US011464848B2

(12) United States Patent
Ciaramella et al.

(10) Patent No.: US 11,464,848 B2
(45) **Date of Patent: *Oct. 11, 2022**

(54) RESPIRATORY SYNCYTIAL VIRUS VACCINE

(71) Applicant: ModernaTX, Inc., Cambridge, MA (US)

(72) Inventors: Giuseppe Ciaramella, Sudbury, MA (US); Kapil Bahl, Medford, MA (US); Amy Espeseth, Chalfont, PA (US); Dai Wang, Blue Bell, PA (US); Andrew J. Bett, Lansdale, PA (US)

(73) Assignee: ModernaTX, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/494,103

(22) PCT Filed: Mar. 15, 2018

(86) PCT No.: PCT/US2018/022630

§ 371 (c)(1),
(2) Date: Sep. 13, 2019

(87) PCT Pub. No.: WO2018/170260

PCT Pub. Date: Sep. 20, 2018

(65) Prior Publication Data

US 2020/0129608 A1 Apr. 30, 2020

Related U.S. Application Data

(60) Provisional application No. 62/471,801, filed on Mar. 15, 2017.

(51) Int. Cl.

| | |
|---|---|
| ***A61K 39/12*** | (2006.01) |
| ***A61P 31/14*** | (2006.01) |
| ***A61K 9/00*** | (2006.01) |
| ***A61K 9/51*** | (2006.01) |
| ***C07K 16/10*** | (2006.01) |
| ***C12N 7/00*** | (2006.01) |
| ***A61K 39/00*** | (2006.01) |

(52) U.S. Cl.

CPC ............ *A61K 39/12* (2013.01); *A61K 9/0019* (2013.01); *A61K 9/5123* (2013.01); *A61K 9/5146* (2013.01); *A61P 31/14* (2018.01); *C07K 16/1027* (2013.01); *C12N 7/00* (2013.01); *A61K 2039/53* (2013.01); *A61K 2039/54* (2013.01); *A61K 2039/545* (2013.01); *A61K 2039/70* (2013.01); *C07K 2317/10* (2013.01); *C07K 2317/76* (2013.01); *C12N 2760/18533* (2013.01)

(58) Field of Classification Search

CPC .... A61K 39/12; A61K 9/0019; A61K 9/5123; A61K 9/5146; A61K 2039/53; A61K 2039/54; A61K 2039/545; A61K 2039/70; A61K 2039/572; A61K 9/1272; A61K 31/7105; A61K 31/7115; A61P 31/14; C07K 16/1027; C07K 2317/10; C07K 2317/76; C12N 7/00; C12N 2760/18533; C12N 2760/18534

See application file for complete search history.

(56) References Cited

U.S. PATENT DOCUMENTS

| | | | |
|---|---|---|---|
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |
| 8,569,256 | B2 | 10/2013 | Heyes et al. |
| 8,609,142 | B2 | 12/2013 | Troiano et al. |
| 8,613,954 | B2 | 12/2013 | Zale et al. |
| 8,617,608 | B2 | 12/2013 | Zale et al. |
| 8,691,966 | B2 | 4/2014 | Kariko et al. |
| 8,710,200 | B2 | 4/2014 | Schrum et al. |
| 8,734,832 | B2 | 5/2014 | O'Hagan et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,999,380 | B2 | 4/2015 | Bancel et al. |
| 9,221,891 | B2 | 12/2015 | Bancel et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,597,380 | B2 | 3/2017 | Chakraborty et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

Chen S, Tam YYC, Lin PJC, Sung MMH, Tam YK, Cullis PR. Influence of particle size on the in vivo potency of lipid nanoparticle formulations of siRNA. J Control Release. Aug. 10, 2016;235:236-244. (Year: 2016).*

(Continued)

*Primary Examiner* — Rachel B Gill

(74) *Attorney, Agent, or Firm* — Wolf, Greenfield & Sacks, P.C.

(57) ABSTRACT

The disclosure describes respiratory syncytial virus (RSV) ribonucleic acid (RNA) vaccines, as well as methods of using the vaccines and compositions comprising the vaccines.

17 Claims, 20 Drawing Sheets

Specification includes a Sequence Listing.

(56) References Cited

U.S. PATENT DOCUMENTS

| | | | |
|---|---|---|---|
| 9,803,199 | B2 | 10/2017 | Koizumi et al. |
| 9,868,691 | B2 | 1/2018 | Benenato et al. |
| 9,872,900 | B2 | 1/2018 | Ciaramella et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,045,540 | B2 | 6/2021 | Ciaramella |
| 11,103,578 | B2 | 8/2021 | Ciaramella et al. |
| 2001/0001066 | A1 | 5/2001 | Cezayirli et al. |
| 2003/0032615 | A1 | 2/2003 | Felgner et al. |
| 2005/0032730 | A1 | 2/2005 | Von Der Mulbe et al. |
| 2005/0059624 | A1 | 3/2005 | Hoerr et al. |
| 2005/0250723 | A1 | 11/2005 | Hoerr et al. |
| 2006/0172003 | A1 | 8/2006 | Meers et al. |
| 2006/0172966 | A1 | 8/2006 | Lipford et al. |
| 2007/0280929 | A1 | 12/2007 | Hoerr et al. |
| 2010/0068226 | A1 | 3/2010 | Taylor et al. |
| 2010/0130588 | A1 | 5/2010 | Yaworski et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mulbe et al. |
| 2010/0303851 | A1 | 12/2010 | Hoerr et al. |
| 2011/0250225 | A1 | 10/2011 | Fotin-Mleczek et al. |
| 2011/0269950 | A1 | 11/2011 | Von Der Mulbe et al. |
| 2011/0311472 | A1 | 12/2011 | Hoerr et al. |
| 2012/0189700 | A1 | 7/2012 | Aguilar et al. |
| 2012/0258046 | A1 | 10/2012 | Mutske |
| 2012/0263648 | A1 | 10/2012 | Shapiro et al. |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0171241 | A1 | 7/2013 | Geall |
| 2013/0183355 | A1 | 7/2013 | Jain et al. |
| 2013/0189351 | A1 | 7/2013 | Geall |
| 2013/0195867 | A1 | 8/2013 | Hoerr et al. |
| 2013/0195968 | A1 | 8/2013 | Geall et al. |
| 2013/0195969 | A1 | 8/2013 | Geall et al. |
| 2013/0202684 | A1 | 8/2013 | Geall et al. |
| 2013/0236533 | A1 | 9/2013 | Von Andrian et al. |
| 2013/0236974 | A1 | 9/2013 | De Fougerolles |
| 2013/0245103 | A1 | 9/2013 | de Fougerolles et al. |
| 2013/0245107 | A1 | 9/2013 | De Fougerolles et al. |
| 2013/0259923 | A1 | 10/2013 | Bancel et al. |
| 2013/0266640 | A1 | 10/2013 | De Fougerolles et al. |
| 2013/0295043 | A1 | 11/2013 | Kallen et al. |
| 2013/0336998 | A1 | 12/2013 | Kallen et al. |
| 2014/0065228 | A1 | 3/2014 | Yarowoski et al. |
| 2014/0134201 | A1 | 5/2014 | Tureci et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0248314 | A1 | 9/2014 | Swanson et al. |
| 2014/0255472 | A1 | 9/2014 | Geall et al. |
| 2014/0271699 | A1 | 9/2014 | Kwong et al. |
| 2014/0271829 | A1 | 9/2014 | Lilja et al. |
| 2014/0378538 | A1 | 12/2014 | Bancel |
| 2015/0030622 | A1 | 1/2015 | Marshall et al. |
| 2015/0051268 | A1 | 2/2015 | Bancel et al. |
| 2015/0056253 | A1 | 2/2015 | Bancel et al. |
| 2015/0079121 | A1 | 3/2015 | Weiner et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2015/0376115 | A1 | 12/2015 | Ansell et al. |
| 2016/0022580 | A1 | 1/2016 | Ramsay et al. |
| 2016/0024140 | A1 | 1/2016 | Issa et al. |
| 2016/0024141 | A1 | 1/2016 | Issa et al. |
| 2016/0151284 | A1 | 1/2016 | Heyes et al. |
| 2016/0032273 | A1 | 2/2016 | Shahrokh et al. |
| 2016/0038612 | A1 | 2/2016 | Hoge et al. |
| 2016/0151474 | A1 | 6/2016 | Kallen et al. |
| 2016/0243221 | A1 | 8/2016 | Hoge et al. |
| 2016/0317647 | A1 | 11/2016 | Ciaramella et al. |
| 2016/0376224 | A1 | 12/2016 | Du et al. |
| 2017/0043037 | A1 | 2/2017 | Kariko et al. |
| 2017/0202979 | A1 | 7/2017 | Chakraborty et al. |
| 2017/0204152 | A1 | 7/2017 | Nelson et al. |
| 2017/0210697 | A1* | 7/2017 | Benenato ................ A61P 37/06 |
| 2017/0239371 | A1 | 8/2017 | Guild et al. |
| 2017/0130255 | A1 | 10/2017 | Wang et al. |
| 2017/0340724 | A1* | 11/2017 | Ciaramella ............ A61K 39/12 |
| 2018/0000953 | A1 | 1/2018 | Almarsson et al. |
| 2018/0002393 | A1 | 1/2018 | Bancel et al. |
| 2018/0028645 | A1* | 2/2018 | Ciaramella ............ A61K 39/39 |
| 2018/0028664 | A1 | 2/2018 | Besin et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0289792 | A1* | 10/2018 | Ciaramella .......... A61K 39/118 |
| 2018/0303925 | A1 | 10/2018 | Weissman et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0363019 | A1 | 12/2018 | Hoge |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0099481 | A1 | 4/2019 | Ciaramella et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0314493 | A1* | 10/2019 | Ciaramella ............ A61K 39/12 |
| 2019/0336452 | A1 | 11/2019 | Brader |
| 2019/0336595 | A1* | 11/2019 | Ciaramella ............ A61K 39/12 |
| 2019/0351040 | A1 | 11/2019 | Valiante et al. |
| 2019/0382774 | A1* | 12/2019 | Hoge ..................... C12N 15/85 |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1* | 3/2020 | Smith ................ A61K 48/0075 |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2021/0023199 | A1 | 1/2021 | Kallen et al. |

(56) References Cited

U.S. PATENT DOCUMENTS

| | | | |
|---|---|---|---|
| 2021/0030866 | A1 | 2/2021 | Kallen et al. |
| 2021/0046173 | A1 | 2/2021 | Ciaramella et al. |
| 2021/0060175 | A1 | 3/2021 | Baumhof et al. |
| 2021/0163919 | A1 | 6/2021 | Issa et al. |
| 2021/0187097 | A1 | 6/2021 | Ciaramella et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0309976 | A1 | 10/2021 | Dousis et al. |
| 2022/0031631 | A1 | 2/2022 | Almarsson et al. |
| 2022/0047518 | A1 | 3/2022 | Hennessy et al. |
| 2022/0054653 | A1 | 3/2022 | Martini et al. |

FOREIGN PATENT DOCUMENTS

| | | | |
|---|---|---|---|
| CA | 2473135 | A1 | 6/2003 |
| EP | 1083232 | B1 | 2/2005 |
| EP | 1301614 | B1 | 11/2006 |
| EP | 1383556 | B1 | 10/2007 |
| EP | 1905844 | A2 | 2/2008 |
| EP | 1026253 | B2 | 12/2012 |
| EP | 2188379 | B1 | 1/2013 |
| WO | WO 1990/011092 | A1 | 10/1990 |
| WO | WO 1996/040945 | A2 | 12/1996 |
| WO | WO 1999/052503 | A2 | 10/1999 |
| WO | WO 2001/021810 | A1 | 3/2001 |
| WO | WO 2004/058166 | A2 | 7/2004 |
| WO | WO 2005/007689 | A1 | 1/2005 |
| WO | WO 2005/120152 | | 12/2005 |
| WO | WO 2006/050280 | A2 | 5/2006 |
| WO | WO 2007/094854 | A2 | 8/2007 |
| WO | WO 2008/014979 | A3 | 2/2008 |
| WO | WO 2008/052770 | A2 | 5/2008 |
| WO | WO 2008/083949 | A2 | 7/2008 |
| WO | WO 2008/103276 | A2 | 8/2008 |
| WO | WO 2010/037408 | A1 | 4/2010 |
| WO | WO 2010/042877 | A1 | 4/2010 |
| WO | WO 2010/054406 | A1 | 5/2010 |
| WO | WO 2010/077717 | A1 | 7/2010 |
| WO | WO 2010/088927 | A1 | 8/2010 |
| WO | WO 2010/115046 | A2 | 10/2010 |
| WO | WO 2011/005799 | A2 | 1/2011 |
| WO | WO 2011/069529 | A1 | 6/2011 |
| WO | WO 2011/069586 | A1 | 6/2011 |
| WO | WO 2011/140627 | A1 | 11/2011 |
| WO | WO 2011/144358 | A1 | 11/2011 |
| WO | WO 2012/006369 | A2 | 1/2012 |
| WO | WO 2012/006376 | A2 | 1/2012 |
| WO | WO 2012/006378 | A1 | 1/2012 |
| WO | WO 2012/006380 | A2 | 1/2012 |
| WO | WO 2012/019630 | A1 | 2/2012 |
| WO | WO 2012/019780 | A1 | 2/2012 |
| WO | WO 2012/030901 | A1 | 3/2012 |
| WO | WO 2012/075040 | A2 | 6/2012 |
| WO | WO 2012/089225 | A1 | 7/2012 |
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2013/006825 | A1 | 1/2013 |
| WO | WO 2013/006837 | A1 | 1/2013 |
| WO | WO 2013/006838 | A1 | 1/2013 |
| WO | WO 2013/006842 | A2 | 1/2013 |
| WO | WO 2013/030778 | A2 | 3/2013 |
| WO | WO 2013/052167 | A2 | 4/2013 |
| WO | WO 2013/056132 | A2 | 4/2013 |
| WO | WO 2013/059496 | A1 | 4/2013 |
| WO | WO 2013/113502 | A1 | 8/2013 |
| WO | WO 2013/174409 | A1 | 11/2013 |
| WO | WO 2013/185069 | A1 | 12/2013 |
| WO | WO 2014/071963 | A1 | 5/2014 |
| WO | WO 2014/072061 | A1 | 5/2014 |
| WO | WO 2014/089239 | A1 | 6/2014 |
| WO | WO 2014/089486 | A1 | 6/2014 |
| WO | WO 2014/127917 | A1 | 8/2014 |
| WO | WO 2014/136086 | A1 | 9/2014 |
| WO | WO 2014/144196 | A1 | 9/2014 |
| WO | WO 2014/152027 | A1 | 9/2014 |
| WO | WO 2014/152774 | A1 | 9/2014 |
| WO | WO 2014/160243 | A1 | 10/2014 |
| WO | WO 2014/160463 | A1 | 10/2014 |
| WO | WO 2014/174018 | A1 | 10/2014 |
| WO | WO 2014/202570 | A1 | 12/2014 |
| WO | WO 2015/013551 | A1 | 1/2015 |
| WO | WO 2015/024667 | A1 | 2/2015 |
| WO | WO 2015/024668 | A2 | 2/2015 |
| WO | WO 2015/024669 | A1 | 2/2015 |
| WO | WO 2015/095340 | A1 | 6/2015 |
| WO | WO 2015/095346 | A1 | 6/2015 |
| WO | WO 2015/189425 | A1 | 12/2015 |
| WO | WO 2015/199952 | A1 | 12/2015 |
| WO | WO 2016/037053 | A1 | 3/2016 |
| WO | WO 2016/164762 | A1 | 10/2016 |
| WO | WO 2016/176330 | A1 | 11/2016 |
| WO | WO 2016/201377 | A1 | 12/2016 |
| WO | WO 2016/203025 | A1 | 12/2016 |
| WO | WO 2017/015457 | A1 | 1/2017 |
| WO | WO 2017/015463 | A1 | 1/2017 |
| WO | WO 2017/019935 | A1 | 2/2017 |
| WO | WO 2017/020026 | A1 | 2/2017 |
| WO | WO 2017/153936 | | 3/2017 |
| WO | WO 2017/172890 | A1 | 3/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/070616 | A1 | 4/2017 |
| WO | WO 2017/070618 | A1 | 4/2017 |
| WO | WO 2017/070620 | A1 | 4/2017 |
| WO | WO 2017/070622 | A1 | 4/2017 |
| WO | WO 2017/070623 | A1 | 4/2017 |
| WO | WO 2017/070626 | A2 | 4/2017 |
| WO | WO 2017/075531 | A1 | 5/2017 |
| WO | WO 2017/127750 | A1 | 7/2017 |
| WO | WO 2017/174564 | A1 | 10/2017 |
| WO | WO 2017/201333 | A1 | 11/2017 |
| WO | WO 2017/201340 | A1 | 11/2017 |
| WO | WO 2017/201342 | A1 | 11/2017 |
| WO | WO 2017/201347 | A1 | 11/2017 |
| WO | WO 2017/201349 | A1 | 11/2017 |
| WO | WO 2018/053209 | A1 | 3/2018 |
| WO | WO 2018/075980 | A1 | 4/2018 |
| WO | WO 2018/078053 | A1 | 5/2018 |
| WO | WO 2018/081459 | A1 | 5/2018 |
| WO | WO 2018/081462 | A1 | 5/2018 |
| WO | WO 2018/081638 | A1 | 5/2018 |
| WO | WO 2018/089801 | A1 | 5/2018 |
| WO | WO 2018/089851 | A1 | 5/2018 |
| WO | WO 2018/107088 | A1 | 6/2018 |
| WO | WO 2018/111967 | A1 | 6/2018 |
| WO | WO 2018/144082 | A1 | 8/2018 |
| WO | WO 2018/144778 | A1 | 8/2018 |
| WO | WO 2018/151816 | A1 | 8/2018 |
| WO | WO 2018/157009 | A1 | 8/2018 |
| WO | WO 2018/170245 | A1 | 9/2018 |
| WO | WO 2018/170256 | A1 | 9/2018 |
| WO | WO 2018/170260 | A1 | 9/2018 |
| WO | WO 2018/170270 | A1 | 9/2018 |
| WO | WO 2018/170347 | A1 | 9/2018 |
| WO | WO 2018/175783 | A1 | 9/2018 |
| WO | WO 2018/187590 | A2 | 10/2018 |
| WO | WO 2018/200737 | A1 | 11/2018 |
| WO | WO 2018/232355 | A1 | 12/2018 |
| WO | WO 2018/232357 | A1 | 12/2018 |
| WO | WO 2019/036670 | A1 | 2/2019 |
| WO | WO 2019/036683 | A1 | 2/2019 |
| WO | WO 2019/036685 | A1 | 2/2019 |
| WO | WO 2019/103993 | A1 | 5/2019 |
| WO | WO 2019/148101 | A1 | 8/2019 |
| WO | WO 2019/202035 | A1 | 10/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |

(56) References Cited

FOREIGN PATENT DOCUMENTS

| | | | |
|---|---|---|---|
| WO | WO 2020/061367 | A1 | 3/2020 |
| WO | WO 2020/097291 | A1 | 5/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/155243 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/046898 | A1 | 3/2022 |

OTHER PUBLICATIONS

Sabnis S, Kumarasinghe ES, Salerno T, Mihai C, Ketova T, Senn JJ, Lynn A, Bulychev A, McFadyen I, Chan J, Almarsson Ö, Stanton MG, Benenato KE. A Novel Amino Lipid Series for mRNA Delivery: Improved Endosomal Escape and Sustained Pharmacology and Safety in Non-human Primates. Mol Ther. Jun. 6, 2018;26(6):1509-1519.*

Xue HY, Guo P, Wen WC, Wong HL. Lipid-Based Nanocarriers for RNA Delivery. Curr Pharm Des. 2015;21(22):3140-7. doi: 10.2174/1381612821666150531164540. PMID: 26027572; PMCID: PMC4618487.*

Kumar V, Qin J, Jiang Y, Duncan RG, Brigham B, Fishman S, Nair JK, Akinc A, Barros SA, Kasperkovitz PV. Shielding of Lipid Nanoparticles for siRNA Delivery: Impact on Physicochemical Properties, Cytokine Induction, and Efficacy. Mol Ther Nucleic Acids. Nov. 18, 2014;3(11):e210.*

Hassett KJ, Benenato KE, Jacquinet E, Lee A, Woods A, Yuzhakov O, Himansu S, Deterling J, Geilich BM, Ketova T, Mihai C, Lynn A, McFadyen I, Moore MJ, Senn JJ, et al.Optimization of Lipid Nanoparticles for Intramuscular Administration of mRNA Vaccines. Mol Ther Nucleic Acids. Apr. 15, 2019;15:1-11. Epub Feb. 7, 2019.*

Kurimoto S, Yoshinaga N, Igarashi K, Matsumoto Y, Cabral H, Uchida S. PEG-OligoRNA Hybridization of mRNA for Developing Sterically Stable Lipid Nanoparticles toward In Vivo Administration. Molecules. Apr. 3, 2019;24(7):1303.*

Graham BS, Modjarrad K, McLellan JS. Novel antigens for RSV vaccines. Curr Opin Immunol. Aug. 2015;35:30-8. Epub Jun. 10, 2015.*

Glenn GM, Smith G, Fries L, Raghunandan R, Lu H, Zhou B, Thomas DN, Hickman SP, Kpamegan E, Boddapati S, Piedra PA. Safety and immunogenicity of a Sf9 insect cell-derived respiratory syncytial virus fusion protein nanoparticle vaccine. Vaccine. Jan. 7, 2013;31(3):524-32. Epub Nov. 12, 2012.*

Espeseth AS, Cejas PJ, Citron MP, Wang D, DiStefano DJ, Callahan C, Donnell GO, Galli JD, Swoyer R, et al. Modified mRNA/lipid nanoparticle-based vaccines expressing respiratory syncytial virus F protein variants are immunogenic and protective in rodent models of RSV infection. NPJ Vaccines. Feb. 14, 2020;5:16.*

Jorquera PA, Choi Y, Oakley KE, Powell TJ, Boyd JG, Palath N, Haynes LM, Anderson LJ, Tripp RA. Nanoparticle vaccines encompassing the respiratory syncytial virus (RSV) G protein CX3C chemokine motif induce robust immunity protecting from challenge and disease. PLoS One. Sep. 10, 2013;8(9):e74905.*

Liang B, Surman S, Amaro-Carambot E, Kabatova B, et al. Enhanced Neutralizing Antibody Response Induced by Respiratory Syncytial Virus Prefusion F Protein Expressed by a Vaccine Candidate. J Virol. Sep. 2015;89(18):9499-510. Epub Jul. 8, 2015.*

Leroueil PR, Berry SA, Duthie K, Han G, Rotello VM, McNerny DQ, Baker JR Jr, Orr BG, Holl MM. Wide varieties of cationic nanoparticles induce defects in supported lipid bilayers. Nano Lett. Feb. 2008;8(2):420-4. doi: 10.1021/nl0722929. Epub Jan. 25, 2008. PMID: 18217783.*

Szebeni J, Muggia F, Gabizon A, Barenholz Y. Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011. PMID: 21787819.*

Szebeni J. Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014. PMID: 25124145.*

Szebeni J, Storm G. Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015. PMID: 26182876.*

Ernsting MJ, Murakami M, Roy A, Li SD. Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013. PMID: 24075927; PMCID: PMC3891171.*

U.S. Appl. No. 16/048,154, filed Jul. 27, 2018, Ciaramella et al.

U.S. Appl. No. 90/014,395, filed Oct. 24, 2019, Ciaramella et al.

U.S. Appl. No. 15/753,297, filed Feb. 17, 2018, Thompson.

U.S. Appl. No. 16/450,882, filed Jun. 24, 2019, Ciaramella.

U.S. Appl. No. 16/136,503, filed Sep. 20, 2018, Ciaramella et al.

U.S. Appl. No. 16/009,880, filed Jun. 15, 2018, Ciaramella et al.

U.S. Appl. No. 15/981,762, filed May 16, 2018, Bancel et al.

U.S. Appl. No. 16/582,621, filed Sep. 25, 2019, Chen et al.

U.S. Appl. No. 16/001,786, filed Jun. 6, 2018, Hoge et al.

U.S. Appl. No. 16/389,545, filed Apr. 19, 2019, Ciaramella et al.

U.S. Appl. No. 16/368,270, filed Mar. 28, 2019, Ciaramella et al.

U.S. Appl. No. 16/805,587, filed Feb. 28, 2020, Ciaramella et al.

U.S. Appl. No. 16/348,943, filed May 10, 2019, Ciaramella.

U.S. Appl. No. 16/131,793, filed Sep. 14, 2018, Ciaramella et al.

U.S. Appl. No. 16/608,451, filed Oct. 25, 2019, Ciaramella et al.

PCT/US2018/022630, Jun. 26, 2018, International Search Report and Written Opinion.

International Search Report and Written Opinion for Application No. PCT/US2018/022630, dated Jun. 28, 2018.

Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.

Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Cheng et al., Multifunctional triblock copolymers for intracellular messenger RNA delivery. Biomaterials. Oct. 2012; 33(28): 6868-6876.

Cross et al., Can mRNA disrupt the drug industry? C&EN, 2018: 96(35);35-40.

Cu et al., Enhanced Delivery and Potency of Self-Amplifying mRNA Vaccines by Electroporation in Situ, Vaccines, 2013, 1, 367-383. Abstract Only.

Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

(56) References Cited

OTHER PUBLICATIONS

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Ewert et al., Cationic liposome-nucleic acid complexes for gene delivery and silencing: pathways and mechanisms for plasmid DNA and siRNA. Top Curr Chem. 2010;296:191-226.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Holtkamp et al., Modification of antigen-encoding RNA increases stability, translational efficacy, and T-cell stimulatory capacity of dendritic cells. Blood. Dec. 15, 2006;108(13):4009-17.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kuhn et al., mRNA as a versatile tool for exogenous protein expression. Current Gene Therapy. Oct. 2012; 12 (5): 347-361.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Leitner et al., DNA and RNA-based vaccines: principles, progress and prospects. Vaccine. Dec. 10, 1999;18 (9-10):765-77.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.
Lorenzi et al., Intranasal vaccination with messenger RNA as a new approach in gene therapy: Use against tuberculosis. BMC Biotechnol. Oct. 2010; 10(77): 1-11.
MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Martinon et al., Induction of virus-specific cytotoxic T lymphocytes in vivo by liposome-entrapped mRNA. EurJ Immunol. Jul. 1993;23(7):1719-22.
McKenzie et al., Nucleic acid vaccines: tasks and tactics. lmmunol Res. 2001 ;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mol Ther. Apr. 2000;2(2):176-81.
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Pollard et al., Type I IFN counteracts the induction of antigen-specific immune responses by lipid-based delivery of mRNA vaccines. Mol Ther. Jan. 2013; 21 (1): 251-259.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Vassilev et al., Microparticle-mediated RNA immunization against bovine viral diarrhea virus. Vaccine. Feb. 28, 2001;19(15-16):2012-9.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 16/467,142, filed Jun. 6, 2019, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.

(56) References Cited

OTHER PUBLICATIONS

U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/848,318, filed Apr. 14, 2020, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 16/788,182, filed Feb. 11, 2020, Panther et al.
U.S. Appl. No. 16/794,318, filed Feb. 19, 2020, Mauger et al.
U.S. Appl. No. 17/145,164, filed Jan. 8, 2021, Giessel et al.
U.S. Appl. No. 17/000,201, filed Aug. 21, 2020, Stewart-Jones et al.
U.S. Appl. No. 17/000,215, filed Aug. 21, 2020, Stewart-Jones et al.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kowalski et al., Delivering the Messenger: Advances in Technologies for Therapeutic mRNA Delivery. Molecular Therapy vol. 27 No. 4 Apr. 2019.
Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Reichmuth et al., mRNA Vaccine Delivery Using Lipid Nanoparticles. Ther Deliv. 2016;7(5):319-34. doi: 10.4155/tde-2016-0006.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.
[No Author Listed], Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive (ModernaTX, Inc.) First Posted Aug. 27, 2020. Retrieved online on Mar. 15, 2021 at https://www.clinicaltrials.gov/ct2/show/NCT04528719?term=NCT04528719&draw=2&rank=1. 9 pages.
McLellan et al., Structure of respiratory syncytial virus fusion glycoprotein in the postfusion conformation reveals preservation of neutralizing epitopes. J Virol. Aug. 2011;85(15):7788-96. doi: 10.1128/JVI.00555-11. Epub May 25, 2011.
Michel T. et al.: "Cationic Nanoliposomes Meet mRNA: Efficient Delivery of Modified mRNA Using Hemocompatible and Stable Vectors for Therapeutic Applications" Molecular Therapy Nucleic Acids, 2017, vol. 8, pp. 459-468, http://dx.doi.org/10.1016/j.omtn.2017.07.013.
Shin et al., Recent Advances in RNA Therapeutics and RNA Delivery Systems Based on Nanoparticles. Adv. Therap., Nov. 2018;1(7):1800065. Review.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Zeng et al., Formulation and Delivery Technologies for mRNA Vaccines. Curr Top Microbiol Immunol. Jun. 2, 2020;10.1007/82_2020_217. doi: 10.1007/82_2020_217.

* cited by examiner

Fig. 3A
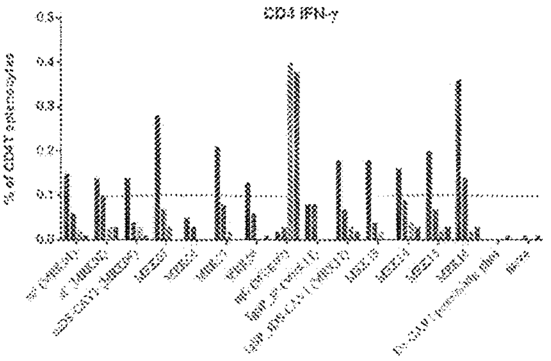
Fig. 3B
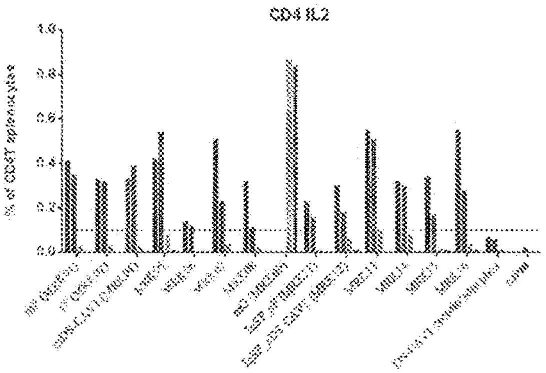
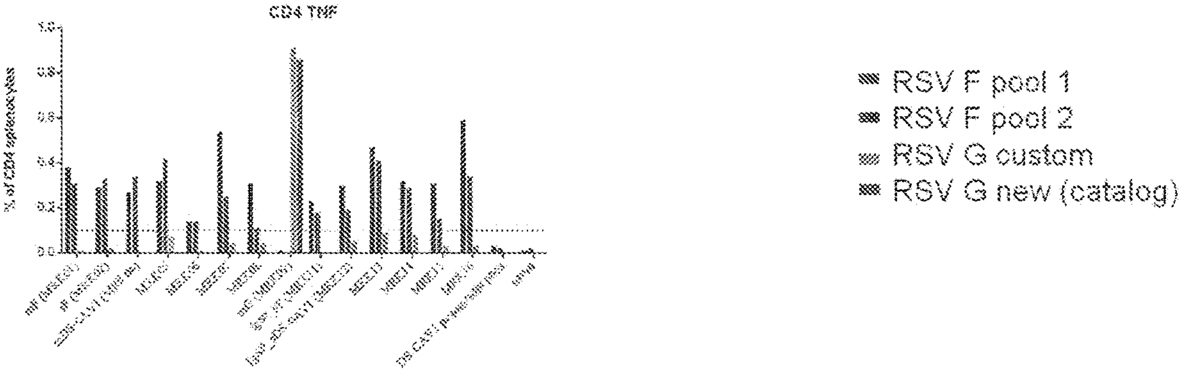
Fig. 3C

Fig. 4A
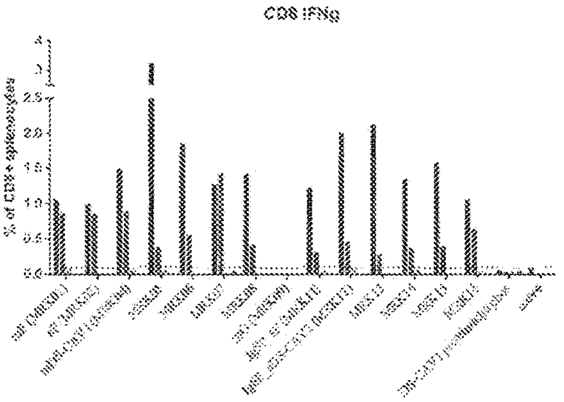
Fig. 4B
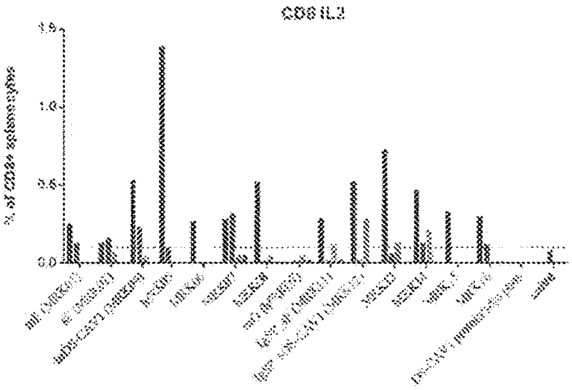
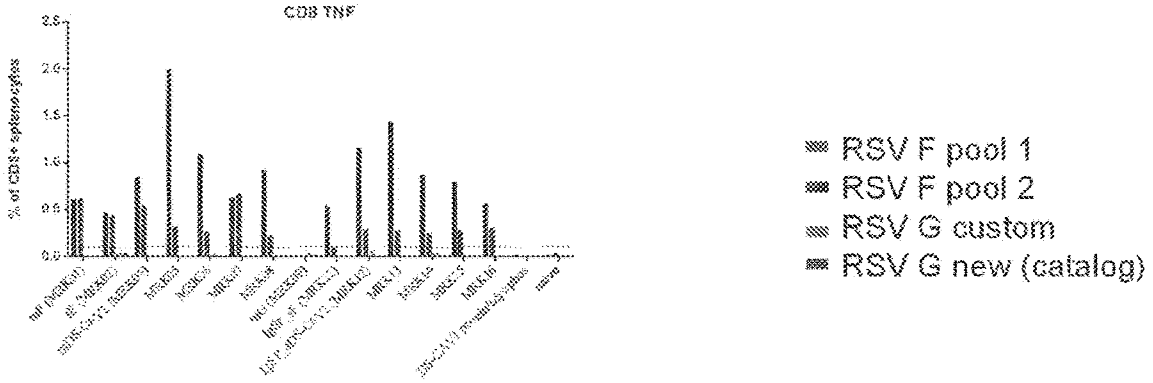
Fig. 4C

Fig 10. Competition ELISA from Cotton Rat Immunogenicity Study

RESPIRATORY SYNCYTIAL VIRUS VACCINE

RELATED APPLICATIONS

This application is a national stage filing under 35 U.S.C. § 371 of international application number PCT/US2018/022630, filed Mar. 15, 2018, which was published under PCT Article 21(2) in English and claims the benefit under 35 U.S.C. § 119(e) of U.S. provisional application No. 62/471,801, filed Mar. 15, 2017, each of which is herein incorporated by reference in its entirety.

BACKGROUND

The human respiratory syncytial virus (RSV) is a negative-sense, single-stranded RNA virus of the genus *Pneumovirinae* and of the family Paramyxoviridae. Symptoms in adults typically resemble a sinus infection or the common cold, although the infection may be asymptomatic. In older adults (e.g., >60 years), RSV infection may progress to bronchiolitis or pneumonia. Symptoms in children are often more severe, including bronchiolitis and pneumonia. It is estimated that in the United States, most children are infected with RSV by the age of three. The RSV virion consists of an internal nucleocapsid comprised of the viral RNA bound to nucleoprotein (N), phosphoprotein (P), and large polymerase protein (L). The nucleocapsid is surrounded by matrix protein (M) and is encapsulated by a lipid bilayer into which the viral fusion (F) and attachment (G) proteins as well as the small hydrophobic protein (SH) are incorporated. The viral genome also encodes two nonstructural proteins (NS1 and NS2), which inhibit type I interferon activity as well as the M-2 protein.

Deoxyribonucleic acid (DNA) vaccination is one technique used to stimulate humoral and cellular immune responses to foreign antigens, such as RSV antigens. The direct injection of genetically engineered DNA (e.g., naked plasmid DNA) into a living host results in a small number of host cells directly producing an antigen, resulting in a protective immunological response. With this technique, however, comes potential problems, including the possibility of insertional mutagenesis, which could lead to the activation of oncogenes or the inhibition of tumor suppressor genes.

SUMMARY

The RNA vaccines of the present disclosure may be used to induce a balanced immune response against RSV, comprising both cellular and humoral immunity, without risking the possibility of insertional mutagenesis, for example.

The RNA (e.g., mRNA) vaccines may be utilized in various settings, depending on the prevalence of the infection, or the degree or level of unmet medical need. The RNA vaccines may be utilized to treat and/or prevent an infection by various genotypes, strains, and isolates of RSV. The RNA vaccines as provided herein have superior properties in that they produce much larger antibody titers and produce responses earlier than commercially-available anti-viral therapeutic treatments. While not wishing to be bound by theory, it is believed that the RNA vaccines of the present disclosure are better designed to produce the appropriate protein conformation upon translation, as the RNA vaccines co-opt natural cellular machinery. Unlike traditional vaccines, which are manufactured ex vivo and may trigger unwanted cellular responses, RNA vaccines as provided herein are presented to the cellular system in a more native fashion.

Some embodiments of the present disclosure provide respiratory syncytial virus (RSV) vaccines that include (i) at least one ribonucleic acid (RNA) polynucleotide having an open reading frame encoding at least one RSV antigenic polypeptide (including immunogenic fragments thereof, e.g., immunogenic fragments capable of raising an immune response to RSV), and (ii) a pharmaceutically acceptable carrier.

In some embodiments, the at least one RNA polynucleotide has at least one chemical modification.

In some embodiments, an antigenic polypeptide is glycoprotein G.

In some embodiments, an antigenic polypeptide is glycoprotein F.

In some embodiments, at least one antigenic polypeptide is glycoprotein F and at least one antigenic polypeptide is selected from G, M, N, P, L, SH, M2, NS1 and NS2.

In some embodiments, at least one antigenic polypeptide is glycoprotein F and at least two antigenic polypeptides are selected from G, M, N, P, L, SH, M2, NS1 and NS2.

In some embodiments, the RNA vaccines further comprise an adjuvant.

In some embodiments, at least one RNA polynucleotide is encoded by at least one nucleic acid sequence set forth as SEQ ID NO: 1, 2, 5, 7, 9, 11, 13, 15, 17, 19, 21, 23, 25, 27, 242, 246, 257, 258, or 259, or homologs having at least 80% identity with a nucleic acid sequence set forth as SEQ ID NO: 1, 2, 5, 7, 9, 11, 13, 15, 17, 19, 21, 23, 25, 27, 242, 246, 257, 258, or 259. In some embodiments, at least one RNA polynucleotide is encoded by at least one nucleic acid sequence set forth as SEQ ID NO: 1, 2, 5, 7, 9, 11, 13, 15, 17, 19, 21, 23, 25, 27, 242, 246, 257, 258, or 259, or homologs having at least 90% (e.g. 90%, 91%, 92%, 93%, 94%, 95%, 96%, 97%, 98%, 99%, 99.8% or 99.9%) identity with a nucleic acid sequence set forth as SEQ ID NO: 1, 2, 5, 7, 9, 11, 13, 15, 17, 19, 21, 23, 25, 27, 242, 246, 257, 258, or 259. In some embodiments, at least one RNA polynucleotide is encoded by at least one fragment of a nucleic acid sequence (e.g., a fragment having at least one antigenic sequence or at least one epitope) set forth as SEQ ID NO: 1, 2, 5, 7, 9, 11, 13, 15, 17, 19, 21, 23, 25, 27, 242, 246, 257, 258, or 259.

In some embodiments, at least one RNA polynucleotide comprises at least one nucleic acid sequence set forth as any of SEQ ID NO: 260-280, or homologs having at least 80% identity with a nucleic acid sequence set forth as any of SEQ ID NO: 260-280. In some embodiments, at least one RNA polynucleotide comprises at least one nucleic acid sequence set forth as any of SEQ ID NO: 260-280, or homologs having at least 90% (e.g. 90%, 91%, 92%, 93%, 94%, 95%, 96%, 97%, 98%, 99%, 99.8% or 99.9%) identity with a nucleic acid sequence set forth as any of SEQ ID NO: 260-280. In some embodiments, at least one RNA polynucleotide comprises at least one fragment of a nucleic acid sequence (e.g., a fragment having at least one antigenic sequence or at least one epitope) set forth as any of SEQ ID NO: 260-280.

In some embodiments, the amino acid sequence of the RSV antigenic polypeptide is, or is a fragment of, or is a homolog having at least 80% (e.g., 85%, 90%, 95%, 98%, 99%) identity to, the amino acid sequence set forth as SEQ ID NO: 3 or SEQ ID NO: 4.

In some embodiments, the amino acid sequence of the RSV antigenic polypeptide is, or is a fragment of, or is a homolog having at least 80% (e.g., 85%, 90%, 95%, 98%, 99%) identity to, the amino acid sequence set forth as SEQ ID NO: 3, 4, 6, 8, 10, 12, 14, 16, 18, 20, 22, 24, 26, 28, 243, or 245.

In some embodiments, at least one RNA (e.g., mRNA) polynucleotide encodes an antigenic polypeptide having at least 90% identity to an amino acid sequence of the present disclosure and having membrane fusion activity. In some embodiments, at least one RNA polynucleotide encodes an antigenic polypeptide having at least 95% identity to an amino acid sequence of the present disclosure and having membrane fusion activity. In some embodiments, at least one RNA polynucleotide encodes an antigenic polypeptide having at least 96% identity to an amino acid sequence of the present disclosure and having membrane fusion activity. In some embodiments, at least one RNA polynucleotide encodes an antigenic polypeptide having at least 97% identity to an amino acid sequence of the present disclosure and having membrane fusion activity. In some embodiments, at least one RNA polynucleotide encodes an antigenic polypeptide having at least 98% identity to an amino acid sequence of the present disclosure and having membrane fusion activity. In some embodiments, at least one RNA polynucleotide encodes an antigenic polypeptide having at least 99% identity to an amino acid sequence of the present disclosure and having membrane fusion activity. In some embodiments, at least one RNA polynucleotide encodes an antigenic polypeptide having 95-99% identity to an amino acid sequence of the present disclosure and having membrane fusion activity.

In some embodiments, at least one RNA (e.g., mRNA) polynucleotide encodes an antigenic polypeptide having an amino acid sequence of the present disclosure and is codon optimized mRNA.

In some embodiments, at least one RNA (e.g., mRNA) polynucleotide encodes an antigenic polypeptide having an amino acid sequence of the present disclosure and has less than 80% identity to (corresponding) wild-type mRNA sequence. In some embodiments, at least one RNA polynucleotide encodes an antigenic polypeptide having an amino acid sequence of the present disclosure and has less than 75%, 85% or 95% identity to wild-type mRNA sequence. In some embodiments, at least one RNA polynucleotide encodes an antigenic polypeptide having an amino acid sequence of the present disclosure and has 30-80%, 40-80%, 50-80%, 60-80%, 70-80%, 75-80% or 78-80% identity to wild-type mRNA sequence. In some embodiments, at least one RNA polynucleotide encodes an antigenic polypeptide having an amino acid sequence of the present disclosure and has 30-85%, 40-85%, 50-85%, 60-85%, 70-85%, 75-85%, or 80-85% identity to wild-type mRNA sequence. In some embodiments, at least one RNA polynucleotide encodes an antigenic polypeptide having an amino acid sequence of the present disclosure and has 30-90%, 40-90%, 50-90%, 60-90%, 70-90%, 75-90%, 80-90%, or 85-90% identity to wild-type mRNA sequence.

In some embodiments, at least one RNA (e.g., mRNA) polynucleotide is encoded by a nucleic acid (e.g., DNA) having at least 90% identity to a nucleic acid sequence of the present disclosure. In some embodiments, at least one RNA polynucleotide is encoded by a nucleic acid having at least 95% identity to a nucleic acid sequence of the present disclosure. In some embodiments, at least one RNA polynucleotide is encoded by a nucleic acid having at least 96% identity to a nucleic acid sequence of the present disclosure. In some embodiments, at least one RNA polynucleotide is encoded by a nucleic acid having at least 97% identity to a nucleic acid sequence of the present disclosure. In some embodiments, at least one RNA polynucleotide is encoded by a nucleic acid having at least 98% identity to a nucleic acid sequence of the present disclosure. In some embodiments, at least one RNA polynucleotide is encoded by a nucleic acid having at least 99% identity to a nucleic acid sequence of the present disclosure. In some embodiments, at least one RNA polynucleotide is encoded by a nucleic acid having 95-99% identity to a nucleic acid sequence of the present disclosure.

In some embodiments, at least one mRNA polynucleotide is encoded by a nucleic acid having a sequence of the present disclosure and has less than 80% identity to wild-type mRNA sequence. In some embodiments, at least one mRNA polynucleotide is encoded by a nucleic acid having a sequence of the present disclosure and has less than 75%, 85% or 95% identity to a wild-type mRNA sequence. In some embodiments, at least one mRNA polynucleotide is encoded by a nucleic acid having a sequence of the present disclosure and has less than 30-80%, 40-80%, 50-80%, 60-80%, 70-80%, 75-80% or 78-80% identity to wild-type mRNA sequence. In some embodiments, at least one mRNA polynucleotide is encoded by a nucleic acid having a sequence of the present disclosure and has less than 30-85%, 40-85%, 50-85%, 60-85%, 70-85%, 75-85% or 80-85% identity to wild-type mRNA sequence. In some embodiments, at least one mRNA polynucleotide is encoded by a nucleic acid having a sequence of the present disclosure and has less than 30-90%, 40-90%, 50-90%, 60-90%, 70-90%, 75-90%, 80-90%, or 85-90% identity to wild-type mRNA sequence.

In some embodiments, at least one RNA (e.g., mRNA) polynucleotide encodes an antigenic polypeptide having an amino acid sequence of the present disclosure and having at least 80% identity to wild-type mRNA sequence, but does not include wild-type mRNA sequence.

In some embodiments, the RSV vaccine includes at least one RNA (e.g., mRNA) polynucleotide having an open reading frame encoding at least one RSV antigenic polypeptide, said RNA polynucleotide having at least one chemical modification.

In some embodiments, the RSV vaccine includes at least one RNA (e.g., mRNA) polynucleotide having an open reading frame encoding at least one RSV antigenic polypeptide, said RNA polynucleotide having at least one chemical modification and at least one 5' terminal cap, wherein the RSV vaccine is formulated within a lipid nanoparticle.

In some embodiments, a 5' terminal cap is 7 mG(5')ppp (5')N1mpNp.

In some embodiments, at least one chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z, 15Z)—N,N-dimethyl-2-nonylhenicosa-12,15-dien-1-amine, and N,N-dimethyl-1-[(1 S,2R)-2-octylcyclopropyl]heptadecan-8-amine.

In some embodiments, the cationic lipid is

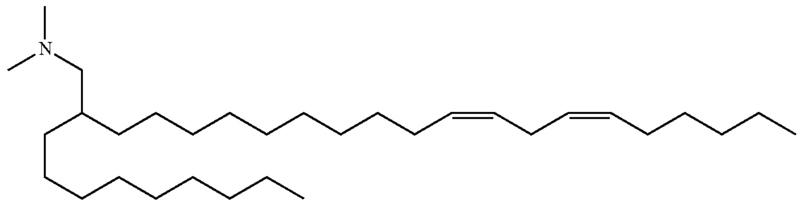 [SMILES: CCCCC/C=C\C/C=C\CCCCCCCCCC(CCCCCCCCC)CN(C)C]
.

In some embodiments, the cationic lipid is

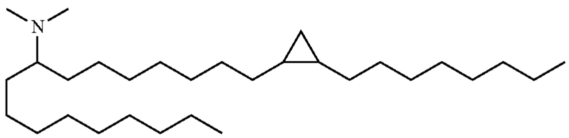
.

In some embodiments, at least one cationic lipid selected from compounds of Formula (I):

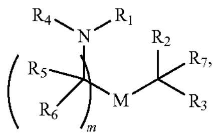
(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$—N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$—OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$—CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_n$—OR, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —$N(OR)S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$) $N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$—CHQR in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —$N(OR)S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$—CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

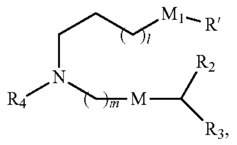

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(═$NR_9$)$N(R)_2$, —NHC(═$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

Some embodiments of the present disclosure provide a respiratory syncytial virus (RSV) vaccine that includes at least one ribonucleic acid (RNA) polynucleotide having an open reading frame encoding at least one RSV antigenic polypeptide, wherein at least 80% of the uracil in the open reading frame have a chemical modification, optionally wherein the RSV vaccine is formulated in a lipid nanoparticle.

In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, a chemical modification is a N1-methyl pseudouridine in the 5-position of the uracil. In some embodiments, 100% of the uracil in the open reading frame are modified to include N1-methyl pseudouridine.

Some embodiments of the present disclosure provide methods of inducing an antigen specific immune response in a subject, comprising administering to the subject a RSV RNA (e.g., mRNA) vaccine in an amount effective to produce an antigen specific immune response.

In some embodiments, an antigen specific immune response comprises a T cell response or a B cell response or both.

In some embodiments, a method of producing an antigen specific immune response involves a single administration of the RSV RNA (e.g., mRNA) vaccine. In some embodiments, a method further includes administering to the subject a booster dose of the RSV RNA (e.g., mRNA) vaccine. A booster vaccine according to this invention may comprise any RSV RNA (e.g., mRNA) vaccine disclosed herein and may be the same as the RSV RNA vaccine initially administered. In some embodiments, the same RSV RNA vaccine is administered annually for every RSV season.

In some embodiments, a RSV RNA (e.g., mRNA) vaccine is administered to the subject by intradermal, intranasal, or intramuscular injection. In some embodiments, a RSV RNA vaccine is administered to the subject by intramuscular injection.

Also provided herein are RSV RNA (e.g., mRNA) vaccines for use in a method of inducing an antigen specific immune response in a subject, the method comprising administering the RSV vaccine to the subject in an amount effective to produce an antigen specific immune response.

Further provided herein are uses of RSV RNA (e.g., mRNA) vaccines in the manufacture of a medicament for use in a method of inducing an antigen specific immune response in a subject, the method comprising administering the RSV vaccine to the subject in an amount effective to produce an antigen specific immune response.

Some aspects of the present disclosure provide RSV RNA (e.g., mRNA) vaccines formulated in an effective amount to produce an antigen specific immune response in a subject.

Other aspects of the present disclosure provide methods of inducing an antigen specific immune response in a subject, the method comprising administering to a subject the RSV RNA (e.g., mRNA) vaccine described herein in an effective amount to produce an antigen specific immune response in a subject.

In some embodiments, an anti-RSV antigenic polypeptide antibody titer produced in the subject is increased by at least 1 log relative to a control (e.g., a control vaccine). In some embodiments, the anti-RSV antigenic polypeptide antibody titer produced in the subject is increased by 1-3 log relative to a control (e.g., a control vaccine).

In some embodiments, the anti-RSV antigenic polypeptide antibody titer produced in the subject is increased at least 2 times relative to a control (e.g., a control vaccine). In some embodiments, the anti-RSV antigenic polypeptide antibody titer produced in the subject is increased at least 5 times relative to a control (e.g., a control vaccine). In some embodiments, the anti-RSV antigenic polypeptide antibody titer produced in the subject is increased at least 10 times relative to a control (e.g., a control vaccine). In some embodiments, the anti-RSV antigenic polypeptide antibody titer produced in the subject is increased 2-10 times relative to a control (e.g., a control vaccine).

In some embodiments, the control is an anti-RSV antigenic polypeptide antibody titer produced in a subject who has not been administered RSV vaccine. In some embodiments, the control is an anti-RSV antigenic polypeptide antibody titer produced in a subject who has been administered a live attenuated or inactivated RSV vaccine. In some embodiments, the control is an anti-RSV antigenic polypeptide antibody titer produced in a subject who has been administered a recombinant or purified RSV protein vaccine. In some embodiments, the control is an anti-RSV antigenic polypeptide antibody titer produced in a subject who has been administered an RSV virus-like particle (VLP) vaccine.

In some embodiments, the effective amount is a dose equivalent to at least a 2-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a dose equivalent to at least a 4-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a dose equivalent to at least a 10-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a dose equivalent to at least a 100-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a dose equivalent to at least a 1000-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a dose equivalent to a 2-fold to 1000-fold reduction in the standard of care dose of a recombinant RSV protein vaccine, wherein an anti-RSV antigenic polypeptide antibody titer produced in the subject is equivalent to an anti-RSV antigenic polypeptide antibody titer produced in a control subject administered the standard of care dose of a recombinant or purified RSV protein vaccine, a live attenuated or inactivated RSV vaccine, or a RSV VLP vaccine.

In some embodiments, the effective amount is a total dose of 25 μg to 1000 μg, or 50 μg to 1000 μg, or 25 to 200 μg. In some embodiments, the effective amount is a total dose of 50 μg, 100 μg, 200 μg, 400 μg, 800 μg, or 1000 μg. In some embodiments, the effective amount is a dose of 25 μg administered to the subject a total of two times. In some embodiments, the effective amount is a dose of 50 μg administered to the subject a total of two times. In some embodiments, the effective amount is a dose of 100 μg administered to the subject a total of two times. In some embodiments, the effective amount is a dose of 200 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the effective amount administered to a subject is a total dose (of RSV RNA, e.g., mRNA, vaccine) of 50 μg to 1000 μg.

In some embodiments, the efficacy (or effectiveness) of the RSV RNA (e.g., mRNA) vaccine against RSV is greater than 60%.

Vaccine efficacy may be assessed using standard analyses (see, e.g., Weinberg et al., *J Infect Dis.* 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100;\ \text{and}$$

$$\text{Efficacy}=(1-\text{RR})\times 100.$$

Likewise, vaccine effectiveness may be assessed using standard analyses (see, e.g., Weinberg et al., *J Infect Dis.* 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, the efficacy (or effectiveness) of the RSV RNA (e.g., mRNA) vaccine against RSV is greater than 65%. In some embodiments, the efficacy (or effectiveness) of the vaccine against RSV is greater than 70%. In some embodiments, the efficacy (or effectiveness) of the vaccine against RSV is greater than 75%. In some embodiments, the efficacy (or effectiveness) of the vaccine against RSV is greater than 80%. In some embodiments, the efficacy (or effectiveness) of the vaccine against RSV is greater than 85%. In some embodiments, the efficacy (or effectiveness) of the vaccine against RSV is greater than 90%.

In some embodiments, the vaccine immunizes the subject against RSV up to 1 year (e.g. for a single RSV season). In some embodiments, the vaccine immunizes the subject against RSV for up to 2 years. In some embodiments, the vaccine immunizes the subject against RSV for more than 2 years. In some embodiments, the vaccine immunizes the subject against RSV for more than 3 years. In some embodiments, the vaccine immunizes the subject against RSV for more than 4 years. In some embodiments, the vaccine immunizes the subject against RSV for 5-10 years.

In some embodiments, the subject administered an RSV RNA (e.g., mRNA) vaccine is about 5 years old or younger, is between the ages of about 1 year and about 5 years (e.g., about 1, 2, 3, 4, 5 or 6 years), is between the ages of about 6 months and about 1 year (e.g., about 6, 7, 8, 9, 10, 11 or 12 months), is about 6 months or younger, or is about 12 months or younger (e.g., 12, 11, 10, 9, 8, 7, 6, 5, 4, 3, 2 months or 1 month). In some embodiments, the subject was born full term (e.g., about 37-42 weeks). In some embodiments, the subject was born prematurely at about 36 weeks of gestation or earlier (e.g., about 36, 35, 34, 33, 32, 31, 30, 29, 28, 27, 26 or 25 weeks), the subject was born prematurely at about 32 weeks of gestation or earlier, or the subject was born prematurely between about 32 weeks and about 36 weeks of gestation.

In some embodiments, the subject is pregnant (e.g., in the first, second or third trimester) when administered an RSV RNA (e.g., mRNA) vaccine. RSV causes infections of the lower respiratory tract, mainly in infants and young children. One-third of RSV related deaths occur in the first year of life, with 99 percent of these deaths occurring in low-resource countries. It's so widespread in the United States that nearly all children become infected with the virus before their second birthdays. Thus, the present disclosure provides RSV vaccines for maternal immunization to improve mother-to-child transmission of protection against RSV.

In some embodiments, the subject has a chronic pulmonary disease (e.g., chronic obstructive pulmonary disease (COPD) or asthma). Two forms of COPD include chronic bronchitis, which involves a long-term cough with mucus, and emphysema, which involves damage to the lungs over time. Thus, a subject administered a RSV RNA (e.g., mRNA) vaccine may have chronic bronchitis or emphysema.

In some embodiments, the subject has been exposed to RSV, is infected with (has) RSV, or is at risk of infection by RSV.

In some embodiments, the subject is immunocompromised (has an impaired immune system, e.g., has an immune disorder or autoimmune disorder).

In some embodiments, the subject is an elderly subject about 60 years old, about 70 years old, or older (e.g., about 60, 65, 70, 75, 80, 85 or 90 years old).

In some embodiments, the subject is a young adult between the ages of about 20 years and about 50 years (e.g., about 20, 25, 30, 35, 40, 45 or 50 years old).

Some aspects of the present disclosure provide Respiratory Syncytial Virus (RSV) RNA (e.g., mRNA) vaccines containing a signal peptide linked to a RSV antigenic polypeptide. Thus, in some embodiments, the RSV RNA (e.g., mRNA) vaccines contain at least one ribonucleic acid (RNA) polynucleotide having an open reading frame encoding a signal peptide linked to a RSV antigenic peptide. Also provided herein are nucleic acids encoding the RSV RNA (e.g., mRNA) vaccines disclosed herein.

In some embodiments, the RSV antigenic peptide is RSV attachment protein (G). In some embodiments, the RSV antigenic peptide is RSV Fusion (F) glycoprotein. In some embodiments, the RSV antigenic peptide is nucleoprotein (N). In some embodiments, the RSV antigenic peptide is phosphoprotein (P). In some embodiments, the RSV antigenic peptide is large polymerase protein (L). In some embodiments, the RSV antigenic peptide is matrix protein (M). In some embodiments, the RSV antigenic peptide is small hydrophobic protein (SH). In some embodiments, the RSV antigenic peptide is nonstructural protein1(NS1). In some embodiments, the RSV antigenic peptide is nonstructural protein 2 (NS2).

In some embodiments, the signal peptide is a IgE signal peptide. In some embodiments, the signal peptide is an IgE HC (Ig heavy chain epsilon-1) signal peptide. In some embodiments, the signal peptide has the sequence MDWTWILFLVAAATRVHS (SEQ ID NO: 281). In some embodiments, the signal peptide is an IgGκ signal peptide. In some embodiments, the signal peptide has the sequence METPAQLLFLLLLWLPDTTG (SEQ ID NO: 282). In some embodiments, the signal peptide is encoded by sequence TGGA-GACTCCCGCTCAGCTGCTGTTTTTGCTCCTCC-TATGGCTGCCGGATACCACC GGC (SEQ ID NO: 287) or AUGGAGACUCCCGCUCAGCUGCUGUUUUUG-CUCCU CCUAUGGCUGCCGGAUACCACCGGC (SEQ ID NO: 288). In some embodiments, the signal peptide is selected from: a Japanese encephalitis PRM signal sequence (MLGSNSGQRVVFTILLLLVAPAYS; SEQ ID NO: 283), VSVg protein signal sequence (MKCLLYLAFLFIGVNCA; SEQ ID NO: 284) and Japanese encephalitis JEV signal sequence (MWLVSLAIVTACAGA; SEQ ID NO: 285). In some embodiments, the signal peptide is MELLILKANAITTILTAVTFC (SEQ ID NO: 289).

Also provided herein are respiratory syncytial virus (RSV) vaccines, comprising at least one ribonucleic acid (RNA) polynucleotide having an open reading frame encoding membrane-bound RSV F protein, membrane-bound DS-Cav1 (stabilized prefusion RSV F protein), or a combination of membrane-bound RSV F protein and membrane-bound DS-Cav1, and a pharmaceutically acceptable carrier.

In some embodiments, a RNA polynucleotide comprises the sequence of SEQ ID NO: 5 and/or the sequence of SEQ ID NO: 7.

In some embodiments, an effective amount of an RSV RNA (e.g., mRNA) vaccine (e.g., a single dose of the RSV vaccine) results in a 2 fold to 200 fold (e.g., about 2, 3, 4, 5, 6, 7, 8, 9, 10, 20, 30, 40, 50, 60, 70, 80, 90, 100, 110, 120, 130, 140, 150, 160, 170, 180, 190 or 200 fold) increase in serum neutralizing antibodies against RSV, relative to a control (e.g., a control vaccine). In some embodiments, a single dose of the RSV RNA (e.g., mRNA) vaccine results in an about 5 fold, 50 fold, or 150 fold increase in serum neutralizing antibodies against RSV, relative to a control (e.g., a control vaccine). In some embodiments, a single dose of the RSV RNA (e.g., mRNA) vaccine results in an about 2 fold to 10 fold, or an about 40 to 60 fold increase in serum neutralizing antibodies against RSV, relative to a control (e.g., a control vaccine).

In some embodiments, the serum neutralizing antibodies are against RSV A and/or RSV B.

In some embodiments, the RSV vaccine is formulated in a MC3 lipid nanoparticle (see, e.g., U.S. Publication No. 2013/0245107 A1 and International Publication No. WO 2010/054401).

Also provided herein are methods of inducing an antigen specific immune response in a subject, the method comprising administering to a subject the RSV RNA (e.g., mRNA) vaccine comprising at least one ribonucleic acid (RNA) polynucleotide having an open reading frame encoding membrane-bound RSV F protein, membrane-bound DS-Cav1 (stabilized prefusion RSV F protein), or a combination of membrane-bound RSV F protein and membrane-bound DS-Cav1, and a pharmaceutically acceptable carrier, in an effective amount to produce an antigen specific immune response in a subject.

In some embodiments, the methods further comprise administering a booster dose of the RSV RNA (e.g., mRNA) vaccine. In some embodiments, the methods further comprise administering a second booster dose of the RSV vaccine.

In some embodiments, efficacy of RNA vaccines RNA (e.g., mRNA) can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide (including immunogenic fragments thereof, e.g., immunogenic fragments capable of raising an immune response to RSV) and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different RNA polynucleotide.

In some embodiments at least one flagellin polypeptide has at least 80%, at least 85%, at least 90%, or at least 95% identity to a flagellin polypeptide having a sequence of SEQ ID NO: 173-175.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first respiratory virus antigenic polypeptide, wherein the RNA polynucleotide does not include a stabilization element, and wherein an adjuvant is not co-formulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 µg/kg and 400 µg/kg of the nucleic acid vaccine is administered to the subject. In some embodiments the dosage of the RNA polynucleotide is 1-5 µg, 5-10 µg, 10-15 µg, 15-20 µg, 10-25 µg, 20-25 µg, 20-50 µg, 30-50 µg, 40-50 µg, 40-60 µg, 60-80 µg, 60-100 µg, 50-100 µg, 80-120 µg, 40-120 µg, 40-150 µg, 50-150 µg, 50-200 µg, 80-200 µg, 100-200 µg, 120-250 µg, 150-250 µg, 180-280 µg, 200-300 µg, 50-300 µg, 80-300 µg, 100-300 µg, 40-300 µg, 50-350 µg, 100-350 µg, 200-350 µg, 300-350 µg, 320-400 µg, 40-380 µg, 40-100 µg, 100-400 µg, 200-400 µg, or 300-400 µg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 μg of one or more RNA polynucleotides having an open reading frame comprising at least one chemical modification or optionally no nucleotide modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a respiratory virus strain in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Both chemically modified and unmodified RNA vaccines are useful in the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a respiratory virus antigenic polypeptide in an effective amount to vaccinate the subject.

In some aspects the invention is a method of vaccinating a subject with a combination vaccine including at least two nucleic acid sequences encoding respiratory antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

In some embodiments, the RNA polynucleotide is one of SEQ ID NO: 1, 2, 5, 7, 9, 11, 13, 15, 17, 19, 21, 23, 25, 27, 242, 246, 257, 258, or 259 and includes at least one chemical modification. In other embodiments, the RNA polynucleotide is one of SEQ ID NO: 1, 2, 5, 7, 9, 11, 13, 15, 17, 19, 21, 23, 25, 27, 242, 246, 257, 258, or 259 and does not include any nucleotide modifications, or is unmodified. In yet other embodiments, the at least one RNA polynucleotide encodes an antigenic protein of any of SEQ ID NO: 3, 4, 6, 8, 10, 12, 14, 16, 18, 20, 22, 24, 26, 28, 243, or 245 and includes at least one chemical modification. In other embodiments, the RNA polynucleotide encodes an antigenic protein of any of SEQ ID NO: 3, 4, 6, 8, 10, 12, 14, 16, 18, 20, 22, 24, 26, 28, 243, or 245 and does not include any nucleotide modifications, or is unmodified.

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIGS. 3A-3C show data from an intracellular cytokine staining assay to test immunogenicity in mice, demonstrating that RSV-F mRNA/NLP vaccines and RSV-G mRNA/LNP vaccines, but not DS-CAV1 protein antigens, elicit robust Th1 biased CD4+ immune responses in mice.

FIGS. 4A-4C show data from an intracellular cytokine staining assay to test immunogenicity in mice, demonstrating that RSV-F mRNA/NLP vaccines and RSV-G mRNA/LNP vaccines, but not DS-CAV1 protein antigens, elicit robust Th1 biased CD8+ immune responses in mice.

DETAILED DESCRIPTION

Figure 1:
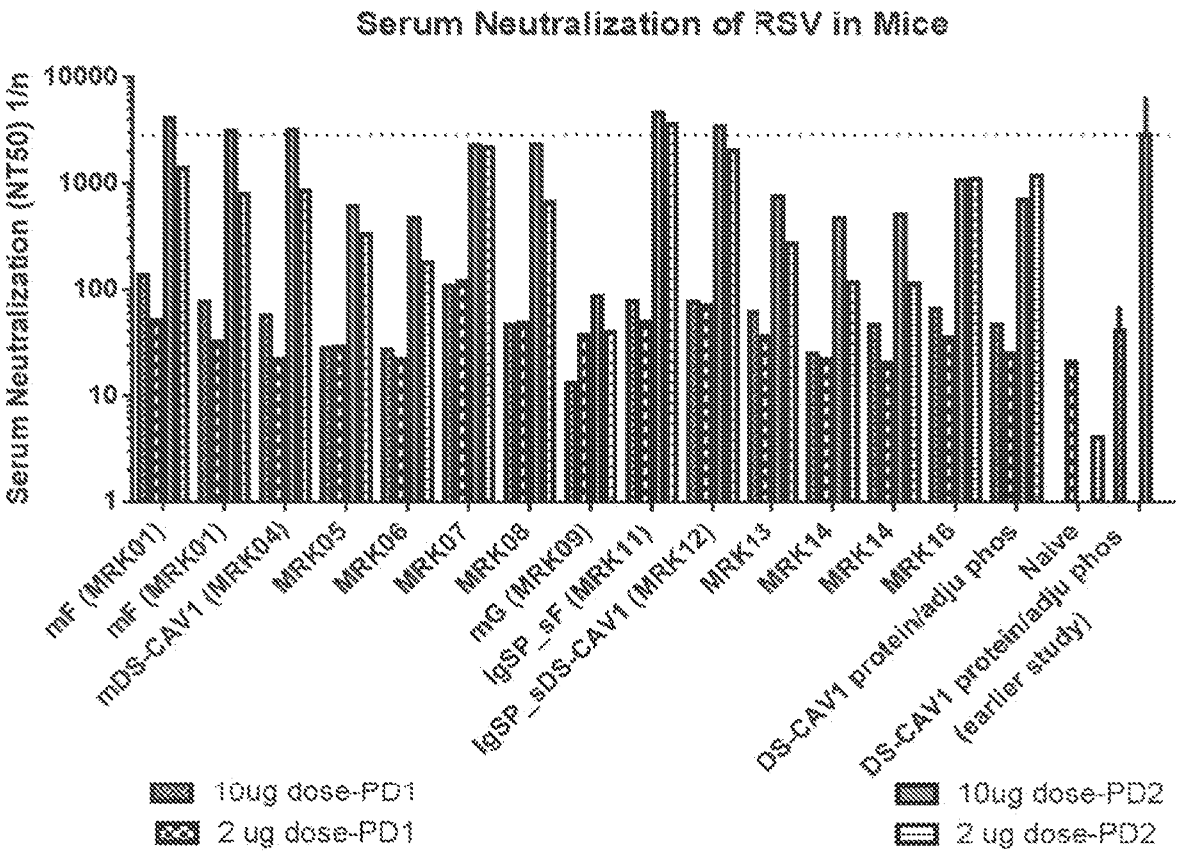
FIG. 1 shows data from an immunogenicity study in mice, designed to evaluate the immune response to RSV vaccine antigens delivered using various mRNA vaccines formulated with MC3 LNP in comparison to protein antigens. The data demonstrated strong neutralizing antibody titers.

Embodiments of the present disclosure provide RNA (e.g., mRNA) vaccines that include a (at least one) polynucleotide encoding a respiratory syncytial virus (RSV) antigen. RSV is a negative-sense, single-stranded RNA virus of the genus *Pneumovirinae*. The virus is present in at least two antigenic subgroups, known as Group A and Group B, primarily resulting from differences in the surface G glycoproteins. Two RSV surface glycoproteins—G and F—mediate attachment with and attachment to cells of the respiratory epithelium. F surface glycoproteins mediate coalescence of neighboring cells. This results in the formation of syncytial cells. RSV is the most common cause of bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

The genome of RSV encodes at least three surface glycoproteins, including F, G, and SH, four nucleocapsid proteins, including L, P, N, and M2, and one matrix protein, M. Glycoprotein F directs viral penetration by fusion between the virion and the host membrane. Glycoprotein G is a type II transmembrane glycoprotein and is the major attachment protein. SH is a short integral membrane protein. Matrix protein M is found in the inner layer of the lipid bilayer and assists virion formation. Nucleocapsid proteins L, P, N, and M2 modulate replication and transcription of the RSV genome. It is thought that glycoprotein G tethers and stabilizes the virus particle at the surface of bronchial epithelial cells, while glycoprotein F interacts with cellular glycosaminoglycans to mediate fusion and delivery of the RSV virion contents into the host cell (Krzyzaniak M A et al. *PLoS Pathog* 2013; 9(4)).

RSV RNA (e.g., mRNA) vaccines, as provided herein, may be used to induce a balanced immune response, comprising both cellular and humoral immunity, without many of the risks associated with DNA vaccination.

The entire contents of International Application No. PCT/US2015/027400, International Publication No. WO2015164674A, are incorporated herein by reference.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers.

The data described herein demonstrate that the formulations of the invention produced significant unexpected improvements over existing antigen vaccines. Additionally, the mRNA-LNP formulations of the invention are superior to other vaccines even when the dose of mRNA is lower than other vaccines. Various mRNA vaccines formulated with MC3 LNP were compared in mice to protein antigen vaccination. The data demonstrated that in comparison to existing vaccines, the mRNA vaccines produced stronger neutralizing antibody titers, much higher cellular immune responses than the protein antigen, elicited robust Th1 biased CD4+ and CD8+ immune responses in mice and reduction in virus in the lungs. No virus was recovered from lungs of any of mice immunized with RSV mRNA vaccines formulated with MC3 LNP, in contrast to only one animal at the lower dose of protein/adjuvant vaccine formulation. Significant neutralizing antibody titers were also achieved in rats and monkeys.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Antigens/Antigenic Polypeptides

At least two antigenic subgroups (A and B) of RSV are known to exist. This antigenic dimorphism is due primarily to difference in the surface G glycoproteins. Two surface glycoproteins, G and F, are present in the envelope and mediate attachment and fusion with cells of the respiratory epithelium. The F proteins also mediate coalescence of neighboring cells to form the characteristic syncytial cells for which the virus receives its name. The epidemiologic and biologic significance of the two antigenic variants of RSV is uncertain. Nonetheless, there is some evidence to suggest that Group A infections tend to be more severe.

The RSV genome is 15,000 nucleotides in length and is composed of a single strand of RNA with negative polarity. It has 10 genes encoding 11 proteins—there are 2 open reading frames of M2. The genome is transcribed sequentially from NS1 to L with reduction in expression levels along its length.

NS1 and NS2 inhibit type I interferon activity. In some embodiments, a RSV vaccine comprises at least one RNA (e.g., mRNA) polynucleotide having an open reading frame encoding products of NS1, or NS2.

N encodes nucleocapsid protein that associates with the genomic RNA forming the nucleocapsid. In some embodiments, a RSV vaccine comprises at least one RNA (e.g., mRNA) polynucleotide having an open reading frame encoding nucleocapsid protein.

M encodes the Matrix protein required for viral assembly. In some embodiments, a RSV vaccine comprises at least one RNA (e.g., mRNA) polynucleotide having an open reading frame encoding Matrix protein.

SH, G and F form the viral coat. The G protein is a surface protein that is heavily glycosylated and functions as the attachment protein. The F protein is another important surface protein that mediates fusion, allowing entry of the virus into the cell cytoplasm and also allowing the formation of syncytia. The F protein is homologous in both subtypes of RSV; antibodies directed at the F protein are neutralizing. In contrast, the G protein differs considerably between the two subtypes. In some embodiments, a RSV vaccine comprises at least one RNA (e.g., mRNA) polynucleotide having an open reading frame encoding SH, G or F protein, or a combination thereof.

Nucleolin at the cell surface is the receptor for the RSV fusion protein. Interference with the nucleolin-RSV fusion protein interaction has been shown to be therapeutic against RSV infection in cell cultures and animal models. In some embodiments, a RSV vaccine comprises at least one RNA (e.g., mRNA) polynucleotide having an open reading frame encoding nucleolin.

M2 is the second matrix protein also required for transcription and encodes M2-1 (elongation factor) and M2-2 (transcription regulation). M2 contains CD8 epitopes. In some embodiments, a RSV vaccine comprises at least one RNA (e.g., mRNA) polynucleotide having an open reading frame encoding the second matrix protein.

L encodes the RNA polymerase. In some embodiments, a RSV vaccine comprises at least one RNA (e.g., mRNA) polynucleotide having an open reading frame encoding the RNA polymerase (L).

The phosphoprotein P is a cofactor for the L protein. In some embodiments, a RSV vaccine comprises at least one RNA (e.g., mRNA) polynucleotide having an open reading frame encoding phosphoprotein P.

Some embodiments of the present disclosure provide RSV vaccines that include at least one RNA (e.g., mRNA) polynucleotide having an open reading frame encoding glycoprotein G.

Some embodiments of the present disclosure provide RSV vaccines that include at least one RNA (e.g., mRNA) polynucleotide having an open reading frame encoding glycoprotein F.

Some embodiments of the present invention disclose RSV vaccines that include at least one RNA (e.g. mRNA) polynucleotide having an open reading frame encoding a polypeptide in the post-fusion form. Further embodiments of the present invention disclose RSV vaccines that include at least one RNA (e.g. mRNA) polynucleotide having an open reading frame encoding a polypeptide in the pre-fusion form. In some embodiments, the polypeptides comprise glycoproteins in a prefusion conformation, for example, but not limited to, prefusion glycoprotein F or DS-CAV1. Without wishing to be bound by theory, certain polypeptides, when in a prefusion conformation, may contain more epitopes for neutralizing antibodies relative to the post-fusion conformation of the same proteins. For example, prefusion glycoprotein F has a unique antigen site ("antigenic site Ø") at its membrane distal apex. Antigenic site Ø may, but not necessarily, comprise residues 62-69 and 196-209 of a RSV F protein sequence. In some instances, such as, but not limited to, prefusion glycoprotein F, prefusion polypeptides may exhibit many fold greater immune responses than those achieved with post-fusion polypeptides. Prefusion RSV glycoproteins and their methods of use are described in WO2014/160463, incorporated by reference herein its entirety.

In some embodiments, RSV vaccines include at least one RNA (e.g., mRNA) polynucleotide having an open reading frame encoding glycoprotein F or glycoprotein G obtained from RSV strain A2 (RSV A2). Other RSV strains are encompassed by the present disclosure, including subtype A strains and subtype B strains.

In some embodiments, a RSV vaccine has at least one RNA (e.g., mRNA) having at least one modification, including but not limited to at least one chemical modification.

In some embodiments, a RSV antigenic polypeptide is longer than 25 amino acids and shorter than 50 amino acids. The term "antigenic polypeptide" includes immunogenic fragments thereof (e.g., immunogenic fragments capable of raising an immune response to RSV). Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, a "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

Paralogs" are genes (or proteins) related by duplication within a genome. Orthologs retain the same function in the course of evolution, whereas paralogs evolve new functions, even if these are related to the original one.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant," but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In alternative embodiments, sequences for (or encoding) signal sequences, termination sequences, transmembrane domains, linkers, multimerization domains (such as, e.g., foldon regions) and the like may be substituted with alternative sequences that achieve the same or a similar function. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue, such as lysine, arginine or histidine for another, or the substitution of one acidic residue, such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein, when referring to polypeptides the terms "site" as it pertains to amino acid based embodiments, is used synonymously with "amino acid residue" and "amino acid side chain." As used herein, when referring to polynucleotides the terms "site" as it pertains to nucleotide based embodiments, is used synonymously with "nucleotide." A site represents a position within a peptide or polypeptide or polynucleotide that may be modified, manipulated, altered, derivatized or varied within the polypeptide or polynucleotide based molecules.

As used herein, the terms "termini" or "terminus," when referring to polypeptides or polynucleotides, refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N-termini and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids that are 40%, 50%, 60%, 70%, 80%, 90%, 95%, or 100% identical to any of the sequences described herein can be utilized in accordance with the present disclosure. In some embodiments, a polypeptide includes 2, 3, 4, 5, 6, 7, 8, 9, 10, or more mutations, as shown in any of the sequences provided or referenced herein. In some embodiments, a protein fragment is longer than 25 amino acids and shorter than 50 amino acids.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication.

Nucleic Acids/Polynucleotides

RSV vaccines, as provided herein, comprise at least one (one or more) ribonucleic acid (RNA) polynucleotide having an open reading frame encoding at least one RSV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide is encoded by at least one nucleic acid sequence set forth as SEQ ID NO: 1, 2, 5, 7, 9, 11, 13, 15, 17, 19, 21, 23, 25, 27, 242, 246, 257, 258, or 259, or homologs having at least 80% identity with a nucleic acid sequence set forth as SEQ ID NO: 1, 2, 5, 7, 9, 11, 13, 15, 17, 19, 21, 23, 25, 27, 242, 246, 257, 258, or 259. In some embodiments, at least one RNA polynucleotide is encoded by at least one nucleic acid sequence set forth as SEQ ID NO: 1, 2, 5, 7, 9, 11, 13, 15, 17, 19, 21, 23, 25, 27, 242, 246, 257, 258, or 259, or homologs having at least 90% (e.g. 90%, 91%, 92%, 93%, 94%, 95%, 96%, 97%, 98%, 99%, 99.8% or 99.9%) identity with a nucleic acid sequence set forth as SEQ ID NO: 1, 2, 5, 7, 9, 11, 13, 15, 17, 19, 21, 23, 25, 27, 242, 246, 257, 258, or 259. In some embodiments, at least one RNA polynucleotide is encoded by at least one fragment of a nucleic acid sequence (e.g., a fragment having at least one antigenic sequence or at least one epitope) set forth as SEQ ID NO: 1, 2, 5, 7, 9, 11, 13, 15, 17, 19, 21, 23, 25, 27, 242, 246, 257, 258, or 259. In some embodiments, the at least one RNA polynucleotide has at least one chemical modification. In some embodiments, the at least one RNA polynucleotide is an mRNA polynucleotide, wherein each uracil (100% of the uracils) of the mRNA polynucleotide is chemically modified. In some embodiments, the at least one RNA polynucleotide is an mRNA polynucleotide, wherein each uracil (100% of the uracils) of the mRNA polynucleotide is chemically modified to include a N1-methyl pseudouridine.

In some embodiments, the amino acid sequence of the RSV antigenic polypeptide is, or is a (antigenic) fragment of, or is a homolog having at least 80% (e.g., 85%, 90%, 95%, 98%, 99%) identity to, the amino acid sequence set forth as SEQ ID NO: 3, 4, 6, 8, 10, 12, 14, 16, 18, 20, 22, 24, 26, 28, 243, or 245.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs), including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

It should be understood that the mRNA polynucleotides of the vaccines as provided herein are synthetic molecules, i.e., they are not naturally-occurring molecules. That is, the mRNA polynucleotides of the present disclosure are isolated mRNA polynucleotides. As is known in the art, "isolated polynucleotides" refer to polynucleotides that are substantially physically separated from other cellular material (e.g., separated from cells and/or systems that produce the polynucleotides) or from other material that hinders their use in the vaccines of the present disclosure. Isolated polynucleotides are substantially pure in that they have been substantially separated from the substances with which they may be associated in living or viral systems. Thus, mRNA polynucleotide vaccines are not associated with living or viral systems, such as cells or viruses. The mRNA polynucleotide vaccines do not include viral components (e.g., viral capsids, viral enzymes, or other viral proteins, for example, those needed for viral-based replication), and the mRNA polynucleotide vaccines are not packaged within, encapsulated within, linked to, or otherwise associated with a virus or viral particle. In some embodiments, the mRNA vaccines comprise a lipid nanoparticle that consists of, or consists essentially of, one or more mRNA polynucleotides (e.g., mRNA polynucleotides encoding one or more RSV antigen (s)).

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics. In some embodiments, the RNA is a messenger RNA (mRNA) having an open reading frame encoding at least one RSV antigen. In some embodiments, the RNA (e.g., mRNA) further comprises a (at least one) 5' UTR, 3' UTR, a polyA tail and/or a 5' cap.

In some embodiments, a RNA polynucleotide (e.g., mRNA) of a RSV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide (e.g., mRNA) of a RSV RNA (e.g., mRNA) vaccine encodes at least 10, 20, 30, 40, 50, 60, 70, 80, 90 or 100 antigenic polypeptides. In some embodiments, a RNA polynucleotide (e.g., mRNA) of a RSV vaccine encodes at least 100 antigenic polypeptides, or at least 200 antigenic polypeptides. In some embodiments, a RNA polynucleotide (e.g., mRNA) of a RSV vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides (e.g., mRNAs) of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares between 65% and 75% or about 80% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, the RSV vaccine includes at least one RNA polynucleotide having an open reading frame encoding at least one RSV antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3"-O-Me-m7G(5)ppp (5') G [the ARCA cap]; G(5)ppp(5')A; G(5')ppp(5')G; m7G (5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G (5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source.

When transfected into mammalian cells, the modified mRNAs have a stability of between 12-18 hours, or greater than 18 hours, e.g., 24, 36, 48, 60, 72, or greater than 72 hours.

In some embodiments a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Signal Peptides

In some embodiments, antigenic polypeptides encoded by RSV polynucleotides comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include of three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodominance of certain signal peptides are much more versatile than previously anticipated.

Signal peptides typically function to facilitate the targeting of newly synthesized protein to the endoplasmic reticulum (ER) for processing. ER processing produces a mature Envelope protein, wherein the signal peptide is cleaved, typically by a signal peptidase of the host cell. A signal peptide may also facilitate the targeting of the protein to the cell membrane. RSV vaccines of the present disclosure may comprise, for example, RNA polynucleotides encoding an artificial signal peptide, wherein the signal peptide coding sequence is operably linked to and is in frame with the coding sequence of the RSV antigenic polypeptide. Thus, RSV vaccines of the present disclosure, in some embodiments, produce an antigenic polypeptide comprising a RSV antigenic polypeptide fused to a signal peptide. In some embodiments, a signal peptide is fused to the N-terminus of the RSV antigenic polypeptide. In some embodiments, a signal peptide is fused to the C-terminus of the RSV antigenic polypeptide.

In some embodiments, the signal peptide fused to the RSV antigenic polypeptide is an artificial signal peptide. In some embodiments, an artificial signal peptide fused to the RSV antigenic polypeptide encoded by the RSV RNA (e.g., mRNA) vaccine is obtained from an immunoglobulin protein, e.g., an IgE signal peptide or an IgG signal peptide. In some embodiments, a signal peptide fused to the RSV antigenic polypeptide encoded by a RSV RNA (e.g., mRNA) vaccine is an Ig heavy chain epsilon-1 signal peptide (IgE HC SP) having the sequence of: MDWTWILFLVAAATRVHS (SEQ ID NO: 281). In some embodiments, a signal peptide fused to a RSV antigenic polypeptide encoded by the RSV RNA (e.g., mRNA) vaccine is an IgGk chain V-III region HAH signal peptide (IgGk SP) having the sequence of METPAQLLFLLLLWLPDTTG (SEQ ID NO: 282). In some embodiments, the RSV antigenic polypeptide encoded by a RSV RNA (e.g., mRNA) vaccine has an amino acid sequence set forth in one of SEQ ID NO: 1 to SEQ ID NO: 28 fused to a signal peptide of SEQ ID NO: 281 or SEQ ID NO: 282. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature RSV antigenic polypeptide produce by RSV RNA vaccine of the present disclosure typically does not comprise a signal peptide.

Chemical Modifications

RNA (e.g., mRNA) vaccines of the present disclosure comprise, in some embodiments, at least one ribonucleic acid (RNA) polynucleotide having an open reading frame encoding at least one respiratory syncytial virus (RSV) antigenic polypeptide, wherein said RNA comprises at least one chemical modification.

The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population. Generally, these terms do not refer to the ribonucleotide modifications in naturally occurring 5'-terminal mRNA cap moieties.

Modifications of polynucleotides include, without limitation, those described herein, and include, but are expressly not limited to, those modifications that comprise chemical modifications. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

With respect to a polypeptide, the term "modification" refers to a modification relative to the canonical set of 20 amino acids. Polypeptides, as provided herein, are also considered "modified" if they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those polynucleotides having at least one chemical modification. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides), including but not limited to chemical modification, that are useful in the compositions, vaccines, methods and synthetic processes of the present disclosure include, but are not limited to the following: 2-methylthio-N6-(cis-hydroxyisopentenyl)adenosine; 2-methylthio-N6-methyladenosine; 2-methylthio-N6-threonylcarbamoyladenosine; N6-glycinylcarbamoyladenosine; N6-isopentenyladenosine; N6-methyl adenosine; N6-threonylcarbamoyladenosine; 1,2'-O-dimethyl adenosine; 1-methyladenosine; 2'-O-methyladenosine; 2'-O-ribosyladenosine (phosphate); 2-methyl adenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyl adenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formyl cytidine; 5-hydroxymethylcytidine; 5-methylcytidine; N4-acetylcytidine; 2'-O-methyl cytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thioguanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8

(alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio) pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonyl ethyl enyl)-4 (thio)pseudouracil; 1 (aminocarbonyl ethyl enyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio)uracil; 5 (propynyl)uracil; 5 (trifluoromethyl)uracil; 5-(2-aminopropyl)uracil; 5-(alkyl)-2-(thio) pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP;

1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1 (4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{(2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethyiwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin- 2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), 2-thiouridine (s2U), 4'-thiouridine, 5-methyl cytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carb amoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and combinations of two or more thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polyribonucleotide includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine (m5C). In some embodiments, the polyribonucleotides (e.g., RNA, such as mRNA) comprise 1-methyl-pseudouridine (m1ψ). In some embodiments, the polyribonucleotides (e.g., RNA, such as mRNA) comprise 1-ethyl-pseudouridine (e1ψ). In some embodiments, the polyribonucleotides (e.g., RNA, such as mRNA) comprise 1-methyl-pseudouridine (m1ψ) and 5-methyl-cytidine (m5C). In some embodiments, the polyribonucleotides (e.g., RNA, such as mRNA) comprise 1-ethyl-pseudouridine (e1ψ) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O- methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (m1ψ), 1-ethyl-pseudouridine (e1ψ), 5-methoxy uridine, 2-thio uridine, 5-cyano uridine, 2'-O-methyl uridine and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, and 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5 se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m^5$ $s^2U$), 1-taurinomethyl-4-thio-pseudouridine, 5-methyl-uridine ($m^5U$, i.e., having the nucleobase deoxythymine), 1-methyl-pseudouridine ($m^1\psi$), 1-ethyl-pseudouridine (e1ψ), 5-methyl-2-thio-uridine ($m^5$ $s^2U$), 1-methyl-4-thio-pseudouridine ($m^1s^4\psi$) 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3- carboxypropyl)uridine ($acp^3U$), 1-methyl-3-(3-amino-3-carboxypropyl)pseudouridine ($acp^3$ $\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine ($\psi m$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-0H-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2$ $m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6{}_2Am$), 1,2'-O-dimethyl-adenosine (m'Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2{}_2G$), N2,7-dimethyl-guanosine ($m^{2,7}G$), N2, N2,7-dimethyl-guanosine 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, O6-methyl-guanosine, 2'-F-ara-guanosine, and 2'-F-guanosine.

In some embodiments, the RNA vaccines comprise a 5'UTR element, an optionally codon optimized open reading frame, and a 3'UTR element, a poly(A) sequence and/or a polyadenylation signal, wherein the RNA is not chemically modified.

RSV RNA Vaccines—In Vitro Transcription of RNA (e.g., mRNA)

RSV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, the at least one RNA polynucleotide has at least one chemical modification. The at least one chemical modification may include, but is expressly not limited to, any modification described herein.

In vitro transcription of RNA is known in the art and is described in International Publication WO2014/152027, which is incorporated by reference herein in its entirety. For example, in some embodiments, the RNA transcript is generated using a non-amplified, linearized DNA template in an in vitro transcription reaction to generate the RNA transcript. In some embodiments the RNA transcript is capped via enzymatic capping. In some embodiments the RNA transcript is purified via chromatographic methods, e.g., use of an oligo dT substrate. Some embodiments exclude the use of DNase. In some embodiments the RNA transcript is synthesized from a non-amplified, linear DNA template coding for the gene of interest via an enzymatic in vitro transcription reaction utilizing a T7 phage RNA polymerase and nucleotide triphosphates of the desired chemistry. Any number of RNA polymerases or variants may be used in the method of the present invention. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides.

In some embodiments a non-amplified, linearized plasmid DNA is utilized as the template DNA for in vitro transcription. In some embodiments, the template DNA is isolated DNA. In some embodiments, the template DNA is cDNA. In some embodiments, the cDNA is formed by reverse transcription of a RNA polynucleotide, for example, but not limited to RSV RNA, e.g. RSV mRNA. In some embodiments, Cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA or RNA beginning with a start codon (e.g., methionine (ATG or AUG)), and ending with a stop codon (e.g., TAA, TAG or TGA, or UAA, UAG or UGA) and typically encodes a polypeptide (e.g., protein). It will be understood that the sequences disclosed herein may further comprise additional elements, e.g., 5' and 3' UTRs, but that those elements, unlike the ORF, need not necessarily be present in a vaccine of the present disclosure.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Methods of Treatment

Provided herein are compositions (e.g., pharmaceutical compositions), methods, kits and reagents for prevention and/or treatment of RSV in humans and other mammals. RSV RNA (e.g. mRNA) vaccines can be used as therapeutic or prophylactic agents. They may be used in medicine to prevent and/or treat infectious disease. In exemplary aspects, the RSV RNA vaccines of the present disclosure are used to provide prophylactic protection from RSV. Prophylactic protection from RSV can be achieved following administration of a RSV RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against a RSV is provided in aspects of the invention. The method involves administering to the subject a RSV RNA vaccine comprising at least one RNA polynucleotide having an open reading frame encoding at least one RSV antigenic polypeptide, thereby inducing in the subject an immune response specific to RSV antigenic polypeptide, wherein anti-antigenic polypeptide antibody titer in the subject is increased following vaccination relative to anti-antigenic polypeptide antibody titer in a subject vaccinated with a prophylactically effective dose of a traditional (e.g., non-nucleic acid) vaccine against the RSV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc.

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the RSV.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the RSV.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the RSV.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the RSV.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the RSV.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the RSV.

A method of eliciting an immune response in a subject against a RSV is provided in other aspects of the invention. The method involves administering to the subject a RSV RNA vaccine comprising at least one RNA polynucleotide having an open reading frame encoding at least one RSV antigenic polypeptide, thereby inducing in the subject an immune response specific to RSV antigenic polypeptide, wherein the immune response in the subject is equivalent to an immune response in a subject vaccinated with a traditional vaccine against the RSV at 2 times to 100 times the dosage level relative to the RNA vaccine.

In some embodiments the immune response in the subject is equivalent to an immune response in a subject vaccinated with a traditional vaccine at twice the dosage level relative to the RSV RNA vaccine.

In some embodiments the immune response in the subject is equivalent to an immune response in a subject vaccinated with a traditional vaccine at three times the dosage level relative to the RSV RNA vaccine.

In some embodiments the immune response in the subject is equivalent to an immune response in a subject vaccinated with a traditional vaccine at 4 times the dosage level relative to the RSV RNA vaccine.

In some embodiments the immune response in the subject is equivalent to an immune response in a subject vaccinated with a traditional vaccine at 5 times the dosage level relative to the RSV RNA vaccine.

In some embodiments the immune response in the subject is equivalent to an immune response in a subject vaccinated with a traditional vaccine at 10 times the dosage level relative to the RSV RNA vaccine.

In some embodiments the immune response in the subject is equivalent to an immune response in a subject vaccinated with a traditional vaccine at 50 times the dosage level relative to the RSV RNA vaccine.

In some embodiments the immune response in the subject is equivalent to an immune response in a subject vaccinated with a traditional vaccine at 100 times the dosage level relative to the RSV RNA vaccine.

In some embodiments the immune response in the subject is equivalent to an immune response in a subject vaccinated with a traditional vaccine at 10 times to 1000 times the dosage level relative to the RSV RNA vaccine.

In some embodiments the immune response in the subject is equivalent to an immune response in a subject vaccinated with a traditional vaccine at 100 times to 1000 times the dosage level relative to the RSV RNA vaccine.

In other embodiments the immune response is assessed by determining [protein] antibody titer in the subject.

In other aspects the invention is a method of eliciting an immune response in a subject against a RSV by administering to the subject a RSV RNA vaccine comprising at least one RNA polynucleotide having an open reading frame encoding at least one RSV antigenic polypeptide, thereby inducing in the subject an immune response specific to RSV antigenic polypeptide, wherein the immune response in the subject is induced 2 days to 10 weeks earlier relative to an immune response induced in a subject vaccinated with a prophylactically effective dose of a traditional vaccine against the RSV. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

Multiprotein and Multicomponent Vaccines

The present disclosure encompasses RSV vaccines comprising multiple RNA (e.g., mRNA) polynucleotides, each encoding a single antigenic polypeptide, as well as RSV vaccines comprising a single RNA polynucleotide encoding more than one antigenic polypeptide (e.g., as a fusion polypeptide). Thus, it should be understood that a vaccine composition comprising a RNA polynucleotide having an open reading frame encoding a first RSV antigenic polypeptide and a RNA polynucleotide having an open reading frame encoding a second RSV antigenic polypeptide encompasses (a) vaccines that comprise a first RNA polynucleotide encoding a first RSV antigenic polypeptide and a second RNA polynucleotide encoding a second RSV antigenic polypeptide, and (b) vaccines that comprise a single RNA polynucleotide encoding a first and second RSV antigenic polypeptide (e.g., as a fusion polypeptide). RSV RNA vaccines of the present disclosure, in some embodiments, comprise 2-10 (e.g., 2, 3, 4, 5, 6, 7, 8, 9 or 10), or more, RNA polynucleotides having an open reading frame, each of which encodes a different RSV antigenic polypeptide (or a single RNA polynucleotide encoding 2-10, or more, different RSV antigenic polypeptides). In some embodiments, a RSV RNA vaccine comprises a RNA polynucleotide having an open reading frame encoding a RSV Fusion (F) glycoprotein, a RNA polynucleotide having an open reading frame encoding a RSV attachment (G) protein, a RNA polynucleotide having an open reading frame encoding a RSV nucleoprotein (N), a RNA polynucleotide having an open reading frame encoding a RSV phosphoprotein (P), a RNA polynucleotide having an open reading frame encoding a RSV large polymerase protein (L), a RNA polynucleotide having an open reading frame encoding a RSV matrix protein (M), a RNA polynucleotide having an open reading frame encoding a RSV small hydrophobic protein (SH), a RNA polynucleotide having an open reading frame encoding a RSV nonstructural protein 1 (NS1), and a RNA polynucleotide having an open reading frame encoding a RSV nonstructure protein 2 (NS2). In some embodiments, a RSV RNA vaccine comprises a RNA polynucleotide having an open reading frame encoding a RSV fusion (F) protein and a RNA polynucleotide having an open reading frame encoding a RSV attachment protein (G). In some embodiments, a RSV RNA vaccine comprises a RNA polynucleotide having an open reading frame encoding a RSV F protein. In some embodiments, a RSV RNA vaccine comprises a RNA polynucleotide having an open reading frame encoding a RSV N protein. In some embodiments, a RSV RNA vaccine comprises a RNA polynucleotide having an open reading frame encoding a RSV M protein. In some embodiments, a RSV RNA vaccine comprises a RNA polynucleotide having an open reading frame encoding a RSV L protein. In some embodiments, a RSV RNA vaccine comprises a RNA polynucleotide having an open reading frame encoding a RSV P protein. In some embodiments, a RSV RNA vaccine comprises a RNA polynucleotide having an open reading frame encoding a RSV SH protein. In some embodiments, a RSV RNA vaccine comprises a RNA polynucleotide having an open reading frame encoding a RSV NS1 protein. In some embodiments, a RSV RNA vaccine comprises a RNA polynucleotide having an open reading frame encoding a RSV NS2 protein.

In some embodiments, a RNA polynucleotide encodes a RSV antigenic polypeptide fused to a signal peptide (e.g., SEQ ID NO: 281 or SEQ ID NO:282). Thus, RSV vaccines comprising at least one ribonucleic acid (RNA) polynucleotide having an open reading frame encoding a signal peptide linked to a RSV antigenic peptide are provided.

Further provided herein are RSV vaccines comprising any RSV antigenic polypeptides disclosed herein (e.g., F, G, M, N, L, P, SH, NS1, NS2, or any antigenic fragment thereof) fused to signal peptides. The signal peptide may be fused to the N- or C-terminus of the RSV antigenic polypeptides.

Broad Spectrum RSV Vaccines

It is envisioned that there may be situations where persons are at risk for infection with more than one strain of RSV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of RSV, a combination vaccine can be administered that includes RNA encoding at least one antigenic polypeptide protein (or antigenic portion thereof) of a first RSV and further includes RNA encoding at least one antigenic polypeptide protein (or antigenic portion thereof) of a second RSV. RNAs (mRNAs) can be co-formulated, for example, in a single lipid nanoparticle (LNP) or can be formulated in separate LNPs destined for co-administration.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. Typhimurium, H. Pylori, V. Cholera, S. marcesens, S. flexneri, T. Pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and SEQ ID NO: 173-175. In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 286).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Therapeutic and Prophylactic Compositions

Provided herein are compositions (e.g., pharmaceutical compositions), methods, kits and reagents for prevention, treatment or diagnosis of RSV in humans and other mammals, for example. RSV RNA (e.g., mRNA) vaccines can be used as therapeutic or prophylactic agents. They may be used in medicine to prevent and/or treat infectious disease. In some embodiments, the RSV vaccines of the invention can be envisioned for use in the priming of immune effector cells, for example, to activate peripheral blood mononuclear cells (PBMCs) ex vivo, which are then infused (re-infused) into a subject.

In exemplary embodiments, a RSV vaccine containing RNA polynucleotides as described herein can be administered to a subject (e.g., a mammalian subject, such as a human subject), and the RNA polynucleotides are translated in vivo to produce an antigenic polypeptide.

The RSV RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a RSV RNA vaccine that contains a polynucleotide that has at least one a translatable region encoding an antigenic polypeptide.

An "effective amount" of the RSV RNA vaccine is provided based, at least in part, on the target tissue, target cell type, means of administration, physical characteristics of the polynucleotide (e.g., size, and extent of modified nucleosides) and other components of the RSV RNA vaccine, and other determinants. In general, an effective amount of the RSV RNA vaccine composition provides an induced or boosted immune response as a function of antigen production in the cell. In general, an effective amount of the RSV RNA vaccine containing RNA polynucleotides having at least one chemical modifications are preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of RSV.

RSV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

RSV RNA (e.g., mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, RSV RNA vaccines may be administered intramuscularly, intranasally or intradermally, similarly to the administration of inactivated vaccines known in the art.

The RSV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines, in many instances, have superior properties in that they produce much larger antibody titers and produce responses early than commercially available anti-virals.

Provided herein are pharmaceutical compositions including RSV RNA vaccines and RNA vaccine compositions and/or complexes optionally in combination with one or more pharmaceutically acceptable excipients.

RSV RNA (e.g., mRNA) vaccines may be formulated or administered alone or in conjunction with one or more other components. For instance, RSV RNA vaccines (vaccine compositions) may comprise other components including, but not limited to, adjuvants.

In some embodiments, RSV RNA vaccines do not include an adjuvant (they are adjuvant free).

RSV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, RSV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

RSV RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with RSV RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intra-molecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

In some embodiments, the RNA polynucleotide does not include a stabilization element.

Nanoparticle Formulations

In some embodiments, RSV RNA (e.g., mRNA) vaccines are formulated in a nanoparticle. In some embodiments, RSV RNA vaccines are formulated in a lipid nanoparticle. In some embodiments, RSV RNA vaccines are formulated in a lipid-polycation complex, referred to as a cationic lipid nanoparticle. The formation of the lipid nanoparticle may be accomplished by methods known in the art and/or as described in U.S. Publication No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Publication No. WO2012013326 or U.S. Publication No. US20130142818; each of which is herein incorporated by reference in its entirety. In some embodiments, RSV RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid was shown to more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA (see, e.g., U.S. Publication No. 20130245107 A1).

In some embodiments, a RSV RNA (e.g., mRNA) vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, or N,N-dimethyl-1-[(1S,2R)-2-octylcyclopropyl]heptadecan-8-amine and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine; (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid: 5-25% neutral lipid (non-cationic lipid): 25-55% sterol; 0.5-15% PEG-lipid.

In some embodiments, a lipid nanoparticle formulation includes 25% to 75% on a molar basis of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino) butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine, e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-cDMA (further discussed in Reyes et al. *J. Controlled Release,* 107, 276-287 (2005) the content of which is herein incorporated by reference in its entirety).

In some embodiments, lipid nanoparticle formulations include 25-75% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 7.5% of the neutral lipid, 31% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 10% of the neutral lipid, 38.5% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 15% of the neutral lipid, 40% of the sterol, and 5% of the PEG or PEG-modified lipid on a molar basis.

In some embodiments, lipid nanoparticle formulations include 57.2% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl] heptadecan-8-amine, 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the content of which is herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid: 5-25% neutral lipid (non-cationic lipid): 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethyl amino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, 2,2-dilinoleyl-4-dimethylaminoethyl[1,3]-dioxolane (DLin-KC2-DMA), dilinoleyl-methyl-4-dimethylaminobutyrate (DLin-MC3-DMA), di((Z)-non-2-en-1-yl) 9-((4-(dimethyl amino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid di((Z)-non-2-en-1-yl) 9-((4-(dimethyl amino)butanoyl)oxy)heptadecanedioate, (12Z,15Z)—N,N-dimethyl-2-nonylhenicosa-12,15-dien-1-amine, or N,N-dimethyl-1-[(1S,2R)-2-octylcyclopropyl]heptadecan-8-amine, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising DLin-MC3-DMA, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding RSV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. US2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Publication No. 2013/0059360, the content of which is herein incorporated by reference in its entirety. In some aspects, polymer conjugates with the polynucleotides of the present invention may be made using the methods and/or segmented polymeric reagents described in U.S. Publication No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In other embodiments, the nanoparticle may comprise PEG and a conjugate of CD47 or a derivative thereof. In yet other embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate, which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121, the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm to 500 nm in diameter) which have been coated densely with a low molecular weight polyethylene glycol (PEG) diffused through mucus only 4 to 6-fold lower than the same particles diffusing in water (Lai et al. *PNAS* 2007 104(5):1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (e.g., a polymeric core) and/or a polymer-vitamin conjugate and/or a tri-block copolymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718, U.S. Publication 2010/0003337 and U.S. Pat. No. 8,263,665, each of which is herein incorporated by reference in its entirety). The copolymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:25972600, the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

In some embodiments, the RNA (e.g., mRNA) vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. *Cancer Biology & Therapy* 2006 5(12)1708-1713, herein incorporated by reference in its entirety)) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. 2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Application No. 2013/0059360, the content of which is herein incorporated by reference in its entirety. In some aspects, polymer conjugates with the polynucleotides of the present invention may be made using the methods and/or segmented polymeric reagents described in U.S. Patent Application No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the content of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al. (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles that comprise a conjugate to enhance the delivery of the nanoparticles of the present disclosure in a subject. The conjugate may be the CD47 membrane or the conjugate may be derived from the CD47 membrane protein, such as the "self" peptide described previously. In other aspects the nanoparticle may comprise PEG and a conjugate of CD47 or a derivative thereof. In yet other aspects, the nanoparticle may comprise both the "self" peptide described above and the membrane protein CD47.

In other aspects, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA (e.g., mRNA) vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121; the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbo.

In some embodiments, an immune response may be elicited by delivering a lipid nanoparticle which may include a nanospecies, a polymer and an immunogen. (U.S. Publication No. 2012/0189700 and International Publication No. WO2012/099805, each of which is herein incorporated by reference in its entirety).

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. *PNAS* 2007 104(5):1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718 and U.S. Publication 2010/0003337 and U.S. Pat. No. 8,263,665; each of which is herein incorporated by reference in its entirety). The copolymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:25972600; the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle (see e.g., U.S. Publication 2010/0215580 and U.S. Publication 2008/0166414 and US2013/0164343 the content of each of which is herein incorporated by reference in its entirety).

In some embodiments, the mucus penetrating lipid nanoparticles may comprise at least one polynucleotide described herein. The polynucleotide may be encapsulated in the lipid nanoparticle and/or disposed on the surface of the paricle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In other embodiments, the mucus penetrating lipid nanoparticles may be a hypotonic formulation comprising a mucosal penetration enhancing coating. The formulation may be hypotonic for the epithelium to which it is being delivered.

Non-limiting examples of hypotonic formulations may be found in International Publication No. WO2013/110028, the content of which is herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. *Biomaterials* 2013, 34(28):6922-9, the content of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. *Cancer Res.* 2008 68:9788-9798; Strumberg et al. *Int J Clin Pharmacol Ther* 2012 50:76-78; Santel et al., *Gene Ther* 2006 13:1222-1234; Santel et al., *Gene Ther* 2006 13:1360-1370; Gutbier et al., *Pulm Pharmacol. Ther.* 2010 23:334-344; Kaufmann et al. *Microvasc Res* 2010 80:286-293; Weide et al. *J Immunother.* 2009 32:498-507; Weide et al. *J Immunother.* 2008 31:180-188; Pascolo, *Expert Opin. Biol. Ther.* 4:1285-1294; Fotin-Mleczek et al., 2011 *J. Immunother.* 34:1-15; Song et al., *Nature Biotechnol.* 2005, 23:709-717; Peer et al., *Proc Natl Acad Sci USA.* 2007 6; 104:4095-4100; deFougerolles *Hum Gene Ther.* 2008 19:125-132; each of which is incorporated herein by reference in its entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. *Mol Ther.* 2010 18:1357-1364; Song et al., *Nat Biotechnol.* 2005 23:709-717; Judge et al., *J Clin Invest.* 2009 119:661-673; Kaufmann et al., *Microvasc Res* 2010 80:286-293; Santel et al., *Gene Ther* 2006 13:1222-1234; Santel et al., *Gene Ther* 2006 13:1360-1370; Gutbier et al., *Pulm Pharmacol. Ther.* 2010 23:334-344; Basha et al., *Mol. Ther.* 2011 19:2186-2200; Fenske and Cullis, *Expert Opin Drug Deliv.* 2008 5:25-44; Peer et al., *Science.* 2008 319:627-630; Peer and Lieberman, *Gene Ther.* 2011 18:1127-1133; each of which is incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. *Mol Ther.* 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., *Curr Drug Discov Technol.* 2011 8:197-206; Musacchio and Torchilin, *Front Biosci.* 2011 16:1388-1412; Yu et al., *Mot Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116; Ben-Arie et al., *Methods Mol Biol.* 2012 757:497-507; Peer 2010 *J Control Release.* 20:63-68; Peer et al., *Proc Natl Acad Sci USA.* 2007 104:4095-4100; Kim et al., *Methods Mol Biol.* 2011 721:339-353; Subramanya et al., *Mol Ther.* 2010 18:2028-2037; Song et al., *Nat Biotechnol.* 2005 23:709-717; Peer et al., *Science.* 2008 319:627-630; Peer and Lieberman, *Gene Ther.* 2011 18:1127-1133; each of which is incorporated herein by reference in its entirety).

In some embodiments, the RNA (e.g., mRNA) vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In other embodiments, the lipid nanoparticle may be a self-assembly lipid-polymer nanoparticle (see Zhang et al., *ACS Nano,* 2008, 2 (8), pp 1696-1702; the content of which is herein incorporated by reference in its entirety). As a non-limiting example, the SLN may be the SLN described in International Publication No. WO2013/105101, the content of which is herein incorporated by reference in its entirety. As another non-limiting example, the SLN may be made by the methods or processes described in International Publication No. WO2013/105101, the content of which is herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., *Mol Ther.* 2007 15:713-720; herein incorporated by reference in its entirety). The liposomes, lipoplexes, or lipid nanoparticles may also be used to increase the stability of the polynucleotide.

In some embodiments, the RNA (e.g., mRNA) vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the present disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012/131104 and WO2012/131106; the contents of each of which is herein incorporated by reference in its entirety).

In other embodiments, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (halozyme Therapeutics, San Diego Calif.), surgical sealants such as fibrinogen polymers (Ethicon Inc. Cornelia, Ga.), TISSELL® (Baxter International, Inc. Deerfield, Ill.), PEG-based sealants, and COSEAL® (Baxter International, Inc Deerfield, Ill.).

In other embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In other embodiments, the RNA vaccine controlled release delivery formulation comprising at least one polynucleotide may be the controlled release polymer system described in U.S. Publication No. 2013/0130348, herein incorporated by reference in its entirety.

In some embodiments, the RNA (e.g., mRNA)vaccines of the present invention may be encapsulated in a therapeutic nanoparticle, referred to herein as "therapeutic nanoparticle RNA vaccines." Therapeutic nanoparticles may be formulated by methods described herein and known in the art such as, but not limited to, International Publication Nos. WO2010/005740, WO2010/030763, WO2010/005721, WO2010/005723, WO2012/054923, U.S. Publication Nos. US2011/0262491, US2010/0104645, US2010/0087337, US2010/0068285, US2011/0274759, US2010/0068286, US2012/0288541, US2013/0123351 and US2013/0230567 and U.S. Pat. Nos. 8,206,747, 8,293,276, 8,318,208 and 8,318,211, the content of each of which is herein incorporated by reference in its entirety. In other embodiments, therapeutic polymer nanoparticles may be identified by the methods described in U.S. Publication No. US2012/0140790, the content of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Publication No. WO2010/075072 and U.S. Publication Nos. US2010/0216804, US2011/0217377 and US2012/0201859, each of which is herein incorporated by reference in its entirety). In another non-limiting example, the sustained release formulation may comprise agents which permit persistent bioavailability such as, but not limited to, crystals, macromolecular gels and/or particulate suspensions (see U.S. Publication No. US2013/0150295, the content of which is herein incorporated by reference in its entirety).

In some embodiments, the therapeutic nanoparticle RNA vaccines may be formulated to be target specific. As a non-limiting example, the therapeutic nanoparticles may include a corticosteroid (see International Publication No. WO2011/084518, herein incorporated by reference in its entirety). As a non-limiting example, the therapeutic nanoparticles may be formulated in nanoparticles described in International Publication Nos. WO2008/121949, WO2010/005726, WO2010/005725, WO2011/084521 and U.S. Publication Nos. US2010/0069426, US2012/0004293 and US2010/0104655, each of which is herein incorporated by reference in its entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly (4-hydroxy-L-proline ester) or combinations thereof. In yet other embodiments, the diblock copolymer may be a high-X diblock copolymer such as those described in International Publication No. WO2013120052, the content of which is herein incorporated by reference in its entirety.

As a non-limiting example, the therapeutic nanoparticle comprises a PLGA-PEG block copolymer (see U.S. Publication No. US2012/0004293 and U.S. Pat. No. 8,236,330, each of which is herein incorporated by reference in its entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012/166923, the content of each of which is herein incorporated by reference in its entirety). In yet another non-limiting example, the therapeutic nanoparticle is a stealth nanoparticle or a target-specific stealth nanoparticle as described in U.S. Publication No. 2013/0172406, the content of which is herein incorporated by reference in its entirety. In some embodiments, the therapeutic nanoparticle may comprise a multiblock copolymer (see e.g., U.S. Pat. Nos. 8,263,665 and 8,287,910 and U.S. Publication No. 2013/0195987, the content of each of which is herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) used as a TGF-beta1 gene delivery vehicle in Lee et al. "Thermosensitive Hydrogel as a TGF-β1 Gene Delivery Vehicle Enhances Diabetic Wound Healing." *Pharmaceutical Research,* 2003 20(12): 1995-2000; and used as a controlled gene delivery system in Li et al. "Controlled Gene Delivery System Based on Thermosensitive Biodegradable Hydrogel" *Pharmaceutical Research* 2003 20(6):884-888; and Chang et al., "Non-ionic amphiphilic biodegradable PEG-PLGA-PEG copolymer enhances gene delivery efficiency in rat skeletal muscle." *J Controlled Release.* 2007 118:245-253; each of which is herein incorporated by reference in its entirety). The RNA (e.g., mRNA) vaccines of the present disclosure may be formulated in lipid nanoparticles comprising the PEG-PLGA-PEG block copolymer.

In some embodiments, the block copolymers described herein may be included in a polyion complex comprising a non-polymeric micelle and the block copolymer. (see e.g., U.S. Publication No. 2012/0076836, herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Publication No. WO2013/032829 or U.S. Publication No. 2013/0121954, the content of which is herein incorporated by reference in its entirety. In some aspects, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly (ethylene)glycol copolymer (see e.g., International Publication No. WO2013/044219; herein incorporated by reference in its entirety). As a non-limiting example, the therapeutic nanoparticle may be used to treat cancer (see International publication No. WO2013/044219, herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethyleneimine, poly(amidoamine) dendrimers, poly(beta-amino esters) (see e.g., U.S. Pat. No. 8,287,849, herein incorporated by reference in its entirety) and combinations thereof. In other embodiments, the nanoparticles described herein may comprise an amine cationic lipid such as those described in International Publication No. WO2013/059496, the content of which is herein incorporated by reference in its entirety. In some aspects the cationic lipids may have an amino-amine or an amino-amide moiety.

In some embodiments, the therapeutic nanoparticles may comprise at least one degradable polyester, which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In other embodiments, the therapeutic nanoparticle may include a conjugation of at least one targeting ligand. The targeting ligand may be any ligand known in the art such as, but not limited to, a monoclonal antibody (Kirpotin et al, *Cancer Res.* 2006 66:6732-6740, herein incorporated by reference in its entirety).

In some embodiments, the therapeutic nanoparticle may be formulated in an aqueous solution, which may be used to target cancer (see International Publication No. WO2011/084513 and U.S. Publication No. 2011/0294717, each of which is herein incorporated by reference in its entirety).

In some embodiments, the therapeutic nanoparticle RNA vaccines, e.g., therapeutic nanoparticles comprising at least one RNA vaccine may be formulated using the methods described by Podobinski et al in U.S. Pat. No. 8,404,799, the content of which is herein incorporated by reference in its entirety.

In some embodiments, the RNA (e.g., mRNA) vaccines may be encapsulated in, linked to and/or associated with synthetic nanocarriers. Synthetic nanocarriers include, but are not limited to, those described in International Publication Nos. WO2010/005740, WO2012/149454 and WO2013/019669, and U.S. Publication Nos. US2011/0262491, US2010/0104645, US2010/0087337 and US2012/0244222, each of which is herein incorporated by reference in its entirety. The synthetic nanocarriers may be formulated using methods known in the art and/or described herein. As a non-limiting example, the synthetic nanocarriers may be formulated by the methods described in International Publication Nos. WO2010/005740, WO2010/030763 and WO2012/13501, and U.S. Publication Nos. US2011/0262491, US2010/0104645, US2010/0087337 and US2012/024422, each of which is herein incorporated by reference in its entirety. In other embodiments, the synthetic nanocarrier formulations may be lyophilized by methods described in International Publication No. WO2011/072218 and U.S. Pat. No. 8,211,473, the content of each of which is herein incorporated by reference in its entirety. In yet other embodiments, formulations of the present invention, including, but not limited to, synthetic nanocarriers, may be lyophilized or reconstituted by the methods described in U.S. Publication No. 2013/0230568, the content of which is herein incorporated by reference in its entirety.

In some embodiments, the synthetic nanocarriers may contain reactive groups to release the polynucleotides described herein (see International Publication No. WO2012/092552 and U.S. Publication No. US2012/0171229, each of which is herein incorporated by reference in its entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Publication No. WO2010/123569 and U.S. Publication No. 2011/0223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Publication Nos. WO2010/138193 and WO2010/138194 and U.S. Publication Nos. US2011/0020388 and US2011/0027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Publication No. WO2010/138192 and U.S. Publication No. 2010/0303850, each of which is herein incorporated by reference in its entirety.

In some embodiments, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Publication No. WO2011/150264 and U.S. Publication No. 2011/0293723, each of which is herein incorporated by reference in its entirety). As another non-limiting example, a vaccine dosage form may include at least two synthetic nanocarriers with the same or different antigens and an excipient (see International Publication No. WO2011/150249 and U.S. Publication No. 2011/0293701, each of which is herein incorporated by reference in its entirety). The vaccine dosage form may be selected by methods described herein, known in the art and/or described in International Publication No. WO2011/150258 and U.S. Publication No. US2012/0027806, each of which is herein incorporated by reference in its entirety).

In some embodiments, the synthetic nanocarrier may comprise at least one polynucleotide which encodes at least one adjuvant (e.g., a flagellin protein). In some embodiments, the synthetic nanocarrier may comprise at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g., U.S. Pat. No. 8,241,610; herein incorporated by reference in its entirety). In other embodiments, the synthetic nanocarrier may comprise at least one polynucleotide and an adjuvant. As a non-limiting example, the synthetic nanocarrier comprising, optionally comprising an adjuvant, may be formulated by the methods described in International Publication No. WO2011/150240 and U.S. Publication No. US2011/0293700, each of which is herein incorporated by reference in its entirety.

In some embodiments, the synthetic nanocarrier may encapsulate at least one polynucleotide which encodes a peptide, fragment or region from a virus. As a non-limiting example, the synthetic nanocarrier may include, but is not limited to, the nanocarriers described in International Publication Nos. WO2012/024621, WO2012/02629, WO2012/024632 and U.S. Publication No. US2012/0064110, US2012/0058153 and US2012/0058154, each of which is herein incorporated by reference in its entirety.

In some embodiments, the synthetic nanocarrier may be coupled to a polynucleotide which may be able to trigger a humoral and/or cytotoxic T lymphocyte (CTL) response (See e.g., International Publication No. WO2013/019669, herein incorporated by reference in its entirety).

In some embodiments, the RNA vaccine may be encapsulated in, linked to and/or associated with zwitterionic lipids. Non-limiting examples of zwitterionic lipids and methods of using zwitterionic lipids are described in U.S. Publication No. 2013/0216607, the content of which is herein incorporated by reference in its entirety. In some aspects, the zwitterionic lipids may be used in the liposomes and lipid nanoparticles described herein.

In some embodiments, the RNA vaccine may be formulated in colloid nanocarriers as described in U.S. Publication No. 2013/0197100, the content of which is herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 2012/0282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, or less than 975 μm.

In other embodiments, RNA (e.g., mRNA) vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. *Molecular Therapy-Nucleic Acids*. 2012. 1:e37; Chen, D. et al., Rapid discovery of potent siRNA-containing lipid nanoparticles enabled by controlled microfluidic formulation. *J Am Chem Soc*. 2012. 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In some embodiments, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see Whitesides, George M. The Origins and the Future of Microfluidics. *Nature,* 2006 442: 368-373; and Abraham et al. Chaotic Mixer for Microchannels. *Science,* 2002 295: 647-651; each of which is herein incorporated by reference in its entirety). As a non-limiting example, controlled microfluidic formulation includes a passive method for mixing streams of steady pressure-driven flows in micro channels at a low Reynolds number (see e.g., Abraham et al. *Chaotic* Mixer for Microchannels. *Science,* 2002 295: 647651; which is herein incorporated by reference in its entirety).

In some embodiments, the RNA (e.g., mRNA) vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA (e.g., mRNA) vaccines of the invention may be formulated for delivery using the drug encapsulating microspheres described in International Publication No. WO2013/063468 or U.S. Pat. No. 8,440,614, each of which is herein incorporated by reference in its entirety. The microspheres may comprise a compound of the formula (I), (II), (III), (IV), (V) or (VI) as described in International Publication No. WO2013063468, the content of which is herein incorporated by reference in its entirety. In other aspects, the amino acid, peptide, polypeptide, lipids (APPL) are useful in delivering the RNA vaccines of the invention to cells (see International Publication No. WO2013/063468, the contents of which is herein incorporated by reference in its entirety).

In some embodiments, the RNA (e.g., mRNA) vaccines of the present disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some aspects, the lipid nanoparticle may be a limit size lipid nanoparticle described in International Publication No. WO2013/059922, the content of which is herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In other aspects the limit size lipid nanoparticle may comprise a polyethylene glycol-lipid such as, but not limited to, DLPE-PEG, DMPE-PEG, DPPC-PEG and DSPE-PEG.

In some embodiments, the RNA vaccines may be delivered, localized and/or concentrated in a specific location using the delivery methods described in International Publication No. WO2013/063530, the content of which is herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In some embodiments, the RNA vaccines may be formulated in an active substance release system (see e.g., U.S. Publication No. US2013/0102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Publication No. WO2013/052167, herein incorporated by reference in its entirety. As another non-limiting example, the nanoparticle described in International Publication No. WO2013/052167, herein incorporated by reference in its entirety, may be used to deliver the RNA vaccines described herein.

In some embodiments, the RNA vaccines may be formulated in porous nanoparticle-supported lipid bilayers (protocells). Protocells are described in International Publication No. WO2013/056132, the content of which is herein incorporated by reference in its entirety.

In some embodiments, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the content of which is herein incorporated by reference in its entirety. As another non-limiting example, the polymer nanoparticle for oral and parenteral formulations may be made by the methods described in European Patent No. EP2073848B1, the content of which is herein incorporated by reference in its entirety.

In other embodiments, the RNA (e.g., mRNA) vaccines described herein may be formulated in nanoparticles used in imaging. The nanoparticles may be liposome nanoparticles such as those described in U.S. Publication No. 2013/0129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., U.S. Publication No US2013/0129636, the contents of which is herein incorporated by reference in its entirety).

In some embodiments, the nanoparticles which may be used in the present invention are formed by the methods described in U.S. Patent Application No. 2013/0130348, the contents of which is herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No. WO2013/072929, the contents of which is herein incorporated by reference in its entirety). As a non-limiting example, the nutrient may be iron in the form of ferrous, ferric salts or elemental iron, iodine, folic acid, vitamins or micronutrients.

In some embodiments, the RNA (e.g., mRNA) vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA (e.g., mRNA) vaccines of the present invention to the pulmonary system (see e.g., U.S. Pat. No. 8,440,231, the contents of which is herein incorporated by reference in its entirety).

The RNA (e.g., mRNA) vaccines of the present invention may be formulated in polyanhydride nanoparticles such as, but not limited to, those described in U.S. Pat. No. 8,449,916, the contents of which is herein incorporated by reference in its entirety. The nanoparticles and microparticles of the present invention may be geometrically engineered to modulate macrophage and/or the immune response. In some aspects, the geometrically engineered particles may have varied shapes, sizes and/or surface charges in order to incorporated the polynucleotides of the present invention for targeted delivery such as, but not limited to, pulmonary delivery (see e.g., International Publication No. WO2013/082111, the content of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No. WO2013/082111, the contents of which is herein incorporated by reference in its entirety.

In some embodiments, the nanoparticles of the present invention may be water soluble nanoparticles such as, but not limited to, those described in International Publication No. WO2013/090601, the content of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present invention may be developed by the methods described in U.S. Publication No. US2013/0172406, the content of which is herein incorporated by reference in its entirety.

In some embodiments, the nanoparticles of the present invention are stealth nanoparticles or target-specific stealth nanoparticles such as, but not limited to, those described in U.S. Publication No. 2013/0172406, the content of which is herein incorporated by reference in its entirety. The nanoparticles of the present invention may be made by the methods described in U.S. Publication No. 2013/0172406, the content of which is herein incorporated by reference in its entirety.

In other embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Publication No. 2013/0171646, the content of which is herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Publication No. WO2013/123523, the content of which is herein incorporated by reference in its entirety.

In some embodiments, a nanoparticle comprises compounds of Formula (I):

(I)

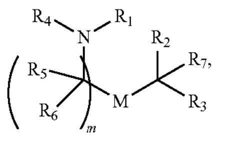

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)N(R)_2$, $—C({=}NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_n$—OR, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

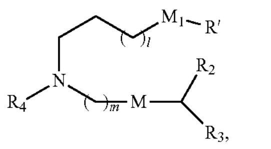

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S)$N(R)_2$, —NHC(O)$N(R)_2$, —N(R)C(O)R, —N(R)$S(O)_2R$, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

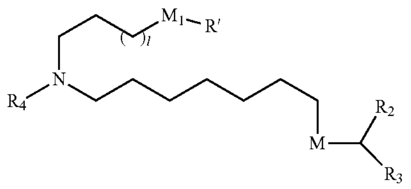

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —NHC(S)$N(R)_2$, —NHC(O)$N(R)_2$, —N(R)C(O)R, —N(R)$S(O)_2R$, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

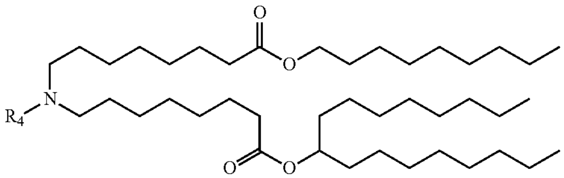

, (IIb)

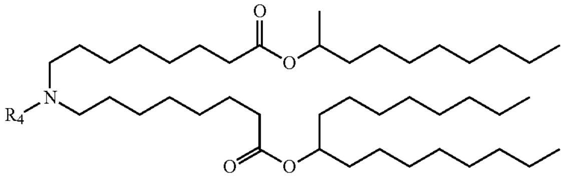

, (IIc)

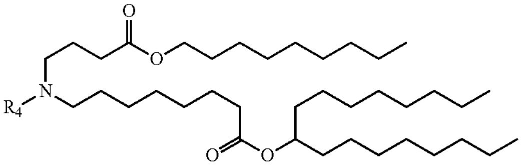

, or

-continued (IIe)

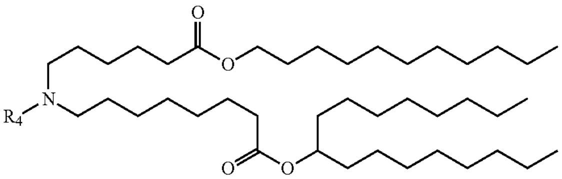

, or a salt or isomer thereof, wherein $R_4$ is as described herein.

In some embodiments, a subset of compounds of Formula (I) includes those of Formula (IId):

(IId)

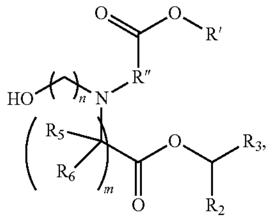

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)

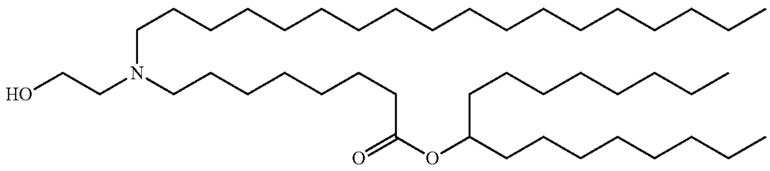

, (Compound 2)

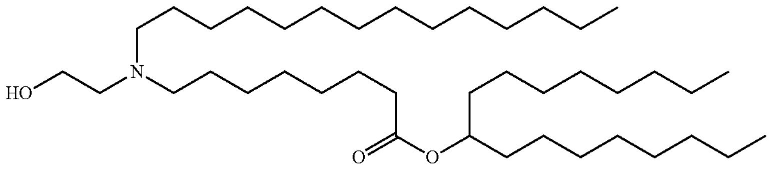

, (Compound 3)

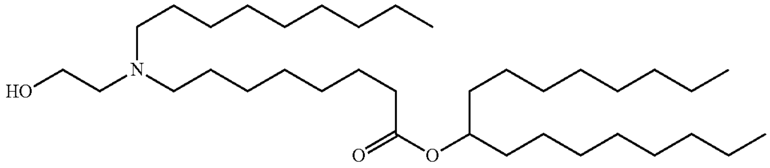

, (Compound 4)

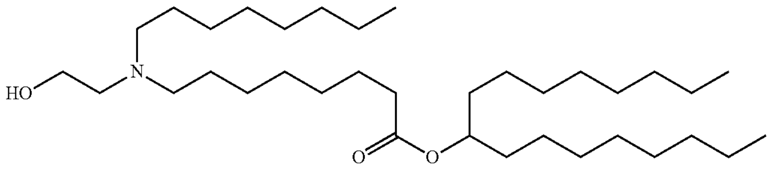

,

-continued
(Compound 5)
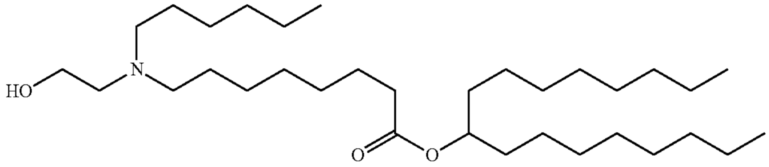
,
(Compound 6)
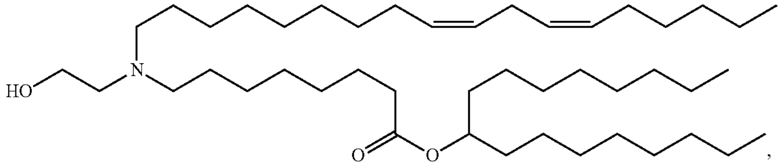
,
(Compound 7)
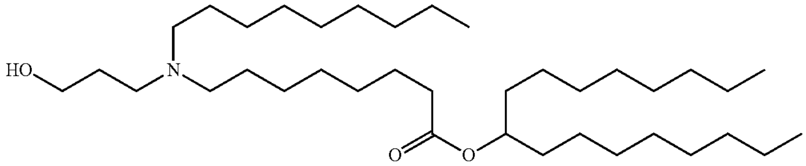
,
(Compound 8)
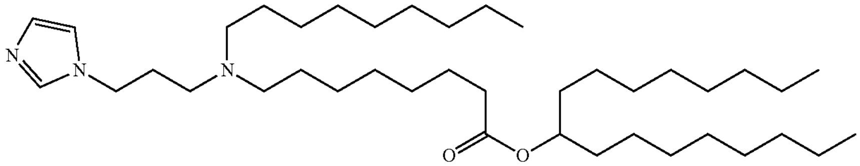
,
(Compound 9)
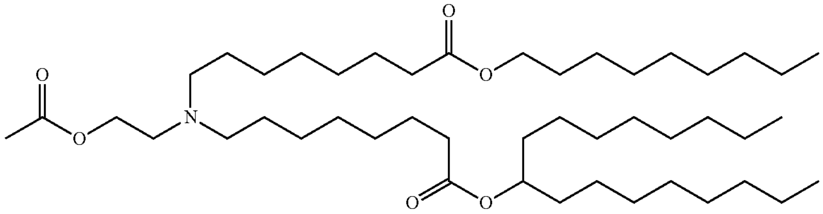
,
(Compound 10)
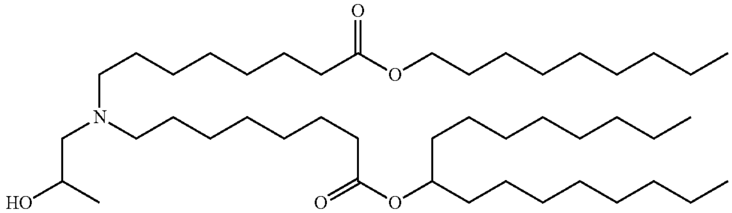
,
(Compound 11)
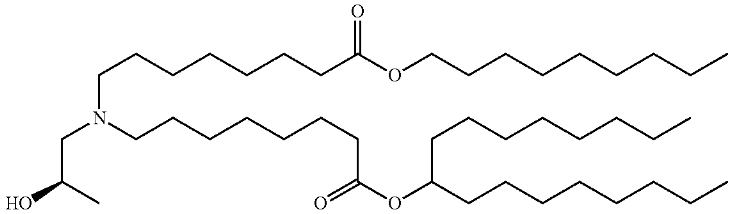
,
(Compound 12)
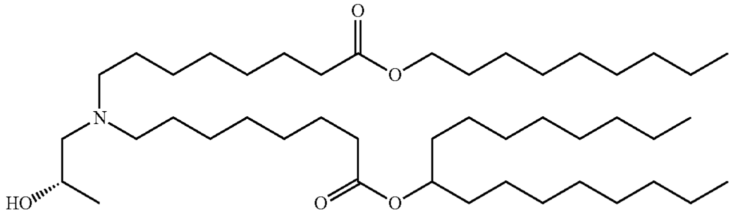
, -continued
(Compound 13)
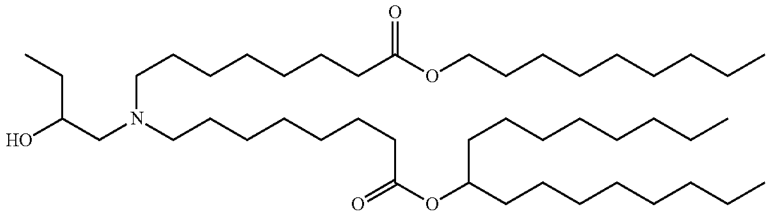
,
(Compound 14)
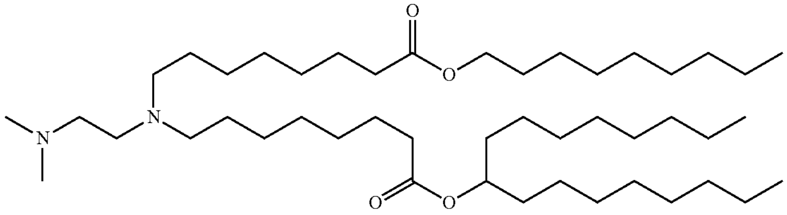
.
(Compound 15)
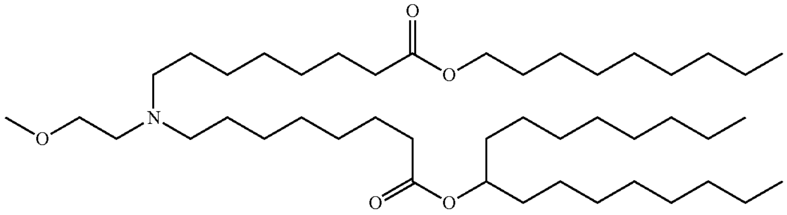
,
(Compound 16)
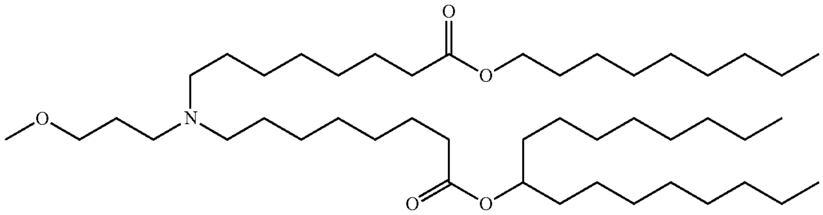
,
(Compound 17)
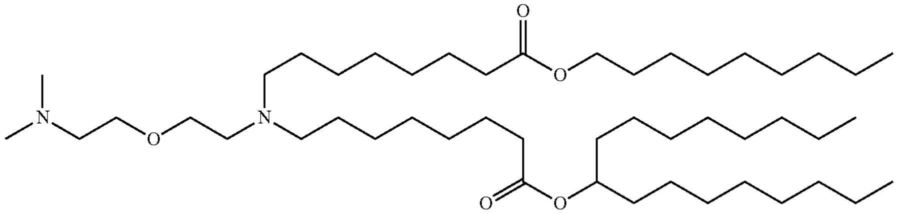
,
(Compound 18)
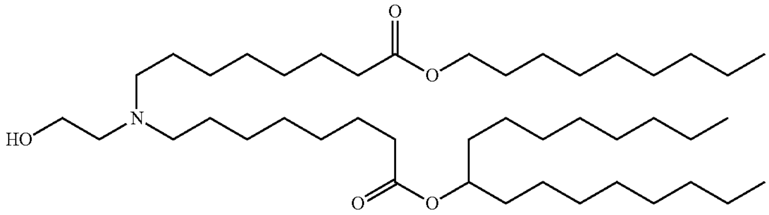
,
(Compound 19)
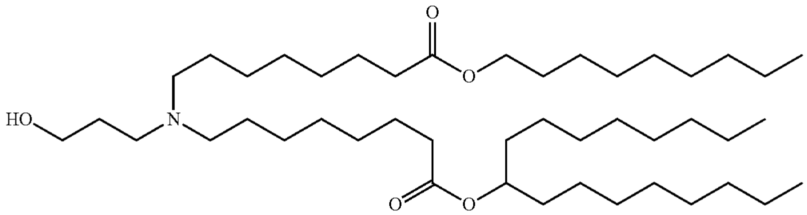
, -continued
(Compound 20)
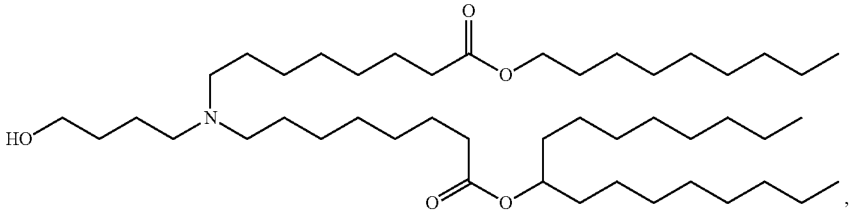
(Compound 21)
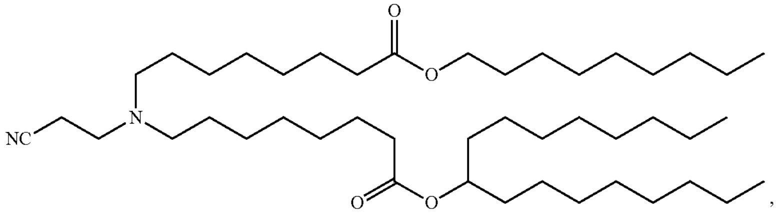
(Compound 22)
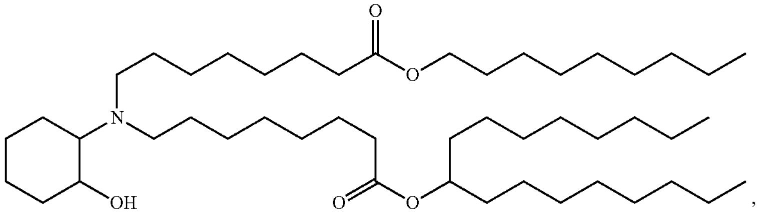
(Compound 23)
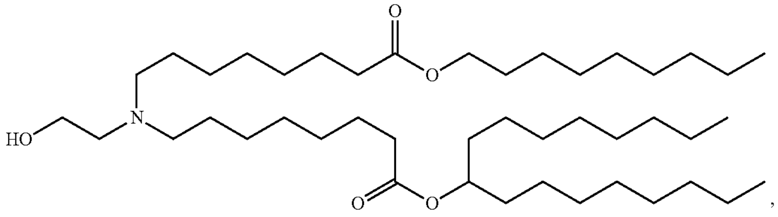
(Compound 24)
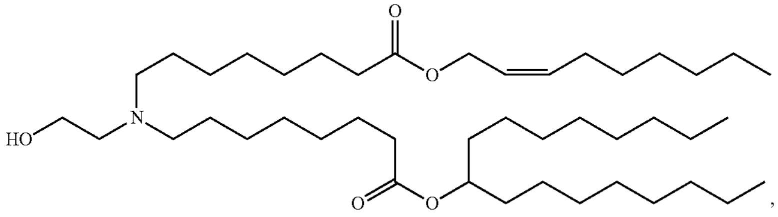
(Compound 25)
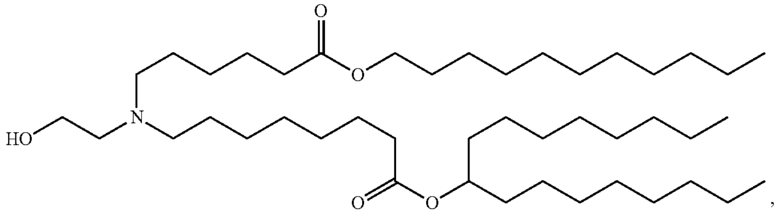
(Compound 26)
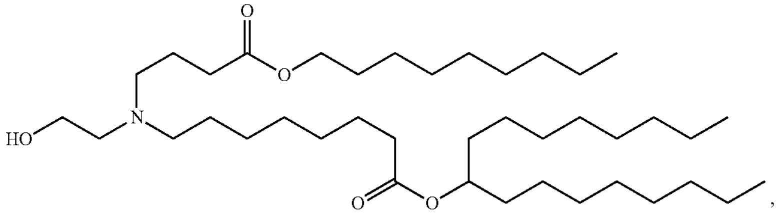

-continued
(Compound 27)
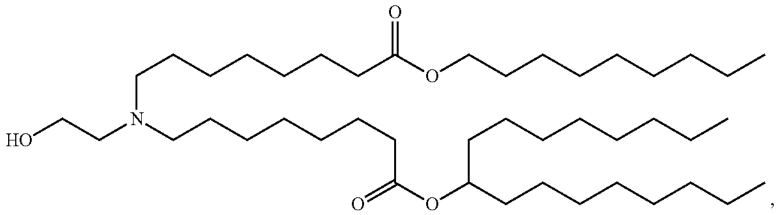
(Compound 28)
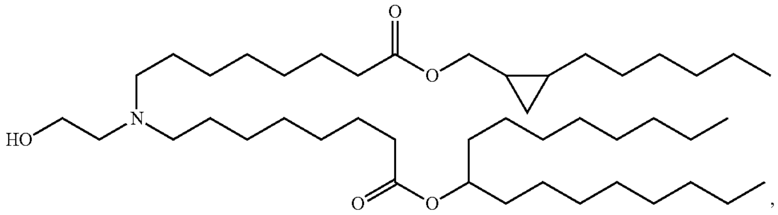
(Compound 29)
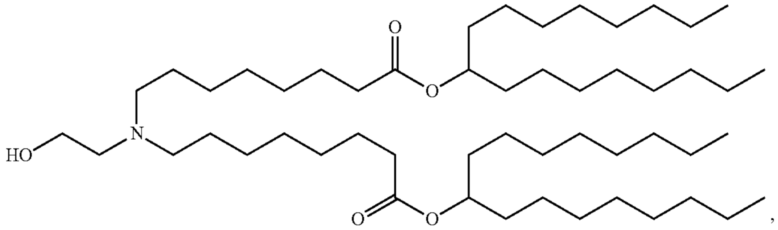
(Compound 30)
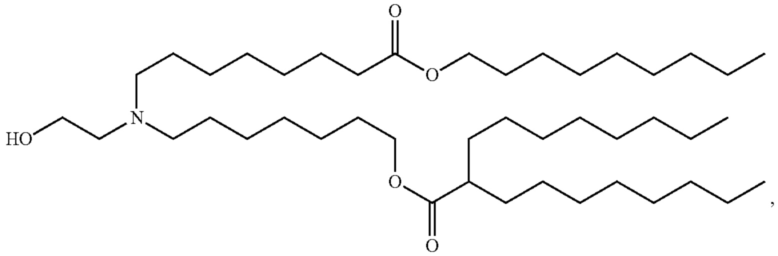
(Compound 31)
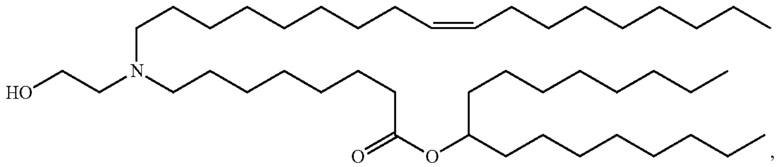
(Compound 32)
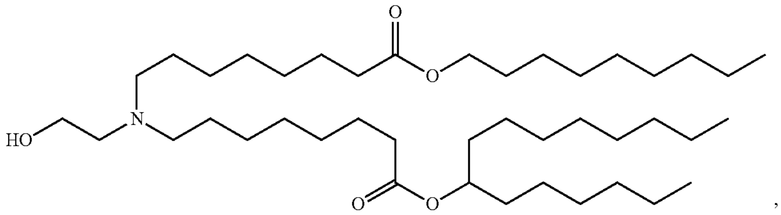
(Compound 33)
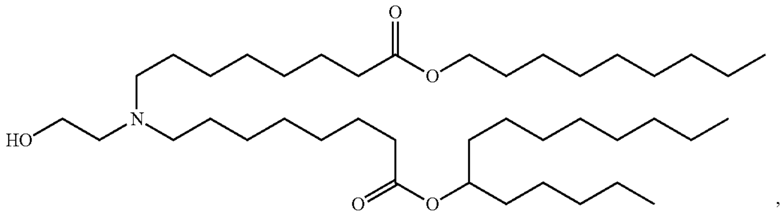
, -continued
(Compound 34)
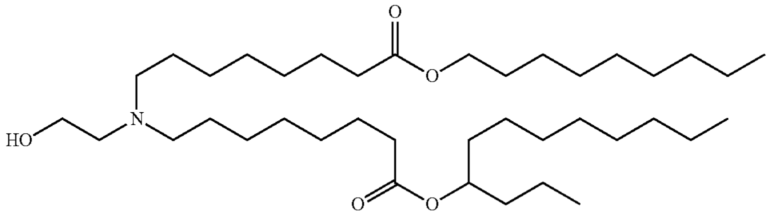
,
(Compound 35)
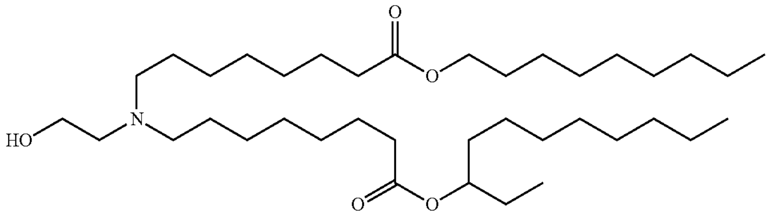
,
(Compound 36)
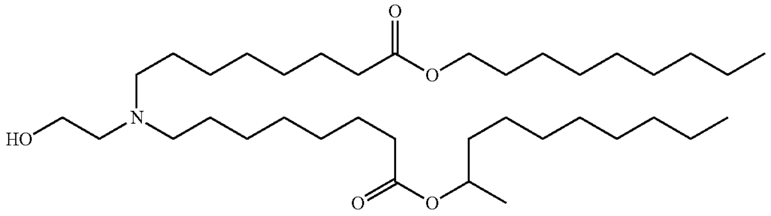
,
(Compound 37)
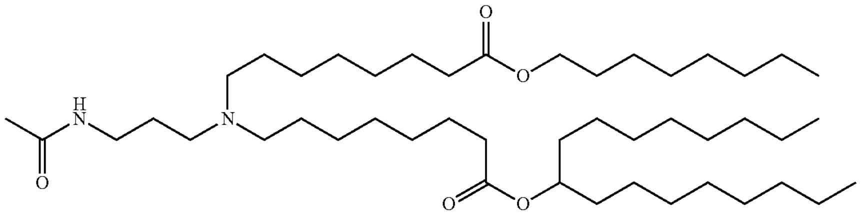
,
(Compound 38)
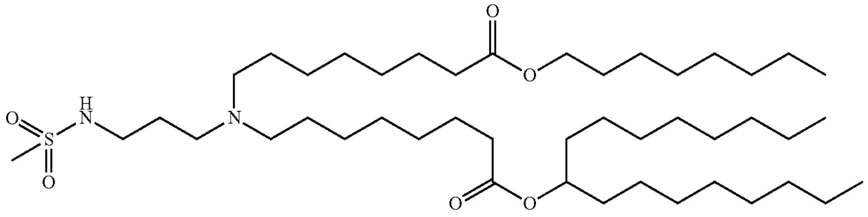
,
(Compound 39)
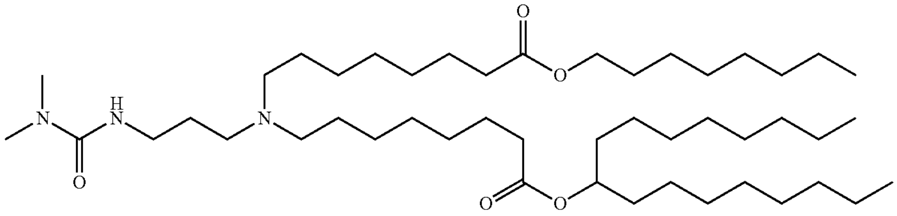
,
(Compound 40)
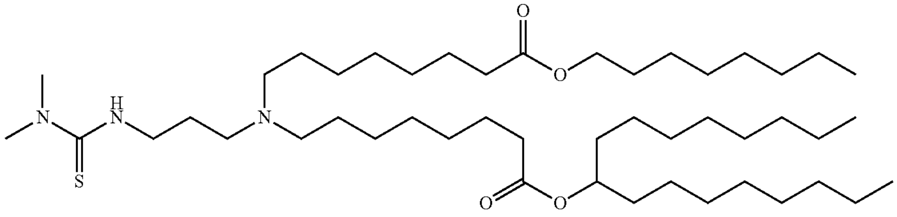
, -continued
(Compound 41)
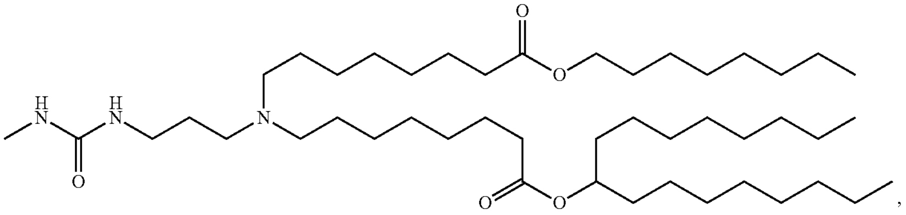
(Compound 42)
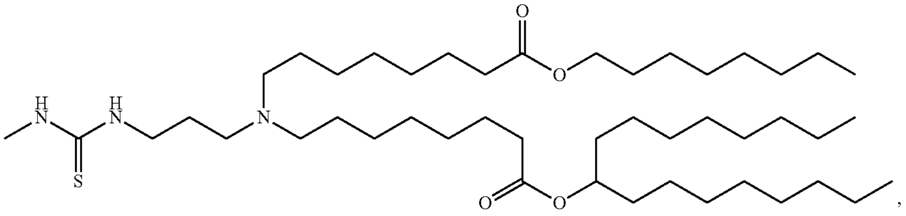
(Compound 43)
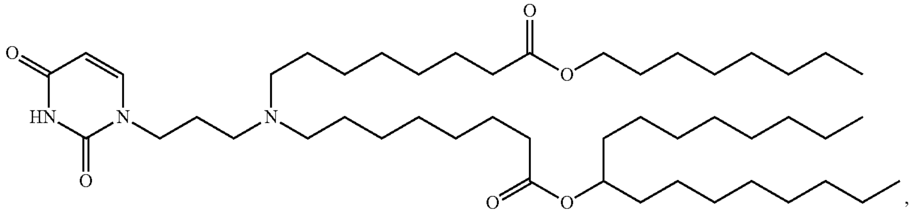
(Compound 44)
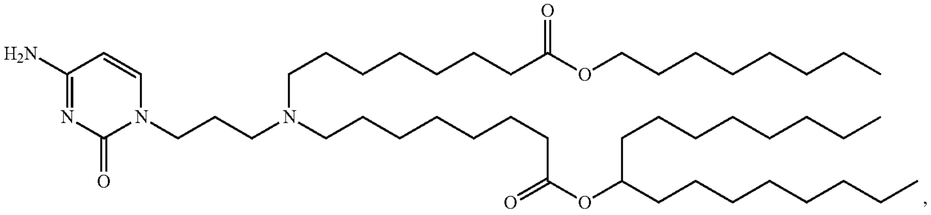
(Compound 45)
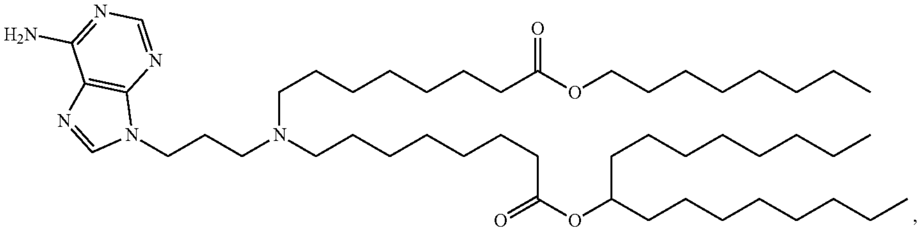
(Compound 46)
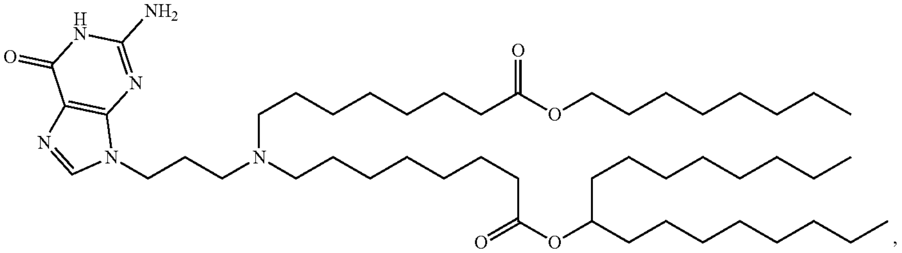
(Compound 47)
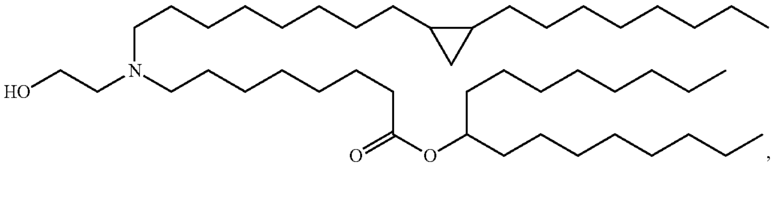
, -continued
(Compound 48)
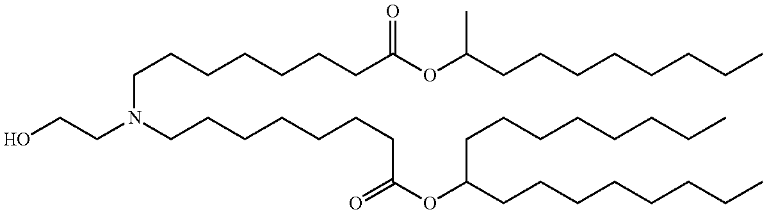
,
(Compound 49)
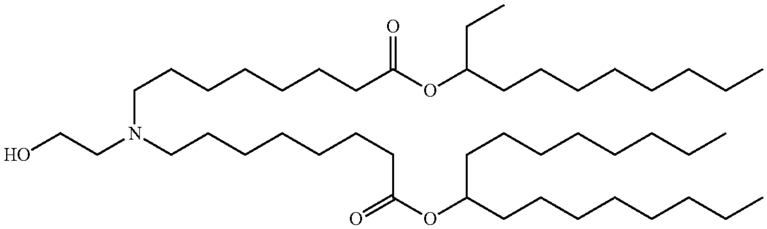
,
(Compound 50)
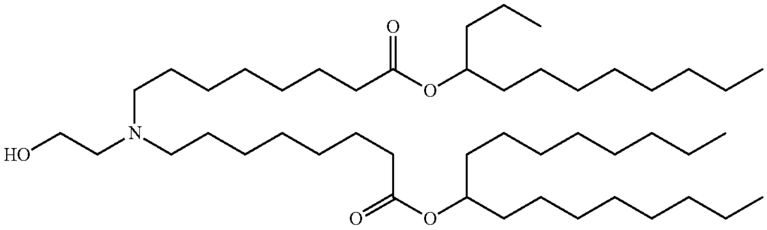
,
(Compound 51)
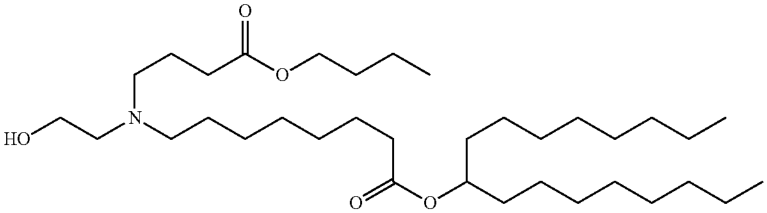
,
(Compound 52)
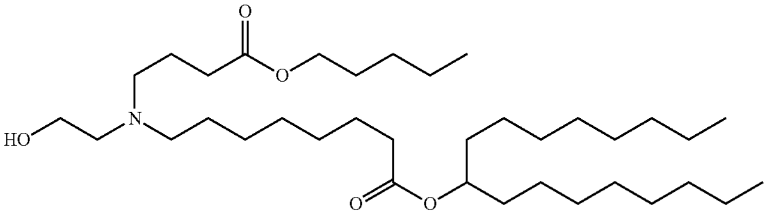
,
(Compound 53)
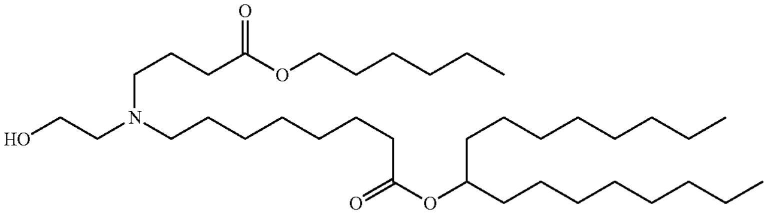
,
(Compound 54)
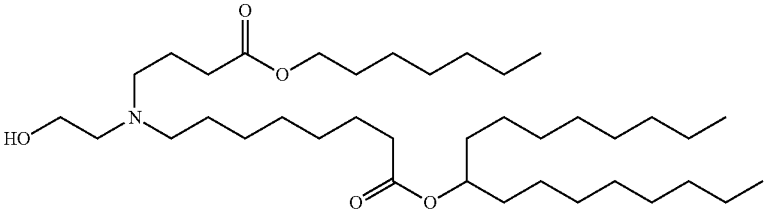
, -continued
(Compound 55)
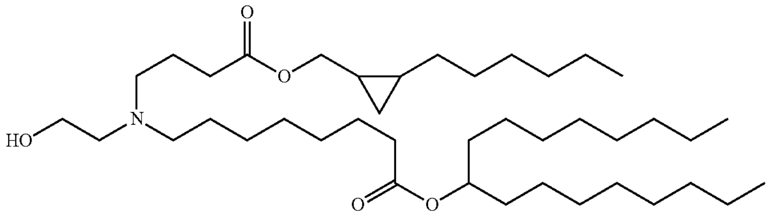
,
(Compound 56)
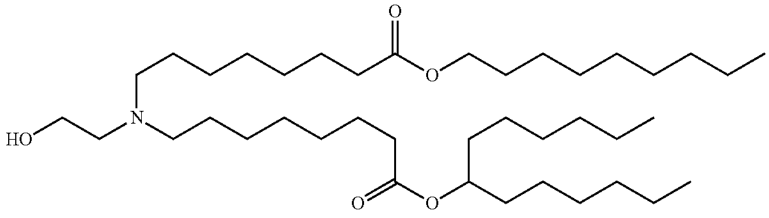
,
(Compound 57)
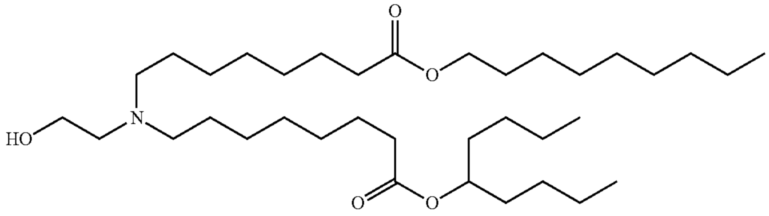
,
(Compound 58)
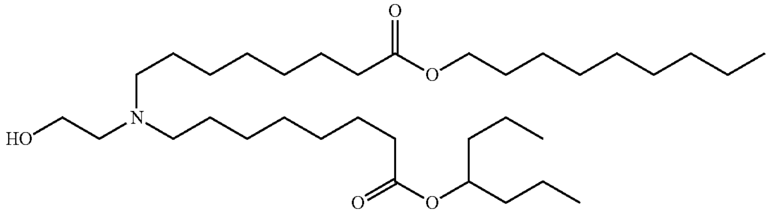
,
(Compound 59)
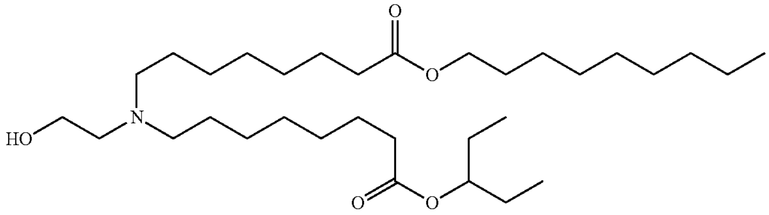
,
(Compound 60)
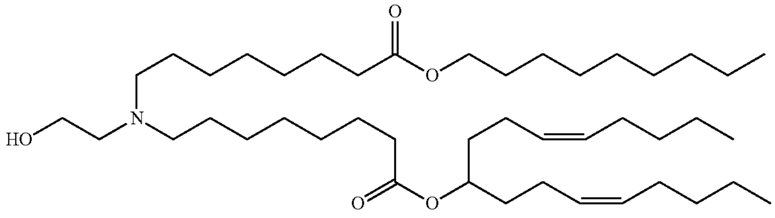
, and
(Compound 61)
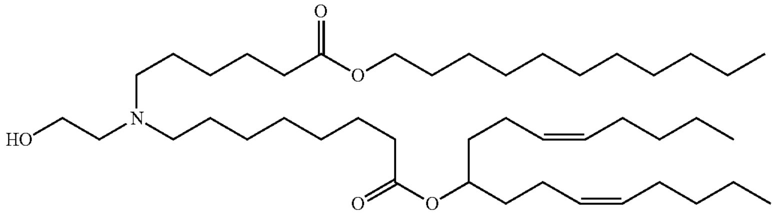
.

In further embodiments, the compound of Formula (I) is selected from the group consisting of:
(Compound 62)
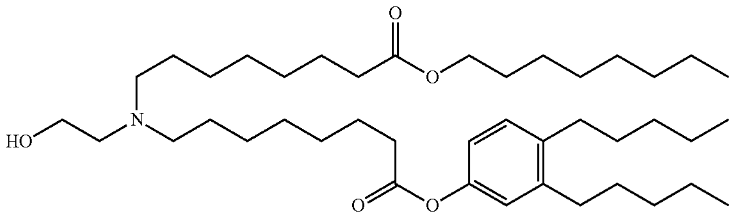
,
(Compound 63)
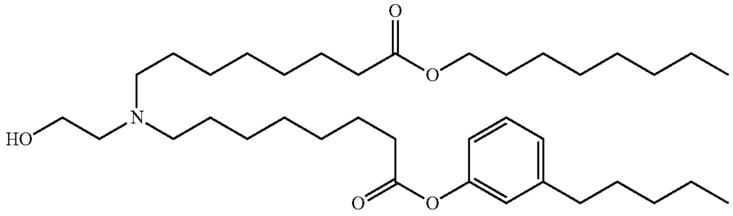
, and
(Compound 64)
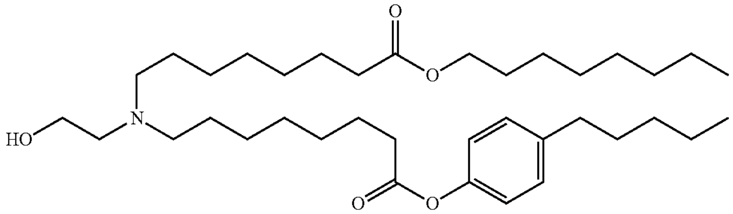
.
In some embodiments, the compound of Formula (I) is selected from the group consisting of:
(Compound 65)
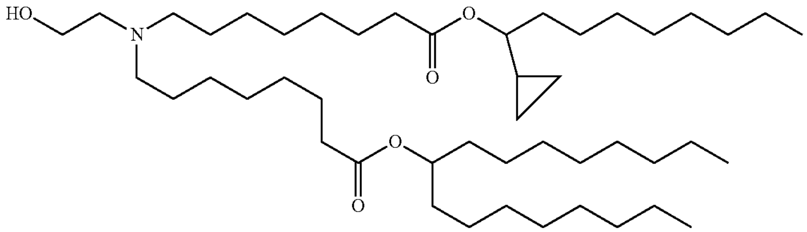
,
(Compound 66)
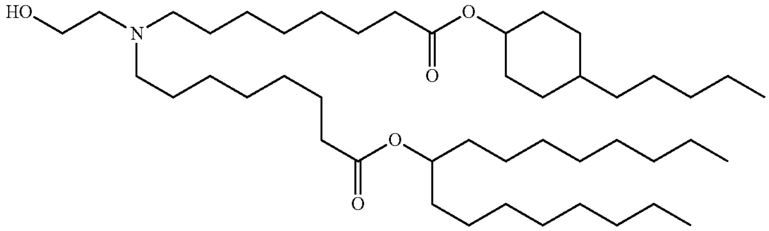
,
(Compound 67)
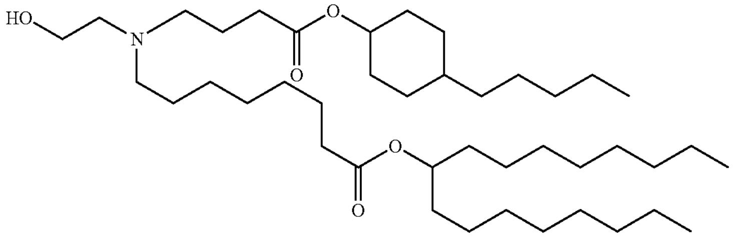
, -continued
(Compound 68)
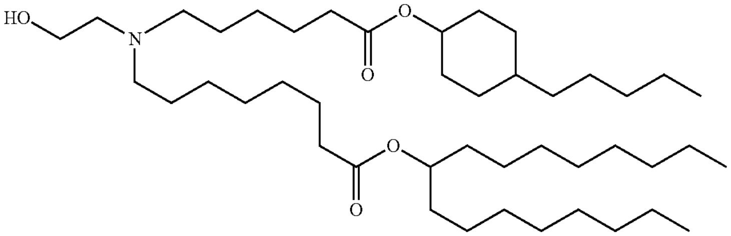
,
(Compound 69)
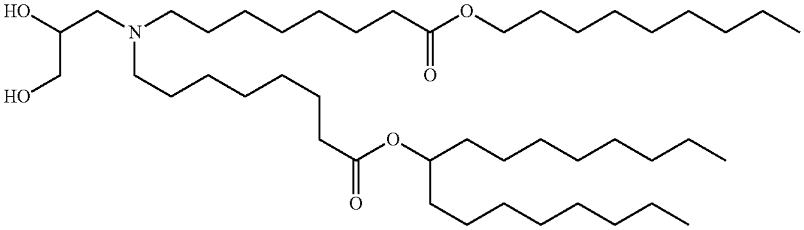
,
(Compound 70)
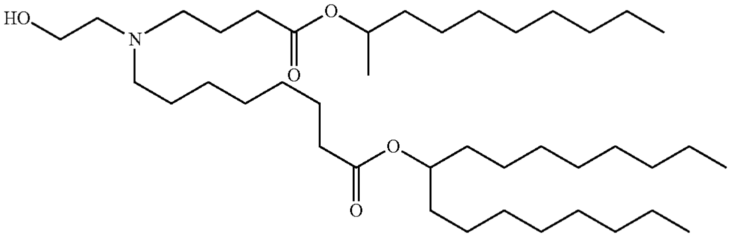
,
(Compound 71)
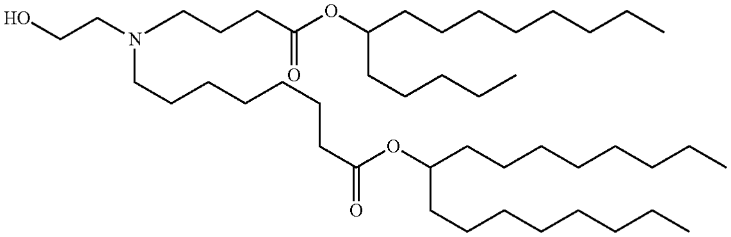
,
(Compound 72)
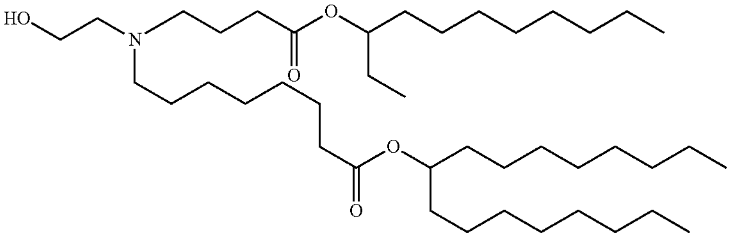
,
(Compound 73)
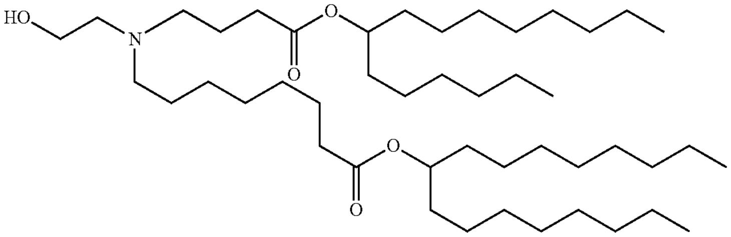
, -continued
(Compound 74)
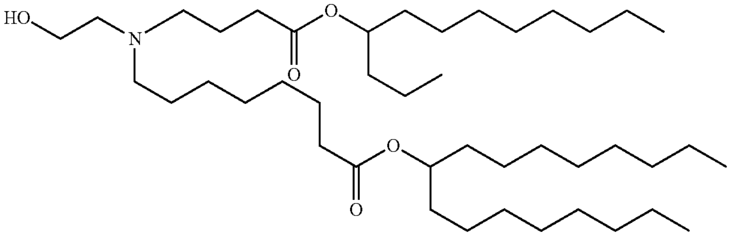
,
(Compound 75)
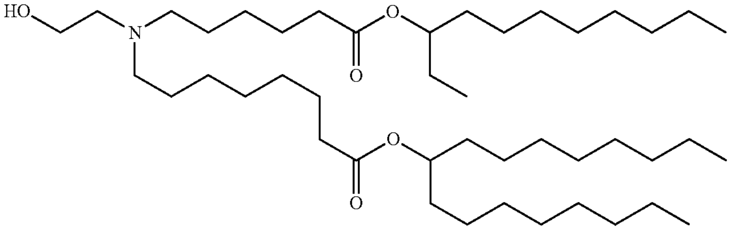
,
(Compound 76)
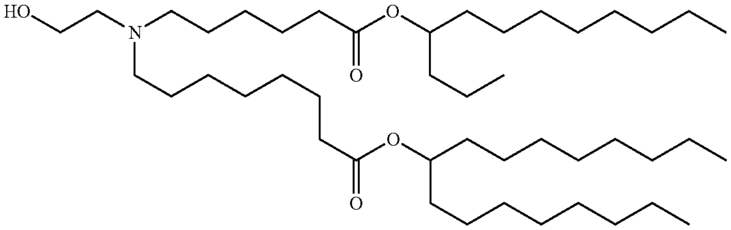
,
(Compound 77)
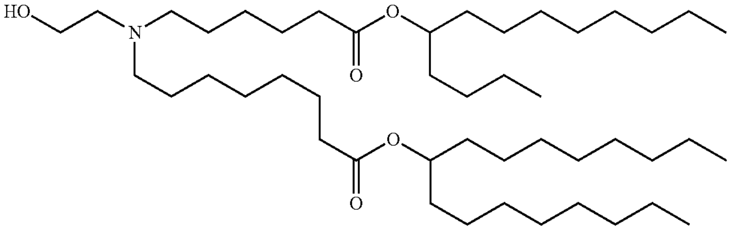
,
(Compound 78)
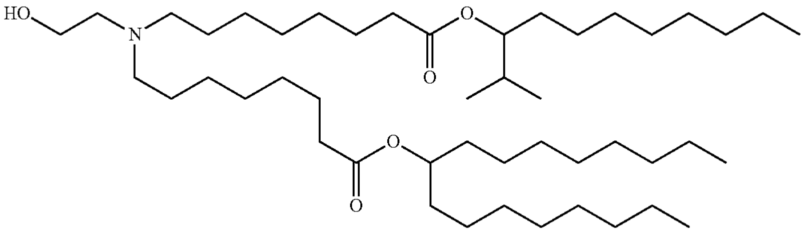
,
(Compound 79)
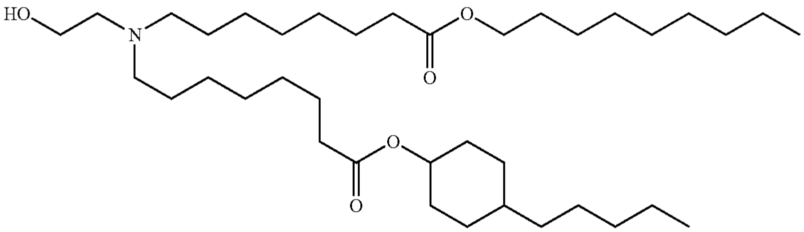
, -continued
(Compound 80)
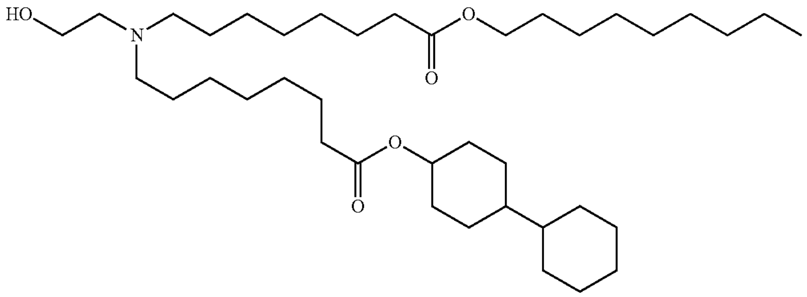
,
(Compound 81)
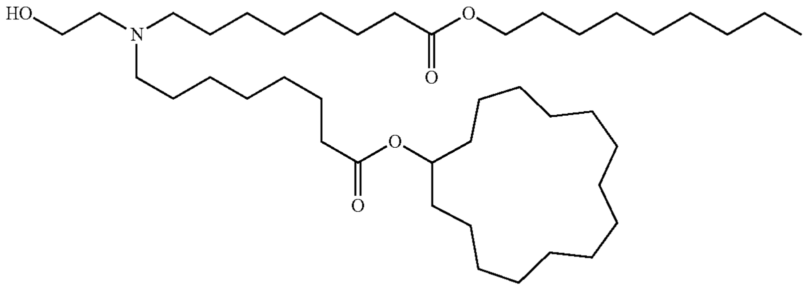
,
(Compound 82)
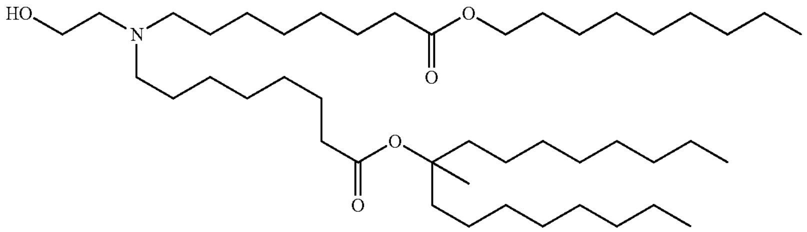
,
(Compound 83)
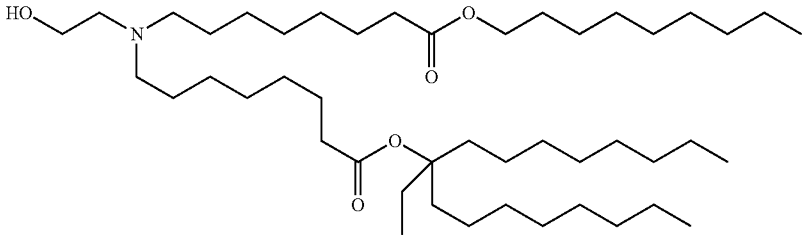
,
(Compound 84)
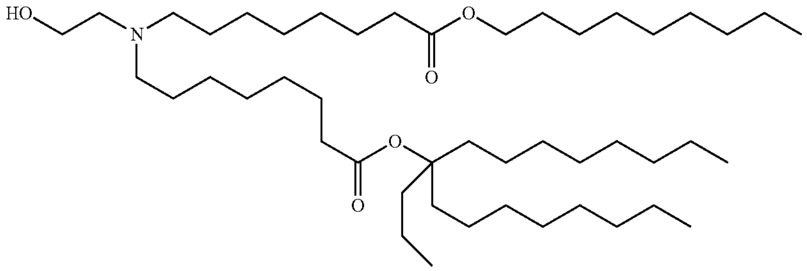
,
(Compound 85)
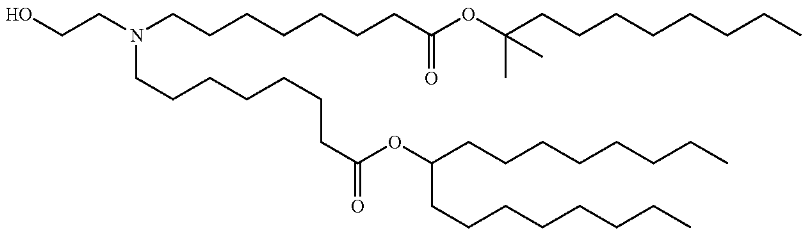
, -continued
(Compound 86)
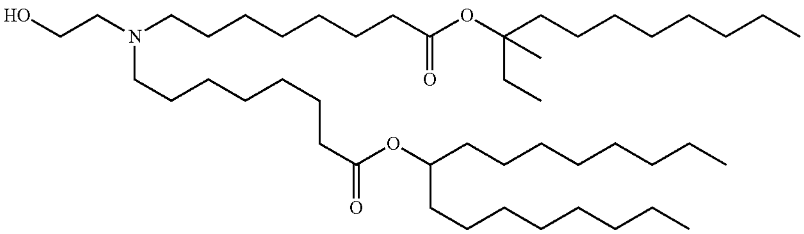
,
(Compound 87)
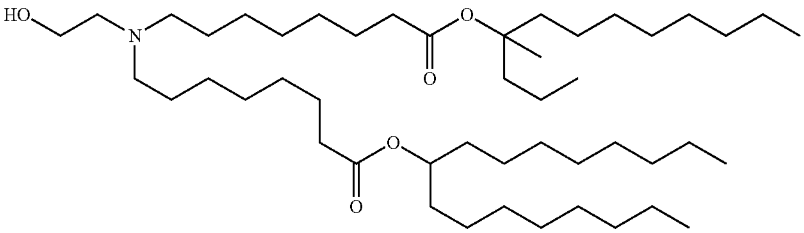
,
(Compound 88)
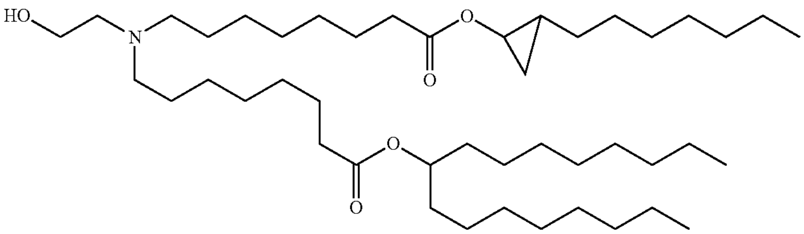
,
(Compound 89)
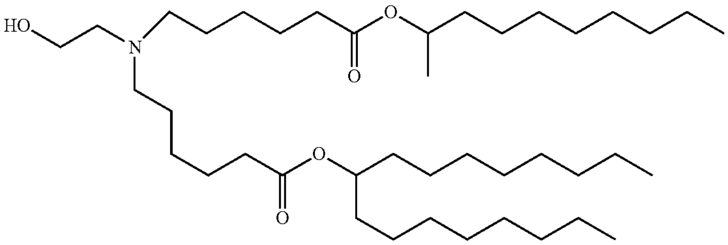
,
(Compound 90)
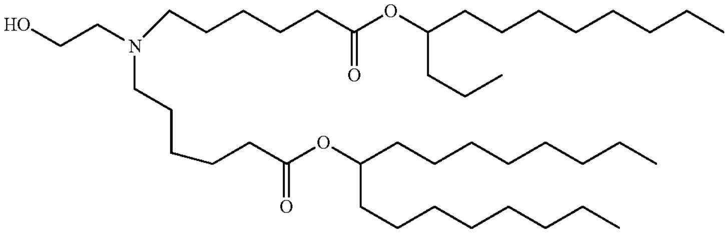
,
(Compound 91)
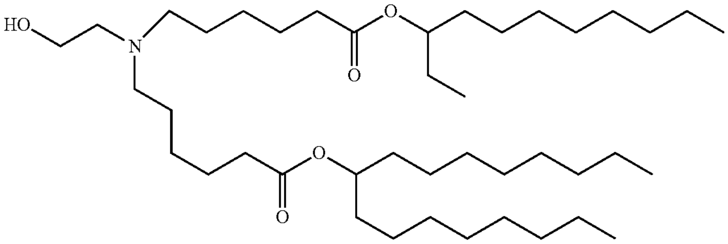
, -continued
(Compound 92)
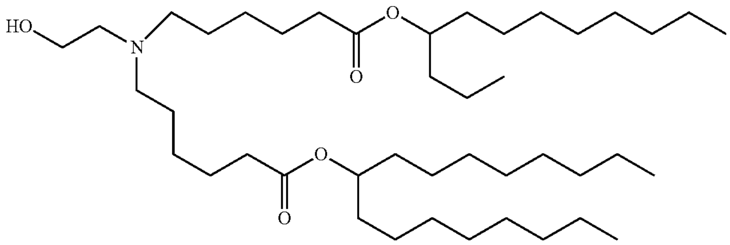
,
(Compound 93)
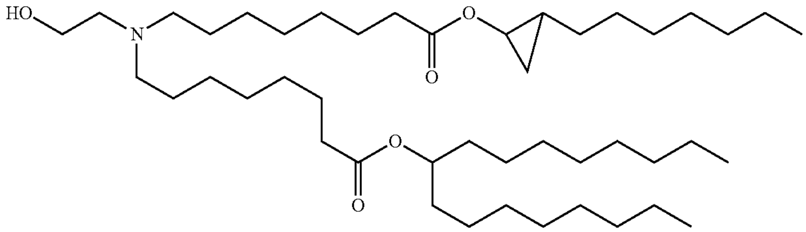
,
(Compound 94)
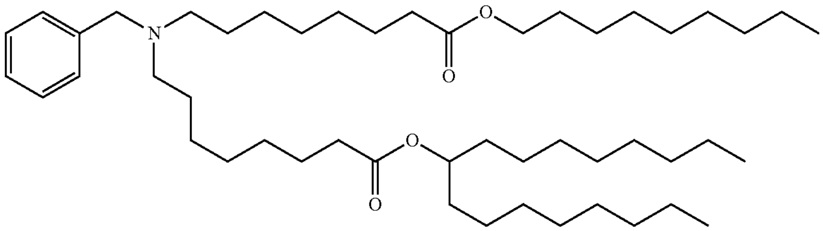
,
(Compound 95)
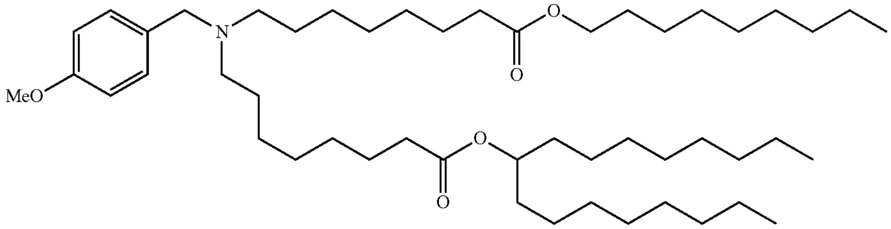
,
(Compound 96)
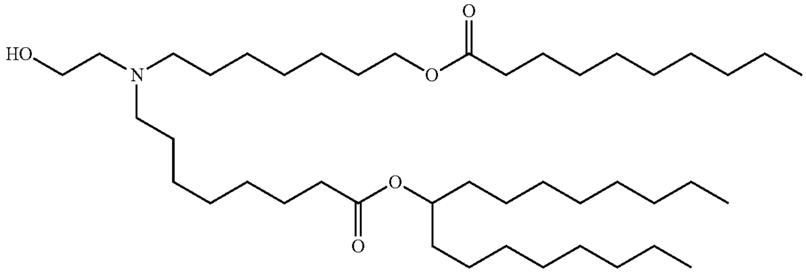
,
(Compound 97)
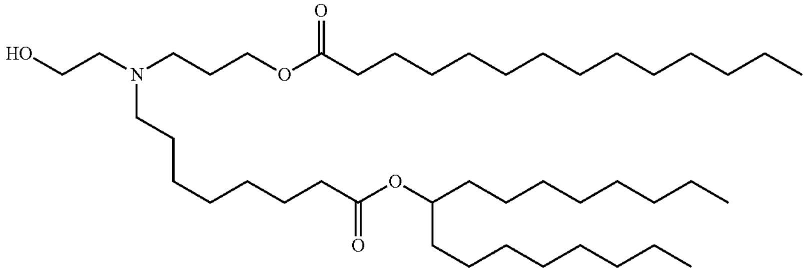
, -continued
(Compound 98)
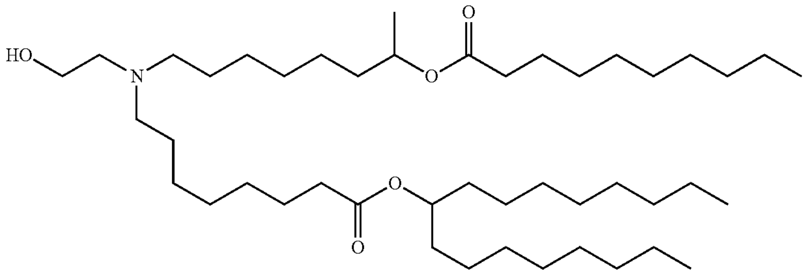
,
(Compound 99)
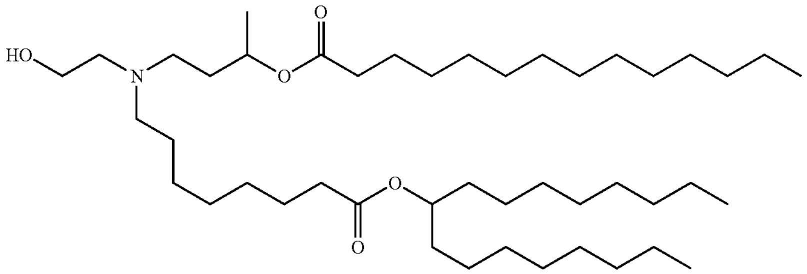
,
(Compound 100)
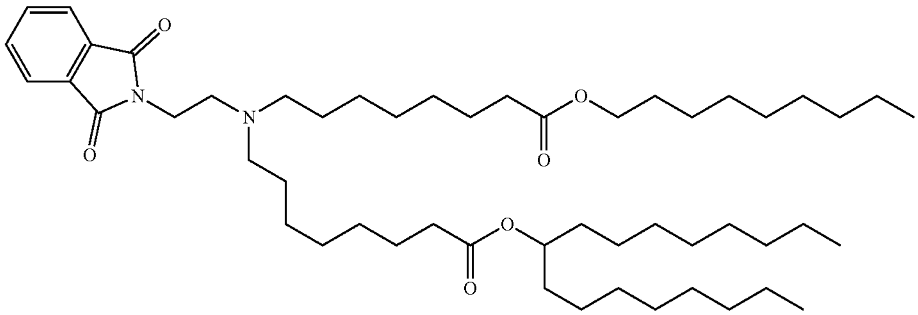
,
(Compoud 101)
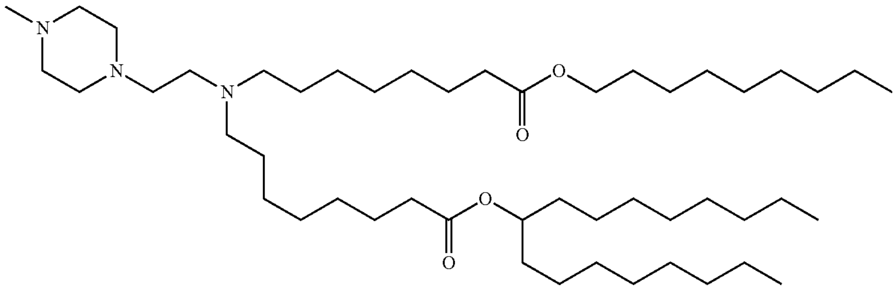
,
(Compound 102)
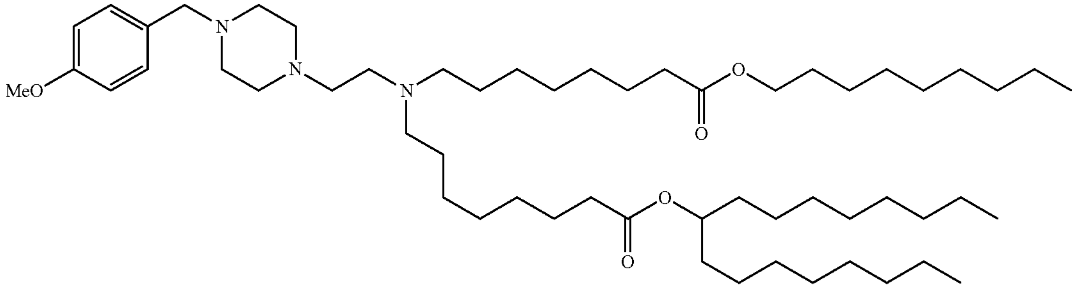
, -continued
(Compound 103)
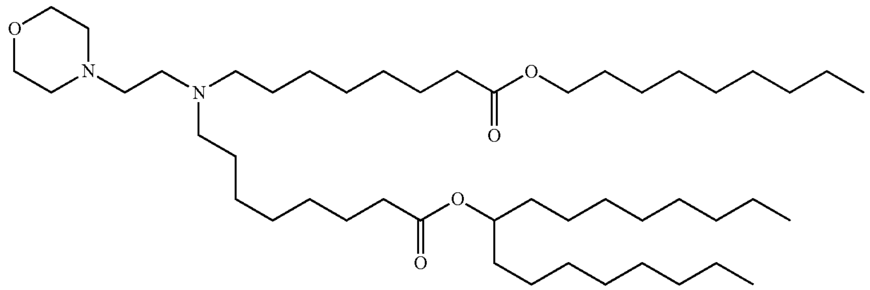
,
(Compound 104)
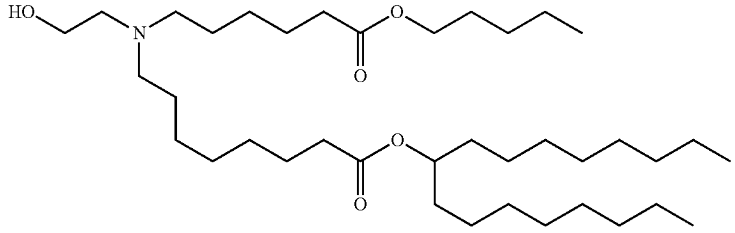
,
(Compound 105)
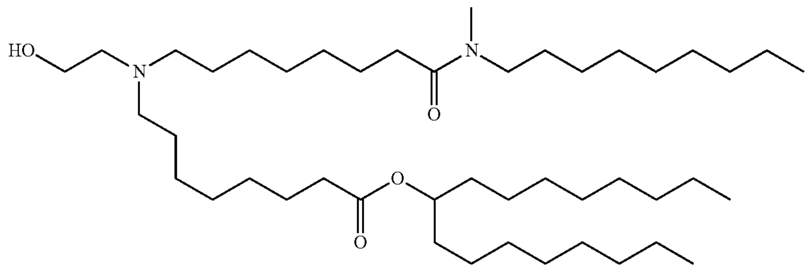
,
(Compound 106)
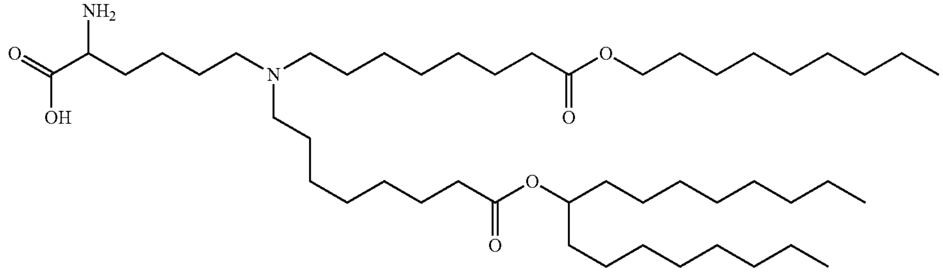
,
(Compound 107)
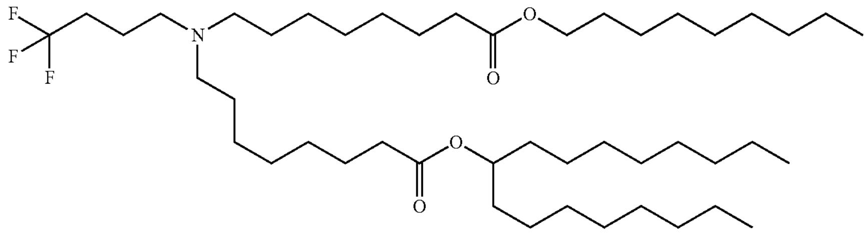
,
(Compound 108)
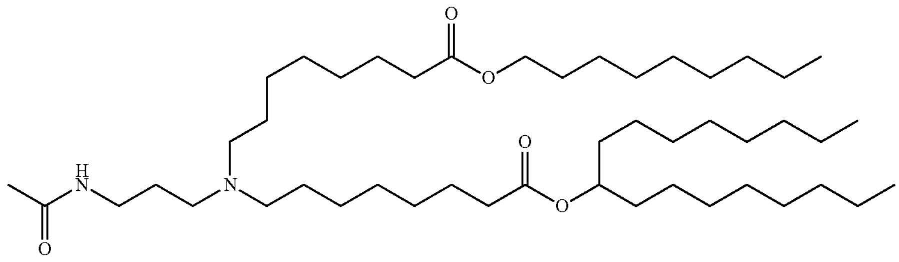
, -continued
(Compoound 109)
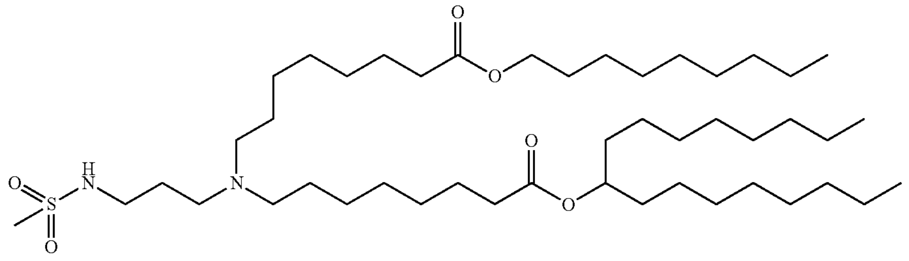
,
(Compound 110)
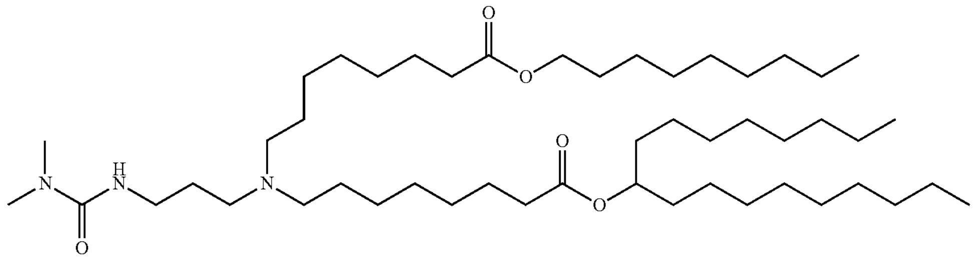
,
(Compound 111)
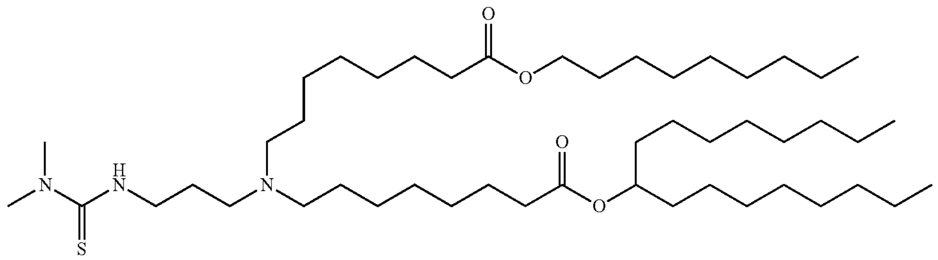
,
(Compound 112)
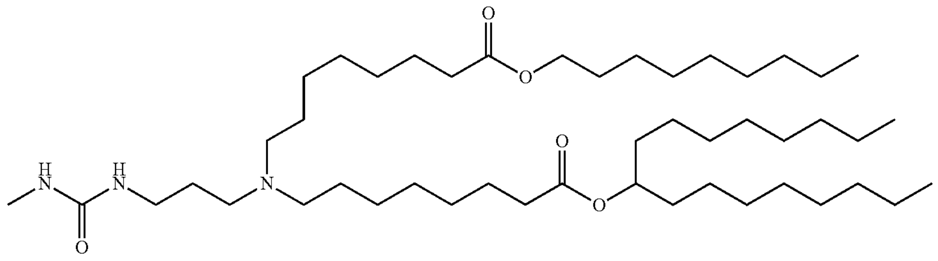
,
(Compound 113)
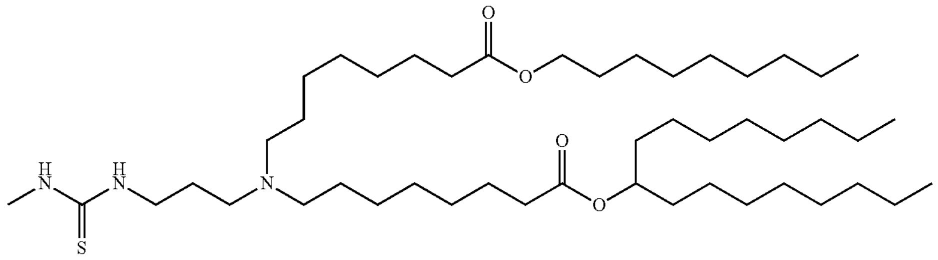
,
(Compound 114)
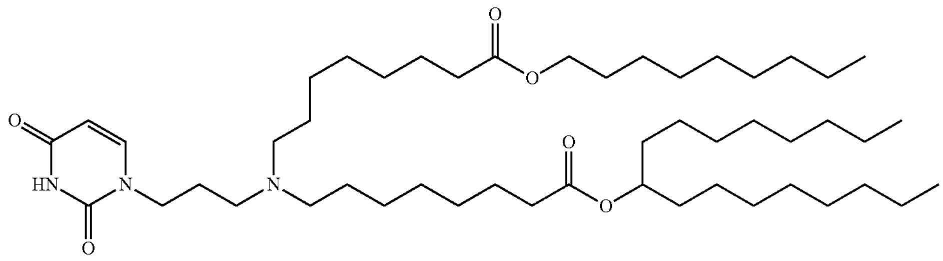
, -continued
(Compound 115)
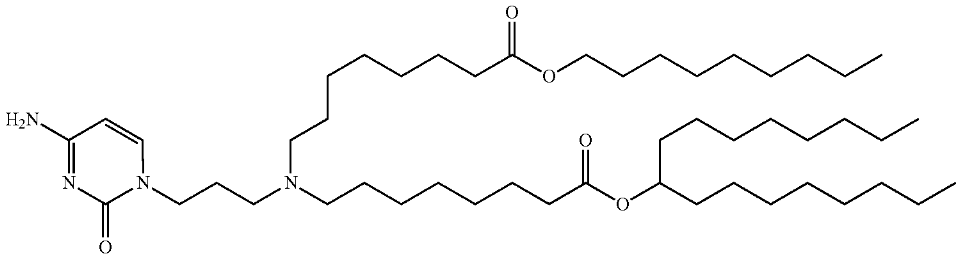
,
(Compound 116)
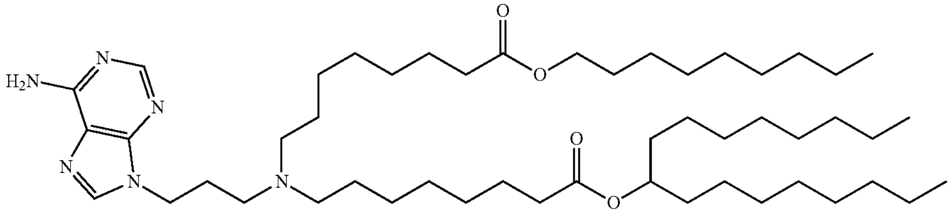
,
(Compound 117)
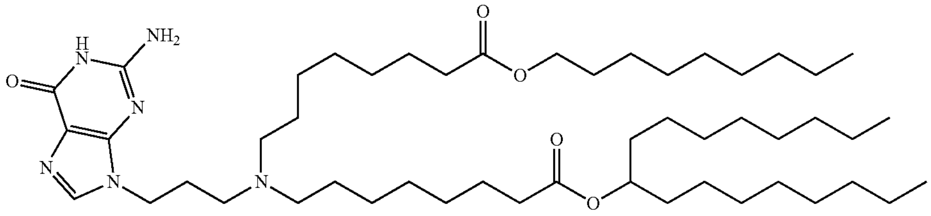
,
(Compound 118)
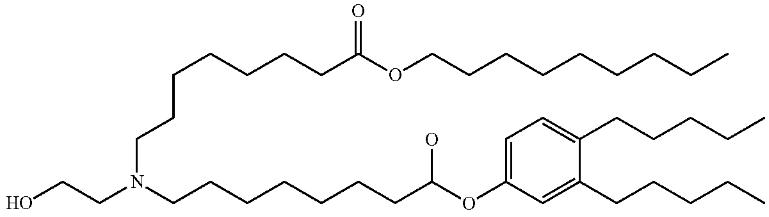
,
(Compound 119)
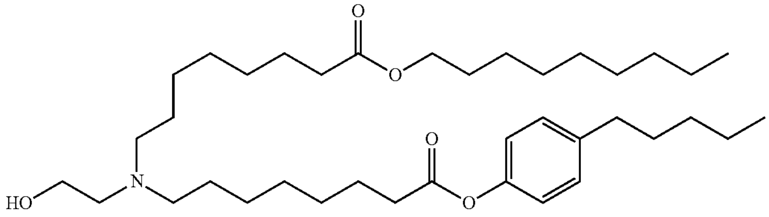
,
(Compound 120)
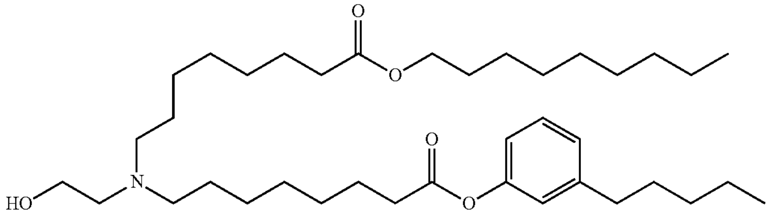
,
(Compound 121)
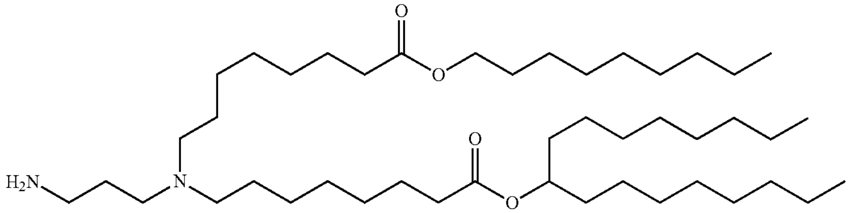
, -continued
(Compound 122)
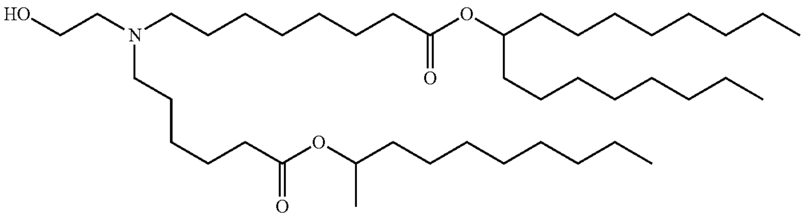
,
(Compound 123)
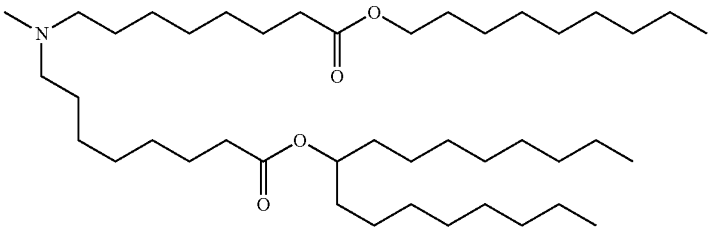
,
(Compound 124)
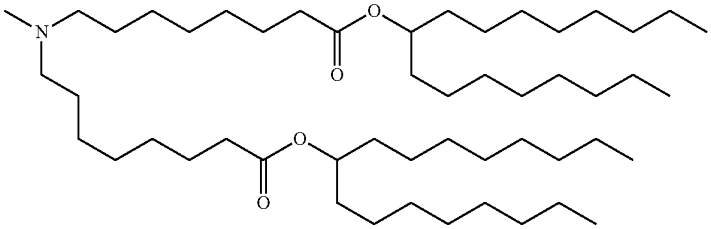
,
(Compound 125)
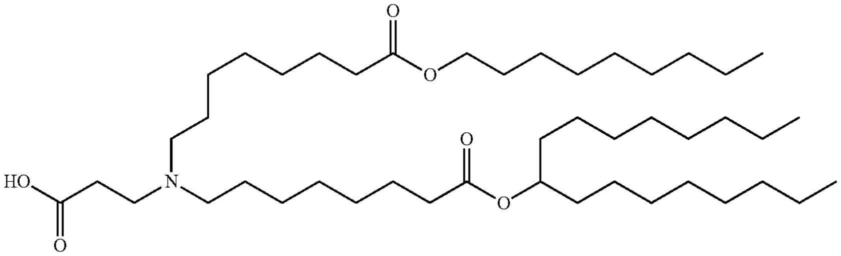
,
(Compound 126)
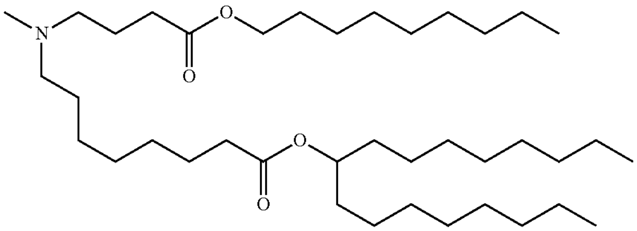
,
(Compound 127)
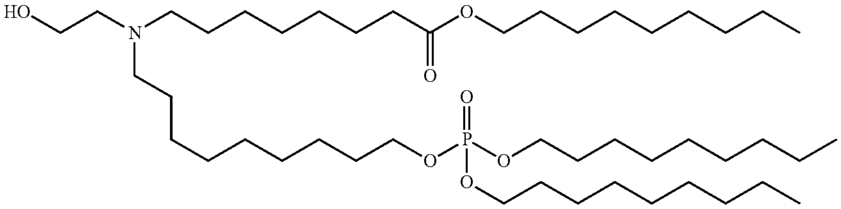
, -continued
(Compound 128)
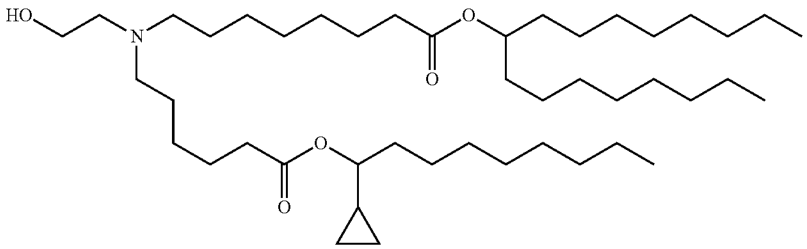
,
(Compound 129)
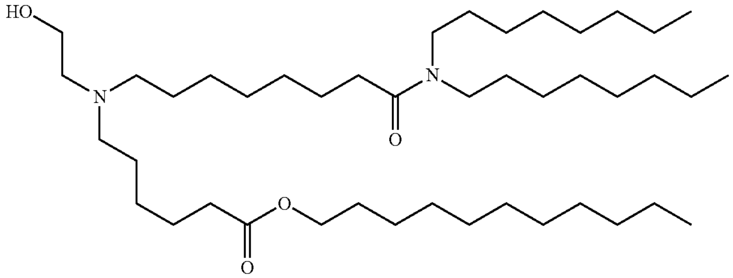
,
(Compound 130)
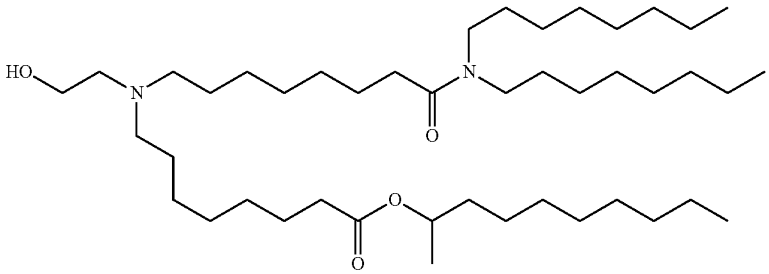
,
(Compound 131)
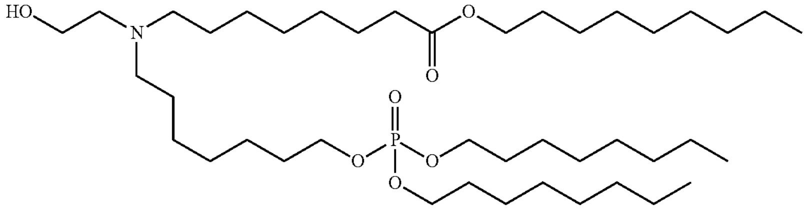
,
(Compound 132)
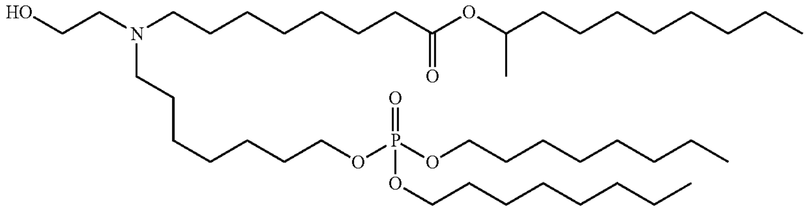
,
(Compound 133)
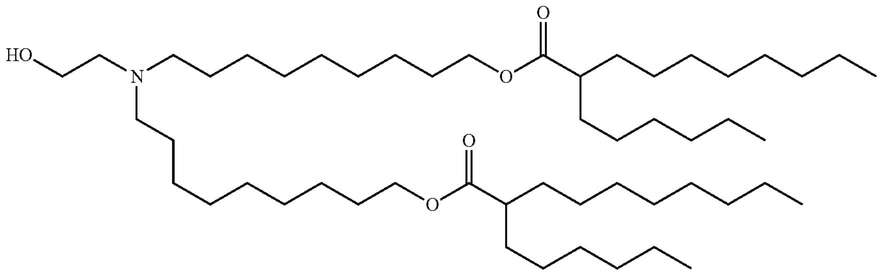
, -continued
(Compound 134)
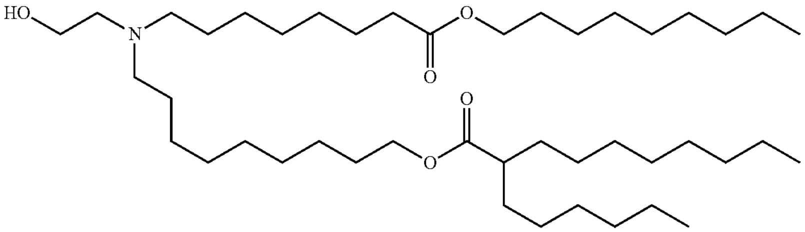
,
(Compound 135)
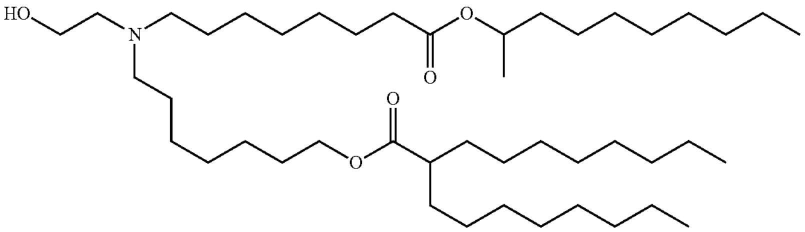
,
(Compound 136)
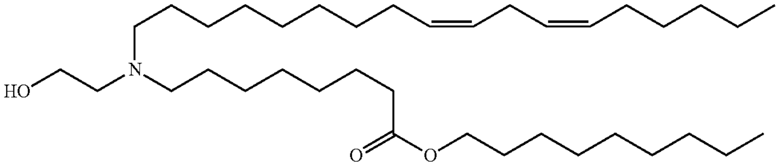
,
(Compound 137)
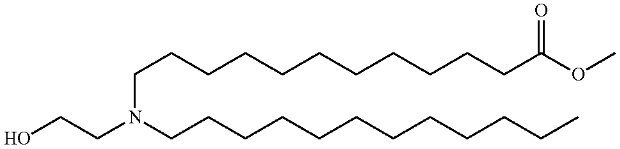
,
(Compound 138)
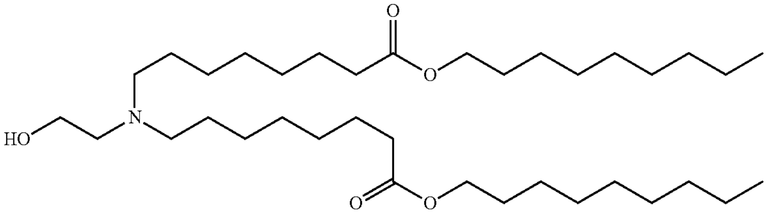
,
(Compound 139)
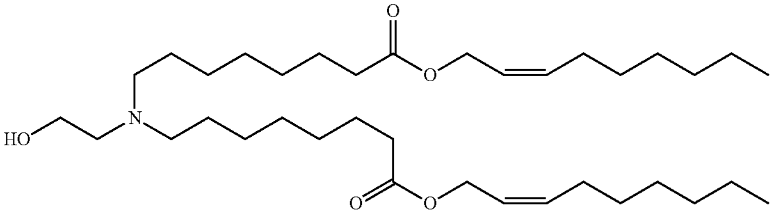
,
(Compound 140)
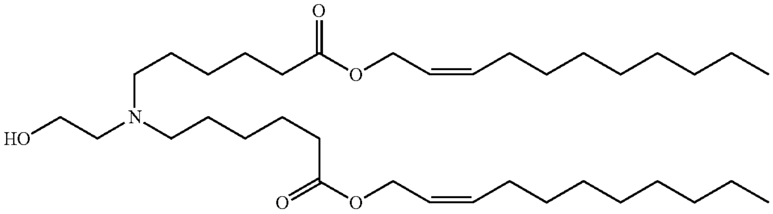
, -continued
(Compound 141)
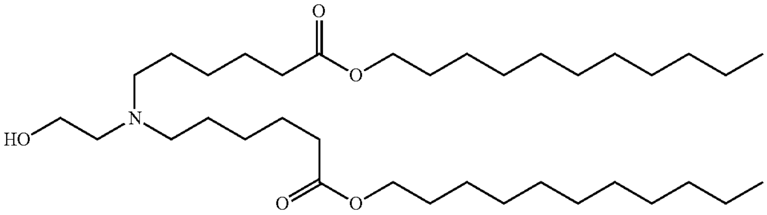
,
(Compound 142)
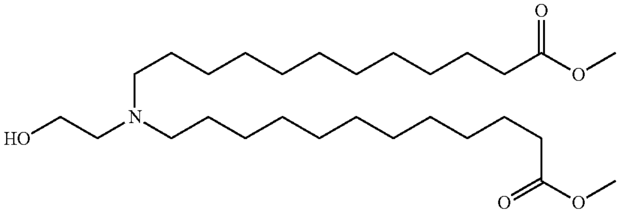
,
(Compound 143)
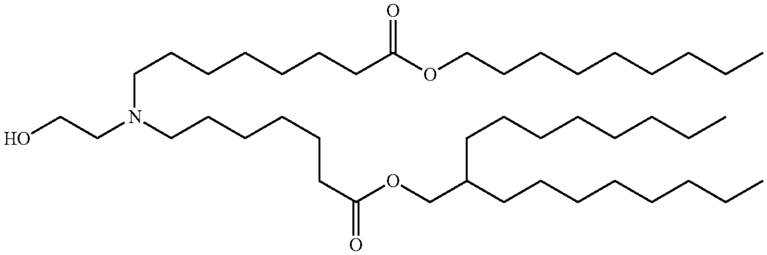
,
(Compound 144)
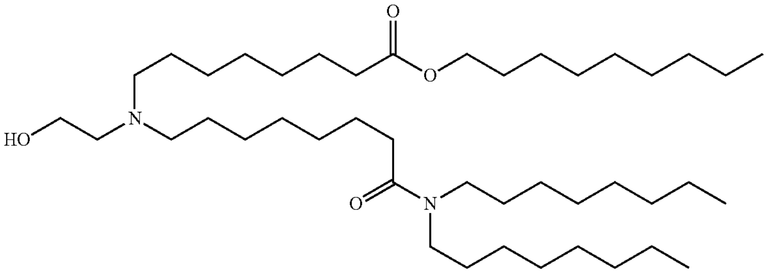
,
(Compound 145)
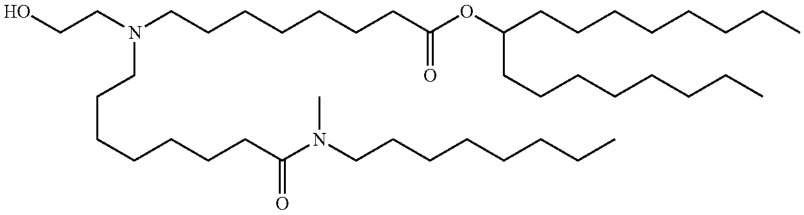
,
(Compound 146)
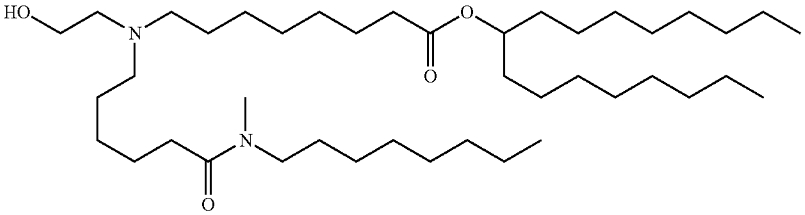
, -continued
(Compound 147)
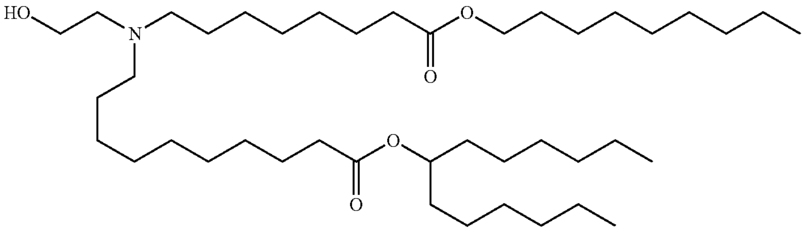
,
(Compound 148)
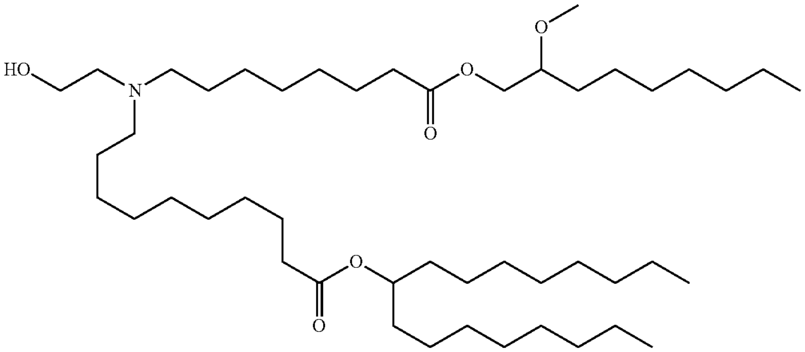
,
(Compound 149)
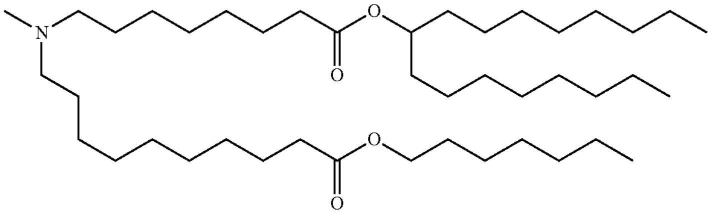
,
(Compound 150)
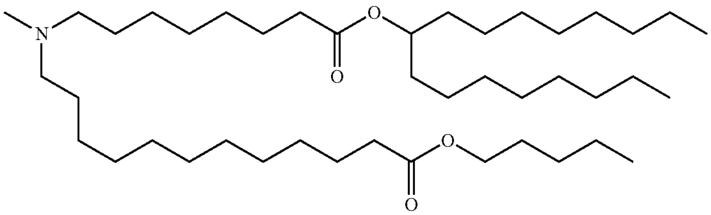
,
(Compound 151)
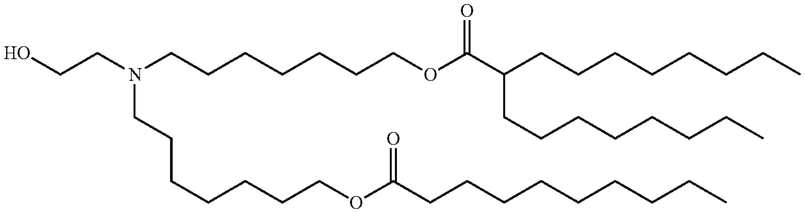
,
(Compound 152)
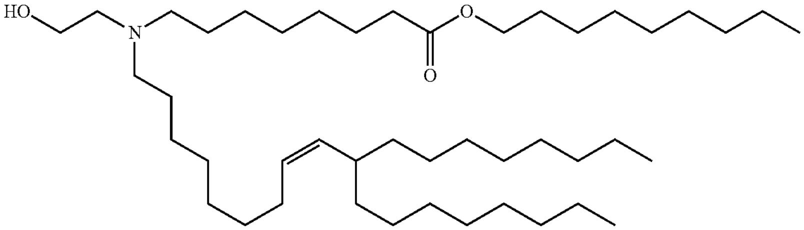
, -continued
(Compound 153)
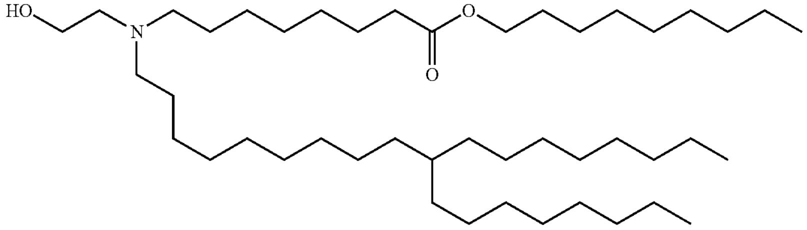
,
(Compound 154)
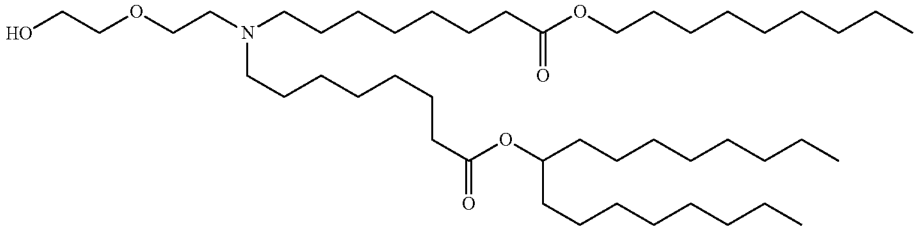
,
(Compound 155)
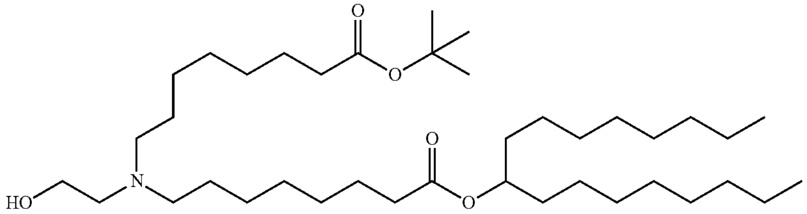
,
(Compound 156)
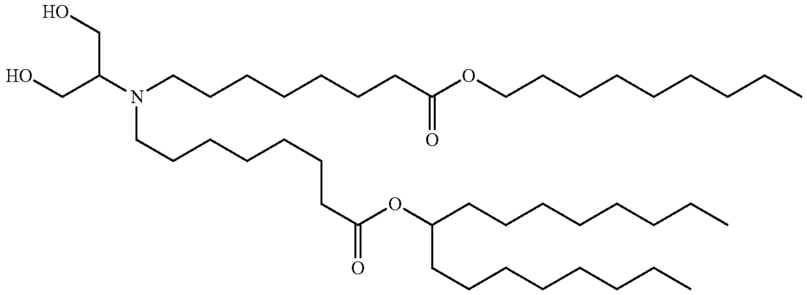
,
(Compound 157)
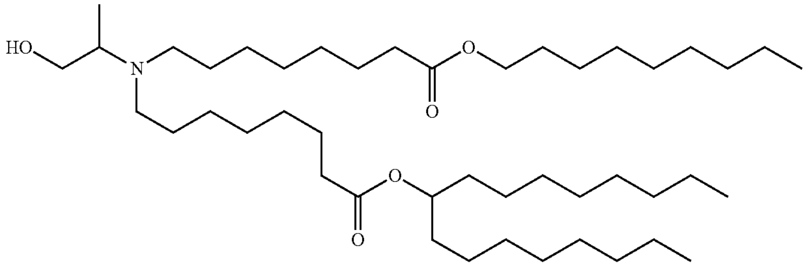
,
(Compound 158)
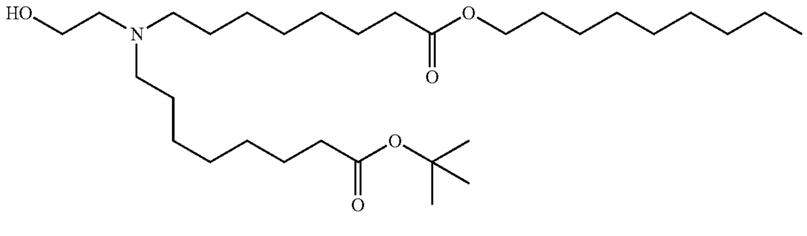
, -continued
(Compound 159)
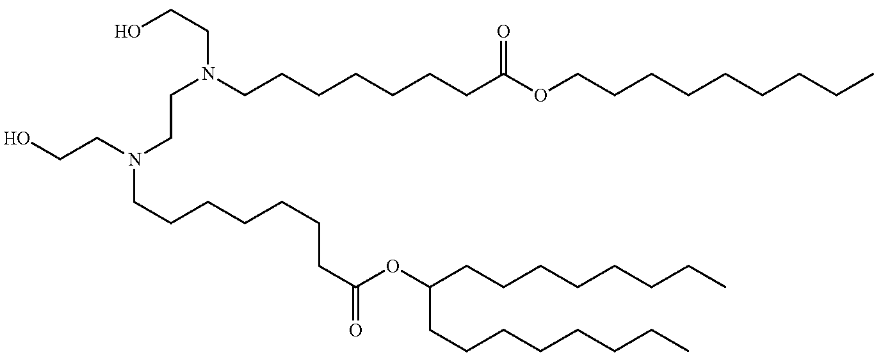
,
(Compound 160)
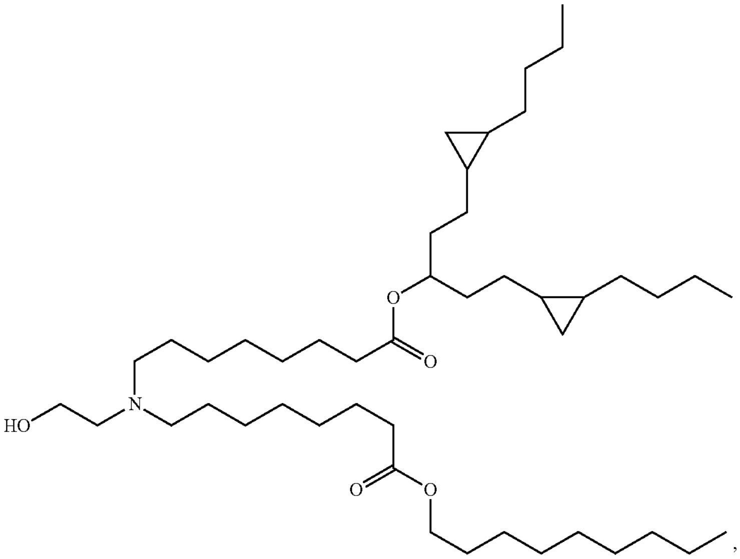
,
(Compound 161)
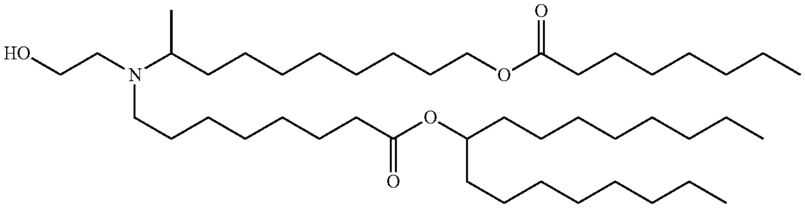
,
(Compound 162)
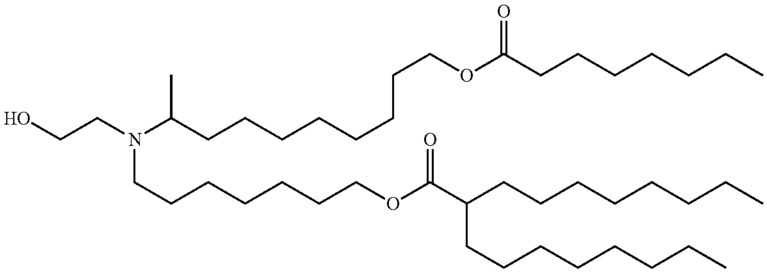
, -continued
(Compound 163)
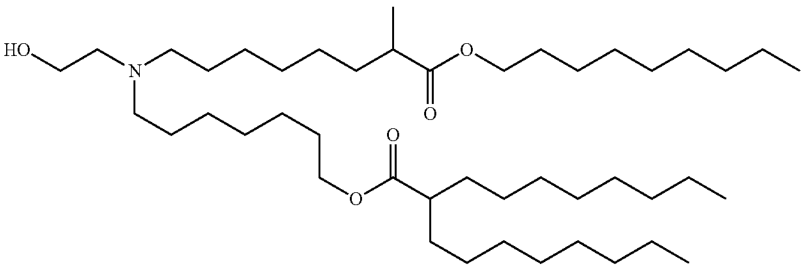
,
(Compound 164)
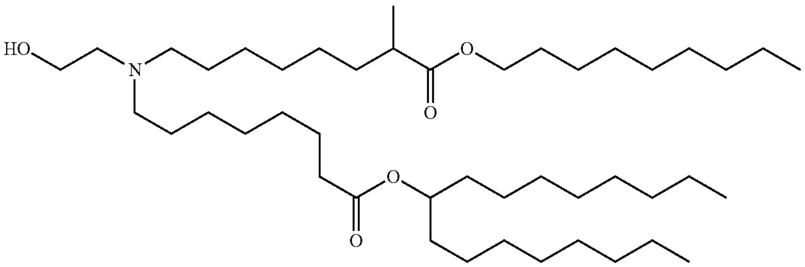
,
(Compound 165)
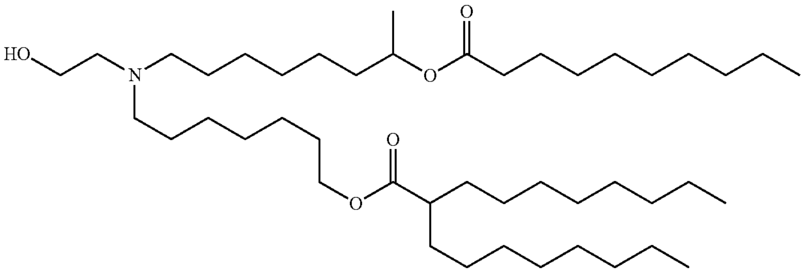
,
(Compound 166)
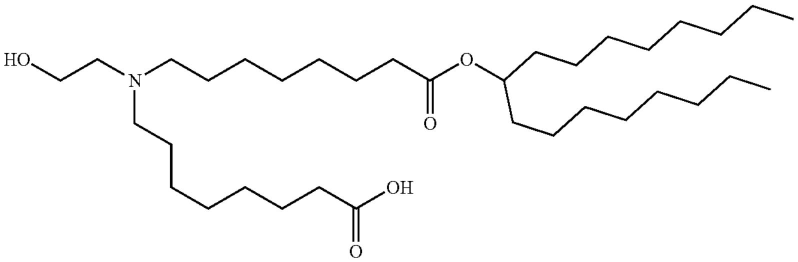
,
(Compound 167)
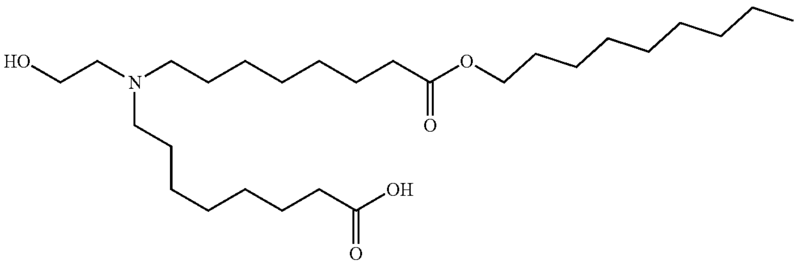
, -continued
(Compound 168)
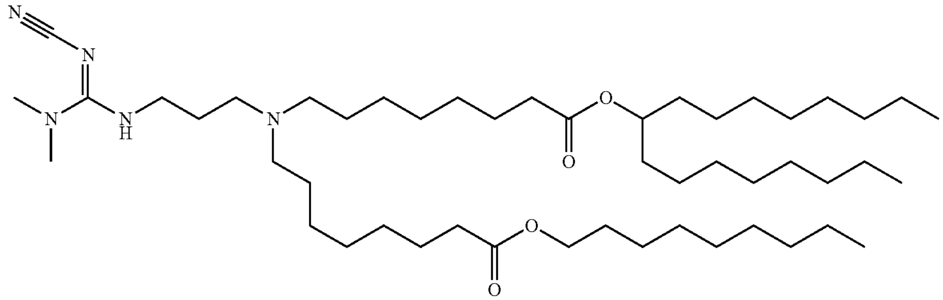
,
(Compound 169)
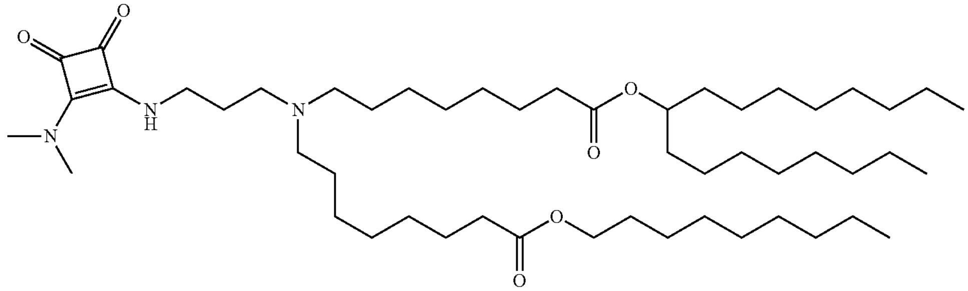
,
(Compound 170)
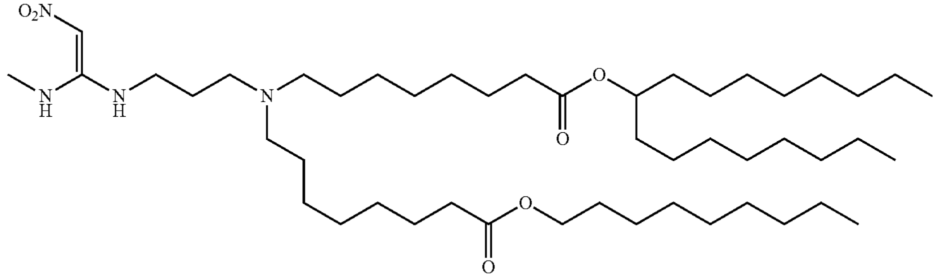
,
(Compound 171)
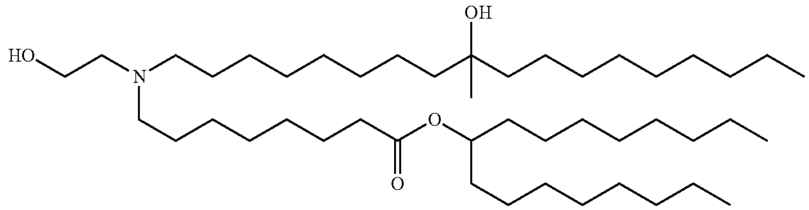
,
(Compound 172)
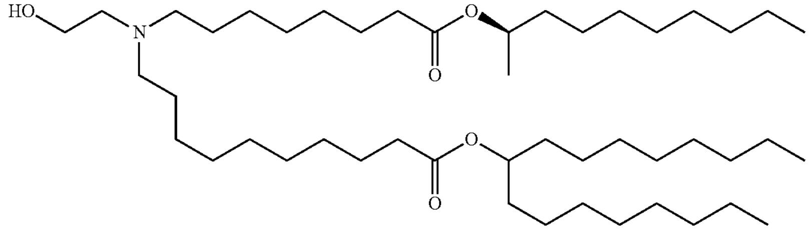
,
(Compound 173)
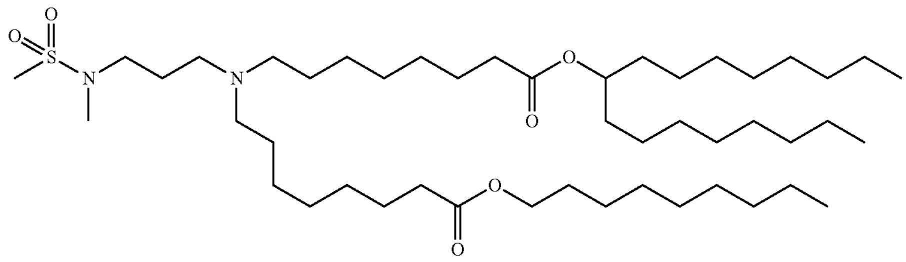
, -continued
(Compound 174)
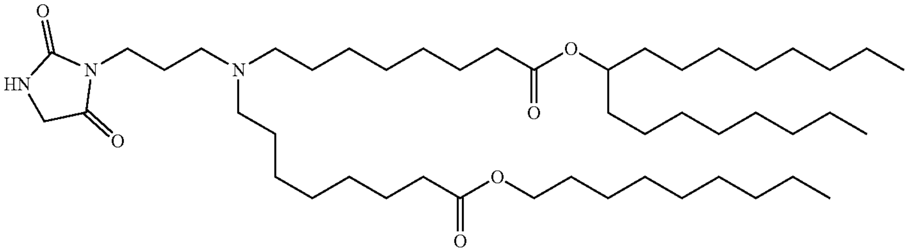
,
(Compound 175)
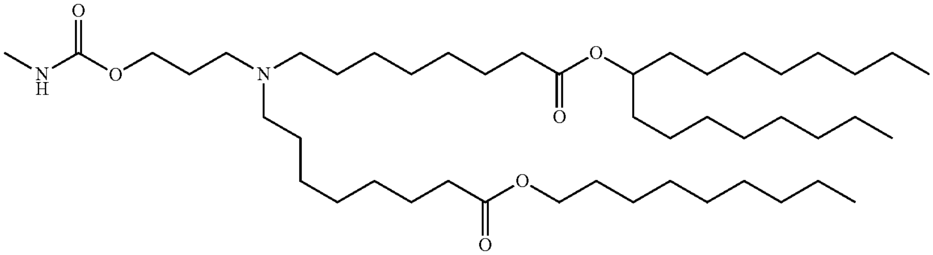
,
(Compound 176)
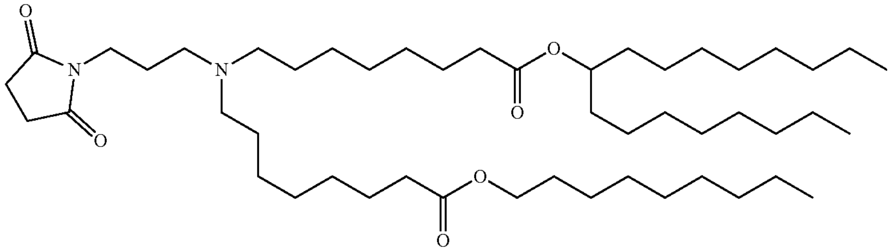
,
(Compound 177)
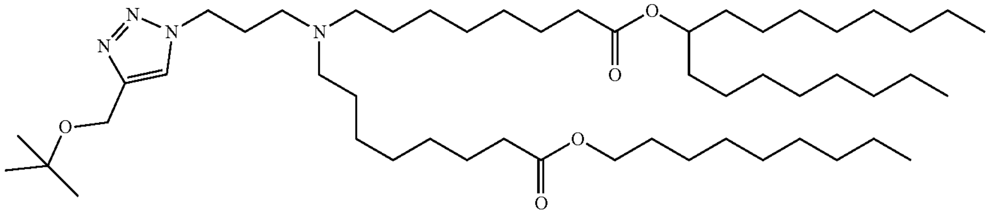
,
(Compound 178)
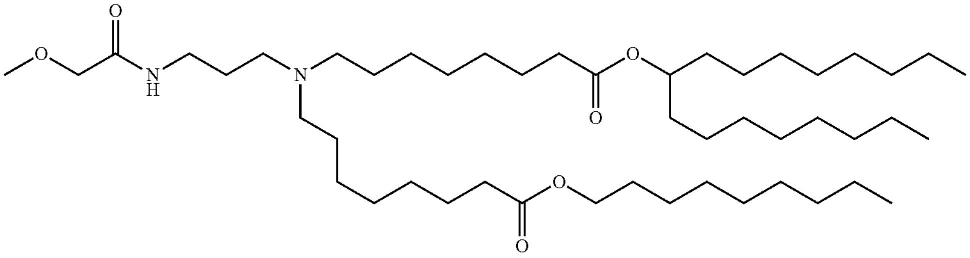
,
(Compound 179)
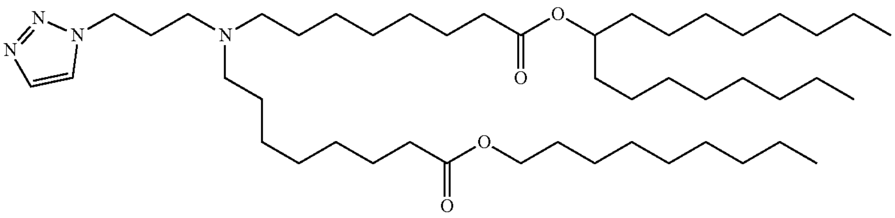
, -continued
(Compound 180)
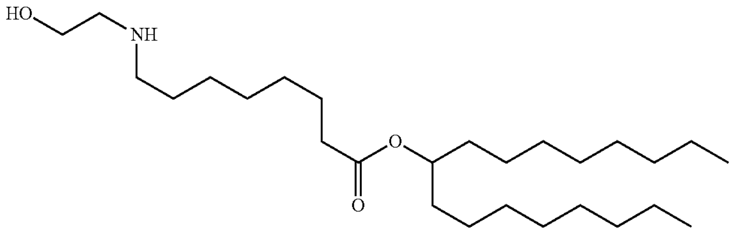
,
(Compound 181)
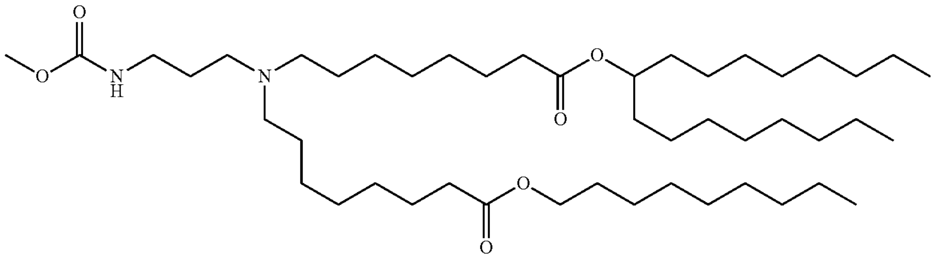
,
(Compound 182)
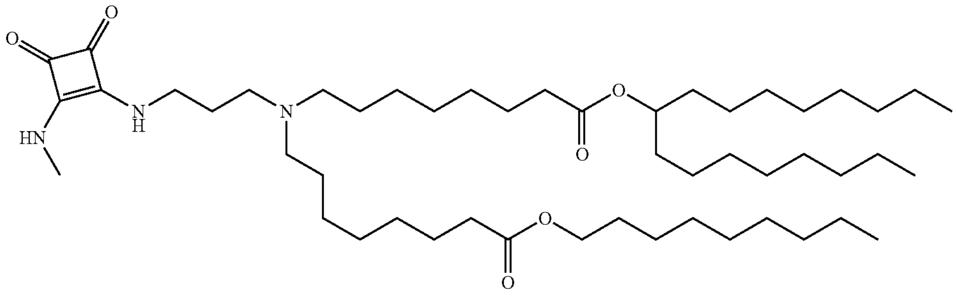
,
(Compound 183)
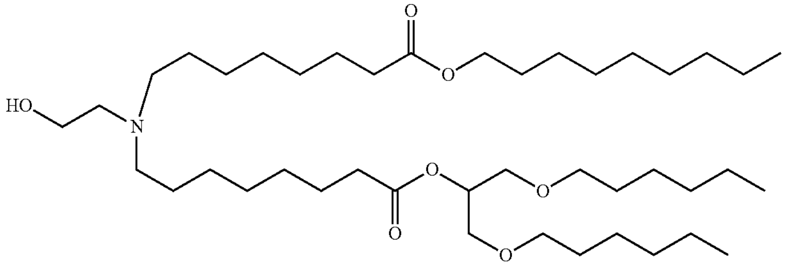
,
(Compound 184)
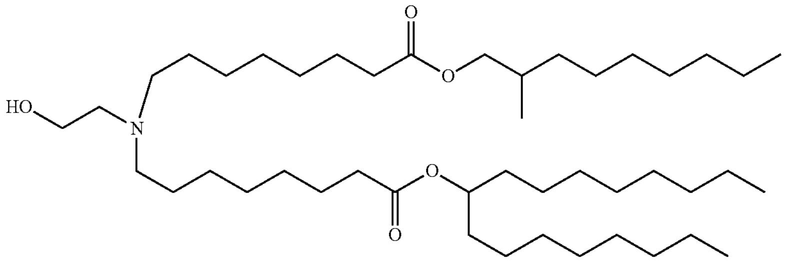
,
(Compound 185)
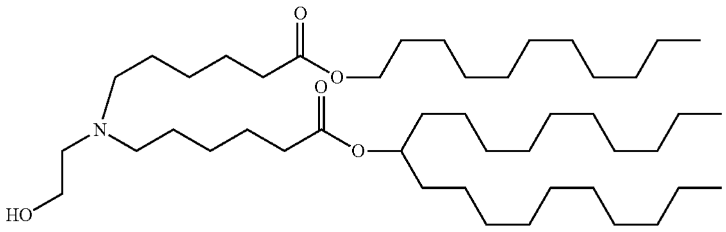
, -continued
(Compound 186)
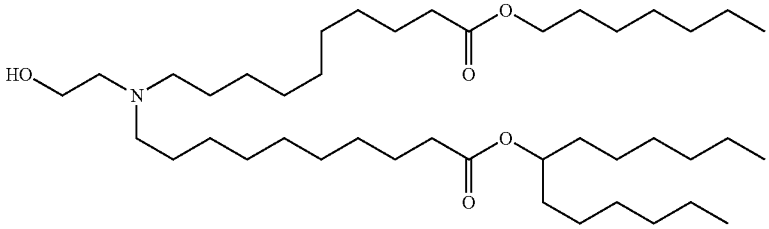
,
(Compound 187)
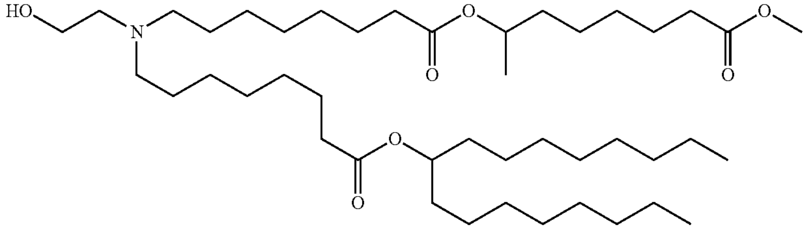
,
(Compound 188)
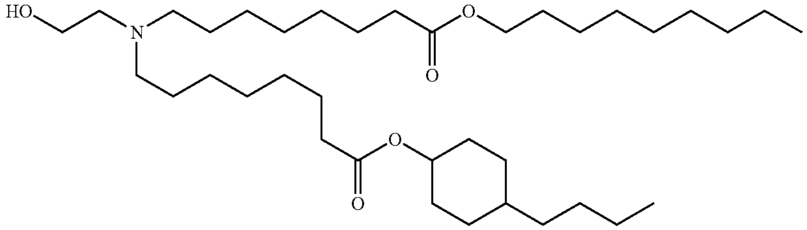
,
(Compund 189)
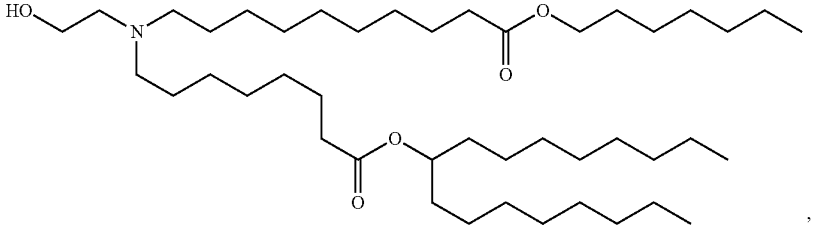
,
(Compound 190)
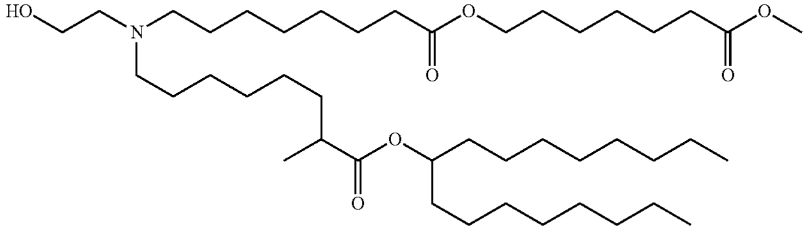
,
(Compound 191)
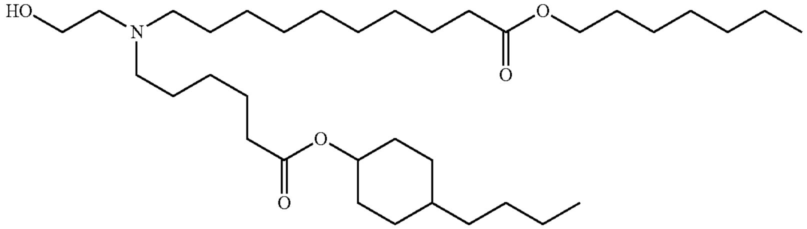
, -continued
(Compound 192)
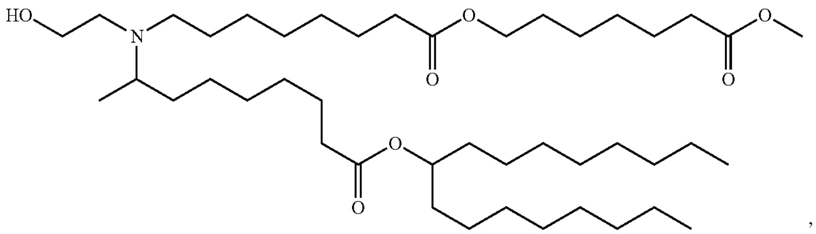
,
(Compound 193)
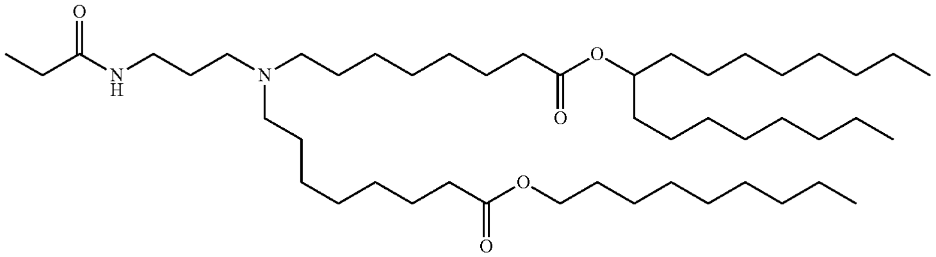
,
(Compound 194)
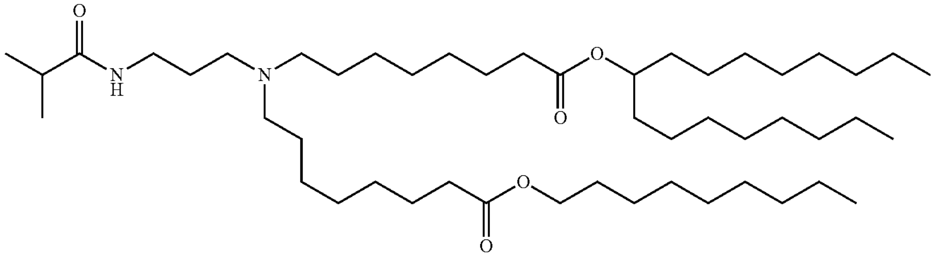
,
(Compound 195)
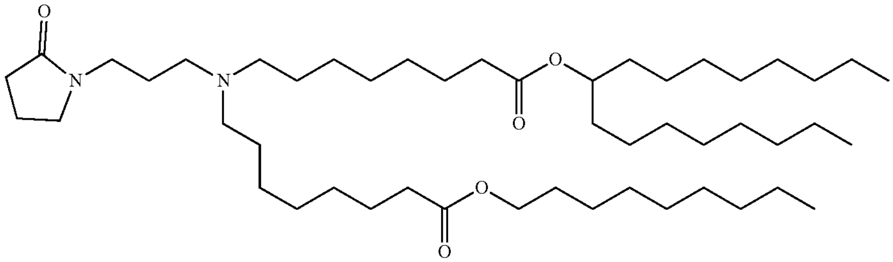
,
(Compound 196)
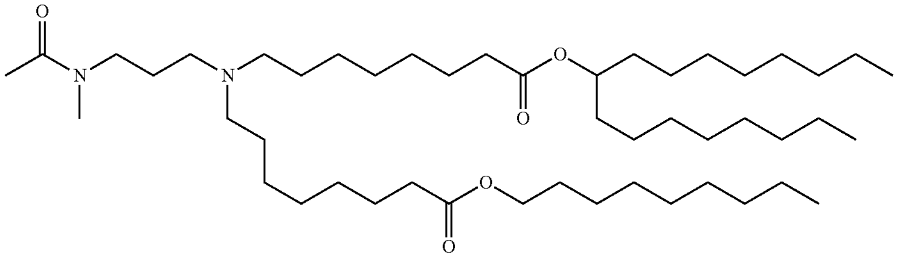
,
(Compound 197)
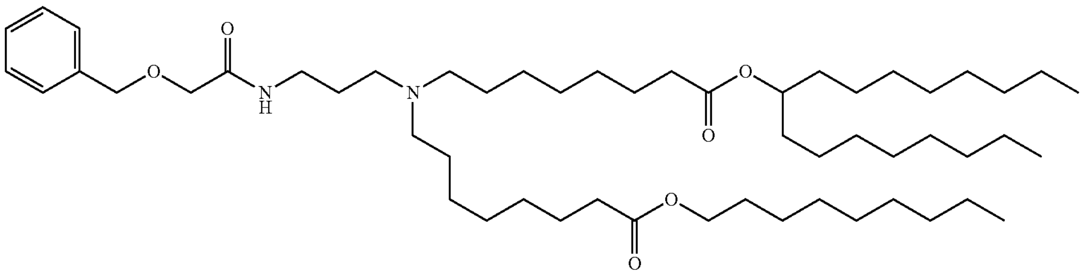
, -continued
(Compound 198)
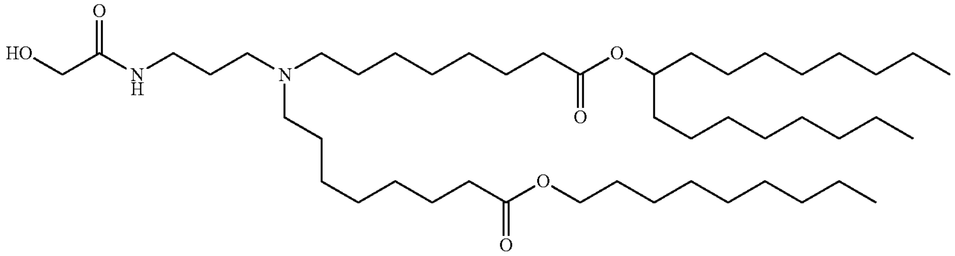
,
(Compound 199)
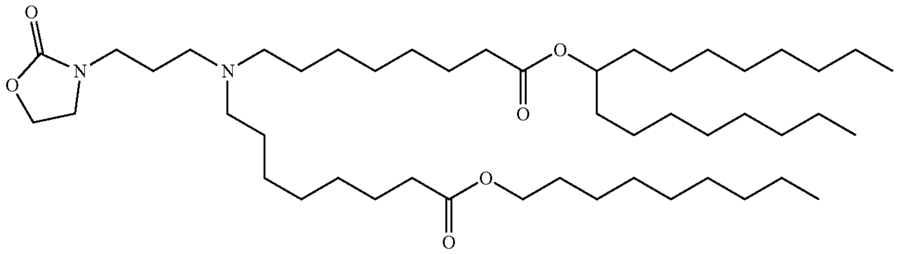
,
(Compound 200)
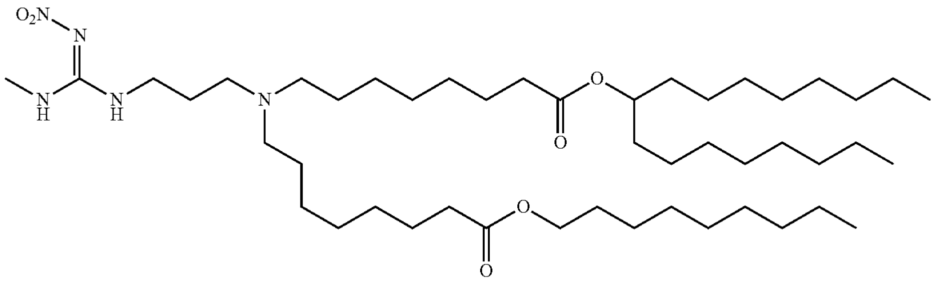
,
(Compound 201)
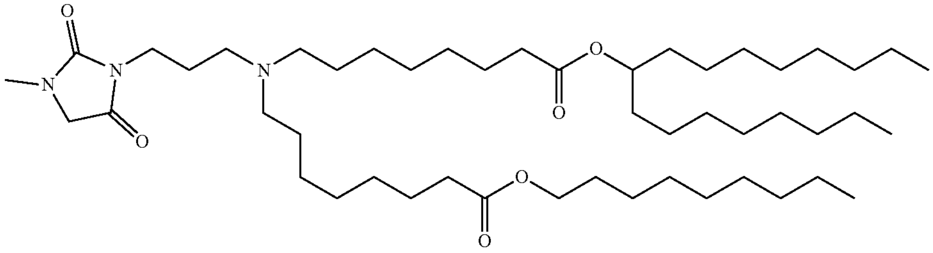
,
(Compound 202)
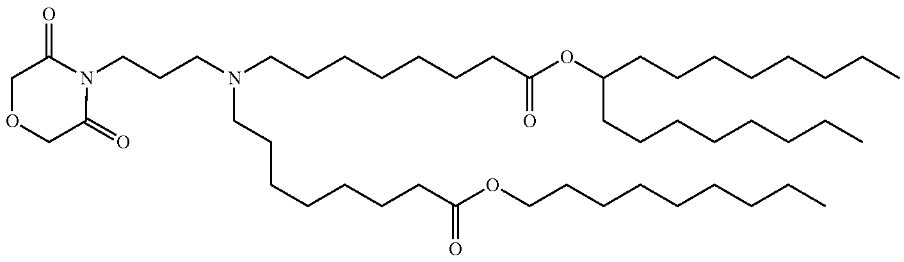
, -continued
(Compound 203)
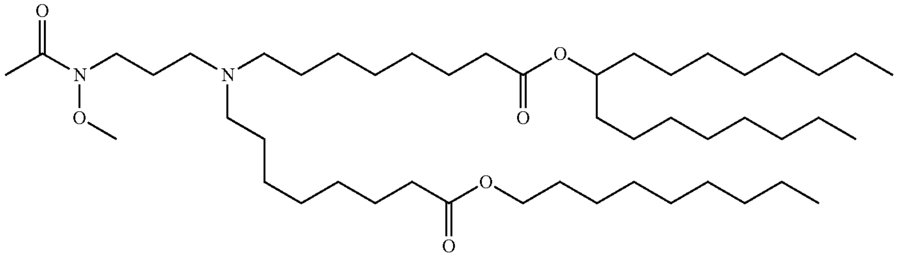
,
(Compound 204)
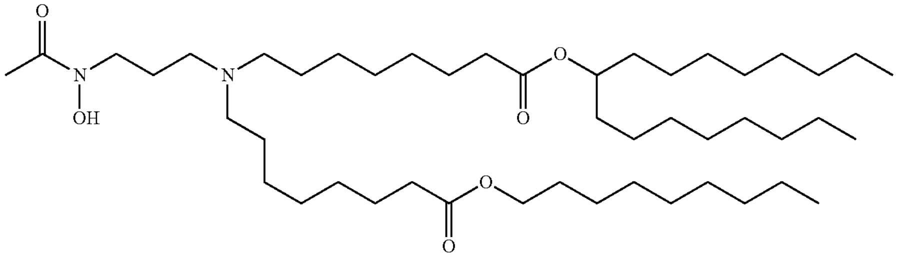
,
(Compound 205)
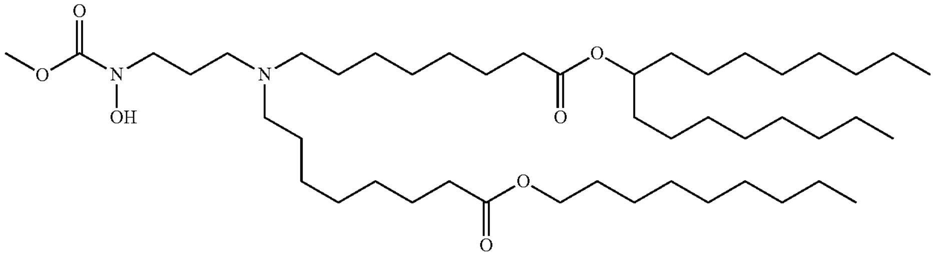
,
(Compound 206)
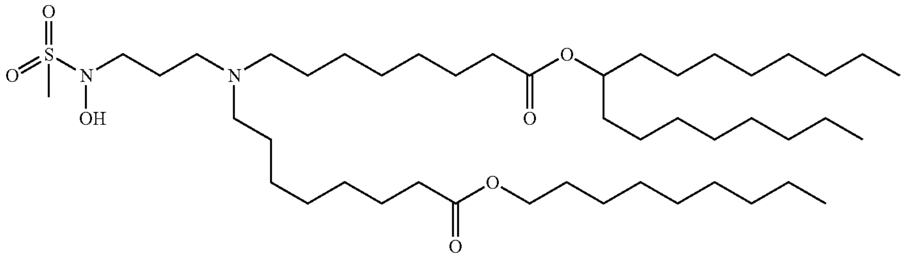
,
(Compound 207)
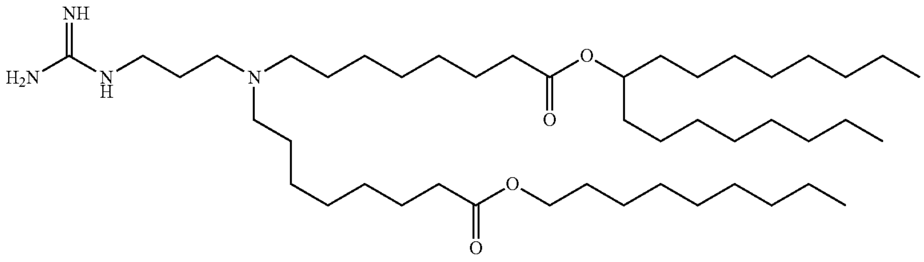
, -continued
(Compound 208)
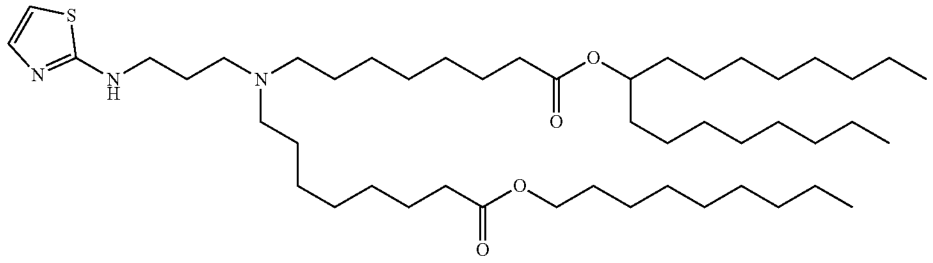
,
(Compound 209)
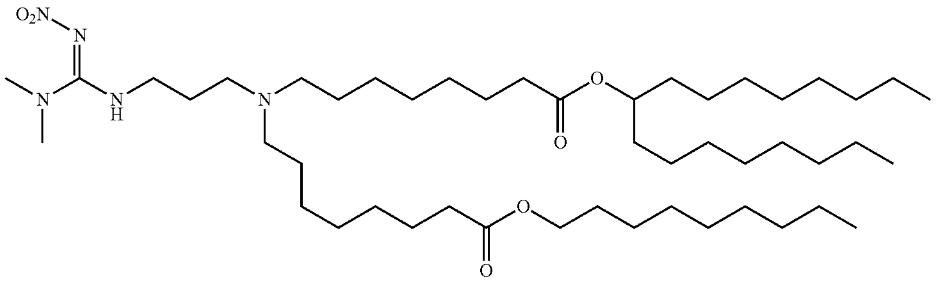
,
(Compound 210)
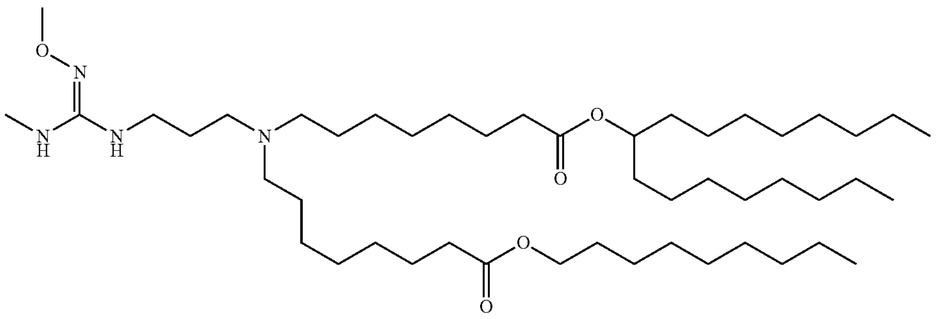
,
(Compound 211)
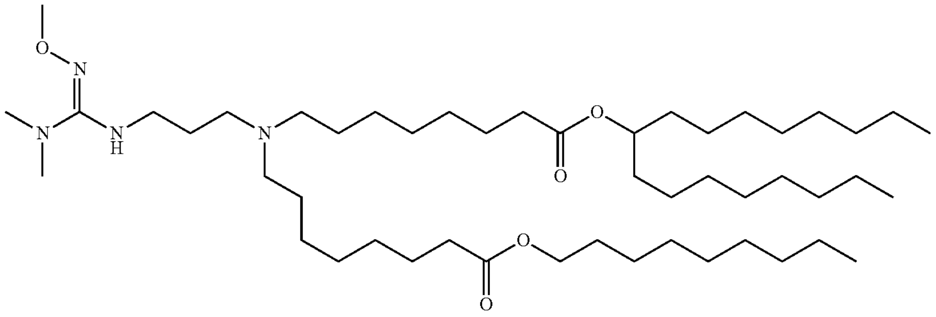
,
(Compound 212)
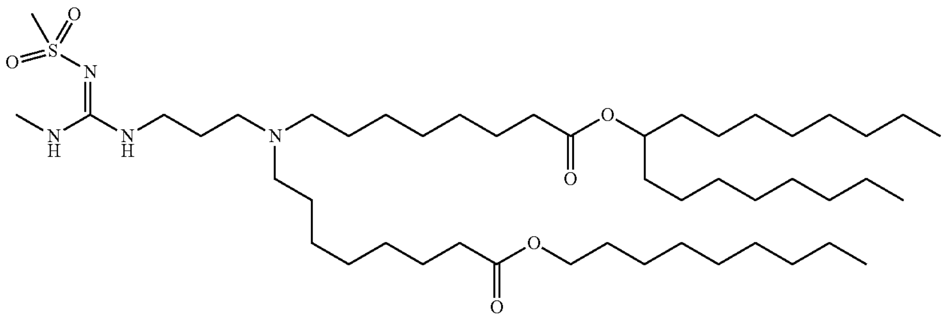
, -continued
(Compound 213)
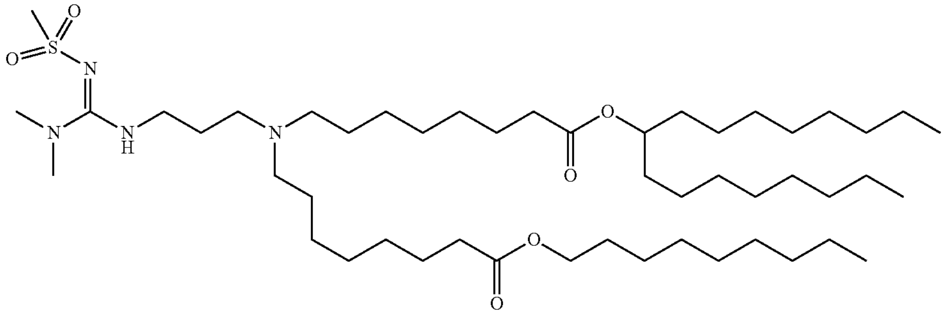
,
(Compound 214)
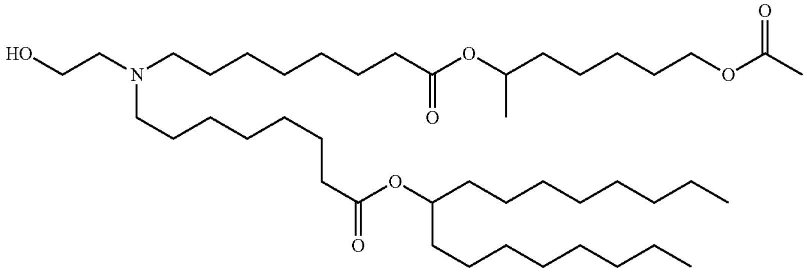
,
(Compound 215)
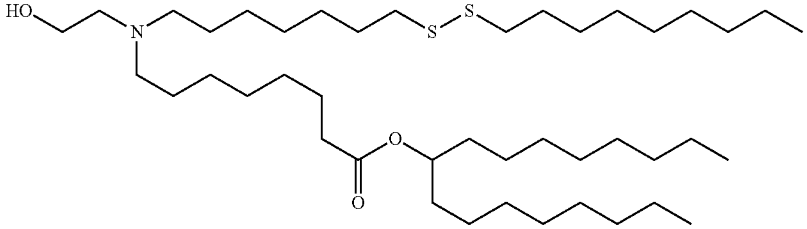
,
(Compound 216)
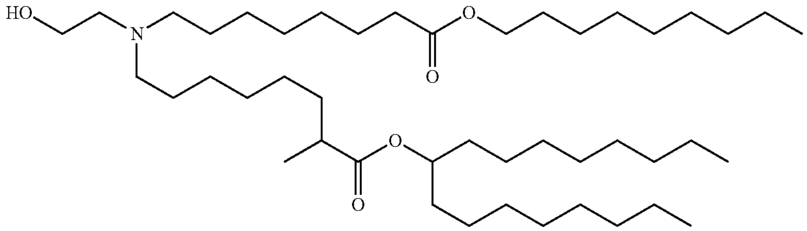
,
(Compound 217)
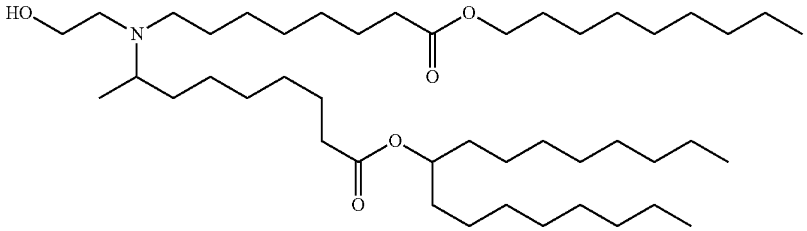
,
(Compound 218)
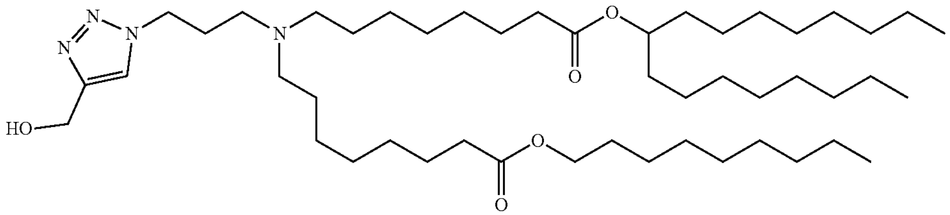
, -continued
(Compound 219)
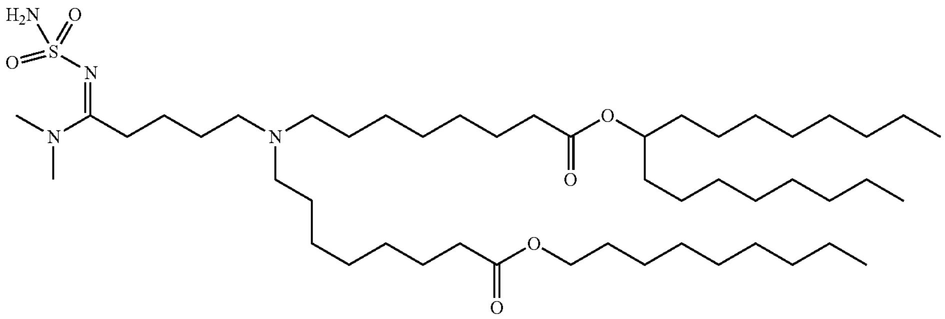
,
(Compound 220)
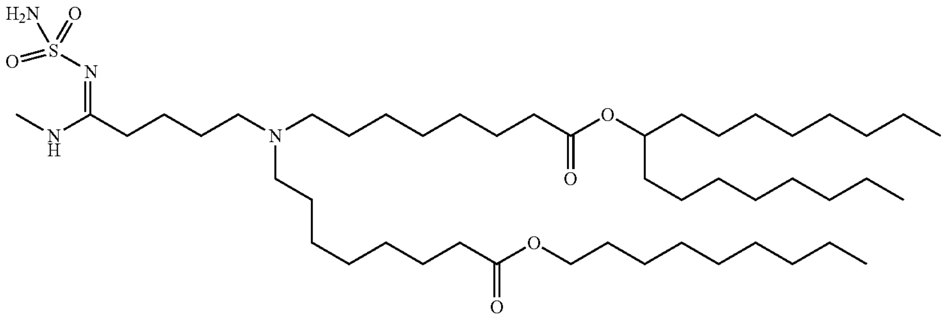
,
(Compound 221)
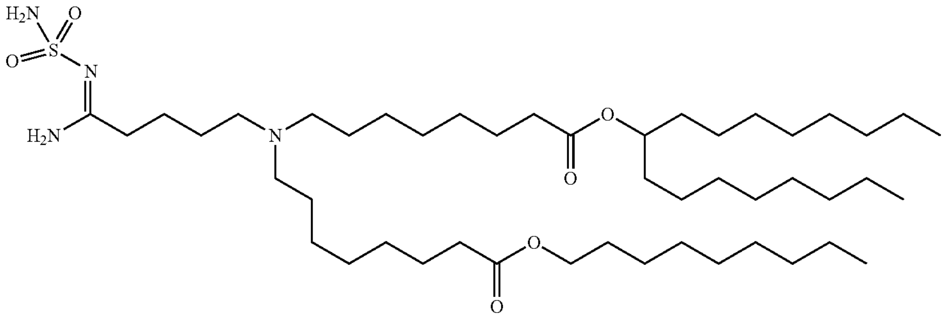
,
(Compound 222)
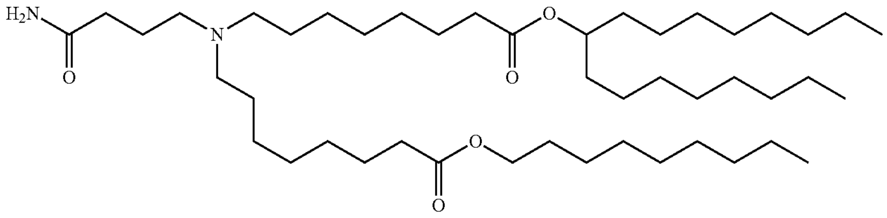
,
(Compound 223)
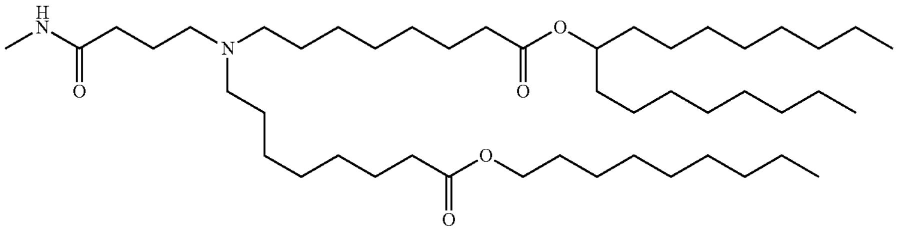
, -continued
(Compound 224)
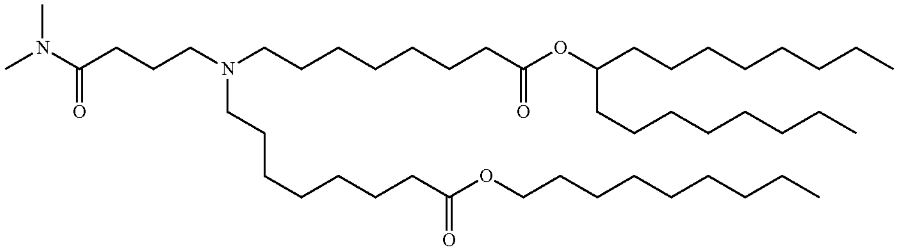
,
(Compound 225)
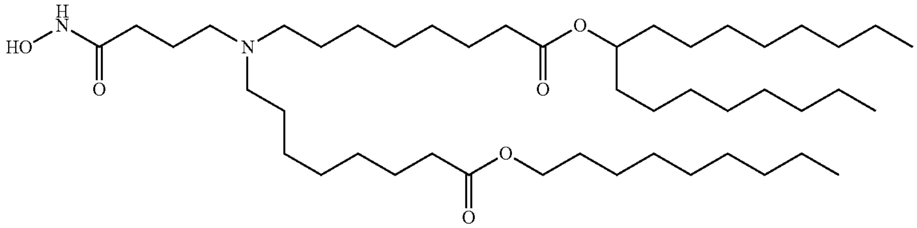
,
(Compound 226)
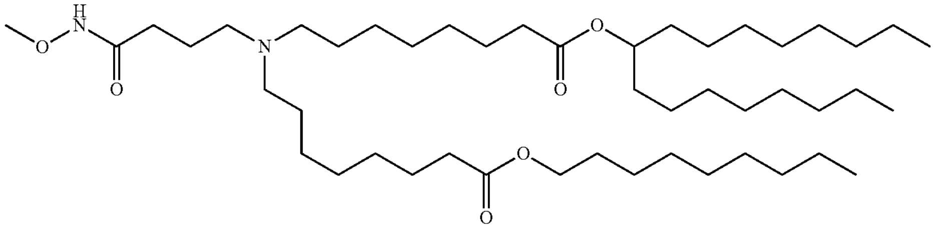
,
(Compound 227)
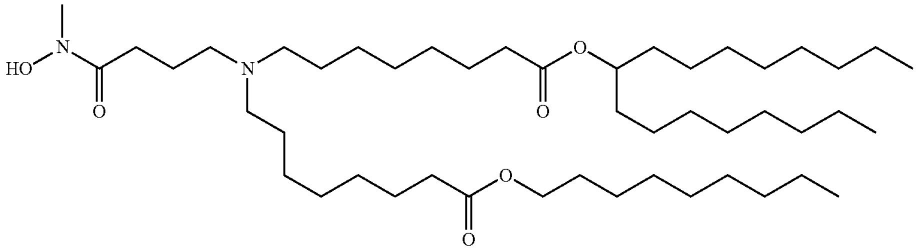
,
(Compound 228)
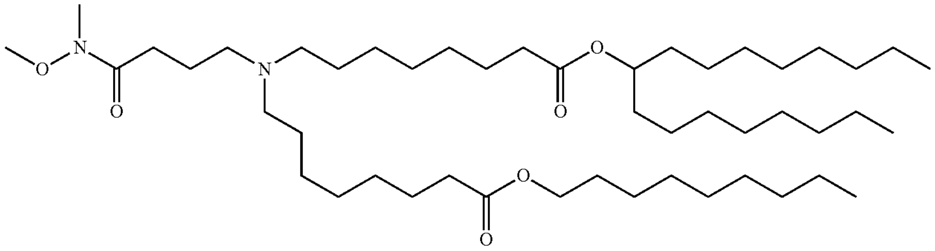
,
(Compound 229)
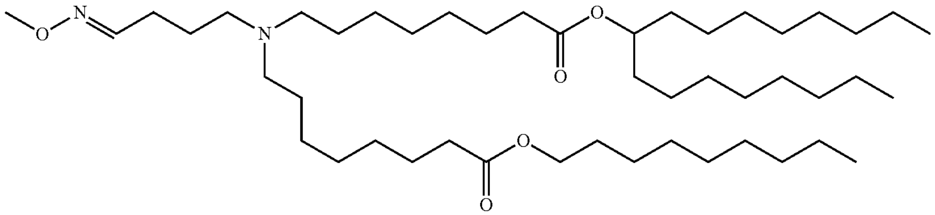
, -continued (Compound 230)

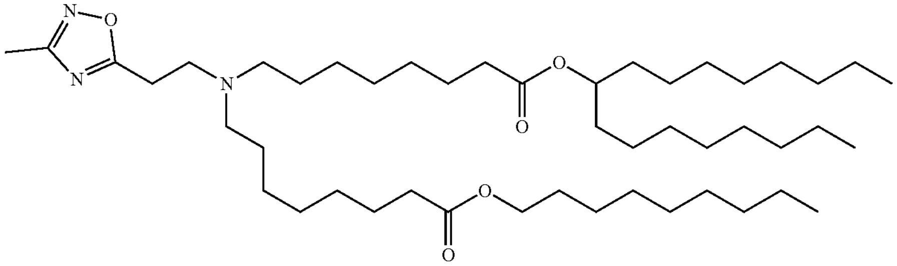

, (Compound 231)

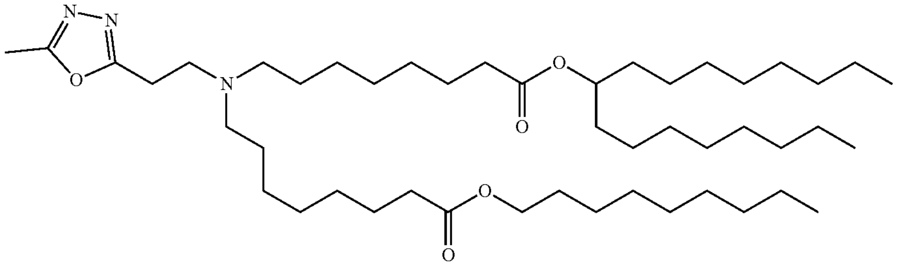

, (Compound 232)

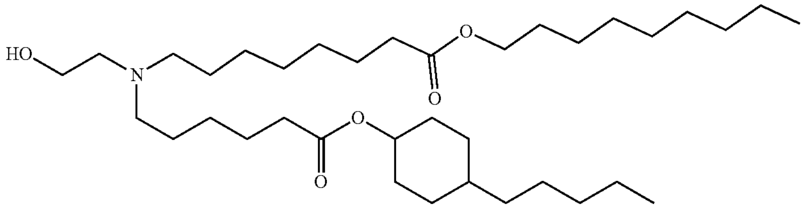

, and salts and isomers thereof.

In some embodiments, a nanoparticle comprises the following compound:

(Compound 233)

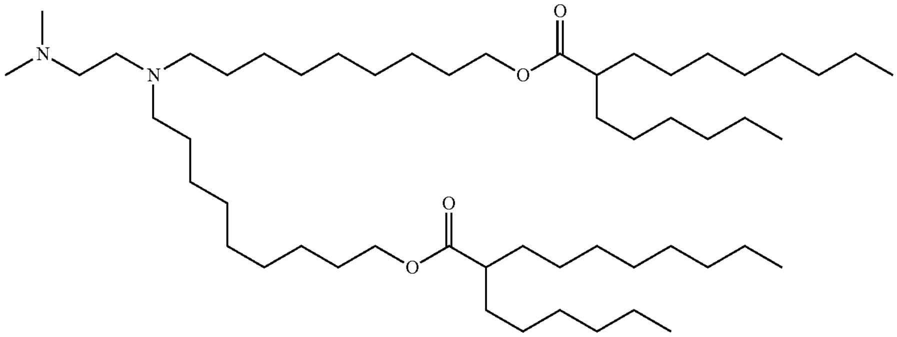

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

Modes of Vaccine Administration

RSV RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. RSV RNA (e.g., mRNA) vaccines compositions are typically formulated in dosage unit form for ease of administration and uniformity of dosage. It will be understood, however, that the total daily usage of RSV RNA (e.g., mRNA)vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, RSV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, RSV RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RSV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, RSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a RSV RNA (e.g., mRNA) vaccine composition may be administered three or four times.

In some embodiments, RSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RSV RNA (e.g., mRNA) vaccine for use in a method of vaccinating a subject is administered the subject a single dosage of between 10 μg/kg and 400 μg/kg of the nucleic acid vaccine in an effective amount to vaccinate the subject. In some embodiments the RNA vaccine for use in a method of vaccinating a subject is administered the subject a single dosage of between 10 μg and 400 μg of the nucleic acid vaccine in an effective amount to vaccinate the subject. In some embodiments, a RSV RNA (e.g., mRNA) vaccine for use in a method of vaccinating a subject is administered to the subject as a single dosage of 25-1000 μg (e.g., a single dosage of mRNA encoding an RSV antigen). In some embodiments, a RSV RNA vaccine is administered to the subject as a single dosage of 25, 50, 100, 150, 200, 250, 300, 350, 400, 450, 500, 550, 600, 650, 700, 750, 800, 850, 900, 950 or 1000 μg. For example, a RSV RNA vaccine may be administered to a subject as a single dose of 25-100, 25-500, 50-100, 50-500, 50-1000, 100-500, 100-1000, 250-500, 250-1000, or 500-1000 μg. In some embodiments, a RSV RNA (e.g., mRNA) vaccine for use in a method of vaccinating a subject is administered to the subject as two dosages, the combination of which equals 25-1000 μg of the RSV RNA (e.g., mRNA) vaccine.

A RSV RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

RSV RNA Vaccine Formulations and Methods of Use

Some aspects of the present disclosure provide formulations of the RSV RNA (e.g., mRNA) vaccine, wherein the RSV RNA vaccine is formulated in an effective amount to produce an antigen specific immune response in a subject (e.g., production of antibodies specific to an anti-RSV antigenic polypeptide). "An effective amount" is a dose of an RSV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-RSV antigenic polypeptide antibody titer produced in a subject administered a RSV RNA (e.g., mRNA) vaccine as provided herein. An antibody titer is a measurement of the amount of antibodies within a subject, for example, antibodies that are specific to a particular antigen (e.g., an anti-RSV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the RSV RNA (e.g., mRNA) vaccine.

In some embodiments, an anti-RSV antigenic polypeptide antibody titer produced in a subject is increased by at least 1 log relative to a control (e.g., a control vaccine). For example, anti-RSV antigenic polypeptide antibody titer produced in a subject may be increased by at least 1.5, at least 2, at least 2.5, or at least 3 log relative to a control (e.g., a control vaccine). In some embodiments, the anti-RSV antigenic polypeptide antibody titer produced in the subject is increased by 1, 1.5, 2, 2.5 or 3 log relative to a control (e.g., a control vaccine). In some embodiments, the anti-RSV antigenic polypeptide antibody titer produced in the subject is increased by 1-3 log relative to a control (e.g., a control vaccine). For example, the anti-RSV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control (e.g., a control vaccine).

In some embodiments, the anti-RSV antigenic polypeptide antibody titer produced in a subject is increased at least 2 times relative to a control (e.g., a control vaccine). For example, the anti-RSV antigenic polypeptide antibody titer produced in a subject may be increased at least 3 times, at least 4 times, at least 5 times, at least 6 times, at least 7 times, at least 8 times, at least 9 times, or at least 10 times relative to a control (e.g., a control vaccine). In some embodiments, the anti-RSV antigenic polypeptide antibody titer produced in the subject is increased 2, 3, 4, 5, 6, 7, 8, 9, or 10 times relative to a control (e.g., a control vaccine). In some embodiments, the anti-RSV antigenic polypeptide antibody titer produced in a subject is increased 2-10 times relative to a control (e.g., a control vaccine). For example, the anti-RSV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control (e.g., a control vaccine).

A control, in some embodiments, is the anti-RSV antigenic polypeptide antibody titer produced in a subject who has not been administered a RSV RNA (e.g., mRNA) vaccine. In some embodiments, a control is an anti-RSV antigenic polypeptide antibody titer produced in a subject who has been administered a live attenuated RSV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-RSV antigenic polypeptide antibody titer produced in a subject administered inactivated RSV vaccine. In some embodiments, a control is an anti-RSV antigenic polypeptide antibody titer produced in a subject administered a recombinant or purified RSV protein vaccine. Recombinant protein vaccines typically include protein antigens that either have been produced in a heterologous expression system (e.g., bacteria or yeast) or purified from large amounts of the pathogenic organism. In some embodiments, a control is an anti-RSV antigenic polypeptide antibody titer produced in a subject who has been administered a RSV virus-like particle (VLP) vaccine (e.g., particles that contain viral capsid protein but lack a viral genome and, therefore, cannot replicate/produce progeny virus). In some embodiments, the control is a VLP RSV vaccine that comprises prefusion or postfusion F proteins, or that comprises a combination of the two.

In some embodiments, an effective amount of a RSV RNA (e.g., mRNA) vaccine is a dose that is reduced compared to the standard of care dose of a recombinant RSV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified RSV protein vaccine, or a live attenuated or inactivated RSV vaccine, or a RSV VLP vaccine, that a physician/clinician or other medical professional would administer to a subject to treat or prevent RSV, or a RSV-related condition, while following the standard of care guideline for treating or preventing RSV, or a RSV-related condition.

In some embodiments, the anti-RSV antigenic polypeptide antibody titer produced in a subject administered an effective amount of a RSV RNA vaccine is equivalent to an anti-RSV antigenic polypeptide antibody titer produced in a control subject administered a standard of care dose of a recombinant or purified RSV protein vaccine, or a live attenuated or inactivated RSV vaccine, or a RSV VLP vaccine.

In some embodiments, an effective amount of a RSV RNA (e.g., mRNA) vaccine is a dose equivalent to an at least 2-fold reduction in a standard of care dose of a recombinant or purified RSV protein vaccine. For example, an effective amount of a RSV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified RSV protein vaccine. In some embodiments, an effective amount of a RSV RNA vaccine is a dose equivalent to an at least at least 100-fold, at least 500-fold, or at least 1000-fold reduction in a standard of care dose of a recombinant or purified RSV protein vaccine. In some embodiments, an effective amount of a RSV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified RSV protein vaccine. In some embodiments, the anti-RSV antigenic polypeptide antibody titer produced in a subject administered an effective amount of a RSV RNA vaccine is equivalent to an anti-RSV antigenic polypeptide antibody titer produced in a control subject administered the standard of care dose of a recombinant or purified RSV protein vaccine, or a live attenuated or inactivated RSV vaccine, or a RSV VLP vaccine. In some embodiments, an effective amount of a RSV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified RSV protein vaccine, wherein the anti-RSV antigenic polypeptide antibody titer produced in the subject is equivalent to an anti-RSV antigenic polypeptide antibody titer produced in a control subject administered the standard of care dose of a recombinant or purified RSV protein vaccine, or a live attenuated or inactivated RSV vaccine, or a RSV VLP vaccine.

In some embodiments, the effective amount of a RSV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 300-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant RSV protein vaccine. In some embodiments, such as the foregoing, the anti-RSV antigenic polypeptide antibody titer produced in the subject is equivalent to an anti-RSV antigenic polypeptide antibody titer produced in a control subject administered the standard of care dose of a recombinant or purified RSV protein vaccine, or a live attenuated or inactivated RSV vaccine, or a RSV VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant RSV protein vaccine. In some embodiments, such as the foregoing, an anti-RSV antigenic polypeptide antibody titer produced in the subject is equivalent to an anti-RSV antigenic polypeptide antibody titer produced in a control subject administered the standard of care dose of a recombinant or purified RSV protein vaccine, or a live attenuated or inactivated RSV vaccine, or a RSV VLP vaccine.

In some embodiments, the effective amount of a RSV RNA (e.g., mRNA) vaccine is a total dose of 50-1000 μg. In some embodiments, the effective amount of a RSV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a RSV RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 μg administered to the subject a total of two times. In some embodiments, the effective amount of a RSV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a RSV RNA (e.g., mRNA) vaccine is a total dose of 25, 50, 100, 150, 200, 250, 300, 350, 400, 450, or 500 μg administered to the subject a total of two times.

Additional Embodiments

1. A respiratory syncytial virus (RSV) vaccine, comprising: at least one messenger ribonucleic acid (mRNA) polynucleotide having a 5' terminal cap, an open reading frame encoding at least one RSV antigenic polypeptide, and a 3' polyA tail.

2. The vaccine of paragraph 1, wherein the at least one mRNA polynucleotide is encoded by a sequence identified by SEQ ID NO: 257.

3. The vaccine of paragraph 1, wherein the at least one mRNA polynucleotide is encoded by a sequence identified by SEQ ID NO: 258.

4. The vaccine of paragraph 1, wherein the at least one mRNA polynucleotide is encoded by a sequence identified by SEQ ID NO: 259.

5. The vaccine of paragraph 1, wherein the at least one mRNA polynucleotide comprises a sequence identified by SEQ ID NO: 278.

6. The vaccine of paragraph 1, wherein the at least one mRNA polynucleotide comprises a sequence identified by SEQ ID NO: 279.

7. The vaccine of paragraph 1, wherein the at least one mRNA polynucleotide comprises a sequence identified by SEQ ID NO: 280.

8. The vaccine of any one of paragraphs 1-7, wherein the 5' terminal cap is or comprises 7 mG(5')ppp(5')NlmpNp.

9. The vaccine of any one of paragraphs 1-8, wherein 100% of the uracil in the open reading frame is modified to include N1-methyl pseudouridine at the 5-position of the uracil.

10. The vaccine of any one of paragraphs 1-9, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG) 2000-DMG.

11. The vaccine of paragraph 10, wherein the lipid nanoparticle further comprises trisodium citrate buffer, sucrose and water.

12. A respiratory syncytial virus (RSV) vaccine, comprising: at least one messenger ribonucleic acid (mRNA) polynucleotide having a 5' terminal cap 7 mG(5')ppp(5') NlmpNp, a sequence identified by SEQ ID NO: 278 and a 3' polyA tail, wherein the uracil nucleotides of the sequence identified by SEQ ID NO: 278 are modified to include N1-methyl pseudouridine at the 5-position of the uracil nucleotide, optionally wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

13. A respiratory syncytial virus (RSV) vaccine, comprising: at least one messenger ribonucleic acid (mRNA) polynucleotide having a 5' terminal cap 7 mG(5')ppp(5') NlmpNp, a sequence identified by SEQ ID NO: 279 and a 3' polyA tail, wherein the uracil nucleotides of the sequence identified by SEQ ID NO: 279 are modified to include N1-methyl pseudouridine at the 5-position of the uracil nucleotide, optionally wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

14. A respiratory syncytial virus (RSV) vaccine, comprising:

at least one messenger ribonucleic acid (mRNA) polynucleotide having a 5' terminal cap 7 mG(5')ppp(5') NlmpNp, a sequence identified by SEQ ID NO: 280 and a 3' polyA tail, wherein the uracil nucleotides of the sequence identified by SEQ ID NO: 280 are modified to include N1-methyl pseudouridine at the 5-position of the uracil nucleotide, optionally wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

15. A respiratory syncytial virus (RSV) vaccine, comprising:

at least one messenger ribonucleic acid (mRNA) polynucleotide having a 5' terminal cap, an open reading frame encoding at least one RSV antigenic polypeptide, and a 3' polyA tail.

16. The vaccine of paragraph 15, wherein the at least one mRNA polynucleotide is encoded by a sequence identified by SEQ ID NO: 5.

17. The vaccine of paragraph 15, wherein the at least one mRNA polynucleotide comprises a sequence identified by SEQ ID NO: 262.

18. The vaccine of paragraph 15, wherein the at least one RSV antigenic polypeptide comprises a sequence identified by SEQ ID NO: 6.

19. The vaccine of paragraph 15, wherein the at least one RSV antigenic polypeptide comprises a sequence identified by SEQ ID NO: 290.

20. The vaccine of paragraph 15, wherein the mRNA polynucleotide is encoded by a sequence identified by SEQ ID NO: 7.

21. The vaccine of paragraph 15, wherein the mRNA polynucleotide comprises a sequence identified by SEQ ID NO: 263.

22. The vaccine of paragraph 15, wherein the at least one RSV antigenic polypeptide comprises a sequence identified by SEQ ID NO: 8.

23. The vaccine of paragraph 15, wherein the at least one RSV antigenic polypeptide comprises a sequence identified by SEQ ID NO: 291.

24. The vaccine of any one of paragraphs 15-23, wherein the 5' terminal cap is or comprises 7 mG(5')ppp(5')NlmpNp.

25. The vaccine of any one of paragraphs 15-24, wherein 100% of the uracil in the open reading frame is modified to include N1-methyl pseudouridine at the 5-position of the uracil.

26. The vaccine of any one of paragraphs 15-25, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG) 2000-DMG.

27. The vaccine of paragraph 26, wherein the lipid nanoparticle further comprises trisodium citrate buffer, sucrose and water.

28. A respiratory syncytial virus (RSV) vaccine, comprising:

at least one messenger ribonucleic acid (mRNA) polynucleotide having a 5' terminal cap 7 mG(5')ppp(5') NlmpNp, a sequence identified by SEQ ID NO: 262, and a 3' polyA tail, wherein the uracil nucleotides of the sequence identified by SEQ ID NO: 262 are modified to include N1-methyl pseudouridine at the 5-position of the uracil nucleotide, optionally wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

29. A respiratory syncytial virus (RSV) vaccine, comprising:

at least one messenger ribonucleic acid (mRNA) polynucleotide having a 5' terminal cap 7 mG(5')ppp(5') NlmpNp, a sequence identified by SEQ ID NO: 263, and a 3' polyA tail, wherein the uracil nucleotides of the sequence identified by SEQ ID NO: 263 are modified to include N1-methyl pseudouridine at the 5-position of the uracil nucleotide, optionally wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

30. The vaccine of any one of paragraphs 1-29 formulated in a lipid nanoparticle comprising at least one cationic lipid selected from compounds of Formula (I):

(I)

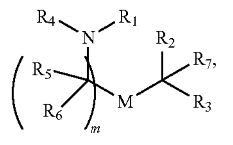

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)—N(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_n—OR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

31. The vaccine of paragraph 29, wherein a subset of compounds of Formula (I) includes those in which when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

32. The vaccine of paragraph 19, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)N(R)_2$, $—C({=}NR_9)R$, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

33. The vaccine of paragraph 29, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C({=}NR_9)N(R)_2$, $—N(R)C({=}CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C({=}NR_9)N(R)_2$, $—N(OR)C({=}CHR_9)N(R)_2$, $—C({=}NR_9)R$, —C(O)N(R)OR, and $—C({=}NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

34. The vaccine of paragraph 29, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

35. The vaccine of paragraph 29, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

36. The vaccine of paragraph 29, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

37. The vaccine of paragraph 29, wherein a subset of compounds of Formula (I) includes those of Formula (IA):

(IA)

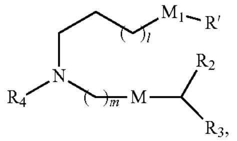

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)S$(O)_2$R, —N(R)$R_8$, —NHC(=$NR_9$)N$(R)_2$, —NHC(=$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3' desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG.2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2×KAPA HIFI™ HotStart ReadyMix by Kapa Biosystems (Woburn, Mass.). This system includes 2× KAPA ReadyMix 12.5 μl; Forward Primer (10 μM) 0.75 μl; Reverse Primer (10 μM) 0.75 μl; Template cDNA 100 ng; and $dH_2O$ diluted to 25.0 μl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, Calif.) per manufacturer's instructions (up to 5 μg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 μg |
| 2) | 10x transcription buffer (400 mM Tris-HCl pH 8.0, 190 mM $MgCl_2$, 50 mM DTT, 10 mM Spermidine) | 2.0 μl |
| 3) | Custom NTPs (25 mM each) | 0.2 μl |
| 4) | RNase Inhibitor | 20 U |
| 5) | T7 RNA polymerase | 3000 U |
| 6) | $dH_2O$ | up to 20.0 μl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, Tex.) following the manufacturer's instructions. This kit can purify up to 500 μg of RNA. Following the cleanup, the RNA polynucleotide may be quantified using the NANODROP™ and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 μg-180 μg and $dH_2O$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μs RNA or up to 2 hours for 180 μg of RNA.

The RNA polynucleotide may then be purified using Ambion's MEGACLEAR™ Kit (Austin, Tex.) following the manufacturer's instructions. Following the cleanup, the RNA may be quantified using the NANODROP™ (ThermoFisher, Waltham, Mass.) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 μg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 8: Agarose Gel Electrophoresis of Modified RNA or RT PCR Products

Individual RNA polynucleotides (200-400 ng in a 20 μl volume) or reverse transcribed PCR products (200-400 ng) may be loaded into a well on a non-denaturing 1.2% Agarose E-Gel (Invitrogen, Carlsbad, Calif.) and run for 12-15 minutes, according to the manufacturer protocol.

Example 9: NANODROP™ Modified RNA Quantification and UV Spectral Data

Chemically modified RNA polynucleotides in TE buffer (1 μl) are used for NANODROP™ UV absorbance readings to quantitate the yield of each polynucleotide from an chemical synthesis or in vitro transcription reaction.

Example 10: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 11: RSV RNA Vaccine

A RSV RNA (e.g., mRNA) vaccine may comprise, for example, at least one RNA polynucleotide encoded by at least one of the following sequences, or by at least one fragment of the following sequences, or by derivatives and variants thereof. A RSV RNA vaccine may comprise, for example, at least one RNA (e.g., mRNA) polynucleotide having at least one chemical modification, e.g. the RSV vaccine may comprise, for example, at least one chemically modified RNA (e.g., mRNA) polynucleotide encoded by at least one of the following (DNA) sequences or by at least one fragment of the following sequences or by derivatives or variants thereof:

RSV # 1

(SEQ ID NO: 1)

```
ATGGAGCTGCTCATCCTCAAAGCAAATGCCATCACCACTATCCTGACCGCC
GTCACTTTCTGCTTCGCCTCCGGCCAAAATATCACCGAAGAGTTCTATCAG
TCCACCTGCTCTGCCGTTTCTAAAGGTTACCTGTCAGCCCTTAGAACAGGG
TGGTATACCTCTGTTATTACCATTGAGTTGTCCAACATTAAGAAGAACAAG
TGCAATGGCACAGACGCTAAGGTTAAGCTCATCAAGCAGGAGCTCGACAAA
TATAAAAATGCCGTCACGGAGCTGCAGTTATTGATGCAGAGCACCCAGGCG
ACAAACAACCGTGCACGACGCGAGCTACCCCGATTCATGAACTACACCCTC
AATAATGCAAAGAAGACAAATGTGACGCTCTCTAAGAAGCGCAAGCGTCGC
TTTCTGGGCTTTCTTCTCGGGGTTGGGAGCGCGATCGCAAGCGGCGTGGCT
GTATCAAAAGTGCTTCATCTTGAGGGAGAAGTGAATAAAATCAAAAGTGCT
CTGCTATCTACAAACAAAGCCGTTGTATCACTGTCCAACGGAGTGTCCGTG
CTCACGTCCAAAGTGCTAGATTTGAAGAATTACATCGATAAGCAGCTGCTC
CCTATTGTGAACAAACAATCATGTTCCATCAGTAACATTGAAACAGTCATC
GAGTTTCAACAGAAAAACAATAGACTGCTGGAGATTACCAGAGAATTTTCG
```

-continued

```
GTTAACGCCGGCGTGACTACCCCTGTAAGCACCTACATGTTGACAAACTCC
GAACTTTTGTCACTGATAAACGATATGCCTATTACTAATGATCAGAAAAAA
TTGATGTCCAATAATGTCCAAATCGTCAGGCAACAGTCCTACAGTATCATG
TCTATTATTAAGGAGGAGGTCCTTGCATACGTGGTGCAACTGCCATTATAC
GGAGTCATTGATACTCCCTGTTGGAAACTCCATACAAGCCCCCTGTGCACT
ACTAACACTAAAGAGGGATCAAATATTTGTCTCACTCGGACAGATAGAGGT
TGGTACTGTGATAATGCTGGCTCAGTGTCATTCTTTCCACAGGCTGAAACC
TGCAAGGTTCAGTCAAACAGGGTGTTTTGCGATACCATGAATTCTCTAACC
CTCCCCAGTGAGGTGAACCTGTGTAATGTGGATATATTCAACCCCAAGTAT
GATTGTAAGATCATGACCTCCAAGACGGACGTGAGTAGCAGTGTTATCACC
TCCCTGGGGGCCATTGTATCCTGCTACGGAAAAACGAAATGTACTGCCTCG
AACAAAAATAGGGGAATCATCAAAACTTTTAGTAATGGATGCGACTACGTA
TCTAATAAAGGTGTTGACACAGTGTCAGTCGGCAACACACTGTATTACGTG
AATAAGCAAGAAGGGAAGTCGCTGTATGTCAAAGGGGAGCCTATCATTAAT
TTTTATGACCCACTGGTTTTCCCCAGCGATGAGTTCGACGCCAGCATTAGT
CAGGTTAATGAGAAAATCAACCAGTCCTTGGCATTTATTCGTAAGAGTGAT
GAATTGCTCCATAATGTGAACGCTGGTAAATCCACTACCAACATTATGATA
ACTACCATCATCATAGTAATAATAGTAATTTTACTGTCTCTGATCGCTGTG
GGCCTGTTACTGTATTGCAAAGCCCGCAGTACTCCTGTCACCTTATCAAAG
GACCAGCTGTCTGGGATAAACAACATCGCGTTCTCCAAT
```

RSV # 2

(SEQ ID NO: 2)

```
ATGGAACTGCTCATTTTGAAGGCAAACGCTATCACGACAATACTCACTGCA
GTGACCTTCTGTTTTGCCTCAGGCCAGAACATAACCGAGGAGTTTTATCAA
TCTACATGCAGCGCTGTATCTAAAGGCTACCTGAGTGCGCTCCGCACAGGA
TGGTACACCTCCGTGATCACCATCGAGCTCAGCAATATTAAAGAGAACAAG
TGCAATGGTACCGACGCTAAAGTCAAACTTATCAAGCAGGAACTCGACAAA
TATAAAAACGCTGTGACCGAGCTGCAGTTATTGATGCAGAGTACACCTGCC
ACCAATAACAGAGCTAGGAGGGAGTTGCCTAGGTTTATGAACTACACTCTC
AACAACGCGAAAAAAACCAATGTGACGCTATCCAAGAAACGGAAGAGGAGG
TTCCTGGGGTTTCTTTTAGGGGTGGGCTCTGCCATTGCTTCCGGCGTGGCT
GTATGTAAAGTTCTCCACCTCGAGGGAGAGGTTAATAAGATTAAGTCGGCC
CTGCTGAGTACTAACAAAGCAGTGGTGTCGCTGAGTAACGGAGTAAGTGTG
TTAACATTTAAGGTGCTGGACCTCAAGAATTATATTGACAAACAGTTGCTT
CCTATTCTAAACAAACAGAGCTGTTCAATAAGTAATATTGAAACTGTTATT
GAGTTTCAGCAGAAGAACAACAGGCTTCTTGAGATTACACGCGAGTTCAGT
GTCAATGCCGGCGTTACAACACCCGTGTCTACCTACATGCTGACGAATTCT
GAGCTTCTCTCTCTCATAAACGACATGCCCATTACGAATGACCAAAAAAAA
CTTATGTCCAACAACGTGCAGATTGTGCGACAGCAATCCTATAGCATTATG
TGTATCATCAAGGAAGAGGTACTCGCTTATGTTGTGCAGCTACCACTCTAT
GGTGTGATTGACACCCCCTGTTGGAAGCTGCATACCAGTCCACTCTGCACC
ACTAACACAAAGGAAGGGAGCAATATTTGCCTCACTCGAACCGACAGGGGG
```

-continued

TGGTATTGCGATAATGCGGGCTCCGTGTCCTTCTTTCCACAGGCTGAAACT

TGTAAGGTACAGTCAAACCGCGTGTTCTGTGATACTATGAATTCTCTGACT

CTTCCCAGCGAGGTTAATCTCTGCAACGTCGACATTTTCAATCCTAAATAT

GACTGCAAGATCATGACCAGCAAGACCGACGTCTCCAGCTCAGTAATCACT

AGCCTAGGGGCCATTGTAAGCTGCTATGGCAAAACCAAGTGTACTGCCTCT

AATAAGAACAGAGGCATAATTAAAACCTTTTCAAATGGCTGTGACTATGTG

TCGAATAAGGGCGTCGACACGGTCTCAGTAGGGAATACCCTCTACTACGTT

AACAAACAGGAAGGCAAATCCCTTTATGTAAAGGGCGAGCCCATCATAAAT

TTCTACGACCCACTTGTGTTCCCCAGTGATGAATTCGATGCATCAATCTCC

CAGGTGAACGAAAAGATCAATCAATCCCTTGCTTTTATACGAAAGTCAGAT

GAACTCCTGCATAACGTGAATGCTGGGAAATCTACAACCAACATCATGATC

ACTACCATCATTATTGTGATTATCGTAATTCTGCTATCCTTGATTGCTGTC

GGGCTGCTTCTGTACTGTAAGGCCAGATCGACGCCTGTGACCCTTTCAAAA

GACCAACTTAGCGGTATCAATAATATTGCCTTTAGCAAT

A RSV vaccine may comprise, for example, at least one RNA (e.g., mRNA) polynucleotide having an open reading frame that encodes at least one of the following antigenic polypeptide sequences or at least one fragment of the following sequences:

RSV # 1

(SEQ ID NO: 3)

MELLILKANAITTILTAVTFCFASGQNITEEFYQSTCSAVSKGYLSALRTG

WYTSVITIELSNIKKNKCNGTDAKVKLIKQELDKYKNAVTELQLLMQSTQA

TNNRARRELPRFMNYTLNNAKKTNVTLSKKRKRRFLGFLLGVGSAIASGVA

VSKVLHLEGEVNKIKSALLSTNKAVVSLSNGVSVLTSKVLDLKNYIDKQLL

PIVNKQSCSISNIETVIEFQQKNNRLLEITREFSVNAGVTTPVSTYMLTNS

ELLSLINDMPITNDQKKLMSNNVQIVRQQSYSIMSIIKEEVLAYVVQLPLY

GVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVIT

SLGAIVSCYGKTKCTASNKNRGIIKTFSNGCDYVSNKGVDTVSVGNTLYYV

NKQEGKSLYVKGEPIINFYDPLVFPSDEFDASISQVNEKINQSLAFIRKSD

ELLHNVNAGKSTTNIMITTIIIVIIVILLSLIAVGLLLYCKARSTPVTLSK

DQLSGINNIAFSN

The underlined region represents a signal peptide sequence. The underlined regions can be substituted with alternative sequences that achieve the same or similar functions, or it can be deleted.

RSV #2

(SEQ ID NO: 4)

MELLILKANAITTILTAVTFCFASGQNITEEFYQSTCSAVSKGYLSALRTG

WYTSVITIELSNIKENKCNGTDAKVKLIKQELDKYKNAVTELQLLMQSTPA

TNNRARRELPRFMNYTLNNAKKTNVTLSKKRKRRFLGFLLGVGSAIASGVA

VCKVLHLEGEVNKIKSALLSTNKAVVSLSNGVSVLTFKVLDLKNYIDKQLL

-continued

PILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLY

GVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVIT

SLGAIVSCYGKTKCTASNKNRGIIKTFSNGCDYVSNKGVDTVSVGNTLYYV

NKQEGKSLYVKGEPIINFYDPLVFPSDEFDASISQVNEKINQSLAFIRKSD

ELLHNVNAGKSTTNIMITTIIIVIIVILLSLIAVGLLLYCKARSTPVTLSK

DQLSGINNIAFSN

The underlined region represents a signal peptide sequence. The underlined regions can be substituted with alternative sequences that achieve the same or similar functions, or it can be deleted.

Example 12: Mouse Immunogenicity

In this example, assays were carried out to evaluate the immune response to RSV vaccine antigens delivered using an mRNA/LNP platform in comparison to protein antigens.

Female Balb/c (CRL) mice (6-8 weeks old; N=10 mice per group) were administered RSV mRNA vaccines or protein vaccines. The mRNA vaccines were generated and formulated in MC3 lipid nanoparticles. The mRNA vaccines evaluated in this study included:

MRK-1 membrane-bound RSV F protein (SEQ ID NO: 262)

MRK-4 membrane-bound DS-CAV1 (stabilized prefusion F protein) (SEQ ID NO: 263)

MRK-5 RSV F construct (SEQ ID NO: 264)

MRK-6 RSV F construct

MRK-7 RSV F construct (SEQ ID NO: 266)

MRK-8 RSV F construct (SEQ ID NO: 267)

MRK-9 membrane-bound RSV G protein (SEQ ID NO: 268)

MRK-11 truncated RSV F protein (ectodomain only); construct modified to include an Ig secretion peptide signal sequence (SEQ ID NO: 269)

MRK-12 DS-CAV1 (non-membrane bound form); modified to include an Ig secretion peptide signal sequence (SEQ ID NO: 270)

MRK-13: MRK-5 construct modified to include an Ig secretion peptide signal sequence (SEQ ID NO: 271)

MRK-14: MRK-6 construct modified to include an Ig secretion peptide signal sequence (SEQ ID NO: 272)

MRK-16: MRK-8 construct modified to include an Ig secretion peptide signal sequence (SEQ ID NO: 273)

The DNA sequences encoding the above-mentioned 12 mRNAs and related amino acid sequences are listed below.

MRK-1 membrane-bound RSV F protein/MRK_01_F (full length, Merck A2 strain)/SQ-030268:

(SEQ ID NO: 5)

ATGGAGCTGCTCATCCTCAAAGCAAATGCCATCACCACTATCCTGACCGCC

GTCACTTTCTGCTTCGCCTCCGGCCAAAATATCACCGAAGAGTTCTATCAG

TCCACCTGCTCTGCCGTTTCTAAAGGTTACCTGTCAGCCCTTAGAACAGGG

TGGTATACCTCTGTTATTACCATTGAGTTGTCCAACATTAAGAAGAACAAG

TGCAATGGCACAGACGCTAAGGTTAAGCTCATCAAGCAGGAGCTCGACAAA

-continued

TATAAAAATGCCGTCACGGAGCTGCAGTTATTGATGCAGAGCACCCAGGCG
ACAAACAACCGTGCACGACGCGAGCTACCCCGATTCATGAACTACACCCTC
AATAATGCAAAGAAGACAAATGTGACGCTCTCTAAGAAGCGCAAGCGTCGC
TTTCTGGGCTTTCTTCTCGGGGTTGGGAGCGCGATCGCAAGCGGCGTGGCT
GTATCAAAAGTGCTTCATCTTGAGGGAGAAGTGAATAAAATCAAAAGTGCT
CTGCTATCTACAAACAAAGCCGTTGTATCACTGTCCAACGGAGTGTCCGTG
CTCACGTCCAAAGTGCTAGATTTGAAGAATTACATCGATAAGCAGCTGCTC
CCTATTGTGAACAAACAATCATGTTCCATCAGTAACATTGAAACAGTCATC
GAGTTTCAACAGAAAAACAATAGACTGCTGGAGATTACCAGAGAATTTTCG
GTTAACGCCGGCGTGACTACCCCTGTAAGCACCTACATGTTGACAAACTCC
GAACTTTTGTCACTGATAAACGATATGCCTATTACTAATGATCAGAAAAAA
TTGATGTCCAATAATGTCCAAATCGTCAGGCAACAGTCCTACAGTATCATG
TCTATTATTAAGGAGGAGGTCCTTGCATACGTGGTGCAACTGCCATTATAC
GGAGTCATTGATACTCCCTGTTGGAAACTCCATACAAGCCCCCTGTGCACT
ACTAACACTAAAGAGGGATCAAATATTTGTCTCACTCGGACAGATAGAGGT
TGGTACTGTGATAATGCTGGCTCAGTGTCATTCTTTCCACAGGCTGAAACC
TGCAAGGTTCAGTCAAACAGGGTGTTTTGCGATACCATGAATTCTCTAACC
CTCCCCAGTGAGGTGAACCTGTGTAATGTGGATATATTCAACCCCAAGTAT
GATTGTAAGATCATGACCTCCAAGACGGACGTGAGTAGCAGTGTTATCACC
TCCCTGGGGGCCATTGTATCCTGCTACGGAAAAACGAAATGTACTGCCTCG
AACAAAAATAGGGGAATCATCAAAACTTTTAGTAATGGATGCGACTACGTA
TCTAATAAAGGTGTTGACACAGTGTCAGTCGGCAACACACTGTATTACGTG
AATAAGCAAGAAGGGAAGTCGCTGTATGTCAAAGGGGAGCCTATCATTAAT
TTTTATGACCCACTGGTTTTCCCCAGCGATGAGTTCGACGCCAGCATTAGT
CAGGTTAATGAGAAAATCAACCAGTCCTTGGCATTTATTCGTAAGAGTGAT
GAATTGCTCCATAATGTGAACGCTGGTAAATCCACTACCAACATTATGATA
ACTACCATCATCATAGTAATAATAGTAATTTTACTGTCTCTGATCGCTGTG
GGCCTGTTACTGTATTGCAAAGCCCGCAGTACTCCTGTCACCTTATCAAAG
GACCAGCTGTCTGGGATAAACAACATCGCGTTCTCCAAT (SEQ ID NO: 6)
<u>MELLILKANAITTILTAVTFC</u>FASGQNITEEFYQSTCSAVSKGYLSALRTG
WYTSVITIELSNIKKNKCNGTDAKVKLIKQELDKYKNAVTELQLLMQSTQA
TNNRARRELPRFMNYTLNNAKKTNVTLSKKRKRRFLGFLLGVGSAIASGVA
VSKVLHLEGEVNKIKSALLSTNKAVVSLSNGVSVLTSKVLDLKNYIDKQLL
PIVNKQSCSISNIETVIEFQQKNNRLLEITREFSVNAGVTTPVSTYMLTNS
ELLSLINDMPITNDQKKLMSNNVQIVRQQSYSIMSIIKEEVLAYVVQLPLY
GVIDTPCWKLHTSPLCTTNTKEGSNICLTRTDRGWYCDNAGSVSFFPQAET
CKVQSNRVFCDTMNSLTLPSEVNLCNVDIFNPKYDCKIMTSKTDVSSSVIT
SLGAIVSCYGKTKCTASNKNRGIIKTFSNGCDYVSNKGVDTVSVGNTLYYV
NKQEGKSLYVKGEPIINFYDPLVFPSDEFDASISQVNEKINQSLAFIRKSD
ELLHNVNAGKSTTNIMITTIIIVIIVILLSLIAVGLLLYCKARSTPVTLSK
DQLSGINNIAFSN

The underlined region represents a signal peptide sequence. The underlined regions can be substituted with alternative sequences that achieve the same or similar functions, or can be deleted, as shown below.

(SEQ ID NO: 290)
FASGQNITEEFYQSTCSAVSKGYLSALRTGWYTSVITIELSNIKKNKCNGT
DAKVKLIKQELDKYKNAVTELQLLMQSTQATNNRARRELPRFMNYTLNNAK
KTNVTLSKKRKRRFLGFLLGVGSAIASGVAVSKVLHLEGEVNKIKSALLST
NKAVVSLSNGVSVLTSKVLDLKNYIDKQLLPIVNKQSCSISNIETVIEFQQ
KNNRLLEITREFSVNAGVTTPVSTYMLTNSELLSLINDMPITNDQKKLMSN
NVQIVRQQSYSIMSIIKEEVLAYVVQLPLYGVIDTPCWKLHTSPLCTTNTK
EGSNICLTRTDRGWYCDNAGSVSFFPQAETCKVQSNRVFCDTMNSLTLPSE
VNLCNVDIFNPKYDCKIMTSKTDVSSSVITSLGAIVSCYGKTKCTASNKNR
GIIKTFSNGCDYVSNKGVDTVSVGNTLYYVNKQEGKSLYVKGEPIINFYDP
LVFPSDEFDASISQVNEKINQSLAFIRKSDELLHNVNAGKSTTNIMITTII
IVIIVILLSLIAVGLLLYCKARSTPVTLSKDQLSGINNIAFSN

MRK-4 membrane-bound DS-CAV1 (stabilized prefusion F protein)/MRK_04_Prefusion F/DS-CAV1 (Full length, S155C/S290C/S190F/V207L)/SQ-030271:

(SEQ ID NO: 7)
ATGGAACTGCTCATTTTGAAGGCAAACGCTATCACGACAATACTCACTGCA
GTGACCTTCTGTTTTGCCTCAGGCCAGAACATAACCGAGGAGTTTTATCAA
TCTACATGCAGCGCTGTATCTAAAGGCTACCTGAGTGCGCTCCGCACAGGA
TGGTACACCTCCGTGATCACCATCGAGCTCAGCAATATTAAAGAGAACAAG
TGCAATGGTACCGACGCTAAAGTCAAACTTATCAAGCAGGAACTCGACAAA
TATAAAAACGCTGTGACCGAGCTGCAGTTATTGATGCAGAGTACACCTGCC
ACCAATAACAGAGCTAGGAGGGAGTTGCCTAGGTTTATGAACTACACTCTC
AACAACGCGAAAAAAACCAATGTGACGCTATCCAAGAAACGGAAGAGGAGG
TTCCTGGGGTTTCTTTTAGGGGTGGGCTCTGCCATTGCTTCCGGCGTGGCT
GTATGTAAAGTTCTCCACCTCGAGGGAGAGGTTAATAAGATTAAGTCGGCC
CTGCTGAGTACTAACAAAGCAGTGGTGTCGCTGAGTAACGGAGTAAGTGTG
TTAACATTTAAGGTGCTGGACCTCAAGAATTATATTGACAAACAGTTGCTT
CCTATTCTAAACAAACAGAGCTGTTCAATAAGTAATATTGAAACTGTTATT
GAGTTTCAGCAGAAGAACAACAGGCTTCTTGAGATTACACGCGAGTTCAGT
GTCAATGCCGGCGTTACAACACCCGTGTCTACCTACATGCTGACGAATTCT
GAGCTTCTCTCTCTCATAAACGACATGCCCATTACGAATGACCAAAAAAAA
CTTATGTCCAACAACGTGCAGATTGTGCGACAGCAATCCTATAGCATTATG
TGTATCATCAAGGAAGAGGTACTCGCTTATGTTGTGCAGCTACCACTCTAT
GGTGTGATTGACACCCCCTGTTGGAAGCTGCATACCAGTCCACTCTGCACC
ACTAACACAAAGGAAGGGAGCAATATTTGCCTCACTCGAACCGACAGGGGG
TGGTATTGCGATAATGCGGGCTCCGTGTCCTTCTTTCCACAGGCTGAAACT

-continued

TGTAAGGTACAGTCAAACCGCGTGTTCTGTGATACTATGAATTCTCTGACT

CTTCCCAGCGAGGTTAATCTCTGCAACGTCGACATTTTCAATCCTAAATAT

GACTGCAAGATCATGACCAGCAAGACCGACGTCTCCAGCTCAGTAATCACT

AGCCTAGGGGCCATTGTAAGCTGCTATGGCAAAACCAAGTGTACTGCCTCT

AATAAGAACAGAGGCATAATTAAAACCTTTTCAAATGGCTGTGACTATGTG

TCGAATAAGGGCGTCGACACGGTCTCAGTAGGGAATACCCTCTACTACGTT

AACAAACAGGAAGGCAAATCCCTTTATGTAAAGGGCGAGCCCATCATAAAT

TTCTACGACCCACTTGTGTTCCCCAGTGATGAATTCGATGCATCAATCTCC

CAGGTGAACGAAAAGATCAATCAATCCCTTGCTTTTATACGAAAGTCAGAT

GAACTCCTGCATAACGTGAATGCTGGGAAATCTACAACCAACATCATGATC

ACTACCATCATTATTGTGATTATCGTAATTCTGCTATCCTTGATTGCTGTC

GGGCTGCTTCTGTACTGTAAGGCCAGATCGACGCCTGTGACCCTTTCAAAA

GACCAACTTAGCGGTATCAATAATATTGCCTTTAGCAAT (SEQ ID NO: 8)

MELLILKANAITTILTAVTFCFASGQNITEEFYQSTCSAVSKGYLSALRTG

WYTSVITIELSNIKENKCNGTDAKVKLIKQELDKYKNAVTELQLLMQSTPA

TNNRARRELPRFMNYTLNNAKKTNVTLSKKRKRRFLGFLLGVGSAIASGVA

VCKVLHLEGEVNKIKSALLSTNKAVVSLSNGVSVLTFKVLDLKNYIDKQLL

PILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLY

GVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVIT

SLGAIVSCYGKTKCTASNKNRGIIKTFSNGCDYVSNKGVDTVSVGNTLYYV

NKQEGKSLYVKGEPIINFYDPLVFPSDEFDASISQVNEKINQSLAFIRKSD

ELLHNVNAGKSTTNIMITTIIIVIIVILLSLIAVGLLLYCKARSTPVTLSK

DQLSGINNIAFSN

The underlined region represents a signal peptide sequence. The underlined regions can be substituted with alternative sequences that achieve the same or similar functions, or can be deleted, as shown below.

(SEQ ID NO: 291)

FASGQNITEEFYQSTCSAVSKGYLSALRTGWYTSVITIELSNIKENKCNGT

DAKVKLIKQELDKYKNAVTELQLLMQSTPATNNRARRELPRFMNYTLNNAK

KTNVTLSKKRKRRFLGFLLGVGSAIASGVAVCKVLHLEGEVNKIKSALLST

NKAVVSLSNGVSVLTFKVLDLKNYIDKQLLPILNKQSCSISNIETVIEFQQ

KNNRLLEITREFSVNAGVTTPVSTYMLTNSELLSLINDMPITNDQKKLMSN

NVQIVRQQSYSIMCIIKEEVLAYVVQLPLYGVIDTPCWKLHTSPLCTTNTK

EGSNICLTRTDRGWYCDNAGSVSFFPQAETCKVQSNRVFCDTMNSLTLPSE

VNLCNVDIFNPKYDCKIMTSKTDVSSSVITSLGAIVSCYGKTKCTASNKNR

GIIKTFSNGCDYVSNKGVDTVSVGNTLYYVNKQEGKSLYVKGEPIINFYDP

LVFPSDEFDASISQVNEKINQSLAFIRKSDELLHNVNAGKSTTNIMITTII

IVIIVILLSLIAVGLLLYCKARSTPVTLSKDQLSGINNIAFSN

MRK-5 RSV F Construct:

(SEQ ID NO: 9)

ATGGAACTGCTCATCCTTAAAGCCAACGCGATAACGACCATTCTGACCGCC

GTGACCTTCTGCTTCGCCAGCGGCCAGAACATTACCGAAGAGTTTTACCAG

AGCACGTGCTCTGCCGTGAGCAAAGGTTATCTGAGCGCTTTAAGAACTGGC

TGGTACACCAGTGTTATTACTATAGAGCTGTCAAATATTAAAAAGAATAAA

TGCAACGGGACCGATGCCAAAGTAAAATTAATTAAGCAGGAATTGGACAAG

TATAAGAATGCAGTGACAGAGTTGCAGCTCCTGATGCAGAGCACACAAGCT

ACAAACAATCGCGCTCGCCAGCAGCAACAGCGGTTTTTAGGGTTCCTGCTA

GGGGTGGGGTCAGCCATTGCCTCTGGAGTGGCAGTGTCCAAAGTGCTGCAT

CTGGAAGGGGAAGTTAACAAGATAAAATCCGCACTCCTCAGCACCAATAAA

GCCGTGGTCTCCCTGTCCAATGGAGTATCAGTTTTGACAAGCAAGGTGCTG

GACCTGAAGAATTATATAGATAAGCAGTTACTGCCAATAGTGAATAAACAG

TCATGCTCAATTAGCAACATTGAGACAGTTATCGAATTCCAGCAGAAAAAT

AATAGGCTTCTGGAAATAACTCGCGAATTCTCAGTAAATGCCGGAGTGACC

ACACCCGTATCGACTTATATGCTTACAAACTCTGAACTGTTGTCCTTGATT

AACGATATGCCAATAACAAATGACCAGAAGAAGCTAATGAGCAACAATGTG

CAGATTGTAAGACAGCAGTCTTACTCAATAATGTCTATAATAAAAGAGGAG

GTGTTGGCATATGTGGTGCAACTGCCTCTCTATGGCGTGATCGATACTCCT

TGCTGGAAGTTACATACATCTCCACTGTGTACAACTAATACTAAGGAGGGT

AGCAATATTTGTCTGACACGCACAGATCGGGGTTGGTATTGCGACAACGCG

GGCAGTGTGAGCTTTTTCCCTCAGGCCGAAACCTGTAAGGTTCAATCTAAT

CGGGTATTTTGCGACACAATGAACAGCCTGACCCTTCCGTCCGAAGTTAAT

TTGTGCAACGTCGACATCTTCAATCCTAAATATGACTGCAAAATCATGACT

TCTAAAACCGACGTATCCAGCTCAGTGATAACAAGCCTTGGGGCAATTGTA

AGCTGCTATGGCAAGACGAAGTGCACCGCTAGTAACAAGAACCGGGGGATT

ATTAAGACTTTTTCGAACGGATGCGATTACGTCTCCAACAAAGGCGTCGAT

ACTGTGTCCGTGGGAAACACCCTCTACTATGTGAACAAGCAGGAAGGCAAA

AGCCTCTACGTCAAAGGAGAGCCTATCATCAATTTCTACGACCCTCTAGTA

TTCCCTTCAGACGAATTTGACGCATCAATTTCCCAGGTGAACGAGAAAATA

AATCAAAGCTTAGCCTTTATCCGCAAGAGTGATGAGTTGCTTCACAACGTC

AACGCCGGCAAATCAACCACTAAT (SEQ ID NO: 10)

MELLILKANAITTILTAVTFCFASGQNITEEFYQSTCSAVSKGYLSALRTG

WYTSVITIELSNIKKNKCNGTDAKVKLIKQELDKYKNAVTELQLLMQSTQA

TNNRARQQQQRFLGFLLGVGSAIASGVAVSKVLHLEGEVNKIKSALLSTNK

AVVSLSNGVSVLTSKVLDLKNYIDKQLLPIVNKQSCSISNIETVIEFQQKN

NRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEG

SNICLTRTDRGWYCDNAGSVSFFPQAETCKVQSNRVFCDTMNSLTLPSEVN

LCNVDIFNPKYDCKIMTSKTDVSSSVITSLGAIVSCYGKTKCTASNKNRGI

-continued

IKTFSNGCDYVSNKGVDTVSVGNTLYYVNKQEGKSLYVKGEPIINFYDPLV

FPSDEFDASISQVNEKINQSLAFIRKSDELLHNVNAGKSTTN

The underlined region represents a signal peptide sequence. The underlined regions can be substituted with alternative sequences that achieve the same or similar functions, or it can be deleted, as shown below.

(SEQ ID NO: 292)

FASGQNITEEFYQSTCSAVSKGYLSALRTGWYTSVITIELSNIKKNKCNGT

DAKVKLIKQELDKYKNAVTELQLLMQSTQATNNRARQQQQRFLGFLLGVGS

AIASGVAVSKVLHLEGEVNKIKSALLTNKAVVSLSNGVSVLTSKVLDLKNY

IDKQLLPIVNKQSCSISNIETVIEFQQKNNRLLEITREFSVNAGVTTPVST

YMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSF

FPQAETCKVQSNRVFCDTMNSLTLPSEVNLCNVDIFNPKYDCKIMTSKTDV

SSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLA

FIRKSDELLHNVNAGKSTTN

MRK-6 RSV F Construct:

(SEQ ID NO: 11)

ATGGAACTCTTGATCCTGAAGGCTAATGCAATAACAACAATTCTGACAGCA

GTCACCTTTTGCTTCGCCAGCGGACAGAATATTACGGAGGAGTTTTATCAA

TCTACCTGTAGTGCCGTGAGCAAGGGGTACCTGTCTGCCCTGAGGACGGGA

TGGTACACATCCGTGATCACCATCGAGTTGTCTAACATTAAAAAGAACAAG

TGCAACGGAACTGACGCCAAGGTGAAGCTCATTAAGCAAGAGCTCGACAAA

TATAAGAATGCGGTTACAGAACTACAGCTACTAATGCAGTCCACACAGGCA

ACCAATAACCGAGCACGTCAGCAGCAGCAACGCTTCCTTGGCTTCCTGCTC

GGGGTTGGCTCGGCAATTGCATCCGGAGTGGCTGTTTCCAAGGTTTTGCAC

CTTGAGGGAGAGGTCAATAAGATCAAGAGCGCCCTCCTGTCAACTAATAAG

GCCGTGGTCAGCCTTTCCAACGGTGTTTCTGTGTTAACCTCAAAAGTGCTC

GACCTTAAAAACTATATCGATAAGCAGCTGCTGCCCATAGTGAACAAACAG

TCCTGTTCTATCAGTAATATCGAGACAGTGATCGAATTCCAGCAGAAGAAC

AATCGTCTGCTGGAAATTACAAGGGAGTTCAGCGTAAACGCTGGAGTCACA

ACCCCCGTGTCCACTTACATGCTGACCAATTCCGAGCTGCTGAGTTTGATT

AATGATATGCCCATTACGAACGATCAGAAGAAACTGATGTCGAATAATGTT

CAGATCGTTAGGCAGCAGTCTTATAGCATCATGAGTATTATCAAAGAGGAG

GTCCTCGCCTATGTGGTTCAGCTGCCTCTCTACGGCGTTATAGACACCCCA

TGCTGGAAGCTTCACACCTCTCCTCTGTGTACGACCAATACAAAGGAGGGC

TCAAACATTTGCCTTACCCGCACAGATAGAGGATGGTACTGCGATAATGCT

GGCTCTGTGTCTTTCTTTCCTCAGGCCGAAACATGTAAGGTACAGTCCAAT

AGGGTATTTTGCGACACCATGAACTCCCTAACCTTACCAAGTGAAGTGAAC

CTCTGCAATGTGGACATCTTTAACCCGAAGTATGACTGCAAAATCATGACT

-continued

TCCAAGACAGACGTGTCCAGTAGTGTGATTACCTCACTGGGCGCAATCGTT

TCATGCTATGGGAAGACAAAGTGCACCGCAAGCAACAAGAATCGGGGCATC

ATCAAAACCTTCAGTAACGGTTGTGACTATGTTTCAAACAAGGGAGTCGAT

ACCGTGTCGGTGGGCAATACTCTTTACTACGTGAATAAACAGGAGGGGAAA

TCACTGTATGTGAAAGGTGAGCCGATCATTAACTTTTACGACCCTCTCGTG

TTTCCCTCCGATGAGTTCGACGCATCCATCAGTCAGGTCAATGAGAAAATC

AACCAATCTCTCGCCTTCATTAGAAAATCTGACGAATTACTGAGTGCCATT

GGAGGATATATTCCGGAGGCTCCCAGGGACGGGCAGGCTTACGTCCGAAAG

GATGGAGAATGGGTCCTACTGAGCACATTTCTA

The underlined region represents a sequence coding for foldon. The underlined region can be substituted with alternative sequences which achieve a same or similar function, or can be deleted.

(SEQ ID NO: 12)

MELLILKANAITTILTAVTFCFASGQNITEEFYQSTCSAVSKGYLSALRTG

WYTSVITIELSNIKKNKCNGTDAKVKLIKQELDKYKNAVTELQLLMQSTQA

TNNRARQQQQRFLGFLLGVGSAIASGVAVSKVLHLEGEVNKIKSALLSTNK

AVVSLSNGVSVLTSKVLDLKNYIDKQLLPIVNKQSCSISNIETVIEFQQKN

NRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEG

SNICLTRTDRGWYCDNAGSVSFFPQAETCKVQSNRVFCDTMNSLTLPSEVN

LCNVDIFNPKYDCKIMTSKTDVSSSVITSLGAIVSCYGKTKCTASNKNRGI

IKTFSNGCDYVSNKGVDTVSVGNTLYYVNKQEGKSLYVKGEPIINFYDPLV

FPSDEFDASISQVNEKINQSLAFIRKSDELLSAIGGYIPEAPRDGQAYVRK

DGEWVLLSTFL

The first underlined region represents a signal peptide sequence. The first underlined regions can be substituted with alternative sequences that achieve the same or similar functions, or it can be deleted, as shown below. The second underlined region represents a foldon. The second underlined region can be substituted with alternative sequences which achieve a same or similar function.

(SEQ ID NO: 293)

FASGQNITEEFYQSTCSAVSKGYLSALRTGWYTSVITIELSNIKKNKCNGT

DAKVKLIKQELDKYKNAVTELQLLMQSTQATNNRARQQQQRFLGFLLGVGS

AIASGVAVSKVLHLEGEVNKIKSALLSTNKAVVSLSNGVSVLTSKVLDLKN

YIDKQLLPIVNKQSCSISNIETVIEFQQKNNRLLEITREFSVNAGVTTPVS

TYMLTNSELLSLINDMPITNDQKKLMSNNVQIVRQQSYSIMSIIKEEVLAY

VVQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKTD

VSSSVITSLGAIVSCYGKTKCTASNKNRGIIKTFSNGCDYVSNKGVDTVSV

GNTLYYVNKQEGKSLYVKGEPIINFYDPLVFPSDEFDASISQVNEKINQSL

AFIRKSDELL

MRK-7 RSV F Construct:

(SEQ ID NO: 13)

ATGGAGCTCCTGATCTTGAAGGCGAATGCCATTACCACCATCCTCACCGCA
GTAACTTTCTGTTTCGCAAGTGGCCAGAATATAACAGAAGAGTTCTATCAG
TCAACCTGTAGCGCAGTCTCAAAGGGGTATTTATCAGCACTGAGAACCGGT
TGGTATACCAGTGTTATTACAATAGAGCTGAGTAACATAAAGGAGAATAAG
TGCAACGGCACTGACGCCAAGGTCAAGCTCATCAAACAGGAACTCGATAAA
TACAAGAACGCTGTCACTGAACTGCAGCTGCTGATGCAAAGCACCCCCGCC
ACCAACAATAGGGCCCGCAGAGAGCTTCCTAGATTTATGAACTACACTCTG
AACAACGCCAAAAAGACCAATGTAACACTGTCAAAGAAACAGAAACAGCAG
GCTATTGCAAGCGGTGTGGCTGTGTCTAAAGTGCTGCATCTCGAGGGGGAG
GTCAACAAGATCAAATCCGCATTGCTCAGCACCAACAAGGCTGTGGTGAGC
CTGTCCAATGGTGTCTCAGTGCTCACCAGCAAAGTGCTGGACCTGAAGAAT
TATATTGATAAGCAGCTGCTACCCATAGTCAACAAACAGTCATGCTCCATA
TCTAATATTGAGACTGTCATCGAGTTCCAACAGAAGAACAATCGCCTGCTG
GAGATTACCAGGGAGTTCTCAGTCAATGCCGGGGTCACGACACCCGTTAGT
ACTTATATGCTTACCAACTCCGAGCTTCTCTCTTTGATCAATGACATGCCA
ATTACTAACGACCAGAAGAAGTTGATGTCTAACAATGTACAGATCGTTCGC
CAGCAGTCCTATTCCATTATGTCGATTATTAAAGAGGAGGTTCTTGCATAC
GTCGTGCAGTTGCCATTATATGGAGTCATCGACACCCCCTGCTGGAAACTG
CATACGTCACCATTATGCACCACGAATACAAAGGAGGGCAGTAATATTTGT
CTTACACGGACTGATCGAGGCTGGTATTGTGATAACGCAGGCTCGGTGTCA
TTCTTTCCACAGGCTGAAACCTGTAAGGTGCAATCTAATAGGGTGTTTTGC
GATACCATGAATTCTCTGACTCTGCCCAGTGAGGTCAATTTGTGTAACGTG
GACATCTTCAACCCCAAAGTACGACTGCAAGATCATGACATCTAAGACAGAT
GTGTCATCCAGCGTTATCACGAGCCTCGGCGCTATAGTCTCCTGTTACGGC
AAGACCAAGTGCACCGCTAGCAACAAGAATCGGGGAATCATCAAAACCTTT
TCTAACGGTTGTGACTACGTGAGCAACAAGGGGGTGGATACCGTCTCAGTC
GGTAACACCCTGTACTACGTGAATAAACAGGAGGGGAAGTCATTGTACGTG
AAGGGTGAACCTATCATCAACTTTTATGACCCCCTCGTCTTCCCATCAGAC
GAGTTTGACGCGTCCATCTCTCAGGTGAATGAGAAGATTAACCAGAGCCTG
GCTTTTATCCGCAAATCAGACGAACTACTGCACAATGTCAACGCTGGCAAG
AGCACAACAAATATAATGATAACAACCATCATCATCGTCATTATTGTGATC
TTGTTATCACTGATCGCTGTGGGGCTCCTCCTTTATTGCAAGGCTCGTAGC
ACCCCTGTCACCCTCAGTAAAGATCAGCTGTCAGGGATCAATAATATCGCG
TTTAGCAAC (SEQ ID NO: 14)

MELLILKANAITTILTAVTFCFASGQNITEEFYQSTCSAVSKGYLSALRTG
WYTSVITIELSNIKENKCNGTDAKVKLIKQELDKYKNAVTELQLLMQSTPA
TNNRARRELPRFMNYTLNNAKKTNVTLSKKQKQQAIASGVAVSKVLHLEGE
VNKIKSALLSTNKAVVSLSNGVSVLTSKVLDLKNYIDKQLLPIVNKQSCSI

-continued

SNIETVIEFQQKNNRLLEITREFSVNAGVTTPVSTYMLTNSELLSLINDMP
ITNDQKKLMSNNVQIVRQQSYSIMSIIKEEVLAYVVQLPLYGVIDTPCWKL
HTSPLCTTNTKEGSNICLTRTDRGWYCDNAGSVSFFPQAETCKVQSNRVFC
DTMNSLTLPSEVNLCNVDIFNPKYDCKIMTSKTDVSSSVITSLGAIVSCYG
KTKCTASNKNRGIIKTFSNGCDYVSNKGVDTVSVGNTLYYVNKQEGKSLYV
KGEPIINFYDPLVFPSDEFDASISQVNEKINQSLAFIRKSDELLHNVNAGK
STTNIMITTIIIVIIVILLSLIAVGLLLYCKARSTPVTLSKDQLSGINNIA
FSN

The underlined region represents a signal peptide sequence. The underlined regions can be substituted with alternative sequences that achieve the same or similar functions, or it can be deleted, as shown below.

(SEQ ID NO: 294)

FASGQNITEEFYQSTCSAVSKGYLSALRTGWYTSVITIELSNIKENKCNGT
DAKVKLIKQELDKYKNAVTELQLLMQSTPATNNRARRELPRFMNYTLNNAK
KTNVTLSKKQKQQAIASGVAVSKVLHLEGEVNKIKSALLSTNKAVVSLSNG
VSVLTSKVLDLKNYIDKQLLPIVNKQSCSISNIETVIEFQQKNNRLLEITR
EFSVNAGVTTPVSTYMLTNSELLSLINDMPITNDQKKLMSNNVQIVRQQSY
SIMSIIKEEVLAYVVQLPLYGVIDTPCWKLHTSPLCTTNTKEGSNICLTRT
DRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGC
DYVSNKGVDTVSVGNTLYYVNKQEGKSLYVKGEPIINFYDPLVFPSDEFDA
SISQVNEKINQSLAFIRKSDELLHNVNAGKSTTNIMITTIIIVIIVILLSL
IAVGLLLYCKARSTPVTLSKDQLSGINNIAFSN

MRK-8 RSV F Construct:

(SEQ ID NO: 15)

ATGGAATTATTAATTTTGAAGACAAATGCTATAACCGCGATACTAGCGGCT
GTGACTCTTTGTTTCGCATCAAGCCAGAATATTACAGAAGAATTTTATCAA
TCCACCTGCAGCGCTGTATCGAAAGGTTACCTCAGCGCGCTTAGGACAGGA
TGGTATACCTCCGTTATCACGATTGAACTGAGTAATATCAAGGAAAACAAG
TGTAACGGAACAGACGCCAAGGTCAAACTTATTAAACAAGAACTGGACAAG
TATAAGTCTGCAGTGACCGAATTGCAGCTCCTGATGCAGAGTACCCCTGCA
ACTAACAACAAGTTTTTGGGCTTTCTGCAAGGCGTGGGTAGCGCGATCGCC
TCCGGAATCGCGGTCTCCAAAGTGTTGCACCTGGAGGGAGAAGTTAACAAG
ATCAAATCGGCTCTGTTGAGTACCAACAAGGCAGTGGTGTCACTGAGCAAC
GGTGTAAGCGTGTTAACAAGCAAGGTATTGGACTTAAAGAACTATATTGAC
AAACAGCTGCTCCCCATCGTGAACAAACAGAGCTGCTCAATCTCCAATATA
GAGACGGTGATAGAGTTCCAGCAAAAAAATAATCGGCTCCTTGAGATCACC
CGCGAATTCTCAGTTAATGCCGGCGTCACAACTCCGGTGTCTACATACATG
CTGACCAACTCGGAGCTGTTATCCTTAATAAATGACATGCCCATCACCAAT
GATCAAAAAAAACTGATGTCAAATAACGTCCAGATAGTAAGACAGCAGAGC

-continued

TACAGCATCATGTCGATTATCAAAGAGGAGGTGCTGGCGTACGTGGTGCAG

CTGCCCCTGTATGGGGTGATTGACACCCCTTGTTGGAAGCTGCACACCTCC

CCACTATGTACTACCAATACCAAAGAAGGATCCAACATCTGCCTTACCCGC

ACCGATAGGGGATGGTATTGCGACAACGCCGGATCCGTCAGCTTCTTTCCA

CTTGCCGAAACTTGCAAGGTTCAGTCAAACCGGGTGTTCTGCGATACAATG

AATTCCCTTACCTTGCCCAGCGAAGTTAATCTCTGTAATATTGACATCTTT

AACCCCAAATACGATTGCAAAATTATGACGTCAAAAACCGATGTCAGTTCA

AGCGTTATCACCAGCTTGGGTGCTATCGTTTCATGCTATGGCAAAACCAAG

TGTACGGCTAGTAACAAAAACCGCGGAATAATTAAGACATTCAGCAATGGT

TGCGACTACGTATCAAATAAGGGTGTCGACACCGTTTCCGTGGGCAATACG

CTGTACTATGTTAATAAACAGGAAGGCAAGTCACTGTATGTTAAAGGTGAA

CCCATCATCAACTTCTACGACCCCCTGGTTTTCCCCTCCGACGAGTTTGAT

GCCAGCATATCACAGGTTAATGAAAAAATAAACGGCACATTGGCGTTTATC

AGAAAGTCTGACGAGAAACTTCATAACGTGGAAGACAAGATAGAAGAGATA

TTGAGCAAAATCTATCATATTGAGAACGAGATCGCCAGGATCAAAAAGCTT

ATTGGGGAG

The underlined region represents a region coding for GCN4. The underlined region can be substituted with alternative sequences which achieve a same or similar function.

(SEQ ID NO: 16)

MELLILKTNAITAILAAVTLCFASSQNITEEFYQSTCSAVSKGYLSALRTG

WYTSVITIELSNIKENKCNGTDAKVKLIKQELDKYKSAVTELQLLMQSTPA

TNNKFLGFLQGVGSAIASGIAVSKVLHLEGEVNKIKSALLSTNKAVVSLSN

GVSVLTSKVLDLKNYIDKQLLPIVNKQSCSISNIETVIEFQQKNNRLLEIT

REFSVNAGVTTPVSTYMLTNSELLSLINDMPITNDQKKLMSNNVQIVRQQS

YSIMSIIKEEVLAYVVQLPLYGVIDTPCWKLHTSPLCTTNTKEGSNICLTR

TDRGWYCDNAGSVSFFPLAETCKVQSNRVFCDTMNSLTLPSEVNLCNIDIF

NPKYDCKIMTSKTDVSSSVITSLGAIVSCYGKTKCTASNKNRGIIKTFSNG

CDYVSNKGVDTVSVGNTLYYVNKQEGKSLYVKGEPIINFYDPLVFPSDEFD

ASISQVNEKINGTLAFIRKSDEKLHNVEDKIEEILSKIYHIENEIARIKKL

IGE

The first underlined region represents a signal peptide sequence. The underlined region can be substituted with alternative sequences that achieve the same or similar functions, or it can be deleted, as shown below. The second underlined region represents GCN4. The underlined region can be substituted with alternative sequences which achieve a same or similar function, or can be deleted.

(SEQ ID NO: 295)

FASSQNITEEFYQSTCSAVSKGYLSALRTGWYTSVITIELSNIKENKCNGT

DAKVKLIKQELDKYKSAVTELQLLMQSTPATNNKFLGFLQGVGSAIASGIA

VSKVLHLEGEVNKIKSALLSTNKAVVSLSNGVSVLTSKVLDLKNYIDKQLL

PIVNKQSCSISNIETVIEFQQKNNRLLEITREFSVNAGVTTPVSTYMLTNS

-continued

ELLSLINDMPITNDQKKLMSNNVQIVRQQSYSIMSIIKEEVLAYVVQLPLY

GVIDTPCWKLHTSPLCTTNTKEGSNICLTRTDRGWYCDNAGSVSFFPLAET

CKVQSNRVFCDTMNSLTLPSEVNLCNIDIFNPKYDCKIMTSKTDVSSSVIT

SLGAIVSCYGKTKCTASNKNRGIIKTFSNGCDYVSNKGVDTVSVGNTLYYV

NKQEGKSLYVKGEPIINFYDPLVFPSDEFDASISQVNEKINGTLAFIRKSD

EKLHN

MRK-9 membrane-bound RSV G protein:

(SEQ ID NO: 17)

ATGTCTAAAAACAAGGACCAGCGCACTGCTAAGACGCTGGAACGCACATGG

GATACCCTGAACCATCTGTTATTCATTTCCAGCTGCCTCTACAAGCTAAAC

CTTAAAAGTGTTGCACAAATCACACTCAGCATCCTGGCAATGATTATTTCA

ACATCCCTGATCATAGCCGCAATCATATTTATCGCCTCAGCAAATCACAAA

GTTACCCCGACCACAGCCATTATCCAGGACGCTACATCCCAAATCAAAAAC

ACCACACCTACATATCTCACTCAGAACCCGCAGCTGGGCATTTCACCATCC

AACCCTTCC*GAGATCACCTCTCAAAT*CACCACCATTCTCGCCTCTACTACC

CCGGGAGTAAAGAGCACTCTTCAGAGCACAACCGTTAAAACTAAAAATACC

ACCACCACTCAGACTCAGCCTTCGAAACCAACGACTAAACAGCGGCAAAAT

AAGCCTCCATCCAAACCGAATAACGACTTTCATTTCGAAGTCTTTAACTTT

GTGCCATGCAGTATTTGCTCCAATAATCCTACTTGCTGGGCTATCTGCAAG

AGAATCCCTAACAAGAAGCCTGGAAAGAAGACAACGACAAAGCCAACTAAG

AAGCCGACACTTAAGACTACCAAAAAAGACCCTAAGCCGCAGACTACCAAG

AGCAAGGAGGTTCCCACAACCAAGCCTACAGAGGAGCCGACTATTAACACA

ACAAAGACCAACATCATCACCACCCTGCTTACTTCTAATACTACCGGAAAC

CCAGAGCTGACGTCCCAGATGGAGACGTTCCATTCCACATCTTCCGAAGGG

AATCCTAGTCCCAGCCAGGTGAGCACAACCTCAGAATACCCGTCCCAGCCC

TCATCACCTCCTAATACCCCCCGGCAG

The underlined region represents a region coding for transmembrane domain. The underlined region can be substituted with alternative sequences which achieve a same or similar function, or can be deleted.

(SEQ ID NO: 18)

MSKNKDQRTAKTLERTWDTLNHLLFISSCLYKLNLKSVAQITLSILAMIIS

TSLIIAAIIFIASANHKVTPTTAIIQDATSQIKNTTPTYLTQNPQLGISPS

NPSEITSQITTILASTTPGVKSTLQSTTVKTKNTTTTQTQPSKPTTKQRQN

KPPSKPNNDFHFEVFNFVPCSICSNNPTCWAICKRIPNKKPGKKTTTKPTK

KPTLKTTKKDPKPQTTKSKEVPTTKPTEEPTINTTKTNIITTLLTSNTTGN

PELTSQMETFHSTSSEGNPSPSQVSTTSEYPSQPSSPPNTPRQ

The underlined region represents a transmembrane domain. The underlined region can be substituted with alternative sequences which achieve a same or similar function.

MRK-11 truncated RSV F protein (ectodomain only); construct modified to include an Ig secretion peptide signal sequence:

(SEQ ID NO: 19)
ATGGAGACGCCTGCCCAGCTGCTGTTCCTGCTGTTGTTGTGGCTGCCAGATACTACTGGGTTTGCAAGCGGACAAAACATTACCGAAGAGTTCTATCAATCCACATGCTCTGCAGTGTCTAAGGGCTACCTTAGTGCATTACGAACCGGGTGGTATACGAGTGTAATCACCATTGAGCTGTCCAACATCAAGAAGAACAAGTGCAATGGGACTGATGCCAAGGTGAAACTTATCAAACAAGAGCTCGACAAGTATAAGAACGCCGTGACCGAACTACAACTCCTGATGCAATCGACTCAGGCTACTAACAACAGAGCTCGGAGGGAGCTGCCCAGATTCATGAATTATACCTTAAACAACGCTAAAAAAACAAATGTGACCCTGAGTAAGAAGCGGAAACGAAGGTTCCTGGGCTTCCTGCTCGGTGTGGGGTCTGCAATAGCAAGCGGCGTCGCTGTGTCCAAGGTCCTTCACTTAGAAGGTGAGGTCAATAAGATCAAGTCCGCTCTCCTCTCTACCAACAAGGCAGTGGTGAGCCTGTCTAACGGTGTGTCCGTGCTGACATCGAAGGTACTGGACCTGAAAAACTACATCGACAAGCAGCTGCTGCCTATTGTGAATAAGCAATCCTGCAGTATCTCCAACATTGAGACAGTGATTGAATTTCAGCAAAAGAACAATCGTTTGTTGGAGATAACAAGAGAATTCAGTGTTAATGCCGGCGTTACCACTCCCGTGTCGACATACATGCTAACAAATAGCGAGCTGCTATCTCTCATTAATGATATGCCTATCACCAATGACCAGAAAAAACTTATGTCCAATAACGTGCAGATAGTCAGGCAGCAGTCCTACAGCATTATGAGCATAATTAAAGAGGAAGTGTTGGCTTACGTCGTCCAGCTTCCACTGTATGGCGTGATCGATACCCCTTGTTGGAAGCTGCATACTTCCCCCCTTTGTACAACTAATACCAAAGAAGGGAGTAATATATGCCTCACAAGGACTGACAGAGGCTGGTACTGCGACAACGCCGGGAGCGTCAGCTTTTTCCCGCAGGCCGAGACATGTAAGGTGCAGAGCAACCGTGTCTTTTGCGACACCATGAATAGCCTGACTTTGCCAAGTGAGGTCAACCTTTGCAACGTGGATATTTTTAACCCTAAGTACGATTGTAAGATAATGACATCCAAAACCGATGTTAGTAGCTCCGTGATCACTTCGCTGGGTGCGATAGTTAGCTGCTATGGAAAGACAAAGTGTACCGCAAGTAACAAGAACCGCGGGATTATTAAAACATTTAGCAATGGGTGCGACTACGTATCAAACAAGGGGGTGGATACAGTCAGCGTGGGAAACACACTTTACTACGTTAACAAGCAGGAAGGGAAATCCCTTTATGTGAAGGGAGAACCAATTATCAACTTTTATGATCCCCTCGTGTTTCCAAGTGATGAATTCGACGCAAGCATCTCGCAGGTGAACGAGAAAATCAATCAGAGTCTAGCTTTCATAAGGAAGTCTGATGAACTGCTTAGTGCCATTGGCGGGTACATACCGGAAGCCCCACGCGACGGTCAGGCTTACGTGAGGAAGGACGGCGAGTGGGTTCTGCTGTCCACTTTCCTT

The first underlined region represents region coding for human Igκ signal peptide, second underlined region represents region coding for foldon. The underlined regions can be substituted with alternative sequences which achieves same or similar functions, or can be deleted.

(SEQ ID NO: 20)
METPAQLLFLLLLWLPDTTGFASGQNITEEFYQSTCSAVSKGYLSALRTGWYTSVITIELSNIKKNKCNGTDAKVKLIKQELDKYKNAVTELQLLMQSTQATNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEVNLCNVDIFNPKYDCKIMTSKTDVSSSVITSLGAIVSCYGKTKCTASNKNRGIIKTFSNGCDYVSNKGVDTVSVGNTLYYVNKQEGKSLYVKGEPIINFYDPLVFPSDEFDASISQVNEKINQSLAFIRKSDELLSAIGGYIPEAPRDGQAYVRKDGEWVLLSTFL

The first underlined region represents human Igκ signal peptide, second underlined region represents foldon. The underlined regions can be substituted with alternative sequences which achieves same or similar functions, or can be deleted, as shown below.

(SEQ ID NO: 296)
FASGQNITEEFYQSTCSAVSKGYLSALRTGWYTSVITIELSNIKKNKCNGTDAKVKLIKQELDKYKNAVTELQLLMQSTQATNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEVNLCNVDIFNPKYDCKIMTSKTDVSSSVITSLGAIVSCYGKTKCTASNKNRGIIKTFSNGCDYVSNKGVDTVSVGNTLYYVNKQEGKSLYVKGEPIINFYDPLVFPSDEFDASISQVNEKINQSLAFRKSDELL

MRK-12 DS-CAV1 (non-membrane bound form); modified to include an Ig secretion peptide signal sequence:

(SEQ ID NO: 21)
ATGGAGACTCCCGCTCAGCTGCTGTTTTTGCTCCTCCTATGGCTGCCGGATACCACCGGCTTTGCCTCTGGACAGAACATTACCGAGGAATTCTATCAGTCGACTTGTTCCGCAGTCTCGAAGGGGTACCTGAGTGCCCTGCGCACCGGGTGGTACACCAGTGTTATCACTATTGAGCTGTCCAACATTAAAGAAAATAAGTGTAATGGAACTGACGCGAAGGTGAAGTTGATAAAACAGGAGCTGGATAAATACAAGAATGCAGTGACCGAACTGCAGCTCCTGATGCAGTCCACTCCAGCAACAAATAATCGCGCGAGACGCGAACTCCCCCGCTTTATGAACTACACTCTGAATAATGCGAAGAAAACGAATGTGACACTAAGTAAGAAAAGAAAACGGCGATTTTCTTGGGTTCCTGCTCGGGGTGGGATCTGCCATAGCAAGCGGGGTGGCGGATGTAAAGTCCTTCACCTAGAAGGGGAGGTGAACAAAATTAAGAGTGCCCTGCTGAGCACCAACAAGGCTGTGGTTTCACTGTCAAACGGAGTAAGCGTGCTAACATTTAAAGTCTTGGACCTGAAGAATTATATTGACAAGCAGCTCCTGCCCATTCTCAACAAACAGTCATGTTCCATTAGCAACATCGAAACAGTCATTGAGTTTCAGCAAAAAAACAACCGCCTCCTTGAGATTACGCGTGAGTTTTCCGTCAATGCTGGAGTCACGACACCGGTGTCCACTTACATGCTGACTAACAGCGAA

-continued

CTCCTGAGCCTAATCAATGACATGCCCATTACTAACGACCAGAAAAAATTG
ATGTCCAATAACGTGCAGATAGTGCGCCAGCAATCTTACTCCATAATGTGC
ATTATCAAGGAGGAAGTCCTGGCGTACGTTGTTCAGCTGCCGCTGTATGGT
GTGATAGATACGCCATGCTGGAAACTGCACACATCCCCCCTTTGCACAACG
AATACTAAAGAGGGAAGTAACATTTGCTTGACCAGAACAGATCGGGGCTGG
TACTGCGACAACGCTGGTAGTGTGTCATTTTTCCCCCAGGCAGAAACGTGT
AAAGTCCAGAGCAATCGCGTGTTCTGCGACACAATGAACTCACTTACTTTG
CCCTCAGAGGTCAATTTGTGTAATGTGGATATCTTCAACCCGAAATACGAT
TGTAAGATTATGACGAGCAAAACAGACGTGTCTTCATCAGTGATAACAAGT
CTGGGCGCAATAGTGTCATGCTATGGTAAGACTAAGTGCACTGCCTCCAAT
AAAAACCGCGGCATCATCAAGACATTTTCAAATGGATGCGACTACGTGTCA
AACAAGGGCGTCGACACAGTAAGCGTTGGGAACACCCTATACTACGTCAAC
AAGCAGGAGGGGAAAAGCCTATACGTGAAAGGCGAGCCAATCATCAATTTC
TACGATCCACTGGTCTTTCCAAGTGACGAATTTGATGCCAGCATATCGCAG
GTGAACGAGAAAATAAATCAGTCACTCGCCTTCATCAGGAAGTCAGATGAG
CTGCTGTCCGCCATCGGAGGATACATTCCAGAAGCCCCACGCGACGGCCAG
GCATACGTGCGGAAGGACGGCGAATGGGTCCTTTTGAGCACTTTTCTA

The first underlined region represents a region coding for human Igκ signal peptide, the second underlined region represents a region coding for a foldon. The underlined regions can be substituted with alternative sequences which achieves same or similar functions, or can be deleted.

(SEQ ID NO: 22)

METPAQLLFLLLLWLPDTTGFASGQNITEEFYQSTCSAVSKGYLSALRTGW
YTSVITIELSNIKENKCNGTDAKVKLIKQELDKYKNAVTELQLLMQSTPAT
NNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLP
ILNKQSCSISNIETVIEFQQKNNRLLEITREFSVNAGVTTPVSTYMLTNSE
LLSLINDMPITNDQKKLMSNNVQIVRQQSYSIMCIIKEEVLAYVVQLPLYG
VIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITS
LGAIVSCYGKTKCTASNKNRGIIKTFSNGCDYVSNKGVDTVSVGNTLYYVN
KQEGKSLYVKGEPIINFYDPLVFPSDEFDASISQVNEKINQSLAFIRKSDE
LLSAIGGYIPEAPRDGQAYVRKDGEWVLLSTFL

The first underlined region represents human Igκ signal peptide, the second underlined region represents foldon. The underlined regions can be substituted with alternative sequences which achieves same or similar functions, or can be deleted, as shown below.

(SEQ ID NO: 297)

FASGQNITEEFYQSTCSAVSKGYLSALRTGWYTSVITIELSNIKENKCNGT
DAKVKLIKQELDKYKNAVTELQLLMQSTPATNNRARRELPRFMNYTLNNAK
KTNVTLSKKRKRRFLGFLLGVGSAIASGVAVCKVLHLEGEVNKIKSALLST

-continued

NKAVVSLSNGVSVLTFKVLDLKNYIDKQLLPILNKQSCSISNIETVIEFQQ
KNNRLLEITREFSVNAGVTTPVSTYMLTNSELLSLINDMPITNDQKKLMSN
NVQIVRQQSYSIMCIIKEEVLAYVVQLPLYGVIDTPCWKLHTSPLCTTNTK
EGSNICLTRTDRGWYCDNAGSVSFFPQAETCKVQSNRVFCDTMNSLTLPSE
VNLCNVDIFNPKYDCKIMTSKTDVSSSVITSLGAIVSCYGKTKCTASNKNR
GIIKTFSNGCDYVSNKGVDTVSVGNTLYYVNKQEGKSLYVKGEPIINFYDP
LVFPSDEFDASISQVNEKINQSLAFIRKSDELL

MRK-13 MRK-5 construct modified to include an Ig secretion peptide signal sequence:

(SEQ ID NO: 23)

ATGGAGACTCCAGCCCAATTACTGTTCCTGCTACTCCTTTGGCTGCCCGAT
ACTACTGGATTCGCTTCGGGTCAGAATATTACAGAGGAGTTCTACCAAAGT
ACTTGCTCTGCAGTCTCCAAGGGATACCTGTCCGCTCTGCGGACGGGATGG
TATACCAGTGTTATAACGATCGAGTTGAGCAACATCAAGAAGAACAAATGT
AATGGAACAGATGCCAAGGTGAAACTGATCAAACAGGAGTTGGATAAATAT
AAGAATGCTGTCACCGAACTGCAGCTATTGATGCAGTCCACCCAGGCTACC
AACAACCGGGCCAGGCAGCAACAACAGAGATTTTTGGGTTTCTTGCTGGGC
GTGGGGTCTGCCATCGCTTCAGGGGTGGCCGTGAGTAAAGTCCTGCACCTG
GAAGGCGAAGTCAACAAGATCAAGTCTGCATTACTAAGTACCAATAAGGCT
GTAGTTAGCCTGTCCAATGGCGTGAGTGTGCTTACTTCTAAGGTACTGGAC
CTGAAGAACTACATCGACAAGCAACTACTACCCATTGTAAATAAGCAGTCA
TGTAGCATATCAAACATCGAGACAGTGATCGAATTTCAACAGAAGAATAAC
CGGCTGTTGGAGATAACACGGGAGTTCTCTGTAAATGCCGGCGTGACGACC
CCTGTCAGCACCTACATGCTCACGAATAGCGAGTTGCTTTCCCTGATTAAT
GATATGCCGATTACAAATGACCAGAAGAAGCTGATGAGTAATAATGTCCAA
ATTGTCCGTCAGCAGAGCTATTCGATTATGTCCATCATCAAGGAGGAAGTC
TTAGCCTATG*TGGTGCAGCTCCCCCTC*TACGGAGTGATTGACACACCGTGC
TGGAAGCTGCACACCTCCCCTTTGTGTACAACCAATACCAAGGAGGGCTCC
AACATCTGCCTTACTAGGACCGACAGGGGATGGTATTGCGACAACGCCGGG
TCCGTCTCATTTTTTCCTCAGGCGGAAACCTGTAAGGTACAGTCGAATCGA
GTGTTTTGTGACACTATGAACAGCCTGACCTTGCCTAGCGAGGTGAATCTG
TGTAACGTTGATATCTTCAACCCTAAGTATGACTGTAAGATCATGACTTCA
AAAACTGATGTCTCCTCAAGCGTGATCACCTCTTTGGGCGCCATCGTGTCA
TGCTACGGAAAGACGAAGTGCACCGCCTCTAACAAGAACCGAGGGATCATC
AAAACATTCTCCAATGGCTGTGATTACGTCAGTAACAAAGGTGTGGACACA
GTCTCCGTGGGCAATACGTTATATTATGTGAATAAGCAGGAGGGAAAAAGT
CTCTATGTGAAGGGTGAACCGATAATCAATTTCTACGATCCCTTGGTGTTT
CCAAGCGACGAGTTCGACGCCTCGATCAGCCAGGTGAACGAGAAAATCAAC
CAGTCTTTGGCATTCATCCGCAAGAGCGACGAGCTACTGCATAACGTGAAC
GCAGGCAAGAGTACTACCAAT

The underlined region represents a region coding for human Igκ signal peptide. The underlined region can be substituted with alternative sequences which achieve a same or similar function, or can be deleted.

(SEQ ID NO: 24)

METPAQLLFLLLLWLPDTTGFASGQNITEEFYQSTCSAVSKGYLSALRTGW
YTSVITIELSNIKKNKCNGTDAKVKLIKQELDKYKNAVTELQLLMQSTQAT
NNRARQQQQRFLGFLLGVGSAIASGVAVSKVLHLEGEVNKIKSALLSTNKA
VVSLSNGVSVLTSKVLDLKNYIDKQLLPIVNKQSCSISNIETVIEFQQKNN
RLLEITREFSVNAGVTTPVSTYMLTNSELLSLINDMPITNDQKKLMSNNVQ
IVRQQSYSIMSIIKEEVLAYVVQLPLYGVIDTPCWKLHTSPLCTTNTKEGS
NICLTRTDRGWYCDNAGSVSFFPQAETCKVQSNRVFCDTMNSLTLPSEVNL
CNVDIFNPKYDCKIMTSKTDVSSSVITSLGAIVSCYGKTKCTASNKNRGII
KTFSNGCDYVSNKGVDTVSVGNTLYYVNKQEGKSLYVKGEPIINFYDPLVF
PSDEFDASISQVNEKINQSLAFIRKSDELLHNVNAGKSTTN

The underlined region represents human Igκ signal peptide. The underlined region can be substituted with alternative sequences which achieve a same or similar function, or can be deleted, as shown below.

(SEQ ID NO: 298)

FASGQNITEEFYQSTCSAVSKGYLSALRTGWYTSVITIELSNIKKNKCNGT
DAKVKLIKQELDKYKNAVTELQLLMQSTQATNNRARQQQQRFLGFLLGVGS
AIASGVAVSKVLHLEGEVNKIKSALLSTNKAVVSLSNGVSVLTSKVLDLKN
YIDKQLLPIVNKQSCSISNIETVIEFQQKNNRLLEITREFSVNAGVTTPVS
TYMLTNSELLSLINDMPITNDQKKLMSNNVQIVRQQSYSIMSIIKEEVLAY
VVQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKTD
VSSSVITSLGAIVSCYGKTKCTASNKNRGIIKTFSNGCDYVSNKGVDTVSV
GNTLYYVNKQEGKSLYVKGEPIINFYDPLVFPSDEFDASISQVNEKINQSL
AFIRKSDELLHNVNAGKSTTN

MRK-14 MRK-6 construct modified to include an Ig secretion peptide signal sequence:

(SEQ ID NO: 25)

ATGGAGACTCCCGCTCAGTTGTTGTTCCTGCTACTGCTGTGGCTGCCTGAT
ACAACCGGATTTGCTAGTGGGCAGAATATCACCGAAGAATTCTATCAGAGC
ACTTGCAGTGCAGTGTCCAAAGGATATTTGAGCGCCCTGCGCACTGGGTGG
TACACAAGTGTCATCACAATCGAGCTAAGTAACATTAAAAAAAACAAATGC
AACGGGACTGACGCAAAGGTCAAACTCATTAAGCAAGAACTTGACAAATAT
AAGAACGCTGTTACAGAGTTGCAGCTGCTAATGCAAAGCACTCAGGCTACC
AATAACCGAGCGAGACAGCAGCAGCAACGTTTCCTGGGTTTCCTGTTAGGT
GTGGGTAGCGCAATTGCCAGTGGTGTAGCCGTGTCCAAGGTGCTGCACCTG
GAAGGGGAAGTGAATAAGATCAAGTCTGCACTGCTGTCCACCAATAAGGCG
GTCGTTTCGCTGTCTAACGGCGTCTCGGTCCTAACAAGTAAAGTTCTGGAT

-continued

TTAAAGAACTATATTGATAAGCAATTGCTGCCTATCGTAAATAAGCAGAGT
TGCAGCATTAGCAATATCGAGACAGTGATAGAATTTCAGCAAAAGAACAAT
CGATTACTCGAAATCACACGCGAATTCAGTGTCAATGCCGGGGTTACAACC
CCTGTGTCGACCTACATGCTTACCAATTCCGAGCTTCTGTCTCTTATTAAC
GATATGCCCATCACGAACGATCAGAAGAAACTGATGTCAAATAACGTCCAA
ATTGTGCGGCAGCAAAGCTACAGTATCATGAGCATCATCAAAGAGGAGGTG
CTCGCCTATGTGGTCCAATTGCCGCTATACGGGGTCATTGATACACCCTGT
TGGAAGCTCCATACATCCCCACTTTGTACAACGAATACCAAGGAGGGGTCT
AACATTTGTCTGACCCGGACCGACAGAGGCTGGTATTGCGATAATGCTGGA
AGCGTTAGTTTCTTTCCTCAGGCAGAAACATGCAAGGTGCAGTCAAACAGA
GTTTTCTGTGACACCATGAATTCCTTGACGCTGCCTTCAGAAGTGAATCTG
TGTAACGTGGATATCTTTAATCCGAAGTACGATTGTAAAATTATGACTAGC
AAGACAGATGTCTCGTCCTCTGTGATCACTAGCCTGGGAGCGATTGTGAGC
TGTTATGGTAAAACAAAGTGTACTGCTAGCAATAAGAACAGGGGGATTATC
AAAACGTTCAGTAACGGCTGTGATTACGTATCCAACAAGGGGGTGGACACC
GTGTCAGTCGGGAACACGCTCTACTACGTGAACAAGCAGGAAGGTAAGTCG
CTATACGTGAAGGGGGAACCCATAATCAATTTCTACGATCCGCTCGTGTTT
CCTAGCGACGAATTCGACGCATCTATCAGCCAGGTGAACGAGAAGATCAAT
CAGAGTCTGGCCTTCATCCGCAAGTCCGACGAGCTGCTTAGTGCTATCGGA
GGTTATATCCCTGAGGCCCCGAGGGACGGCCAAGCGTATGTGAGAAAGGAC
GGGGAATGGGTACTGTTGTCAACTTTCCTA

The first underlined region represents a region coding for human Igκ signal peptide, the second underlined region represents a region coding for a foldon. The underlined regions can be substituted with alternative sequences which achieves same or similar functions, or can be deleted.

(SEQ ID NO: 26)

METPAQLLFLLLLWLPDTTGFASGQNITEEFYQSTCSAVSKGYLSALRTGW
YTSVITIELSNIKKNKCNGTDAKVKLIKQELDKYKNAVTELQLLMQSTQAT
NNRARQQQQRFLGFLLGVGSAIASGVAVSKVLHLEGEVNKIKSALLSTNKA
VVSLSNGVSVLTSKVLDLKNYIDKQLLPIVNKQSCSISNIETVIEFQQKNN
RLLEITREFSVNAGVTTPVSTYMLTNSELLSLINDMPITNDQKKLMSNNVQ
IVRQQSYSIMSIIKEEVLAYVVQLPLYGVIDTPCWKLHTSPLCTTNTKEGS
NICLTRTDRGWYCDNAGSVSFFPQAETCKVQSNRVFCDTMNSLTLPSEVNL
CNVDIFNPKYDCKIMTSKTDVSSSVITSLGAIVSCYGKTKCTASNKNRGII
KTFSNGCDYVSNKGVDTVSVGNTLYYVNKQEGKSLYVKGEPIINFYDPLVF
PSDEFDASISQVNEKINQSLAFIRKSDELLSAIGGYIPEAPRDGQAYVRKD
GEWVLLSTFL

The first underlined region represents human Igκ signal peptide, second underlined region represents a foldon. The underlined regions can be substituted with alternative sequences which achieves same or similar functions, or can be deleted, as shown below.

(SEQ ID NO: 299)
FASGQNITEEFYQSTCSAVSKGYLSALRTGWYTSVITIELSNIKKNKCNGT

DAKVKLIKQELDKYKNAVTELQLLMQSTQATNNRARQQQQRFLGFLLGVGS

AIASGVAVSKVLHLEGEVNKIKSALLSTNKAVVSLSNGVSVLTSKVLDLKN

YIDKQLLPIVNKQSCSISNIETVIEFQQKNNRLLEITREFSVNAGVTTPVS

TYMLTNSELLSLINDMPITNDQKKLMSNNVQIVRQQSYSIMSIIKEEVLAY

VVQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKTD

VSSSVITSLGAIVSCYGKTKCTASNKNRGIIKTFSNGCDYVSNKGVDTVSV

GNTLYYVNKQEGKSLYVKGEPIINFYDPLVFPSDEFDASISQVNEKINQSL

AFIRKSDELL

MRK-16 MRK-8 construct modified to include an Ig secretion peptide signal sequence:

(SEQ ID NO: 27)
ATGGAGACACCTGCCCAACTTCTGTTCCTTCTTTTGCTCTGGCTGCCTGA

CACAACCGGCTTCGCATCTTCACAAAACATCACGGAAGAGTTTTACCAGA

GCACATGCTCCGCGGTCTCTAAAGGCTATCTTTCTGCCCTGCGGACTGGC

TGGTATACCAGCGTCATCACCATAGAGCTGTCAAACATCAAGGAGAACAA

GTGTAACGGCACTGACGCCAAGGTCAAGCTTATAAAGCAGGAACTGGACA

AGTATAAGAGTGCTGTTACCGAGCTCCAGTTGCTTATGCAGTCCACCCCC

GCAACAAACAATAAATTTCTGGGCTTTCTACAGGGCGTCGGAAGCGCCAT

CGCAAGCGGCATCGCTGTGAGCAAGGTGTTGCATCTGGAGGGAGAGGTGA

ATAAGATAAAGAGTGCTCTGCTTTCCACTAACAAAGCCGTGGTGAGCCTG

AGCAATGGCGTATCTGTTCTGACTTCTAAAGTCCTGGATCTCAAGAACTA

TATCGACAAGCAGCTCTTGCCCATTGTCAACAAACAGTCCTGCTCCATTT

CCAATATTGAGACCGTCATTGAGTTCCAACAGAAGAATAACCGTTTGCTG

GAAATTACAAGGGAATTCAGTGTTAATGCCGGTGTAACCACCCCTGTGAG

CACCTATATGCTCACCAACTCTGAACTGCTGAGTCTGATTAACGATATGC

CCATTACTAATGATCAGAAGAAACTAATGAGTAACAATGTCCAGATAGTT

CGGCAGCAGTCATATTCCATTATGAGTATAATCAAGGAGGAAGTGCTAGC

CTACGTAGTTCAGCTCCCCCTCTACGGCGTTATAGACACGCCATGTTGGA

AGCTGCATACGAGTCCTCTGTGCACTACAAATACCAAGGAGGGCAGTAAC

ATATGCTTGACTAGAACTGATAGAGGCTGGTACTGCGACAATGCAGGCTC

CGTGTCATTCTTTCCTCTCGCCGAGACGTGTAAAGTGCAGAGTAACAGAG

TGTTTTGTGACACAATGAACTCATTGACCCTGCCTAGCGAAGTGAACTTA

TGCAACATCGACATTTTTAACCCAAAATACGATTGCAAGATTATGACCTC

TAAGACTGACGTATCTTCATCCGTCATAACTTCTCTAGGAGCGATCGTGA

GCTGCTACGGTAAGACTAAATGCACGGCTAGTAATAAAAATAGAGGTATC

ATTAAGACTTTTAGTAACGGTTGCGATTATGTGTCAAACAAGGGAGTCGA

CACTGTTTCAGTGGGCAATACTCTCTACTACGTTAACAAACAGGAGGGTA

AATCCCTTTATGTGAAAGGGGAACCCATCATTAATTTTTATGACCCACTT

-continued

GTGTTTCCTAGTGACGAGTTTGACGCTTCAATCAGTCAAGTGAACGAAAA

AATTAATGGCACGCTCGCGTTTATCAGGAAAAGCGACGAGAAGCTGCATA

ACGTGGAAGATAAGATCGAGGAGATTCTCTCGAAAATTTATCATATAGAG

AATGAAATCGCAAGAATCAAAAAGCTTATTGGGGAG

The first underlined region represents a region coding for human Igκ signal peptide, the second underlined region represents a region coding for GCN4. The underlined regions can be substituted with alternative sequences which achieves same or similar functions, or can be deleted.

(SEQ ID NO: 28)
METPAQLLFLLLLWLPDTTGFASSQNITEEFYQSTCSAVSKGYLSALRT

GWYTSVITIELSNIKENKCNGTDAKVKLIKQELDKYKSAVTELQLLMQS

TPATNNKFLGFLQGVGSAIASGIAVSKVLHLEGEVNKIKSALLSTNKAV

VSLSNGVSVLTSKVLDLKNYIDKQLLPIVNKQSCSISNIETVIEFQQKN

NRLLEITREFSVNAGVTTPVSTYMLTNSELLSLINDMPITNDQKKLMSN

NVQIVRQQSYSIMSIIKEEVLAYVVQLPLYGVIDTPCWKLHTSPLCTTN

TKEGSNICLTRTDRGWYCDNAGSVSFFPLAETCKVQSNRVFCDTMNSLT

LPSEVNLCNIDIFNPKYDCKIMTSKTDVSSSVITSLGAIVSCYGKTKCT

ASNKNRGIIKTFSNGCDYVSNKGVDTVSVGNTLYYVNKQEGKSLYVKGE

PIINFYDPLVFPSDEFDASISQVNEKINGTLAFIRKSDEKLHNVEDKIE

EILSKIYHIENEIARIKKLIGE

The first underlined region represents human Igκ signal peptide, second underlined region represents GCN4. The underlined regions can be substituted with alternative sequences which achieves same or similar functions, or can be deleted, as shown below.

(SEQ ID NO: 300)
FASSQNITEEFYQSTCSAVSKGYLSALRTGWYTSVITIELSNIKENKCNG

TDAKVKLIKQELDKYKSAVTELQLLMQSTPATNNKFLGFLQGVGSAIASG

IAVSKVLHLEGEVNKIKSALLSTNKAVVSLSNGVSVLTSKVLDLKNYIDK

QLLPIVNKQSCSISNIETVIEFQQKNNRLLEITREFSVNAGVTTPVSTYM

LTNSELLSLINDMPITNDQKKLMSNNVQIVRQQSYSIMSIIKEEVLAYVV

QLPLYGVIDTPCWKLHTSPLCTTNTKEGSNICLTRTDRGWYCDNAGSVSF

FPLAETCKVQSNRVFCDTMNSLTLPSEVNLCNIDIFNPKYDCKIMTSKTD

VSSSVITSLGAIVSCYGKTKCTASNKNRGIIKTFSNGCDYVSNKGVDTVS

VGNTLYYVNKQEGKSLYVKGEPIINFYDPLVFPSDEFDASISQVNEKING

TLAFIRKSDEKLHN.

The protein vaccine evaluated in this study was DS-CAV1 stabilized prefusion F protein (1 mg/mL), as described in McLellan et al. *Science* 342, 592 (2013). The protein was buffered in 50 mM Hepes, 300 mM NaCl and was formulated with Adju-phos.

Briefly, groups of 10 mice were immunized intramuscularly with the following vaccines:

| Group | N | Vaccine | Concentration (μg/ml) | Total dose/ mouse (μg) |
|---|---|---|---|---|
| 1 | 10 | mF (MRK-1) | 100 | 10 |
| 3 | " | mDS-CAV1 (MRK-4) | 100 | 10 |
| 4 | " | MRK-5 | 100 | 10 |
| 5 | " | MRK-6 | 100 | 10 |
| 6 | " | MRK-7 | 100 | 10 |
| 7 | " | MRK-8 | 100 | 10 |
| 8 | " | mG (MRK-9) | 100 | 10 |
| 9 | " | IgSP_sF (MRK-11) | 100 | 10 |
| 10 | " | IgSP_sDS-CAV1 (MRK-12) | 100 | 10 |
| 11 | " | MRK-13 | 100 | 10 |
| 12 | " | MRK-14 | 100 | 10 |
| 14 | " | MRK-16 | 100 | 10 |
| 15 | " | DS-CAV1 protein/adju phos | 100 | 10 |
| 16 | 10 | mF (MRK-1) | 20 | 2 |
| 18 | " | mDS-CAV1 (MRK-4) | 20 | 2 |
| 19 | " | MRK-5 | 20 | 2 |
| 20 | " | MRK-6 | 20 | 2 |
| 21 | " | MRK-7 | 20 | 2 |
| 22 | " | MRK-8 | 20 | 2 |
| 23 | " | mG (MRK-9) | 20 | 2 |
| 24 | " | IgSP_sF (MRK-11) | 20 | 2 |
| 25 | " | IgSP_sDS-CAV1 (MRK-12) | 20 | 2 |
| 26 | " | MRK-13 | 20 | 2 |
| 27 | " | MRK-14 | 20 | 2 |
| 29 | " | MRK-16 | 20 | 2 |
| 30 | " | DS-CAV1 protein/adju phos | 20 | 2 |
| 31 | " | naive | | |

The animals were immunized on day 0 and day 21 of the experiment. On days 14 and 35, blood was drawn from each animal and used for serological assays. On days 42 and 49, a subset of the animals were sacrificed and spleens were harvested to support ELISPOT and intracellular cytokine staining studies.

A. RSV Neutralization Assay:

Mouse sera from each group were pooled and evaluated for neutralization of RSV-A (Long strain) using the following procedures:

1. All sera samples were heat inactivated by placing in dry bath incubator set at 56° C. for 30 minutes. Samples and control sera were then diluted 1:3 in virus diluent (2% FBS in EMEM) and duplicate samples were added to an assay plate and serially diluted.
2. RSV-Long stock virus was removed from the freezer and quickly thawed in 37° C. water bath. Viruses were diluted to 2000 pfu/mL in virus diluent
3. Diluted virus was added to each well of the 96-well plate, with the exception of one column of cells.
4. HEp-2 cells were trypsinized, washed, resuspended at $1.5\times10^5$ cells/ml in virus diluent, and 100 mL of the suspended cells were added to each well of the 96-well plate. The plates were then incubated for 72 hours at 37° C., 5% $CO_2$.
5. Following the 72 hour incubation, the cells were washed with PBS, and fixed using 80% acetone dissolved in PBS for 10-20 minutes at 16-24° C. The fixative was removed and the plates were allowed to air-dry.
6. Plates were then washed thoroughly with PBS+0.05% Tween. The detections monoclonal antibodies, 143-F3-1B8 and 34C9 were diluted to 2.5 plates were then washed thoroughly with PBS+0.05%. 50 plates were then washed thoroughly with PBS+0.well of the 96-well plate. The plates were then incubated in a humid chamber at 16-24° C. for 60-75 minutes on rocker
7. Following the incubation, the plates were thoroughly washed.

8. Biotinylated horse anti-mouse IgG was diluted 1:200 in assay diluent and added to each well of the 96-well plate. Plates were incubated as above and washed.
9. A cocktail of IRDye 800CW Streptavidin (1:1000 final dilution), Sapphire 700 (1:1000 dilution) and 5 mM DRAQS solution (1:10,000 dilution) was prepared in assay diluent and 50 mL of the cocktail was added to each well of the 96-well plate. Plates were incubated as above in the dark, washed, and allowed to air dry.
10. Plates were then read using an Aerius Imager. Serum neutralizing titers were then calculated using a 4 parameter curve fit in Graphpad Prism.

The serum neutralizing antibody titers for the mouse immunogenicity study measured post dose 1 (PD1) and post dose 2 (PD2) are shown in FIG. 1. The PD2 serum neutralizing antibody titers are also provided in tabular form below:

| Description | 10 μg dose | 2 μg dose |
|---|---|---|
| mF (MRK-1) | 4075 | 1391 |
| mDS-CAV1 (MRK-4) | 3160 | 846 |
| MRK-5 | 600 | 331 |
| MRK-6 | 465 | 178 |
| MRK-7 | 2259 | 2168 |
| MRK-8 | 2318 | 656 |
| mG (MRK-9) | 86 | 39 |
| IgSP_sF (MRK-11) | 4559 | 3597 |
| IgSP_sDS-CAV1 (MRK-12) | 3458 | 2007 |
| MRK-13 | 750 | 269 |
| MRK-14 | 471 | 116 |
| MRK-16 | 1077 | 1088 |
| DS-CAV1 protein/adju phos | 692 | 1166 |
| Naive | | <4 |

The results indicated that the neutralizing antibody titers are robust and several of the mRNA vaccines, including the RSV mF vaccine and the RSVmDS-CAV1 mRNA vaccine elicited neutralizing antibody titers higher than DS-CAV1 protein/adjuv-phos vaccine.

B. Assays for Cellular Immune Response:

Mouse IFN-γ ELISPOT Assay Procedures

I. Preparation of Splenocytes:

Spleens were placed in a 60-mm tissue culture dish and palpated up and down with a syringe handle to remove the cells. Minced spleens were then transferred to 15-mL tubes, centrifuged at 1200 rpm for 10 min, resuspended in an Ammonium-Chloride-Potassium (ACK) Lysing Buffer and incubated at room temperature for 5 minutes. R10 media was added to the tubes and cells were centrifuged at 1200 rpm for 10 minutes, and then washed once more with R10 media. Following a second centrifugation, the cells were resuspended in 10 mL of R10 media and filtered through a 70 μm nylon cell strainer into a 50 mL centrifuge tube. The strainer was rinsed with an additional 10 mL of media and this was added to the cells. The cells were counted on a hemocytometer and the cell concentration was normalized across the groups.

II. ELISPOT Assay:

1) 96-well MultiScreen-IP sterile white filtration plates were coated with MABTECH purified anti-mouse IFN-γ, clone AN18 at 10 μg/ml PBS in Bio-Hood (1:100 dilution) and incubated at 4° C. overnight
2) The following morning, the plates were washed with sterile PBS and blocked with R10 medium at 37° C. for 4 hrs.

3) Splenocytes were added to the plate at $4\times10^5$ cells/well, and the cells were stimulated with peptide pools for RSV-F and RSV-G. The peptide pools were as follows.

For RSV-F:

| Sequence = sequence in FM | peptide ID | SEQ ID No: |
|---|---|---|
| MELPILKANAITTIL | RSV_F_1-15 | 29 |
| ILKANAITTILTAVT | RSV_F_5-19 | 30 |
| NAITTILTAVTFCFA | RSV_F_9-23 | 31 |
| TILTAVTFCFASSQN | RSV_F_13-27 | 32 |
| AVTFCFASSQNITEE | RSV_F_17-31 | 33 |
| CFASSQNITEEFYQS | RSV_F_21-35 | 34 |
| SQNITEEFYQSTCSA | RSV_F_25-39 | 35 |
| TEEFYQSTCSAVSKG | RSV_F_29-43 | 36 |
| YQSTCSAVSKGYLSA | RSV_F_33-47 | 37 |
| CSAVSKGYLSALRTG | RSV_F_37-51 | 38 |
| SKGYLSALRTGWYTS | RSV_F_41-55 | 39 |
| LSALRTGWYTSVITI | RSV_F_45-59 | 40 |
| RTGWYTSVITIELSN | RSV_F_49-63 | 41 |
| YTSVITIELSNIKEN | RSV_F_53-67 | 42 |
| ITIELSNIKENKCNG | RSV_F_57-71 | 43 |
| LSNIKENKCNGTDAK | RSV_F_61-75 | 44 |
| KENKCNGTDAKVKLI | RSV_F_65-79 | 45 |
| CNGTDAKVKLIKQEL | RSV_F_69-83 | 46 |
| DAKVKLIKQELDKYK | RSV_F_73-87 | 47 |
| KLIKQELDKYKNAVT | RSV_F_77-91 | 48 |
| QELDKYKNAVTELQL | RSV_F_81-95 | 49 |
| KYKNAVTELQLLMQS | RSV_F_85-99 | 50 |
| AVTELQLLMQSTPAA | RSV_F_89-103 | 51 |
| LQLLMQSTPAANNRA | RSV_F_93-107 | 52 |
| MQSTPAANNRARREL | RSV_F_97-111 | 53 |
| PAANNRARRELPRFM | RSV_F_101-115 | 54 |
| NRARRELPRFMNYTL | RSV_F_105-119 | 55 |
| RELPRFMNYTLNNAK | RSV_F_109-123 | 56 |
| RFMNYTLNNAKKTNV | RSV_F_113-127 | 57 |
| YTLNNAKKTNVTLSK | RSV_F_117-131 | 58 |
| NAKKTNVTLSKKRKR | RSV_F_121-135 | 59 |
| TNVTLSKKRKRRFLG | RSV_F_125-139 | 60 |
| LSKKRKRRFLGFLLG | RSV_F_129-143 | 61 |
| RKRRFLGFLLGVGSA | RSV_F_133-147 | 62 |
| FLGFLLGVGSAIASG | RSV_F_137-151 | 63 |
| LLGVGSAIASGIAVS | RSV_F_141-155 | 64 |
| GSAIASGIAVSKVLH | RSV_F_145-159 | 65 |
| ASGIAVSKVLHLEGE | RSV_F_149-163 | 66 |
| AVSKVLHLEGEVNKI | RSV_F_153-167 | 67 |
| VLHLEGEVNKIKSAL | RSV_F_157-171 | 68 |
| EGEVNKIKSALLSTN | RSV_F_161-175 | 69 |
| NKIKSALLSTNKAVV | RSV_F_165-179 | 70 |
| SALLSTNKAVVSLSN | RSV_F_169-183 | 71 |
| STNKAVVSLSNGVSV | RSV_F_173-187 | 72 |
| AVVSLSNGVSVLTSK | RSV_F_177-191 | 73 |
| LSNGVSVLTSKVLDL | RSV_F_181-195 | 74 |
| VSVLTSKVLDLKNYI | RSV_F_185-199 | 75 |
| TSKVLDLKNYIDKQL | RSV_F_189-203 | 76 |
| LDLKNYIDKQLLPIV | RSV_F_193-207 | 77 |
| NYIDKQLLPIVNKQS | RSV_F_197-211 | 78 |
| KQLLPIVNKQSCSIS | RSV_F_201-215 | 79 |
| PIVNKQSCSISNIET | RSV_F_205-219 | 80 |
| KQSCSISNIETVIEF | RSV_F_209-223 | 81 |
| SISNIETVIEFQQKN | RSV_F_213-227 | 82 |
| IETVIEFQQKNNRLL | RSV_F_217-231 | 83 |
| IEFQQKNNRLLEITR | RSV_F_221-235 | 84 |
| QKNNRLLEITREFSV | RSV_F_225-239 | 85 |
| RLLEITREFSVNAGV | RSV_F_229-243 | 86 |
| ITREFSVNAGVTTPV | RSV_F_233-247 | 87 |
| FSVNAGVTTPVSTYM | RSV_F_237-251 | 88 |
| AGVTTPVSTYMLTNS | RSV_F_241-255 | 89 |
| TPVSTYMLTNSELLS | RSV_F_245-259 | 90 |
| TYMLTNSELLSLIND | RSV_F_249-263 | 91 |
| TNSELLSLINDMPIT | RSV_F_253-267 | 92 |
| LLSLINDMPITNDQK | RSV_F_257-271 | 93 |
| INDMPITNDQKKLMS | RSV_F_261-275 | 94 |
| PITNDQKKLMSNNVQ | RSV_F_265-279 | 95 |
| DQKKLMSNNVQIVRQ | RSV_F_269-283 | 96 |
| LMSNNVQIVRQQSYS | RSV_F_273-287 | 97 |
| NVQIVRQQSYSIMSI | RSV_F_277-291 | 98 |
| VRQQSYSIMSIIKKE | RSV_F_281-295 | 99 |
| SYSIMSIIKKEVLAY | RSV_F_285-299 | 100 |
| MSIIKKEVLAYVVQL | RSV_F_289-303 | 101 |
| KKEVLAYVVQLPLYG | RSV_F_293-307 | 102 |

-continued

| Sequence = sequence in FM | peptide ID | SEQ ID No: |
|---|---|---|
| LAYVVQLPLYGVIDT | RSV_F_297-311 | 103 |
| VQLPLYGVIDTPCWK | RSV_F_301-315 | 104 |
| LYGVIDTPCWKLHTS | RSV_F_305-319 | 105 |
| IDTPCWKLHTSPLCT | RSV_F_309- 323 | 106 |
| CWKLHTSPLCTTNTK | RSV_F_313-327 | 107 |
| HTSPLCTTNTKEGSN | RSV_F_317-331 | 108 |
| LCTTNTKEGSNICLT | RSV_F_321-335 | 109 |
| NTKEGSNICLTRTDR | RSV_F_325-339 | 110 |
| GSNICLTRTDRGWYC | RSV_F_329-343 | 111 |
| CLTRTDRGWYCDNAG | RSV_F_333-347 | 112 |
| TDRGWYCDNAGSVSF | RSV_F_337-351 | 113 |
| WYCDNAGSVSFFPQA | RSV_F_341-355 | 114 |
| NAGSVSFFPQAETCK | RSV_F_345-359 | 115 |
| VSFFPQAETCKVQSN | RSV_F_349-363 | 116 |
| PQAETCKVQSNRVFC | RSV_F_353-367 | 117 |
| TCKVQSNRVFCDTMN | RSV_F_357-371 | 118 |
| QSNRVFCDTMNSLTL | RSV_F_361-375 | 119 |
| VFCDTMNSLTLPSEV | RSV_F_365-379 | 120 |
| TMNSLTLPSEVNLCN | RSV_F_369-383 | 121 |
| LTLPSEVNLCNVDIF | RSV_F_373-387 | 122 |
| SEVNLCNVDIFNPKY | RSV_F_377-391 | 123 |
| LCNVDIFNPKYDCKI | RSV_F_381-395 | 124 |
| DIFNPKYDCKIMTSK | RSV_F_385-399 | 125 |
| PKYDCKIMTSKTDVS | RSV_F_389-403 | 126 |
| CKIMTSKTDVSSSVI | RSV_F_393-407 | 127 |
| TSKTDVSSSVITSLG | RSV_F_397-411 | 128 |
| DVSSSVITSLGAIVS | RSV_F_401-415 | 129 |
| SVITSLGAIVSCYGK | RSV_F_405-419 | 130 |
| SLGAIVSCYGKTKCT | RSV_F_409-423 | 131 |
| IVSCYGKTKCTASNK | RSV_F_413-427 | 132 |
| YGKTKCTASNKNRGI | RSV_F_417-431 | 133 |
| KCTASNKNRGIIKTF | RSV_F_421-435 | 134 |
| SNKNRGIIKTFSNGC | RSV_F_425-439 | 135 |
| RGIIKTFSNGCDYVS | RSV_F_429-443 | 136 |
| KTFSNGCDYVSNKGV | RSV_F_433-447 | 137 |
| NGCDYVSNKGVDTVS | RSV_F_437-451 | 138 |
| YVSNKGVDTVSVGNT | RSV_F_441-455 | 139 |
| KGVDTVSVGNTLYYV | RSV_F_445-459 | 140 |

-continued

| Sequence = sequence in FM | peptide ID | SEQ ID No: |
|---|---|---|
| TVSVGNTLYYVNKQE | RSV_F_449-463 | 141 |
| GNTLYYVNKQEGKSL | RSV_F_453-467 | 142 |
| YYVNKQEGKSLYVKG | RSV_F_457-471 | 143 |
| KQEGKSLYVKGEPII | RSV_F_461-475 | 144 |
| KSLYVKGEPIINFYD | RSV_F_465-479 | 145 |
| VKGEPIINFYDPLVF | RSV_F_469-483 | 146 |
| PIINFYDPLVFPSGE | RSV_F_473-487 | 147 |
| FYDPLVFPSGEFDAS | RSV_F_477-491 | 148 |
| LVFPSGEFDASISQV | RSV_F_481-495 | 149 |
| SGEFDASISQVNEKI | RSV_F_485-499 | 150 |
| DASISQVNEKINQSL | RSV_F_489-503 | 151 |
| SQVNEKINQSLAFIR | RSV_F_493-507 | 152 |
| EKINQSLAFIRKSDE | RSV_F_497-511 | 153 |
| QSLAFIRKSDELLHN | RSV_F_501-515 | 154 |
| FIRKSDELLHNVNAG | RSV_F_505-519 | 155 |
| SDELLHNVNAGKSTT | RSV_F_509-523 | 156 |
| LHNVNAGKSTTNIMI | RSV_F_513-527 | 157 |
| NAGKSTTNIMITAII | RSV_F_517-531 | 158 |
| STTNIMITAIIIVIV | RSV_F_521-535 | 159 |
| IMITAIIIVIVVILL | RSV_F_525-539 | 160 |
| AIIIVIVVILLSLIA | RSV_F_529-543 | 161 |
| VIVVILLSLIAVGLL | RSV_F_533-547 | 162 |
| ILLSLIAVGLLLYCK | RSV_F_537-551 | 163 |
| LIAVGLLLYCKARST | RSV_F_541-555 | 164 |
| GLLLYCKARSTPVTL | RSV_F_545-559 | 165 |
| YCKARSTPVTLSKDQ | RSV_G_549-563 | 166 |
| RSTPVTLSKDQLSGI | RSV_F_553-567 | 167 |
| VTLSKDQLSGINNIA | RSV_F_557-571 | 168 |
| KDQLSGINNIAFSN | RSV_F_561-574 | 169 |

For RSV-G:

| Sequence | peptide ID | SEQ ID No: |
|---|---|---|
| MSKNKDQRTAKTLER | RSV_G_1-15 | 170 |
| KDQRTAKTLERTWDT | RSV_G_5-19 | 171 |
| TAKTLERTWDTLNHL | RSV_G_9-23 | 172 |
| LERTWDTLNHLLFIS | RSV_G_13-27 | 173 |
| WDTLNHLLFISSCLY | RSV_G_17-31 | 174 |
| NHLLFISSCLYKLNL | RSV_G_21-35 | 175 |

-continued

| Sequence | peptide ID | SEQ ID No: |
|---|---|---|
| FISSCLYKLNLKSVA | RSV_G_25-39 | 176 |
| CLYKLNLKSVAQITL | RSV_G_29-43 | 177 |
| LNLKSVAQITLSILA | RSV_G_33-47 | 178 |
| SVAQITLSILAMIIS | RSV_G_37-51 | 179 |
| ITLSILAMIISTSLI | RSV_G_41-55 | 180 |
| ILAMIISTSLIIAAI | RSV_G_45-59 | 181 |
| IISTSLIIAAIIFIA | RSV_G_49-63 | 182 |
| SLIIAAIIFIASANH | RSV_G_53-67 | 183 |
| AAIIFIASANHKVTS | RSV_G_57-71 | 184 |
| FIASANHKVTSTTTI | RSV_G_61-75 | 185 |
| ANHKVTSTTTIIQDA | RSV_G_65-79 | 186 |
| VTSTTTIIQDATSQI | RSV_G_69-83 | 187 |
| TTIIQDATSQIKNTT | RSV_G_73-87 | 188 |
| QDATSQIKNTTPTYL | RSV_G_77-91 | 189 |
| SQIKNTTPTYLTQSP | RSV_G_81-95 | 190 |
| NTTPTYLTQSPQLGI | RSV_G_85-99 | 191 |
| TYLTQSPQLGISPSN | RSV_G_89-103 | 192 |
| QSPQLGISPSNPSEI | RSV_G_93-107 | 193 |
| LGISPSNPSEITSQI | RSV_G_97-111 | 194 |
| PSNPSEITSQITTIL | RSV_G_101-115 | 195 |
| SEITSQITTILASTT | RSV_G_105-119 | 196 |
| SQITTILASTTPGVK | RSV_G_109-123 | 197 |
| TILASTTPGVKSTLQ | RSV_G_113-127 | 198 |
| STTPGVKSTLQSTTV | RSV_G_117-131 | 199 |
| GVKSTLQSTTVGTKN | RSV_G_121-135 | 200 |
| TLQSTTVGTKNTTTT | RSV_G_125-139 | 201 |
| TTVGTKNTTTTQAQP | RSV_G_129-143 | 202 |
| TKNTTTTQAQPSKPT | RSV_G_133-147 | 203 |
| TTTQAQPSKPTTKQR | RSV_G_137-151 | 204 |
| AQPSKPTTKQRQNKP | RSV_G_141-155 | 205 |
| KPTTKQRQNKPPSKP | RSV_G_145-159 | 206 |
| KQRQNKPPSKPNNDF | RSV_G_149-163 | 207 |
| NKPPSKPNNDFHFEV | RSV_G_153-167 | 208 |
| SKPNNDFHFEVFNFV | RSV_G_157-171 | 209 |
| NDFHFEVFNFVPCSI | RSV_G_161-175 | 210 |
| FEVFNFVPCSICSNN | RSV_G_165-179 | 211 |
| NFVPCSICSNNPTCW | RSV_G_169-183 | 212 |
| CSICSNNPTCWAICK | RSV_G_173-187 | 213 |
| SNNPTCWAICKRIPN | RSV_G_177-191 | 214 |

-continued

| Sequence | peptide ID | SEQ ID No: |
|---|---|---|
| TCWAICKRIPNKKPG | RSV_G_181-195 | 215 |
| ICKRIPNKKPGKKTT | RSV_G_185-199 | 216 |
| IPNKKPGKKTTTKPT | RSV_G_189-203 | 217 |
| KPGKKTTTKPTEEPT | RSV_G_193-207 | 218 |
| KTTTKPTEEPTFKTA | RSV_G_197-211 | 219 |
| KPTEEPTFKTAKEDP | RSV_G_201-215 | 220 |
| EPTFKTAKEDPKPQT | RSV_G_205-219 | 221 |
| KTAKEDPKPQTTGSG | RSV_G_209-223 | 222 |
| EDPKPQTTGSGEVPT | RSV_G_213-227 | 223 |
| PQTTGSGEVPTTKPT | RSV_G_217-231 | 224 |
| GSGEVPTTKPTGEPT | RSV_G_221-235 | 225 |
| VPTTKPTGEPTINTT | RSV_G_225-239 | 226 |
| KPTGEPTINTTKTNI | RSV_G_229-243 | 227 |
| EPTINTTKTNITTTL | RSV_G_233-247 | 228 |
| NTTKTNITTTLLTSN | RSV_G_237-251 | 229 |
| TNITTTLLTSNTTRN | RSV_G_241-255 | 230 |
| TTLLTSNTTRNPELT | RSV_G_245-259 | 231 |
| TSNTTRNPELTSQME | RSV_G_249-263 | 232 |
| TRNPELTSQMETFHS | RSV_G_253-267 | 233 |
| ELTSQMETFHSTSSE | RSV_G_257-271 | 234 |
| QMETFHSTSSEGNPS | RSV_G_261-275 | 235 |
| FHSTSSEGNPSPSQV | RSV_G_265-279 | 236 |
| SSEGNPSPSQVSITS | RSV_G_269-283 | 237 |
| NPSPSQVSITSEYLS | RSV_G_273-287 | 238 |
| SQVSITSEYLSQPSS | RSV_G_277-291 | 239 |
| ITSEYLSQPSSPPNT | RSV_G_281-295 | 240 |
| YLSQPSSPPNTPR | RSV_G_285-297 | 241 |

4) Plates were incubated at 37° C., 5% $CO_2$ for 20-24 hrs.
5) The following day, the plates were thoroughly washed and 100 µL/well MABTECH detection antibody, clone R4-6A2 was added to 0.25 µg/ml in PBS/1% FBS (1:4000 dilution) in each well. Plates were incubated for 2 hrs and then washed thoroughly with PBS/0.05% Tween 20
6) Streptavidin-AP was diluted 1:3000 in PBS/1% FBS and 100 µL was added to each well.
7) Plates were incubated for 60 min at room temperature and washed thoroughly with PBS/Tween 20 (0.05%).
8) 100 µl of 1-STEP NBT/BCIP was added to each well, plates were held at room temperature for several minutes, washed with tap water, and allowed to dry overnight.
9) Plates were imaged using AID imager system and data were processed to calculate the number of IFN-γ secreting cells per million splenocytes.

Figure 2:
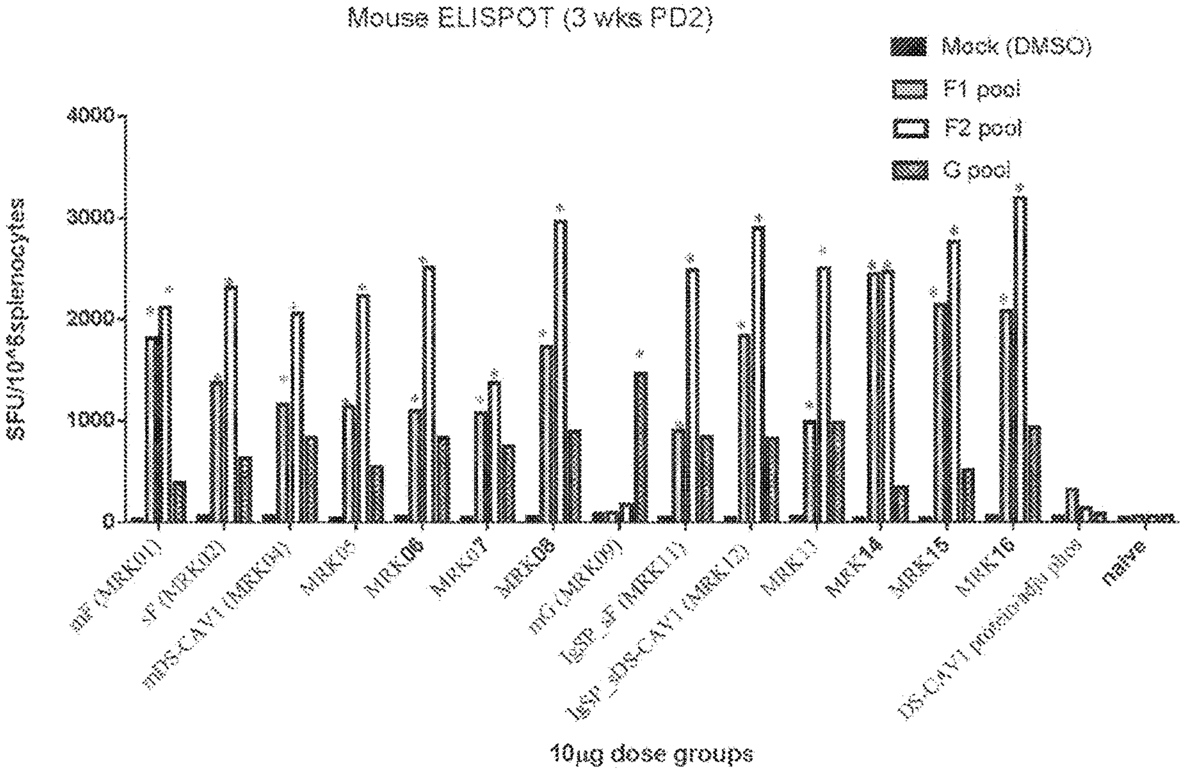
FIG. 2 shows that that RNA/LNP vaccines gave much higher cellular immune responses than the protein antigen.

The data showed that RNA/LNP vaccines gave much higher cellular immune responses than the protein antigen formulated with alum, which elicited little to no detectable cellular immune responses. See FIG. 2, where columns with a * indicate that the number of sots of interferon gamma were too high to count accurately.

III. Intracellular Cytokine Staining:

Splenocytes were harvested as described above. Freshly harvested splenocytes were rested overnight in R10 media at $1\times10^7$ cells per mL. The following morning, 100 μL of cells were added to each well according to plate template for a final number of $1\times10^6$ cells/well. Pooled RSV-F or RSV-G peptides were used to stimulate the cells. The RSV-F peptide pools were as described above. The RSV-G peptide pools were either as described above or purchased from JPT (catalog PM-RSV-MSG). Cells were incubated for 1 hr at 37° C., and BFA and monensin were added to each well to a final concentration of 5 μg each.

To stain the cells, 20 μL of 20 mM EDTA was added to each cell well, and the cells were incubated for 15 minutes at Room Temperature (RT). The plates were centrifuged at 500×g for 5 minutes and the supernatant was aspirated. The plates were then washed with PBS and centrifuged again. ViVidye was reconstituted with DMSO and diluted in PBS. 125 μL diluted Vividye was added to each well and incubated at room temperature for 15 minutes. The plates were centrifuged, the supernatant was removed and the plates were washed again with 175 μL FACSWash. A BD cytofix/cytoperm solution was added to each well, and the plates were incubated for 20-25 minutes at 2-8° C. The plates were then centrifuged and washed twice with a BD perm wash buffer. Finally, FC block was added to a final concentration of 0.01 mg/mL in a volume of 125 mL per well in the BD perm wash buffer. The cells were stained with an intracellular antibody cocktail made as follows:

a) IL-10 FITC:
b) IL-17A PE:
c) IL-2 PCF594:
d) CD4 PerCPcy5.5:
e) TNF PE Cy7:
f) IFNg APC:
g) CD8a BV510:
h) CD3 APC Cy7:
i) Perm Wash:

The cells were incubated with the antibody cocktail (20 μL per test well) at 2-8° C. for 35 minutes, washed twice with the BD perm wash buffer, and resuspended in 200 μL per well of BD stabilizing fixative. Samples were acquired on an LSRII and data were analyzed using Flojo software. The percentage of CD4+ splenocytes that respond to the peptide pools and produced IFN-γ, IL-2, or TNFα are shown in FIGS. 3A, 3B, and 3C and the percentage of CD8+ splenocytes that respond to the peptide pools and produce Ifn-γ, IL-2 or TNFα are shown in FIGS. 4A, 4B, and 4C The data were a that RSV-F mRNA/LNP vaccines and RSV-G mRNA/LNP vaccines but not DS-CAV1 protein antigens elicit robust Th1 biased CD4+ immune responses in mice. In addition, RSV-F mRNA/LNP vaccines but not RSV-G mRNA/LNP vaccines or DS-CAV1 protein antigens elicit robust Th1 biased CD8+ immune responses in mice.

Example 13: Mouse Immunogenicity

In this example, additional assays were carried out to evaluate the immune response to RSV vaccine antigens delivered using an mRNA/LNP platform in comparison to protein antigens.

Again, female Balb/c (CRL) mice (6-8 weeks old; N=10 mice per group) were administered mRNA vaccines or protein vaccines. The mRNA vaccines were generated and formulated in MC3 lipid nanoparticles. The mRNA vaccines evaluated in this study included the followings:

MRK-1 membrane-bound RSV F protein
MRK-2 secreted RSV F protein
MRK-3 secreted DS-CAV1
MRK-4 membrane-bound DS-CAV1 (stabilized prefusion F protein)
MRK-5 RSV F construct
MRK-7 RSV F construct
MRK-8 RSV F construct
MRK-9 membrane-bound RSV G protein
Influenza M1

Listed below are the DNA sequences encoding the mRNA sequences for MRK-2, MRK-3 and Influenza M1. Also shown are the corresponding amino acid sequences. All other sequences are provided elsewhere herein.

MRK-2 non-membrane bound form RSV F protein/MRK_02_F (soluble, Merck A2 strain)/

(SEQ ID NO: 242)

```
ATGGAGCTGTTGATCCTTAAGGCCAACGCCATCACTACTATTCTCACCGC
GGTAACATTCTGCTTCGCCTCCGGGCAGAACATCACCGAGGAGTTCTACC
AGTCTACGTGCTCCGCCGTCTCCAAAGGTTACCTGTCCGCATTAAGGACG
GGGTGGTACACTTCCGTCATAACTATTGAACTGAGTAACATAAAAAAGAA
CAAGTGTAATGGGACGGATGCCAAGGTGAAGCTCATCAAGCAAGAGCTTG
ACAAATACAAGAATGCAGTGACAGAGCTCCAACTTCTCATGCAGTCTACA
CAGGCCACGAATAACCGTGCCCGAAGAGAACTGCCTAGATTTATGAATTA
CACTTTGAACAACGCCAAAAAGACCAACGTGACTCTAAGCAAAAAAAGGA
AACGGCGTTTTCTGGGCTTTCTGCTGGGGGTTGGTAGCGCCATCGCATCT
GGCGTGGCAGTCAGTAAAGTTTTGCACCTTGAGGGGGAGGTCAACAAAAT
CAAGAGCGCGCTGTTATCAACAAACAAGGCAGTCGTGTCCCTCTCCAATG
GCGTGTCTGTCCTGACCTCTAAAGTACTGGATCTCAAGAACTATATCGAC
AAACAACTGCTACCAATCGTCAATAAGCAGAGTTGCTCTATTTCCAATAT
TGAGACCGTGATCGAGTTTCAACAGAAGAATAACAGATTGTTGGAGATCA
CCAGGGAATTCAGCGTCAATGCAGGGGTGACCACACCCGTATCTACCTAC
ATGCTGACCAACTCGGAACTCCTCTCCTTAATAAACGACATGCCTATTAC
TAACGACCAAAAAAAGTTGATGTCCAACAATGTCCAGATCGTGCGACAGC
AATCTTATTCAATTATGTCCATTATAAAAGAGGAGGTGCTGGCGTACGTA
GTGCAGCTGCCCCTTTACGGAGTGATCGACACCCCATGCTGGAAGCTCCA
CACCTCCCCCCTGTGCACCACTAATACCAAAGAAGGCAGCAACATCTGTC
TGACCCGTACCGACCGCGGATGGTACTGCGATAATGCAGGTAGCGTCTCT
TTTTTTCCCCAGGCTGAAACTTGCAAGGTTCAGTCCAACCGGGTATTCTG
TGACACGATGAACAGTCTCACCCTACCATCAGAGGTGAACCTGTGCAATG
TGGACATATTTAACCCTAAATATGACTGTAAGATCATGACCTCCAAAACT
GACGTTTCCAGCAGTGTCATAACCTCACTGGGCGCAATAGTTTCATGCTA
TGGAAAGACTAAGTGCACTGCCTCTAACAAAAATCGAGGTATTATTAAGA
```

-continued

CCTTTAGCAATGGCTGCGATTATGTCAGTAACAAAGGTGTTGATACAGTG
AGTGTGGGCAACACATTATACTATGTTAACAAGCAAGAAGGCAAGAGCCT
CTATGTGAAGGGAGAACCAATCATTAATTTTTACGATCCGCTGGTCTTTC
CCAGCGATGAGTTCGATGCATCCATCTCTCAGGTGAATGAAAAAATTAAC
CAATCACTGGCTTTCATACGGAAGAGCGATGAACTGCTGAGCGCCATCGG
GGGATACATCCCTGAAGCTCCGAGGGACGGCCAAGCTTATGTCCGCAAAG
ACGGAGAGTGGGTGTTGCTCAGTACCTTCCTC

The underlined region represents a region coding for a foldon. The underlined region can be substituted with alternative sequences which achieve a same or similar function.

(SEQ ID NO: 243)

MELLILKANAITTILTAVTFCFASGQNITEEFYQSTCSAVSKGYLSALRT
GWYTSVITIELSNIKKNKCNGTDAKVKLIKQELDKYKNAVTELQLLMQST
QATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLSAIGGYIPEAPRDGQAYVRKDGEWVLLSTFL

The first underlined region represents a signal peptide sequence. The first underlined regions can be substituted with alternative sequences that achieve the same or similar functions, or it can be deleted. The second underlined region represents a foldon. The second underlined region can be substituted with alternative sequences which achieve a same or similar function.

MRK-3 non-membrane bound form DS-CAV1 (stabilized prefusion F protein)//MRK_03_DS-CAV1 (soluble, S155C/S290C/S190F/V207L)/SQ-030271:

(SEQ ID NO: 244)

ATGGAACTGCTGATTCTTAAGGCGAATGCCATAACCACTATCTTGACCGC
AGTTACTTTTTGCTTCGCCTCTGGGCAGAATATTACCGAAGAGTTCTACC
AGTCCACGTGCAGTGCCGTGTCTAAGGGCTACCTTTCCGCGCTTCGCACT
GGCTGGTACACGTCAGTCATAACGATCGAACTCTCTAATATAAAGGAAAA
TAAGTGTAACGGAACAGACGCTAAGGTCAAGTTAATCAAGCAGGAGCTGG
ACAAATATAAGAATGCCGTAACGGAGCTCCAGCTGCTCATGCAGAGCACG
CCAGCTACAAACAACAGGGCACGCCGTGAGCTCCCCCGATTTATGAACTA
CACATTGAACAACGCCAAGAAAACTAACGTGACTTTGTCCAAGAAGAGGA
AGCGGCGATTCTTAGGGTTCCTTTTGGGGGTAGGCTCGGCGATTGCCAGT
GGGGTTGCCGTATGCAAGGTGCTCCACCTGGAAGGGGAGGTGAACAAGAT
TAAGTCGGCTCTGCTCAGTACAAACAAAGCTGTCGTCTCATTGTCAAACG

-continued

GAGTCAGTGTATTGACATTTAAAGTCCTCGACCTGAAGAACTATATAGAT
AAACAGTTACTCCCAATCTTGAATAAGCAGTCCTGTAGCATCAGCAACAT
TGAGACAGTGATCGAGTTCCAGCAGAAGAATAATCGCCTACTCGAGATCA
CCAGAGAATTCTCAGTCAATGCCGGAGTAACCACTCCTGTCAGCACATAC
ATGCTCACAAACTCTGAACTCCTAAGCCTGATTAATGATATGCCTATCAC
AAATGATCAGAAGAAACTCATGAGCAATAATGTGCAGATTGTAAGACAGC
AGAGTTATTCTATAATGTGTATTATTAAGGAGGAGGTACTGGCCTATGTG
GTTCAACTTCCTCTGTATGGGGTGATAGATACACCATGCTGGAAGCTGCA
CACCAGCCCACTGTGTACGACCAATACAAAGGAGGGCTCCAATATTTGCT
TAACACGGACTGACCGGGGGTGGTATTGCGACAATGCCGGATCAGTCTCC
TTCTTCCCCCAAGCAGAGACCTGCAAGGTGCAGTCCAATAGAGTTTTCTG
CGACACAATGAACTCGCTGACCCTACCTAGCGAAGTTAACTTATGCAACG
TGGATATTTTTAATCCGAAGTATGATTGTAAAATCATGACTAGCAAAACG
GATGTTAGCTCCAGCGTAATCACCTCCCTAGGCGCTATCGTGAGCTGTTA
TGGCAAGACGAAGTGCACTGCATCTAATAAAAATAGGGGTATTATTAAAA
CCTTCAGCAATGGCTGCGACTATGTGAGCAATAAGGGCGTGGACACCGTG
TCAGTGGGAAACACCCTCTATTATGTGAACAAGCAGGAGGGAAAATCCCT
TTATGTAAAGGGCGAACCCATTATCAATTTCTATGACCCCCTGGTTTTCC
CAAGCGACGAGTTCGACGCATCTATCTCTCAAGTGAACGAGAAAATCAAT
CAGAGTCTTGCCTTTATCAGAAAATCCGATGAGCTGCTTTCCGCCATCGG
TGGCTATATCCCAGAAGCCCCAAGAGACGGACAAGCGTACGTCCGGAAAG
ATGGTGAGTGGGTCCTCCTCTCTACCTTTCTT

The underlined region represents a region coding for a foldon. The underlined region can be substituted with alternative sequences which achieve a same or similar function.

(SEQ ID NO: 245)

MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVCKVLHLEGEVNKIKSALLSTNKAVVSLSNGVSVLTFKVLDLKNYID
KQLLPILNKQSCSISNIETVIEFQQKNNRLLEITREFSVNAGVTTPVSTY
MLTNSELLSLINDMPITNDQKKLMSNNVQIVRQQSYSIMCIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLSAIGGYIPEAPRDGQAYVRKDGEWVLLSTFL

The first underlined region represents a signal peptide sequence. The first underlined regions can be substituted with alternative sequences that achieve the same or similar functions, or it can be deleted. The second underlined region represents a foldon. The second underlined region can be substituted with alternative sequences which achieve a same or similar function.

Influenza M-1 (A/California/04/2009(H1N1), ACP44152)+hIgκ

(SEQ ID NO: 246)

ATGGAGACTCCTGCACAGCTGCTGTTTCTGCTATTGTTGTGGCTTCCGGA

CACTACTGGGTCCCTCCTCACCGAGGTGGAAACATACGTGCTGTCCATCA

TACCATCCGGGCCCTTGAAAGCCGAGATCGCCCAGAGACTCGAATCTGTA

TTCGCAGGAAAGAACACGGATTTGGAGGCACTAATGGAATGGCTGAAGAC

CCGTCCGATCCTGTCTCCTCTCACAAAGGGGATTCTTGGATTTGTCTTTA

CCCTCACCGTCCCGAGCGAGCGCGGTCTCCAGCGCAGACGTTTTGTACAG

AATGCACTGAATGGCAACGGCGATCCCAATAACATGGATCGTGCGGTAAA

GCTTTATAAAAAGCTGAAGAGAGAAATCACTTTCCATGGGGCTAAAGAGG

TGAGTCTCTCCTATTCAACCGGGGCATTGGCCTCTTGCATGGGTCTTATA

TACAATCGAATGGGCACCGTTACCACCGAGGCCGCATTTGGTCTGGTTTG

TGCTACGTGCGAGCAAATCGCAGATAGCCAGCATCGGTCCCATCGGCAGA

TGGCCACCACTACGAACCCTCTAATTCGACATGAAAATCGCATGGTCCTG

GCTAGCACCACCGCAAAGGCAATGGAGCAGATGGCGGGCTCTAGTGAACA

GGCAGCCGAGGCAATGGAAGTGGCCAATCAGACCAGGCAGATGGTCCATG

CTATGCGGACTATTGGTACCCACCCGTCCAGCAGTGCTGGACTGAAGGAT

GACCTCCTTGAGAACCTGCAGGCATACCAGAAACGAATGGGGGTGCAAAT

GCAGAGATTCAAG

The underlined region represents a region coding for human Igκ signal peptide. The underlined region can be substituted with alternative sequences which achieve a same or similar function.

(SEQ ID NO: 247)

METPAQLLFLLLLWLPDTTGSLLTEVETYVLSIIPSGPLKAEIAQRLESV

FAGKNTDLEALMEWLKTRPILSPLTKGILGFVFTLTVPSERGLQRRRFVQ

NALNGNGDPNNMDRAVKLYKKLKREITFHGAKEVSLSYSTGALASCMGLI

YNRIVIGTVTTEAAFGLVCATCEQIADSQHRSHRQMATTTNPLIRHENRM

VLASTTAKAMEQMAGSSEQAAEAMEVANQTRQMVHAMRTIGTHPSSSAGL

KDDLLENLQAYQKRMGVQMQRFK

The underlined region represents human Igκ signal peptide. The underlined region can be substituted with alternative sequences which achieve a same or similar function.

The influenza M1 mRNA was combined with MRK-1, MRK-4 or MRK-9 in an effort to increase the immune response by having the cells that take up the mRNAs make virus like particles (VLPs).

Protein vaccine evaluated in this study was DS-CAV1 stabilized prefusion F protein as described in McLellan et al. *Science* 342, 592 (2013); 1 mg/mL. The protein was buffered in 50 mM Hepes, 300 mM NaCl and was formulated with Adju-phos.

Groups of 10 mice were immunized intramuscularly with 100 groups of 10 mice were immunized intramuscularly with 100 μL of vaccine, delivered with 50 μL injections into each quadriceps. The groups were vaccinated with the following vaccines:

TABLE 1

Vaccines

| Group | Vaccine | Concentration (μg/ml) | Total dose/mouse (μg) |
|---|---|---|---|
| 1 | mF (MRK-1) | 100 | 10 |
| 2 | sF (MRK-2) | 100 | 10 |
| 3 | mDS-CAV1 (MRK-4) | 100 | 10 |
| 4 | sDS-CAV1 (MRK-3) | 100 | 10 |
| 5 | mG (MRK-9) | 100 | 10 |
| 6 | mF (MRK-1) + Influenza M1 (1:1 mixture) | 100 | 10 |
| 7 | mDS-CAV1 (MRK-4) + Influenza M1 (1:1 mixture) | 100 | 10 |
| 8 | mG (MRK-9) + Influenza M1 (1:1 mixture) | 100 | 10 |
| 9 | MRK-5 | 100 | 10 |
| 10 | MRK-7 | 100 | 10 |
| 11 | MRK-8 | 100 | 10 |
| 12 | DS-CAV1 protein/adju phos | 100 | 10 |
| 13 | mF (MRK-1) | 20 | 2 |
| 14 | sF (MRK-2) | 20 | 2 |
| 15 | mDS-CAV1 (MRK-4) | 20 | 2 |
| 16 | sDS-CAV1 (MRK-3) | 20 | 2 |
| 17 | mG (MRK-9) | 20 | 2 |
| 18 | VLP/mF (MRK-1) | 20 | 2 |
| 19 | VLP/mDS-CAV1 (MRK-4) | 20 | 2 |
| 20 | VLP/G (MRK-9) | 20 | 2 |
| 21 | MRK-5 | 20 | 2 |
| 22 | MRK-7 | 20 | 2 |
| 23 | MRK-8 | 20 | 2 |
| 24 | DS-CAV1 protein/adju phos | 20 | 2 |
| 25 | naive | N/A | N/A |

The animals were immunized on day 0 and day 21 of the experiment. On days 14 and 35, blood was drawn from each animal and used for serological assays. On day 42, a subset of the animals were sacrificed and spleens were harvested to support ELISPOT and intracellular cytokine staining studies.

On day 27, the mice were challenged intranasally with $1\times10^6$PFU RSV A2. Four days post inoculation, the animals were sacrificed by $CO_2$ inhalation and lung and nasal turbinates were removed and homogenized in 10 volumes of Hanks Balanced Salt Solution (Lonza) containing SPG on wet ice. The samples were clarified by centrifugation at 2000 rpm for 10 minutes, aliquotted, flash frozen, and immediately stored frozen at −70° C.

Figure 5:
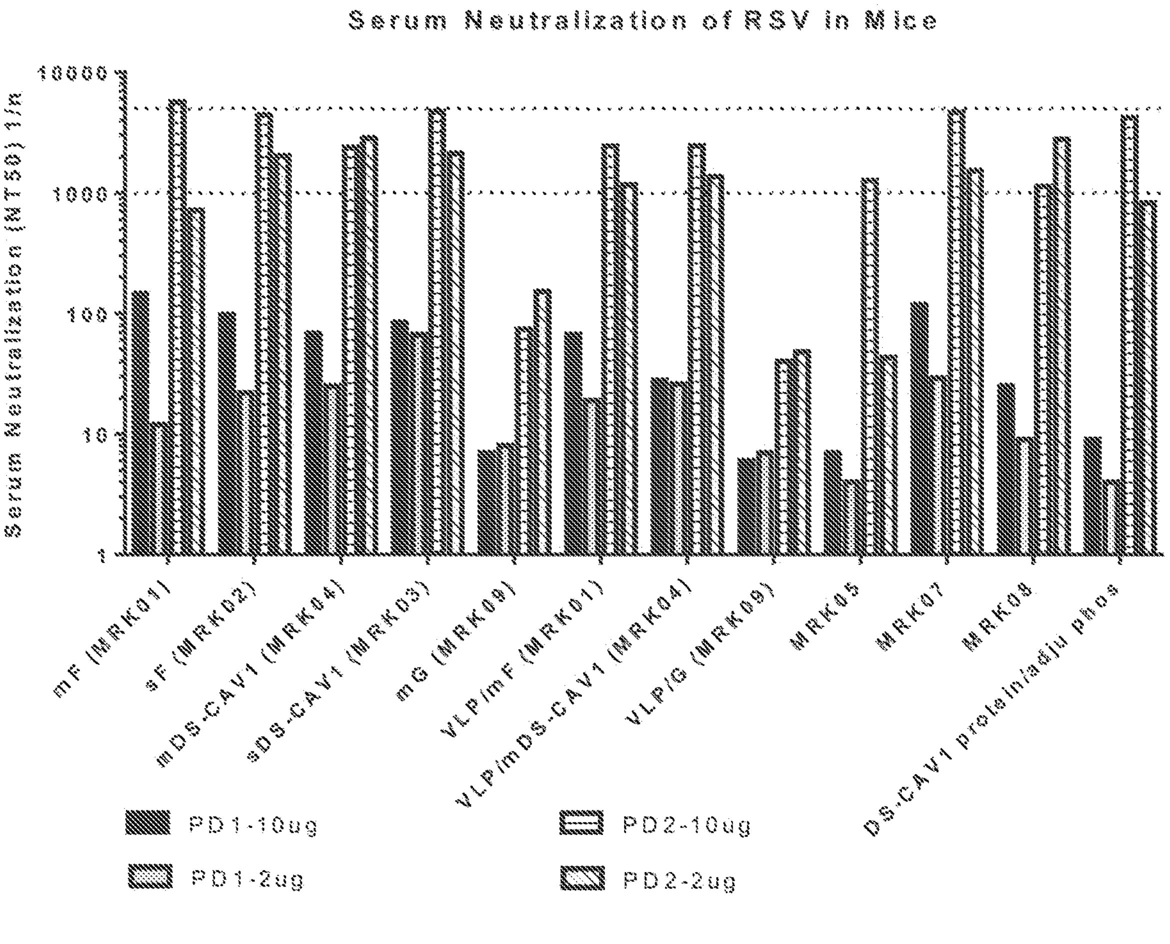
FIG. 5 shows data from an immunogenicity study in mice, demonstrating strong neutralizing antibody titers equivalent to those achieved with a protein antigen adjuvanted with ADJU-PHOS®.

A. RSV Neutralization Assay:

Neutralizing antibody titers were determined as described above. The titers are shown in FIG. 5 (PD1=samples taken post-dose 1, PD2=samples taken post-dose2). The results showed that mRNA/LNP vaccines were strongly immunogenic and elicited high neutralizing antibody titers, as was demonstrated in the previous experiment. Attempts to generate a significantly higher neutralizing antibody by co-delivering mRNAs expressing influenza M1 with mRNAs expressing membrane-bound protein antigen were not successful.

B. Intracellular Cytokine Staining.

Figure 6A:
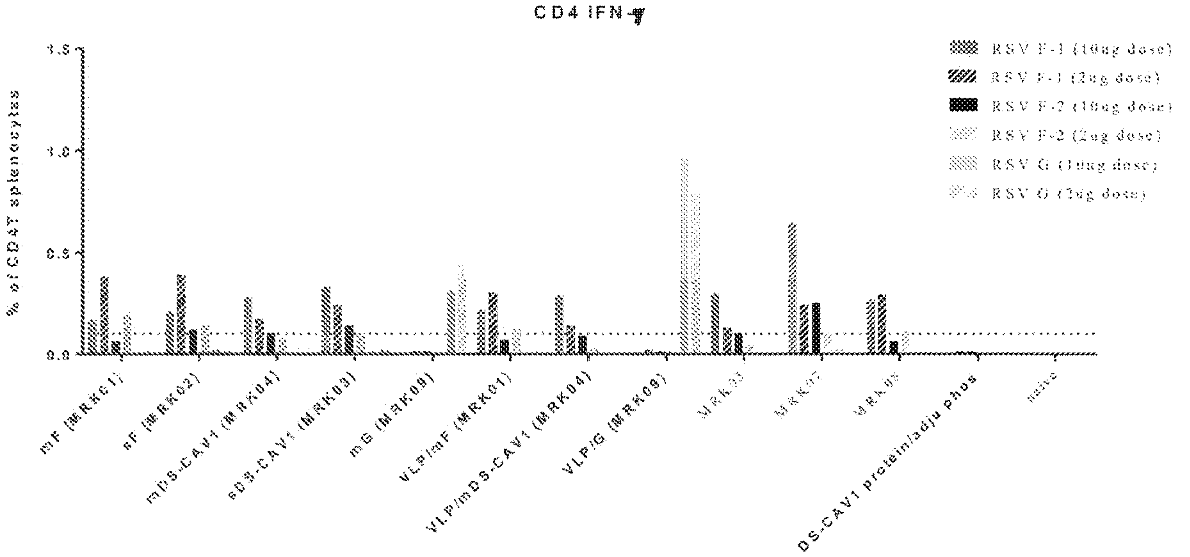
FIGS. 6A-6C show data from an intracellular cytokine staining assay to test immunogenicity in mice, demonstrating that RSV-F mRNA/LNP vaccines and RSV-G mRNA/LNP vaccines, but not DS-CAV1 protein antigens, elicit robust Th1 biased CD4+ immune responses in mice.
Figure 6B:
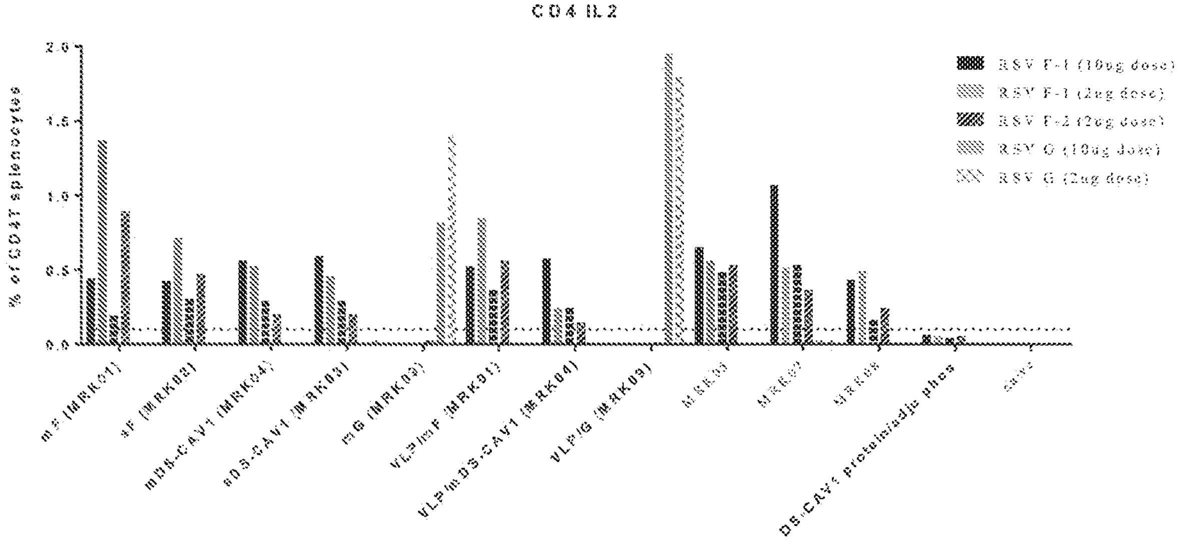
Figure 6C:
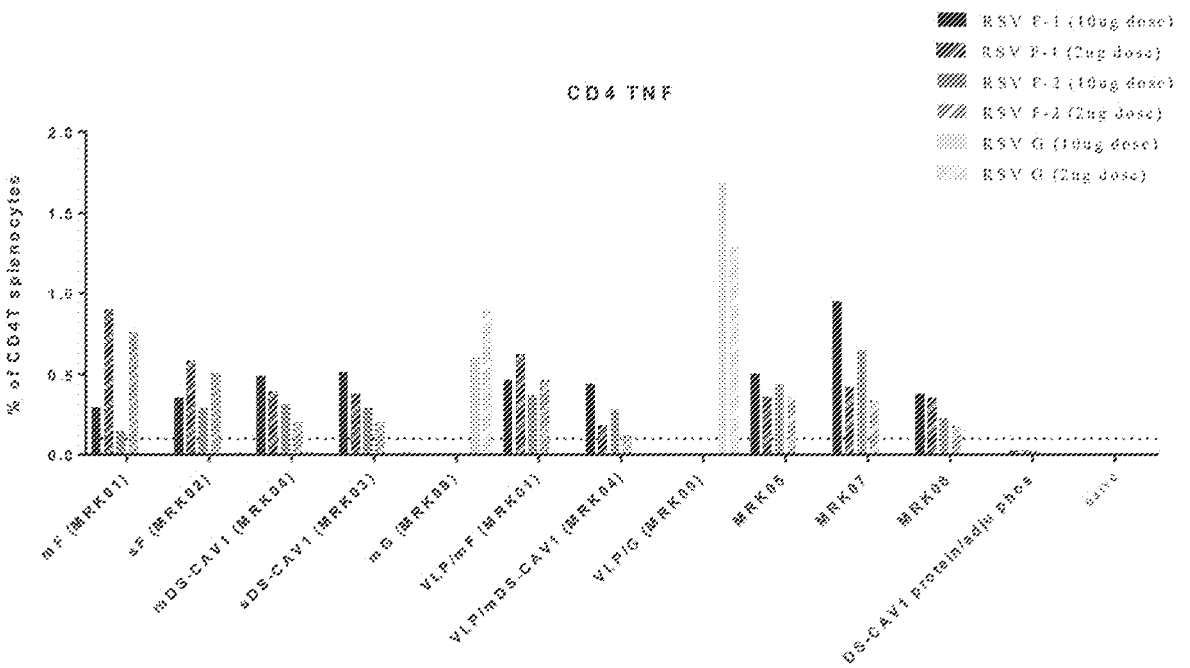

Intracellular cytokine staining was conducted in the same manner described above in Examples 13. The CD4 ICS responses to RSV-F and G peptide pools are shown in FIGS. 6A, 6B, and 6C. As in the previous study, the ICS results showed that mRNA vaccines expressing RSV-F and RSV-G elicited robust Th1-biased CD4 immune responses.

Figure 7A:
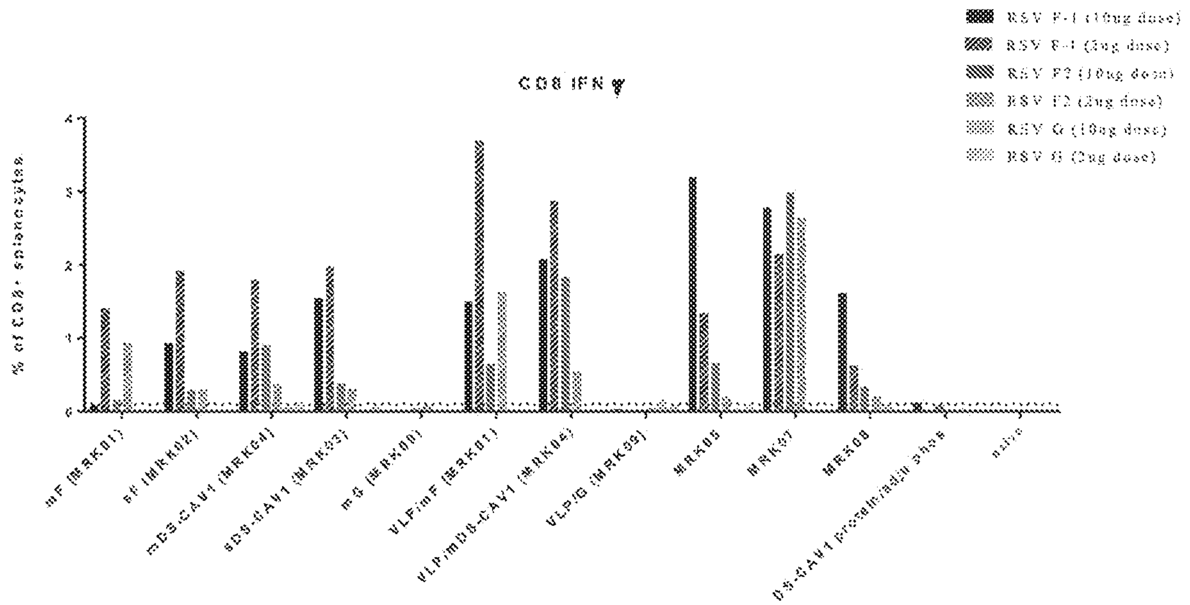
FIGS. 7A-7C show data from an intracellular cytokine staining assay to test immunogenicity in mice, confirming that RSV-F mRNA/LNP vaccines, but not RSV-G mRNA/LNP vaccines or DS-CAV1 protein antigens, elicit robust TH1 biased CD8+ immune responses in mice.
Figure 7B:
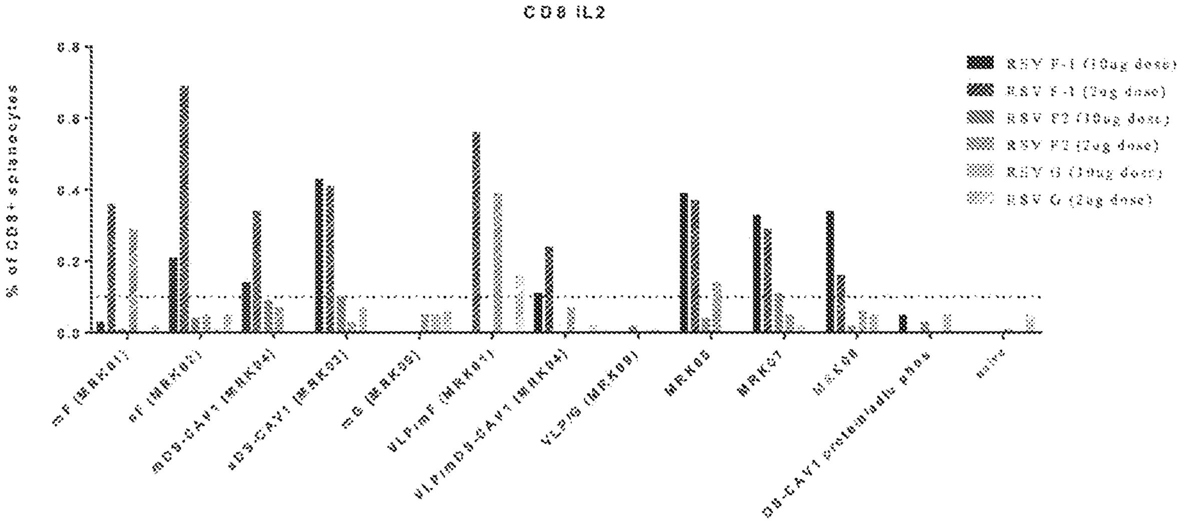
Figure 7C:
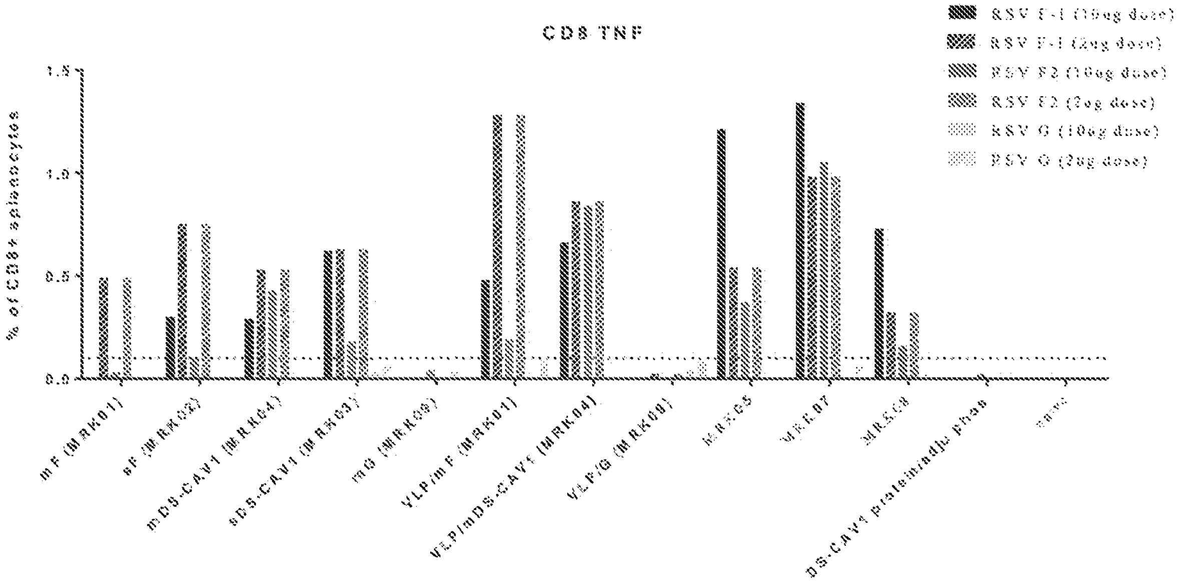

The CD8 ICS responses are shown in FIGS. 7A, 7B, and 7C. The data confirm the previous observation that mRNAs expressing RSV-F antigens but not mRNAs expressing RSV-G or DS-CAV1 protein/adju phos elicited robust Th1 biased CD8 responses.

C. Mouse Challenge Results

Figure 8:
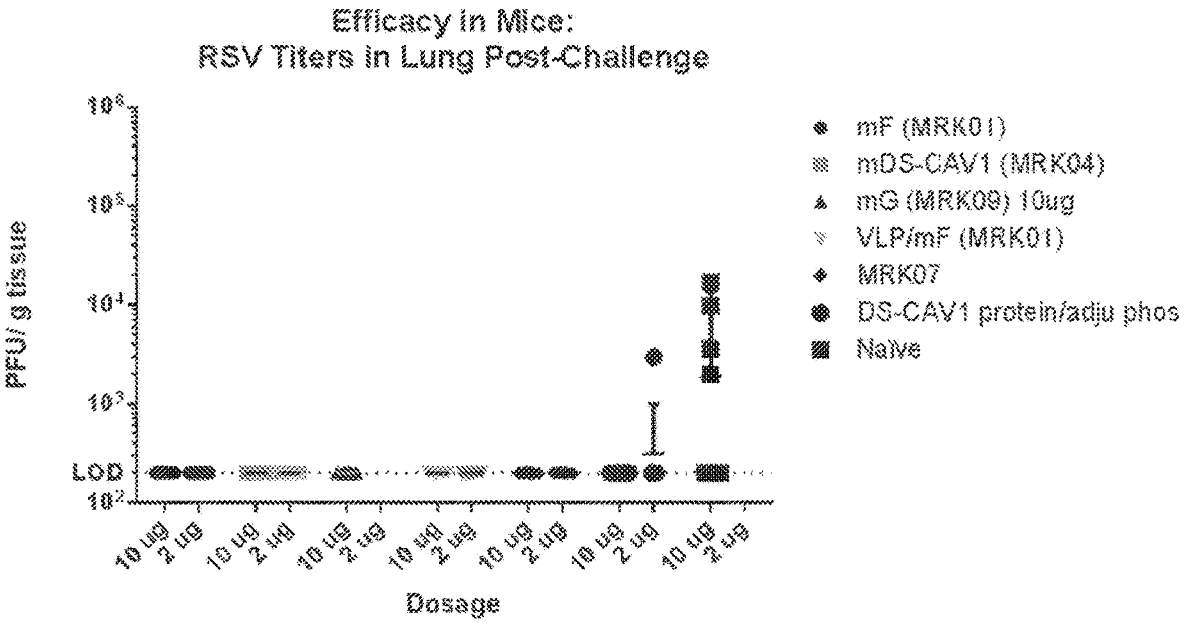
FIG. 8 shows data from an assay, demonstrating that no virus was recovered from lungs of any of mice immunized with RSV mRNA vaccines formulated with MC3 LNP, and only one animal at the lower dose of DS-CAV1 protein/ADJU-PHOS® vaccine had any virus detectable in the nose.

The procedure for measuring viral titers is outlined below. Briefly, samples were diluted and added in duplicate to 24-well plates containing confluent HEp-2 cell monolayers. The plates were incubated at 37° C. for one hour. Following the one hour incubation, sample inoculum was aspirated and lml of overlay containing 0.75% methylcellulose was added. The plates were incubated at 37° C. for 5 days. Following the 5 day incubation, the cells were fixed and stained with crystal violet/glutaraldehyde solution. Plaques were counted and titers were expressed as pfu/gram of tissue. As shown in FIG. 8, no virus was recovered from the lungs of any of the mice immunized with the mRNA vaccines formulated with MC3 LNP and only one animal at the lower dose of DS-CAV1 protein/adju phos vaccine had any virus detectable in the nose.

Example 14: Cotton Rat Immunogenicity and Efficacy

In this example, assays were carried out to test the immunogenicity and efficacy of mRNA/LNP vaccines in the cotton rat RSV challenge model.

More specifically, female cotton rats (SAGE) were used and immunizations began at 3-7 weeks of age. The mRNA vaccines used were generated and formulated in MC3 lipid nanoparticles. The mRNA vaccines evaluated in this study included:

MRK-1 membrane-bound RSV F protein

MRK-2 secreted RSV F protein (truncated ectodomain)

MRK-3 secreted DS-CAV1 (trimeric ectodomain)

MRK-4 membrane-bound DS-CAV1 (stabilized prefusion F protein)

MRK-9 membrane-bound RSV G protein

Influenza M1 protein

Protein vaccine evaluated in this study was DS-CAV1 stabilized prefusion F protein as described in McLellan et al. *Science* 342, 592 (2013); 1 mg/mL. The protein was buffered in 50 mM Hepes, 300 mM NaCl and was formulated with Adju-phos.

Groups of 10 cotton rats were immunized intramuscularly with 120 μL of vaccine, delivered with 60 μL injections into each quadricep. The groups were vaccinated with the following vaccines as set out in Table 2:

TABLE 2

Vaccine Formulations Tested for Immunogenicity in Cotton Rats

| Group | Vaccine | Conc (μg/ml) | Dose (μg) |
|---|---|---|---|
| 1 | mF (MRK-1), I.M. | 250 | 30 |
| 2 | sF (MRK-2) I.M. | 250 | 30 |
| 3 | mDS-CAV1 (MRK-4), I.M. | 250 | 30 |
| 4 | sDS-CAV1 (MRK-3), I.M. | 250 | 30 |
| 5 | mG (MRK-9), I.M. | 250 | 30 |
| 6 | VLP/mF (MRK10 + MRK-1), I.M. | 250 | 30 |
| 7 | VLP/mG (MRK10 + MRK-9), I.M. | 250 | 30 |
| 8 | VLP/mDS-CAV1 (MRK10 + MRK-4), I.M. | 250 | 30 |
| 9 | DS-CAV1 protein/adju phos, I.M. | 250 | 30 |
| 10 | RSV A2 5.5log10 pfu, I.N. | NA | NA |
| 11 | None | NA | NA |

The animals were immunized on day 0 and day 28 of the experiment. On days 28 and 56, blood was drawn from each animal and used for serological assays. On day 56, the cotton rats were challenged intranasally with $1\times10^{5.5}$PFU RSV A2. Four days post inoculation, animals were sacrificed by $CO_2$ inhalation and lung (left lobes) and nasal turbinates were removed and homogenized in 10 volumes of Hanks Balanced Salt Solution (Lonza) containing SPG on wet ice. The samples were clarified by centrifugation at 2000 rpm for 10 minutes, aliquoted, flash frozen, and immediately stored frozen at −70° C.

A. RSV Neutralization Assay

Neutralizing antibody titers were determined as described above.

Figure 9:
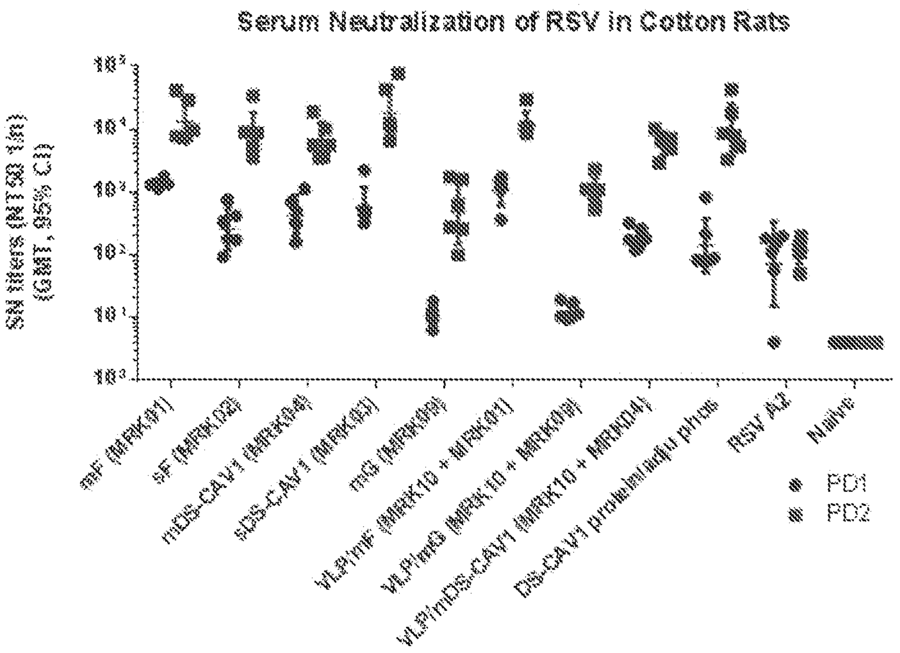
FIG. 9 shows data from an immunogenicity study in cotton rats, demonstrating strong neutralizing antibody titers in animals immunized with various RSV mRNA vaccines formulated with MC3 LNP.

The titers determined post dose 1 and post dose 2 are shown in FIG. 9. The neutralizing titers were robust in cotton rats following a single immunization and overall were several fold higher than those elicited by the DS-CAV1 protein antigen formulated with adju-phos or with infection with RSV A2 virus. The highest neutralizing antibody titers were elicited by RNA vaccines expressing full length RSV-F protein, truncated F-protein (ectodomain), mDS-CAV1 (stabilized prefusion F protein containing the RSV F transmembrane domain), and sDS-CAV1 (a truncated form of the stabilized prefusion F protein) as well as mRNA combination, including full length F protein and influenza M1 (termed "VLP/mF" in the graph above).

Titers determined post-dose two indicate that overall, neutralizing antibody titers were quite high for both mRNA vaccines and for the DS-CAV1 protein comparitor. Surprisingly, in this study, as in the two mouse immunogenicity studies, relatively high neutralizing antibody titers were observed for the mG and mG+influenza M1 mRNA vaccine groups after the second dose of vaccine. With other vaccine modalities used to delivery RSV-G antigens, it was reported that neutralizing antibody activity is not observed in vitro unless complement is included in the assay.

B. Competition ELISA

The immune response to specific epitopes on RSV F-protein for neutralizing antibodies was characterized. The antigenic site II is the binding site for palivizumab, a monoclonal antibody developed for the prevention of lower respiratory infection with RSV in at risk infants and toddlers. Antigenic site Ø is a binding site for more potent neutralizing antibodies that are elicited by natural infection with RSV. A competition ELISA was developed to characterize the antigenic site Ø and antigenic site II response to the various mRNA-based vaccines.

Methods

Figure 10:
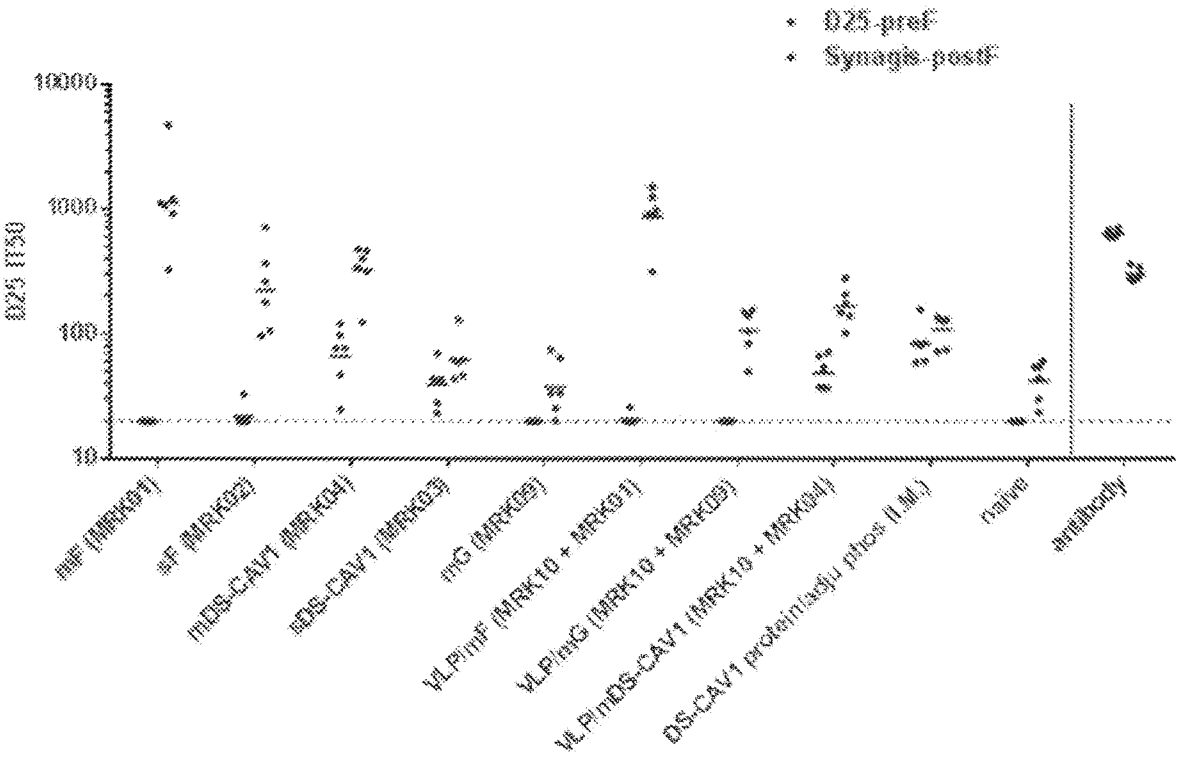
FIG. 10 shows data from a cotton rat competition ELISA, characterizing the antigenic Ø and antigenic site II response to various RSV mRNA vaccines.

ELISA plates were coated with either prefusion F protein or postfusion F protein (McLellan et al., 2013). After coating, the plates were washed and blocked with blocking buffer (PBST/3% nonfat dried milk). Test sera from the cotton rat challenge study was then diluted with blocking buffer and titrated in the ELISA plate. Biotinylated D25 (a monoclonal antibody that binds to antigenic site Ø) or biotinylated palivizumab (a monoclonal antibody that binds to antigenic site II) were diluted in blocking buffer and added to each well of the ELISA plate (biotinylated D25 is only used with plates coated with prefusion F protein; biotinylated palivizumab may be used with plates coated with prefusion or postfusion F protein as antigenic site II is present on both forms of the antigen). Following incubation, plates were washed and streptavidin-tagged horse radish peroxidase was added to each well of the ELISA plate. Plates were incubated at room temperature for 1 hr, washed, and incubated with TMB substrate (ThermoScientific). The color was allowed to develop for 10 minutes and then quenched with 100 μL of 2N sulfuric acid and the plates were read at 450 nM on a microplate reader. The results are shown in FIG. 10. FIG. 10 illustrates the ability of cotton rat sera to compete with either D25 binding to prefusion F protein or palivizumab binding to postfusion F protein.

Background binding titers were seen in both the naïve mice and in those immunized with mG or with VLP/mG (neither of which will express the epitopes bound by D25 or palivizumab). The unlabeled monoclonal antibodies were included in the experiment as positive controls and those data are shown in the right-hand column of FIG. 10. No D25 competing titers were evident in cotton rats immunized with MRK-1, MRK-2, MRK-9, MRK10+MRK-1, or MRK10+MRK-9. Only immunization with a mRNA encoding the DS-CAV1 sequence (MRK-4, MRK-3, and MRK10+MRK-4) elicited D25-competing antibody titers, illustrating that these mRNAs produce a form of RSV F protein that is primarily in the prefusion conformation. In contrast, palivizumab competing titers were far higher in animals immunized with MRK-1 or MKR02 mRNAs, illustrating that these mRNAs were produced as postfusion RSV F protein in cotton rats.

C. Cotton Rat Challenge Results

Figure 11:
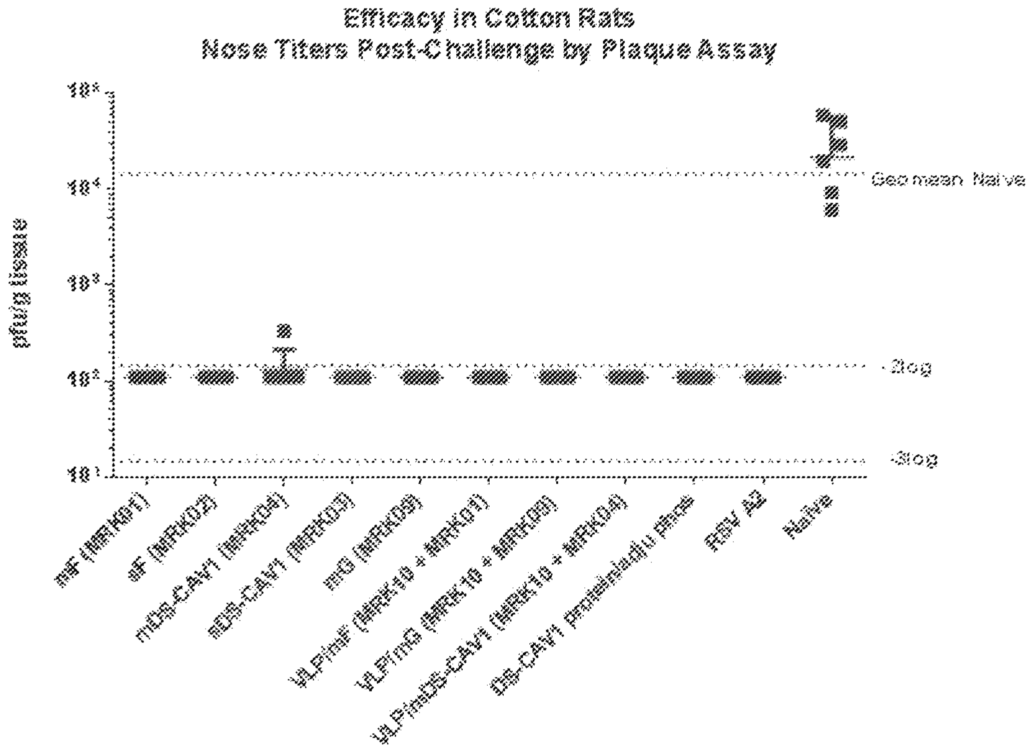
FIG. 11 shows data from a cotton rat challenge assay, demonstrating protective effects of RSV mRNA vaccines formulated with MC3 LNP.

Procedures for measuring RSV titers in the cotton rat nose were followed as described above for mice. Nasal titers are shown in FIG. 11. In this assay, the limit of detection was 40 pfu/g of tissue. It was found that only one vaccinated animal (one mouse vaccinated with mDS-CAV1 (MRK4) mRNA encapsulated with MC3 LNP) had any detectable virus presence in the nose. In contrast, the geometric mean titer of RSV A2 virus in animals that were not vaccinated but were challenged in the same study was >10,000 pfu/g tissue.

Example 15: African Green Monkey Immunogenicity and Efficacy

In this example, assays were carried out to test the immunogenicity and efficacy of mRNA/LNP vaccines in the African Green Monkey RSV challenge model.

More specifically, male and female adult African Green Monkeys with body weights ranging from 1.3 to 3.75 kg, which were confirmed to be RSV-negative by neutralizing antibody titer, were used. The mRNA vaccines used were generated and formulated in MC3 lipid nanoparticles. The mRNA vaccines evaluated in this study included:

MRK-1 membrane-bound RSV F protein

MRK-4 membrane-bound DS-Cav1 (stabilized prefusion F protein)

Groups of four African Green Monkeys were immunized intramuscularly with 1000 μL of vaccine, delivered with 500 μL injections into each deltoid. The groups were vaccinated with the following vaccines as set out in Table 3.

TABLE 3

Vaccine Formulations Tested for Immunogenicity in African Green Monkeys

| Group | Vaccine | Conc (μg/ml) | Dose (μg) |
|---|---|---|---|
| 1 | mF (MRK-1), I.M. | 125 | 125 |
| 2 | mDS-Cav1 (MRK-4), I.M. | 125 | 125 |
| 3 | mF (MRK-1) + mDS-Cav1 (MRK-4), I.M. | 125 | 125 (62.5 μg each mRNA) |
| 4 | RSV A2 5.5log10 pfu, I.N. | NA | NA |
| 5 | None | NA | NA |

The animals were immunized on day 0, day 28, and day 56 of the experiment. On days 0, 14, 28, 42, 56 and 70, blood was drawn from each animal and used for serological assays.

On day 70, the African Green Monkeys were challenged intranasally with $1\times10^{5-5}$ PFU RSV A2. Nasopharyngeal swabs were collected on days 1-12, 14, and on day 18 post challenge, and lung lavage samples were collected on days 3, 5, 7, 9, 12, 14, and 18 post challenge to test for viral replication.

A. RSV Neutralization Assay

Neutralizing antibody titers ($NT_{50}$) were determined as described above.

Figure 12:
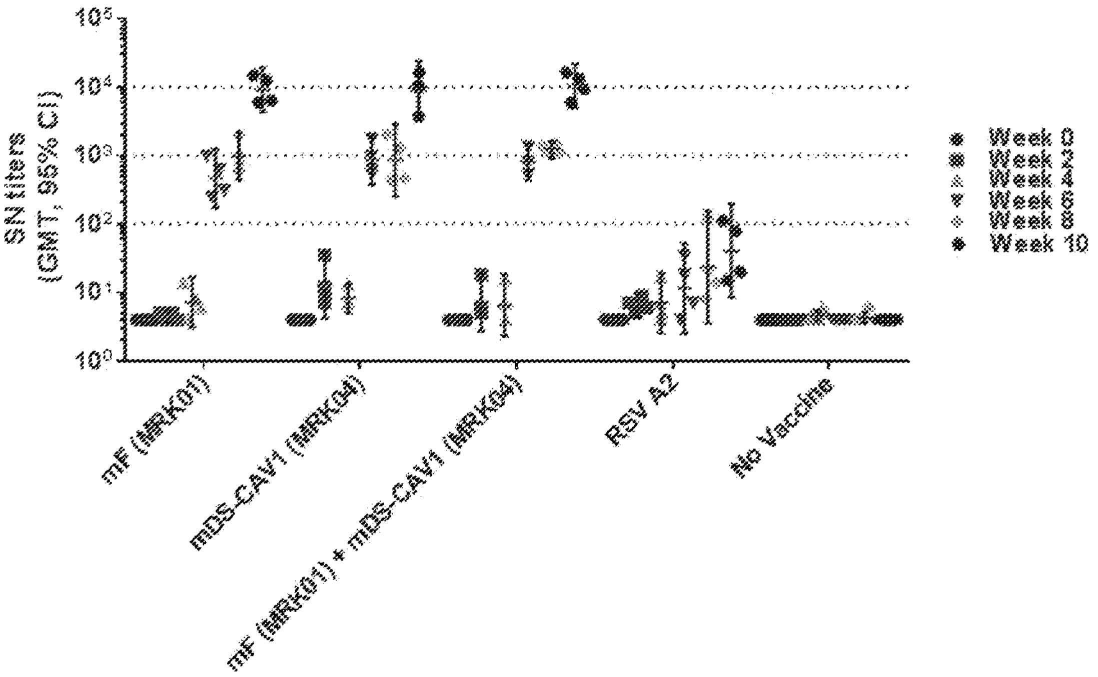
FIG. 12 shows a graph representative of serum neutralizing antibody titers (NT50 individual and GMT with 95% confidence intervals) to RSV A induced in African Green Monkeys by RSV mRNA vaccines and control formulations.

The $NT_{50}$ titers determined post dose 1 and post dose 2 are shown in FIG. 12. Titers were seen to increase after each dose for both groups receiving mRNA vaccines as well as the group receiving RSV A2. The GMTs obtained with mRNA vaccines at week 10 (2 weeks post-dose 3) were more than 2 orders of magnitude higher than in the animals that received RSV A2.

B. Competition ELISA

The immune response to specific epitopes on RSV F-protein for neutralizing antibodies was characterized using the competition assays described above.

Figure 13A:
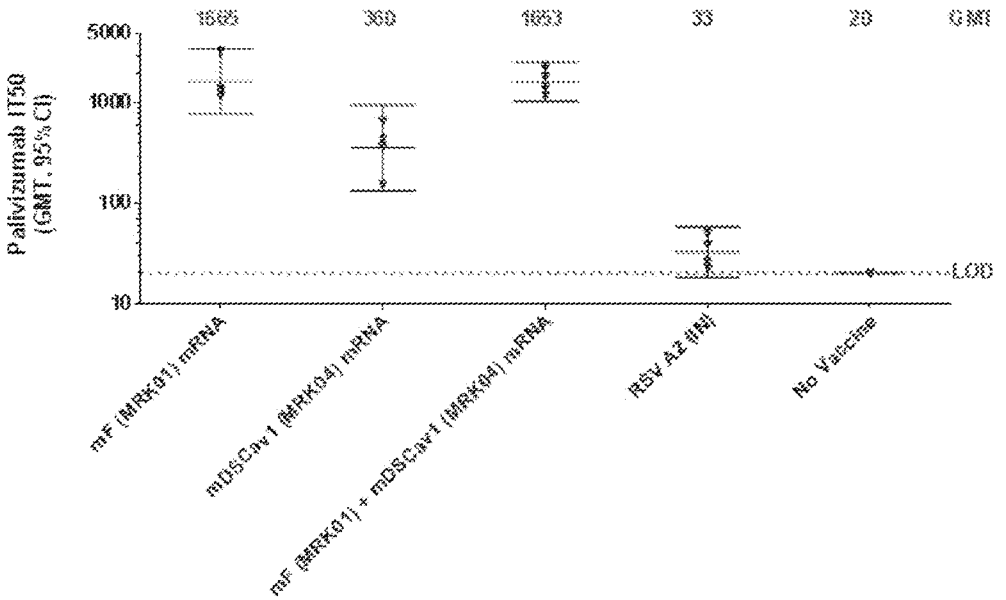
FIGS. 13A-13B show graphs representative of serum antibody competition ELISA titers (IT50 individual and GMT with 95% confidence intervals) against palivizumab (site II) (FIG. 13A) and D25 (site Ø) (FIG. 13B) measured at week 10 (2 weeks PD3).
Figure 13B:
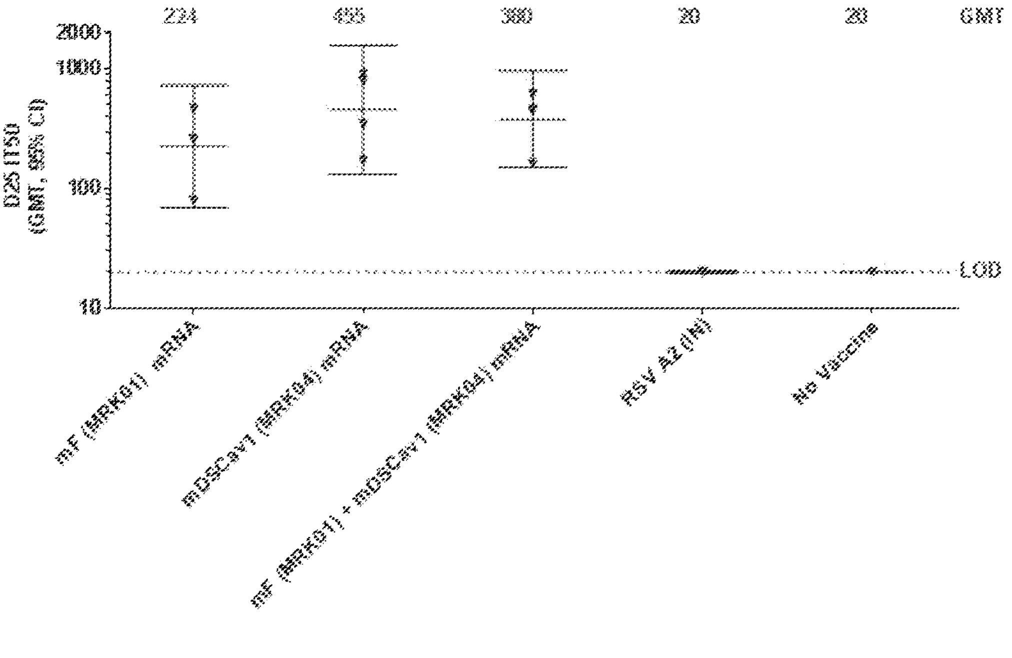

The palivizumab and D25 competing antibody titers measured at week 10 (2 weeks PD3) are presented in FIGS. 13A-13B. The GMT palivizumab competing titers were 5 fold higher in the groups that received mF or the combination of mF+mDS-Cav1 compared to the group that received mDS-Cav1. While the GMT D25 competing antibody titers were 2 fold higher in the groups that received mDS-Cav1 or the combination of mF+mDS-Cav1 than in the group that received mF mRNA. The prefusion F stabilized antigen (mDS-Cav1), was able to elicit prefusion specific responses.

C. African Green Monkey Challenge Results

As mentioned above, in order to evaluate vaccine efficacy African Green Monkeys were challenged intranasally with $1\times10^{5.5}$PFU RSV A2 on day 70 post vaccination and nasopharyngeal swabs and lung lavage samples were collected post challenge to test for the presence of virus.

In order to measure RSV titers in the African Green Monkey nasopharyngeal swabs and lung lavage samples an RSV RT-qPCR assay to detect RSV A was carried out as follows:

1) Equipment and Materials:

A. Equipment

1. Stratagene Mx3005P Real Time PCR system and MxPro Software
2. Jouan GR422 centrifuge or equivalent
3. Jouan Plate carriers or equivalent B. Reagents 1. Quantitect® Probe RT-PCR kit (1000) catalog #204445
2. Water, Molecular Biology Grade DNAase-free and Protease free, 5 Prime, catalog #2900136
3. TE buffer, 10 mM Tris 1 mM EDTA ph 8.0, Fisher Bioreagents, catalog #BP2473-100
4. Viral primers: RSV A Forward and Reverse primers, Sigma custom, HPLC purified. Primer stocks are reconstituted to 100 μM in Molecular grade water and stored at −20° C.
5. RSV dual labeled probe, Sigma custom, HPLC purified. Probe stocks are reconstituted to 100 μM in TE buffer and stored at −20° C. protected from light.
6. RSV A standard were generated in-house and stored at −20° C. Standards for the assay were generated by designing primer pairs to the N gene of RSV A. The product length for the RSV A standard is 885 bp. QIAGEN OneStep RT-PCR was used to generate this standard.

TABLE 4

| Primers | |
|---|---|
| Primers | Sequences |
| RSV A F N gene | 5' CTC AAT TTC CTC ACT TCT CCA GTG T (SEQ ID NO: 248) |
| RSV A R N gene | 5' CTT GAT TCC TCG GTG TAC CTC TGT (SEQ ID NO: 249) |
| RSV A FAM N gene | 5'FAM-TCC CAT TAT GCC TAG GCC AGC A (BHQ1) (SEQ ID NO: 250) |

7. Promega, Maxwell® 16 Viral Total Nucleic Acid Purification Kit (Product #AS1150)

C. Supplies

1. Stratagene Optical cap 8× strip, catalog #401425
2. Stratagene Mx3000P 96 well plates, skirted, catalog #401334
3. ART filtered pipet tips 2) RT-PCR Reactions and Set Up A. Preparation of Complete Master Mix 1. Prepare complete Master Mix following the set up below for a final reaction volume of 50 μL. The following table is volume per well. Final primer concentration is 300 nM and final probe concentration is 200 nM.

TABLE 5

| Reagents | |
|---|---|
| Reagent | mL |
| 2X Master Mix | 25 |
| RSV A F 100 uM | 0.2 |
| RSV A R 100 uM | 0.2 |
| RSV A FAM 100 uM | 0.1 |
| RT enzyme mix | 0.5 |
| Water | 19 |

2. Add 45 μL of complete master mix to each well. Cover plate with plate cover and wrap in aluminum foil to protect from light.

B. Preparation of Standard curve

1. Remove standard from −20° C.
2. Dilute standards to final concentrations of $1\times10^6$ copy/5 μL to 1 copy/5 μL using 10-fold dilutions.

C. Sample preparation

1. Nasopharyngeal swab and lung lavage samples are prepared for the RT-PCR reaction using the Maxwell® 16 Viral Total Nucleic Acid Purification Kit (Promega, product #AS1150)
2. 200 μL of sample is extracted following the manufactures protocol and eluted into 50 μL to be used in PCR reactions.

D. Additions of samples

1. Add 5 μL of extracted samples to appropriate wells. After addition of samples, carefully cap sample wells before adding standard curves.
2. Add 5 μL of diluted standard to appropriate wells and cap.
3. Add 5 μL of molecular grade water to No Template Control (NTC) wells.
4. Wrap plates in aluminum foil and transfer plates to centrifuge.
5. Spin plates for 2 mins at 100 rpm to pull down any samples or master mix that may be on the sides of well.
6. Wrap plates in aluminum foil and transfer to Stratagene instrument.

E. Thermo cycler: Stratagene MX 3005P

1. Place plates in Stratagene Mx3005P and set thermal profile conditions to:

TABLE 6

| Thermocycler Steps | | |
|---|---|---|
| Step | Time | Temperature |
| Reverse Transcription | 30 min | 50 |
| PCR initial activation step | 15 min | 95 |
| 2-step cycling: | | |
| Denaturation | 16 sec | 94 |
| Combined annealing/extension | 60 sec | 62 |
| Number of cycles | 40 | |

2. Analyze results using the Stratagene Mx3005p software

Figure 14A:
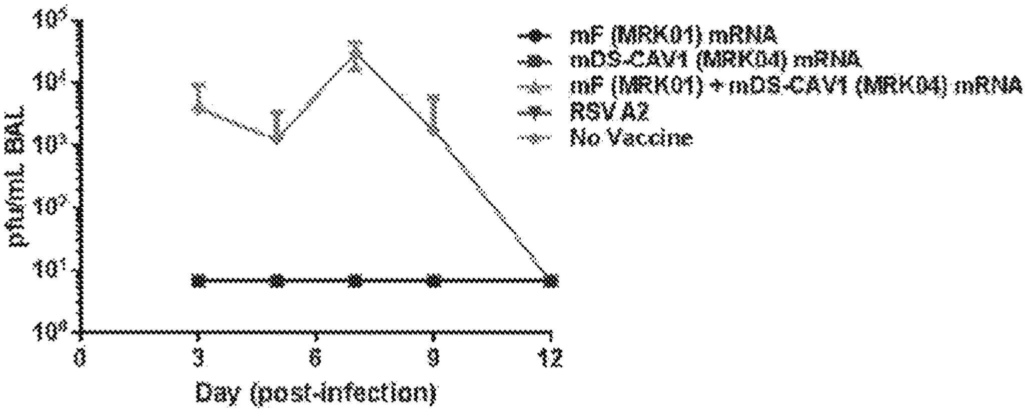
FIGS. 14A-14B show graphs representative of mean lung viremia detected post challenge (FIG. 13A) and mean nasal viremia detected post challenge (FIG. 13B) in African Green Monkeys with 95% confidence intervals.
Figure 14B:
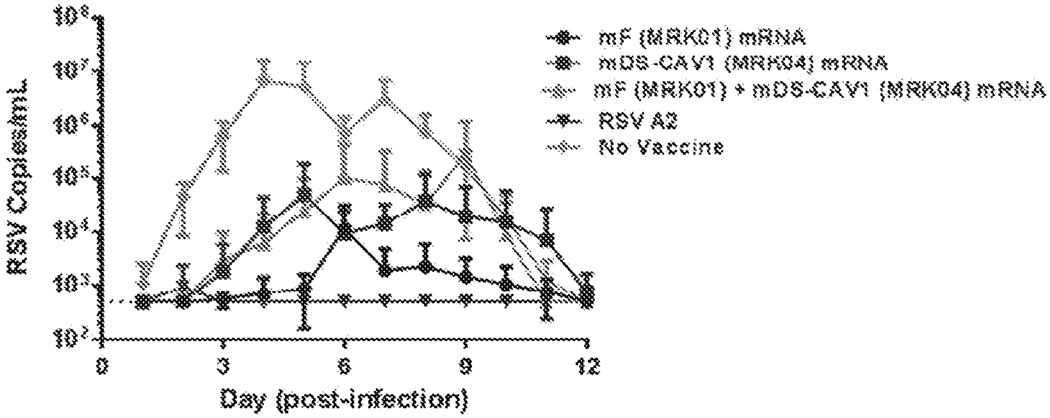

The mean RNA copy number detected in the lung and nose samples are presented in FIGS. 14A-14B. The animals that received mRNA encoding mF, mDS-Cav1 or mF+mDS-Cav1 formulated in MC3 showed complete protection (no virus detected) in lungs similar to the control group immunized with RSV A2. The animals that received mRNA vaccines also showed a greater than 2 log reduction in virus detected in the nose on the majority of the assay days compared to the no vaccine control group.

Example 16: Immunogenicity in RSV-Experienced African Green Monkeys

The immunogenicity of mRNA vaccines formulated in MC3 LNP was tested in RSV-experienced African Green Monkeys.

Healthy adult, African Green Monkeys of either sex (n=5/group), weighing more than 1.3 kg, that were confirmed to be RSV seropositive by ELISA and neutralizing antibody titers, were selected for the study. The pool of animals selected for this study had been experimentally infected with RSV in previous vaccine studies and were distributed across study groups based on their pre-study RSV neutralization titers so that all groups would have similar group GMTs at study start. RSV-experienced animals provide a model of immune memory recall response to vaccination that may reflect the responses that can be anticipated in seropositive human adults.

A single vaccine dose was administered to each animal at week 0 by the intramuscular (IM) route. A control group receiving only the MC3 LNP was also included in the study design. Vaccines were administered as described in Table 7. After vaccination, the animals were observed daily for any changes at the inoculation site or other changes in activity or feeding habits that might indicate an adverse reaction to the vaccine, but none were noted. Serum samples were collected for assessment of RSV neutralizing antibody titers, as well as palivizumab (site II) and D25 (site Ø) competing antibody titers. PBMC samples were collected to assess cell-mediated immune responses.

TABLE 7

| Vaccine Formulations Tested for Immunogenicity in RSV Seropositive African Green Monkeys | | | |
|---|---|---|---|
| Group | Vaccine | Conc (μg/ml) | Dose (μg) |
| 1 | mF (MRK-1), I.M. | 125 | 125 |
| 2 | mDS-Cav1 (MRK-4), I.M. | 125 | 125 |
| 3 | mF (MRK-1) + mDS-Cav1 (MRK-4), I.M. | 125 | 125 (62.5 μg each mRNA) |
| 4 | RSV A2 $5.5_{log10}$ pfu, I.N. | NA | NA |
| 5 | None | NA | NA |

Figure 15:
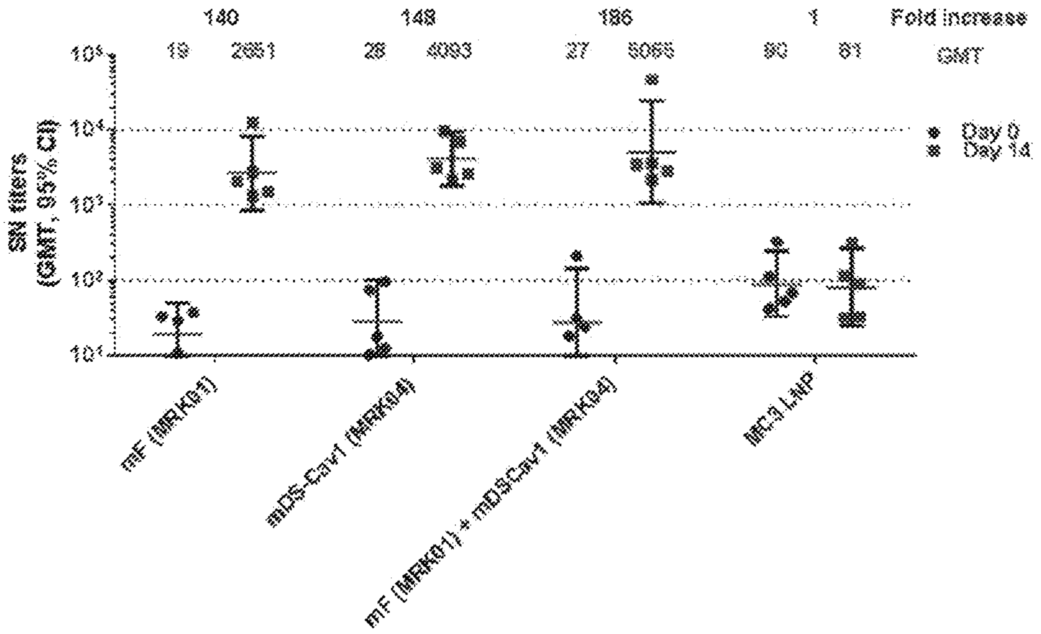
FIG. 15 shows a graph representative of serum neutralizing antibody titers (NT50 individual and GMT with 95% confidence intervals) to RSV A induced in RSV-experienced African Green Monkeys by various RSV mRNA vaccine and control formulations at 2 weeks post vaccination.
Figure 16:
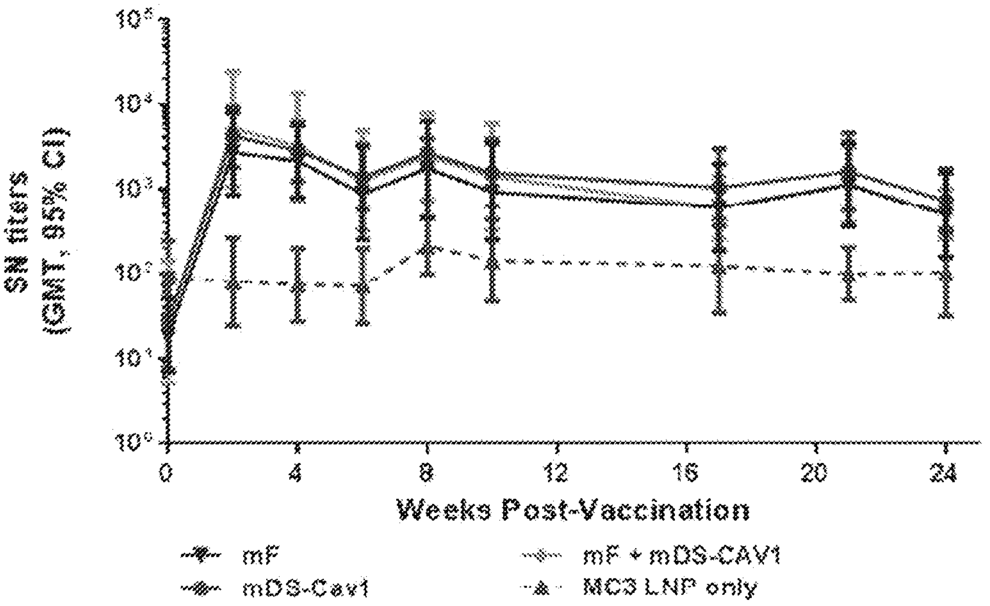
FIG. 16 shows a graph representative of serum neutralizing antibody titers (GMT with 95% confidence intervals) to RSV A induced in RSV-experienced African Green Monkeys by various RSV mRNA vaccine and control formulations.

Individual animal $NT_{50}$ titers were measured in serum samples collected at baseline and 2 weeks post vaccination using methods described above, and the results are shown in FIG. 15. Vaccination with the mRNA vaccines resulted in, on average, a 150-fold increase in serum neutralization titers. The fold increase was comparable for all mRNA vaccines. No increase in titers was observed in the LNP only vaccine control group. The durability of the serum neutralization titers was assessed by measuring the titers every 2 to 4 weeks post vaccination. The GMTs for each group measured out to week 24 post vaccination are presented in FIG. 16. The titers remain about 50 fold higher than baseline at week 24.

Figure 17A:
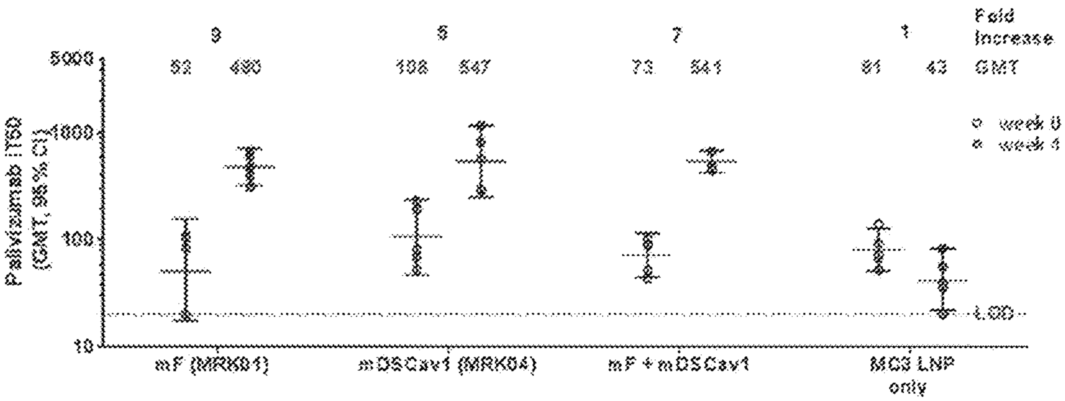
FIGS. 17A-17B show graphs representative of serum antibody competition ELISA titers (IT50 individual and GMT with 95% confidence intervals) against palivizumab (site II) (FIG. 17A) and D25 (site Ø) (FIG. 17B) measured at baseline and 4 weeks post immunization.
Figure 17B:
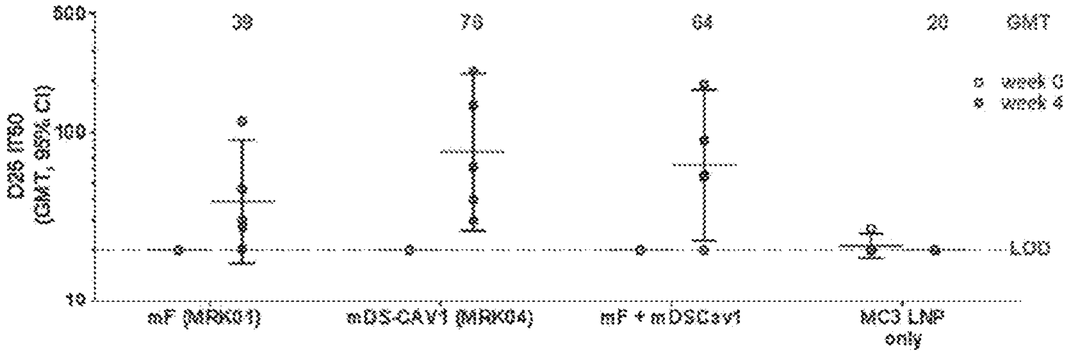

To evaluate the quality of the boosted responses in the vaccinated animals, both palivizumab (site II) and D25 (site Ø) competing antibody titers were determined. As described above, antigenic site II is a neutralization epitope found on both the prefusion and the postfusion conformation of the F protein, while site Ø is a prefusion specific neutralization epitope. The palivizumab (site II) and D25 (site Ø) competing antibody titers measured 4 weeks post vaccination using the methods described above are summarized in FIGS. 17A-17B. All of the mRNA vaccines resulted in a boost in palivizumab competing titers of approximately 7 fold from baseline. Although D25 competing antibody titers were below the limit of detection of the assay before immunization in all but one animal in the MC3 LNP only control group, D25 competing antibody titers were elicited in all animals receiving an mRNA based vaccine. The GMTs were highest in the groups receiving mDS-Cav1 or the combination of mF+mDS-Cav1. No increase in palivizumab or D25 (site Ø) competing antibody titers were seen in the LNP only control group.

Figure 18A:
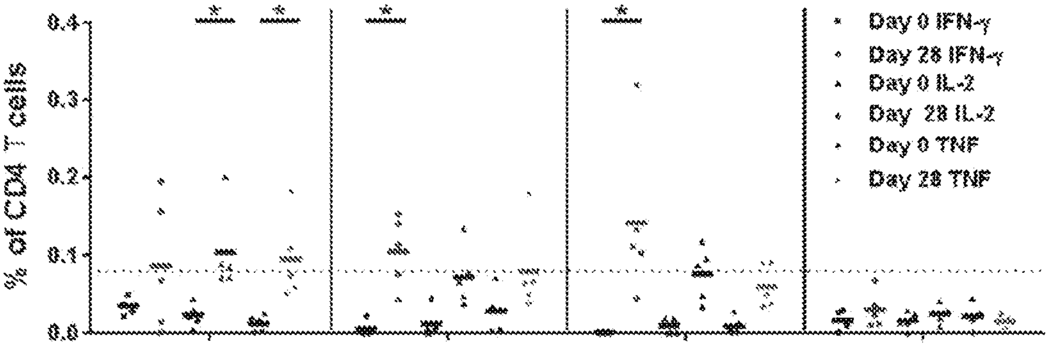
FIGS. 18A-18B show graphs representative of RSV F-specific CD4+(FIG. 18A) and CD8+(FIG. 18B) T cell responses induced in RSV experienced African Green Monkeys by various vaccine and control formulations.
Figure 18B:
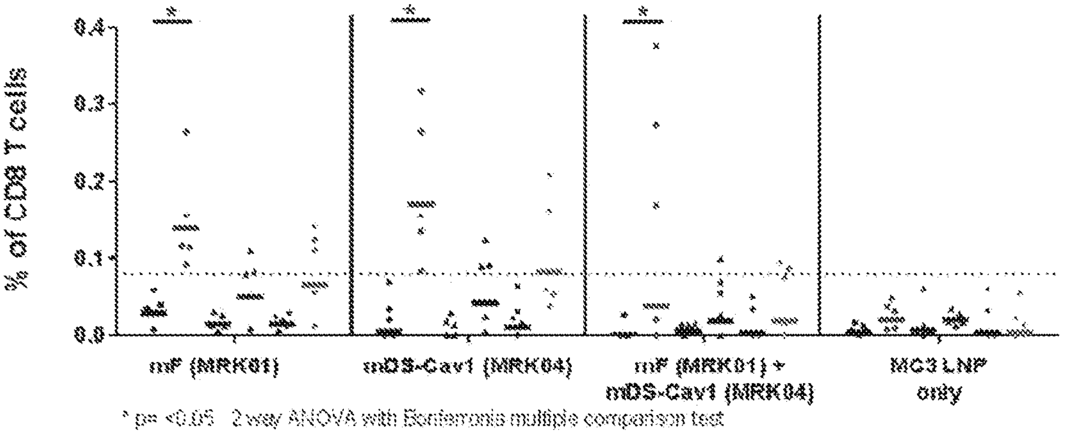

The mRNA vaccines were also found to boost T cell responses in the RSV-experienced African green monkeys as determined by ICS assay at week 6 post vaccination (FIGS. 18A-18B).

ICS assays for African Green Monkeys were conducted as follows:

A. Day 1: Thawing PBMCs

1. PBMC vials were removed from liquid nitrogen and placed on dry ice until ready to thaw.
2. Cells were thawed quickly with gentle agitation in 37° C. set point water bath.
3. For each subject, cell suspension was transferred to an appropriately labeled 15 mL or 50 mL tube, using a serologic pipette.
4. Approximately 0.5 mL R10 medium was slowly added to the cells, which were then swirled gently to mix the media and cell suspension.
5. Three times the frozen cell volume of R10 media was then added drop wise to each tube, swirling each after 0.5 mL to 1.0 mL of R10 media were added.
6. R10 Media was then added at a rate of 1.0 mL to 2.0 mL at a time until approximately 10 to 15 mL was added to each tube.
7. The tubes were swirled to mix the media and cell suspension, and then centrifuged at 250×g (setpoint) for 8 to 10 minutes at room temperature.
8. The supernatant was removed and the cells were gently resuspended in 5 mL of R10 medium.
9. The cell suspensions were then transferred into a 12 well tissue culture plate.
10. The tissue culture plates were placed in a 37° C.+/−2° C., 4% to 6% $CO_2$ incubator overnight.

B. Day 2: Counting and Stimulation Procedure for PBMC

PBMC Counting

1. PBMCs from each well of the 12-well tissue culture plate were placed into labeled 50 mL conical tubes.
2. Cells were then counted by trypan blue exclusion on a hemacytometer or by Guava PC and resuspended to $1\times10^7$ cells per mL.

Stimulation Set-up 1. 100 μL of the resuspended PBMCs were then added to each well of a 96-well sterile U bottom tissue culture plate for a final number of $1\times10^6$ cells/well.
2. Peptide pools corresponding to the RSV F protein sequence were generated as follows. For optimal results the peptides were combined into two pools, RSV F1 and RSV F2. RSVF1 includes the first 71 peptides in the following list, and RSV F2 includes the following 70 peptides:

TABLE 8

| Peptides | | | | |
|---|---|---|---|---|
| First aa number | 15-mer | aa # | | SEQ ID NO: |
| 1 | MELPILKANAITTIL | 1-15 | start F protein pool 1 | 29 |
| 5 | ILKANAITTILTAVT | 5-19 | | 30 |
| 9 | NAITTILTAVTFCFA | 9-23 | | 31 |
| 13 | TILTAVTFCFASSQN | 13-27 | | 32 |
| 17 | AVTFCFASSQNITEE | 17-31 | | 33 |
| 21 | CFASSQNITEEFYQS | 21-35 | | 34 |
| 25 | SQNITEEFYQSTCSA | 25-39 | | 35 |
| 29 | TEEFYQSTCSAVSKG | 29-43 | | 36 |
| 33 | YQSTCSAVSKGYLSA | 33-47 | | 37 |
| 37 | CSAVSKGYLSALRTG | 37-51 | | 38 |
| 41 | SKGYLSALRTGWYTS | 41-55 | | 39 |
| 45 | LSALRTGWYTSVITI | 45-59 | | 40 |
| 49 | RTGWYTSVITIELSN | 49-63 | | 41 |
| 53 | YTSVITIELSNIKEN | 53-67 | | 42 |
| 57 | ITIELSNIKENKCNG | 57-71 | | 43 |
| 61 | LSNIKENKCNGTDAK | 61-75 | | 44 |
| 65 | KENKCNGTDAKVKLI | 65-79 | | 45 |
| 69 | CNGTDAKVKLIKQEL | 69-83 | | 46 |

TABLE 8-continued

| Peptides | | | |
|---|---|---|---|
| First aa number | 15-mer | aa # | SEQ ID NO: |
| 73 | DAKVKLIKQELDKYK | 73-87 | 47 |
| 77 | KLIKQELDKYKNAVT | 77-91 | 48 |
| 81 | QELDKYKNAVTELQL | 81-95 | 49 |
| 85 | KYKNAVTELQLLMQS | 85-99 | 50 |
| 89 | AVTELQLLMQSTPAA | 89-103 | 51 |
| 93 | LQLLMQSTPAANNRA | 93-107 | 52 |
| 97 | MQSTPAANNRARREL | 97-111 | 53 |
| 101 | PAANNRARRELPRFM | 101-115 | 54 |
| 105 | NRARRELPRFMNYTL | 105-119 | 55 |
| 109 | RELPRFMNYTLNNAK | 109-123 | 56 |
| 113 | RFMNYTLNNAKKTNV | 113-127 | 57 |
| 117 | YTLNNAKKTNVTLSK | 117-131 | 58 |
| 121 | NAKKTNVTLSKKRKR | 121-135 | 59 |
| 125 | TNVTLSKKRKRRFLG | 125-139 | 60 |
| 129 | LSKKRKRRFLGFLLG | 129-143 | 61 |
| 133 | RKRRFLGFLLGVGSA | 133-147 | 62 |
| 137 | FLGFLLGVGSAIASG | 137-151 | 63 |
| 141 | LLGVGSAIASGIAVS | 141-155 | 64 |
| 145 | GSAIASGIAVSKVLH | 145-159 | 65 |
| 149 | ASGIAVSKVLHLEGE | 149-163 | 66 |
| 153 | AVSKVLHLEGEVNKI | 153-167 | 67 |
| 157 | VLHLEGEVNKIKSAL | 157-171 | 68 |
| 161 | EGEVNKIKSALLSTN | 161-175 | 69 |
| 165 | NKIKSALLSTNKAVV | 165-179 | 70 |
| 169 | SALLSTNKAVVSLSN | 169-183 | 71 |
| 173 | STNKAVVSLSNGVSV | 173-187 | 72 |
| 177 | AVVSLSNGVSVLTSK | 177-191 | 73 |
| 181 | LSNGVSVLTSKVLDL | 181-195 | 74 |
| 185 | VSVLTSKVLDLKNYI | 185-199 | 75 |
| 189 | TSKVLDLKNYIDKQL | 189-203 | 76 |
| 193 | LDLKNYIDKQLLPIV | 193-207 | 77 |
| 197 | NYIDKQLLPIVNKQS | 197-211 | 78 |
| 201 | KQLLPIVNKQSCSIS | 201-215 | 79 |
| 205 | PIVNKQSCSISNIET | 205-219 | 80 |
| 209 | KQSCSISNIETVIEF | 209-223 | 81 |
| 213 | SISNIETVIEFQQKN | 213-227 | 82 |
| 217 | IETVIEFQQKNNRLL | 217-231 | 83 |

TABLE 8-continued

| Peptides | | | | |
|---|---|---|---|---|
| First aa number | 15-mer | aa # | | SEQ ID NO: |
| 221 | IEFQQKNNRLLEITR | 221-235 | | 84 |
| 225 | QKNNRLLEITREFSV | 225-239 | | 85 |
| 229 | RLLEITREFSVNAGV | 229-243 | | 86 |
| 233 | ITREFSVNAGVTTPV | 233-247 | | 87 |
| 237 | FSVNAGVTTPVSTYM | 237-251 | | 88 |
| 241 | AGVTTPVSTYMLTNS | 241-255 | | 89 |
| 245 | TPVSTYMLTNSELLS | 245-259 | | 90 |
| 249 | TYMLTNSELLSLIND | 249-263 | | 91 |
| 253 | TNSELLSLINDMPIT | 253-267 | | 92 |
| 257 | LLSLINDMPITNDQK | 257-271 | | 93 |
| 261 | INDMPITNDQKKLMS | 261-275 | | 94 |
| 265 | PITNDQKKLMSNNVQ | 265-279 | | 95 |
| 269 | DQKKLMSNNVQIVRQ | 269-283 | | 96 |
| 273 | LMSNNVQIVRQQSYS | 273-287 | | 97 |
| 277 | NVQIVRQQSYSIMSI | 277-291 | | 98 |
| 281 | VRQQSYSIMSIIKKE | 281-295 | | 99 |
| 285 | SYSIMSIIKKEVLAY | 285-299 | start F protein pool 2 | 100 |
| 289 | MSIIKKEVLAYVVQL | 289-303 | | 101 |
| 293 | KKEVLAYVVQLPLYG | 293-307 | | 102 |
| 297 | LAYVVQLPLYGVIDT | 297-311 | | 103 |
| 301 | VQLPLYGVIDTPCWK | 301-315 | | 104 |
| 305 | LYGVIDTPCWKLHTS | 305-319 | | 105 |
| 309 | IDTPCWKLHTSPLCT | 309-323 | | 106 |
| 313 | CWKLHTSPLCTTNTK | 313-327 | | 107 |
| 317 | HTSPLCTTNTKEGSN | 317-331 | | 108 |
| 321 | LCTTNTKEGSNICLT | 321-335 | | 109 |
| 325 | NTKEGSNICLTRTDR | 325-339 | | 110 |
| 329 | GSNICLTRTDRGWYC | 329-343 | | 111 |
| 333 | CLTRTDRGWYCDNAG | 333-347 | | 112 |
| 337 | TDRGWYCDNAGSVSF | 337-351 | | 113 |
| 341 | WYCDNAGSVSFFPQA | 341-355 | | 114 |
| 345 | NAGSVSFFPQAETCK | 345-359 | | 115 |
| 349 | VSFFPQAETCKVQSN | 349-363 | | 116 |
| 353 | PQAETCKVQSNRVFC | 353-367 | | 117 |
| 357 | TCKVQSNRVFCDTMN | 357-371 | | 118 |
| 361 | QSNRVFCDTMNSLTL | 361-375 | | 119 |
| 365 | VFCDTMNSLTLPSEV | 365-379 | | 120 |

TABLE 8-continued

| Peptides | | | |
|---|---|---|---|
| First aa number | 15-mer | aa # | SEQ ID NO: |
| 369 | TMNSLTLPSEVNLCN | 369-383 | 121 |
| 373 | LTLPSEVNLCNVDIF | 373-387 | 122 |
| 377 | SEVNLCNVDIFNPKY | 377-391 | 123 |
| 381 | LCNVDIFNPKYDCKI | 381-395 | 124 |
| 385 | DIFNPKYDCKIMTSK | 385-399 | 125 |
| 389 | PKYDCKIMTSKTDVS | 389-403 | 126 |
| 393 | CKIMTSKTDVSSSVI | 393-407 | 127 |
| 397 | TSKTDVSSSVITSLG | 397-411 | 128 |
| 401 | DVSSSVITSLGAIVS | 401-415 | 129 |
| 405 | SVITSLGAIVSCYGK | 405-419 | 130 |
| 409 | SLGAIVSCYGKTKCT | 409-423 | 131 |
| 413 | IVSCYGKTKCTASNK | 413-427 | 132 |
| 417 | YGKTKCTASNKNRGI | 417-431 | 133 |
| 421 | KCTASNKNRGIIKTF | 421-435 | 134 |
| 425 | SNKNRGIIKTFSNGC | 425-439 | 135 |
| 429 | RGIIKTFSNGCDYVS | 429-443 | 136 |
| 433 | KTFSNGCDYVSNKGV | 433-447 | 137 |
| 437 | NGCDYVSNKGVDTVS | 437-451 | 138 |
| 441 | YVSNKGVDTVSVGNT | 441-455 | 139 |
| 445 | KGVDTVSVGNTLYYV | 445-459 | 140 |
| 449 | TVSVGNTLYYVNKQE | 449-463 | 141 |
| 453 | GNTLYYVNKQEGKSL | 453-467 | 142 |
| 457 | YYVNKQEGKSLYVKG | 457-471 | 143 |
| 461 | KQEGKSLYVKGEPII | 461-475 | 144 |
| 465 | KSLYVKGEPIINFYD | 465-479 | 145 |
| 469 | VKGEPIINFYDPLVF | 469-483 | 146 |
| 473 | PIINFYDPLVFPSGE | 473-487 | 147 |
| 477 | FYDPLVFPSGEFDAS | 477-491 | 148 |
| 481 | LVFPSGEFDASISQV | 481-495 | 149 |
| 485 | SGEFDASISQVNEKI | 485-499 | 150 |
| 489 | DASISQVNEKINQSL | 489-503 | 151 |
| 493 | SQVNEKINQSLAFIR | 493-507 | 152 |
| 497 | EKINQSLAFIRKSDE | 497-511 | 153 |
| 501 | QSLAFIRKSDELLHN | 501-515 | 154 |
| 505 | FIRKSDELLHNVNAG | 505-519 | 155 |
| 509 | SDELLHNVNAGKSTT | 509-523 | 156 |
| 513 | LHNVNAGKSTTNIMI | 513-527 | 157 |

TABLE 8-continued

| Peptides | | | |
|---|---|---|---|
| First aa number | 15-mer | aa # | SEQ ID NO: |
| 517 | NAGKSTTNIMITAII | 517-531 | 158 |
| 521 | STTNIMITAIIIVIV | 521-535 | 159 |
| 525 | IMITAIIIVIVVILL | 525-539 | 160 |
| 529 | AIIIVIVVILLSLIA | 529-543 | 161 |
| 533 | VIVVILLSLIAVGLL | 533-547 | 162 |
| 537 | ILLSLIAVGLLLYCK | 537-551 | 163 |
| 541 | LIAVGLLLYCKARST | 541-555 | 164 |
| 545 | GLLLYCKARSTPVTL | 545-559 | 165 |
| 549 | YCKARSTPVTLSKDQ | 549-563 | 166 |
| 553 | RSTPVTLSKDQLSGI | 553-567 | 167 |
| 557 | VTLSKDQLSGINNIA | 557-571 | 168 |
| 561 | KDQLSGINNIAFSN | 561-575 14mer<br>561-574 | 169<br>— |

3. Peptide pools (either RSV F1 or RSV F2 pool) were added to the cells to a final concentration of 2.5 μg/mL.
4. One mock well was prepared for each subject. The volume of DMSO corresponding to the volume of the peptide pool was added to the mock well.
5. Positive control wells were stimulated with a solution of PMA (20 ng/mL)/Ionomycin (1.25 μg/mL).
6. CD28/CD49d cocktail was added to each well at a final concentration of 2 μg/mL.
7. Following the addition of peptides and the CD28/CD49d cocktail, the plates were incubated 30-60 minutes in 37 degree incubator.
8. 5 mL of Brefeldin A (0.5 mg/mL) was then added to each well, and the plates were then incubated for an additional 4-5 hours in 37° C. 5% $CO_2$ incubator.
9. Plates were then removed and 20 μL of 20 mM EDTA (dissolved in 1×PBS) was added to each cell well.
10. The plates were then held at 4° C. overnight.

C. Day 3: Staining

1. Plates were centrifuged at 500×g for 5 min, and the supernatant was removed.
2. Each well was washed with 175 mL of FACS Wash, and the plate was centrifuged again at 500×g for 5 min, and the supernatant was removed.
3. The PBMCs were stained with the extracellular antibodies as follows according to manufacturer recommended volume:
   i. CD8 APCH7: 5 μL per test
   ii. CD3 PE: 20 μL per test
   iii. CD4 PCF594: 5 μL per test
   iv. ViViDye: 3 μL per test
4. After the cocktail was added to all wells, 120 μL of FACSwash was added to each well and mixed. The plates were incubated in the dark at room temperature for 25-30 minutes.
5. Plates were then centrifuged plate at 500×g for 5 minutes and washed with 175 μL per well of FACS wash.
6. 200 μL of BD Cytofix/cytoperm solution was added to each well and the plates were incubated 20 to 25 minutes 4° C.

7. Plates were then centrifuged plate at 500×g for 5 minutes and washed twice with 175 μL per well of PD perm wash buffer.
8. The PBMCs were then stained with the intracellular antibodies as follows:
   i. IFN-g FITC 20 μL per test
   ii. TNF PEcy7 5 μL per test
   iii. IL-2 APC 20 μL per test
9. After the cocktail was added to all wells, 120 μL of BD PermWash was added to each well, and the plates were incubated in the dark at room temperature for 25 minutes.
10. Following the incubation, the plates were centrifuged at 500×g for 5 minutes, washed with 175 μL BD perm wash buffer and the cells were then resuspended in 200 μL per well of BD stabilizing fixative. Samples were then stored overnight at 4° C. and acquired on an LSRII within 24 hrs of fixing.

As shown in FIGS. 18A-18B, mRNA vaccines (mF, mDS-Cav1 or mF+mDS-Cav1) resulted in increases in RSV F specific CD4+ and CD8+ T cell responses that were positive for IFN-γ, IL-2, and TNF-α. Overall the responses were comparable across all mRNA vaccine groups. T cell responses were not boosted in the MC3 LNP only control group.

Example 17: Immunogenicity and Efficacy Against RSV-B in Cotton Rat; Effectiveness of mRNA Vaccine Encapsulated with MC3

The immunogenicity and efficacy of experimental mRNA RSV vaccine formulations against challenge with RSV-B was tested in cotton rats. The study compared mRNAs encoding different forms of RSV-F protein encapsulated in MC3 lipid nanoparticle.

More specifically, female cotton rats (SAGE) were used and immunizations began at 3-7 weeks of age. The mRNA vaccines evaluated in this study included:

MRK-1 membrane-bound RSV F protein

MRK-4 membrane-bound DS-Cav1 (stabilized prefusion F protein)

The groups included in the study are as summarized in Table 9. The study evaluated all mRNA vaccines at a single dose of 25 mg. Control groups included in the study received either RSV A2 ($1\times10^{5.5}$ pfu) or no vaccine. Two doses of vaccine were administered to each animal (at week 0 and 4) except for the group receiving RSV A2 which received a single intranasal inoculum at week 0. Serum samples were collected for assessment of RSV neutralizing antibody titers. At week 8 cotton rats were challenged intranasally with RSV B strain RSV 18537. Four days post challenge the animals were euthanized and nose and lung tissue were collected to assess vaccine efficacy by measuring RSV levels in the tissue.

TABLE 9

Vaccine Formulations Tested for Immunogenicity and Efficacy in Cotton Rats

| Group | No. of Cotton Rats | Vaccine Formulation (mRNA/LNP) | Concentration (μg/mL) | Final mRNA Dose (μg) |
|---|---|---|---|---|
| 1 | 6 | mF (MRK-1) mRNA/MC3, I.M. | 250 | 25 |
| 2 | 6 | mDS-Cav1 (MRK-4) mRNA/MC3, I.M. | 250 | 25 |
| 3 | 6 | RSV A2 (intranasal) | NA | 5.5 log 10 pfu |
| 4 | 6 | No Vaccine | NA | NA |

Figure 19:
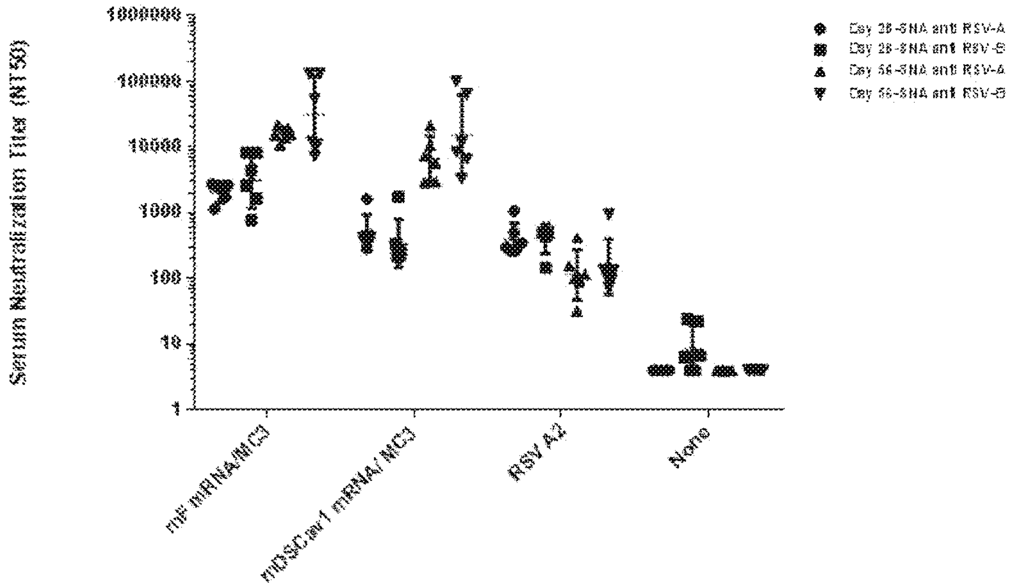
FIG. 19 shows a graph representative of serum neutralizing antibody titers (NT50 individual and GMT with 95% confidence intervals) to RSV A and RSV B induced in cotton rats at weeks 4 (4 weeks post dose 1 against RSV A (circle) and RSV B (square)) and 8 (4 weeks post dose 2 against RSV A (triangle pointing up) and RSV B (triangle pointing down) by various vaccine and control formulations.

Individual animal neutralizing antibody ($NT_{50}$) titers were measured in serum samples collected at week 4 (4 weeks post-dose 1) and week 8 (4 weeks post-dose 2; day of challenge). At week 4 all of the animals responded to vaccination with mRNA vaccines as well as with the RSV A2 challenge. Titers increased in both mRNA vaccine groups following the second immunization. Both the mRNA vaccines and the RSV A2 infection resulted in roughly equivalent neutralizing antibody titers against RSV A and RSV B. The individual animal and group geometric mean $NT_{50}$ titers measured at weeks 4 and 8 (4 weeks post-dose 1 (PD1) and 4 weeks post-dose 2 (PD2; day of challenge)) are presented in FIG. 19.

Figure 20:
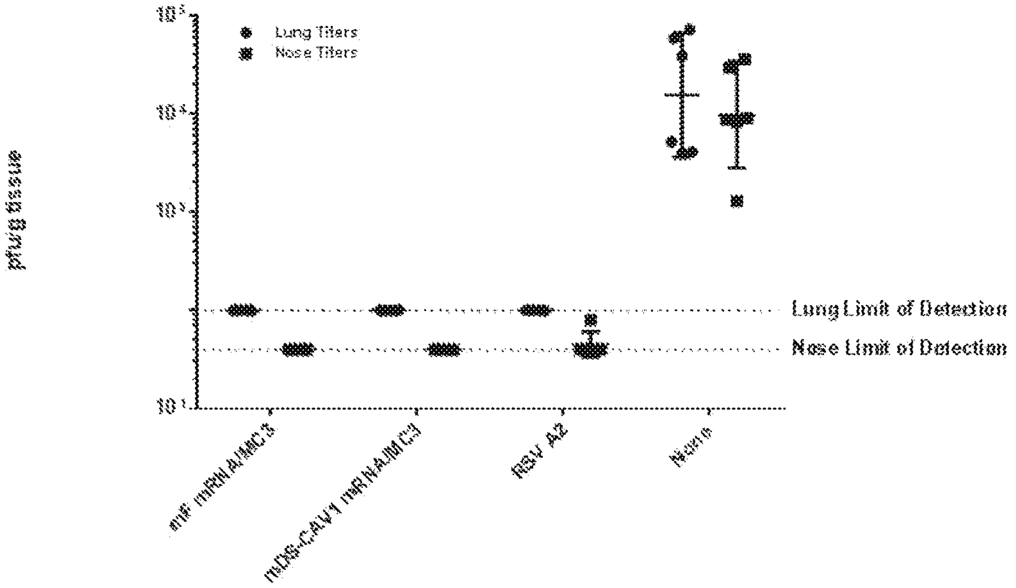
FIG. 20 shows a graph representative of mean lung (circles) and nose (squares) viral copies with 95% confidence intervals measured in cotton rats post challenge with RSV B 18357.

The in vivo efficacy of the various vaccine formulations was evaluated by measuring inhibition of viral replication in the lungs and nasal passages of the immunized cotton rats after challenge with RSV B strain 18537 using the methods described above. The data are shown in FIG. 20. Complete inhibition of virus replication was observed in the lungs and the nose of cotton rats immunized with wt RSV A2. Both mF and mDS-Cav1 mRNAs completely protected both the lung and the nose from challenge with RSV B 18537, despite being designed based on sequences from RSV A. Both mF and mDS-Cav1 mRNA vaccines were equally effective against RSV B challenge when formulated with MC3 lipid nanoparticles.

Each of the sequences described herein encompasses a chemically modified sequence or an unmodified sequence which includes no nucleotide modifications.

Example 18: Mouse Immunogenicity

In this example, assays are carried out to evaluate the immune response to RSV vaccine antigens delivered using an chemically unmodified mRNA/LNP platform in comparison to protein antigens.

Female Balb/c (CRL) mice (6-8 weeks old; N=10 mice per group) are administered RSV mRNA vaccines or protein vaccines. The mRNA vaccines are generated and formulated in MC3 lipid nanoparticles. The mRNA vaccines to be evaluated in this study include (each in a chemically unmodifed form):

MRK-1 membrane-bound RSV F protein

MRK-4 membrane-bound DS-CAV1 (stabilized prefusion F protein)

MRK-5 RSV F construct

MRK-6 RSV F construct

MRK-7 RSV F construct

MRK-8 RSV F construct

MRK-9 membrane-bound RSV G protein

MRK-11 truncated RSV F protein (ectodomain only); construct modified to include an Ig secretion peptide signal sequence MRK-12 DS-CAV1 (non-membrane bound form); modified to include an Ig secretion peptide signal sequence MRK-13: MRK-5 construct modified to include an Ig secretion peptide signal sequence MRK-14: MRK-6 construct modified to include an Ig secretion peptide signal sequence MRK-16: MRK-8 construct modified to include an Ig secretion peptide signal sequence The animals are immunized on day 0 and day 21 of the experiment. On days 14 and 35, blood is drawn from each animal and used for serological assays. On days 42 and 49, a subset of the animals are sacrificed and spleens are harvested to support ELISPOT and intracellular cytokine staining studies.

A. RSV Neutralization Assay:

Mouse sera from each group are pooled and evaluated for neutralization of RSV-A (Long strain) using the following procedures:

11. All sera samples are heat inactivated by placing in dry bath incubator set at 56° C. for 30 minutes. Samples and control sera are then diluted 1:3 in virus diluent (2% FBS in EMEM) and duplicate samples are added to an assay plate and serially diluted.
12. RSV-Long stock virus is removed from the freezer and quickly thawed in 37° C. water bath. Viruses are diluted to 2000 pfu/mL in virus diluent
13. Diluted virus is added to each well of the 96-well plate, with the exception of one column of cells.
14. HEp-2 cells are trypsinized, washed, resuspended at $1.5\times10^5$ cells/ml in virus diluent, and 100 mL of the suspended cells are added to each well of the 96-well plate. The plates are then incubated for 72 hours at 37° C., 5% $CO_2$.
15. Following the 72 hour incubation, the cells are washed with PBS, and fixed using 80% acetone dissolved in PBS for 10-20 minutes at 16-24° C. The fixative is removed and the plates are allowed to air-dry.
16. Plates are then washed thoroughly with PBS+0.05% Tween. The detections monoclonal antibodies, 143-F3-1B8 and 34C9 are diluted to 2.5 plates are then washed thoroughly with PBS+0.05%. 50 plates are then washed thoroughly with PBS+0.well of the 96-well plate. The plates are then incubated in a humid chamber at 16-24° C. for 60-75 minutes on rocker
17. Following the incubation, the plates are thoroughly washed.
18. Biotinylated horse anti-mouse IgG is diluted 1:200 in assay diluent and added to each well of the 96-well plate. Plates are incubated as above and washed.
19. A cocktail of IRDye 800CW Streptavidin (1:1000 final dilution), Sapphire 700 (1:1000 dilution) and 5 mM DRAQS solution (1:10,000 dilution) is prepared in assay diluent and 50 mL of the cocktail is added to each well of the 96-well plate. Plates are incubated as above in the dark, washed, and allowed to air dry.
20. Plates are then read using an Aerius Imager. Serum neutralizing titers are then calculated using a 4 parameter curve fit in Graphpad Prism.

The serum neutralizing antibody titers for the mouse immunogenicity study are measured post dose 1 (PD1) and post dose 2 (PD2).

TABLE 10

Flagellin Nucleic Acid Sequences

| Name | Sequence | SEQ ID NO: |
|---|---|---|
| NT (5' UTR, ORF, 3' UTR) | TCAAGCTTTTGGACCCTCGTACAGAAGCTAATACGACTCACTAT AGGGAAATAAGAGAGAAAAGAAGAGTAAGAAGAAATATAAG AGCCACCATGGCACAAGTCATTAATACAAACAGCCTGTCGCTG TTGACCCAGAATAACCTGAACAAATCCCAGTCCGCACTGGGCA CTGCTATCGAGCGTTTGTCTTCCGGTCTGCGTATCAACAGCGCG AAAGACGATGCGGCAGGACAGGCGATTGCTAACCGTTTTACCG CGAACATCAAAGGTCTGACTCAGGCTTCCCGTAACGCTAACGA CGGTATCTCCATTGCGCAGACCACTGAAGGCGCGCTGAACGAA ATCAACAACAACCTGCAGCGTGTGCGTGAACTGGCGGTTCAGT CTGCGAATGGTACTAACTCCCAGTCTGACCTCGACTCCATCCAG GCTGAAATCACCCAGCGCCTGAACGAAATCGACCGTGTATCCG GCCAGACTCAGTTCAACGGCGTGAAAGTCCTGGCGCAGGACAA CACCCTGACCATCCAGGTTGGTGCCAACGACGGTGAAACTATC GATATTGATTTAAAAGAAATCAGCTCTAAAACACTGGGACTTG ATAAGCTTAATGTCCAAGATGCCTACACCCCGAAAGAAACTGC TGTAACCGTTGATAAAACTACCTATAAAAATGGTACAGATCCT ATTACAGCCCAGAGCAATACTGATATCCAAACTGCAATTGGCG GTGGTGCAACGGGGGTTACTGGGGCTGATATCAAATTTAAAGA TGGTCAATACTATTTAGATGTTAAAGGCGGTGCTTCTGCTGGTG TTTATAAAGCCACTTATGATGAAACTACAAAGAAAGTTAATAT TGATACGACTGATAAAACTCCGTTGGCAACTGCGGAAGCTACA GCTATTCGGGGAACGGCCACTATAACCCACAACCAAATTGCTG AAGTAACAAAAGAGGGTGTTGATACGACCACAGTTGCGGCTCA ACTTGCTGCAGCAGGGGTTACTGGCGCCGATAAGGACAATACT AGCCTTGTAAAACTATCGTTTGAGGATAAAAACGGTAAGGTTA TTGATGGTGGCTATGCAGTGAAAATGGGCGACGATTTCTATGC CGCTACATATGATGAGAAAACAGGTGCAATTACTGCTAAAACC ACTACTTATACAGATGGTACTGGCGTTGCTCAAACTGGAGCTGT GAAATTTGGTGGCGCAAATGGTAAATCTGAAGTTGTTACTGCT ACCGATGGTAAGACTTACTTAGCAAGCGACCTTGACAAACATA ACTTCAGAACAGGCGGTGAGCTTAAAGAGGTTAATACAGATAA GACTGAAAACCCACTGCAGAAAATTGATGCTGCCTTGGCACAG GTTGATACACTTCGTTCTGACCTGGGTGCGGTTCAGAACCGTTT CAACTCCGCTATCACCAACCTGGGCAATACCGTAAATAACCTG TCTTCTGCCCGTAGCCGTATCGAAGATTCCGACTACGCAACCGA AGTCTCCAACATGTCTCGCGCGCAGATTCTGCAGCAGGCCGGT ACCTCCGTTCTGGCGCAGGCGAACCAGGTTCCGCAAAACGTCC | 251 |

TABLE 10-continued

Flagellin Nucleic Acid Sequences

| Name | Sequence | SEQ ID NO: |
|---|---|---|
| | TCTCTTTACTGCGTTGATAATAGGCTGGAGCCTCGGTGGCCATG<br>CTTCTTGCCCCTTGGGCCTCCCCCCAGCCCCTCCTCCCCTTCCTG<br>CACCCGTACCCCCGTGGTCTTTGAATAAAGTCTGAGTGGGCGG<br>C | |
| ORF Sequence, NT | ATGGCACAAGTCATTAATACAAACAGCCTGTCGCTGTTGACCC<br>AGAATAACCTGAACAAATCCCAGTCCGCACTGGGCACTGCTAT<br>CGAGCGTTTGTCTTCCGGTCTGCGTATCAACAGCGCGAAAGAC<br>GATGCGGCAGGACAGGCGATTGCTAACCGTTTTACCGCGAACA<br>TCAAAGGTCTGACTCAGGCTTCCCGTAACGCTAACGACGGTAT<br>CTCCATTGCGCAGACCACTGAAGGCGCGCTGAACGAAATCAAC<br>AACAACCTGCAGCGTGTGCGTGAACTGGCGGTTCAGTCTGCGA<br>ATGGTACTAACTCCCAGTCTGACCTCGACTCCATCCAGGCTGAA<br>ATCACCCAGCGCCTGAACGAAATCGACCGTGTATCCGGCCAGA<br>CTCAGTTCAACGGCGTGAAAGTCCTGGCGCAGGACAACACCCT<br>GACCATCCAGGTTGGTGCCAACGACGGTGAAACTATCGATATT<br>GATTTAAAAGAAATCAGCTCTAAAACACTGGGACTTGATAAGC<br>TTAATGTCCAAGATGCCTACACCCCGAAAGAAACTGCTGTAAC<br>CGTTGATAAAACTACCTATAAAAATGGTACAGATCCTATTACA<br>GCCCAGAGCAATACTGATATCCAAACTGCAATTGGCGGTGGTG<br>CAACGGGGGTTACTGGGGCTGATATCAAATTTAAAGATGGTCA<br>ATACTATTTAGATGTTAAAGGCGGTGCTTCTGCTGGTGTTTATA<br>AAGCCACTTATGATGAAACTACAAAGAAAGTTAATATTGATAC<br>GACTGATAAAACTCCGTTGGCAACTGCGGAAGCTACAGCTATT<br>CGGGGAACGGCCACTATAACCCACAACCAAATTGCTGAAGTAA<br>CAAAAGAGGGTGTTGATACGACCACAGTTGCGGCTCAACTTGC<br>TGCAGCAGGGGTTACTGGCGCCGATAAGGACAATACTAGCCTT<br>GTAAAACTATCGTTTGAGGATAAAAACGGTAAGGTTATTGATG<br>GTGGCTATGCAGTGAAAATGGGCGACGATTTCTATGCCGCTAC<br>ATATGATGAGAAAACAGGTGCAATTACTGCTAAAACCACTACT<br>TATACAGATGGTACTGGCGTTGCTCAAACTGGAGCTGTGAAAT<br>TTGGTGGCGCAAATGGTAAATCTGAAGTTGTTACTGCTACCGAT<br>GGTAAGACTTACTTAGCAAGCGACCTTGACAAACATAACTTCA<br>GAACAGGCGGTGAGCTTAAAGAGGTTAATACAGATAAGACTG<br>AAAACCCACTGCAGAAAATTGATGCTGCCTTGGCACAGGTTGA<br>TACACTTCGTTCTGACCTGGGTGCGGTTCAGAACCGTTTCAACT<br>CCGCTATCACCAACCTGGGCAATACCGTAAATAACCTGTCTTCT<br>GCCCGTAGCCGTATCGAAGATTCCGACTACGCAACCGAAGTCT<br>CCAACATGTCTCGCGCGCAGATTCTGCAGCAGGCCGGTACCTC<br>CGTTCTGGCGCAGGCGAACCAGGTTCCGCAAAACGTCCTCTCTT<br>TACTGCGT | 252 |
| mRNA Sequence (assumes T100 tail) | G*GGGAAAUAAGAGAGAAAAGAAGAGUAAGAAGAAAUAUAA<br>GAGCCACCAUGGCACAAGUCAUUAAUACAAACAGCCUGUCGC<br>UGUUGACCCAGAAUAACCUGAACAAAUCCCAGUCCGCACUGG<br>GCACUGCUAUCGAGCGUUUGUCUUCCGGUCUGCGUAUCAACA<br>GCGCGAAAGACGAUGCGGCAGGACAGGCGAUUGCUAACCGUU<br>UUACCGCGAACAUCAAAGGUCUGACUCAGGCUUCCCGUAACG<br>CUAACGACGGUAUCUCCAUUGCGCAGACCACUGAAGGCGCGC<br>UGAACGAAAUCAACAACAACCUGCAGCGUGUGCGUGAACUGG<br>CGGUUCAGUCUGCGAAUGGUACUAACUCCCAGUCUGACCUCG<br>ACUCCAUCCAGGCUGAAAUCACCCAGCGCCUGAACGAAAUCG<br>ACCGUGUAUCCGGCCAGACUCAGUUCAACGGCGUGAAAGUCC<br>UGGCGCAGGACAACACCCUGACCAUCCAGGUUGGUGCCAACG<br>ACGGUGAAACUAUCGAUAUUGAUUUAAAAGAAAUCAGCUCU<br>AAAACACUGGGACUUGAUAAGCUUAAUGUCCAAGAUGCCUAC<br>ACCCCGAAAGAAACUGCUGUAACCGUUGAUAAAACUACCUAU<br>AAAAAUGGUACAGAUCCUAUUACAGCCCAGAGCAAUACUGAU<br>AUCCAAACUGCAAUUGGCGGUGGUGCAACGGGGGUUACUGG<br>GGCUGAUAUCAAAUUUAAAGAUGGUCAAUACUAUUUAGAUG<br>UUAAAGGCGGUGCUUCUGCUGGUGUUUAUAAAGCCACUUAU<br>GAUGAAACUACAAAGAAAGUUAAUAUUGAUACGACUGAUAA<br>AACUCCGUUGGCAACUGCGGAAGCUACAGCUAUUCGGGGAAC<br>GGCCACUAUAACCCACAACCAAAUUGCUGAAGUAACAAAAGA<br>GGGUGUUGAUACGACCACAGUUGCGGCUCAACUUGCUGCAGC<br>AGGGGUUACUGGCGCCGAUAAGGACAAUACUAGCCUUGUAA<br>AACUAUCGUUUGAGGAUAAAAACGGUAAGGUUAUUGAUGGU<br>GGCUAUGCAGUGAAAAUGGGCGACGAUUUCUAUGCCGCUACA<br>UAUGAUGAGAAAACAGGUGCAAUUACUGCUAAAACCACUAC<br>UUAUACAGAUGGUACUGGCGUUGCUCAAACUGGAGCUGUGA<br>AAUUUGGUGGCGCAAAUGGUAAAUCUGAAGUUGUUACUGCU<br>ACCGAUGGUAAGACUUACUUAGCAAGCGACCUUGACAAACAU<br>AACUUCAGAACAGGCGGUGAGCUUAAAGAGGUUAAUACAGA<br>UAAGACUGAAAACCCACUGCAGAAAAUUGAUGCUGCCUUGGC<br>ACAGGUUGAUACACUUCGUUCUGACCUGGGUGCGGUUCAGAA | 253 |

TABLE 10-continued

| Flagellin Nucleic Acid Sequences | | |
|---|---|---|
| Name | Sequence | SEQ ID NO: |
| | CCGUUUCAACUCCGCUAUCACCAACCUGGGCAAUACCGUAAA<br>UAACCUGUCUUCUGCCCGUAGCCGUAUCGAAGAUUCCGACUA<br>CGCAACCGAAGUCUCCAACAUGUCUCGCGCGCAGAUUCUGCA<br>GCAGGCCGGUACCUCCGUUCUGGCGCAGGCGAACCAGGUUCC<br>GCAAAACGUCCUCUCUUUACUGCGUUGAUAAUAGGCUGGAGC<br>CUCGGUGGCCAUGCUUCUUGCCCCUUGGGCCUCCCCCCAGCC<br>CCUCCUCCCCUUCCUGCACCCGUACCCCCGUGGUCUUUGAAU<br>AAAGUCUGAGUGGGCGGCAAAAAAAAAAAAAAAAAAAAAAA<br>AAAAAAAAAAAAAAAAAAAAAAAAAAAAAAAAAAAAAAAAA<br>AAAAAAAAAAAAAAAAAAAAAAAAAAAAAAAAAAAAAUCUAG | |

TABLE 11

| Flagellin Amino Acid Sequences | | |
|---|---|---|
| Name | Sequence | SEQ ID NO: |
| ORF Sequence, AA | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANGTNSQSDLDSIQAEITQRLNEIDRVSGQTQFNGVKVL<br>AQDNTLTIQVGANDGETIDIDLKEISSKTLGLDKLNVQDAYTPKET<br>AVTVDKTTYKNGTDPITAQSNTDIQTAIGGGATGVTGADIKFKDG<br>QYYLDVKGGASAGVYKATYDETTKKVNIDTTDKTPLATAEATAI<br>RGTATITHNQIAEVTKEGVDTTTVAAQLAAAGVTGADKDNTSLV<br>KLSFEDKNGKVIDGGYAVKMGDDFYAATYDEKTGAITAKTTTYT<br>DGTGVAQTGAVKFGGANGKSEVVTATDGKTYLASDLDKHNFRT<br>GGELKEVNTDKTENPLQKIDAALAQVDTLRSDLGAVQNRFNSAIT<br>NLGNTVNNLSSARSRIEDSDYATEVSNMSRAQILQQAGTSVLAQA<br>NQVPQNVLSLLR | 254 |
| Flagellin-GS linker-circumsporozoite protein (CSP) | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANSTNSQSDLDSIQAEITQRLNEIDRVSGQTQFNGVKVL<br>AQDNTLTIQVGANDGETIDIDLKQINSQTLGLDTLNVQQKYKVSD<br>TAATVTGYADTTIALDNSTFKASATGLGGTDQKIDGDLKFDDTTG<br>KYYAKVTVTGGTGKDGYYEVSVDKTNGEVTLAGGATSPLTGGLP<br>ATATEDVKNVQVANADLTEAKAALTAAGVTGTASVVKMSYTDN<br>NGKTIDGGLAVKVGDDYYSATQNKDGSISINTTKYTADDGTSKTA<br>LNKLGGADGKTEVVSIGGKTYAASKAEGHNFKAQPDLAEAAATT<br>TENPLQKIDAALAQVDTLRSDLGAVQNRFNSAITNLGNTVNNLTS<br>ARSRIEDSDYATEVSNMSRAQILQQAGTSVLAQANQVPQNVLSLL<br>RGGGGSGGGGSMMAPDPNANPNANPNANPNANPNANPNANPNA<br>NPNANPNANPNANPNANPNANPNANPNANPNANPNANPNANPN<br>ANPNANPNKNNQGNGQGHNMPNDPNRNVDENANANNAVKNNN<br>NEEPSDKHIEQYLKKIKNSISTEWSPCSVTCGNGIQVRIKPGSANKP<br>KDELDYENDIEKKICKMEKCSSVFNVVNS | 255 |
| Flagellin-RPVT linker-circumsporozoite protein (CSP) | MMAPDPNANPNANPNANPNANPNANPNANPNANPNANPNANPN<br>ANPNANPNANPNANPNANPNANPNANPNANPNANPNANPNKNN<br>QGNGQGHNMPNDPNRNVDENANANNAVKNNNNEEPSDKHIEQY<br>LKKIKNSISTEWSPCSVTCGNGIQVRIKPGSANKPKDELDYENDIEK<br>KICKMEKCSSVFNVVNSRPVTMAQVINTNSLSLLTQNNLNKSQSA<br>LGTAIERLSSGLRINSAKDDAAGQAIANRFTANIKGLTQASRNAND<br>GISIAQTTEGALNEINNNLQRVRELAVQSANSTNSQSDLDSIQAEIT<br>QRLNEIDRVSGQTQFNGVKVLAQDNTLTIQVGANDGETIDIDLKQI<br>NSQTLGLDTLNVQQKYKVSDTAATVTGYADTTIALDNSTFKASAT<br>GLGGTDQKIDGDLKFDDTTGKYYAKVTVTGGTGKDGYYEVSVD<br>KTNGEVTLAGGATSPLTGGLPATATEDVKNVQVANADLTEAKAA<br>LTAAGVTGTASVVKMSYTDNNGKTIDGGLAVKVGDDYYSATQN<br>KDGSISINTTKYTADDGTSKTALNKLGGADGKTEVVSIGGKTYAA<br>SKAEGHNFKAQPDLAEAAATTTENPLQKIDAALAQVDTLRSDLG<br>AVQNRFNSAITNLGNTVNNLTSARSRIEDSDYATEVSNMSRAQILQ<br>QAGTSVLAQANQVPQNVLSLLR | 256 |

Additional mRNA Vaccines

MRK_04
SQ-03-0271

(SEQ ID NO: 7)

ATGGAACTGCTCATTTTGAAGGCAAACGCTATCACGACAATACTCACTGC
AGTGACCTTCTGTTTTGCCTCAGGCCAGAACATAACCGAGGAGTTTTATC
AATCTACATGCAGCGCTGTATCTAAAGGCTACCTGAGTGCGCTCCGCACA
GGATGGTACACCTCCGTGATCACCATCGAGCTCAGCAATATTAAAGAGAA
CAAGTGCAATGGTACCGACGCTAAAGTCAAACTTATCAAGCAGGAACTCG
ACAAATATAAAAACGCTGTGACCGAGCTGCAGTTATTGATGCAGAGTACA
CCTGCCACCAATAACAGAGCTAGGAGGGAGTTGCCTAGGTTTATGAACTA
CACTCTCAACAACGCGAAAAAAACCAATGTGACGCTATCCAAGAAACGGA
AGAGGAGGTTCCTGGGGTTTCTTTTAGGGGTGGGCTCTGCCATTGCTTCC
GGCGTGGCTGTATGTAAAGTTCTCCACCTCGAGGGAGAGGTTAATAAGAT
TAAGTCGGCCCTGCTGAGTACTAACAAAGCAGTGGTGTCGCTGAGTAACG
GAGTAAGTGTGTTAACATTTAAGGTGCTGGACCTCAAGAATTATATTGAC
AAACAGTTGCTTCCTATTCTAAACAAACAGAGCTGTTCAATAAGTAATAT
TGAAACTGTTATTGAGTTTCAGCAGAAGAACAACAGGCTTCTTGAGATTA
CACGCGAGTTCAGTGTCAATGCCGGCGTTACAACACCCGTGTCTACCTAC
ATGCTGACGAATTCTGAGCTTCTCTCTCTCATAAACGACATGCCCATTAC
GAATGACCAAAAAAAACTTATGTCCAACAACGTGCAGATTGTGCGACAGC
AATCCTATAGCATTATGTGTATCATCAAGGAAGAGGTACTCGCTTATGTT
GTGCAGCTACCACTCTATGGTGTGATTGACACCCCCTGTTGGAAGCTGCA
TACCAGTCCACTCTGCACCACTAACACAAAGGAAGGGAGCAATATTTGCC
TCACTCGAACCGACAGGGGGTGGTATTGCGATAATGCGGGCTCCGTGTCC
TTCTTTCCACAGGCTGAAACTTGTAAGGTACAGTCAAACCGCGTGTTCTG
TGATACTATGAATTCTCTGACTCTTCCCAGCGAGGTTAATCTCTGCAACG
TCGACATTTTCAATCCTAAATATGACTGCAAGATCATGACCAGCAAGACC
GACGTCTCCAGCTCAGTAATCACTAGCCTAGGGGCCATTGTAAGCTGCTA
TGGCAAAACCAAGTGTACTGCCTCTAATAAGAACAGAGGCATAATTAAAA
CCTTTTCAAATGGCTGTGACTATGTGTCGAATAAGGGCGTCGACACGGTC
TCAGTAGGGAATACCCTCTACTACGTTAACAAACAGGAAGGCAAATCCCT
TTATGTAAAGGGCGAGCCCATCATAAATTTCTACGACCCACTTGTGTTCC
CCAGTGATGAATTCGATGCATCAATCTCCCAGGTGAACGAAAAGATCAAT
CAATCCCTTGCTTTTATACGAAAGTCAGATGAACTCCTGCATAACGTGAA
TGCTGGGAAATCTACAACCAACATCATGATCACTACCATCATTATTGTGA
TTATCGTAATTCTGCTATCCTTGATTGCTGTCGGGCTGCTTCTGTACTGT
AAGGCCAGATCGACGCCTGTGACCCTTTCAAAAGACCAACTTAGCGGTAT
CAATAATATTGCCTTTAGCAAT

-continued

MRK_04_no AAALys
SQ-038059

(SEQ ID NO: 257)

ATGGAACTGCTCATTTTGAAGGCAAACGCTATCACGACAATACTCACTGC
AGTGACCTTCTGTTTTGCCTCAGGCCAGAACATAACCGAGGAGTTTTATC
AATCTACATGCAGCGCTGTATCTAAAGGCTACCTGAGTGCGCTCCGCACA
GGATGGTACACCTCCGTGATCACCATCGAGCTCAGCAATATTAAAGAGAA
CAAGTGCAATGGTACCGACGCTAAAGTCAAACTTATCAAGCAGGAACTCG
ACAAATATAAGAACGCTGTGACCGAGCTGCAGTTATTGATGCAGAGTACA
CCTGCCACCAATAACAGAGCTAGGAGGGAGTTGCCTAGGTTTATGAACTA
CACTCTCAACAACGCGAAGAAGACCAATGTGACGCTATCCAAGAAACGGA
AGAGGAGGTTCCTGGGGTTTCTTTTAGGGGTGGGCTCTGCCATTGCTTCC
GGCGTGGCTGTATGTAAAGTTCTCCACCTCGAGGGAGAGGTTAATAAGAT
TAAGTCGGCCCTGCTGAGTACTAACAAAGCAGTGGTGTCGCTGAGTAACG
GAGTAAGTGTGTTAACATTTAAGGTGCTGGACCTCAAGAATTATATTGAC
AAACAGTTGCTTCCTATTCTAAACAAACAGAGCTGTTCAATAAGTAATAT
TGAAACTGTTATTGAGTTTCAGCAGAAGAACAACAGGCTTCTTGAGATTA
CACGCGAGTTCAGTGTCAATGCCGGCGTTACAACACCCGTGTCTACCTAC
ATGCTGACGAATTCTGAGCTTCTCTCTCTCATAAACGACATGCCCATTAC
GAATGACCAAAAGAAACTTATGTCCAACAACGTGCAGATTGTGCGACAGC
AATCCTATAGCATTATGTGTATCATCAAGGAAGAGGTACTCGCTTATGTT
GTGCAGCTACCACTCTATGGTGTGATTGACACCCCCTGTTGGAAGCTGCA
TACCAGTCCACTCTGCACCACTAACACAAAGGAAGGGAGCAATATTTGCC
TCACTCGAACCGACAGGGGGTGGTATTGCGATAATGCGGGCTCCGTGTCC
TTCTTTCCACAGGCTGAAACTTGTAAGGTACAGTCAAACCGCGTGTTCTG
TGATACTATGAATTCTCTGACTCTTCCCAGCGAGGTTAATCTCTGCAACG
TCGACATTTTCAATCCTAAATATGACTGCAAGATCATGACCAGCAAGACC
GACGTCTCCAGCTCAGTAATCACTAGCCTAGGGGCCATTGTAAGCTGCTA
TGGCAAGACCAAGTGTACTGCCTCTAATAAGAACAGAGGCATAATTAAGA
CCTTTTCAAATGGCTGTGACTATGTGTCGAATAAGGGCGTCGACACGGTC
TCAGTAGGGAATACCCTCTACTACGTTAACAAACAGGAAGGCAAATCCCT
TTATGTAAAGGGCGAGCCCATCATAAATTTCTACGACCCACTTGTGTTCC
CCAGTGATGAATTCGATGCATCAATCTCCCAGGTGAACGAAAAGATCAAT
CAATCCCTTGCTTTTATACGAAAGTCAGATGAACTCCTGCATAACGTGAA
TGCTGGGAAATCTACAACCAACATCATGATCACTACCATCATTATTGTGA
TTATCGTAATTCTGCTATCCTTGATTGCTGTCGGGCTGCTTCTGTACTGT
AAGGCCAGATCGACGCCTGTGACCCTTTCAAAGGACCAACTTAGCGGTAT
CAATAATATTGCCTTTAGCAAT

MRK_04_no4A
SQ-03-805-8

(SEQ ID NO: 258)

ATGGAACTGCTCATTTTGAAGGCAAACGCTATCACGACAATACTCACTGC
AGTGACCTTCTGTTTTGCCTCAGGCCAGAACATAACCGAGGAGTTTTATC

-continued

AATCTACATGCAGCGCTGTATCTAAAGGCTACCTGAGTGCGCTCCGCACA
GGATGGTACACCTCCGTGATCACCATCGAGCTCAGCAATATTAAAGAGAA
CAAGTGCAATGGTACCGACGCTAAAGTCAAACTTATCAAGCAGGAACTCG
ACAAATATAAGAACGCTGTGACCGAGCTGCAGTTATTGATGCAGAGTACA
CCTGCCACCAATAACAGAGCTAGGAGGGAGTTGCCTAGGTTTATGAACTA
CACTCTCAACAACGCGAAGAAGACCAATGTGACGCTATCCAAGAAACGGA
AGAGGAGGTTCCTGGGGTTTCTTTTAGGGGTGGGCTCTGCCATTGCTTCC
GGCGTGGCTGTATGTAAAGTTCTCCACCTCGAGGGAGAGGTTAATAAGAT
TAAGTCGGCCCTGCTGAGTACTAACAAAGCAGTGGTGTCGCTGAGTAACG
GAGTAAGTGTGTTAACATTTAAGGTGCTGGACCTCAAGAATTATATTGAC
AAACAGTTGCTTCCTATTCTAAACAAACAGAGCTGTTCAATAAGTAATAT
TGAAACTGTTATTGAGTTTCAGCAGAAGAACAACAGGCTTCTTGAGATTA
CACGCGAGTTCAGTGTCAATGCCGGCGTTACAACACCCGTGTCTACCTAC
ATGCTGACGAATTCTGAGCTTCTCTCTCTCATAAACGACATGCCCATTAC
GAATGACCAGAAGAAACTTATGTCCAACAACGTGCAGATTGTGCGACAGC
AATCCTATAGCATTATGTGTATCATCAAGGAAGAGGTACTCGCTTATGTT
GTGCAGCTACCACTCTATGGTGTGATTGACACCCCCTGTTGGAAGCTGCA
TACCAGTCCACTCTGCACCACTAACACAAAGGAAGGGAGCAATATTTGCC
TCACTCGAACCGACAGGGGGTGGTATTGCGATAATGCGGGCTCCGTGTCC
TTCTTTCCACAGGCTGAAACTTGTAAGGTACAGTCAAACCGCGTGTTCTG
TGATACTATGAATTCTCTGACTCTTCCCAGCGAGGTTAATCTCTGCAACG
TCGACATTTTCAATCCTAAATATGACTGCAAGATCATGACCAGCAAGACC
GACGTCTCCAGCTCAGTAATCACTAGCCTAGGGGCCATTGTAAGCTGCTA
TGGCAAGACCAAGTGTACTGCCTCTAATAAGAACAGAGGCATAATTAAGA
CCTTTTCAAATGGCTGTGACTATGTGTCGAATAAGGGCGTCGACACGGTC
TCAGTAGGGAATACCCTCTACTACGTTAACAAACAGGAAGGCAAATCCCT
TTATGTAAAGGGCGAGCCCATCATAAATTTCTACGACCCACTTGTGTTCC
CCAGTGATGAATTCGATGCATCAATCTCCCAGGTGAACGAGAAGATCAAT
CAATCCCTTGCTTTTATACGAAAGTCAGATGAACTCCTGCATAACGTGAA
TGCTGGGAAATCTACAACCAACATCATGATCACTACCATCATTATTGTGA
TTATCGTAATTCTGCTATCCTTGATTGCTGTCGGGCTGCTTCTGTACTGT
AAGGCCAGATCGACGCCTGTGACCCTTTCAAAGGACCAACTTAGCGGTAT
CAATAATATTGCCTTTAGCAAT

MRK_04_nopolyA_3mut
SQ-038057

(SEQ ID NO: 259)

ATGGAACTGCTCATTTTGAAGGCAAACGCTATCACGACAATACTCACTGC
AGTGACCTTCTGTTTTGCCTCAGGCCAGAACATAACCGAGGAGTTTTATC
AATCTACATGCAGCGCTGTATCTAAAGGCTACCTGAGTGCGCTCCGCACA
GGATGGTACACCTCCGTGATCACCATCGAGCTCAGCAATATTAAAGAGAA
CAAGTGCAATGGTACCGACGCTAAAGTCAAACTTATCAAGCAGGAACTCG

-continued

ACAAATATAAGAACGCTGTGACCGAGCTGCAGTTATTGATGCAGAGTACA
CCTGCCACCAATAACAGAGCTAGGAGGGAGTTGCCTAGGTTTATGAACTA
CACTCTCAACAACGCGAAGAAAACCAATGTGACGCTATCCAAGAAACGGA
AGAGGAGGTTCCTGGGGTTTCTTTTAGGGGTGGGCTCTGCCATTGCTTCC
GGCGTGGCTGTATGTAAAGTTCTCCACCTCGAGGGAGAGGTTAATAAGAT
TAAGTCGGCCCTGCTGAGTACTAACAAAGCAGTGGTGTCGCTGAGTAACG
GAGTAAGTGTGTTAACATTTAAGGTGCTGGACCTCAAGAATTATATTGAC
AAACAGTTGCTTCCTATTCTAAACAAACAGAGCTGTTCAATAAGTAATAT
TGAAACTGTTATTGAGTTTCAGCAGAAGAACAACAGGCTTCTTGAGATTA
CACGCGAGTTCAGTGTCAATGCCGGCGTTACAACACCCGTGTCTACCTAC
ATGCTGACGAATTCTGAGCTTCTCTCTCTCATAAACGACATGCCCATTAC
GAATGACCAAAAGAAACTTATGTCCAACAACGTGCAGATTGTGCGACAGC
AATCCTATAGCATTATGTGTATCATCAAGGAAGAGGTACTCGCTTATGTT
GTGCAGCTACCACTCTATGGTGTGATTGACACCCCCTGTTGGAAGCTGCA
TACCAGTCCACTCTGCACCACTAACACAAAGGAAGGGAGCAATATTTGCC
TCACTCGAACCGACAGGGGGTGGTATTGCGATAATGCGGGCTCCGTGTCC
TTCTTTCCACAGGCTGAAACTTGTAAGGTACAGTCAAACCGCGTGTTCTG
TGATACTATGAATTCTCTGACTCTTCCCAGCGAGGTTAATCTCTGCAACG
TCGACATTTTCAATCCTAAATATGACTGCAAGATCATGACCAGCAAGACC
GACGTCTCCAGCTCAGTAATCACTAGCCTAGGGGCCATTGTAAGCTGCTA
TGGCAAAACCAAGTGTACTGCCTCTAATAAGAACAGAGGCATAATTAAAA
CCTTTTCAAATGGCTGTGACTATGTGTCGAATAAGGGCGTCGACACGGTC
TCAGTAGGGAATACCCTCTACTACGTTAACAAACAGGAAGGCAAATCCCT
TTATGTAAAGGGCGAGCCCATCATAAATTTCTACGACCCACTTGTGTTCC
CCAGTGATGAATTCGATGCATCAATCTCCCAGGTGAACGAAAAGATCAAT
CAATCCCTTGCTTTTATACGAAAGTCAGATGAACTCCTGCATAACGTGAA
TGCTGGGAAATCTACAACCAACATCATGATCACTACCATCATTATTGTGA
TTATCGTAATTCTGCTATCCTTGATTGCTGTCGGGCTGCTTCTGTACTGT
AAGGCCAGATCGACGCCTGTGACCCTTTCAAAAGACCAACTTAGCGGTAT
CAATAATATTGCCTTTAGCAAT

TABLE 12

RSV mRNA Sequences

| Name | mRNA Sequence | SEQ ID NO: |
|---|---|---|
| RSV #1 | AUGGAGCUGCUCAUCCUCAAAGCAAAUGCCAUCACCACUAUCCU<br>GACCGCCGUCACUUUCUGCUUCGCCUCCGGCCAAAAUAUCACCGA<br>AGAGUUCUAUCAGUCCACCUGCUCUGCCGUUUCUAAAGGUUACC<br>UGUCAGCCCUUAGAACAGGGUGGUAUACCUCUGUUAUUACCAUU<br>GAGUUGUCCAACAUUAAGAAGAACAAGUGCAAUGGCACAGACGC<br>UAAGGUUAAGCUCAUCAAGCAGGAGCUCGACAAAUAUAAAAAUG<br>CCGUCACGGAGCUGCAGUUAUUGAUGCAGAGCACCCAGGCGACA<br>AACAACCGUGCACGACGCGAGCUACCCCGAUUCAUGAACUACAC<br>CCUCAAUAAUGCAAAGAAGACAAAUGUGACGCUCUCUAAGAAGC<br>GCAAGCGUCGCUUUCUGGGCUUUCUUCUCGGGGUUGGGAGCGCG<br>AUCGCAAGCGGCGUGGCUGUAUCAAAAGUGCUUCAUCUUGAGGG<br>AGAAGUGAAUAAAAUCAAAAGUGCUCUGCUAUCUACAAACAAAG<br>CCGUUGUAUCACUGUCCAACGGAGUGUCCGUGCUCACGUCCAAA<br>GUGCUAGAUUUGAAGAAUUACAUCGAUAAGCAGCUGCUCCCUAU<br>UGUGAACAAACAAUCAUGUUCCAUCAGUAACAUUGAAACAGUCA<br>UCGAGUUUCAACAGAAAAACAAUAGACUGCUGGAGAUUACCAGA<br>GAAUUUUCGGUUAACGCCGGCGUGACUACCCCUGUAAGCACCUA<br>CAUGUUGACAAACUCCGAACUUUUGUCACUGAUAAACGAUAUGC<br>CUAUUACUAAUGAUCAGAAAAAAUUGAUGUCCAAUAAUGUCCAA<br>AUCGUCAGGCAACAGUCCUACAGUAUCAUGUCUAUUAUUAAGGA<br>GGAGGUCCUUGCAUACGUGGUGCAACUGCCAUUAUACGGAGUCA<br>UUGAUACUCCCUGUUGGAAACUCCAUACAAGCCCCCUGUGCACU<br>ACUAACACUAAAGAGGGAUCAAAUAUUUGUCUCACUCGGACAGA<br>UAGAGGUUGGUACUGUGAUAAUGCUGGCUCAGUGUCAUUCUUUC<br>CACAGGCUGAAACCUGCAAGGUUCAGUCAAACAGGGUGUUUUGC<br>GAUACCAUGAAUUCUCUAACCCUCCCCAGUGAGGUGAACCUGUG<br>UAAUGUGGAUAUAUUCAACCCCAAGUAUGAUUGUAAGAUCAUGA<br>CCUCCAAGACGGACGUGAGUAGCAGUGUUAUCACCUCCCUGGGG<br>GCCAUUGUAUCCUGCUACGGAAAAACGAAAUGUACUGCCUCGAA<br>CAAAAAUAGGGGAAUCAUCAAAACUUUUAGUAAUGGAUGCGACU<br>ACGUAUCUAAUAAAGGUGUUGACACAGUGUCAGUCGGCAACACA<br>CUGUAUUACGUGAAUAAGCAAGAAGGGAAGUCGCUGUAUGUCAA<br>AGGGGAGCCUAUCAUUAAUUUUUAUGACCCACUGGUUUUCCCCA<br>GCGAUGAGUUCGACGCCAGCAUUAGUCAGGUUAAUGAGAAAAUC<br>AACCAGUCCUUGGCAUUUAUUCGUAAGAGUGAUGAAUUGCUCCA<br>UAAUGUGAACGCUGGUAAAUCCACUACCAACAUUAUGAUAACUA<br>CCAUCAUCAUAGUAAUAAUAGUAAUUUUACUGUCUCUGAUCGCU<br>GUGGGCCUGUUACUGUAUUGCAAAGCCCGCAGUACUCCUGUCAC<br>CUUAUCAAAGGACCAGCUGUCUGGGAUAAACAACAUCGCGUUCU<br>CCAAU | 260 |
| RSV #2 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAAAAC<br>GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAAAAAACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA<br>GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAAAAAAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG<br>GGCCAUUGUAAGCUGCUAUGGCAAAACCAAGUGUACUGCCUCUA<br>AUAAGAACAGAGGCAUAAUUAAAACCUUUUCAAAUGGCUGUGAC<br>UAUGUGUCGAAUAAGGGCGUCGACACGGUCUCAGUAGGGAAUAC<br>CCUCUACUACGUUAACAAACAGGAAGGCAAAUCCCUUUAUGUAA<br>AGGGCGAGCCCAUCAUAAAUUUCUACGACCCACUUGUGUUCCCC<br>AGUGAUGAAUUCGAUGCAUCAAUCUCCCAGGUGAACGAAAAGAU | 261 |

TABLE 12-continued

RSV mRNA Sequences

| Name | mRNA Sequence | SEQ ID NO: |
|---|---|---|
| | CAAUCAAUCCCUUGCUUUUAUACGAAAGUCAGAUGAACUCCUGC<br>AUAACGUGAAUGCUGGGAAAUCUACAACCAACAUCAUGAUCACU<br>ACCAUCAUUAUUGUGAUUAUCGUAAUUCUGCUAUCCUUGAUUGC<br>UGUCGGGCUGCUUCUGUACUGUAAGGCCAGAUCGACGCCUGUGA<br>CCCUUUCAAAAGACCAACUUAGCGGUAUCAAUAAUAUUGCCUUU<br>AGCAAU | |
| MRK-1 membrane-bound RSV F protein/MRK_01_ F (full length, Merck A2 strain)/SQ-030268 | AUGGAGCUGCUCAUCCUCAAAGCAAAUGCCAUCACCACUAUCCUG<br>ACCGCCGUCACUUUCUGCUUCGCCUCCGGCCAAAAUAUCACCGAA<br>GAGUUCUAUCAGUCCACCUGCUCUGCCGUUUCUAAAGGUUACCUG<br>UCAGCCCUUAGAACAGGGUGGUAUACCUCUGUUAUUACCAUUGAG<br>UUGUCCAACAUUAAGAAGAACAAGUGCAAUGGCACAGACGCUAAG<br>GUUAAGCUCAUCAAGCAGGAGCUCGACAAAUAUAAAAAUGCCGUC<br>ACGGAGCUGCAGUUAUUGAUGCAGAGCACCCAGGCGACAAACAAC<br>CGUGCACGACGCGAGCUACCCCGAUUCAUGAACUACACCCUCAAU<br>AAUGCAAAGAAGACAAAUGUGACGCUCUCUAAGAAGCGCAAGCGU<br>CGCUUUCUGGGCUUUCUUCUCGGGGUUGGGAGCGCGAUCGCAAGC<br>GGCGUGGCUGUAUCAAAAGUGCUUCAUCUUGAGGGAGAAGUGAAU<br>AAAAUCAAAAGUGCUCUGCUAUCUACAAACAAAGCCGUUGUAUCA<br>CUGUCCAACGGAGUGUCCGUGCUCACGUCCAAAGUGCUAGAUUUG<br>AAGAAUUACAUCGAUAAGCAGCUGCUCCCUAUUGUGAACAAACAA<br>UCAUGUUCCAUCAGUAACAUUGAAACAGUCAUCGAGUUUCAACAG<br>AAAAACAAUAGACUGCUGGAGAUUACCAGAGAAUUUUCGGUUAAC<br>GCCGGCGUGACUACCCCUGUAAGCACCUACAUGUUGACAAACUCC<br>GAACUUUUGUCACUGAUAAACGAUAUGCCUAUUACUAAUGAUCAG<br>AAAAAAUUGAUGUCCAAUAAUGUCCAAAUCGUCAGGCAACAGUCC<br>UACAGUAUCAUGUCUAUUAUUAAGGAGGAGGUCCUUGCAUACGUG<br>GUGCAACUGCCAUUAUACGGAGUCAUUGAUACUCCCUGUUGGAAA<br>CUCCAUACAAGCCCCCUGUGCACUACUAACACUAAAGAGGGAUCA<br>AAUAUUUGUCUCACUCGGACAGAUAGAGGUUGGUACUGUGAUAAU<br>GCUGGCUCAGUGUCAUUCUUUCCACAGGCUGAAACCUGCAAGGUU<br>CAGUCAAACAGGGUGUUUUGCGAUACCAUGAAUUCUCUAACCCUC<br>CCCAGUGAGGUGAACCUGUGUAAUGUGGAUAUAUUCAACCCCAAG<br>UAUGAUUGUAAGAUCAUGACCUCCAAGACGGACGUGAGUAGCAGU<br>GUUAUCACCUCCCUGGGGGCCAUUGUAUCCUGCUACGGAAAAACG<br>AAAUGUACUGCCUCGAACAAAAAUAGGGGAAUCAUCAAAACUUUU<br>AGUAAUGGAUGCGACUACGUAUCUAAUAAAGGUGUUGACACAGUG<br>UCAGUCGGCAACACACUGUAUUACGUGAAUAAGCAAGAAGGGAAG<br>UCGCUGUAUGUCAAAGGGGAGCCUAUCAUUAAUUUUUAUGACCCA<br>CUGGUUUUCCCCAGCGAUGAGUUCGACGCCAGCAUUAGUCAGGUU<br>AAUGAGAAAAUCAACCAGUCCUUGGCAUUUAUUCGUAAGAGUGAU<br>GAAUUGCUCCAUAAUGUGAACGCUGGUAAAUCCACUACCAACAUU<br>AUGAUAACUACCAUCAUCAUAGUAAUAAUAGUAAUUUUACUGUCU<br>CUGAUCGCUGUGGGCCUGUUACUGUAUUGCAAAGCCCGCAGUACU<br>CCUGUCACCUUAUCAAAGGACCAGCUGUCUGGGAUAAACAACAUC<br>GCGUUCUCCAAU | 262 |
| MRK-4 membrane-bound DS-CAV1 (stabilized prefusion F protein)/MRK_04_ Prefusion F/DS-CAV1 (Full length, S155C/S290C/ S190F/V207L)/ SQ-030271 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAAAAC<br>GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAAAAAACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA<br>GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAAAAAAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG | 263 |

TABLE 12-continued

| RSV mRNA Sequences | | |
|---|---|---|
| Name | mRNA Sequence | SEQ ID NO: |
| | GGCCAUUGUAAGCUGCUAUGGCAAAACCAAGUGUACUGCCUCUA AUAAGAACAGAGGCAUAAUUAAAACCUUUUCAAAUGGCUGUGAC UAUGUGUCGAAUAAGGGCGUCGACACGGUCUCAGUAGGGAAUAC CCUCUACUACGUUAACAAACAGGAAGGCAAAUCCCUUUAUGUAA AGGGCGAGCCCAUCAUAAAUUUCUACGACCCACUUGUGUUCCCC AGUGAUGAAUUCGAUGCAUCAAUCUCCCAGGUGAACGAAAAGAU CAAUCAAUCCCUUGCUUUUAUACGAAAGUCAGAUGAACUCCUGC AUAACGUGAAUGCUGGGAAAUCUACAACCAACAUCAUGAUCACU ACCAUCAUUAUUGUGAUUAUCGUAAUUCUGCUAUCCUUGAUUGC UGUCGGGCUGCUUCUGUACUGUAAGGCCAGAUCGACGCCUGUGA CCCUUUCAAAAGACCAACUUAGCGGUAUCAAUAAUAUUGCCUUU AGCAAU | |
| MRK-5 RSV F Construct | AUGGAACUGCUCAUCCUUAAAGCCAACGCGAUAACGACCAUUCU GACCGCCGUGACCUUCUGCUUCGCCAGCGGCCAGAACAUUACCG AAGAGUUUUACCAGAGCACGUGCUCUGCCGUGAGCAAAGGUUAU CUGAGCGCUUUAAGAACUGGCUGGUACACCAGUGUUAUUACUAU AGAGCUGUCAAAUAUUAAAAAGAAUAAAUGCAACGGGACCGAUG CCAAAGUAAAAUUAAUUAAGCAGGAAUUGGACAAGUAUAAGAAU GCAGUGACAGAGUUGCAGCUCCUGAUGCAGAGCACACAAGCUAC AAACAAUCGCGCUCGCCAGCAGCAACAGCGGUUUUUAGGGUUCC UGCUAGGGGUGGGGUCAGCCAUUGCCUCUGGAGUGGCAGUGUCC AAAGUGCUGCAUCUGGAAGGGGAAGUUAACAAGAUAAAAUCCGC ACUCCUCAGCACCAAUAAAGCCGUGGUCUCCCUGUCCAAUGGAG UAUCAGUUUUGACAAGCAAGGUGCUGGACCUGAAGAAUUAUAUA GAUAAGCAGUUACUGCCAAUAGUGAAUAAACAGUCAUGCUCAAU UAGCAACAUUGAGACAGUUAUCGAAUUCCAGCAGAAAAAUAAUA GGCUUCUGGAAAUAACUCGCGAAUUCUCAGUAAAUGCCGGAGUG ACCACACCCGUAUCGACUUAUAUGCUUACAAACUCUGAACUGUU GUCCUUGAUUAACGAUAUGCCAAUAACAAAUGACCAGAAGAAGC UAAUGAGCAACAAUGUGCAGAUUGUAAGACAGCAGUCUUACUCA AUAAUGUCUAUAAUAAAAGAGGAGGUGUUGGCAUAUGUGGUGC AACUGCCUCUCUAUGGCGUGAUCGAUACUCCUUGCUGGAAGUUA CAUACAUCUCCACUGUGUACAACUAAUACUAAGGAGGGUAGCAA UAUUUGUCUGACACGCACAGAUCGGGGUUGGUAUUGCGACAACG CGGGCAGUGUGAGCUUUUUCCCUCAGGCCGAAACCUGUAAGGUU CAAUCUAAUCGGGUAUUUUGCGACACAAUGAACAGCCUGACCCU UCCGUCCGAAGUUAAUUUGUGCAACGUCGACAUCUUCAAUCCUA AAUAUGACUGCAAAAUCAUGACUUCUAAAACCGACGUAUCCAGC UCAGUGAUAACAAGCCUUGGGGCAAUUGUAAGCUGCUAUGGCAA GACGAAGUGCACCGCUAGUAACAAGAACCGGGGGAUUAUUAAGA CUUUUUCGAACGGAUGCGAUUACGUCUCCAACAAAGGCGUCGAU ACUGUGUCCGUGGGAAACACCCUCUACUAUGUGAACAAGCAGGA AGGCAAAAGCCUCUACGUCAAAGGAGAGCCUAUCAUCAAUUUCU ACGACCCUCUAGUAUUCCCUUCAGACGAAUUUGACGCAUCAAUU UCCCAGGUGAACGAGAAAAUAAAUCAAAGCUUAGCCUUUAUCCG CAAGAGUGAUGAGUUGCUUCACAACGUCAACGCCGGCAAAUCAA CCACUAAU | 264 |
| MRK-6 RSV F Construct | AUGGAACUCUUGAUCCUGAAGGCUAAUGCAAUAACAACAAUUCU GACAGCAGUCACCUUUUGCUUCGCCAGCGGACAGAAUAUUACGG AGGAGUUUUAUCAAUCUACCUGUAGUGCCGUGAGCAAGGGGUAC CUGUCUGCCCUGAGGACGGGAUGGUACACAUCCGUGAUCACCAU CGAGUUGUCUAACAUUAAAAAGAACAAGUGCAACGGAACUGACG CCAAGGUGAAGCUCAUUAAGCAAGAGCUCGACAAAUAUAAGAAU GCGGUUACAGAACUACAGCUACUAAUGCAGUCCACACAGGCAAC CAAUAACCGAGCACGUCAGCAGCAGCAACGCUUCCUUGGCUUCC UGCUCGGGGUUGGCUCGGCAAUUGCAUCCGGAGUGGCUGUUUCC AAGGUUUUGCACCUUGAGGGAGAGGUCAAUAAGAUCAAGAGCGC CCUCCUGUCAACUAAUAAGGCCGUGGUCAGCCUUUCCAACGGUG UUUCUGUGUUAACCUCAAAAGUGCUCGACCUUAAAAACUAUAUC GAUAAGCAGCUGCUGCCCAUAGUGAACAAACAGUCCUGUUCUAU CAGUAAUAUCGAGACAGUGAUCGAAUUCCAGCAGAAGAACAAUC GUCUGCUGGAAAUUACAAGGGAGUUCAGCGUAAACGCUGGAGUC ACAACCCCCGUGUCCACUUACAUGCUGACCAAUUCCGAGCUGCU GAGUUUGAUUAAUGAUAUGCCCAUUACGAACGAUCAGAAGAAAC UGAUGUCGAAUAAUGUUCAGAUCGUUAGGCAGCAGUCUUAUAGC AUCAUGAGUAUUAUCAAAGAGGAGGUCCUCGCCUAUGUGGUUCA GCUGCCUCUCUACGGCGUUAUAGACACCCCAUGCUGGAAGCUUC ACACCUCUCCUCUGUGUACGACCAAUACAAAGGAGGGCUCAAAC AUUUGCCUUACCCGCACAGAUAGAGGAUGGUACUGCGAUAAUGC UGGCUCUGUGUCUUUCUUUCCUCAGGCCGAAACAUGUAAGGUAC AGUCCAAUAGGGUAUUUUGCGACACCAUGAACUCCCUAACCUUA CCAAGUGAAGUGAACCUCUGCAAUGUGGACAUCUUUAACCCGAA GUAUGACUGCAAAAUCAUGACUUCCAAGACAGACGUGUCCAGUA | 265 |

TABLE 12-continued

RSV mRNA Sequences

| Name | mRNA Sequence | SEQ ID NO: |
|---|---|---|
| | GUGUGAUUACCUCACUGGGCGCAAUCGUUUCAUGCUAUGGGAAG<br>ACAAAGUGCACCGCAAGCAACAAGAAUCGGGGCAUCAUCAAAAC<br>CUUCAGUAACGGUUGUGACUAUGUUUCAAACAAGGGAGUCGAUA<br>CCGUGUCGGUGGGCAAUACUCUUUACUACGUGAAUAAACAGGAG<br>GGGAAAUCACUGUAUGUGAAAGGUGAGCCGAUCAUUAACUUUUA<br>CGACCCUCUCGUGUUUCCCUCCGAUGAGUUCGACGCAUCCAUCA<br>GUCAGGUCAAUGAGAAAAUCAACCAAUCUCUCGCCUUCAUUAGA<br>AAAUCUGACGAAUUACUGAGUGCCAUUGGAGGAUAUAUUCCGGA<br>GGCUCCCAGGGACGGGCAGGCUUACGUCCGAAAGGAUGGAGAAU<br>GGGUCCUACUGAGCACAUUUCUA (The underlined region<br>represents a sequence coding for foldon. The<br>underlined region can be substituted with<br>alternative sequences which achieve a same or<br>similar function.) | |
| MRK-7 RSV F<br>Construct | AUGGAGCUCCUGAUCUUGAAGGCGAAUGCCAUUACCACCAUCCU<br>CACCGCAGUAACUUUCUGUUUCGCAAGUGGCCAGAAUAUAACAG<br>AAGAGUUCUAUCAGUCAACCUGUAGCGCAGUCUCAAAGGGGUAU<br>UUAUCAGCACUGAGAACCGGUUGGUAUACCAGUGUUAUUACAAU<br>AGAGCUGAGUAACAUAAAGGAGAAUAAGUGCAACGGCACUGACG<br>CCAAGGUCAAGCUCAUCAAACAGGAACUCGAUAAAUACAAGAAC<br>GCUGUCACUGAACUGCAGCUGCUGAUGCAAAGCACCCCCGCCACC<br>AACAAUAGGGCCCGCAGAGAGCUUCCUAGAUUUAUGAACUACAC<br>UCUGAACAACGCCAAAAAGACCAAUGUAACACUGUCAAAGAAAC<br>AGAAACAGCAGGCUAUUGCAAGCGGUGUGGCUGUGUCUAAAGUG<br>CUGCAUCUCGAGGGGGAGGUCAACAAGAUCAAAUCCGCAUUGCU<br>CAGCACCAACAAGGCUGUGGUGAGCCUGUCCAAUGGUGUCUCAG<br>UGCUCACCAGCAAAGUGCUGGACCUGAAGAAUUAUAUUGAUAAG<br>CAGCUGCUACCCAUAGUCAACAAACAGUCAUGCUCCAUAUCUAA<br>UAUUGAGACUGUCAUCGAGUUCCAACAGAAGAACAAUCGCCUGC<br>UGGAGAUUACCAGGGAGUUCUCAGUCAAUGCCGGGGUCACGACA<br>CCCGUUAGUACUUAUAUGCUUACCAACUCCGAGCUUCUCUCUUU<br>GAUCAAUGACAUGCCAAUUACUAACGACCAGAAGAAGUUGAUGU<br>CUAACAAUGUACAGAUCGUUCGCCAGCAGUCCUAUUCCAUUAUG<br>UCGAUUAUUAAAGAGGAGGUUCUUGCAUACGUCGUGCAGUUGCC<br>AUUAUAUGGAGUCAUCGACACCCCCUGCUGGAAACUGCAUACGU<br>CACCAUUAUGCACCACGAAUACAAAGGAGGGCAGUAAUAUUUGU<br>CUUACACGGACUGAUCGAGGCUGGUAUUGUGAUAACGCAGGCUC<br>GGUGUCAUUCUUUCCACAGGCUGAAACCUGUAAGGUGCAAUCUA<br>AUAGGGUGUUUUGCGAUACCAUGAAUUCUCUGACUCUGCCCAGU<br>GAGGUCAAUUUGUGUAACGUGGACAUCUUCAACCCAAAGUACGA<br>CUGCAAGAUCAUGACAUCUAAGACAGAUGUGUCAUCCAGCGUUA<br>UCACGAGCCUCGGCGCUAUAGUCUCCUGUUACGGCAAGACCAAG<br>UGCACCGCUAGCAACAAGAAUCGGGGAAUCAUCAAAACCUUUUC<br>UAACGGUUGUGACUACGUGAGCAACAAGGGGGUGGAUACCGUCU<br>CAGUCGGUAACACCCUGUACUACGUGAAUAAACAGGAGGGGAAG<br>UCAUUGUACGUGAAGGGUGAACCUAUCAUCAACUUUUAUGACCC<br>CCUCGUCUUCCCAUCAGACGAGUUUGACGCGUCCAUCUCUCAGG<br>UGAAUGAGAAGAUUAACCAGAGCCUGGCUUUUAUCCGCAAAUCA<br>GACGAACUACUGCACAAUGUCAACGCUGGCAAGAGCACAACAAA<br>UAUAAUGAUAACAACCAUCAUCAUCGUCAUUAUUGUGAUCUUGU<br>UAUCACUGAUCGCUGUGGGGCUCCUCCUUUAUUGCAAGGCUCGU<br>AGCACCCCUGUCACCCUCAGUAAAGAUCAGCUGUCAGGGAUCAA<br>UAAUAUCGCGUUUAGCAAC | 266 |
| MRK-8 RSV F<br>Construct | AUGGAAUUAUUAAUUUUGAAGACAAAUGCUAUAACCGCGAUACUA<br>GCGGCUGUGACUCUUUGUUUCGCAUCAAGCCAGAAUAUUACAGAA<br>GAAUUUUAUCAAUCCACCUGCAGCGCUGUAUCGAAAGGUUACCUC<br>AGCGCGCUUAGGACAGGAUGGUAUACCUCCGUUAUCACGAUUGAA<br>CUGAGUAAUAUCAAGGAAAACAAGUGUAACGGAACAGACGCCAAG<br>GUCAAACUUAUUAAACAAGAACUGGACAAGUAUAAGUCUGCAGUG<br>ACCGAAUUGCAGCUCCUGAUGCAGAGUACCCCUGCAACUAACAAC<br>AAGUUUUUGGGCUUUCUGCAAGGCGUGGGUAGCGCGAUCGCCUCC<br>GGAAUCGCGGUCUCCAAAGUGUUGCACCUGGAGGGAGAAGUUAAC<br>AAGAUCAAAUCGGCUCUGUUGAGUACCAACAAGGCAGUGGUGUCA<br>CUGAGCAACGGUGUAAGCGUGUUAACAAGCAAGGUAUUGGACUUA<br>AAGAACUAUAUUGACAAACAGCUGCUCCCCAUCGUGAACAAACAG<br>AGCUGCUCAAUCUCCAAUAUAGAGACGGUGAUAGAGUUCCAGCAA<br>AAAAAUAAUCGGCUCCUUGAGAUCACCCGCGAAUUCUCAGUUAAU<br>GCCGGCGUCACAACUCCGGUGUCUACAUACAUGCUGACCAACUCG<br>GAGCUGUUAUCCUUAAUAAAUGACAUGCCCAUCACCAAUGAUCAA<br>AAAAAACUGAUGUCAAAUAACGUCCAGAUAGUAAGACAGCAGAGC<br>UACAGCAUCAUGUCGAUUAUCAAAGAGGAGGUGCUGGCGUACGUG<br>GUGCAGCUGCCCCUGUAUGGGGUGAUUGACACCCCUUGUUGGAAG<br>CUGCACACCUCCCCACUAUGUACUACCAAUACCAAAGAAGGAUCC | 267 |

TABLE 12-continued

| RSV mRNA Sequences | | |
|---|---|---|
| Name | mRNA Sequence | SEQ ID NO: |
| | AACAUCUGCCUUACCCGCACCGAUAGGGGAUGGUAUUGCGACAAC<br>GCCGGAUCCGUCAGCUUCUUUCCACUUGCCGAAACUUGCAAGGUU<br>CAGUCAAACCGGGUGUUCUGCGAUACAAUGAAUUCCCUUACCUUG<br>CCCAGCGAAGUUAAUCUCUGUAAUAUUGACAUCUUUAACCCCAAA<br>UACGAUUGCAAAAUUAUGACGUCAAAAACCGAUGUCAGUUCAAGC<br>GUUAUCACCAGCUUGGGUGCUAUCGUUUCAUGCUAUGGCAAAACC<br>AAGUGUACGGCUAGUAACAAAAACCGCGGAAUAAUUAAGACAUUC<br>AGCAAUGGUUGCGACUACGUAUCAAAUAAGGGUGUCGACACCGUU<br>UCCGUGGGCAAUACGCUGUACUAUGUUAAUAAACAGGAAGGCAAG<br>UCACUGUAUGUUAAAGGUGAACCCAUCAUCAACUUCUACGACCCC<br>CUGGUUUUCCCCUCCGACGAGUUUGAUGCCAGCAUAUCACAGGUU<br>AAUGAAAAAAUAAACGGCACAUUGGCGUUUAUCAGAAAGUCUGAC<br>GAGAAACUUCAUAACGUGGAAGACAAGAUAGAAGAGAUAUUGAG<br>CAAAAUCUAUCAUAUUGAGAACGAGAUCGCCAGGAUCAAAAAGCU<br>UAUUGGGGAG (The underlined region represents a<br>region coding for GCN4. The underlined region can<br>be substituted with alternative sequences which<br>achieve a same or similar function.) | |
| MRK-9<br>membrane-bound<br>RSV G protein | AUGUCUAAAAACAAGGACCAGCGCACUGCUAAGACGCUGGAACG<br>CACAUGGGAUACCCUGAACCAUCUGUUAUUCAUUUCCAGCUGCC<br>UCUACAAGCUAAACCUUAAAAGUGUUGCACAAAUCACACUCAGC<br>AUCCUGGCAAUGAUUAUUUCAACAUCCCUGAUCAUAGCCGCAAU<br>CAUAUUUAUCGCCUCAGCAAAUCACAAAGUUACCCCGACCACAG<br>CCAUUAUCCAGGACGCUACAUCCCAAAUCAAAAACACCACACCU<br>ACAUAUCUCACUCAGAACCCGCAGCUGGGCAUUUCACCAUCCAA<br>CCCUUCC*GAGAUCACCUCUCAAAU*CACCACCAUUCUCGCCUCUACU<br>ACCCCGGGAGUAAAGAGCACUCUUCAGAGCACAACCGUUAAAAC<br>UAAAAAUACCACCACCACUCAGACUCAGCCUUCGAAACCAACGA<br>CUAAACAGCGGCAAAAUAAGCCUCCAUCCAAACCGAAUAACGAC<br>UUUCAUUUCGAAGUCUUUAACUUUGUGCCAUGCAGUAUUUGCUC<br>CAAUAAUCCUACUUGCUGGGCUAUCUGCAAGAGAAUCCCUAACA<br>AGAAGCCUGGAAAGAAGACAACGACAAAGCCAACUAAGAAGCCG<br>ACACUUAAGACUACCAAAAAAGACCCUAAGCCGCAGACUACCAA<br>GAGCAAGGAGGUUCCCACAACCAAGCCUACAGAGGAGCCGACUA<br>UUAACACAACAAAGACCAACAUCAUCACCACCCUGCUUACUUCU<br>AAUACUACCGGAAACCCAGAGCUGACGUCCCAGAUGGAGACGUU<br>CCAUUCCACAUCUUCCGAAGGGAAUCCUAGUCCCAGCCAGGUGA<br>GCACAACCUCAGAAUACCCGUCCCAGCCCUCAUCACCUCCUAAUA<br>CCCCCCGGCAG (The underlined region represents a<br>region coding for transmembrane domain The<br>underlined region can be substituted with<br>alternative sequences which achieve a same or<br>similar function.) | 268 |
| MRK-11<br>truncated RSV F<br>protein<br>(ectodomain<br>only); construct<br>modified to<br>include an Ig<br>secretion peptide<br>signal sequence | AUGGAGACGCCUGCCCAGCUGCUGUUCCUGCUGUUGUUGUGGCU<br>GCCAGAUACUACUGGGUUUGCAAGCGGACAAAACAUUACCGAAG<br>AGUUCUAUCAAUCCACAUGCUCUGCAGUGUCUAAGGGCUACCUU<br>AGUGCAUUACGAACCGGGUGGUAUACGAGUGUAAUCACCAUUGA<br>GCUGUCCAACAUCAAGAAGAACAAGUGCAAUGGGACUGAUGCCA<br>AGGUGAAACUUAUCAAACAAGAGCUCGACAAGUAUAAGAACGCC<br>GUGACCGAACUACAACUCCUGAUGCAAUCGACUCAGGCUACUAA<br>CAACAGAGCUCGGAGGGAGCUGCCCAGAUUCAUGAAUUAUACCU<br>UAAACAACGCUAAAAAAACAAAUGUGACCCUGAGUAAGAAGCGG<br>AAACGAAGGUUCCUGGGCUUCCUGCUCGGUGUGGGGUCUGCAAU<br>AGCAAGCGGCGUCGCUGUGUCCAAGGUCCUUCACUUAGAAGGUG<br>AGGUCAAUAAGAUCAAGUCCGCUCUCCUCUCUACCAACAAGGCA<br>GUGGUGAGCCUGUCUAACGGUGUGUCCGUGCUGACAUCGAAGGU<br>ACUGGACCUGAAAAACUACAUCGACAAGCAGCUGCUGCCUAUUG<br>UGAAUAAGCAAUCCUGCAGUAUCUCCAACAUUGAGACAGUGAUU<br>GAAUUUCAGCAAAAGAACAAUCGUUUGUUGGAGAUAACAAGAGA<br>AUUCAGUGUUAAUGCCGGCGUUACCACUCCCGUGUCGACAUACA<br>UGCUAACAAAUAGCGAGCUGCUAUCUCUCAUUAAUGAUAUGCCU<br>AUCACCAAUGACCAGAAAAAACUUAUGUCCAAUAACGUGCAGAU<br>AGUCAGGCAGCAGUCCUACAGCAUUAUGAGCAUAAUUAAAGAGG<br>AAGUGUUGGCUUACGUCGUCCAGCUUCCACUGUAUGGCGUGAUC<br>GAUACCCCUUGUUGGAAGCUGCAUACUUCCCCCCUUUGUACAAC<br>UAAUACCAAAGAAGGGAGUAAUAUAUGCCUCACAAGGACUGACA<br>GAGGCUGGUACUGCGACAACGCCGGGAGCGUCAGCUUUUUCCCG<br>CAGGCCGAGACAUGUAAGGUGCAGAGCAACCGUGUCUUUUGCGA<br>CACCAUGAAUAGCCUGACUUUGCCAAGUGAGGUCAACCUUUGCA<br>ACGUGGAUAUUUUUAACCCUAAGUACGAUUGUAAGAUAAUGACA<br>UCCAAAACCGAUGUUAGUAGCUCCGUGAUCACUUCGCUGGGUGC<br>GAUAGUUAGCUGCUAUGGAAAGACAAAGUGUACCGCAAGUAACA<br>AGAACCGCGGAUUAUUAAAACAUUUAGCAAUGGGUGCGACUAC | 269 |

TABLE 12-continued

RSV mRNA Sequences

| Name | mRNA Sequence | SEQ ID NO: |
|---|---|---|
| | GUAUCAAACAAGGGGGGUGGAUACAGUCAGCGUGGGAAACACACU<br>UUACUACGUUAACAAGCAGGAAGGGAAAUCCCUUUAUGUGAAGG<br>GAGAACCAAUUAUCAACUUUUAUGAUCCCCUCGUGUUUCCAAGU<br>GAUGAAUUCGACGCAAGCAUCUCGCAGGUGAACGAGAAAAUCAA<br>UCAGAGUCUAGCUUUCAUAAGGAAGUCUGAUGAACUGCUUAGUG<br>CCAUUGGCGGGUACAUACCGGAAGCCCCACGCGACGGUCAGGCU<br>UACGUGAGGAAGGACGGCGAGUGGGUUCUGCUGUCCACUUUCCU<br>U (The first underlined region represents region coding for human Igκ signal peptide, second underlined region represents region coding for foldon. The underlined regions can be substituted with alternative sequences which achieves same or similar functions.) | |
| MRK-12 DS-CAV1 (non-membrane bound form); modified to include an Ig secretion peptide signal sequence | AUGGAGACUCCCGCUCAGCUGCUGUUUUUGCUCCUCCUAUGGCUG<br>CCGGAUACCACCGGCUUUGCCUCUGGACAGAACAUUACCGAGGAA<br>UUCUAUCAGUCGACUUGUUCCGCAGUCUCGAAGGGGUACCUGAGU<br>GCCCUGCGCACCGGGUGGUACACCAGUGUUAUCACUAUUGAGCUG<br>UCCAACAUUAAAGAAAAUAAGUGUAAUGGAACUGACGCGAAGGUG<br>AAGUUGAUAAAACAGGAGCUGGAUAAAUACAAGAAUGCAGUGACC<br>GAACUGCAGCUCCUGAUGCAGUCCACUCCAGCAACAAAUAAUCGC<br>GCGAGACGCGAACUCCCCCGCUUUAUGAACUACACUCUGAAUAAU<br>GCGAAGAAAACGAAUGUGACACUAAGUAAGAAAAGAAAACGGCGA<br>UUUCUUGGGUUCCUGCUCGGGGUGGGAUCUGCCAUAGCAAGCGGG<br>GUGGCGGUAUGUAAAGUCCUUCACCUAGAAGGGGAGGUGAACAAA<br>AUUAAGAGUGCCCUGCUGAGCACCAACAAGGCUGUGGUUUCACUG<br>UCAAACGGAGUAAGCGUGCUAACAUUUAAAGUCUUGGACCUGAAG<br>AAUUAUAUUGACAAGCAGCUCCUGCCCAUUCUCAACAAACAGUCA<br>UGUUCCAUUAGCAACAUCGAAACAGUCAUUGAGUUUCAGCAAAAA<br>AACAACCGCCUCCUUGAGAUUACGCGUGAGUUUUCCGUCAAUGCU<br>GGAGUCACGACACCGGUGUCCACUUACAUGCUGACUAACAGCGAA<br>CUCCUGAGCCUAAUCAAUGACAUGCCCAUUACUAACGACCAGAAA<br>AAAUUGAUGUCCAAUAACGUGCAGAUAGUGCGCCAGCAAUCUUAC<br>UCCAUAAUGUGCAUUAUCAAGGAGGAAGUCCUGGCGUACGUUGUU<br>CAGCUGCCGCUGUAUGGUGUGAUAGAUACGCCAUGCUGGAAACUG<br>CACACAUCCCCCCUUUGCACAACGAAUACUAAAGAGGGAAGUAAC<br>AUUUGCUUGACCAGAACAGAUCGGGGCUGGUACUGCGACAACGCU<br>GGUAGUGUGUCAUUUUUCCCCCAGGCAGAAACGUGUAAAGUCCAG<br>AGCAAUCGCGUGUUCUGCGACACAAUGAACUCACUUACUUUGCCC<br>UCAGAGGUCAAUUUGUGUAAUGUGGAUAUCUUCAACCCGAAAUAC<br>GAUUGUAAGAUUAUGACGAGCAAAACAGACGUGUCUUCAUCAGUG<br>AUAACAAGUCUGGGCGCAAUAGUGUCAUGCUAUGGUAAGACUAAG<br>UGCACUGCCUCCAAUAAAAACCGCGGCAUCAUCAAGACAUUUUCA<br>AAUGGAUGCGACUACGUGUCAAACAAGGGCGUCGACACAGUAAGC<br>GUUGGGAACACCCUAUACUACGUCAACAAGCAGGAGGGGAAAAGC<br>CUAUACGUGAAAGGCGAGCCAAUCAUCAAUUUCUACGAUCCACUG<br>GUCUUUCCAAGUGACGAAUUUGAUGCCAGCAUAUCGCAGGUGAAC<br>GAGAAAAUAAAUCAGUCACUCGCCUUCAUCAGGAAGUCAGAUGAG<br>CUGCUGUCCGCCAUCGGAGGAUACAUUCCAGAAGCCCCACGCGAC<br>GGCCAGGCAUACGUGCGGAAGGACGGCGAAUGGGUCCUUUUGAGC<br>ACUUUUCUA (The first underlined region represents a region coding for human Igκ signal peptide, The second underlined region represents a region coding for a foldon. The underlined regions can be substituted with alternative sequences which achieves same or similar functions.) | 270 |
| MRK-13 MRK-5 construct modified to include an Ig secretion peptide signal sequence | AUGGAGACUCCAGCCCAAUUACUGUUCCUGCUACUCCUUUGGCU<br>GCCCGAUACUACUGGAUUCGCUUCGGGUCAGAAUAUUACAGAGG<br>AGUUCUACCAAAGUACUUGCUCUGCAGUCUCCAAGGGAUACCUG<br>UCCGCUCUGCGGACGGGAUGGUAUACCAGUGUUAUAACGAUCGA<br>GUUGAGCAACAUCAAGAAGAACAAAUGUAAUGGAACAGAUGCCA<br>AGGUGAAACUGAUCAAACAGGAGUUGGAUAAAUAUAAGAAUGCU<br>GUCACCGAACUGCAGCUAUUGAUGCAGUCCACCCAGGCUACCAA<br>CAACCGGGCCAGGCAGCAACAACAGAGAUUUUUGGGUUUCUUGC<br>UGGGCGUGGGGUCUGCCAUCGCUUCAGGGGUGGCCGUGAGUAAA<br>GUCCUGCACCUGGAAGGCGAAGUCAACAAGAUCAAGUCUGCAUU<br>ACUAAGUACCAAUAAGGCUGUAGUUAGCCUGUCCAAUGGCGUGA<br>GUGUGCUUACUUCUAAGGUACUGGACCUGAAGAACUACAUCGAC<br>AAGCAACUACUACCCAUUGUAAAUAAGCAGUCAUGUAGCAUAUC<br>AAACAUCGAGACAGUGAUCGAAUUUCAACAGAAGAAUAACCGGC<br>UGUUGGAGAUAACACGGGAGUUCUCUGUAAAUGCCGGCGUGACG<br>ACCCCUGUCAGCACCUACAUGCUCACGAAUAGCGAGUUGCUUUC<br>CCUGAUUAAUGAUAUGCCGAUUACAAAUGACCAGAAGAAGCUGA<br>UGAGUAAUAAUGUCCAAAUUGUCCGUCAGCAGAGCUAUUCGAUU | 271 |

TABLE 12-continued

RSV mRNA Sequences

| Name | mRNA Sequence | SEQ ID NO: |
|---|---|---|
| | AUGUCCAUCAUCAAGGAGGAAGUCUUAGCCUAUG*UGGUGCAGCUCCCCCUC*UACGGAGUGAUUGACACACCGUGCUGGAAGCUGCACACCUCCCCUUUGUGUACAACCAAUACCAAGGAGGGCUCCAACAUCUGCCUUACUAGGACCGACAGGGGAUGGUAUUGCGACAACGCCGGGUCCGUCUCAUUUUUUCCUCAGGCGGAAACCUGUAAGGUACAGUCGAAUCGAGUGUUUUGUGACACUAUGAACAGCCUGACCUUGCCUAGCGAGGUGAAUCUGUGUAACGUUGAUAUCUUCAACCCUAAGUAUGACUGUAAGAUCAUGACUUCAAAAACUGAUGUCUCCUCAAGCGUGAUCACCUCUUUGGGCGCCAUCGUGUCAUGCUACGGAAAGACGAAGUGCACCGCCUCUAACAAGAACCGAGGGAUCAUCAAAACAUUCUCCAAUGGCUGUGAUUACGUCAGUAACAAAGGUGUGGACACAGUCUCCGUGGGCAAUACGUUAUAUUAUGUGAAUAAGCAGGAGGGAAAAAGUCUCUAUGUGAAGGGUGAACCGAUAAUCAAUUUCUACGAUCCCUUGGUGUUUCCAAGCGACGAGUUCGACGCCUCGAUCAGCCAGGUGAACGAGAAAAUCAACCAGUCUUUGGCAUUCAUCCGCAAGAGCGACGAGCUACUGCAUAACGUGAACGCAGGCAAGAGUACUACCAAU (The underlined region represents a region coding for human Igκ signal peptide. The underlined region can be substituted with alternative sequences which achieve a same or similar function) | |
| MRK-14 MRK-6 construct modified to include an Ig secretion peptide signal sequence: | AUGGAGACUCCCGCUCAGUUGUUGUUCCUGCUACUGCUGUGGCUGCCUGAUACAACCGGAUUUGCUAGUGGGCAGAAUAUCACCGAAGAAUUCUAUCAGAGCACUUGCAGUGCAGUGUCCAAAGGAUAUUUGAGCGCCCUGCGCACUGGGUGGUACACAAGUGUCAUCACAAUCGAGCUAAGUAACAUUAAAAAAAACAAAUGCAACGGGACUGACGCAAAGGUCAAACUCAUUAAGCAAGAACUUGACAAAUAUAAGAACGCUGUUACAGAGUUGCAGCUGCUAAUGCAAAGCACUCAGGCUACCAAUAACCGAGCGAGACAGCAGCAGCAACGUUUCCUGGGUUUCCUGUUAGGUGUGGGUAGCGCAAUUGCCAGUGGUGUAGCCGUGUCCAAGGUGCUGCACCUGGAAGGGGAAGUGAAUAAGAUCAAGUCUGCACUGCUGUCCACCAAUAAGGCGGUCGUUUCGCUGUCUAACGGCGUCUCGGUCCUAACAAGUAAAGUUCUGGAUUUAAAGAACUAUAUUGAUAAGCAAUUGCUGCCUAUCGUAAAUAAGCAGAGUUGCAGCAUUAGCAAUAUCGAGACAGUGAUAGAAUUUCAGCAAAAGAACAAUCGAUUACUCGAAAUCACACGCGAAUUCAGUGUCAAUGCCGGGGUUACAACCCCUGUGUCGACCUACAUGCUUACCAAUUCCGAGCUUCUGUCUCUUAUUAACGAUAUGCCCAUCACGAACGAUCAGAAGAAACUGAUGUCAAAUAACGUCCAAAUUGUGCGGCAGCAAAGCUACAGUAUCAUGAGCAUCAUCAAAGAGGAGGUGCUCGCCUAUGUGGUCCAAUUGCCGCUAUACGGGGUCAUUGAUACACCCUGUUGGAAGCUCCAUACAUCCCCACUUUGUACAACGAAUACCAAGGAGGGGUCUAACAUUUGUCUGACCCGGACCGACAGAGGCUGGUAUUGCGAUAAUGCUGGAAGCGUUAGUUUCUUUCCUCAGGCAGAAACAUGCAAGGUGCAGUCAAACAGAGUUUUCUGUGACACCAUGAAUUCCUUGACGCUGCCUUCAGAAGUGAAUCUGUGUAACGUGGAUAUCUUUAAUCCGAAGUACGAUUGUAAAAUUAUGACUAGCAAGACAGAUGUCUCGUCCUCUGUGAUCACUAGCCUGGGAGCGAUUGUGAGCUGUUAUGGUAAAACAAAGUGUACUGCUAGCAAUAAGAACAGGGGGAUUAUCAAAACGUUCAGUAACGGCUGUGAUUACGUAUCCAACAAGGGGGUGGACACCGUGUCAGUCGGGAACACGCUCUACUACGUGAACAAGCAGGAAGGUAAGUCGCUAUACGUGAAGGGGGAACCCAUAAUCAAUUUCUACGAUCCGCUCGUGUUUCCUAGCGACGAAUUCGACGCAUCUAUCAGCCAGGUGAACGAGAAGAUCAAUCAGAGUCUGGCCUUCAUCCGCAAGUCCGACGAGCUGCUUAGUGCUAUCGGAGGUUAUAUCCCUGAGGCCCCGAGGGACGGCCAAGCGUAUGUGAGAAAGGACGGGGAAUGGGUACUGUUGUCAACUUUCCUA (The first underlined region represents a region coding for human Igκ signal peptide, The second underlined region represents a region coding for a foldon. The underlined regions can be substituted with alternative sequences which achieves same or similar functions.) | 272 |
| MRK-16 MRK-8 construct modified to include an Ig secretion peptide signal sequence: | AUGGAGACACCUGCCCAACUUCUGUUCCUUCUUUUGCUCUGGCUGCCUGACACAACCGGCUUCGCAUCUUCACAAAACAUCACGGAAGAGUUUUACCAGAGCACAUGCUCCGCGGUCUCUAAAGGCUAUCUUUCUGCCCUGCGGACUGGCUGGUAUACCAGCGUCAUCACCAUAGAGCUGUCAAACAUCAAGGAGAACAAGUGUAACGGCACUGACGCCAAGGUCAAGCUUAUAAAGCAGGAACUGGACAAGUAUAAGAGUGCUGUUACCGAGCUCCAGUUGCUUAUGCAGUCCACCCCCGCAACAAACAAUAAAUUUCUGGGCUUUCUACAGGGCGUCGGAAGCGCCAUCGCAAGCGGCAUCGCUGUGAGCAAGGUGUUGCAUCUGGAGGGAGAGGUGAAUAAGAUAAAGAGUGCUCUGCUUUCCACUAACAAAGCCGUGGUGAGCCUGAGCAAUGGCGUAUCUGUUCUGACUUCUAAAGUCCUGGAUCUCAAGAACUAUAUCGACAAGCAGCUCUUGCCCAUUGUC | 273 |

TABLE 12-continued

RSV mRNA Sequences

| Name | mRNA Sequence | SEQ ID NO: |
|---|---|---|
| | AACAAACAGUCCUGCUCCAUUUCCAAUAUUGAGACCGUCAUUGA<br>GUUCCAACAGAAGAAUAACCGUUUGCUGGAAAUUACAAGGGAAU<br>UCAGUGUUAAUGCCGGUGUAACCACCCCUGUGAGCACCUAUAUG<br>CUCACCAACUCUGAACUGCUGAGUCUGAUUAACGAUAUGCCCAU<br>UACUAAUGAUCAGAAGAAACUAAUGAGUAACAAUGUCCAGAUAG<br>UUCGGCAGCAGUCAUAUUCCAUUAUGAGUAUAAUCAAGGAGGAA<br>GUGCUAGCCUACG*UAGUUCAGCUCCCCCUC*UACGGCGUUAUAGAC<br>ACGCCAUGUUGGAAGCUGCAUACGAGUCCUCUGUGCACUACAAA<br>UACCAAGGAGGGCAGUAACAUAUGCUUGACUAGAACUGAUAGAG<br>GCUGGUACUGCGACAAUGCAGGCUCCGUGUCAUUCUUUCCUCUC<br>GCCGAGACGUGUAAAGUGCAGAGUAACAGAGUGUUUUGUGACAC<br>AAUGAACUCAUUGACCCUGCCUAGCGAAGUGAACUUAUGCAACA<br>UCGACAUUUUUAACCCAAAAUACGAUUGCAAGAUUAUGACCUCU<br>AAGACUGACGUAUCUUCAUCCGUCAUAACUUCUCUAGGAGCGAU<br>CGUGAGCUGCUACGGUAAGACUAAAUGCACGGCUAGUAAUAAAA<br>AUAGAGGUAUCAUUAAGACUUUUAGUAACGGUUGCGAUUAUGUG<br>UCAAACAAGGGAGUCGACACUGUUUCAGUGGGCAAUACUCUCUA<br>CUACGUUAACAAACAGGAGGGUAAAUCCCUUUAUGUGAAAGGGG<br>AACCCAUCAUUAAUUUUUAUGACCCACUUGUGUUUCCUAGUGAC<br>GAGUUUGACGCUUCAAUCAGUCAAGUGAACGAAAAAAUUAAUGG<br>CACGCUCGCGUUUAUCAGGAAAAGCGACGAGAAGCUGCAUAACG<br>UGGAAGAUAAGAUCGAGGAGAUUCUCUCGAAAAUUUAUCAUAUA<br>GAGAAUGAAAUCGCAAGAAUCAAAAAGCUUAUUGGGGAG (The first underlined region represents a region coding for human Igκ signal peptide, The second underlined region represents a region coding for GCN4. The underlined regions can be substituted with alternative sequences which achieves same or similar functions.) | |
| MRK-2 non-membrane bound form RSV F protein/MRK_02_F (soluble, Merck A2 strain)/ | AUGGAGCUGUUGAUCCUUAAGGCCAACGCCAUCACUACUAUUCU<br>CACCGCGGUAACAUUCUGCUUCGCCUCCGGGCAGAACAUCACCG<br>AGGAGUUCUACCAGUCUACGUGCUCCGCCGUCUCCAAAGGUUAC<br>CUGUCCGCAUUAAGGACGGGGUGGUACACUUCCGUCAUAACUAU<br>UGAACUGAGUAACAUAAAAAAGAACAAGUGUAAUGGGACGGAUG<br>CCAAGGUGAAGCUCAUCAAGCAAGAGCUUGACAAAUACAAGAAU<br>GCAGUGACAGAGCUCCAACUUCUCAUGCAGUCUACACAGGCCAC<br>GAAUAACCGUGCCCGAAGAGAACUGCCUAGAUUUAUGAAUUACA<br>CUUUGAACAACGCCAAAAAGACCAACGUGACUCUAAGCAAAAAA<br>AGGAAACGGCGUUUUCUGGGCUUUCUGCUGGGGGUUGGUAGCGC<br>CAUCGCAUCUGGCGUGGCAGUCAGUAAAGUUUUGCACCUUGAGG<br>GGGAGGUCAACAAAAUCAAGAGCGCGCUGUUAUCAACAAACAAG<br>GCAGUCGUGUCCCUCUCCAAUGGCGUGUCUGUCCUGACCUCUAA<br>AGUACUGGAUCUCAAGAACUAUAUCGACAAACAACUGCUACCAA<br>UCGUCAAUAAGCAGAGUUGCUCUAUUUCCAAUAUUGAGACCGUG<br>AUCGAGUUUCAACAGAAGAAUAACAGAUUGUUGGAGAUCACCAG<br>GGAAUUCAGCGUCAAUGCAGGGGUGACCACACCCGUAUCUACCU<br>ACAUGCUGACCAACUCGGAACUCCUCUCCUUAAUAAACGACAUG<br>CCUAUUACUAACGACCAAAAAAAGUUGAUGUCCAACAAUGUCCA<br>GAUCGUGCGACAGCAAUCUUAUUCAAUUAUGUCCAUUAUAAAAG<br>AGGAGGUGCUGGCGUACGUAGUGCAGCUGCCCCUUUACGGAGUG<br>AUCGACACCCCAUGCUGGAAGCUCCACACCUCCCCCCUGUGCACC<br>ACUAAUACCAAAGAAGGCAGCAACAUCUGUCUGACCCGUACCGA<br>CCGCGGAUGGUACUGCGAUAAUGCAGGUAGCGUCUCUUUUUUUC<br>CCCAGGCUGAAACUUGCAAGGUUCAGUCCAACCGGGUAUUCUGU<br>GACACGAUGAACAGUCUCACCCUACCAUCAGAGGUGAACCUGUG<br>CAAUGUGGACAUAUUUAACCCUAAAUAUGACUGUAAGAUCAUGA<br>CCUCCAAAACUGACGUUUCCAGCAGUGUCAUAACCUCACUGGGC<br>GCAAUAGUUUCAUGCUAUGGAAAGACUAAGUGCACUGCCUCUAA<br>CAAAAAUCGAGGUAUUAUUAAGACCUUUAGCAAUGGCUGCGAUU<br>AUGUCAGUAACAAAGGUGUUGAUACAGUGAGUGUGGGCAACACA<br>UUAUACUAUGUUAACAAGCAAGAAGGCAAGAGCCUCUAUGUGAA<br>GGGAGAACCAAUCAUUAAUUUUUACGAUCCGCUGGUCUUUCCCA<br>GCGAUGAGUUCGAUGCAUCCAUCUCUCAGGUGAAUGAAAAAAUU<br>AACCAAUCACUGGCUUUCAUACGGAAGAGCGAUGAACUGCUGAG<br>CGCCAUCGGGGGAUACAUCCCUGAAGCUCCGAGGGACGGCCAAG<br>CUUAUGUCCGCAAAGACGGAGAGUGGGUGUUGCUCAGUACCUUC<br>CUC (The underlined region represents a region coding for a foldon. The underlined region can be substituted with alternative sequences which achieve a same or similar function.) | 274 |
| MRK-3 non-membrane bound form DS-CAV1 | AUGGAACUGCUGAUUCUUAAGGCGAAUGCCAUAACCACUAUCUU<br>GACCGCAGUUACUUUUUGCUUCGCCUCUGGGCAGAAUAUUACCG<br>AAGAGUUCUACCAGUCCACGUGCAGUGCCGUGUCUAAGGGCUAC | 275 |

TABLE 12-continued

RSV mRNA Sequences

| Name | mRNA Sequence | SEQ ID NO: |
|---|---|---|
| (stabilized prefusion F protein)//MRK_03_ DS-CAV1 (soluble, S155C/S290C/ S190F/V207L)/ SQ-030271 | CUUUCCGCGCUUCGCACUGGCUGGUACACGUCAGUCAUAACGAU<br>CGAACUCUCUAAUAUAAAGGAAAAUAAGUGUAACGGAACAGACG<br>CUAAGGUCAAGUUAAUCAAGCAGGAGCUGGACAAAUAUAAGAAU<br>GCCGUAACGGAGCUCCAGCUGCUCAUGCAGAGCACGCCAGCUAC<br>AAACAACAGGGCACGCCGUGAGCUCCCCCGAUUUAUGAACUACA<br>CAUUGAACAACGCCAAGAAAACUAACGUGACUUUGUCCAAGAAG<br>AGGAAGCGGCGAUUCUUAGGGUUCCUUUUGGGGGUAGGCUCGGC<br>GAUUGCCAGUGGGGUUGCCGUAUGCAAGGUGCUCCACCUGGAAG<br>GGGAGGUGAACAAGAUUAAGUCGGCUCUGCUCAGUACAAACAAA<br>GCUGUCGUCUCAUUGUCAAACGGAGUCAGUGUAUUGACAUUUAA<br>AGUCCUCGACCUGAAGAACUAUAUAGAUAAACAGUUACUCCCAA<br>UCUUGAAUAAGCAGUCCUGUAGCAUCAGCAACAUUGAGACAGUG<br>AUCGAGUUCCAGCAGAAGAAUAAUCGCCUACUCGAGAUCACCAG<br>AGAAUUCUCAGUCAAUGCCGGAGUAACCACUCCUGUCAGCACAU<br>ACAUGCUCACAAACUCUGAACUCCUAAGCCUGAUUAAUGAUAUG<br>CCUAUCACAAAUGAUCAGAAGAAACUCAUGAGCAAUAAUGUGCA<br>GAUUGUAAGACAGCAGAGUUAUUCUAUAAUGUGUAUUAUUAAG<br>GAGGAGGUACUGGCCUAUGUGGUUCAACUUCCUCUGUAUGGGGU<br>GAUAGAUACACCAUGCUGGAAGCUGCACACCAGCCCACUGUGUA<br>CGACCAAUACAAAGGAGGGCUCCAAUAUUUGCUUAACACGGACU<br>GACCGGGGGUGGUAUUGCGACAAUGCCGGAUCAGUCUCCUUCUU<br>CCCCCAAGCAGAGACCUGCAAGGUGCAGUCCAAUAGAGUUUUCU<br>GCGACACAAUGAACUCGCUGACCCUACCUAGCGAAGUUAACUUA<br>UGCAACGUGGAUAUUUUUAAUCCGAAGUAUGAUUGUAAAAUCAU<br>GACUAGCAAAACGGAUGUUAGCUCCAGCGUAAUCACCUCCCUAG<br>GCGCUAUCGUGAGCUGUUAUGGCAAGACGAAGUGCACUGCAUCU<br>AAUAAAAAUAGGGGUAUUAUUAAAACCUUCAGCAAUGGCUGCGA<br>CUAUGUGAGCAAUAAGGGCGUGGACACCGUGUCAGUGGGAAACA<br>CCCUCUAUUAUGUGAACAAGCAGGAGGGAAAAUCCCUUUAUGUA<br>AAGGGCGAACCCAUUAUCAAUUUCUAUGACCCCCUGGUUUUCCC<br>AAGCGACGAGUUCGACGCAUCUAUCUCUCAAGUGAACGAGAAAA<br>UCAAUCAGAGUCUUGCCUUUAUCAGAAAAUCCGAUGAGCUGCUU<br>UCCGCCAUCGGUGGCUAUAUCCCAGAAGCCCCAAGAGACGGACA<br>AGCGUACGUCCGGAAAGAUGGUGAGUGGGUCCUCCUCUCUACCU<br>UUCUU (The underlined region represents a region coding for a foldon. The underlined region can be substituted with alternative sequences which achieve a same or similar function) | |
| Influenza M-1 (A/California/04/ 2009(H1N1), ACP44152) + hIgκ | AUGGAGACUCCUGCACAGCUGCUGUUUCUGCUAUUGUUGUGGCUU<br>CCGGACACUACUGGGUCCCUCCUCACCGAGGUGGAAACAUACGUG<br>CUGUCCAUCAUACCAUCCGGGCCCUUGAAAGCCGAGAUCGCCCAG<br>AGACUCGAAUCUGUAUUCGCAGGAAAGAACACGGAUUUGGAGGCA<br>CUAAUGGAAUGGCUGAAGACCCGUCCGAUCCUGUCUCCUCUCACA<br>AAGGGGAUUCUUGGAUUUGUCUUUACCCUCACCGUCCCGAGCGAG<br>CGCGGUCUCCAGCGCAGACGUUUUGUACAGAAUGCACUGAAUGGC<br>AACGGCGAUCCCAAUAACAUGGAUCGUGCGGUAAAGCUUUAUAAA<br>AAGCUGAAGAGAGAAAUCACUUUCCAUGGGGCUAAAGAGGUGAGU<br>CUCUCCUAUUCAACCGGGGCAUUGGCCUCUUGCAUGGGUCUUAUA<br>UACAAUCGAAUGGGCACCGUUACCACCGAGGCCGCAUUUGGUCUG<br>GUUUGUGCUACGUGCGAGCAAAUCGCAGAUAGCCAGCAUCGGUCC<br>CAUCGGCAGAUGGCCACCACUACGAACCCUCUAAUUCGACAUGAA<br>AAUCGCAUGGUCCUGGCUAGCACCACCGCAAAGGCAAUGGAGCAG<br>AUGGCGGGCUCUAGUGAACAGGCAGCCGAGGCAAUGGAAGUGGCC<br>AAUCAGACCAGGCAGAUGGUCCAUGCUAUGCGGACUAUUGGUACC<br>CACCCGUCCAGCAGUGCUGGACUGAAGGAUGACCUCCUUGAGAAC<br>CUGCAGGCAUACCAGAAACGAAUGGGGGUGCAAAUGCAGAGAUUC<br>AAG (The underlined region represents a region coding for human Igκ signal peptide. The underlined region can be substituted with alternative sequences which achieve a same or similar function) | 276 |
| MRK_04 SQ-030271 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAAAAC<br>GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAAAAAACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA | 277 |

TABLE 12-continued

RSV mRNA Sequences

| Name | mRNA Sequence | SEQ ID NO: |
|---|---|---|
| | GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAAAAAAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG<br>GGCCAUUGUAAGCUGCUAUGGCAAAACCAAGUGUACUGCCUCUA<br>AUAAGAACAGAGGCAUAAUUAAAACCUUUUCAAAUGGCUGUGAC<br>UAUGUGUCGAAUAAGGGCGUCGACACGGUCUCAGUAGGGAAUAC<br>CCUCUACUACGUUAACAAACAGGAAGGCAAAUCCCUUUAUGUAA<br>AGGGCGAGCCCAUCAUAAAUUUCUACGACCCACUUGUGUUCCCC<br>AGUGAUGAAUUCGAUGCAUCAAUCUCCCAGGUGAACGAAAAGAU<br>CAAUCAAUCCCUUGCUUUUAUACGAAAGUCAGAUGAACUCCUGC<br>AUAACGUGAAUGCUGGGAAAUCUACAACCAACAUCAUGAUCACU<br>ACCAUCAUUAUUGUGAUUAUCGUAAUUCUGCUAUCCUUGAUUGC<br>UGUCGGGCUGCUUCUGUACUGUAAGGCCAGAUCGACGCCUGUGA<br>CCCUUUCAAAAGACCAACUUAGCGGUAUCAAUAAUAUUGCCUUU<br>AGCAAU | |
| MRK_04_no<br>AAALys<br>SQ-038059 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAGAAC<br>GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAGAAGACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA<br>GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAAAAGAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG<br>GGCCAUUGUAAGCUGCUAUGGCAAGACCAAGUGUACUGCCUCUA<br>AUAAGAACAGAGGCAUAAUUAAGACCUUUUCAAAUGGCUGUGAC<br>UAUGUGUCGAAUAAGGGCGUCGACACGGUCUCAGUAGGGAAUAC<br>CCUCUACUACGUUAACAAACAGGAAGGCAAAUCCCUUUAUGUAA<br>AGGGCGAGCCCAUCAUAAAUUUCUACGACCCACUUGUGUUCCCC<br>AGUGAUGAAUUCGAUGCAUCAAUCUCCCAGGUGAACGAAAAGAU<br>CAAUCAAUCCCUUGCUUUUAUACGAAAGUCAGAUGAACUCCUGC<br>AUAACGUGAAUGCUGGGAAAUCUACAACCAACAUCAUGAUCACU<br>ACCAUCAUUAUUGUGAUUAUCGUAAUUCUGCUAUCCUUGAUUGC<br>UGUCGGGCUGCUUCUGUACUGUAAGGCCAGAUCGACGCCUGUGA<br>CCCUUUCAAAGGACCAACUUAGCGGUAUCAAUAAUAUUGCCUUU<br>AGCAAU | 278 |
| MRK_04_no4A<br>SQ-038058 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAGAAC | 279 |

TABLE 12-continued

| RSV mRNA Sequences | | |
|---|---|---|
| Name | mRNA Sequence | SEQ ID NO: |
| | GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAGAAGACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA<br>GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAGAAGAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG<br>GGCCAUUGUAAGCUGCUAUGGCAAGACCAAGUGUACUGCCUCUA<br>AUAAGAACAGAGGCAUAAUUAAGACCUUUUCAAAUGGCUGUGAC<br>UAUGUGUCGAAUAAGGGCGUCGACACGGUCUCAGUAGGGAAUAC<br>CCU CUACUACGUUAACAAACAGGAAGGCAAAUCCCUUUAUGUAA<br>AGGGCGAGCCCAUCAUAAAUUUCUACGACCCACUUGUGUUCCCC<br>AGUGAUGAAUUCGAUGCAUCAAUCUCCCAGGUGAACGAGAAGAU<br>CAAUCAAUCCCUUGCUUUUAUACGAAAGUCAGAUGAACUCCUGC<br>AUAACGUGAAUGCUGGGAAAUCUACAACCAACAUCAUGAUCACU<br>ACCAUCAUUAUUGUGAUUAUCGUAAUUCUGCUAUCCUUGAUUGC<br>UGUCGGGCUGCUUCUGUACUGUAAGGCCAGAUCGACGCCUGUGA<br>CCCUUUCAAAGGACCAACUUAGCGGUAUCAAUAAUAUUGCCUUU<br>AGCAAU | |
| MRK_04_nopolyA_<br>3mut<br>SQ-038057 | AUGGAACUGCUCAUUUUGAAGGCAAACGCUAUCACGACAAUACU<br>CACUGCAGUGACCUUCUGUUUUGCCUCAGGCCAGAACAUAACCG<br>AGGAGUUUUAUCAAUCUACAUGCAGCGCUGUAUCUAAAGGCUAC<br>CUGAGUGCGCUCCGCACAGGAUGGUACACCUCCGUGAUCACCAU<br>CGAGCUCAGCAAUAUUAAAGAGAACAAGUGCAAUGGUACCGACG<br>CUAAAGUCAAACUUAUCAAGCAGGAACUCGACAAAUAUAAGAAC<br>GCUGUGACCGAGCUGCAGUUAUUGAUGCAGAGUACACCUGCCAC<br>CAAUAACAGAGCUAGGAGGGAGUUGCCUAGGUUUAUGAACUACA<br>CUCUCAACAACGCGAAGAAAACCAAUGUGACGCUAUCCAAGAAA<br>CGGAAGAGGAGGUUCCUGGGGUUUCUUUUAGGGGUGGGCUCUGC<br>CAUUGCUUCCGGCGUGGCUGUAUGUAAAGUUCUCCACCUCGAGG<br>GAGAGGUUAAUAAGAUUAAGUCGGCCCUGCUGAGUACUAACAAA<br>GCAGUGGUGUCGCUGAGUAACGGAGUAAGUGUGUUAACAUUUAA<br>GGUGCUGGACCUCAAGAAUUAUAUUGACAAACAGUUGCUUCCUA<br>UUCUAAACAAACAGAGCUGUUCAAUAAGUAAUAUUGAAACUGUU<br>AUUGAGUUUCAGCAGAAGAACAACAGGCUUCUUGAGAUUACACG<br>CGAGUUCAGUGUCAAUGCCGGCGUUACAACACCCGUGUCUACCU<br>ACAUGCUGACGAAUUCUGAGCUUCUCUCUCUCAUAAACGACAUG<br>CCCAUUACGAAUGACCAAAAGAAACUUAUGUCCAACAACGUGCA<br>GAUUGUGCGACAGCAAUCCUAUAGCAUUAUGUGUAUCAUCAAGG<br>AAGAGGUACUCGCUUAUGUUGUGCAGCUACCACUCUAUGGUGUG<br>AUUGACACCCCCUGUUGGAAGCUGCAUACCAGUCCACUCUGCAC<br>CACUAACACAAAGGAAGGGAGCAAUAUUUGCCUCACUCGAACCG<br>ACAGGGGGUGGUAUUGCGAUAAUGCGGGCUCCGUGUCCUUCUUU<br>CCACAGGCUGAAACUUGUAAGGUACAGUCAAACCGCGUGUUCUG<br>UGAUACUAUGAAUUCUCUGACUCUUCCCAGCGAGGUUAAUCUCU<br>GCAACGUCGACAUUUUCAAUCCUAAAUAUGACUGCAAGAUCAUG<br>ACCAGCAAGACCGACGUCUCCAGCUCAGUAAUCACUAGCCUAGG<br>GGCCAUUGUAAGCUGCUAUGGCAAAACCAAGUGUACUGCCUCUA<br>AUAAGAACAGAGGCAUAAUUAAAACCUUUUCAAAUGGCUGUGAC<br>UAUGUGUCGAAUAAGGGCGUCGACACGGUCUCAGUAGGGAAUAC<br>CCUCUACUACGUUAACAAACAGGAAGGCAAAUCCCUUUAUGUAA<br>AGGGCGAGCCCAUCAUAAAUUUCUACGACCCACUUGUGUUCCCC<br>AGUGAUGAAUUCGAUGCAUCAAUCUCCCAGGUGAACGAAAAGAU<br>CAAUCAAUCCCUUGCUUUUAUACGAAAGUCAGAUGAACUCCUGC<br>AUAACGUGAAUGCUGGGAAAUCUACAACCAACAUCAUGAUCACU | 280 |

TABLE 12-continued

RSV mRNA Sequences

| Name | mRNA Sequence | SEQ ID NO: |
|---|---|---|
| | ACCAUCAUUAUUGUGAUUAUCGUAAUUCUGCUAUCCUUGAUUGC UGUCGGGCUGCUUCUGUACUGUAAGGCCAGAUCGACGCCUGUGA CCCUUUCAAAAGACCAACUUAGCGGUAUCAAUAAUAUUGCCUUU AGCAAU | |

It should be understood that each of the ORF sequences provided herein may be combined with a 5' and/or 3' UTR, such as those described herein. It should also be understood that the 5' and/or 3' UTR for each construct may be omitted, modified or substituted for a different UTR sequences in any one of the vaccines as provided herein.

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A composition comprising a ribonucleic acid (RNA) polynucleotide having an open reading frame encoding a respiratory syncytial virus (RSV) antigenic polypeptide and a lipid nanoparticle comprising 10-20 mol % neutral lipid, 35-45 mol % cholesterol, 1-5% PEG-modified lipid, and 40-50 mol % ionizable cationic lipid, wherein the ionizable cationic lipid comprises Compound 25:

(Compound 25)

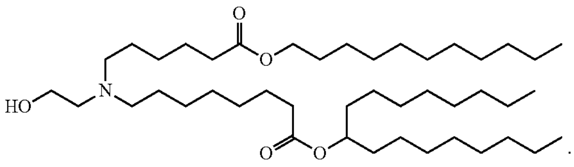

2. The composition of claim 1, wherein the antigenic polypeptide is glycoprotein G.

3. The composition of claim 1, wherein the antigenic polypeptide is glycoprotein F.

4. The composition of claim 1, further comprising an adjuvant.

5. The composition of claim 1, further comprising a pharmaceutically acceptable carrier.

6. The composition of claim 1, wherein the open reading frame is codon-optimized.

7. The composition of claim 1, wherein the vaccine is multivalent.

8. The composition of claim 1, wherein the RNA polynucleotide encodes at least 2 antigenic polypeptides.

9. The composition of claim 1, wherein the RNA polynucleotide comprises a chemical modification.

10. The composition of claim 9, wherein the chemical modification is selected from the group consisting of pseudouridine, 1-methylpseudouridine, 1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

11. The composition of claim 1, wherein the nanoparticle has a mean diameter of 50-200 nm.

12. The composition of claim 1, wherein the sterol is a cholesterol.

13. The composition of claim 1, wherein the nanoparticle has a polydispersity value of less than 0.4.

14. The composition of claim 1, wherein the nanoparticle has a net neutral charge at a neutral pH value.

15. A method of administering to a subject the RSV composition of claim 1.

16. The composition of claim 3, wherein the glycoprotein F is a stabilized prefusion form of glycoprotein F.

17. The composition of claim 10, wherein the chemical modification is 1-methylpseudouridine.

* * * * *

SEQUENCE LISTING

<160> NUMBER OF SEQ ID NOS: 300

<210> SEQ ID NO 1
<211> LENGTH: 1722
<212> TYPE: DNA
<213> ORGANISM: Respiratory Syncytial Virus

<400> SEQUENCE: 1

```
atggagctgc tcatcctcaa agcaaatgcc atcaccacta tcctgaccgc cgtcactttc     60
tgcttcgcct ccggccaaaa tatcaccgaa gagttctatc agtccacctg ctctgccgtt    120
tctaaaggtt acctgtcagc ccttagaaca gggtggtata cctctgttat taccattgag    180
ttgtccaaca ttaagaagaa caagtgcaat ggcacagacg ctaaggttaa gctcatcaag    240
caggagctcg acaaatataa aaatgccgtc acggagctgc agttattgat gcagagcacc    300
caggcgacaa acaaccgtgc acgacgcgag ctaccccgat tcatgaacta caccctcaat    360
aatgcaaaga agacaaatgt gacgctctct aagaagcgca agcgtcgctt tctgggcttt    420
cttctcgggg ttgggagcgc gatcgcaagc ggcgtggctg tatcaaaagt gcttcatctt    480
gagggagaag tgaataaaat caaaagtgct ctgctatcta caaacaaagc cgttgtatca    540
ctgtccaacg gagtgtccgt gctcacgtcc aaagtgctag atttgaagaa ttacatcgat    600
aagcagctgc tccctattgt gaacaaacaa tcatgttcca tcagtaacat tgaaacagtc    660
atcgagtttc aacagaaaaa caatagactg ctggagatta ccagagaatt ttcggttaac    720
gccggcgtga ctacccctgt aagcacctac atgttgacaa actccgaact tttgtcactg    780
ataaacgata tgcctattac taatgatcag aaaaaattga tgtccaataa tgtccaaatc    840
gtcaggcaac agtcctacag tatcatgtct attattaagg aggaggtcct tgcatacgtg    900
gtgcaactgc cattatacgg agtcattgat actccctgtt ggaaactcca tacaagcccc    960
ctgtgcacta ctaacactaa agagggatca aatatttgtc tcactcggac agatagaggt   1020
tggtactgtg ataatgctgg ctcagtgtca ttctttccac aggctgaaac ctgcaaggtt   1080
cagtcaaaca gggtgttttg cgataccatg aattctctaa ccctccccag tgaggtgaac   1140
ctgtgtaatg tggatatatt caaccccaag tatgattgta agatcatgac ctccaagacg   1200
gacgtgagta gcagtgttat cacctccctg ggggccattg tatcctgcta cggaaaaacg   1260
```

-continued

```
aaatgtactg cctcgaacaa aaatagggga atcatcaaaa cttttagtaa tggatgcgac   1320

tacgtatcta ataaaggtgt tgacacagtg tcagtcggca acacactgta ttacgtgaat   1380

aagcaagaag ggaagtcgct gtatgtcaaa ggggagccta tcattaattt ttatgaccca   1440

ctggttttcc ccagcgatga gttcgacgcc agcattagtc aggttaatga gaaaatcaac   1500

cagtccttgg catttattcg taagagtgat gaattgctcc ataatgtgaa cgctggtaaa   1560

tccactacca acattatgat aactaccatc atcatagtaa taatagtaat tttactgtct   1620

ctgatcgctg tgggcctgtt actgtattgc aaagcccgca gtactcctgt caccttatca   1680

aaggaccagc tgtctgggat aaacaacatc gcgttctcca at                      1722
```

<210> SEQ ID NO 2
<211> LENGTH: 1722
<212> TYPE: DNA
<213> ORGANISM: Respiratory Syncytial Virus

<400> SEQUENCE: 2

```
atggaactgc tcattttgaa ggcaaacgct atcacgacaa tactcactgc agtgaccttc     60

tgttttgcct caggccagaa cataaccgag gagttttatc aatctacatg cagcgctgta    120

tctaaaggct acctgagtgc gctccgcaca ggatggtaca cctccgtgat caccatcgag    180

ctcagcaata ttaaagagaa caagtgcaat ggtaccgacg ctaaagtcaa acttatcaag    240

caggaactcg acaaatataa aaacgctgtg accgagctgc agttattgat gcagagtaca    300

cctgccacca ataacagagc taggagggag ttgcctaggt ttatgaacta cactctcaac    360

aacgcgaaaa aaaccaatgt gacgctatcc aagaaacgga agaggaggtt cctggggttt    420

cttttagggg tgggctctgc cattgcttcc ggcgtggctg tatgtaaagt tctccacctc    480

gagggagagg ttaataagat taagtcggcc ctgctgagta ctaacaaagc agtggtgtcg    540

ctgagtaacg gagtaagtgt gttaacattt aaggtgctgg acctcaagaa ttatattgac    600

aaacagttgc ttcctattct aaacaaacag agctgttcaa taagtaatat tgaaactgtt    660

attgagtttc agcagaagaa caacaggctt cttgagatta cacgcgagtt cagtgtcaat    720

gccggcgtta caacacccgt gtctacctac atgctgacga attctgagct tctctctctc    780

ataaacgaca tgcccattac gaatgaccaa aaaaaactta tgtccaacaa cgtgcagatt    840

gtgcgacagc aatcctatag cattatgtgt atcatcaagg aagaggtact cgcttatgtt    900

gtgcagctac cactctatgg tgtgattgac accccctgtt ggaagctgca taccagtcca    960

ctctgcacca ctaacacaaa ggaagggagc aatatttgcc tcactcgaac cgacaggggg   1020

tggtattgcg ataatgcggg ctccgtgtcc ttctttccac aggctgaaac ttgtaaggta   1080

cagtcaaacc gcgtgttctg tgatactatg aattctctga ctcttcccag cgaggttaat   1140

ctctgcaacg tcgacatttt caatcctaaa tatgactgca agatcatgac cagcaagacc   1200

gacgtctcca gctcagtaat cactagccta ggggccattg taagctgcta tggcaaaacc   1260

aagtgtactg cctctaataa gaacagaggc ataattaaaa ccttttcaaa tggctgtgac   1320

tatgtgtcga ataagggcgt cgacacggtc tcagtaggga ataccctcta ctacgttaac   1380

aaacaggaag gcaaatccct ttatgtaaag ggcgagccca tcataaattt ctacgaccca   1440

cttgtgttcc ccagtgatga attcgatgca tcaatctccc aggtgaacga aaagatcaat   1500

caatcccttg cttttatacg aaagtcagat gaactcctgc ataacgtgaa tgctgggaaa   1560

tctacaacca acatcatgat cactaccatc attattgtga ttatcgtaat tctgctatcc   1620
```

-continued

```
ttgattgctg tcgggctgct tctgtactgt aaggccagat cgacgcctgt gacccttca   1680

aaagaccaac ttagcggtat caataatatt gcctttagca at                      1722


<210> SEQ ID NO 3
<211> LENGTH: 574
<212> TYPE: PRT
<213> ORGANISM: Respiratory Syncytial Virus

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
```

355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn Ile Met Ile Thr
515 520 525

Thr Ile Ile Ile Val Ile Ile Val Ile Leu Leu Ser Leu Ile Ala Val
530 535 540

Gly Leu Leu Leu Tyr Cys Lys Ala Arg Ser Thr Pro Val Thr Leu Ser
545 550 555 560

Lys Asp Gln Leu Ser Gly Ile Asn Asn Ile Ala Phe Ser Asn
565 570

<210> SEQ ID NO 4
<211> LENGTH: 574
<212> TYPE: PRT
<213> ORGANISM: Respiratory Syncytial Virus

<400> SEQUENCE: 4

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Cys Lys Val Leu His Leu
145 150 155 160

-continued

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 5
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 5

```
atggagctgc tcatcctcaa agcaaatgcc atcaccacta tcctgaccgc cgtcactttc     60
tgcttcgcct ccggccaaaa tatcaccgaa gagttctatc agtccacctg ctctgccgtt    120
tctaaaggtt acctgtcagc ccttagaaca gggtggtata cctctgttat taccattgag    180
ttgtccaaca ttaagaagaa caagtgcaat ggcacagacg ctaaggttaa gctcatcaag    240
caggagctcg acaaatataa aaatgccgtc acggagctgc agttattgat gcagagcacc    300
caggcgacaa acaaccgtgc acgacgcgag ctaccccgat tcatgaacta caccctcaat    360
aatgcaaaga agacaaatgt gacgctctct aagaagcgca agcgtcgctt tctgggcttt    420
cttctcgggg ttgggagcgc gatcgcaagc ggcgtggctg tatcaaaagt gcttcatctt    480
gagggagaag tgaataaaat caaaagtgct ctgctatcta caaacaaagc cgttgtatca    540
ctgtccaacg gagtgtccgt gctcacgtcc aaagtgctag atttgaagaa ttacatcgat    600
aagcagctgc tccctattgt gaacaaacaa tcatgttcca tcagtaacat tgaaacagtc    660
atcgagtttc aacagaaaaa caatagactg ctggagatta ccagagaatt ttcggttaac    720
gccggcgtga ctacccctgt aagcacctac atgttgacaa actccgaact tttgtcactg    780
ataaacgata tgcctattac taatgatcag aaaaaattga tgtccaataa tgtccaaatc    840
gtcaggcaac agtcctacag tatcatgtct attattaagg aggaggtcct tgcatacgtg    900
gtgcaactgc cattatacgg agtcattgat actccctgtt ggaaactcca tacaagcccc    960
ctgtgcacta ctaacactaa agagggatca aatatttgtc tcactcggac agatagaggt   1020
tggtactgtg ataatgctgg ctcagtgtca ttctttccac aggctgaaac ctgcaaggtt   1080
cagtcaaaca gggtgttttg cgataccatg aattctctaa ccctccccag tgaggtgaac   1140
ctgtgtaatg tggatatatt caaccccaag tatgattgta agatcatgac ctccaagacg   1200
gacgtgagta gcagtgttat cacctccctg ggggccattg tatcctgcta cggaaaaacg   1260
aaatgtactg cctcgaacaa aaataggggga atcatcaaaa cttttagtaa tggatgcgac   1320
tacgtatcta ataaaggtgt tgacacagtg tcagtcggca acacactgta ttacgtgaat   1380
aagcaagaag ggaagtcgct gtatgtcaaa ggggagccta tcattaattt ttatgaccca   1440
ctggttttcc ccagcgatga gttcgacgcc agcattagtc aggttaatga gaaaatcaac   1500
cagtccttgg catttattcg taagagtgat gaattgctcc ataatgtgaa cgctggtaaa   1560
tccactacca acattatgat aactaccatc atcatagtaa taatagtaat tttactgtct   1620
ctgatcgctg tgggcctgtt actgtattgc aaagcccgca gtactcctgt caccttatca   1680
aaggaccagc tgtctgggat aaacaacatc gcgttctcca at                      1722
```

<210> SEQ ID NO 6
<211> LENGTH: 574
<212> TYPE: PRT
<213> ORGANISM: Artificial Sequence
<220> FEATURE:
<223> OTHER INFORMATION: Synthetic Polypeptide

<400> SEQUENCE: 6

```
Met Glu Leu Leu Ile Leu Lys Ala Asn Ala Ile Thr Thr Ile Leu Thr
1               5                   10                  15
```

-continued

```
Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430
```

```
Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 7
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 7

```
atggaactgc tcattttgaa ggcaaacgct atcacgacaa tactcactgc agtgaccttc      60

tgttttgcct caggccagaa cataaccgag gagttttatc aatctacatg cagcgctgta     120

tctaaaggct acctgagtgc gctccgcaca ggatggtaca cctccgtgat caccatcgag     180

ctcagcaata ttaaagagaa caagtgcaat ggtaccgacg ctaaagtcaa acttatcaag     240

caggaactcg acaaatataa aaacgctgtg accgagctgc agttattgat gcagagtaca     300

cctgccacca ataacagagc taggagggag ttgcctaggt ttatgaacta cactctcaac     360

aacgcgaaaa aaaccaatgt gacgctatcc aagaaacgga agaggaggtt cctggggttt     420

cttttagggg tgggctctgc cattgcttcc ggcgtggctg tatgtaaagt tctccacctc     480

gagggagagg ttaataagat taagtcggcc ctgctgagta ctaacaaagc agtggtgtcg     540

ctgagtaacg gagtaagtgt gttaacattt aaggtgctgg acctcaagaa ttatattgac     600

aaacagttgc ttcctattct aaacaaacag agctgttcaa taagtaatat tgaaactgtt     660

attgagtttc agcagaagaa caacaggctt cttgagatta cacgcgagtt cagtgtcaat     720

gccggcgtta caacacccgt gtctacctac atgctgacga attctgagct tctctctctc     780

ataaacgaca tgcccattac gaatgaccaa aaaaaactta tgtccaacaa cgtgcagatt     840

gtgcgacagc aatcctatag cattatgtgt atcatcaagg aagaggtact cgcttatgtt     900

gtgcagctac cactctatgg tgtgattgac accccctgtt ggaagctgca taccagtcca     960

ctctgcacca ctaacacaaa ggaagggagc aatatttgcc tcactcgaac cgacaggggg    1020

tggtattgcg ataatgcggg ctccgtgtcc ttctttccac aggctgaaac ttgtaaggta    1080

cagtcaaacc gcgtgttctg tgatactatg aattctctga ctcttcccag cgaggttaat    1140

ctctgcaacg tcgacatttt caatcctaaa tatgactgca agatcatgac cagcaagacc    1200

gacgtctcca gctcagtaat cactagccta ggggccattg taagctgcta tggcaaaacc    1260
```

-continued

```
aagtgtactg cctctaataa gaacagaggc ataattaaaa ccttttcaaa tggctgtgac   1320

tatgtgtcga ataagggcgt cgacacggtc tcagtaggga ataccctcta ctacgttaac   1380

aaacaggaag gcaaatccct ttatgtaaag ggcgagccca tcataaattt ctacgaccca   1440

cttgtgttcc ccagtgatga attcgatgca tcaatctccc aggtgaacga aaagatcaat   1500

caatcccttg cttttatacg aaagtcagat gaactcctgc ataacgtgaa tgctgggaaa   1560

tctacaacca acatcatgat cactaccatc attattgtga ttatcgtaat tctgctatcc   1620

ttgattgctg tcgggctgct tctgtactgt aaggccagat cgacgcctgt gaccctttca   1680

aaagaccaac ttagcggtat caataatatt gcctttagca at                      1722
```

<210> SEQ ID NO 8
<211> LENGTH: 574
<212> TYPE: PRT
<213> ORGANISM: Artificial Sequence
<220> FEATURE:
<223> OTHER INFORMATION: Synthetic Polypeptide

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

```
Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 9
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 9

```
atggaactgc tcatccttaa agccaacgcg ataacgacca ttctgaccgc cgtgaccttc      60

tgcttcgcca gcggccagaa cattaccgaa gagttttacc agagcacgtg ctctgccgtg     120

agcaaaggtt atctgagcgc tttaagaact ggctggtaca ccagtgttat tactatagag     180

ctgtcaaata ttaaaaagaa taaatgcaac gggaccgatg ccaaagtaaa attaattaag     240

caggaattgg acaagtataa gaatgcagtg acagagttgc agctcctgat gcagagcaca     300

caagctacaa acaatcgcgc tcgccagcag caacagcggt ttttagggtt cctgctaggg     360

gtggggtcag ccattgcctc tggagtggca gtgtccaaag tgctgcatct ggaaggggaa     420
```

-continued

```
gttaacaaga taaaatccgc actcctcagc accaataaag ccgtggtctc cctgtccaat     480

ggagtatcag ttttgacaag caaggtgctg gacctgaaga attatataga taagcagtta     540

ctgccaatag tgaataaaca gtcatgctca attagcaaca ttgagacagt tatcgaattc     600

cagcagaaaa ataataggct tctggaaata actcgcgaat tctcagtaaa tgccggagtg     660

accacacccg tatcgactta tatgcttaca aactctgaac tgttgtcctt gattaacgat     720

atgccaataa caaatgacca gaagaagcta atgagcaaca atgtgcagat tgtaagacag     780

cagtcttact caataatgtc tataataaaa gaggaggtgt tggcatatgt ggtgcaactg     840

cctctctatg gcgtgatcga tactccttgc tggaagttac atacatctcc actgtgtaca     900

actaatacta aggagggtag caatatttgt ctgacacgca cagatcgggg ttggtattgc     960

gacaacgcgg gcagtgtgag ctttttccct caggccgaaa cctgtaaggt tcaatctaat    1020

cgggtatttt gcgacacaat gaacagcctg acccttccgt ccgaagttaa tttgtgcaac    1080

gtcgacatct tcaatcctaa atatgactgc aaaatcatga cttctaaaac cgacgtatcc    1140

agctcagtga taacaagcct tggggcaatt gtaagctgct atggcaagac gaagtgcacc    1200

gctagtaaca agaaccgggg gattattaag actttttcga acggatgcga ttacgtctcc    1260

aacaaaggcg tcgatactgt gtccgtggga aacaccctct actatgtgaa caagcaggaa    1320

ggcaaaagcc tctacgtcaa aggagagcct atcatcaatt tctacgaccc tctagtattc    1380

ccttcagacg aatttgacgc atcaatttcc caggtgaacg agaaaataaa tcaaagctta    1440

gcctttatcc gcaagagtga tgagttgctt cacaacgtca acgccggcaa atcaaccact    1500

aat                                                                  1503
```

```
<210> SEQ ID NO 10
<211> LENGTH: 501
<212> TYPE: PRT
<213> ORGANISM: Artificial Sequence
<220> FEATURE:
<223> OTHER INFORMATION: Synthetic Polypeptide

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Gln Gln Gln Gln
            100                 105                 110

Arg Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
```

```
                165                 170                 175

Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
        195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
        275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Ala Gly
                485                 490                 495

Lys Ser Thr Thr Asn
            500
```

<210> SEQ ID NO 11
<211> LENGTH: 1563
<212> TYPE: DNA
<213> ORGANISM: Artificial Sequence
<220> FEATURE:
<223> OTHER INFORMATION: Synthetic Polynucleotide

<400> SEQUENCE: 11

```
atggaactct tgatcctgaa ggctaatgca ataacaacaa ttctgacagc agtcaccttt      60

tgcttcgcca gcggacagaa tattacggag gagttttatc aatctacctg tagtgccgtg     120
```

```
agcaaggggt acctgtctgc cctgaggacg ggatggtaca catccgtgat caccatcgag    180

ttgtctaaca ttaaaaagaa caagtgcaac ggaactgacg ccaaggtgaa gctcattaag    240

caagagctcg acaaatataa gaatgcggtt acagaactac agctactaat gcagtccaca    300

caggcaacca ataaccgagc acgtcagcag cagcaacgct tccttggctt cctgctcggg    360

gttggctcgg caattgcatc cggagtggct gtttccaagg ttttgcacct tgagggagag    420

gtcaataaga tcaagagcgc cctcctgtca actaataagg ccgtggtcag cctttccaac    480

ggtgtttctg tgttaacctc aaaagtgctc gaccttaaaa actatatcga taagcagctg    540

ctgcccatag tgaacaaaca gtcctgttct atcagtaata tcgagacagt gatcgaattc    600

cagcagaaga acaatcgtct gctggaaatt acaagggagt tcagcgtaaa cgctggagtc    660

acaacccccg tgtccactta catgctgacc aattccgagc tgctgagttt gattaatgat    720

atgcccatta cgaacgatca gaagaaactg atgtcgaata atgttcagat cgttaggcag    780

cagtcttata gcatcatgag tattatcaaa gaggaggtcc tcgcctatgt ggttcagctg    840

cctctctacg gcgttataga caccccatgc tggaagcttc acacctctcc tctgtgtacg    900

accaatacaa aggagggctc aaacatttgc cttacccgca cagatagagg atggtactgc    960

gataatgctg gctctgtgtc tttctttcct caggccgaaa catgtaaggt acagtccaat   1020

agggtatttt gcgacaccat gaactcccta accttaccaa gtgaagtgaa cctctgcaat   1080

gtggacatct ttaacccgaa gtatgactgc aaaatcatga cttccaagac agacgtgtcc   1140

agtagtgtga ttacctcact gggcgcaatc gtttcatgct atgggaagac aaagtgcacc   1200

gcaagcaaca agaatcgggg catcatcaaa accttcagta acggttgtga ctatgtttca   1260

aacaagggag tcgataccgt gtcggtgggc aatactcttt actacgtgaa taaacaggag   1320

gggaaatcac tgtatgtgaa aggtgagccg atcattaact tttacgaccc tctcgtgttt   1380

ccctccgatg agttcgacgc atccatcagt caggtcaatg agaaaatcaa ccaatctctc   1440

gccttcatta gaaaatctga cgaattactg agtgccattg gaggatatat tccggaggct   1500

cccagggacg ggcaggctta cgtccgaaag gatggagaat gggtcctact gagcacattt   1560

cta                                                                  1563
```

<210> SEQ ID NO 12
<211> LENGTH: 521
<212> TYPE: PRT
<213> ORGANISM: Artificial Sequence
<220> FEATURE:
<223> OTHER INFORMATION: Synthetic Polypeptide

<400> SEQUENCE: 12

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Gln Gln Gln Gln
```

```
            100                 105                 110

Arg Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
        195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
        275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu Ser Ala Ile Gly Gly Tyr
                485                 490                 495

Ile Pro Glu Ala Pro Arg Asp Gly Gln Ala Tyr Val Arg Lys Asp Gly
            500                 505                 510

Glu Trp Val Leu Leu Ser Thr Phe Leu
        515                 520
```

<210> SEQ ID NO 13
<211> LENGTH: 1692
<212> TYPE: DNA
<213> ORGANISM: Artificial Sequence
<220> FEATURE:
<223> OTHER INFORMATION: Synthetic Polynucleotide

<400> SEQUENCE: 13
atggagctcc tgatcttgaa ggcgaatgcc attaccacca tcctcaccgc agtaactttc 60
tgtttcgcaa gtggccagaa tataacagaa gagttctatc agtcaacctg tagcgcagtc 120
tcaaaggggt atttatcagc actgagaacc ggttggtata ccagtgttat tacaatagag 180
ctgagtaaca taaaggagaa taagtgcaac ggcactgacg ccaaggtcaa gctcatcaaa 240
caggaactcg ataaatacaa gaacgctgtc actgaactgc agctgctgat gcaaagcacc 300
cccgccacca acaatagggc ccgcagagag cttcctagat ttatgaacta cactctgaac 360
aacgccaaaa agaccaatgt aacactgtca aagaaacaga aacagcaggc tattgcaagc 420
ggtgtggctg tgtctaaagt gctgcatctc gaggggggagg tcaacaagat caaatccgca 480
ttgctcagca ccaacaaggc tgtggtgagc ctgtccaatg gtgtctcagt gctcaccagc 540
aaagtgctgg acctgaagaa ttatattgat aagcagctgc tacccatagt caacaaacag 600
tcatgctcca tatctaatat tgagactgtc atcgagttcc aacagaagaa caatcgcctg 660
ctggagatta ccagggagtt ctcagtcaat gccggggtca cgacacccgt tagtacttat 720
atgcttacca actccgagct tctctctttg atcaatgaca tgccaattac taacgaccag 780
aagaagttga tgtctaacaa tgtacagatc gttcgccagc agtcctattc cattatgtcg 840
attattaaag aggaggttct tgcatacgtc gtgcagttgc cattatatgg agtcatcgac 900
accccctgct ggaaactgca tacgtcacca ttatgcacca cgaatacaaa ggagggcagt 960
aatatttgtc ttacacggac tgatcgaggc tggtattgtg ataacgcagg ctcggtgtca 1020
ttctttccac aggctgaaac ctgtaaggtg caatctaata gggtgttttg cgataccatg 1080
aattctctga ctctgcccag tgaggtcaat ttgtgtaacg tggacatctt caacccaaag 1140
tacgactgca agatcatgac atctaagaca gatgtgtcat ccagcgttat cacgagcctc 1200
ggcgctatag tctcctgtta cggcaagacc aagtgcaccg ctagcaacaa gaatcgggga 1260
atcatcaaaa ccttttctaa cggttgtgac tacgtgagca acaagggggt ggataccgtc 1320
tcagtcggta acaccctgta ctacgtgaat aaacaggagg ggaagtcatt gtacgtgaag 1380
ggtgaaccta tcatcaactt ttatgacccc ctcgtcttcc catcagacga gtttgacgcg 1440
tccatctctc aggtgaatga gaagattaac cagagcctgg cttttatccg caaatcagac 1500
gaactactgc acaatgtcaa cgctggcaag agcacaacaa atataatgat aacaaccatc 1560
atcatcgtca ttattgtgat cttgttatca ctgatcgctg tggggctcct cctttattgc 1620
aaggctcgta gcacccctgt caccctcagt aaagatcagc tgtcagggat caataatatc 1680
gcgtttagca ac 1692

<210> SEQ ID NO 14
<211> LENGTH: 564
<212> TYPE: PRT
<213> ORGANISM: Artificial Sequence
<220> FEATURE:
<223> OTHER INFORMATION: Synthetic Polypeptide

<400> SEQUENCE: 14

-continued

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ala Ile Ala Ser Gly Val Ala Val
    130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Ser Ile Ser Asn Ile Glu
        195                 200                 205

Thr Val Ile Glu Phe Gln Gln Lys Asn Asn Arg Leu Leu Glu Ile Thr
    210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270

Gln Gln Ser Tyr Ser Ile Met Ser Ile Ile Lys Glu Glu Val Leu Ala
        275                 280                 285

Tyr Val Val Gln Leu Pro Leu Tyr Gly Val Ile Asp Thr Pro Cys Trp
    290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
        355                 360                 365

Val Asn Leu Cys Asn Val Asp Ile Phe Asn Pro Lys Tyr Asp Cys Lys
    370                 375                 380

Ile Met Thr Ser Lys Thr Asp Val Ser Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
```

-continued

```
            420                 425                 430

Ser Asn Lys Gly Val Asp Thr Val Ser Val Gly Asn Thr Leu Tyr Tyr
        435                 440                 445

Val Asn Lys Gln Glu Gly Lys Ser Leu Tyr Val Lys Gly Glu Pro Ile
    450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn Ile Met Ile Thr Thr Ile Ile Ile Val Ile Ile Val Ile Leu
        515                 520                 525

Leu Ser Leu Ile Ala Val Gly Leu Leu Leu Tyr Cys Lys Ala Arg Ser
    530                 535                 540

Thr Pro Val Thr Leu Ser Lys Asp Gln Leu Ser Gly Ile Asn Asn Ile
545                 550                 555                 560

Ala Phe Ser Asn
```

<210> SEQ ID NO 15
<211> LENGTH: 1539
<212> TYPE: DNA
<213> ORGANISM: Artificial Sequence
<220> FEATURE:
<223> OTHER INFORMATION: Synthetic Polynucleotide

<400> SEQUENCE: 15

```
atggaattat taattttgaa gacaaatgct ataaccgcga tactagcggc tgtgactctt     60

tgtttcgcat caagccagaa tattacagaa gaattttatc aatccacctg cagcgctgta    120

tcgaaaggtt acctcagcgc gcttaggaca ggatggtata cctccgttat cacgattgaa    180

ctgagtaata tcaaggaaaa caagtgtaac ggaacagacg ccaaggtcaa acttattaaa    240

caagaactgg acaagtataa gtctgcagtg accgaattgc agctcctgat gcagagtacc    300

cctgcaacta acaacaagtt tttgggcttt ctgcaaggcg tgggtagcgc gatcgcctcc    360

ggaatcgcgg tctccaaagt gttgcacctg gagggagaag ttaacaagat caaatcggct    420

ctgttgagta ccaacaaggc agtggtgtca ctgagcaacg gtgtaagcgt gttaacaagc    480

aaggtattgg acttaaagaa ctatattgac aaacagctgc tccccatcgt gaacaaacag    540

agctgctcaa tctccaatat agagacggtg atagagttcc agcaaaaaaa taatcggctc    600

cttgagatca cccgcgaatt ctcagttaat gccggcgtca caactccggt gtctacatac    660

atgctgacca actcggagct gttatcctta ataaatgaca tgcccatcac caatgatcaa    720

aaaaaactga tgtcaaataa cgtccagata gtaagacagc agagctacag catcatgtcg    780

attatcaaag aggaggtgct ggcgtacgtg gtgcagctgc ccctgtatgg ggtgattgac    840

accccttgtt ggaagctgca cacctcccca ctatgtacta ccaataccaa agaaggatcc    900

aacatctgcc ttacccgcac cgatagggga tggtattgcg acaacgccgg atccgtcagc    960

ttctttccac ttgccgaaac ttgcaaggtt cagtcaaacc gggtgttctg cgatacaatg   1020

aattccctta ccttgcccag cgaagttaat ctctgtaata ttgacatctt taaccccaaa   1080

tacgattgca aaattatgac gtcaaaaacc gatgtcagtt caagcgttat caccagcttg   1140

ggtgctatcg tttcatgcta tggcaaaacc aagtgtacgg ctagtaacaa aaaccgcgga   1200

ataattaaga cattcagcaa tggttgcgac tacgtatcaa ataagggtgt cgacaccgtt   1260
```

```
tccgtgggca atacgctgta ctatgttaat aaacaggaag gcaagtcact gtatgttaaa   1320

ggtgaaccca tcatcaactt ctacgacccc ctggttttcc cctccgacga gtttgatgcc   1380

agcatatcac aggttaatga aaaaataaac ggcacattgg cgtttatcag aaagtctgac   1440

gagaaacttc ataacgtgga agacaagata gaagagatat tgagcaaaat ctatcatatt   1500

gagaacgaga tcgccaggat caaaaagctt attggggag                          1539


<210> SEQ ID NO 16
<211> LENGTH: 513
<212> TYPE: PRT
<213> ORGANISM: Artificial Sequence
<220> FEATURE:
<223> OTHER INFORMATION: Synthetic Polypeptide

<400> SEQUENCE: 16

Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Gln
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
        195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
        275                 280                 285

Ser Pro Leu Cys Thr Thr Asn Thr Lys Glu Gly Ser Asn Ile Cys Leu
    290                 295                 300

Thr Arg Thr Asp Arg Gly Trp Tyr Cys Asp Asn Ala Gly Ser Val Ser
```

305 310 315 320

Phe Phe Pro Leu Ala Glu Thr Cys Lys Val Gln Ser Asn Arg Val Phe
325 330 335

Cys Asp Thr Met Asn Ser Leu Thr Leu Pro Ser Glu Val Asn Leu Cys
340 345 350

Asn Ile Asp Ile Phe Asn Pro Lys Tyr Asp Cys Lys Ile Met Thr Ser
355 360 365

Lys Thr Asp Val Ser Ser Ser Val Ile Thr Ser Leu Gly Ala Ile Val
370 375 380

Ser Cys Tyr Gly Lys Thr Lys Cys Thr Ala Ser Asn Lys Asn Arg Gly
385 390 395 400

Ile Ile Lys Thr Phe Ser Asn Gly Cys Asp Tyr Val Ser Asn Lys Gly
405 410 415

Val Asp Thr Val Ser Val Gly Asn Thr Leu Tyr Tyr Val Asn Lys Gln
420 425 430

Glu Gly Lys Ser Leu Tyr Val Lys Gly Glu Pro Ile Ile Asn Phe Tyr
435 440 445

Asp Pro Leu Val Phe Pro Ser Asp Glu Phe Asp Ala Ser Ile Ser Gln
450 455 460

Val Asn Glu Lys Ile Asn Gly Thr Leu Ala Phe Ile Arg Lys Ser Asp
465 470 475 480

Glu Lys Leu His Asn Val Glu Asp Lys Ile Glu Glu Ile Leu Ser Lys
485 490 495

Ile Tyr His Ile Glu Asn Glu Ile Ala Arg Ile Lys Lys Leu Ile Gly
500 505 510

Glu

<210> SEQ ID NO 17
<211> LENGTH: 894
<212> TYPE: DNA
<213> ORGANISM: Artificial Sequence
<220> FEATURE:
<223> OTHER INFORMATION: Synthetic Polynucleotide

<400> SEQUENCE: 17
atgtctaaaa acaaggacca gcgcactgct aagacgctgg aacgcacatg ggataccctg 60
aaccatctgt tattcatttc cagctgcctc tacaagctaa accttaaaag tgttgcacaa 120
atcacactca gcatcctggc aatgattatt tcaacatccc tgatcatagc cgcaatcata 180
tttatcgcct cagcaaatca caaagttacc ccgaccacag ccattatcca ggacgctaca 240
tcccaaatca aaaacaccac acctacatat ctcactcaga acccgcagct gggcatttca 300
ccatccaacc cttccgagat cacctctcaa atcaccacca ttctcgcctc tactaccccg 360
ggagtaaaga gcactcttca gagcacaacc gttaaaacta aaaataccac caccactcag 420
actcagcctt cgaaaccaac gactaaacag cggcaaaata agcctccatc caaaccgaat 480
aacgactttc atttcgaagt ctttaacttt gtgccatgca gtatttgctc caataatcct 540
acttgctggg ctatctgcaa gagaatccct aacaagaagc ctggaaagaa gacaacgaca 600
aagccaacta agaagccgac acttaagact accaaaaaag accctaagcc gcagactacc 660
aagagcaagg aggttcccac aaccaagcct acagaggagc cgactattaa cacaacaaag 720
accaacatca tcaccaccct gcttacttct aatactaccg gaaacccaga gctgacgtcc 780
cagatggaga cgttccattc cacatcttcc gaagggaatc ctagtcccag ccaggtgagc 840
acaacctcag aatacccgtc ccagccctca tcacctccta ataccccccg gcag 894

<210> SEQ ID NO 18
<211> LENGTH: 298
<212> TYPE: PRT
<213> ORGANISM: Artificial Sequence
<220> FEATURE:
<223> OTHER INFORMATION: Synthetic Polypeptide

<400> SEQUENCE: 18

Met Ser Lys Asn Lys Asp Gln Arg Thr Ala Lys Thr Leu Glu Arg Thr
1 5 10 15

Trp Asp Thr Leu Asn His Leu Leu Phe Ile Ser Ser Cys Leu Tyr Lys
20 25 30

Leu Asn Leu Lys Ser Val Ala Gln Ile Thr Leu Ser Ile Leu Ala Met
35 40 45

Ile Ile Ser Thr Ser Leu Ile Ile Ala Ala Ile Ile Phe Ile Ala Ser
50 55 60

Ala Asn His Lys Val Thr Pro Thr Thr Ala Ile Ile Gln Asp Ala Thr
65 70 75 80

Ser Gln Ile Lys Asn Thr Thr Pro Thr Tyr Leu Thr Gln Asn Pro Gln
85 90 95

Leu Gly Ile Ser Pro Ser Asn Pro Ser Glu Ile Thr Ser Gln Ile Thr
100 105 110

Thr Ile Leu Ala Ser Thr Thr Pro Gly Val Lys Ser Thr Leu Gln Ser
115 120 125

Thr Thr Val Lys Thr Lys Asn Thr Thr Thr Thr Gln Thr Gln Pro Ser
130 135 140

Lys Pro Thr Thr Lys Gln Arg Gln Asn Lys Pro Pro Ser Lys Pro Asn
145 150 155 160

Asn Asp Phe His Phe Glu Val Phe Asn Phe Val Pro Cys Ser Ile Cys
165 170 175

Ser Asn Asn Pro Thr Cys Trp Ala Ile Cys Lys Arg Ile Pro Asn Lys
180 185 190

Lys Pro Gly Lys Lys Thr Thr Thr Lys Pro Thr Lys Lys Pro Thr Leu
195 200 205

Lys Thr Thr Lys Lys Asp Pro Lys Pro Gln Thr Thr Lys Ser Lys Glu
210 215 220

Val Pro Thr Thr Lys Pro Thr Glu Glu Pro Thr Ile Asn Thr Thr Lys
225 230 235 240

Thr Asn Ile Ile Thr Thr Leu Leu Thr Ser Asn Thr Thr Gly Asn Pro
245 250 255

Glu Leu Thr Ser Gln Met Glu Thr Phe His Ser Thr Ser Ser Glu Gly
260 265 270

Asn Pro Ser Pro Ser Gln Val Ser Thr Thr Ser Glu Tyr Pro Ser Gln
275 280 285

Pro Ser Ser Pro Pro Asn Thr Pro Arg Gln
290 295

<210> SEQ ID NO 19
<211> LENGTH: 1629
<212> TYPE: DNA
<213> ORGANISM: Artificial Sequence
<220> FEATURE:
<223> OTHER INFORMATION: Synthetic Polynucleotide

<400> SEQUENCE: 19
atggagacgc ctgcccagct gctgttcctg ctgttgttgt ggctgccaga tactactggg 60
tttgcaagcg gacaaaacat taccgaagag ttctatcaat ccacatgctc tgcagtgtct 120
aagggctacc ttagtgcatt acgaaccggg tggtatacga gtgtaatcac cattgagctg 180
tccaacatca agaagaacaa gtgcaatggg actgatgcca aggtgaaact tatcaaacaa 240
gagctcgaca agtataagaa cgccgtgacc gaactacaac tcctgatgca atcgactcag 300
gctactaaca acagagctcg gagggagctg cccagattca tgaattatac cttaaacaac 360
gctaaaaaaa caaatgtgac cctgagtaag aagcggaaac gaaggttcct gggcttcctg 420
ctcggtgtgg ggtctgcaat agcaagcggc gtcgctgtgt ccaaggtcct tcacttagaa 480
ggtgaggtca ataagatcaa gtccgctctc ctctctacca acaaggcagt ggtgagcctg 540
tctaacggtg tgtccgtgct gacatcgaag gtactggacc tgaaaaacta catcgacaag 600
cagctgctgc ctattgtgaa taagcaatcc tgcagtatct ccaacattga gacagtgatt 660
gaatttcagc aaaagaacaa tcgtttgttg gagataacaa gagaattcag tgttaatgcc 720
ggcgttacca ctcccgtgtc gacatacatg ctaacaaata gcgagctgct atctctcatt 780
aatgatatgc ctatcaccaa tgaccagaaa aaacttatgt ccaataacgt gcagatagtc 840
aggcagcagt cctacagcat tatgagcata attaaagagg aagtgttggc ttacgtcgtc 900
cagcttccac tgtatggcgt gatcgatacc ccttgttgga agctgcatac ttcccccctt 960
tgtacaacta ataccaaaga agggagtaat atatgcctca caaggactga cagaggctgg 1020
tactgcgaca acgccgggag cgtcagcttt ttcccgcagg ccgagacatg taaggtgcag 1080
agcaaccgtg tcttttgcga caccatgaat agcctgactt tgccaagtga ggtcaacctt 1140
tgcaacgtgg atatttttaa ccctaagtac gattgtaaga taatgacatc caaaaccgat 1200
gttagtagct ccgtgatcac ttcgctgggt gcgatagtta gctgctatgg aaagacaaag 1260
tgtaccgcaa gtaacaagaa ccgcgggatt attaaaacat ttagcaatgg gtgcgactac 1320
gtatcaaaca agggggtgga tacagtcagc gtgggaaaca cactttacta cgttaacaag 1380
caggaaggga aatcccttta tgtgaaggga gaaccaatta tcaactttta tgatcccctc 1440
gtgtttccaa gtgatgaatt cgacgcaagc atctcgcagg tgaacgagaa aatcaatcag 1500
agtctagctt tcataaggaa gtctgatgaa ctgcttagtg ccattggcgg gtacataccg 1560
gaagccccac gcgacggtca ggcttacgtg aggaaggacg gcgagtgggt tctgctgtcc 1620
actttcctt 1629

<210> SEQ ID NO 20
<211> LENGTH: 543
<212> TYPE: PRT
<213> ORGANISM: Artificial Sequence
<220> FEATURE:
<223> OTHER INFORMATION: Synthetic Polypeptide

<400> SEQUENCE: 20

Met Glu Thr Pro Ala Gln Leu Leu Phe Leu Leu Leu Leu Trp Leu Pro
1 5 10 15

Asp Thr Thr Gly Phe Ala Ser Gly Gln Asn Ile Thr Glu Glu Phe Tyr
20 25 30

Gln Ser Thr Cys Ser Ala Val Ser Lys Gly Tyr Leu Ser Ala Leu Arg
35 40 45

Thr Gly Trp Tyr Thr Ser Val Ile Thr Ile Glu Leu Ser Asn Ile Lys
50 55 60

Lys Asn Lys Cys Asn Gly Thr Asp Ala Lys Val Lys Leu Ile Lys Gln
65 70 75 80

-continued

```
Glu Leu Asp Lys Tyr Lys Asn Ala Val Thr Glu Leu Gln Leu Leu Met
                85                  90                  95

Gln Ser Thr Gln Ala Thr Asn Asn Arg Ala Arg Arg Glu Leu Pro Arg
            100                 105                 110

Phe Met Asn Tyr Thr Leu Asn Asn Ala Lys Lys Thr Asn Val Thr Leu
        115                 120                 125

Ser Lys Lys Arg Lys Arg Arg Phe Leu Gly Phe Leu Leu Gly Val Gly
    130                 135                 140

Ser Ala Ile Ala Ser Gly Val Ala Val Ser Lys Val Leu His Leu Glu
145                 150                 155                 160

Gly Glu Val Asn Lys Ile Lys Ser Ala Leu Leu Ser Thr Asn Lys Ala
                165                 170                 175

Val Val Ser Leu Ser Asn Gly Val Ser Val Leu Thr Ser Lys Val Leu
            180                 185                 190

Asp Leu Lys Asn Tyr Ile Asp Lys Gln Leu Leu Pro Ile Val Asn Lys
        195                 200                 205

Gln Ser Cys Ser Ile Ser Asn Ile Glu Thr Val Ile Glu Phe Gln Gln
    210                 215                 220

Lys Asn Asn Arg Leu Leu Glu Ile Thr Arg Glu Phe Ser Val Asn Ala
225                 230                 235                 240

Gly Val Thr Thr Pro Val Ser Thr Tyr Met Leu Thr Asn Ser Glu Leu
                245                 250                 255

Leu Ser Leu Ile Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
        275                 280                 285

Ser Ile Ile Lys Glu Glu Val Leu Ala Tyr Val Val Gln Leu Pro Leu
    290                 295                 300

Tyr Gly Val Ile Asp Thr Pro Cys Trp Lys Leu His Thr Ser Pro Leu
305                 310                 315                 320

Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
        355                 360                 365

Met Asn Ser Leu Thr Leu Pro Ser Glu Val Asn Leu Cys Asn Val Asp
    370                 375                 380

Ile Phe Asn Pro Lys Tyr Asp Cys Lys Ile Met Thr Ser Lys Thr Asp
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
        435                 440                 445

Val Ser Val Gly Asn Thr Leu Tyr Tyr Val Asn Lys Gln Glu Gly Lys
    450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
                485                 490                 495
```

-continued

```
Lys Ile Asn Gln Ser Leu Ala Phe Ile Arg Lys Ser Asp Glu Leu Leu
            500                 505                 510

Ser Ala Ile Gly Gly Tyr Ile Pro Glu Ala Pro Arg Asp Gly Gln Ala
        515                 520                 525

Tyr Val Arg Lys Asp Gly Glu Trp Val Leu Leu Ser Thr Phe Leu
    530                 535                 540
```

```
<210> SEQ ID NO 21
<211> LENGTH: 1629
<212> TYPE: DNA
<213> ORGANISM: Artificial Sequence
<220> FEATURE:
<223> OTHER INFORMATION: Synthetic Polynucleotide

<400> SEQUENCE: 21

atggagactc ccgctcagct gctgtttttg ctcctcctat ggctgccgga taccaccggc      60

tttgcctctg gacagaacat taccgaggaa ttctatcagt cgacttgttc cgcagtctcg     120

aaggggtacc tgagtgccct gcgcaccggg tggtacacca gtgttatcac tattgagctg     180

tccaacatta aagaaaataa gtgtaatgga actgacgcga aggtgaagtt gataaaacag     240

gagctggata aatacaagaa tgcagtgacc gaactgcagc tcctgatgca gtccactcca     300

gcaacaaata atcgcgcgag acgcgaactc ccccgcttta tgaactacac tctgaataat     360

gcgaagaaaa cgaatgtgac actaagtaag aaaagaaaac ggcgatttct tgggttcctg     420

ctcggggtgg gatctgccat agcaagcggg gtggcggtat gtaaagtcct tcacctagaa     480

ggggaggtga acaaaattaa gagtgccctg ctgagcacca acaaggctgt ggtttcactg     540

tcaaacggag taagcgtgct aacatttaaa gtcttggacc tgaagaatta tattgacaag     600

cagctcctgc ccattctcaa caaacagtca tgttccatta gcaacatcga aacagtcatt     660

gagtttcagc aaaaaaacaa ccgcctcctt gagattacgc gtgagttttc cgtcaatgct     720

ggagtcacga caccggtgtc cacttacatg ctgactaaca gcgaactcct gagcctaatc     780

aatgacatgc ccattactaa cgaccagaaa aaattgatgt ccaataacgt gcagatagtg     840

cgccagcaat cttactccat aatgtgcatt atcaaggagg aagtcctggc gtacgttgtt     900

cagctgccgc tgtatggtgt gatagatacg ccatgctgga aactgcacac atcccccctt     960

tgcacaacga atactaaaga gggaagtaac atttgcttga ccagaacaga tcggggctgg    1020

tactgcgaca acgctggtag tgtgtcattt ttcccccagg cagaaacgtg taaagtccag    1080

agcaatcgcg tgttctgcga cacaatgaac tcacttactt tgccctcaga ggtcaatttg    1140

tgtaatgtgg atatcttcaa cccgaaatac gattgtaaga ttatgacgag caaaacagac    1200

gtgtcttcat cagtgataac aagtctgggc gcaatagtgt catgctatgg taagactaag    1260

tgcactgcct ccaataaaaa ccgcggcatc atcaagacat tttcaaatgg atgcgactac    1320

gtgtcaaaca agggcgtcga cacagtaagc gttgggaaca ccctatacta cgtcaacaag    1380

caggagggga aaagcctata cgtgaaaggc gagccaatca tcaatttcta cgatccactg    1440

gtctttccaa gtgacgaatt tgatgccagc atatcgcagg tgaacgagaa aataaatcag    1500

tcactcgcct tcatcaggaa gtcagatgag ctgctgtccg ccatcggagg atacattcca    1560

gaagccccac gcgacggcca ggcatacgtg cggaaggacg gcgaatgggt ccttttgagc    1620

acttttcta                                                            1629
```

```
<210> SEQ ID NO 22
<211> LENGTH: 543
<212> TYPE: PRT
```

<213> ORGANISM: Artificial Sequence
<220> FEATURE:
<223> OTHER INFORMATION: Synthetic Polypeptide

<400> SEQUENCE: 22

Met Glu Thr Pro Ala Gln Leu Leu Phe Leu Leu Leu Leu Trp Leu Pro
1 5 10 15

Asp Thr Thr Gly Phe Ala Ser Gly Gln Asn Ile Thr Glu Glu Phe Tyr
20 25 30

Gln Ser Thr Cys Ser Ala Val Ser Lys Gly Tyr Leu Ser Ala Leu Arg
35 40 45

Thr Gly Trp Tyr Thr Ser Val Ile Thr Ile Glu Leu Ser Asn Ile Lys
50 55 60

Glu Asn Lys Cys Asn Gly Thr Asp Ala Lys Val Lys Leu Ile Lys Gln
65 70 75 80

Glu Leu Asp Lys Tyr Lys Asn Ala Val Thr Glu Leu Gln Leu Leu Met
85 90 95

Gln Ser Thr Pro Ala Thr Asn Asn Arg Ala Arg Arg Glu Leu Pro Arg
100 105 110

Phe Met Asn Tyr Thr Leu Asn Asn Ala Lys Lys Thr Asn Val Thr Leu
115 120 125

Ser Lys Lys Arg Lys Arg Arg Phe Leu Gly Phe Leu Leu Gly Val Gly
130 135 140

Ser Ala Ile Ala Ser Gly Val Ala Val Cys Lys Val Leu His Leu Glu
145 150 155 160

Gly Glu Val Asn Lys Ile Lys Ser Ala Leu Leu Ser Thr Asn Lys Ala
165 170 175

Val Val Ser Leu Ser Asn Gly Val Ser Val Leu Thr Phe Lys Val Leu
180 185 190

Asp Leu Lys Asn Tyr Ile Asp Lys Gln Leu Leu Pro Ile Leu Asn Lys
195 200 205

Gln Ser Cys Ser Ile Ser Asn Ile Glu Thr Val Ile Glu Phe Gln Gln
210 215 220

Lys Asn Asn Arg Leu Leu Glu Ile Thr Arg Glu Phe Ser Val Asn Ala
225 230 235 240

Gly Val Thr Thr Pro Val Ser Thr Tyr Met Leu Thr Asn Ser Glu Leu
245 250 255

Leu Ser Leu Ile Asn Asp Met Pro Ile Thr Asn Asp Gln Lys Lys Leu
260 265 270

Met Ser Asn Asn Val Gln Ile Val Arg Gln Gln Ser Tyr Ser Ile Met
275 280 285

Cys Ile Ile Lys Glu Glu Val Leu Ala Tyr Val Val Gln Leu Pro Leu
290 295 300

Tyr Gly Val Ile Asp Thr Pro Cys Trp Lys Leu His Thr Ser Pro Leu
305 310 315 320

Cys Thr Thr Asn Thr Lys Glu Gly Ser Asn Ile Cys Leu Thr Arg Thr
325 330 335

Asp Arg Gly Trp Tyr Cys Asp Asn Ala Gly Ser Val Ser Phe Phe Pro
340 345 350

Gln Ala Glu Thr Cys Lys Val Gln Ser Asn Arg Val Phe Cys Asp Thr
355 360 365

Met Asn Ser Leu Thr Leu Pro Ser Glu Val Asn Leu Cys Asn Val Asp
370 375 380

Ile Phe Asn Pro Lys Tyr Asp Cys Lys Ile Met Thr Ser Lys Thr Asp

-continued

```
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
        435                 440                 445

Val Ser Val Gly Asn Thr Leu Tyr Tyr Val Asn Lys Gln Glu Gly Lys
    450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
                485                 490                 495

Lys Ile Asn Gln Ser Leu Ala Phe Ile Arg Lys Ser Asp Glu Leu Leu
            500                 505                 510

Ser Ala Ile Gly Gly Tyr Ile Pro Glu Ala Pro Arg Asp Gly Gln Ala
        515                 520                 525

Tyr Val Arg Lys Asp Gly Glu Trp Val Leu Leu Ser Thr Phe Leu
    530                 535                 540
```

<210> SEQ ID NO 23
<211> LENGTH: 1500
<212> TYPE: DNA
<213> ORGANISM: Artificial Sequence
<220> FEATURE:
<223> OTHER INFORMATION: Synthetic Polynucleotide

<400> SEQUENCE: 23

```
atggagactc cagcccaatt actgttcctg ctactccttt ggctgcccga tactactgga     60

ttcgcttcgg gtcagaatat tacagaggag ttctaccaaa gtacttgctc tgcagtctcc    120

aagggatacc tgtccgctct gcggacggga tggtatacca gtgttataac gatcgagttg    180

agcaacatca agaagaacaa atgtaatgga acagatgcca aggtgaaact gatcaaacag    240

gagttggata aatataagaa tgctgtcacc gaactgcagc tattgatgca gtccacccag    300

gctaccaaca accgggccag gcagcaacaa cagagatttt tgggtttctt gctgggcgtg    360

gggtctgcca tcgcttcagg ggtggccgtg agtaaagtcc tgcacctgga aggcgaagtc    420

aacaagatca agtctgcatt actaagtacc aataaggctg tagttagcct gtccaatggc    480

gtgagtgtgc ttacttctaa ggtactggac ctgaagaact acatcgacaa gcaactacta    540

cccattgtaa ataagcagtc atgtagcata tcaaacatcg agacagtgat cgaatttcaa    600

cagaagaata accggctgtt ggagataaca cgggagttct ctgtaaatgc cggcgtgacg    660

acccctgtca gcacctacat gctcacgaat agcgagttgc tttccctgat taatgatatg    720

ccgattacaa atgaccagaa gaagctgatg agtaataatg tccaaattgt ccgtcagcag    780

agctattcga ttatgtccat catcaaggag gaagtcttag cctatgtggt gcagctcccc    840

ctctacggag tgattgacac accgtgctgg aagctgcaca cctccccttt gtgtacaacc    900

aataccaagg agggctccaa catctgcctt actaggaccg acaggggatg gtattgcgac    960

aacgccgggt ccgtctcatt ttttcctcag gcggaaacct gtaaggtaca gtcgaatcga   1020

gtgttttgtg acactatgaa cagcctgacc ttgcctagcg aggtgaatct gtgtaacgtt   1080

gatatcttca accctaagta tgactgtaag atcatgactt caaaaactga tgtctcctca   1140

agcgtgatca cctctttggg cgccatcgtg tcatgctacg gaaagacgaa gtgcaccgcc   1200
```

```
tctaacaaga accgagggat catcaaaaca ttctccaatg gctgtgatta cgtcagtaac   1260

aaaggtgtgg acacagtctc cgtgggcaat acgttatatt atgtgaataa gcaggaggga   1320

aaaagtctct atgtgaaggg tgaaccgata atcaatttct acgatccctt ggtgtttcca   1380

agcgacgagt tcgacgcctc gatcagccag gtgaacgaga aaatcaacca gtctttggca   1440

ttcatccgca agagcgacga gctactgcat aacgtgaacg caggcaagag tactaccaat   1500


<210> SEQ ID NO 24
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 24

Met Glu Thr Pro Ala Gln Leu Leu Phe Leu Leu Leu Leu Trp Leu Pro
1               5                   10                  15

Asp Thr Thr Gly Phe Ala Ser Gly Gln Asn Ile Thr Glu Glu Phe Tyr
            20                  25                  30

Gln Ser Thr Cys Ser Ala Val Ser Lys Gly Tyr Leu Ser Ala Leu Arg
        35                  40                  45

Thr Gly Trp Tyr Thr Ser Val Ile Thr Ile Glu Leu Ser Asn Ile Lys
    50                  55                  60

Lys Asn Lys Cys Asn Gly Thr Asp Ala Lys Val Lys Leu Ile Lys Gln
65                  70                  75                  80

Glu Leu Asp Lys Tyr Lys Asn Ala Val Thr Glu Leu Gln Leu Leu Met
                85                  90                  95

Gln Ser Thr Gln Ala Thr Asn Asn Arg Ala Arg Gln Gln Gln Gln Arg
            100                 105                 110

Phe Leu Gly Phe Leu Leu Gly Val Gly Ser Ala Ile Ala Ser Gly Val
        115                 120                 125

Ala Val Ser Lys Val Leu His Leu Glu Gly Glu Val Asn Lys Ile Lys
    130                 135                 140

Ser Ala Leu Leu Ser Thr Asn Lys Ala Val Val Ser Leu Ser Asn Gly
145                 150                 155                 160

Val Ser Val Leu Thr Ser Lys Val Leu Asp Leu Lys Asn Tyr Ile Asp
                165                 170                 175

Lys Gln Leu Leu Pro Ile Val Asn Lys Gln Ser Cys Ser Ile Ser Asn
            180                 185                 190

Ile Glu Thr Val Ile Glu Phe Gln Gln Lys Asn Asn Arg Leu Leu Glu
        195                 200                 205

Ile Thr Arg Glu Phe Ser Val Asn Ala Gly Val Thr Thr Pro Val Ser
    210                 215                 220

Thr Tyr Met Leu Thr Asn Ser Glu Leu Leu Ser Leu Ile Asn Asp Met
225                 230                 235                 240

Pro Ile Thr Asn Asp Gln Lys Lys Leu Met Ser Asn Asn Val Gln Ile
                245                 250                 255

Val Arg Gln Gln Ser Tyr Ser Ile Met Ser Ile Ile Lys Glu Glu Val
            260                 265                 270

Leu Ala Tyr Val Val Gln Leu Pro Leu Tyr Gly Val Ile Asp Thr Pro
        275                 280                 285

Cys Trp Lys Leu His Thr Ser Pro Leu Cys Thr Thr Asn Thr Lys Glu
    290                 295                 300

Gly Ser Asn Ile Cys Leu Thr Arg Thr Asp Arg Gly Trp Tyr Cys Asp
305                 310                 315                 320
```

```
Asn Ala Gly Ser Val Ser Phe Phe Pro Gln Ala Glu Thr Cys Lys Val
                325                 330                 335

Gln Ser Asn Arg Val Phe Cys Asp Thr Met Asn Ser Leu Thr Leu Pro
            340                 345                 350

Ser Glu Val Asn Leu Cys Asn Val Asp Ile Phe Asn Pro Lys Tyr Asp
        355                 360                 365

Cys Lys Ile Met Thr Ser Lys Thr Asp Val Ser Ser Ser Val Ile Thr
    370                 375                 380

Ser Leu Gly Ala Ile Val Ser Cys Tyr Gly Lys Thr Lys Cys Thr Ala
385                 390                 395                 400

Ser Asn Lys Asn Arg Gly Ile Ile Lys Thr Phe Ser Asn Gly Cys Asp
                405                 410                 415

Tyr Val Ser Asn Lys Gly Val Asp Thr Val Ser Val Gly Asn Thr Leu
            420                 425                 430

Tyr Tyr Val Asn Lys Gln Glu Gly Lys Ser Leu Tyr Val Lys Gly Glu
        435                 440                 445

Pro Ile Ile Asn Phe Tyr Asp Pro Leu Val Phe Pro Ser Asp Glu Phe
    450                 455                 460

Asp Ala Ser Ile Ser Gln Val Asn Glu Lys Ile Asn Gln Ser Leu Ala
465                 470                 475                 480

Phe Ile Arg Lys Ser Asp Glu Leu Leu His Asn Val Asn Ala Gly Lys
                485                 490                 495

Ser Thr Thr Asn
            500


<210> SEQ ID NO 25
<211> LENGTH: 1560
<212> TYPE: DNA
<213> ORGANISM: Artificial Sequence
<220> FEATURE:
<223> OTHER INFORMATION: Synthetic Polynucleotide

<400> SEQUENCE: 25

atggagactc ccgctcagtt gttgttcctg ctactgctgt ggctgcctga tacaaccgga      60

tttgctagtg ggcagaatat caccgaagaa ttctatcaga gcacttgcag tgcagtgtcc     120

aaaggatatt tgagcgccct gcgcactggg tggtacacaa gtgtcatcac aatcgagcta     180

agtaacatta aaaaaaacaa atgcaacggg actgacgcaa aggtcaaact cattaagcaa     240

gaacttgaca aatataagaa cgctgttaca gagttgcagc tgctaatgca aagcactcag     300

gctaccaata accgagcgag acagcagcag caacgtttcc tgggtttcct gttaggtgtg     360

ggtagcgcaa ttgccagtgg tgtagccgtg tccaaggtgc tgcacctgga aggggaagtg     420

aataagatca agtctgcact gctgtccacc aataaggcgg tcgtttcgct gtctaacggc     480

gtctcggtcc taacaagtaa agttctggat ttaaagaact atattgataa gcaattgctg     540

cctatcgtaa ataagcagag ttgcagcatt agcaatatcg agacagtgat agaatttcag     600

caaaagaaca atcgattact cgaaatcaca cgcgaattca gtgtcaatgc cggggttaca     660

acccctgtgt cgacctacat gcttaccaat tccgagcttc tgtctcttat taacgatatg     720

cccatcacga acgatcagaa gaaactgatg tcaaataacg tccaaattgt gcggcagcaa     780

agctacagta tcatgagcat catcaaagag gaggtgctcg cctatgtggt ccaattgccg     840

ctatacgggg tcattgatac accctgttgg aagctccata catccccact ttgtacaacg     900

aataccaagg aggggtctaa catttgtctg acccggaccg acagaggctg gtattgcgat     960
```

aatgctggaa gcgttagttt ctttcctcag gcagaaacat gcaaggtgca gtcaaacaga 1020
gttttctgtg acaccatgaa ttccttgacg ctgccttcag aagtgaatct gtgtaacgtg 1080
gatatcttta atccgaagta cgattgtaaa attatgacta gcaagacaga tgtctcgtcc 1140
tctgtgatca ctagcctggg agcgattgtg agctgttatg gtaaaacaaa gtgtactgct 1200
agcaataaga acagggggat tatcaaaacg ttcagtaacg gctgtgatta cgtatccaac 1260
aagggggtgg acaccgtgtc agtcgggaac acgctctact acgtgaacaa gcaggaaggt 1320
aagtcgctat acgtgaaggg ggaacccata atcaatttct acgatccgct cgtgtttcct 1380
agcgacgaat tcgacgcatc tatcagccag gtgaacgaga agatcaatca gagtctggcc 1440
ttcatccgca agtccgacga gctgcttagt gctatcggag gttatatccc tgaggccccg 1500
agggacggcc aagcgtatgt gagaaaggac ggggaatggg tactgttgtc aactttccta 1560

<210> SEQ ID NO 26
<211> LENGTH: 520
<212> TYPE: PRT
<213> ORGANISM: Artificial Sequence
<220> FEATURE:
<223> OTHER INFORMATION: Synthetic Polypeptide

<400> SEQUENCE: 26

Met Glu Thr Pro Ala Gln Leu Leu Phe Leu Leu Leu Leu Trp Leu Pro
1 5 10 15

Asp Thr Thr Gly Phe Ala Ser Gly Gln Asn Ile Thr Glu Glu Phe Tyr
20 25 30

Gln Ser Thr Cys Ser Ala Val Ser Lys Gly Tyr Leu Ser Ala Leu Arg
35 40 45

Thr Gly Trp Tyr Thr Ser Val Ile Thr Ile Glu Leu Ser Asn Ile Lys
50 55 60

Lys Asn Lys Cys Asn Gly Thr Asp Ala Lys Val Lys Leu Ile Lys Gln
65 70 75 80

Glu Leu Asp Lys Tyr Lys Asn Ala Val Thr Glu Leu Gln Leu Leu Met
85 90 95

Gln Ser Thr Gln Ala Thr Asn Asn Arg Ala Arg Gln Gln Gln Gln Arg
100 105 110

Phe Leu Gly Phe Leu Leu Gly Val Gly Ser Ala Ile Ala Ser Gly Val
115 120 125

Ala Val Ser Lys Val Leu His Leu Glu Gly Glu Val Asn Lys Ile Lys
130 135 140

Ser Ala Leu Leu Ser Thr Asn Lys Ala Val Val Ser Leu Ser Asn Gly
145 150 155 160

Val Ser Val Leu Thr Ser Lys Val Leu Asp Leu Lys Asn Tyr Ile Asp
165 170 175

Lys Gln Leu Leu Pro Ile Val Asn Lys Gln Ser Cys Ser Ile Ser Asn
180 185 190

Ile Glu Thr Val Ile Glu Phe Gln Gln Lys Asn Asn Arg Leu Leu Glu
195 200 205

Ile Thr Arg Glu Phe Ser Val Asn Ala Gly Val Thr Thr Pro Val Ser
210 215 220

Thr Tyr Met Leu Thr Asn Ser Glu Leu Leu Ser Leu Ile Asn Asp Met
225 230 235 240

Pro Ile Thr Asn Asp Gln Lys Lys Leu Met Ser Asn Asn Val Gln Ile
245 250 255

Val Arg Gln Gln Ser Tyr Ser Ile Met Ser Ile Ile Lys Glu Glu Val

```
            260                 265                 270

Leu Ala Tyr Val Val Gln Leu Pro Leu Tyr Gly Val Ile Asp Thr Pro
        275                 280                 285

Cys Trp Lys Leu His Thr Ser Pro Leu Cys Thr Thr Asn Thr Lys Glu
    290                 295                 300

Gly Ser Asn Ile Cys Leu Thr Arg Thr Asp Arg Gly Trp Tyr Cys Asp
305                 310                 315                 320

Asn Ala Gly Ser Val Ser Phe Phe Pro Gln Ala Glu Thr Cys Lys Val
                325                 330                 335

Gln Ser Asn Arg Val Phe Cys Asp Thr Met Asn Ser Leu Thr Leu Pro
            340                 345                 350

Ser Glu Val Asn Leu Cys Asn Val Asp Ile Phe Asn Pro Lys Tyr Asp
        355                 360                 365

Cys Lys Ile Met Thr Ser Lys Thr Asp Val Ser Ser Ser Val Ile Thr
    370                 375                 380

Ser Leu Gly Ala Ile Val Ser Cys Tyr Gly Lys Thr Lys Cys Thr Ala
385                 390                 395                 400

Ser Asn Lys Asn Arg Gly Ile Ile Lys Thr Phe Ser Asn Gly Cys Asp
                405                 410                 415

Tyr Val Ser Asn Lys Gly Val Asp Thr Val Ser Val Gly Asn Thr Leu
            420                 425                 430

Tyr Tyr Val Asn Lys Gln Glu Gly Lys Ser Leu Tyr Val Lys Gly Glu
        435                 440                 445

Pro Ile Ile Asn Phe Tyr Asp Pro Leu Val Phe Pro Ser Asp Glu Phe
    450                 455                 460

Asp Ala Ser Ile Ser Gln Val Asn Glu Lys Ile Asn Gln Ser Leu Ala
465                 470                 475                 480

Phe Ile Arg Lys Ser Asp Glu Leu Leu Ser Ala Ile Gly Gly Tyr Ile
                485                 490                 495

Pro Glu Ala Pro Arg Asp Gly Gln Ala Tyr Val Arg Lys Asp Gly Glu
            500                 505                 510

Trp Val Leu Leu Ser Thr Phe Leu
        515                 520


<210> SEQ ID NO 27
<211> LENGTH: 1536
<212> TYPE: DNA
<213> ORGANISM: Artificial Sequence
<220> FEATURE:
<223> OTHER INFORMATION: Synthetic Polynucleotide

<400> SEQUENCE: 27

atggagacac ctgcccaact tctgttcctt cttttgctct ggctgcctga cacaaccggc      60

ttcgcatctt cacaaaacat cacggaagag ttttaccaga gcacatgctc cgcggtctct     120

aaaggctatc tttctgccct gcggactggc tggtatacca gcgtcatcac catagagctg     180

tcaaacatca aggagaacaa gtgtaacggc actgacgcca aggtcaagct tataaagcag     240

gaactggaca agtataagag tgctgttacc gagctccagt tgcttatgca gtccaccccc     300

gcaacaaaca ataaatttct gggctttcta cagggcgtcg gaagcgccat cgcaagcggc     360

atcgctgtga gcaaggtgtt gcatctggag ggagaggtga ataagataaa gagtgctctg     420

ctttccacta acaaagccgt ggtgagcctg agcaatggcg tatctgttct gacttctaaa     480

gtcctggatc tcaagaacta tatcgacaag cagctcttgc ccattgtcaa caaacagtcc     540

tgctccattt ccaatattga gaccgtcatt gagttccaac agaagaataa ccgtttgctg     600
```

-continued

```
gaaattacaa gggaattcag tgttaatgcc ggtgtaacca cccctgtgag cacctatatg    660

ctcaccaact ctgaactgct gagtctgatt aacgatatgc ccattactaa tgatcagaag    720

aaactaatga gtaacaatgt ccagatagtt cggcagcagt catattccat tatgagtata    780

atcaaggagg aagtgctagc ctacgtagtt cagctccccc tctacggcgt tatagacacg    840

ccatgttgga agctgcatac gagtcctctg tgcactacaa ataccaagga gggcagtaac    900

atatgcttga ctagaactga tagaggctgg tactgcgaca atgcaggctc cgtgtcattc    960

tttcctctcg ccgagacgtg taaagtgcag agtaacagag tgttttgtga cacaatgaac   1020

tcattgaccc tgcctagcga agtgaactta tgcaacatcg acatttttaa cccaaaatac   1080

gattgcaaga ttatgacctc taagactgac gtatcttcat ccgtcataac ttctctagga   1140

gcgatcgtga gctgctacgg taagactaaa tgcacggcta gtaataaaaa tagaggtatc   1200

attaagactt ttagtaacgg ttgcgattat gtgtcaaaca agggagtcga cactgtttca   1260

gtgggcaata ctctctacta cgttaacaaa caggagggta aatcccttta tgtgaaaggg   1320

gaacccatca ttaattttta tgacccactt gtgtttccta gtgacgagtt tgacgcttca   1380

atcagtcaag tgaacgaaaa aattaatggc acgctcgcgt ttatcaggaa aagcgacgag   1440

aagctgcata acgtggaaga taagatcgag gagattctct cgaaaattta tcatatagag   1500

aatgaaatcg caagaatcaa aaagcttatt ggggag                             1536


<210> SEQ ID NO 28
<211> LENGTH: 512
<212> TYPE: PRT
<213> ORGANISM: Artificial Sequence
<220> FEATURE:
<223> OTHER INFORMATION: Synthetic Polypeptide

<400> SEQUENCE: 28

Met Glu Thr Pro Ala Gln Leu Leu Phe Leu Leu Leu Leu Trp Leu Pro
1               5                   10                  15

Asp Thr Thr Gly Phe Ala Ser Ser Gln Asn Ile Thr Glu Glu Phe Tyr
            20                  25                  30

Gln Ser Thr Cys Ser Ala Val Ser Lys Gly Tyr Leu Ser Ala Leu Arg
        35                  40                  45

Thr Gly Trp Tyr Thr Ser Val Ile Thr Ile Glu Leu Ser Asn Ile Lys
    50                  55                  60

Glu Asn Lys Cys Asn Gly Thr Asp Ala Lys Val Lys Leu Ile Lys Gln
65                  70                  75                  80

Glu Leu Asp Lys Tyr Lys Ser Ala Val Thr Glu Leu Gln Leu Leu Met
                85                  90                  95

Gln Ser Thr Pro Ala Thr Asn Asn Lys Phe Leu Gly Phe Leu Gln Gly
            100                 105                 110

Val Gly Ser Ala Ile Ala Ser Gly Ile Ala Val Ser Lys Val Leu His
        115                 120                 125

Leu Glu Gly Glu Val Asn Lys Ile Lys Ser Ala Leu Leu Ser Thr Asn
    130                 135                 140

Lys Ala Val Val Ser Leu Ser Asn Gly Val Ser Val Leu Thr Ser Lys
145                 150                 155                 160

Val Leu Asp Leu Lys Asn Tyr Ile Asp Lys Gln Leu Leu Pro Ile Val
                165                 170                 175

Asn Lys Gln Ser Cys Ser Ile Ser Asn Ile Glu Thr Val Ile Glu Phe
            180                 185                 190
```

```
Gln Gln Lys Asn Asn Arg Leu Leu Glu Ile Thr Arg Glu Phe Ser Val
        195                 200                 205

Asn Ala Gly Val Thr Thr Pro Val Ser Thr Tyr Met Leu Thr Asn Ser
    210                 215                 220

Glu Leu Leu Ser Leu Ile Asn Asp Met Pro Ile Thr Asn Asp Gln Lys
225                 230                 235                 240

Lys Leu Met Ser Asn Asn Val Gln Ile Val Arg Gln Gln Ser Tyr Ser
                245                 250                 255

Ile Met Ser Ile Ile Lys Glu Glu Val Leu Ala Tyr Val Val Gln Leu
            260                 265                 270

Pro Leu Tyr Gly Val Ile Asp Thr Pro Cys Trp Lys Leu His Thr Ser
        275                 280                 285

Pro Leu Cys Thr Thr Asn Thr Lys Glu Gly Ser Asn Ile Cys Leu Thr
    290                 295                 300

Arg Thr Asp Arg Gly Trp Tyr Cys Asp Asn Ala Gly Ser Val Ser Phe
305                 310                 315                 320

Phe Pro Leu Ala Glu Thr Cys Lys Val Gln Ser Asn Arg Val Phe Cys
                325                 330                 335

Asp Thr Met Asn Ser Leu Thr Leu Pro Ser Glu Val Asn Leu Cys Asn
            340                 345                 350

Ile Asp Ile Phe Asn Pro Lys Tyr Asp Cys Lys Ile Met Thr Ser Lys
        355                 360                 365

Thr Asp Val Ser Ser Ser Val Ile Thr Ser Leu Gly Ala Ile Val Ser
    370                 375                 380

Cys Tyr Gly Lys Thr Lys Cys Thr Ala Ser Asn Lys Asn Arg Gly Ile
385                 390                 395                 400

Ile Lys Thr Phe Ser Asn Gly Cys Asp Tyr Val Ser Asn Lys Gly Val
                405                 410                 415

Asp Thr Val Ser Val Gly Asn Thr Leu Tyr Tyr Val Asn Lys Gln Glu
            420                 425                 430

Gly Lys Ser Leu Tyr Val Lys Gly Glu Pro Ile Ile Asn Phe Tyr Asp
        435                 440                 445

Pro Leu Val Phe Pro Ser Asp Glu Phe Asp Ala Ser Ile Ser Gln Val
    450                 455                 460

Asn Glu Lys Ile Asn Gly Thr Leu Ala Phe Ile Arg Lys Ser Asp Glu
465                 470                 475                 480

Lys Leu His Asn Val Glu Asp Lys Ile Glu Glu Ile Leu Ser Lys Ile
                485                 490                 495

Tyr His Ile Glu Asn Glu Ile Ala Arg Ile Lys Lys Leu Ile Gly Glu
            500                 505                 510


<210> SEQ ID NO 29
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 29

Met Glu Leu Pro Ile Leu Lys Ala Asn Ala Ile Thr Thr Ile Leu
1               5                   10                  15


<210> SEQ ID NO 30
<211> LENGTH: 15
<212> TYPE: PRT
<213> ORGANISM: Artificial Sequence
<220> FEATURE:
```

<223> OTHER INFORMATION: Synthetic Polypeptide

<400> SEQUENCE: 30

Ile Leu Lys Ala Asn Ala Ile Thr Thr Ile Leu Thr Ala Val Thr
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31

Asn Ala Ile Thr Thr Ile Leu Thr Ala Val Thr Phe Cys Phe Ala
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 32

Thr Ile Leu Thr Ala Val Thr Phe Cys Phe Ala Ser Ser Gln Asn
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 33

Ala Val Thr Phe Cys Phe Ala Ser Ser Gln Asn Ile Thr Glu Glu
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 34

Cys Phe Ala Ser Ser Gln Asn Ile Thr Glu Glu Phe Tyr Gln Ser
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 35

Ser Gln Asn Ile Thr Glu Glu Phe Tyr Gln Ser Thr Cys Ser Ala
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 36

Thr Glu Glu Phe Tyr Gln Ser Thr Cys Ser Ala Val Ser Lys Gly
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 37

Tyr Gln Ser Thr Cys Ser Ala Val Ser Lys Gly Tyr Leu Ser Ala
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 38

Cys Ser Ala Val Ser Lys Gly Tyr Leu Ser Ala Leu Arg Thr Gly
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 39

Ser Lys Gly Tyr Leu Ser Ala Leu Arg Thr Gly Trp Tyr Thr Ser
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 40

Leu Ser Ala Leu Arg Thr Gly Trp Tyr Thr Ser Val Ile Thr Ile
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 41

Arg Thr Gly Trp Tyr Thr Ser Val Ile Thr Ile Glu Leu Ser Asn
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 42

Tyr Thr Ser Val Ile Thr Ile Glu Leu Ser Asn Ile Lys Glu Asn
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 43

Ile Thr Ile Glu Leu Ser Asn Ile Lys Glu Asn Lys Cys Asn Gly
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 44

Leu Ser Asn Ile Lys Glu Asn Lys Cys Asn Gly Thr Asp Ala Lys
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 45

Lys Glu Asn Lys Cys Asn Gly Thr Asp Ala Lys Val Lys Leu Ile
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 46

Cys Asn Gly Thr Asp Ala Lys Val Lys Leu Ile Lys Gln Glu Leu
1 5 10 15

<210> SEQ ID NO 47
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 47

Asp Ala Lys Val Lys Leu Ile Lys Gln Glu Leu Asp Lys Tyr Lys
1 5 10 15

<210> SEQ ID NO 48
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 48

```
Lys Leu Ile Lys Gln Glu Leu Asp Lys Tyr Lys Asn Ala Val Thr
1               5                   10                  15


<210> SEQ ID NO 49
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 49

Gln Glu Leu Asp Lys Tyr Lys Asn Ala Val Thr Glu Leu Gln Leu
1               5                   10                  15


<210> SEQ ID NO 50
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 50

Lys Tyr Lys Asn Ala Val Thr Glu Leu Gln Leu Leu Met Gln Ser
1               5                   10                  15


<210> SEQ ID NO 51
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 51

Ala Val Thr Glu Leu Gln Leu Leu Met Gln Ser Thr Pro Ala Ala
1               5                   10                  15


<210> SEQ ID NO 52
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 52

Leu Gln Leu Leu Met Gln Ser Thr Pro Ala Ala Asn Asn Arg Ala
1               5                   10                  15


<210> SEQ ID NO 53
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 53

Met Gln Ser Thr Pro Ala Ala Asn Asn Arg Ala Arg Arg Glu Leu
1               5                   10                  15


<210> SEQ ID NO 54
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 54
```

Pro Ala Ala Asn Asn Arg Ala Arg Arg Glu Leu Pro Arg Phe Met
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 55

Asn Arg Ala Arg Arg Glu Leu Pro Arg Phe Met Asn Tyr Thr Leu
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 56

Arg Glu Leu Pro Arg Phe Met Asn Tyr Thr Leu Asn Asn Ala Lys
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 57

Arg Phe Met Asn Tyr Thr Leu Asn Asn Ala Lys Lys Thr Asn Val
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 58

Tyr Thr Leu Asn Asn Ala Lys Lys Thr Asn Val Thr Leu Ser Lys
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 59

Asn Ala Lys Lys Thr Asn Val Thr Leu Ser Lys Lys Arg Lys Arg
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 60

Thr Asn Val Thr Leu Ser Lys Lys Arg Lys Arg Arg Phe Leu Gly 1 5 10 15

<210> SEQ ID NO 61
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 61

Leu Ser Lys Lys Arg Lys Arg Arg Phe Leu Gly Phe Leu Leu Gly
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 62

Arg Lys Arg Arg Phe Leu Gly Phe Leu Leu Gly Val Gly Ser Ala
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 63

Phe Leu Gly Phe Leu Leu Gly Val Gly Ser Ala Ile Ala Ser Gly
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 64

Leu Leu Gly Val Gly Ser Ala Ile Ala Ser Gly Ile Ala Val Ser
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 65

Gly Ser Ala Ile Ala Ser Gly Ile Ala Val Ser Lys Val Leu His
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 66

Ala Ser Gly Ile Ala Val Ser Lys Val Leu His Leu Glu Gly Glu
1 5 10 15

<210> SEQ ID NO 67
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 67

Ala Val Ser Lys Val Leu His Leu Glu Gly Glu Val Asn Lys Ile
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 68

Val Leu His Leu Glu Gly Glu Val Asn Lys Ile Lys Ser Ala Leu
1 5 10 15

<210> SEQ ID NO 69
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 69

Glu Gly Glu Val Asn Lys Ile Lys Ser Ala Leu Leu Ser Thr Asn
1 5 10 15

<210> SEQ ID NO 70
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 70

Asn Lys Ile Lys Ser Ala Leu Leu Ser Thr Asn Lys Ala Val Val
1 5 10 15

<210> SEQ ID NO 71
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 71

Ser Ala Leu Leu Ser Thr Asn Lys Ala Val Val Ser Leu Ser Asn
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 72

Ser Thr Asn Lys Ala Val Val Ser Leu Ser Asn Gly Val Ser Val
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 73

Ala Val Val Ser Leu Ser Asn Gly Val Ser Val Leu Thr Ser Lys
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 74

Leu Ser Asn Gly Val Ser Val Leu Thr Ser Lys Val Leu Asp Leu
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 75

Val Ser Val Leu Thr Ser Lys Val Leu Asp Leu Lys Asn Tyr Ile
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

Thr Ser Lys Val Leu Asp Leu Lys Asn Tyr Ile Asp Lys Gln Leu
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 77

Leu Asp Leu Lys Asn Tyr Ile Asp Lys Gln Leu Leu Pro Ile Val
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 78

Asn Tyr Ile Asp Lys Gln Leu Leu Pro Ile Val Asn Lys Gln Ser
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 79

Lys Gln Leu Leu Pro Ile Val Asn Lys Gln Ser Cys Ser Ile Ser
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 80

Pro Ile Val Asn Lys Gln Ser Cys Ser Ile Ser Asn Ile Glu Thr
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 81

Lys Gln Ser Cys Ser Ile Ser Asn Ile Glu Thr Val Ile Glu Phe
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

Ser Ile Ser Asn Ile Glu Thr Val Ile Glu Phe Gln Gln Lys Asn
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 83

Ile Glu Thr Val Ile Glu Phe Gln Gln Lys Asn Asn Arg Leu Leu
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 84

Ile Glu Phe Gln Gln Lys Asn Asn Arg Leu Leu Glu Ile Thr Arg
1 5 10 15

<210> SEQ ID NO 85

<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

Gln Lys Asn Asn Arg Leu Leu Glu Ile Thr Arg Glu Phe Ser Val
1 5 10 15

<210> SEQ ID NO 86
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 86

Arg Leu Leu Glu Ile Thr Arg Glu Phe Ser Val Asn Ala Gly Val
1 5 10 15

<210> SEQ ID NO 87
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 87

Ile Thr Arg Glu Phe Ser Val Asn Ala Gly Val Thr Thr Pro Val
1 5 10 15

<210> SEQ ID NO 88
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 88

Phe Ser Val Asn Ala Gly Val Thr Thr Pro Val Ser Thr Tyr Met
1 5 10 15

<210> SEQ ID NO 89
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 89

Ala Gly Val Thr Thr Pro Val Ser Thr Tyr Met Leu Thr Asn Ser
1 5 10 15

<210> SEQ ID NO 90
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 90

Thr Pro Val Ser Thr Tyr Met Leu Thr Asn Ser Glu Leu Leu Ser
1 5 10 15

<210> SEQ ID NO 91
<211> LENGTH: 15

<212> TYPE: PRT
<213> ORGANISM: Artificial Sequence
<220> FEATURE:
<223> OTHER INFORMATION: Synthetic Polypeptide

<400> SEQUENCE: 91

Thr Tyr Met Leu Thr Asn Ser Glu Leu Leu Ser Leu Ile Asn Asp
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 92

Thr Asn Ser Glu Leu Leu Ser Leu Ile Asn Asp Met Pro Ile Thr
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 93

Leu Leu Ser Leu Ile Asn Asp Met Pro Ile Thr Asn Asp Gln Lys
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 94

Ile Asn Asp Met Pro Ile Thr Asn Asp Gln Lys Lys Leu Met Ser
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 95

Pro Ile Thr Asn Asp Gln Lys Lys Leu Met Ser Asn Asn Val Gln
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 96

Asp Gln Lys Lys Leu Met Ser Asn Asn Val Gln Ile Val Arg Gln
1 5 10 15

<210> SEQ ID NO 97
<211> LENGTH: 15
<212> TYPE: PRT

<213> ORGANISM: Artificial Sequence
<220> FEATURE:
<223> OTHER INFORMATION: Synthetic Polypeptide

<400> SEQUENCE: 97

Leu Met Ser Asn Asn Val Gln Ile Val Arg Gln Gln Ser Tyr Ser
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 98

Asn Val Gln Ile Val Arg Gln Gln Ser Tyr Ser Ile Met Ser Ile
1 5 10 15

<210> SEQ ID NO 99
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 99

Val Arg Gln Gln Ser Tyr Ser Ile Met Ser Ile Ile Lys Lys Glu
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 100

Ser Tyr Ser Ile Met Ser Ile Ile Lys Lys Glu Val Leu Ala Tyr
1 5 10 15

<210> SEQ ID NO 101
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 101

Met Ser Ile Ile Lys Lys Glu Val Leu Ala Tyr Val Val Gln Leu
1 5 10 15

<210> SEQ ID NO 102
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 102

Lys Lys Glu Val Leu Ala Tyr Val Val Gln Leu Pro Leu Tyr Gly
1 5 10 15

<210> SEQ ID NO 103
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 103

Leu Ala Tyr Val Val Gln Leu Pro Leu Tyr Gly Val Ile Asp Thr
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 104

Val Gln Leu Pro Leu Tyr Gly Val Ile Asp Thr Pro Cys Trp Lys
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 105

Leu Tyr Gly Val Ile Asp Thr Pro Cys Trp Lys Leu His Thr Ser
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 106

Ile Asp Thr Pro Cys Trp Lys Leu His Thr Ser Pro Leu Cys Thr
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 107

Cys Trp Lys Leu His Thr Ser Pro Leu Cys Thr Thr Asn Thr Lys
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 108

His Thr Ser Pro Leu Cys Thr Thr Asn Thr Lys Glu Gly Ser Asn
1 5 10 15

<210> SEQ ID NO 109
<211> LENGTH: 15
<212> TYPE: PRT
<213> ORGANISM: Artificial Sequence
<220> FEATURE:

<223> OTHER INFORMATION: Synthetic Polypeptide

<400> SEQUENCE: 109

Leu Cys Thr Thr Asn Thr Lys Glu Gly Ser Asn Ile Cys Leu Thr
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 110

Asn Thr Lys Glu Gly Ser Asn Ile Cys Leu Thr Arg Thr Asp Arg
1 5 10 15

<210> SEQ ID NO 111
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 111

Gly Ser Asn Ile Cys Leu Thr Arg Thr Asp Arg Gly Trp Tyr Cys
1 5 10 15

<210> SEQ ID NO 112
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 112

Cys Leu Thr Arg Thr Asp Arg Gly Trp Tyr Cys Asp Asn Ala Gly
1 5 10 15

<210> SEQ ID NO 113
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 113

Thr Asp Arg Gly Trp Tyr Cys Asp Asn Ala Gly Ser Val Ser Phe
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 114

Trp Tyr Cys Asp Asn Ala Gly Ser Val Ser Phe Phe Pro Gln Ala
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 115

Asn Ala Gly Ser Val Ser Phe Phe Pro Gln Ala Glu Thr Cys Lys
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 116

Val Ser Phe Phe Pro Gln Ala Glu Thr Cys Lys Val Gln Ser Asn
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 117

Pro Gln Ala Glu Thr Cys Lys Val Gln Ser Asn Arg Val Phe Cys
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 118

Thr Cys Lys Val Gln Ser Asn Arg Val Phe Cys Asp Thr Met Asn
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 119

Gln Ser Asn Arg Val Phe Cys Asp Thr Met Asn Ser Leu Thr Leu
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 120

Val Phe Cys Asp Thr Met Asn Ser Leu Thr Leu Pro Ser Glu Val
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 121

Thr Met Asn Ser Leu Thr Leu Pro Ser Glu Val Asn Leu Cys Asn
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 122

Leu Thr Leu Pro Ser Glu Val Asn Leu Cys Asn Val Asp Ile Phe
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 123

Ser Glu Val Asn Leu Cys Asn Val Asp Ile Phe Asn Pro Lys Tyr
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 124

Leu Cys Asn Val Asp Ile Phe Asn Pro Lys Tyr Asp Cys Lys Ile
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 125

Asp Ile Phe Asn Pro Lys Tyr Asp Cys Lys Ile Met Thr Ser Lys
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 126

Pro Lys Tyr Asp Cys Lys Ile Met Thr Ser Lys Thr Asp Val Ser
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 127

Cys Lys Ile Met Thr Ser Lys Thr Asp Val Ser Ser Ser Val Ile
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 128

Thr Ser Lys Thr Asp Val Ser Ser Ser Val Ile Thr Ser Leu Gly
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 129

Asp Val Ser Ser Ser Val Ile Thr Ser Leu Gly Ala Ile Val Ser
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 130

Ser Val Ile Thr Ser Leu Gly Ala Ile Val Ser Cys Tyr Gly Lys
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 131

Ser Leu Gly Ala Ile Val Ser Cys Tyr Gly Lys Thr Lys Cys Thr
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 132

Ile Val Ser Cys Tyr Gly Lys Thr Lys Cys Thr Ala Ser Asn Lys
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 133

Tyr Gly Lys Thr Lys Cys Thr Ala Ser Asn Lys Asn Arg Gly Ile
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 134

Lys Cys Thr Ala Ser Asn Lys Asn Arg Gly Ile Ile Lys Thr Phe
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 135

Ser Asn Lys Asn Arg Gly Ile Ile Lys Thr Phe Ser Asn Gly Cys
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 136

Arg Gly Ile Ile Lys Thr Phe Ser Asn Gly Cys Asp Tyr Val Ser
1 5 10 15

<210> SEQ ID NO 137
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 137

Lys Thr Phe Ser Asn Gly Cys Asp Tyr Val Ser Asn Lys Gly Val
1 5 10 15

<210> SEQ ID NO 138
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 138

Asn Gly Cys Asp Tyr Val Ser Asn Lys Gly Val Asp Thr Val Ser
1 5 10 15

<210> SEQ ID NO 139
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 139

Tyr Val Ser Asn Lys Gly Val Asp Thr Val Ser Val Gly Asn Thr 1 5 10 15

<210> SEQ ID NO 140
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 140

Lys Gly Val Asp Thr Val Ser Val Gly Asn Thr Leu Tyr Tyr Val
1 5 10 15

<210> SEQ ID NO 141
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 141

Thr Val Ser Val Gly Asn Thr Leu Tyr Tyr Val Asn Lys Gln Glu
1 5 10 15

<210> SEQ ID NO 142
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 142

Gly Asn Thr Leu Tyr Tyr Val Asn Lys Gln Glu Gly Lys Ser Leu
1 5 10 15

<210> SEQ ID NO 143
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 143

Tyr Tyr Val Asn Lys Gln Glu Gly Lys Ser Leu Tyr Val Lys Gly
1 5 10 15

<210> SEQ ID NO 144
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 144

Lys Gln Glu Gly Lys Ser Leu Tyr Val Lys Gly Glu Pro Ile Ile
1 5 10 15

<210> SEQ ID NO 145
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 145

Lys Ser Leu Tyr Val Lys Gly Glu Pro Ile Ile Asn Phe Tyr Asp
1 5 10 15

```
<210> SEQ ID NO 146
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 146

Val Lys Gly Glu Pro Ile Ile Asn Phe Tyr Asp Pro Leu Val Phe
1               5                   10                  15


<210> SEQ ID NO 147
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 147

Pro Ile Ile Asn Phe Tyr Asp Pro Leu Val Phe Pro Ser Gly Glu
1               5                   10                  15


<210> SEQ ID NO 148
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 148

Phe Tyr Asp Pro Leu Val Phe Pro Ser Gly Glu Phe Asp Ala Ser
1               5                   10                  15


<210> SEQ ID NO 149
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 149

Leu Val Phe Pro Ser Gly Glu Phe Asp Ala Ser Ile Ser Gln Val
1               5                   10                  15


<210> SEQ ID NO 150
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 150

Ser Gly Glu Phe Asp Ala Ser Ile Ser Gln Val Asn Glu Lys Ile
1               5                   10                  15


<210> SEQ ID NO 151
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 151

Asp Ala Ser Ile Ser Gln Val Asn Glu Lys Ile Asn Gln Ser Leu
1               5                   10                  15
```

<210> SEQ ID NO 152
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 152

Ser Gln Val Asn Glu Lys Ile Asn Gln Ser Leu Ala Phe Ile Arg
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 153

Glu Lys Ile Asn Gln Ser Leu Ala Phe Ile Arg Lys Ser Asp Glu
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 154

Gln Ser Leu Ala Phe Ile Arg Lys Ser Asp Glu Leu Leu His Asn
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 155

Phe Ile Arg Lys Ser Asp Glu Leu Leu His Asn Val Asn Ala Gly
1 5 10 15

<210> SEQ ID NO 156
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 156

Ser Asp Glu Leu Leu His Asn Val Asn Ala Gly Lys Ser Thr Thr
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 157

Leu His Asn Val Asn Ala Gly Lys Ser Thr Thr Asn Ile Met Ile
1 5 10 15

<210> SEQ ID NO 158
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 158

Asn Ala Gly Lys Ser Thr Thr Asn Ile Met Ile Thr Ala Ile Ile
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 159

Ser Thr Thr Asn Ile Met Ile Thr Ala Ile Ile Ile Val Ile Val
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 160

Ile Met Ile Thr Ala Ile Ile Ile Val Ile Val Val Ile Leu Leu
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 161

Ala Ile Ile Ile Val Ile Val Val Ile Leu Leu Ser Leu Ile Ala
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 162

Val Ile Val Val Ile Leu Leu Ser Leu Ile Ala Val Gly Leu Leu
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 163

Ile Leu Leu Ser Leu Ile Ala Val Gly Leu Leu Leu Tyr Cys Lys
1 5 10 15

<210> SEQ ID NO 164

<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 164

Leu Ile Ala Val Gly Leu Leu Leu Tyr Cys Lys Ala Arg Ser Thr
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 165

Gly Leu Leu Leu Tyr Cys Lys Ala Arg Ser Thr Pro Val Thr Leu
1 5 10 15

<210> SEQ ID NO 166
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 166

Tyr Cys Lys Ala Arg Ser Thr Pro Val Thr Leu Ser Lys Asp Gln
1 5 10 15

<210> SEQ ID NO 167
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 167

Arg Ser Thr Pro Val Thr Leu Ser Lys Asp Gln Leu Ser Gly Ile
1 5 10 15

<210> SEQ ID NO 168
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 168

Val Thr Leu Ser Lys Asp Gln Leu Ser Gly Ile Asn Asn Ile Ala
1 5 10 15

<210> SEQ ID NO 169
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 169

Lys Asp Gln Leu Ser Gly Ile Asn Asn Ile Ala Phe Ser Asn
1 5 10

<210> SEQ ID NO 170
<211> LENGTH: 15

<212> TYPE: PRT
<213> ORGANISM: Artificial Sequence
<220> FEATURE:
<223> OTHER INFORMATION: Synthetic Polypeptide

<400> SEQUENCE: 170

Met Ser Lys Asn Lys Asp Gln Arg Thr Ala Lys Thr Leu Glu Arg
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 171

Lys Asp Gln Arg Thr Ala Lys Thr Leu Glu Arg Thr Trp Asp Thr
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 172

Thr Ala Lys Thr Leu Glu Arg Thr Trp Asp Thr Leu Asn His Leu
1 5 10 15

<210> SEQ ID NO 173
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 173

Leu Glu Arg Thr Trp Asp Thr Leu Asn His Leu Leu Phe Ile Ser
1 5 10 15

<210> SEQ ID NO 174
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 174

Trp Asp Thr Leu Asn His Leu Leu Phe Ile Ser Ser Cys Leu Tyr
1 5 10 15

<210> SEQ ID NO 175
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 175

Asn His Leu Leu Phe Ile Ser Ser Cys Leu Tyr Lys Leu Asn Leu
1 5 10 15

<210> SEQ ID NO 176
<211> LENGTH: 15
<212> TYPE: PRT

<213> ORGANISM: Artificial Sequence
<220> FEATURE:
<223> OTHER INFORMATION: Synthetic Polypeptide

<400> SEQUENCE: 176

Phe Ile Ser Ser Cys Leu Tyr Lys Leu Asn Leu Lys Ser Val Ala
1 5 10 15

<210> SEQ ID NO 177
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 177

Cys Leu Tyr Lys Leu Asn Leu Lys Ser Val Ala Gln Ile Thr Leu
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 178

Leu Asn Leu Lys Ser Val Ala Gln Ile Thr Leu Ser Ile Leu Ala
1 5 10 15

<210> SEQ ID NO 179
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 179

Ser Val Ala Gln Ile Thr Leu Ser Ile Leu Ala Met Ile Ile Ser
1 5 10 15

<210> SEQ ID NO 180
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 180

Ile Thr Leu Ser Ile Leu Ala Met Ile Ile Ser Thr Ser Leu Ile
1 5 10 15

<210> SEQ ID NO 181
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 181

Ile Leu Ala Met Ile Ile Ser Thr Ser Leu Ile Ile Ala Ala Ile
1 5 10 15

<210> SEQ ID NO 182
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 182

Ile Ile Ser Thr Ser Leu Ile Ile Ala Ala Ile Ile Phe Ile Ala
1 5 10 15

<210> SEQ ID NO 183
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 183

Ser Leu Ile Ile Ala Ala Ile Ile Phe Ile Ala Ser Ala Asn His
1 5 10 15

<210> SEQ ID NO 184
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 184

Ala Ala Ile Ile Phe Ile Ala Ser Ala Asn His Lys Val Thr Ser
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 185

Phe Ile Ala Ser Ala Asn His Lys Val Thr Ser Thr Thr Thr Ile
1 5 10 15

<210> SEQ ID NO 186
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 186

Ala Asn His Lys Val Thr Ser Thr Thr Thr Ile Ile Gln Asp Ala
1 5 10 15

<210> SEQ ID NO 187
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 187

Val Thr Ser Thr Thr Thr Ile Ile Gln Asp Ala Thr Ser Gln Ile
1 5 10 15

<210> SEQ ID NO 188
<211> LENGTH: 15
<212> TYPE: PRT
<213> ORGANISM: Artificial Sequence
<220> FEATURE:

-continued

<223> OTHER INFORMATION: Synthetic Polypeptide

<400> SEQUENCE: 188

Thr Thr Ile Ile Gln Asp Ala Thr Ser Gln Ile Lys Asn Thr Thr
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 189

Gln Asp Ala Thr Ser Gln Ile Lys Asn Thr Thr Pro Thr Tyr Leu
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 190

Ser Gln Ile Lys Asn Thr Thr Pro Thr Tyr Leu Thr Gln Ser Pro
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 191

Asn Thr Thr Pro Thr Tyr Leu Thr Gln Ser Pro Gln Leu Gly Ile
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 192

Thr Tyr Leu Thr Gln Ser Pro Gln Leu Gly Ile Ser Pro Ser Asn
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 193

Gln Ser Pro Gln Leu Gly Ile Ser Pro Ser Asn Pro Ser Glu Ile
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 194

Leu Gly Ile Ser Pro Ser Asn Pro Ser Glu Ile Thr Ser Gln Ile
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 195

Pro Ser Asn Pro Ser Glu Ile Thr Ser Gln Ile Thr Thr Ile Leu
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 196

Ser Glu Ile Thr Ser Gln Ile Thr Thr Ile Leu Ala Ser Thr Thr
1 5 10 15

<210> SEQ ID NO 197
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 197

Ser Gln Ile Thr Thr Ile Leu Ala Ser Thr Thr Pro Gly Val Lys
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 198

Thr Ile Leu Ala Ser Thr Thr Pro Gly Val Lys Ser Thr Leu Gln
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 199

Ser Thr Thr Pro Gly Val Lys Ser Thr Leu Gln Ser Thr Thr Val
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 200

Gly Val Lys Ser Thr Leu Gln Ser Thr Thr Val Gly Thr Lys Asn
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 201

Thr Leu Gln Ser Thr Thr Val Gly Thr Lys Asn Thr Thr Thr Thr
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 202

Thr Thr Val Gly Thr Lys Asn Thr Thr Thr Thr Gln Ala Gln Pro
1 5 10 15

<210> SEQ ID NO 203
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 203

Thr Lys Asn Thr Thr Thr Thr Gln Ala Gln Pro Ser Lys Pro Thr
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 204

Thr Thr Thr Gln Ala Gln Pro Ser Lys Pro Thr Thr Lys Gln Arg
1 5 10 15

<210> SEQ ID NO 205
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 205

Ala Gln Pro Ser Lys Pro Thr Thr Lys Gln Arg Gln Asn Lys Pro
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 206

```
Lys Pro Thr Thr Lys Gln Arg Gln Asn Lys Pro Pro Ser Lys Pro
1               5                   10                  15


<210> SEQ ID NO 207
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 207

Lys Gln Arg Gln Asn Lys Pro Pro Ser Lys Pro Asn Asn Asp Phe
1               5                   10                  15


<210> SEQ ID NO 208
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 208

Asn Lys Pro Pro Ser Lys Pro Asn Asn Asp Phe His Phe Glu Val
1               5                   10                  15


<210> SEQ ID NO 209
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 209

Ser Lys Pro Asn Asn Asp Phe His Phe Glu Val Phe Asn Phe Val
1               5                   10                  15


<210> SEQ ID NO 210
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 210

Asn Asp Phe His Phe Glu Val Phe Asn Phe Val Pro Cys Ser Ile
1               5                   10                  15


<210> SEQ ID NO 211
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 211

Phe Glu Val Phe Asn Phe Val Pro Cys Ser Ile Cys Ser Asn Asn
1               5                   10                  15


<210> SEQ ID NO 212
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 212
```

Asn Phe Val Pro Cys Ser Ile Cys Ser Asn Asn Pro Thr Cys Trp
1 5 10 15

<210> SEQ ID NO 213
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 213

Cys Ser Ile Cys Ser Asn Asn Pro Thr Cys Trp Ala Ile Cys Lys
1 5 10 15

<210> SEQ ID NO 214
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 214

Ser Asn Asn Pro Thr Cys Trp Ala Ile Cys Lys Arg Ile Pro Asn
1 5 10 15

<210> SEQ ID NO 215
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 215

Thr Cys Trp Ala Ile Cys Lys Arg Ile Pro Asn Lys Lys Pro Gly
1 5 10 15

<210> SEQ ID NO 216
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 216

Ile Cys Lys Arg Ile Pro Asn Lys Lys Pro Gly Lys Lys Thr Thr
1 5 10 15

<210> SEQ ID NO 217
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 217

Ile Pro Asn Lys Lys Pro Gly Lys Lys Thr Thr Thr Lys Pro Thr
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 218

Lys Pro Gly Lys Lys Thr Thr Thr Lys Pro Thr Glu Glu Pro Thr 1 5 10 15

<210> SEQ ID NO 219
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 219

Lys Thr Thr Thr Lys Pro Thr Glu Glu Pro Thr Phe Lys Thr Ala
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 220

Lys Pro Thr Glu Glu Pro Thr Phe Lys Thr Ala Lys Glu Asp Pro
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 221

Glu Pro Thr Phe Lys Thr Ala Lys Glu Asp Pro Lys Pro Gln Thr
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 222

Lys Thr Ala Lys Glu Asp Pro Lys Pro Gln Thr Thr Gly Ser Gly
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 223

Glu Asp Pro Lys Pro Gln Thr Thr Gly Ser Gly Glu Val Pro Thr
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 224

Pro Gln Thr Thr Gly Ser Gly Glu Val Pro Thr Thr Lys Pro Thr
1 5 10 15

<210> SEQ ID NO 225
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 225

Gly Ser Gly Glu Val Pro Thr Thr Lys Pro Thr Gly Glu Pro Thr
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 226

Val Pro Thr Thr Lys Pro Thr Gly Glu Pro Thr Ile Asn Thr Thr
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 227

Lys Pro Thr Gly Glu Pro Thr Ile Asn Thr Thr Lys Thr Asn Ile
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 228

Glu Pro Thr Ile Asn Thr Thr Lys Thr Asn Ile Thr Thr Thr Leu
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 229

Asn Thr Thr Lys Thr Asn Ile Thr Thr Thr Leu Leu Thr Ser Asn
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 230

Thr Asn Ile Thr Thr Thr Leu Leu Thr Ser Asn Thr Thr Arg Asn
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 231

Thr Thr Leu Leu Thr Ser Asn Thr Thr Arg Asn Pro Glu Leu Thr
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 232

Thr Ser Asn Thr Thr Arg Asn Pro Glu Leu Thr Ser Gln Met Glu
1 5 10 15

<210> SEQ ID NO 233
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 233

Thr Arg Asn Pro Glu Leu Thr Ser Gln Met Glu Thr Phe His Ser
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 234

Glu Leu Thr Ser Gln Met Glu Thr Phe His Ser Thr Ser Ser Glu
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 235

Gln Met Glu Thr Phe His Ser Thr Ser Ser Glu Gly Asn Pro Ser
1 5 10 15

<210> SEQ ID NO 236
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 236

Phe His Ser Thr Ser Ser Glu Gly Asn Pro Ser Pro Ser Gln Val
1 5 10 15

<210> SEQ ID NO 237
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 237

Ser Ser Glu Gly Asn Pro Ser Pro Ser Gln Val Ser Ile Thr Ser
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 238

Asn Pro Ser Pro Ser Gln Val Ser Ile Thr Ser Glu Tyr Leu Ser
1 5 10 15

<210> SEQ ID NO 239
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 239

Ser Gln Val Ser Ile Thr Ser Glu Tyr Leu Ser Gln Pro Ser Ser
1 5 10 15

<210> SEQ ID NO 240
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 240

Ile Thr Ser Glu Tyr Leu Ser Gln Pro Ser Ser Pro Pro Asn Thr
1 5 10 15

<210> SEQ ID NO 241
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 241

Tyr Leu Ser Gln Pro Ser Ser Pro Pro Asn Thr Pro Arg
1 5 10

<210> SEQ ID NO 242
<211> LENGTH: 1632
<212> TYPE: DNA
<213> ORGANISM: Artificial Sequence
<220> FEATURE:
<223> OTHER INFORMATION: Synthetic Polynucleotide

<400> SEQUENCE: 242
atggagctgt tgatccttaa ggccaacgcc atcactacta ttctcaccgc ggtaacattc 60
tgcttcgcct ccgggcagaa catcaccgag gagttctacc agtctacgtg ctccgccgtc 120
tccaaaggtt acctgtccgc attaaggacg gggtggtaca cttccgtcat aactattgaa 180

```
ctgagtaaca taaaaaagaa caagtgtaat gggacggatg ccaaggtgaa gctcatcaag    240
caagagcttg acaaatacaa gaatgcagtg acagagctcc aacttctcat gcagtctaca    300
caggccacga ataaccgtgc ccgaagagaa ctgcctagat ttatgaatta cactttgaac    360
aacgccaaaa agaccaacgt gactctaagc aaaaaaagga aacggcgttt tctgggcttt    420
ctgctggggg ttggtagcgc catcgcatct ggcgtggcag tcagtaaagt tttgcacctt    480
gagggggagg tcaacaaaat caagagcgcg ctgttatcaa caaacaaggc agtcgtgtcc    540
ctctccaatg gcgtgtctgt cctgacctct aaagtactgg atctcaagaa ctatatcgac    600
aaacaactgc taccaatcgt caataagcag agttgctcta tttccaatat tgagaccgtg    660
atcgagtttc aacagaagaa taacagattg ttggagatca ccagggaatt cagcgtcaat    720
gcaggggtga ccacacccgt atctacctac atgctgacca actcggaact cctctcctta    780
ataaacgaca tgcctattac taacgaccaa aaaaagttga tgtccaacaa tgtccagatc    840
gtgcgacagc aatcttattc aattatgtcc attataaaag aggaggtgct ggcgtacgta    900
gtgcagctgc ccctttacgg agtgatcgac accccatgct ggaagctcca cacctccccc    960
ctgtgcacca ctaataccaa agaaggcagc aacatctgtc tgacccgtac cgaccgcgga   1020
tggtactgcg ataatgcagg tagcgtctct ttttttcccc aggctgaaac ttgcaaggtt   1080
cagtccaacc gggtattctg tgacacgatg aacagtctca ccctaccatc agaggtgaac   1140
ctgtgcaatg tggacatatt taaccctaaa tatgactgta agatcatgac ctccaaaact   1200
gacgtttcca gcagtgtcat aacctcactg ggcgcaatag tttcatgcta tggaaagact   1260
aagtgcactg cctctaacaa aaatcgaggt attattaaga cctttagcaa tggctgcgat   1320
tatgtcagta acaaaggtgt tgatacagtg agtgtgggca acacattata ctatgttaac   1380
aagcaagaag gcaagagcct ctatgtgaag ggagaaccaa tcattaattt ttacgatccg   1440
ctggtctttc ccagcgatga gttcgatgca tccatctctc aggtgaatga aaaaattaac   1500
caatcactgg ctttcatacg gaagagcgat gaactgctga gcgccatcgg gggatacatc   1560
cctgaagctc cgagggacgg ccaagcttat gtccgcaaag acggagagtg ggtgttgctc   1620
agtaccttcc tc                                                       1632
```

<210> SEQ ID NO 243
<211> LENGTH: 544
<212> TYPE: PRT
<213> ORGANISM: Artificial Sequence
<220> FEATURE:
<223> OTHER INFORMATION: Synthetic Polypeptide

<400> SEQUENCE: 243

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
```

```
        515                 520                 525

Ala Tyr Val Arg Lys Asp Gly Glu Trp Val Leu Leu Ser Thr Phe Leu
    530                 535                 540
```

```
<210> SEQ ID NO 244
<211> LENGTH: 1632
<212> TYPE: DNA
<213> ORGANISM: Artificial Sequence
<220> FEATURE:
<223> OTHER INFORMATION: Synthetic Polynucleotide

<400> SEQUENCE: 244

atggaactgc tgattcttaa ggcgaatgcc ataaccacta tcttgaccgc agttactttt      60

tgcttcgcct ctgggcagaa tattaccgaa gagttctacc agtccacgtg cagtgccgtg     120

tctaagggct acctttccgc gcttcgcact ggctggtaca cgtcagtcat aacgatcgaa     180

ctctctaata taaaggaaaa taagtgtaac ggaacagacg ctaaggtcaa gttaatcaag     240

caggagctgg acaaatataa gaatgccgta acggagctcc agctgctcat gcagagcacg     300

ccagctacaa acaacagggc acgccgtgag ctcccccgat ttatgaacta cacattgaac     360

aacgccaaga aaactaacgt gactttgtcc aagaagagga agcggcgatt cttagggttc     420

cttttggggg taggctcggc gattgccagt ggggttgccg tatgcaaggt gctccacctg     480

gaaggggagg tgaacaagat taagtcggct ctgctcagta caaacaaagc tgtcgtctca     540

ttgtcaaacg gagtcagtgt attgacattt aaagtcctcg acctgaagaa ctatatagat     600

aaacagttac tcccaatctt gaataagcag tcctgtagca tcagcaacat tgagacagtg     660

atcgagttcc agcagaagaa taatcgccta ctcgagatca ccagagaatt ctcagtcaat     720

gccggagtaa ccactcctgt cagcacatac atgctcacaa actctgaact cctaagcctg     780

attaatgata tgcctatcac aaatgatcag aagaaactca tgagcaataa tgtgcagatt     840

gtaagacagc agagttattc tataatgtgt attattaagg aggaggtact ggcctatgtg     900

gttcaacttc ctctgtatgg ggtgatagat acaccatgct ggaagctgca caccagccca     960

ctgtgtacga ccaatacaaa ggagggctcc aatatttgct taacacggac tgaccggggg    1020

tggtattgcg acaatgccgg atcagtctcc ttcttccccc aagcagagac ctgcaaggtg    1080

cagtccaata gagttttctg cgacacaatg aactcgctga ccctacctag cgaagttaac    1140

ttatgcaacg tggatatttt taatccgaag tatgattgta aaatcatgac tagcaaaacg    1200

gatgttagct ccagcgtaat cacctcccta ggcgctatcg tgagctgtta tggcaagacg    1260

aagtgcactg catctaataa aaataggggt attattaaaa ccttcagcaa tggctgcgac    1320

tatgtgagca ataagggcgt ggacaccgtg tcagtgggaa acaccctcta ttatgtgaac    1380

aagcaggagg gaaaatccct ttatgtaaag ggcgaaccca ttatcaattt ctatgacccc    1440

ctggttttcc caagcgacga gttcgacgca tctatctctc aagtgaacga gaaaatcaat    1500

cagagtcttg cctttatcag aaaatccgat gagctgcttt ccgccatcgg tggctatatc    1560

ccagaagccc caagagacgg acaagcgtac gtccggaaag atggtgagtg ggtcctcctc    1620

tctacctttc tt                                                        1632
```

```
<210> SEQ ID NO 245
<211> LENGTH: 544
<212> TYPE: PRT
<213> ORGANISM: Artificial Sequence
<220> FEATURE:
<223> OTHER INFORMATION: Synthetic Polypeptide
```

<400> SEQUENCE: 245

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540
```

<210> SEQ ID NO 246
<211> LENGTH: 813
<212> TYPE: DNA
<213> ORGANISM: Artificial Sequence
<220> FEATURE:
<223> OTHER INFORMATION: Synthetic Polynucleotide

<400> SEQUENCE: 246

```
atggagactc ctgcacagct gctgtttctg ctattgttgt ggcttccgga cactactggg     60

tccctcctca ccgaggtgga aacatacgtg ctgtccatca taccatccgg gcccttgaaa    120

gccgagatcg cccagagact cgaatctgta ttcgcaggaa agaacacgga tttggaggca    180

ctaatggaat ggctgaagac ccgtccgatc ctgtctcctc tcacaaaggg gattcttgga    240

tttgtcttta ccctcaccgt cccgagcgag cgcggtctcc agcgcagacg ttttgtacag    300

aatgcactga atggcaacgg cgatcccaat aacatggatc gtgcggtaaa gctttataaa    360

aagctgaaga gagaaatcac tttccatggg gctaaagagg tgagtctctc ctattcaacc    420

ggggcattgg cctcttgcat gggtcttata tacaatcgaa tgggcaccgt taccaccgag    480

gccgcatttg gtctggtttg tgctacgtgc gagcaaatcg cagatagcca gcatcggtcc    540

catcggcaga tggccaccac tacgaaccct ctaattcgac atgaaaatcg catggtcctg    600

gctagcacca ccgcaaaggc aatggagcag atggcgggct ctagtgaaca ggcagccgag    660

gcaatggaag tggccaatca gaccaggcag atggtccatg ctatgcggac tattggtacc    720

cacccgtcca gcagtgctgg actgaaggat gacctccttg agaacctgca ggcataccag    780

aaacgaatgg gggtgcaaat gcagagattc aag                                 813
```

<210> SEQ ID NO 247
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 247

```
Met Glu Thr Pro Ala Gln Leu Leu Phe Leu Leu Leu Leu Trp Leu Pro
1               5                   10                  15

Asp Thr Thr Gly Ser Leu Leu Thr Glu Val Glu Thr Tyr Val Leu Ser
            20                  25                  30
```

```
Ile Ile Pro Ser Gly Pro Leu Lys Ala Glu Ile Ala Gln Arg Leu Glu
        35                  40                  45

Ser Val Phe Ala Gly Lys Asn Thr Asp Leu Glu Ala Leu Met Glu Trp
    50                  55                  60

Leu Lys Thr Arg Pro Ile Leu Ser Pro Leu Thr Lys Gly Ile Leu Gly
65                  70                  75                  80

Phe Val Phe Thr Leu Thr Val Pro Ser Glu Arg Gly Leu Gln Arg Arg
                85                  90                  95

Arg Phe Val Gln Asn Ala Leu Asn Gly Asn Gly Asp Pro Asn Asn Met
            100                 105                 110

Asp Arg Ala Val Lys Leu Tyr Lys Lys Leu Lys Arg Glu Ile Thr Phe
        115                 120                 125

His Gly Ala Lys Glu Val Ser Leu Ser Tyr Ser Thr Gly Ala Leu Ala
    130                 135                 140

Ser Cys Met Gly Leu Ile Tyr Asn Arg Met Gly Thr Val Thr Thr Glu
145                 150                 155                 160

Ala Ala Phe Gly Leu Val Cys Ala Thr Cys Glu Gln Ile Ala Asp Ser
                165                 170                 175

Gln His Arg Ser His Arg Gln Met Ala Thr Thr Thr Asn Pro Leu Ile
            180                 185                 190

Arg His Glu Asn Arg Met Val Leu Ala Ser Thr Thr Ala Lys Ala Met
        195                 200                 205

Glu Gln Met Ala Gly Ser Ser Glu Gln Ala Ala Glu Ala Met Glu Val
    210                 215                 220

Ala Asn Gln Thr Arg Gln Met Val His Ala Met Arg Thr Ile Gly Thr
225                 230                 235                 240

His Pro Ser Ser Ser Ala Gly Leu Lys Asp Asp Leu Leu Glu Asn Leu
                245                 250                 255

Gln Ala Tyr Gln Lys Arg Met Gly Val Gln Met Gln Arg Phe Lys
            260                 265                 270
```

<210> SEQ ID NO 248
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 248
ctcaatttcc tcacttctcc agtgt 25

<210> SEQ ID NO 249
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 249
cttgattcct cggtgtacct ctgt 24

<210> SEQ ID NO 250
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 250
tcccattatg cctaggccag cagca 25

<210> SEQ ID NO 251
<211> LENGTH: 1729
<212> TYPE: DNA
<213> ORGANISM: Artificial Sequence
<220> FEATURE:
<223> OTHER INFORMATION: Synthetic Polynucleotide

<400> SEQUENCE: 251
tcaagctttt ggaccctcgt acagaagcta atacgactca ctatagggaa ataagagaga 60
aaagaagagt aagaagaaat ataagagcca ccatggcaca agtcattaat acaaacagcc 120
tgtcgctgtt gacccagaat aacctgaaca aatcccagtc cgcactgggc actgctatcg 180
agcgtttgtc ttccggtctg cgtatcaaca gcgcgaaaga cgatgcggca ggacaggcga 240
ttgctaaccg ttttaccgcg aacatcaaag gtctgactca ggcttcccgt aacgctaacg 300
acggtatctc cattgcgcag accactgaag gcgcgctgaa cgaaatcaac aacaacctgc 360
agcgtgtgcg tgaactggcg gttcagtctg cgaatggtac taactcccag tctgacctcg 420
actccatcca ggctgaaatc acccagcgcc tgaacgaaat cgaccgtgta tccggccaga 480
ctcagttcaa cggcgtgaaa gtcctggcgc aggacaacac cctgaccatc caggttggtg 540
ccaacgacgg tgaaactatc gatattgatt taaaagaaat cagctctaaa acactgggac 600
ttgataagct taatgtccaa gatgcctaca ccccgaaaga aactgctgta accgttgata 660
aaactaccta taaaaatggt acagatccta ttacagccca gagcaatact gatatccaaa 720
ctgcaattgg cggtggtgca acgggggtta ctggggctga tatcaaattt aaagatggtc 780
aatactattt agatgttaaa ggcggtgctt ctgctggtgt ttataaagcc acttatgatg 840
aaactacaaa gaaagttaat attgatacga ctgataaaac tccgttggca actgcggaag 900
ctacagctat tcggggaacg gccactataa cccacaacca aattgctgaa gtaacaaaag 960
agggtgttga tacgaccaca gttgcggctc aacttgctgc agcaggggtt actggcgccg 1020
ataaggacaa tactagcctt gtaaaactat cgtttgagga taaaaacggt aaggttattg 1080
atggtggcta tgcagtgaaa atgggcgacg atttctatgc cgctacatat gatgagaaaa 1140
caggtgcaat tactgctaaa accactactt atacagatgg tactggcgtt gctcaaactg 1200
gagctgtgaa atttggtggc gcaaatggta aatctgaagt tgttactgct accgatggta 1260
agacttactt agcaagcgac cttgacaaac ataacttcag aacaggcggt gagcttaaag 1320
aggttaatac agataagact gaaaacccac tgcagaaaat tgatgctgcc ttggcacagg 1380
ttgatacact tcgttctgac ctgggtgcgg ttcagaaccg tttcaactcc gctatcacca 1440
acctgggcaa taccgtaaat aacctgtctt ctgcccgtag ccgtatcgaa gattccgact 1500
acgcaaccga agtctccaac atgtctcgcg cgcagattct gcagcaggcc ggtacctccg 1560
ttctggcgca ggcgaaccag gttccgcaaa acgtcctctc tttactgcgt tgataatagg 1620
ctggagcctc ggtggccatg cttcttgccc cttgggcctc cccccagccc ctcctcccct 1680
tcctgcaccc gtacccccgt ggtctttgaa taaagtctga gtgggcggc 1729

<210> SEQ ID NO 252
<211> LENGTH: 1518
<212> TYPE: DNA
<213> ORGANISM: Artificial Sequence
<220> FEATURE:
<223> OTHER INFORMATION: Synthetic Polynucleotide

<400> SEQUENCE: 252

```
atggcacaag tcattaatac aaacagcctg tcgctgttga cccagaataa cctgaacaaa     60

tcccagtccg cactgggcac tgctatcgag cgtttgtctt ccggtctgcg tatcaacagc    120

gcgaaagacg atgcggcagg acaggcgatt gctaaccgtt ttaccgcgaa catcaaaggt    180

ctgactcagg cttcccgtaa cgctaacgac ggtatctcca ttgcgcagac cactgaaggc    240

gcgctgaacg aaatcaacaa caacctgcag cgtgtgcgtg aactggcggt tcagtctgcg    300

aatggtacta actcccagtc tgacctcgac tccatccagg ctgaaatcac ccagcgcctg    360

aacgaaatcg accgtgtatc cggccagact cagttcaacg gcgtgaaagt cctggcgcag    420

gacaacaccc tgaccatcca ggttggtgcc aacgacggtg aaactatcga tattgattta    480

aaagaaatca gctctaaaac actgggactt gataagctta atgtccaaga tgcctacacc    540

ccgaaagaaa ctgctgtaac cgttgataaa actacctata aaaatggtac agatcctatt    600

acagcccaga gcaatactga tatccaaact gcaattggcg gtggtgcaac gggggttact    660

ggggctgata tcaaatttaa agatggtcaa tactatttag atgttaaagg cggtgcttct    720

gctggtgttt ataaagccac ttatgatgaa actacaaaga aagttaatat tgatacgact    780

gataaaactc cgttggcaac tgcggaagct acagctattc ggggaacggc cactataacc    840

cacaaccaaa ttgctgaagt aacaaaagag ggtgttgata cgaccacagt tgcggctcaa    900

cttgctgcag caggggttac tggcgccgat aaggacaata ctagccttgt aaaactatcg    960

tttgaggata aaaacggtaa ggttattgat ggtggctatg cagtgaaaat gggcgacgat   1020

ttctatgccg ctacatatga tgagaaaaca ggtgcaatta ctgctaaaac cactacttat   1080

acagatggta ctggcgttgc tcaaactgga gctgtgaaat ttggtggcgc aaatggtaaa   1140

tctgaagttg ttactgctac cgatggtaag acttacttag caagcgacct tgacaaacat   1200

aacttcagaa caggcggtga gcttaaagag gttaatacag ataagactga aaacccactg   1260

cagaaaattg atgctgcctt ggcacaggtt gatacacttc gttctgacct gggtgcggtt   1320

cagaaccgtt tcaactccgc tatcaccaac ctgggcaata ccgtaaataa cctgtcttct   1380

gcccgtagcc gtatcgaaga ttccgactac gcaaccgaag tctccaacat gtctcgcgcg   1440

cagattctgc agcaggccgg tacctccgtt ctggcgcagg cgaaccaggt tccgcaaaac   1500

gtcctctctt tactgcgt                                                 1518
```

<210> SEQ ID NO 253
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 253

```
ggggaaauaa gagagaaaag aagaguaaga agaaauauaa gagccaccau ggcacaaguc     60

auuaauacaa acagccuguc gcuguugacc cagaauaacc ugaacaaauc ccaguccgca    120

cugggcacug cuaucgagcg uuugucuucc ggucugcgua ucaacagcgc gaaagacgau    180

gcggcaggac aggcgauugc uaaccguuuu accgcgaaca ucaaaggucu gacucaggcu    240

ucccguaacg cuaacgacgg uaucuccauu gcgcagacca cugaaggcgc gcugaacgaa    300

aucaacaaca accugcagcg ugugcgugaa cuggcgguuc agucugcgaa ugguacuaac    360

ucccagucug accucgacuc cauccaggcu gaaaucaccc agcgccugaa cgaaaucgac    420

cguguauccg gccagacuca guucaacggc gugaaagucc uggcgcagga caacacccug    480
```

-continued

```
accauccagg uuggugccaa cgacggugaa acuaucgaua uugauuuaaa agaaaucagc    540

ucuaaaacac ugggacuuga uaagcuuaau guccaagaug ccuacacccc gaaagaaacu    600

gcuguaaccg uugauaaaac uaccuauaaa aaugguacag auccuauuac agcccagagc    660

aauacugaua uccaaacugc aauuggcggu ggugcaacgg ggguuacugg ggcugauauc    720

aaauuuaaag auggucaaua cuauuuagau guuaaaggcg gugcuucugc ugguguuuau    780

aaagccacuu augaugaaac uacaaagaaa guuaauauug auacgacuga uaaaacuccg    840

uuggcaacug cggaagcuac agcuauucgg ggaacggcca cuauaaccca caaccaaauu    900

gcugaaguaa caaaagaggg uguugauacg accacaguug cggcucaacu ugcugcagca    960

gggguuacug gcgccgauaa ggacaauacu agccuuguaa aacuaucguu ugaggauaaa   1020

aacgguaagg uuauugaugg uggcuaugca gugaaaaugg gcgacgauuu cuaugccgcu   1080

acauaugaug agaaaacagg ugcaauuacu gcuaaaacca cuacuuauac agaugguacu   1140

ggcguugcuc aaacuggagc ugugaaauuu gguggcgcaa augguaaauc ugaaguuguu   1200

acugcuaccg augguaagac uuacuuagca agcgaccuug acaaacauaa cuucagaaca   1260

ggcggugagc uuaaagaggu uaauacagau aagacugaaa acccacugca gaaaauugau   1320

gcugccuugg cacagguuga uacacuucgu ucugaccugg gugcgguuca gaaccguuuc   1380

aacuccgcua ucaccaaccu gggcaauacc guaaauaacc ugucuucugc ccguagccgu   1440

aucgaagauu ccgacuacgc aaccgaaguc uccaacaugu cucgcgcgca gauucugcag   1500

caggccggua ccuccguucu ggcgcaggcg aaccagguuc cgcaaaacgu ccucucuuua   1560

cugcguugau aauaggcugg agccucggug gccaugcuuc uugccccuug ggccuccccc   1620

cagccccucc uccccuuccu gcacccguac ccccgugguc uuugaauaaa gucugagugg   1680

gcggcaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaucuag              1790
```

<210> SEQ ID NO 254
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 254

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
```

```
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
            340                 345                 350

Ile Thr Ala Lys Thr Thr Thr Tyr Thr Asp Gly Thr Gly Val Ala Gln
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505
```

<210> SEQ ID NO 255
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 255

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

```
Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Gly
                485                 490                 495

Gly Gly Gly Ser Gly Gly Gly Gly Ser Met Met Ala Pro Asp Pro Asn
            500                 505                 510

Ala Asn Pro Asn Ala Asn Pro Asn Ala Asn Pro Asn Ala Asn Pro Asn
        515                 520                 525

Ala Asn Pro Asn Ala Asn Pro Asn Ala Asn Pro Asn Ala Asn Pro Asn
    530                 535                 540

Ala Asn Pro Asn Ala Asn Pro Asn Ala Asn Pro Asn Ala Asn Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Lys Asn Asn Gln
            580                 585                 590

Gly Asn Gly Gln Gly His Asn Met Pro Asn Asp Pro Asn Arg Asn Val
        595                 600                 605

Asp Glu Asn Ala Asn Ala Asn Asn Ala Val Lys Asn Asn Asn Asn Glu
    610                 615                 620

Glu Pro Ser Asp Lys His Ile Glu Gln Tyr Leu Lys Lys Ile Lys Asn
625                 630                 635                 640

Ser Ile Ser Thr Glu Trp Ser Pro Cys Ser Val Thr Cys Gly Asn Gly
                645                 650                 655

Ile Gln Val Arg Ile Lys Pro Gly Ser Ala Asn Lys Pro Lys Asp Glu
            660                 665                 670

Leu Asp Tyr Glu Asn Asp Ile Glu Lys Lys Ile Cys Lys Met Glu Lys
        675                 680                 685

Cys Ser Ser Val Phe Asn Val Val Asn Ser
    690                 695
```

<210> SEQ ID NO 256
<211> LENGTH: 692
<212> TYPE: PRT
<213> ORGANISM: Artificial Sequence
<220> FEATURE:
<223> OTHER INFORMATION: Synthetic Polypeptide

<400> SEQUENCE: 256

```
Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Ala
65                  70                  75                  80
```

```
Asn Pro Asn Lys Asn Asn Gln Gly Asn Gly Gln Gly His Asn Met Pro
                85                  90                  95

Asn Asp Pro Asn Arg Asn Val Asp Glu Asn Ala Asn Ala Asn Asn Ala
            100                 105                 110

Val Lys Asn Asn Asn Asn Glu Glu Pro Ser Asp Lys His Ile Glu Gln
        115                 120                 125

Tyr Leu Lys Lys Ile Lys Asn Ser Ile Ser Thr Glu Trp Ser Pro Cys
    130                 135                 140

Ser Val Thr Cys Gly Asn Gly Ile Gln Val Arg Ile Lys Pro Gly Ser
145                 150                 155                 160

Ala Asn Lys Pro Lys Asp Glu Leu Asp Tyr Glu Asn Asp Ile Glu Lys
                165                 170                 175

Lys Ile Cys Lys Met Glu Lys Cys Ser Ser Val Phe Asn Val Val Asn
            180                 185                 190

Ser Arg Pro Val Thr Met Ala Gln Val Ile Asn Thr Asn Ser Leu Ser
        195                 200                 205

Leu Leu Thr Gln Asn Asn Leu Asn Lys Ser Gln Ser Ala Leu Gly Thr
    210                 215                 220

Ala Ile Glu Arg Leu Ser Ser Gly Leu Arg Ile Asn Ser Ala Lys Asp
225                 230                 235                 240

Asp Ala Ala Gly Gln Ala Ile Ala Asn Arg Phe Thr Ala Asn Ile Lys
                245                 250                 255

Gly Leu Thr Gln Ala Ser Arg Asn Ala Asn Asp Gly Ile Ser Ile Ala
            260                 265                 270

Gln Thr Thr Glu Gly Ala Leu Asn Glu Ile Asn Asn Asn Leu Gln Arg
        275                 280                 285

Val Arg Glu Leu Ala Val Gln Ser Ala Asn Ser Thr Asn Ser Gln Ser
    290                 295                 300

Asp Leu Asp Ser Ile Gln Ala Glu Ile Thr Gln Arg Leu Asn Glu Ile
305                 310                 315                 320

Asp Arg Val Ser Gly Gln Thr Gln Phe Asn Gly Val Lys Val Leu Ala
                325                 330                 335

Gln Asp Asn Thr Leu Thr Ile Gln Val Gly Ala Asn Asp Gly Glu Thr
            340                 345                 350

Ile Asp Ile Asp Leu Lys Gln Ile Asn Ser Gln Thr Leu Gly Leu Asp
        355                 360                 365

Thr Leu Asn Val Gln Gln Lys Tyr Lys Val Ser Asp Thr Ala Ala Thr
    370                 375                 380

Val Thr Gly Tyr Ala Asp Thr Thr Ile Ala Leu Asp Asn Ser Thr Phe
385                 390                 395                 400

Lys Ala Ser Ala Thr Gly Leu Gly Gly Thr Asp Gln Lys Ile Asp Gly
                405                 410                 415

Asp Leu Lys Phe Asp Asp Thr Thr Gly Lys Tyr Tyr Ala Lys Val Thr
            420                 425                 430

Val Thr Gly Gly Thr Gly Lys Asp Gly Tyr Tyr Glu Val Ser Val Asp
        435                 440                 445

Lys Thr Asn Gly Glu Val Thr Leu Ala Gly Gly Ala Thr Ser Pro Leu
    450                 455                 460

Thr Gly Gly Leu Pro Ala Thr Ala Thr Glu Asp Val Lys Asn Val Gln
465                 470                 475                 480

Val Ala Asn Ala Asp Leu Thr Glu Ala Lys Ala Ala Leu Thr Ala Ala
                485                 490                 495
```

-continued

```
Gly Val Thr Gly Thr Ala Ser Val Val Lys Met Ser Tyr Thr Asp Asn
            500                 505                 510

Asn Gly Lys Thr Ile Asp Gly Gly Leu Ala Val Lys Val Gly Asp Asp
        515                 520                 525

Tyr Tyr Ser Ala Thr Gln Asn Lys Asp Gly Ser Ile Ser Ile Asn Thr
    530                 535                 540

Thr Lys Tyr Thr Ala Asp Asp Gly Thr Ser Lys Thr Ala Leu Asn Lys
545                 550                 555                 560

Leu Gly Gly Ala Asp Gly Lys Thr Glu Val Val Ser Ile Gly Gly Lys
                565                 570                 575

Thr Tyr Ala Ala Ser Lys Ala Glu Gly His Asn Phe Lys Ala Gln Pro
            580                 585                 590

Asp Leu Ala Glu Ala Ala Ala Thr Thr Thr Glu Asn Pro Leu Gln Lys
        595                 600                 605

Ile Asp Ala Ala Leu Ala Gln Val Asp Thr Leu Arg Ser Asp Leu Gly
    610                 615                 620

Ala Val Gln Asn Arg Phe Asn Ser Ala Ile Thr Asn Leu Gly Asn Thr
625                 630                 635                 640

Val Asn Asn Leu Thr Ser Ala Arg Ser Arg Ile Glu Asp Ser Asp Tyr
                645                 650                 655

Ala Thr Glu Val Ser Asn Met Ser Arg Ala Gln Ile Leu Gln Gln Ala
            660                 665                 670

Gly Thr Ser Val Leu Ala Gln Ala Asn Gln Val Pro Gln Asn Val Leu
        675                 680                 685

Ser Leu Leu Arg
    690


<210> SEQ ID NO 257
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 257

atggaactgc tcattttgaa ggcaaacgct atcacgacaa tactcactgc agtgaccttc      60

tgttttgcct caggccagaa cataaccgag gagttttatc aatctacatg cagcgctgta     120

tctaaaggct acctgagtgc gctccgcaca ggatggtaca cctccgtgat caccatcgag     180

ctcagcaata ttaaagagaa caagtgcaat ggtaccgacg ctaaagtcaa acttatcaag     240

caggaactcg acaaatataa gaacgctgtg accgagctgc agttattgat gcagagtaca     300

cctgccacca ataacagagc taggagggag ttgcctaggt ttatgaacta cactctcaac     360

aacgcgaaga agaccaatgt gacgctatcc aagaaacgga agaggaggtt cctggggttt     420

cttttagggg tgggctctgc cattgcttcc ggcgtggctg tatgtaaagt tctccacctc     480

gagggagagg ttaataagat taagtcggcc ctgctgagta ctaacaaagc agtggtgtcg     540

ctgagtaacg gagtaagtgt gttaacattt aaggtgctgg acctcaagaa ttatattgac     600

aaacagttgc ttcctattct aaacaaacag agctgttcaa taagtaatat tgaaactgtt     660

attgagtttc agcagaagaa caacaggctt cttgagatta cacgcgagtt cagtgtcaat     720

gccggcgtta caacacccgt gtctacctac atgctgacga attctgagct tctctctctc     780

ataaacgaca tgcccattac gaatgaccaa aagaaactta tgtccaacaa cgtgcagatt     840

gtgcgacagc aatcctatag cattatgtgt atcatcaagg aagaggtact cgcttatgtt     900
```

gtgcagctac cactctatgg tgtgattgac accccctgtt ggaagctgca taccagtcca 960
ctctgcacca ctaacacaaa ggaagggagc aatatttgcc tcactcgaac cgacaggggg 1020
tggtattgcg ataatgcggg ctccgtgtcc ttctttccac aggctgaaac ttgtaaggta 1080
cagtcaaacc gcgtgttctg tgatactatg aattctctga ctcttcccag cgaggttaat 1140
ctctgcaacg tcgacatttt caatcctaaa tatgactgca agatcatgac cagcaagacc 1200
gacgtctcca gctcagtaat cactagccta ggggccattg taagctgcta tggcaagacc 1260
aagtgtactg cctctaataa gaacagaggc ataattaaga ccttttcaaa tggctgtgac 1320
tatgtgtcga ataagggcgt cgacacggtc tcagtaggga ataccctcta ctacgttaac 1380
aaacaggaag gcaaatccct ttatgtaaag ggcgagccca tcataaattt ctacgaccca 1440
cttgtgttcc ccagtgatga attcgatgca tcaatctccc aggtgaacga aaagatcaat 1500
caatcccttg cttttatacg aaagtcagat gaactcctgc ataacgtgaa tgctgggaaa 1560
tctacaacca acatcatgat cactaccatc attattgtga ttatcgtaat tctgctatcc 1620
ttgattgctg tcgggctgct tctgtactgt aaggccagat cgacgcctgt gaccctttca 1680
aaggaccaac ttagcggtat caataatatt gcctttagca at 1722

<210> SEQ ID NO 258
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 258
atggaactgc tcattttgaa ggcaaacgct atcacgacaa tactcactgc agtgaccttc 60
tgttttgcct caggccagaa cataaccgag gagttttatc aatctacatg cagcgctgta 120
tctaaaggct acctgagtgc gctccgcaca ggatggtaca cctccgtgat caccatcgag 180
ctcagcaata ttaaagagaa caagtgcaat ggtaccgacg ctaaagtcaa acttatcaag 240
caggaactcg acaaatataa gaacgctgtg accgagctgc agttattgat gcagagtaca 300
cctgccacca ataacagagc taggagggag ttgcctaggt ttatgaacta cactctcaac 360
aacgcgaaga agaccaatgt gacgctatcc aagaaacgga agaggaggtt cctggggttt 420
cttttagggg tgggctctgc cattgcttcc ggcgtggctg tatgtaaagt tctccacctc 480
gagggagagg ttaataagat taagtcggcc ctgctgagta ctaacaaagc agtggtgtcg 540
ctgagtaacg gagtaagtgt gttaacattt aaggtgctgg acctcaagaa ttatattgac 600
aaacagttgc ttcctattct aaacaaacag agctgttcaa taagtaatat tgaaactgtt 660
attgagtttc agcagaagaa caacaggctt cttgagatta cacgcgagtt cagtgtcaat 720
gccggcgtta caacacccgt gtctacctac atgctgacga attctgagct tctctctctc 780
ataaacgaca tgcccattac gaatgaccag aagaaactta tgtccaacaa cgtgcagatt 840
gtgcgacagc aatcctatag cattatgtgt atcatcaagg aagaggtact cgcttatgtt 900
gtgcagctac cactctatgg tgtgattgac accccctgtt ggaagctgca taccagtcca 960
ctctgcacca ctaacacaaa ggaagggagc aatatttgcc tcactcgaac cgacaggggg 1020
tggtattgcg ataatgcggg ctccgtgtcc ttctttccac aggctgaaac ttgtaaggta 1080
cagtcaaacc gcgtgttctg tgatactatg aattctctga ctcttcccag cgaggttaat 1140
ctctgcaacg tcgacatttt caatcctaaa tatgactgca agatcatgac cagcaagacc 1200
gacgtctcca gctcagtaat cactagccta ggggccattg taagctgcta tggcaagacc 1260

```
aagtgtactg cctctaataa gaacagaggc ataattaaga ccttttcaaa tggctgtgac   1320

tatgtgtcga ataagggcgt cgacacggtc tcagtaggga ataccctcta ctacgttaac   1380

aaacaggaag gcaaatccct ttatgtaaag ggcgagccca tcataaattt ctacgaccca   1440

cttgtgttcc ccagtgatga attcgatgca tcaatctccc aggtgaacga gaagatcaat   1500

caatcccttg cttttatacg aaagtcagat gaactcctgc ataacgtgaa tgctgggaaa   1560

tctacaacca acatcatgat cactaccatc attattgtga ttatcgtaat tctgctatcc   1620

ttgattgctg tcgggctgct tctgtactgt aaggccagat cgacgcctgt gaccctttca   1680

aaggaccaac ttagcggtat caataatatt gcctttagca at                      1722
```

<210> SEQ ID NO 259
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 259

```
atggaactgc tcattttgaa ggcaaacgct atcacgacaa tactcactgc agtgaccttc     60

tgttttgcct caggccagaa cataaccgag gagttttatc aatctacatg cagcgctgta    120

tctaaaggct acctgagtgc gctccgcaca ggatggtaca cctccgtgat caccatcgag    180

ctcagcaata ttaaagagaa caagtgcaat ggtaccgacg ctaaagtcaa acttatcaag    240

caggaactcg acaaatataa gaacgctgtg accgagctgc agttattgat gcagagtaca    300

cctgccacca ataacagagc taggagggag ttgcctaggt ttatgaacta cactctcaac    360

aacgcgaaga aaaccaatgt gacgctatcc aagaaacgga agaggaggtt cctggggttt    420

cttttagggg tgggctctgc cattgcttcc ggcgtggctg tatgtaaagt tctccacctc    480

gagggagagg ttaataagat taagtcggcc ctgctgagta ctaacaaagc agtggtgtcg    540

ctgagtaacg gagtaagtgt gttaacattt aaggtgctgg acctcaagaa ttatattgac    600

aaacagttgc ttcctattct aaacaaacag agctgttcaa taagtaatat tgaaactgtt    660

attgagtttc agcagaagaa caacaggctt cttgagatta cacgcgagtt cagtgtcaat    720

gccggcgtta caacacccgt gtctacctac atgctgacga attctgagct tctctctctc    780

ataaacgaca tgcccattac gaatgaccaa aagaaactta tgtccaacaa cgtgcagatt    840

gtgcgacagc aatcctatag cattatgtgt atcatcaagg aagaggtact cgcttatgtt    900

gtgcagctac cactctatgg tgtgattgac accccctgtt ggaagctgca taccagtcca    960

ctctgcacca ctaacacaaa ggaagggagc aatatttgcc tcactcgaac cgacaggggg   1020

tggtattgcg ataatgcggg ctccgtgtcc ttctttccac aggctgaaac ttgtaaggta   1080

cagtcaaacc gcgtgttctg tgatactatg aattctctga ctcttcccag cgaggttaat   1140

ctctgcaacg tcgacatttt caatcctaaa tatgactgca agatcatgac cagcaagacc   1200

gacgtctcca gctcagtaat cactagccta ggggccattg taagctgcta tggcaaaacc   1260

aagtgtactg cctctaataa gaacagaggc ataattaaaa ccttttcaaa tggctgtgac   1320

tatgtgtcga ataagggcgt cgacacggtc tcagtaggga ataccctcta ctacgttaac   1380

aaacaggaag gcaaatccct ttatgtaaag ggcgagccca tcataaattt ctacgaccca   1440

cttgtgttcc ccagtgatga attcgatgca tcaatctccc aggtgaacga aaagatcaat   1500

caatcccttg cttttatacg aaagtcagat gaactcctgc ataacgtgaa tgctgggaaa   1560
```

-continued tctacaacca acatcatgat cactaccatc attattgtga ttatcgtaat tctgctatcc 1620
ttgattgctg tcgggctgct tctgtactgt aaggccagat cgacgcctgt gaccctttca 1680
aaagaccaac ttagcggtat caataatatt gcctttagca at 1722

<210> SEQ ID NO 260
<211> LENGTH: 1722
<212> TYPE: RNA
<213> ORGANISM: Respiratory Syncytial Virus

<400> SEQUENCE: 260
auggagcugc ucauccucaa agcaaaugcc aucaccacua uccugaccgc cgucacuuuc 60
ugcuucgccu ccggccaaaa uaucaccgaa gaguucuauc aguccaccug cucugccguu 120
ucuaaagguu accugucagc ccuuagaaca gggugguaua ccucuguuau uaccauugag 180
uuguccaaca uuaagaagaa caagugcaau ggcacagacg cuaagguuaa gcucaucaag 240
caggagcucg acaaauauaa aaaugccguc acggagcugc aguuauugau gcagagcacc 300
caggcgacaa acaaccgugc acgacgcgag cuaccccgau ucaugaacua cacccucaau 360
aaugcaaaga agacaaaugu gacgcucucu aagaagcgca agcgucgcuu ucugggcuuu 420
cuucucgggg uugggagcgc gaucgcaagc ggcguggcug uaucaaaagu gcuucaucuu 480
gagggagaag ugaauaaaau caaaagugcu cugcuaucua caaacaaagc cguuguauca 540
cuguccaacg gaguguccgu gcucacgucc aaagugcuag auuugaagaa uuacaucgau 600
aagcagcugc ucccuauugu gaacaaacaa ucauguucca ucaguaacau ugaaacaguc 660
aucgaguuuc aacagaaaaa caauagacug cuggagauua ccagagaauu uucgguuaac 720
gccggcguga cuaccccugu aagcaccuac auguugacaa acuccgaacu uuugucacug 780
auaaacgaua ugccuauuac uaaugaucag aaaaaauuga uguccaauaa uguccaaauc 840
gucaggcaac aguccuacag uaucaugucu auuauuaagg aggagguccu ugcauacgug 900
gugcaacugc cauuauacgg agucauugau acucccuguu ggaaacucca uacaagcccc 960
cugugcacua cuaacacuaa agagggauca aauauuuguc ucacucggac agauagaggu 1020
ugguacugug auaaaugcugg cucaguguca uucuuuccac aggcugaaac cugcaagguu 1080
cagucaaaca ggguguuuug cgauaccaug aauucucuaa cccuccccag ugaggugaac 1140
cuguguaaug uggauauauu caaccccaag uaugauugua agaucaugac cuccaagacg 1200
gacgugagua gcaguguuau caccucccug gggccauug uauccugcua cggaaaaacg 1260
aaauguacug ccucgaacaa aaauagggga aucaucaaaa cuuuuaguaa uggaugcgac 1320
uacguaucua auaaaggugu ugacacagug ucagucggca acacacugua uuacgugaau 1380
aagcaagaag ggaagucgcu guaugucaaa ggggagccua ucauuaauuu uuaugaccca 1440
cugguuuucc ccagcgauga guucgacgcc agcauuaguc agguuaauga gaaaaucaac 1500
caguccuugg cauuuauucg uaagagugau gaauugcucc auaaugugaa cgcugguaaa 1560
uccacuacca acauuaugau aacuaccauc aucauaguaa uaauaguaau uuuacugucu 1620
cugaucgcug ugggccuguu acuguauugc aaagcccgca guacuccugu caccuuauca 1680
aaggaccagc ugucugggau aaacaacauc gcguucucca au 1722

<210> SEQ ID NO 261
<211> LENGTH: 1722
<212> TYPE: RNA
<213> ORGANISM: Respiratory Syncytial Virus

<400> SEQUENCE: 261
auggaacugc ucauuuugaa ggcaaacgcu aucacgacaa uacucacugc agugaccuuc 60
uguuuugccu caggccagaa cauaaccgag gaguuuuauc aaucuacaug cagcgcugua 120
ucuaaaggcu accugagugc gcuccgcaca ggaugguaca ccuccgugau caccaucgag 180
cucagcaaua uuaaagagaa caagugcaau gguaccgacg cuaaagucaa acuuaucaag 240
caggaacucg acaaauauaa aaacgcugug accgagcugc aguuauugau gcagaguaca 300
ccugccacca auaacagagc uaggagggag uugccuaggu uuaugaacua cacucucaac 360
aacgcgaaaa aaaccaaugu gacgcuaucc aagaaacgga agaggagguu ccugggguuu 420
cuuuuagggg ugggcucugc cauugcuucc ggcguggcug uauguaaagu ucuccaccuc 480
gagggagagg uuaauaagau uaagucggcc cugcugagua cuaacaaagc aguggugucg 540
cugaguaacg gaguaagugu guuaacauuu aaggugcugg accucaagaa uuauauugac 600
aaacaguugc uuccuauucu aaacaaacag agcuguucaa uaaguaauau ugaaacuguu 660
auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccaa aaaaaacuua uguccaacaa cgugcagauu 840
gugcgacagc aauccuauag cauuaugugu aucaucaagg aagagguacu cgcuuauguu 900
gugcagcuac cacucuaugg ugugauugac acccccuguu ggaagcugca uaccagucca 960
cucugcacca cuaacacaaa ggaagggagc aauauuugcc ucacucgaac cgacaggggg 1020
ugguauugcg auaaugcggg cuccgugucc uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaaaacc 1260
aaguguacug ccucuaauaa gaacagaggc auaauuaaaa ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga aaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaagaccaac uuagcgguau caauaauauu gccuuuagca au 1722

<210> SEQ ID NO 262
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 262
auggagcugc ucauccucaa agcaaaugcc aucaccacua uccugaccgc cgucacuuuc 60
ugcuucgccu ccggccaaaa uaucaccgaa gaguucuauc aguccaccug cucugccguu 120
ucuaaagguu accugucagc ccuuagaaca gggugguaua ccucuguuau uaccauugag 180
uuguccaaca uuaagaagaa caagugcaau ggcacagacg cuaagguuaa gcucaucaag 240
caggagcucg acaaauauaa aaaugccguc acggagcugc aguuauugau gcagagcacc 300

-continued

```
caggcgacaa acaaccgugc acgacgcgag cuaccccgau ucaugaacua cacccucaau    360
aaugcaaaga agacaaaugu gacgcucucu aagaagcgca agcgucgcuu ucugggcuuu    420
cuucucgggg uugggagcgc gaucgcaagc ggcguggcug uaucaaaagu gcuucaucuu    480
gagggagaag ugaauaaaau caaaagugcu cugcuaucua caaacaaagc cguuguauca    540
cuguccaacg gaguguccgu gcucacgucc aaagugcuag auuugaagaa uuacaucgau    600
aagcagcugc ucccuauugu gaacaaacaa ucauguucca ucaguaacau ugaaacaguc    660
aucgaguuuc aacagaaaaa caauagacug cuggagauua ccagagaauu uucgguuaac    720
gccggcguga cuaccccugu aagcaccuac auguugacaa acuccgaacu uuugucacug    780
auaaacgaua ugccuauuac uaaugaucag aaaaaauuga uguccaauaa uguccaaauc    840
gucaggcaac aguccuacag uaucaugucu auuauuaagg aggagguccu ugcauacgug    900
gugcaacugc cauuauacgg agucauugau acucccuguu ggaaacucca uacaagcccc    960
cugugcacua cuaacacuaa agagggauca aauauuuguc ucacucggac agauagaggu   1020
ugguacugug auaaugcugg cucaguguca uucuuuccac aggcugaaac cugcaagguu   1080
cagucaaaca ggguguuuug cgauaccaug aauucucuaa cccuccccag ugaggugaac   1140
cuguguaaug uggauauauu caaccccaag uaugauugua agaucaugac cuccaagacg   1200
gacgugagua gcaguguuau caccucccug ggggccauug uauccugcua cggaaaaacg   1260
aaauguacug ccucgaacaa aaauagggga aucaucaaaa cuuuuaguaa uggaugcgac   1320
uacguaucua auaaaggugu ugacacagug ucagucggca acacacugua uuacgugaau   1380
aagcaagaag ggaagucgcu guaugucaaa ggggagccua ucauuaauuu uuaugaccca   1440
cugguuuucc ccagcgauga guucgacgcc agcauuaguc agguuaauga gaaaaucaac   1500
caguccuugg cauuuauucg uaagagugau gaauugcucc auaaugugaa cgcugguaaa   1560
uccacuacca acauuaugau aacuaccauc aucauaguaa uaauaguaau uuuacugucu   1620
cugaucgcug ugggccuguu acuguauugc aaagcccgca guacuccugu caccuuauca   1680
aaggaccagc ugucugggau aaacaacauc gcguucucca au                      1722
```

<210> SEQ ID NO 263
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 263

```
auggaacugc ucauuuugaa ggcaaacgcu aucacgacaa uacucacugc agugaccuuc     60
uguuuugccu caggccagaa cauaaccgag gaguuuuauc aaucuacaug cagcgcugua    120
ucuaaaggcu accugagugc gcuccgcaca ggauggguaca ccuccgugau caccaucgag    180
cucagcaaua uuaaagagaa caagugcaau gguaccgacg cuaaagucaa acuuaucaag    240
caggaacucg acaaauauaa aaacgcugug accgagcugc aguuauugau gcagaguaca    300
ccugccacca auaacagagc uaggagggag uugccuaggu uuaugaacua cacucucaac    360
aacgcgaaaa aaaccaaugu gacgcuaucc aagaaacgga agaggagguu ccuggggguuu    420
cuuuuagggg ugggcucugc cauugcuucc ggcguggcug uauguaaagu ucuccaccuc    480
gagggagagg uuaauaagau uaagucggcc cugcugagua cuaacaaagc aguggugucg    540
cugaguaacg gaguaagugu guuaacauuu aaggugcugg accucaagaa uuauauugac    600
aaacaguugc uuccuauucu aaacaaacag agcuguucaa uaaguaauau ugaaacuguu    660
```

auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccaa aaaaaacuua uguccaacaa cgugcagauu 840
gugcgacagc aauccuauag cauuaugugu aucaucaagg aagagguacu cgcuuauguu 900
gugcagcuac cacucuaugg ugugauugac acccccuguu ggaagcugca uaccagucca 960
cucugcacca cuaacacaaa ggaagggagc aauauuugcc ucacucgaac cgacaggggg 1020
ugguauugcg auaaugcggg cuccgugucc uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaaaacc 1260
aaguguacug ccucuaauaa gaacagaggc auaauuaaaa ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga aaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaagaccaac uuagcgguau caauaauauu gccuuuagca au 1722

<210> SEQ ID NO 264
<211> LENGTH: 1503
<212> TYPE: RNA
<213> ORGANISM: Artificial Sequence
<220> FEATURE:
<223> OTHER INFORMATION: Synthetic Polynucleotide

<400> SEQUENCE: 264
auggaacugc ucauccuuaa agccaacgcg auaacgacca uucugaccgc cgugaccuuc 60
ugcuucgcca gcggccagaa cauuaccgaa gaguuuuacc agagcacgug cucugccgug 120
agcaaagguu aucugagcgc uuuaagaacu ggcugguaca ccaguguuau uacuauagag 180
cugucaaaua uuaaaaagaa uaaaugcaac gggaccgaug ccaaaguaaa auuaauuaag 240
caggaauugg acaaguauaa gaaugcagug acagaguugc agcuccugau gcagagcaca 300
caagcuacaa acaaucgcgc ucgccagcag caacagcggu uuuuaggguu ccugcuaggg 360
guggggucag ccauugccuc uggaguggca guguccaaag ugcugcaucu ggaaggggaa 420
guuaacaaga uaaaauccgc acuccucagc accaauaaag ccguggucuc ccuguccaau 480
ggaguaucag uuuugacaag caaggugcug gaccugaaga auuauauaga uaagcaguua 540
cugccaauag ugaauaaaca gucaugcuca auuagcaaca uugagacagu uaucgaauuc 600
cagcagaaaa auaauaggcu ucuggaaaua acucgcgaau ucucaguaaa ugccggagug 660
accacacccg uaucgacuua uaugcuuaca aacucugaac uguuguccuu gauuaacgau 720
augccaauaa caaaugacca gaagaagcua augagcaaca augugcagau uguaagacag 780
cagucuuacu caauaauguc uauaauaaaa gaggaggugu uggcauaugu ggugcaacug 840
ccucucuaug gcgugaucga uacuccuugc uggaaguuac auacaucucc acuguguaca 900
acuaauacua aggaggguag caauauuugu cugacacgca cagaucgggg uugguauugc 960
gacaacgcgg gcagugugag cuuuuucccu caggccgaaa ccuguaaggu ucaaucuaau 1020
cggguauuuu gcgacacaau gaacagccug acccuuccgu ccgaaguuaa uuugugcaac 1080
gucgacaucu ucaauccuaa auaugacugc aaaaucauga cuucuaaaac cgacguaucc 1140
agcucaguga uaacaagccu uggggcaauu guaagcugcu auggcaagac gaagugcacc 1200
gcuaguaaca agaaccgggg gauuauuaag acuuuuucga acggaugcga uuacgucucc 1260
aacaaaggcg ucgauacugu guccguggga aacacccucu acuaugugaa caagcaggaa 1320
ggcaaaagcc ucuacgucaa aggagagccu aucaucaauu ucuacgaccc ucuaguauuc 1380
ccuucagacg aauuugacgc aucaauuucc caggugaacg agaaaauaaa ucaaagcuua 1440
gccuuuaucc gcaagaguga ugaguugcuu cacaacguca acgccggcaa aucaaccacu 1500
aau 1503

<210> SEQ ID NO 265
<211> LENGTH: 1563
<212> TYPE: RNA
<213> ORGANISM: Artificial Sequence
<220> FEATURE:
<223> OTHER INFORMATION: Synthetic Polynucleotide

<400> SEQUENCE: 265
auggaacucu ugauccugaa ggcuaaugca auaacaacaa uucugacagc agucaccuuu 60
ugcuucgcca gcggacagaa uauuacggag gaguuuuauc aaucuaccug uagugccgug 120
agcaaggggu accugucugc ccugaggacg ggaugguaca cauccgugau caccaucgag 180
uugucuaaca uuaaaaagaa caagugcaac ggaacugacg ccaaggugaa gcucauuaag 240
caagagcucg acaaauauaa gaaugcgguu acagaacuac agcuacuaau gcaguccaca 300
caggcaacca auaaccgagc acgucagcag cagcaacgcu uccuuggcuu ccugcucggg 360
guuggcucgg caauugcauc cggaguggcu guuuccaagg uuuugcaccu ugagggagag 420
gucaauaaga ucaagagcgc ccuccuguca acuaauaagg ccguggucag ccuuuccaac 480
gguguuucug uguuaaccuc aaaagugcuc gaccuuaaaa acuauaucga uaagcagcug 540
cugcccauag ugaacaaaca guccuguucu aucaguaaua ucgagacagu gaucgaauuc 600
cagcagaaga acaaucgucu gcuggaaauu acaagggagu ucagcguaaa cgcuggaguc 660
acaacccccg uguccacuua caugcugacc aauuccgagc ugcugaguuu gauuaaugau 720
augcccauua cgaacgauca gaagaaacug augucgaaua auguucagau cguuaggcag 780
cagucuuaua gcaucaugag uauuaucaaa gaggaggucc ucgccuaugu gguucagcug 840
ccucucuacg gcguuauaga caccccaugc uggaagcuuc acaccucucc ucuguguacg 900
accaauacaa aggagggcuc aaacauuugc cuuacccgca cagauagagg augguacugc 960
gauaaugcug gcucuguguc uuucuuuccu caggccgaaa cauguaaggu acaguccaau 1020
aggguauuuu gcgacaccau gaacucccua accuuaccaa gugaagugaa ccucugcaau 1080
guggacaucu uuaacccgaa guaugacugc aaaaucauga cuuccaagac agacgugucc 1140
aguaguguga uuaccucacu gggcgcaauc guuucaugcu augggaagac aaagugcacc 1200
gcaagcaaca agaaucgggg caucaucaaa accuucagua acgguuguga cuauguuuca 1260
aacaagggag ucgauaccgu gucggugggc aauacucuuu acuacgugaa uaaacaggag 1320
gggaaaucac uguaugugaa aggugagccg aucauuaacu uuuacgaccc ucucguguuu 1380
cccuccgaug aguucgacgc auccaucagu caggucaaug agaaaaucaa ccaaucucuc 1440
gccuucauua gaaaaucuga cgaauuacug agugccauug gaggauauau uccggaggcu 1500
cccagggacg ggcaggcuua cguccgaaag gauggagaau ggguccuacu gagcacauuu 1560
cua 1563

<210> SEQ ID NO 266
<211> LENGTH: 1692
<212> TYPE: RNA
<213> ORGANISM: Artificial Sequence
<220> FEATURE:
<223> OTHER INFORMATION: Synthetic Polynucleotide

<400> SEQUENCE: 266
auggagcucc ugaucuugaa ggcgaaugcc auuaccacca uccucaccgc aguaacuuuc 60
uguuucgcaa guggccagaa uauaacagaa gaguucuauc agucaaccug uagcgcaguc 120
ucaaaggggu auuuaucagc acugagaacc gguugguaua ccaguguuau uacaauagag 180
cugaguaaca uaaaggagaa uaagugcaac ggcacugacg ccaaggucaa gcucaucaaa 240
caggaacucg auaaauacaa gaacgcuguc acugaacugc agcugcugau gcaaagcacc 300
cccgccacca acaauagggc ccgcagagag cuuccuagau uuaugaacua cacucugaac 360
aacgccaaaa agaccaaugu aacacuguca aagaaacaga aacagcaggc uauugcaagc 420 ggugugggcug ugucuaaagu gcugcaucuc gagggggagg ucaacaagau caaauccgca 480
uugcucagca ccaacaaggc uguggugagc cuguccaaug gugucucagu gcucaccagc 540
aaagugcugg accugaagaa uuauauugau aagcagcugc uacccauagu caacaaacag 600
ucaugcucca uaucuaauau ugagacuguc aucgaguucc aacagaagaa caaucgccug 660
cuggagauua ccagggaguu cucagucaau gccgggguca cgacacccgu uaguacuuau 720
augcuuacca acuccgagcu ucucucuuug aucaaugaca ugccaauuac uaacgaccag 780
aagaaguuga ugucuaacaa uguacagauc guucgccagc aguccuauuc cauuaugucg 840
auuauuaaag aggagguucu ugcauacguc gugcaguugc cauuauaugg agucaucgac 900
acccccugcu ggaaacugca uacgucacca uuaugcacca cgaauacaaa ggagggcagu 960
aauauuuguc uuacacggac ugaucgaggc ugguauugug auaacgcagg cucgguguca 1020
uucuuuccac aggcugaaac cuguaaggug caaucuaaua ggguguuuug cgauaccaug 1080
aauucucuga cucugcccag ugaggucaau uuguguaacg uggacaucuu caacccaaag 1140
uacgacugca agaucaugac aucuaagaca gaugugucau ccagcguuau cacgagccuc 1200
ggcgcuauag ucuccuguua cggcaagacc aagugcaccg cuagcaacaa gaaucgggga 1260
aucaucaaaa ccuuuucuaa cgguugugac uacgugagca acaagggggu ggauaccguc 1320
ucagucggua acacccugua cuacgugaau aaacaggagg ggaagucauu guacgugaag 1380
ggugaaccua ucaucaacuu uuaugacccc cucgucuucc caucagacga guuugacgcg 1440
uccaucucuc aggugaauga gaagauuaac cagagccugg cuuuuauccg caaaucagac 1500
gaacuacugc acaaugucaa cgcuggcaag agcacaacaa auauaaugau aacaaccauc 1560
aucaucguca uuauugugau cuuguuauca cugaucgcug uggggcuccu ccuuuauugc 1620
aaggcucgua gcaccccugu cacccucagu aaagaucagc ugucagggau caauaauauc 1680
gcguuuagca ac 1692

<210> SEQ ID NO 267
<211> LENGTH: 1539
<212> TYPE: RNA
<213> ORGANISM: Artificial Sequence
<220> FEATURE:

<223> OTHER INFORMATION: Synthetic Polynucleotide

<400> SEQUENCE: 267
auggaauuau uaauuuugaa gacaaaugcu auaaccgcga uacuagcggc ugugacucuu 60
uguuucgcau caagccagaa uauuacagaa gaauuuuauc aauccaccug cagcgcugua 120
ucgaaagguu accucagcgc gcuuaggaca ggaugguaua ccuccguuau cacgauugaa 180
cugaguaaua ucaaggaaaa caaguguaac ggaacagacg ccaaggucaa acuuauuaaa 240
caagaacugg acaaguauaa gucugcagug accgaauugc agcuccugau gcagaguacc 300
ccugcaacua acaacaaguu uuugggcuuu cugcaaggcg uggguagcgc gaucgccucc 360
ggaaucgcgg ucuccaaagu guugcaccug gagggagaag uuaacaagau caaaucggcu 420
cuguugagua ccaacaaggc agugguguca cugagcaacg guguaagcgu guuaacaagc 480
aagguauugg acuuaaagaa cuauauugac aaacagcugc uccccaucgu gaacaaacag 540
agcugcucaa ucuccaauau agagacggug auagaguucc agcaaaaaaa uaaucggcuc 600
cuugagauca cccgcgaauu cucaguuaau gccggcguca caacuccggu gucuacauac 660
augcugacca acucggagcu guuauccuua auaaaugaca ugcccaucac caaugaucaa 720
aaaaaacuga ugucaaauaa cguccagaua guaagacagc agagcuacag caucaugucg 780
auuaucaaag aggaggugcu ggcguacgug gugcagcugc cccuguaugg ggugauugac 840
accccuuguu ggaagcugca caccucccca cuauguacua ccaauaccaa agaaggaucc 900
aacaucugcc uuacccgcac cgauagggga ugguauugcg acaacgccgg auccgucagc 960
uucuuuccac uugccgaaac uugcaagguu cagucaaacc gggguguucug cgauacaaug 1020 aauucccuua ccuugcccag cgaaguuaau cucuguaaua uugacaucuu uaaccccaaa 1080
uacgauugca aaauuaugac gucaaaaacc gaugucaguu caagcguuau caccagcuug 1140
ggugcuaucg uuucaugcua uggcaaaacc aaguguacgg cuaguaacaa aaaccgcgga 1200 auaaauuaaga cauucagcaa ugguugcgac uacguaucaa auaagggugu cgacaccguu 1260
uccgugggca auacgcugua cuauguuaau aaacaggaag gcaagucacu guauguuaaa 1320
ggugaaccca ucaucaacuu cuacgacccc cugguuuucc ccuccgacga guuugaugcc 1380
agcauaucac agguuaauga aaaaauaaac ggcacauugg cguuuaucag aaagucugac 1440
gagaaacuuc auaacgugga agacaagaua gaagagauau ugagcaaaau cuaucauauu 1500
gagaacgaga ucgccaggau caaaaagcuu auuggggag 1539

<210> SEQ ID NO 268
<211> LENGTH: 894
<212> TYPE: RNA
<213> ORGANISM: Artificial Sequence
<220> FEATURE:
<223> OTHER INFORMATION: Synthetic Polynucleotide

<400> SEQUENCE: 268
augucuaaaa acaaggacca gcgcacugcu aagacgcugg aacgcacaug ggauacccug 60
aaccaucugu uauucauuuc cagcugccuc uacaagcuaa accuuaaaag uguugcacaa 120
aucacacuca gcauccuggc aaugauuauu ucaacauccc ugaucauagc cgcaaucaua 180
uuuaucgccu cagcaaauca caaaguuacc ccgaccacag ccauuaucca ggacgcuaca 240
ucccaaauca aaaacaccac accuacauau cucacucaga acccgcagcu gggcauuuca 300
ccauccaacc cuuccgagau caccucucaa aucaccacca uucucgccuc uacuaccccg 360
ggaguaaaga gcacucuuca gagcacaacc guuaaaacua aaaauaccac caccacucag 420

```
acucagccuu cgaaaccaac gacuaaacag cggcaaaaua agccuccauc caaaccgaau    480

aacgacuuuc auuucgaagu cuuuaacuuu gugccaugca guauuugcuc caauaauccu    540

acuugcuggg cuaucugcaa gagaaucccu aacaagaagc cuggaaagaa gacaacgaca    600

aagccaacua agaagccgac acuuaagacu accaaaaaag acccuaagcc gcagacuacc    660

aagagcaagg agguucccac aaccaagccu acagaggagc cgacuauuaa cacaacaaag    720

accaacauca ucaccacccu gcuuacuucu aauacuaccg gaaacccaga gcugacgucc    780

cagauggaga cguuccauuc cacaucuucc gaagggaauc cuaguccag ccaggugagc    840

acaaccucag aauacccguc ccagcccuca ucaccuccua auaccccccg gcag          894
```

```
<210> SEQ ID NO 269
<211> LENGTH: 1629
<212> TYPE: RNA
<213> ORGANISM: Artificial Sequence
<220> FEATURE:
<223> OTHER INFORMATION: Synthetic Polynucleotide

<400> SEQUENCE: 269

auggagacgc cugcccagcu gcuguuccug cuguuguugu ggcugccaga uacuacuggg     60

uuugcaagcg gacaaaacau uaccgaagag uucuaucaau ccacaugcuc ugcagugucu    120

aagggcuacc uuagugcauu acgaaccggg ugguauacga guguaaucac cauugagcug    180

uccaacauca agaagaacaa gugcaauggg acugaugcca aggugaaacu uaucaaacaa    240

gagcucgaca aguauaagaa cgccgugacc gaacuacaac uccugaugca aucgacucag    300

gcuacuaaca acagagcucg gagggagcug cccagauuca ugaauuauac cuuaaacaac    360

gcuaaaaaaa caaaugugac ccugaguaag aagcggaaac gaagguuccu gggcuuccug    420

cucggugugg ggucugcaau agcaagcggc gucgcugugu ccaagguccu ucacuuagaa    480

ggugagguca auaagaucaa guccgcucuc cucucuacca acaaggcagu ggugagccug    540

ucuaacggug uguccgugcu gacaucgaag guacuggacc ugaaaaacua caucgacaag    600

cagcugcugc cuauugugaa uaagcaaucc ugcaguaucu ccaacauuga gacagugauu    660

gaauuucagc aaaagaacaa ucguuuguug gagauaacaa gagaauucag uguuaaugcc    720

ggcguuacca cucccguguc gacauacaug cuaacaaaua gcgagcugcu aucucucauu    780

aaugauaugc cuaucaccaa ugaccagaaa aaacuuaugu ccaauaacgu gcagauaguc    840

aggcagcagu ccuacagcau uaugagcaua auuaaagagg aaguguuggc uuacgucguc    900

cagcuuccac uguauggcgu gaucgauacc ccuuguugga agcugcauac uuccccccuu    960

uguacaacua auaccaaaga agggaguaau auaugccuca caaggacuga cagaggcugg   1020

uacugcgaca acgccgggag cgucagcuuu uucccgcagg ccgagacaug uaaggugcag   1080

agcaaccgug ucuuuugcga caccaugaau agccugacuu ugccaaguga ggucaaccuu   1140

ugcaacgugg auauuuuuaa cccuaaguac gauuguaaga uaaugacauc caaaaccgau   1200

guuaguagcu ccgugaucac uucgcugggu gcgauaguua gcugcuaugg aaagacaaag   1260

uguaccgcaa guaacaagaa ccgcgggauu auuaaaacau uuagcaaugg gugcgacuac   1320

guaucaaaca agggggugga uacagucagc gugggaaaca cacuuuacua cguuaacaag   1380

caggaaggga aaucccuuua ugugaaggga gaaccaauua ucaacuuuua ugauccccuc   1440

guguuuccaa gugaugaauu cgacgcaagc aucucgcagg ugaacgagaa aaucaaucag   1500

agucuagcuu ucauaaggaa gucugaugaa cugcuuagug ccauuggcgg guacauaccg   1560
```

gaagccccac gcgacggguca ggcuuacgug aggaaggacg gcgagugggu ucugcugucc 1620
acuuuccuu 1629

<210> SEQ ID NO 270
<211> LENGTH: 1629
<212> TYPE: RNA
<213> ORGANISM: Artificial Sequence
<220> FEATURE:
<223> OTHER INFORMATION: Synthetic Polynucleotide

<400> SEQUENCE: 270
auggagacuc ccgcucagcu gcuguuuuug cuccuccuau ggcugccgga uaccaccggc 60
uuugccucug gacagaacau uaccgaggaa uucuaucagu cgacuuguuc cgcagucucg 120
aagggguacc ugagugcccu gcgcaccggg ugguacacca guguuaucac uauugagcug 180
uccaacauua aagaaaauaa guguaaugga acugacgcga aggugaaguu gauaaaacag 240
gagcuggaua aauacaagaa ugcagugacc gaacugcagc uccugaugca guccacucca 300
gcaacaaaua aucgcgcgag acgcgaacuc ccccgcuuua ugaacuacac ucugaauaau 360
gcgaagaaaa cgaaugugac acuaaguaag aaaagaaaac ggcgauuucu uggguuccug 420
cucggggugg gaucugccau agcaagcggg guggcgguau guaaagaccu ucaccuagaa 480
ggggagguga acaaaauuaa gagugcccug cugagcacca acaaggcugu gguuucacug 540
ucaaacggag uaagcgugcu aacauuuaaa gucuuggacc ugaagaauua uauugacaag 600
cagcuccugc ccauucucaa caaacaguca uguuccauua gcaacaucga aacagucauu 660
gaguuucagc aaaaaaacaa ccgccuccuu gagauuacgc gugaguuuuc cgucaaugcu 720
ggagucacga caccggugu cacuuacaug cugacuaaca gcgaacuccu gagccuaauc 780
aaugacaugc ccauuacuaa cgaccagaaa aaauugaugu ccaauaacgu gcagauagug 840
cgccagcaau cuuacuccau aaugugcauu aucaaggagg aaguccuggc guacguuguu 900
cagcugccgc uguauggugu gauagauacg ccaugcugga aacugcacac aucccccccuu 960 ugcacaacga auacuaaaga gggaaguaac auuugcuuga ccagaacaga ucggggcugg 1020
uacugcgaca acgcugguag ugugucauuu uucccccagg cagaaacgug uaaaguccag 1080
agcaaucgcg uguucugcga cacaaugaac ucacuuacuu ugcccucaga ggucaauuug 1140
uguaaugugg auaucuucaa cccgaaauac gauuguaaga uuaugacgag caaaacagac 1200
gugucuucau cagugauaac aagucugggc gcaauagugu caugcuaugg uaagacuaag 1260
ugcacugccu ccaauaaaaa ccgcggcauc aucaagacau uuucaaaugg augcgacuac 1320
gugucaaaca agggcgucga cacaguaagc guugggaaca cccuauacua cgucaacaag 1380
caggagggga aaagccuaua cgugaaaggc gagccaauca ucaauuucua cgauccacug 1440
gucuuuccaa gugacgaauu ugaugccagc auaucgcagg ugaacgagaa aauaaaucag 1500
ucacucgccu ucaucaggaa gucagaugag cugcuguccg ccaucggagg auacauucca 1560
gaagccccac gcgacggcca ggcauacgug cggaaggacg gcgaaugggu ccuuuugagc 1620
acuuuucua 1629

<210> SEQ ID NO 271
<211> LENGTH: 1500
<212> TYPE: RNA
<213> ORGANISM: Artificial Sequence
<220> FEATURE:
<223> OTHER INFORMATION: Synthetic Polynucleotide

<400> SEQUENCE: 271

-continued

```
auggagacuc cagcccaauu acuguuccug cuacuccuuu ggcugcccga uacuacugga     60
uucgcuucgg gucagaauau uacagaggag uucuaccaaa guacuugcuc ugcagucucc    120
aagggauacc uguccgcucu gcggacggga ugguauacca guguuauaac gaucgaguug    180
agcaacauca agaagaacaa auguaaugga acagaugcca aggugaaacu gaucaaacag    240
gaguuggaua aauauaagaa ugcugucacc gaacugcagc uauugaugca guccacccag    300
gcuaccaaca accgggccag gcagcaacaa cagagauuuu uggguuucuu gcugggcgug    360
gggucugcca ucgcuucagg gguggccgug aguaaagucc ugcaccugga aggcgaaguc    420
aacaagauca agucugcauu acuaaguacc aauaaggcug uaguuagccu guccaauggc    480
gugagugugc uuacuucuaa gguacuggac cugaagaacu acaucgacaa gcaacuacua    540
cccauuguaa auaagcaguc auguagcaua ucaaacaucg agacagugau cgaauuucaa    600
cagaagaaua accggcuguu ggagauaaca cgggaguucu cuguaaaugc cggcgugacg    660
accccuguca gcaccuacau gcucacgaau agcgaguugc uuucccugau uaaugauaug    720
ccgauuacaa augaccagaa gaagcugaug aguaauaaug uccaaauugu ccgucagcag    780
agcuauucga uuauguccau caucaaggag gaagucuuag ccuauguggu gcagcucccc    840
cucuacggag ugauugacac accgugcugg aagcugcaca ccucccccuu guguacaacc    900
aauaccaagg agggcuccaa caucugccuu acuaggaccg acaggggaug guauugcgac    960
aacgccgggu ccgucucauu uuuuccucag gcggaaaccu guaagguaca gucgaaucga   1020
guguuuugug acacuaugaa cagccugacc uugccuagcg aggugaaucu guguaacguu   1080
gauaucuuca acccuaagua ugacuguaag aucaugacuu caaaaacuga ugucuccuca   1140
agcgugauca ccucuuuggg cgccaucgug ucaugcuacg gaaagacgaa gugcaccgcc   1200
ucuaacaaga accgagggau caucaaaaca uucuccaaug gcugugauua cgucaguaac   1260
aaaggugugg acacagucuc cgugggcaau acguuauauu augugaauaa gcaggaggga   1320
aaaagucucu augugaaggg ugaaccgaua aucaauuucu acgaucccuu gguguuucca   1380
agcgacgagu ucgacgccuc gaucagccag gugaacgaga aaaucaacca gucuuuggca   1440
uucauccgca agagcgacga gcuacugcau aacgugaacg caggcaagag uacuaccaau   1500
```

<210> SEQ ID NO 272
<211> LENGTH: 1560
<212> TYPE: RNA
<213> ORGANISM: Artificial Sequence
<220> FEATURE:
<223> OTHER INFORMATION: Synthetic Polynucleotide

<400> SEQUENCE: 272

```
auggagacuc ccgcucaguu guuguuccug cuacugcugu ggcugccuga uacaaccgga     60
uuugcuagug ggcagaauau caccgaagaa uucuaucaga gcacuugcag ugcagugucc    120
aaaggauauu ugagcgcccu gcgcacuggg ugguacacaa gugucaucac aaucgagcua    180
aguaacauua aaaaaaacaa augcaacggg acugacgcaa aggucaaacu cauuaagcaa    240
gaacuugaca aauauaagaa cgcuguuaca gaguugcagc ugcuaaugca aagcacucag    300
gcuaccaaua accgagcgag acagcagcag caacguuucc uggguuuccu guuaggugug    360
gguagcgcaa uugccagugg uguagccgug uccaaggugc ugcaccugga aggggaagug    420
aauaagauca agucugcacu gcuguccacc aauaaggcgg ucguuucgcu gucuaacggc    480
gucucggucc uaacaaguaa aguucuggau uuaaagaacu auauugauaa gcaauugcug    540
```

ccuaucguaa auaagcagag uugcagcauu agcaauaucg agacagugau agaauuucag 600
caaaagaaca aucgauuacu cgaaaucaca cgcgaauuca gugucaaugc cggggguuaca 660 accccugugu cgaccuacau gcuuaccaau uccgagcuuc ugucucuuau uaacgauaug 720
cccaucacga acgaucagaa gaaacugaug ucaaauaacg uccaaauugu gcggcagcaa 780
agcuacagua ucaugagcau caucaaagag gaggugcucg ccuauguggu ccaauugccg 840
cuauacgggg ucauugauac acccuguugg aagcuccaua cauccccacu uuguacaacg 900
aauaccaagg aggggucuaa cauuugucug acccggaccg acagaggcug guauugcgau 960
aaugcuggaa gcguuaguuu cuuuccucag gcagaaacau gcaaggugca gucaaacaga 1020
guuuucugug acaccaugaa uuccuugacg cugccuucag aagugaaucu guguaacgug 1080
gauaucuuua auccgaagua cgauuguaaa auuaugacua gcaagacaga ugucucgucc 1140
ucugugauca cuagccuggg agcgauugug agcuguuaug guaaaacaaa guguacugcu 1200
agcaauaaga acagggggau uaucaaaacg uucaguaacg gcugugauua cguauccaac 1260 aaggggugg acaccguguc agucgggaac acgcucuacu acgugaacaa gcaggaaggu 1320
aagucgcuau acgugaaggg ggaacccaua aucaauuucu acgauccgcu cguguuuccu 1380
agcgacgaau ucgacgcauc uaucagccag gugaacgaga agaucaauca gagucuggcc 1440
uucauccgca aguccgacga gcugcuuagu gcuaucggag guuauauccc ugaggccccg 1500
agggacggcc aagcguaugu gagaaaggac ggggaauggg uacuguuguc aacuuuccua 1560

<210> SEQ ID NO 273
<211> LENGTH: 1536
<212> TYPE: RNA
<213> ORGANISM: Artificial Sequence
<220> FEATURE:
<223> OTHER INFORMATION: Synthetic Polynucleotide

<400> SEQUENCE: 273
auggagacac cugcccaacu ucuguuccuu cuuuugcucu ggcugccuga cacaaccggc 60
uucgcaucuu cacaaaacau cacggaagag uuuuaccaga gcacaugcuc cgcggucucu 120
aaaggcuauc uuucugcccu gcggacuggc ugguauacca gcgucaucac cauagagcug 180
ucaaacauca aggagaacaa guguaacggc acugacgcca aggucaagcu uauaaagcag 240
gaacuggaca aguauaagag ugcuguuacc gagcuccagu ugcuuaugca guccaccccc 300
gcaacaaaca auaaaauucu gggcuuucua cagggcgucg gaagcgccau cgcaagcggc 360
aucgcuguga gcaaggugu gcaucuggag ggagaggguga auaagauaaa gagugcucug 420
cuuuccacua acaaagccgu ggugagccug agcaauggcg uaucuguucu gacuucuaaa 480
guccuggauc ucaagaacua uaucgacaag cagcucuugc ccauugucaa caaacagucc 540
ugcuccauuu ccaauauuga gaccgucauu gaguuccaac agaagaauaa ccguuugcug 600
gaaauuacaa gggaauucag uguuaaugcc gguguaacca ccccugugag caccuauaug 660
cucaccaacu cugaacugcu gagucugauu aacgauaugc ccauuacuaa ugaucagaag 720
aaacuaauga guaacaaugu ccagauaguu cggcagcagu cauauuccau uaugaguaua 780
aucaaggagg aagugcuagc cuacguaguu cagcuccccc ucuacggcgu uauagacacg 840
ccauguugga agcugcauac gaguccucug ugcacuacaa auaccaagga gggcaguaac 900
auaugcuuga cuagaacuga uagaggcugg uacugcgaca augcaggcuc cgugucauuc 960
uuuccucucg ccgagacgug uaaagugcag aguaacagag uguuuuguga cacaaugaac 1020
ucauugaccc ugccuagcga agugaacuua ugcaacaucg acauuuuuaa cccaaaauac 1080
gauugcaaga uuaugaccuc uaagacugac guaucuucau ccgucauaac uucucuagga 1140
gcgaucguga gcugcuacgg uaagacuaaa ugcacggcua guaauaaaaa uagagguauc 1200
auuaagacuu uuaguaacgg uugcgauuau gugucaaaca agggagucga cacuguuuca 1260
gugggcaaua cucucuacua cguuaacaaa caggagggua aaucccuuua ugugaaaggg 1320
gaacccauca uuaauuuuua ugacccacuu guguuuccua gugacgaguu ugacgcuuca 1380
aucagucaag ugaacgaaaa aauuaauggc acgcucgcgu uuaucaggaa aagcgacgag 1440
aagcugcaua acguggaaga uaagaucgag gagauucucu cgaaaauuua ucauauagag 1500
aaugaaaucg caagaaucaa aaagcuuauu ggggag 1536

<210> SEQ ID NO 274
<211> LENGTH: 1632
<212> TYPE: RNA
<213> ORGANISM: Artificial Sequence
<220> FEATURE:
<223> OTHER INFORMATION: Synthetic Polynucleotide

<400> SEQUENCE: 274
auggagcugu ugauccuuaa ggccaacgcc aucacuacua uucucaccgc gguaacauuc 60
ugcuucgccu ccgggcagaa caucaccgag gaguucuacc agucuacgug cuccgccguc 120
uccaaagguu accuguccgc auuaaggacg gggugguaca cuuccgucau aacuauugaa 180
cugaguaaca uaaaaaagaa caaguguaau gggacggaug ccaaggugaa gcucaucaag 240
caagagcuug acaaauacaa gaaugcagug acagagcucc aacuucucau gcagucuaca 300
caggccacga auaaccgugc ccgaagagaa cugccuagau uuaugaauua cacuuugaac 360
aacgccaaaa agaccaacgu gacucuaagc aaaaaaagga aacggcguuu ucugggcuuu 420
cugcuggggg uugguagcgc caucgcaucu ggcguggcag ucaguaaagu uuugcaccuu 480
gagggggagg ucaacaaaau caagagcgcg cuguuaucaa caaacaaggc agucguguccc 540 cucuccaaug gcgugucugu ccugaccucu aaaguacugg aucucaagaa cuauaucgac 600
aaacaacugc uaccaaucgu caauaagcag aguugcucua uuuccaauau ugagaccgug 660
aucgaguuuc aacagaagaa uaacagauug uuggagauca ccagggaauu cagcgucaau 720
gcagggguga ccacacccgu aucuaccuac augcugacca acucggaacu ccucuccuua 780
auaaacgaca ugccuauuac uaacgaccaa aaaaaguuga uguccaacaa uguccagauc 840
gugcgacagc aaucuuauuc aauuaugucc auuauaaaag aggaggugcu ggcguacgua 900
gugcagcugc cccuuuacgg agugaucgac accccaugcu ggaagcucca caccuccccc 960
cugugcacca cuaauaccaa agaaggcagc aacaucuguc ugacccguac cgaccgcgga 1020
ugguacugcg auaaugcagg uagcgucucu uuuuuucccc aggcugaaac uugcaagguu 1080
caguccaacc ggguauucug ugacacgaug aacagucuca cccuaccauc agaggugaac 1140
cugugcaaug uggacauauu uaacccuaaa uaugacugua agaucaugac cuccaaaacu 1200
gacguuucca gcagugucau aaccucacug ggcgcaauag uuucaugcua uggaaagacu 1260
aagugcacug ccucuaacaa aaaucgaggu auuauuaaga ccuuuagcaa uggcugcgau 1320
uaugucagua acaaaggugu ugauacagug agugugggca acacauuaua cuauguuaac 1380
aagcaagaag gcaagagccu cuaugugaag ggagaaccaa ucauuaauuu uuacgauccg 1440
cuggucuuuc ccagcgauga guucgaugca uccaucucuc aggugaauga aaaaauuaac 1500
caaucacugg cuuucauacg gaagagcgau gaacugcuga gcgccaucgg gggauacauc 1560
ccugaagcuc cgagggacgg ccaagcuuau guccgcaaag acggagagug gguguugcuc 1620
aguaccuucc uc 1632

<210> SEQ ID NO 275
<211> LENGTH: 1632
<212> TYPE: RNA
<213> ORGANISM: Artificial Sequence
<220> FEATURE:
<223> OTHER INFORMATION: Synthetic Polynucleotide

<400> SEQUENCE: 275
auggaacugc ugauucuuaa ggcgaaugcc auaaccacua ucuugaccgc aguuacuuuu 60
ugcuucgccu cugggcagaa uauuaccgaa gaguucuacc aguccacgug cagugccgug 120
ucuaagggcu accuuuccgc gcuucgcacu ggcugguaca cgucagucau aacgaucgaa 180
cucucuaaua uaaaggaaaa uaaguguaac ggaacagacg cuaaggucaa guuaaucaag 240
caggagcugg acaaauauaa gaaugccgua acggagcucc agcugcucau gcagagcacg 300
ccagcuacaa acaacagggc acgccgugag cucccccgau uuaugaacua cacauugaac 360
aacgccaaga aaacuaacgu gacuuugucc aagaagagga agcggcgauu cuuagggguuc 420 cuuuuggggg uaggcucggc gauugccagu ggggguugccg uaugcaaggu gcuccaccug 480
gaaggggagg ugaacaagau uaagucggcu cugcucagua caaacaaagc ugucgucuca 540
uugucaaacg gagucagugu auugacauuu aaaguccucg accugaagaa cuauauagau 600
aaacaguuac ucccaaucuu gaauaagcag uccuguagca ucagcaacau ugagacagug 660
aucgaguucc agcagaagaa uaaucgccua cucgagauca ccagagaauu cucagucaau 720
gccggaguaa ccacuccugu cagcacauac augcucacaa acucugaacu ccuaagccug 780
auuaaugaua ugccuaucac aaaugaucag aagaaacuca ugagcaauaa ugugcagauu 840
guaagacagc agaguuauuc uauaaugugu auuauuaagg aggagguacu ggccuaugug 900
guucaacuuc cucuguaugg ggugauagau acaccaugcu ggaagcugca caccagccca 960
cuguguacga ccaauacaaa ggagggcucc aauauuugcu uaacacggac ugaccggggg 1020
ugguauugcg acaaugccgg aucagucucc uucuuccccc aagcagagac cugcaaggug 1080
caguccaaua gaguuuucug cgacacaaug aacucgcuga cccuaccuag cgaaguuaac 1140
uuaugcaacg uggauauuuu uaauccgaag uaugauugua aaaucaugac uagcaaaacg 1200
gauguuagcu ccagcguaau caccucccua ggcgcuaucg ugagcuguua uggcaagacg 1260
aagugcacug caucuaauaa aaauaggggu auuauuaaaa ccuucagcaa uggcugcgac 1320
uaugugagca auaagggcgu ggacaccgug ucagugggaa acacccucua uuaugugaac 1380
aagcaggagg gaaaaucccu uuauguaaag ggcgaaccca uuaucaauuu cuaugacccc 1440
cugguuuucc caagcgacga guucgacgca ucuaucucuc aagugaacga gaaaaucaau 1500
cagagucuug ccuuuaucag aaaauccgau gagcugcuuu ccgccaucgg uggcuauauc 1560
ccagaagccc caagagacgg acaagcguac guccggaaag auggugagug gguccuccuc 1620
ucuaccuuuc uu 1632

<210> SEQ ID NO 276
<211> LENGTH: 813
<212> TYPE: RNA
<213> ORGANISM: Artificial Sequence
<220> FEATURE:
<223> OTHER INFORMATION: Synthetic Polynucleotide

<400> SEQUENCE: 276

-continued auggagacuc cugcacagcu gcuguuucug cuauuguugu ggcuuccgga cacuacuggg 60
ucccuccuca ccgaggugga aacauacgug cuguccauca uaccauccgg gcccuugaaa 120
gccgagaucg cccagagacu cgaaucugua uucgcaggaa agaacacgga uuuggaggca 180
cuaauggaau ggcugaagac ccguccgauc cugucuccuc ucacaaaggg gauucuugga 240
uuugucuuua cccucaccgu cccgagcgag cgcggucucc agcgcagacg uuuuguacag 300
aaugcacuga auggcaacgg cgaucccaau aacauggauc gugcgguaaa gcuuuauaaa 360
aagcugaaga gagaaaucac uuuccauggg gcuaaagagg ugagucucuc cuauucaacc 420
ggggcauugg ccucuugcau gggucuuaua uacaaucgaa ugggcaccgu uaccaccgag 480
gccgcauuug gucugguuug ugcuacgugc gagcaaaucg cagauagcca gcaucggucc 540
caucggcaga uggccaccac uacgaacccu cuaauucgac augaaaaucg cauggucug 600 gcuagcacca ccgcaaaggc aauggagcag auggcgggcu cuagugaaca ggcagccgag 660
gcaauggaag uggccaauca gaccaggcag augguccaug cuaugcggac uauugguacc 720
cacccgucca gcagugcugg acugaaggau gaccuccuug agaaccugca ggcauaccag 780
aaacgaaugg gggugcaaau gcagagauuc aag 813

<210> SEQ ID NO 277
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 277
auggaacugc ucauuuugaa ggcaaacgcu aucacgacaa uacucacugc agugaccuuc 60
uguuuugccu caggccagaa cauaaccgag gaguuuuauc aaucuacaug cagcgcugua 120
ucuaaaggcu accugagugc gcuccgcaca ggaugguaca ccuccgugau caccaucgag 180
cucagcaaua uuaaagagaa caagugcaau gguaccgacg cuaaagucaa acuuaucaag 240
caggaacucg acaaauauaa aaacgcugug accgagcugc aguuauugau gcagaguaca 300
ccugccacca auaacagagc uaggagggag uugccuaggu uuaugaacua cacucucaac 360
aacgcgaaaa aaaccaaugu gacgcuaucc aagaaacgga agaggagguu ccuggggguu 420
cuuuuagggg ugggcucugc cauugcuucc ggcguggcug uauguaaagu ucuccaccuc 480
gagggagagg uuaauaagau uaagucggcc cugcugagua cuaacaaagc aguggugucg 540
cugaguaacg gaguaagugu guuaacauuu aaggugcugg accucaagaa uuauauugac 600
aaacaguugc uuccuauucu aaacaaacag agcuguucaa uaaguaauau ugaaacuguu 660
auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccaa aaaaaacuua uguccaacaa cgugcagauu 840
gugcgacagc aauccuauag cauuaugugu aucaucaagg aagagguacu cgcuuauguu 900
gugcagcuac cacucuaugg ugugauugac accccuguu ggaagcugca uaccagucca 960
cucugcacca cuaacacaaa ggaagggagc aauauuugcc ucacucgaac cgacaggggg 1020
ugguauugcg auaaaugcggg cuccgugucc uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaaaacc 1260
aaguguacug ccucuaauaa gaacagaggc auaauuaaaa ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga aaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaagaccaac uuagcgguau caauaauauu gccuuuagca au 1722

<210> SEQ ID NO 278
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 278
auggaacugc ucauuuugaa ggcaaacgcu aucacgacaa uacucacugc agugaccuuc 60
uguuuugccu caggccagaa cauaaccgag gaguuuuauc aaucuacaug cagcgcugua 120
ucuaaaggcu accugagugc gcuccgcaca ggaugguaca ccuccgugau caccaucgag 180
cucagcaaua uuaaagagaa caagugcaau gguaccgacg cuaaagucaa acuuaucaag 240
caggaacucg acaaauauaa gaacgcugug accgagcugc aguuauugau gcagaguaca 300
ccugccacca auaacagagc uaggagggag uugccuaggu uuaugaacua cacucucaac 360
aacgcgaaga agaccaaugu gacgcuaucc aagaaacgga agaggagguu ccugggguuu 420
cuuuuagggg ugggcucugc cauugcuucc ggcguggcug uauguaaagu ucuccaccuc 480
gagggagagg uuaauaagau uaagucggcc cugcugagua cuaacaaagc aguggugucg 540
cugaguaacg gaguaagugu guuaacauuu aaggugcugg accucaagaa uuauauugac 600
aaacaguugc uuccuauucu aaacaaacag agcuguucaa uaaguaauau ugaaacuguu 660
auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccaa aagaaacuua uguccaacaa cgugcagauu 840
gugcgacagc aauccuauag cauuaugugu aucaucaagg aagagguacu cgcuuauguu 900
gugcagcuac cacucuaugg ugugauugac acccccuguu ggaagcugca uaccagucca 960
cucugcacca cuaacacaaa ggaagggagc aauauuugcc ucacucgaac cgacaggggg 1020
ugguauugcg auaaugcggg cuccguguec uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaagacc 1260
aaguguacug ccucuaauaa gaacagaggc auaauuaaga ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga aaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaggaccaac uuagcgguau caauaauauu gccuuuagca au 1722

<210> SEQ ID NO 279
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 279
auggaacugc ucauuuugaa ggcaaacgcu aucacgacaa uacucacugc agugaccuuc 60
uguuuugccu caggccagaa cauaaccgag gaguuuuauc aaucuacaug cagcgcugua 120
ucuaaaggcu accugagugc gcuccgcaca ggaugguaca ccuccgugau caccaucgag 180
cucagcaaua uuaaagagaa caagugcaau gguaccgacg cuaaagucaa acuuaucaag 240
caggaacucg acaaauauaa gaacgcugug accgagcugc aguuauugau gcagaguaca 300
ccugccacca auaacagagc uaggagggag uugccuaggu uuaugaacua cacucucaac 360
aacgcgaaga agaccaaugu gacgcuaucc aagaaacgga agaggagguu ccuggggguu 420
cuuuuagggg ugggcucugc cauugcuucc ggcguggcug uauguaaagu ucuccaccuc 480
gagggagagg uuaauaagau uaagucggcc cugcugagua cuaacaaagc aguggugucg 540
cugaguaacg gaguaagugu guuaacauuu aaggugcugg accucaagaa uuauauugac 600
aaacaguugc uuccuauucu aaacaaacag agcuguucaa uaaguaauau ugaaacuguu 660
auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccag aagaaacuua uguccaacaa cgugcagauu 840
gugcgacagc aauccuauag cauuaugugu aucaucaagg aagagguacu cgcuuauguu 900
gugcagcuac cacucuaugg ugugauugac accccccuguu ggaagcugca uaccagucca 960
cucugcacca cuaacacaaa ggaagggagc aauauuugcc ucacucgaac cgacaggggg 1020
ugguauugcg auaaugcggg cuccgugucc uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaagacc 1260
aaguguacug ccucuaauaa gaacagaggc auaauuaaga ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga gaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaggaccaac uuagcgguau caauaauauu gccuuuagca au 1722

<210> SEQ ID NO 280
<211> LENGTH: 1722
<212> TYPE: RNA

<213> ORGANISM: Artificial Sequence
<220> FEATURE:
<223> OTHER INFORMATION: Synthetic Polynucleotide

<400> SEQUENCE: 280
auggaacugc ucauuuugaa ggcaaacgcu aucacgacaa uacucacugc agugaccuuc 60
uguuuugccu caggccagaa cauaaccgag gaguuuuauc aaucuacaug cagcgcugua 120
ucuaaaggcu accugagugc gcuccgcaca ggaugguaca ccuccgugau caccaucgag 180
cucagcaaua uuaaagagaa caagugcaau gguaccgacg cuaaagucaa acuuaucaag 240
caggaacucg acaaauauaa gaacgcugug accgagcugc aguuauugau gcagaguaca 300
ccugccacca auaacagagc uaggagggag uugccuaggu uuaugaacua cacucucaac 360
aacgcgaaga aaaccaaugu gacgcuaucc aagaaacgga agaggagguu ccuggggguu 420
cuuuuagggg ugggcucugc cauugcuucc ggcguggcug uauguaaagu ucuccaccuc 480
gagggagagg uuaauaagau uaagucggcc cugcugagua cuaacaaagc aguggugucg 540
cugaguaacg gaguaagugu guuaacauuu aaggugcugg accucaagaa uuauauugac 600
aaacaguugc uuccuauucu aaacaaacag agcuguucaa uaaguaauau ugaaacuguu 660
auugaguuuc agcagaagaa caacaggcuu cuugagauua cacgcgaguu cagugucaau 720
gccggcguua caacacccgu gucuaccuac augcugacga auucugagcu ucucucucuc 780
auaaacgaca ugcccauuac gaaugaccaa aagaaacuua uguccaacaa cgugcagauu 840
gugcgacagc aauccuauag cauuaugugu aucaucaagg aagagguacu cgcuuauguu 900
gugcagcuac cacucuaugg ugugauugac acccccuguu ggaagcugca uaccagucca 960
cucugcacca cuaacacaaa ggaagggagc aauauuugcc ucacucgaac cgacaggggg 1020
ugguauugcg auaaugcggg cuccgugucc uucuuuccac aggcugaaac uuguaaggua 1080
cagucaaacc gcguguucug ugauacuaug aauucucuga cucuucccag cgagguuaau 1140
cucugcaacg ucgacauuuu caauccuaaa uaugacugca agaucaugac cagcaagacc 1200
gacgucucca gcucaguaau cacuagccua ggggccauug uaagcugcua uggcaaaacc 1260
aaguguacug ccucuaauaa gaacagaggc auaaauuaaaa ccuuuucaaa uggcugugac 1320
uaugugucga auaagggcgu cgacacgguc ucaguaggga auacccucua cuacguuaac 1380
aaacaggaag gcaaaucccu uuauguaaag ggcgagccca ucauaaauuu cuacgaccca 1440
cuuguguucc ccagugauga auucgaugca ucaaucuccc aggugaacga aaagaucaau 1500
caaucccuug cuuuuauacg aaagucagau gaacuccugc auaacgugaa ugcugggaaa 1560
ucuacaacca acaucaugau cacuaccauc auuauuguga uuaucguaau ucugcuaucc 1620
uugauugcug ucgggcugcu ucuguacugu aaggccagau cgacgccugu gacccuuuca 1680
aaagaccaac uuagcgguau caauaauauu gccuuuagca au 1722

<210> SEQ ID NO 281
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 281

Met Asp Trp Thr Trp Ile Leu Phe Leu Val Ala Ala Ala Thr Arg Val
1 5 10 15

His Ser

<210> SEQ ID NO 282
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 282

```
Met Glu Thr Pro Ala Gln Leu Leu Phe Leu Leu Leu Leu Trp Leu Pro
1               5                   10                  15

Asp Thr Thr Gly
            20
```

<210> SEQ ID NO 283
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 283

```
Met Leu Gly Ser Asn Ser Gly Gln Arg Val Val Phe Thr Ile Leu Leu
1               5                   10                  15

Leu Leu Val Ala Pro Ala Tyr Ser
            20
```

<210> SEQ ID NO 284
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 284

```
Met Lys Cys Leu Leu Tyr Leu Ala Phe Leu Phe Ile Gly Val Asn Cys
1               5                   10                  15

Ala
```

<210> SEQ ID NO 285
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 285

```
Met Trp Leu Val Ser Leu Ala Ile Val Thr Ala Cys Ala Gly Ala
1               5                   10                  15
```

<210> SEQ ID NO 286
<211> LENGTH: 13
<212> TYPE: PRT
<213> ORGANISM: Salmonella typhimurium

<400> SEQUENCE: 286

```
Leu Gln Arg Val Arg Glu Leu Ala Val Gln Ser Ala Asn
1               5                   10
```

<210> SEQ ID NO 287
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 287
tggagactcc cgctcagctg ctgtttttgc tcctcctatg gctgccggat accaccggc 59

<210> SEQ ID NO 288
<211> LENGTH: 60
<212> TYPE: RNA
<213> ORGANISM: Artificial Sequence
<220> FEATURE:
<223> OTHER INFORMATION: Synthetic Polynucleotide

<400> SEQUENCE: 288
auggagacuc ccgcucagcu gcuguuuuug cuccuccuau ggcugccgga uaccaccggc 60

<210> SEQ ID NO 289
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 289

Met Glu Leu Leu Ile Leu Lys Ala Asn Ala Ile Thr Thr Ile Leu Thr
1 5 10 15

Ala Val Thr Phe Cys
20

<210> SEQ ID NO 290
<211> LENGTH: 553
<212> TYPE: PRT
<213> ORGANISM: Artificial Sequence
<220> FEATURE:
<223> OTHER INFORMATION: Synthetic Polypeptide

<400> SEQUENCE: 290

Phe Ala Ser Gly Gln Asn Ile Thr Glu Glu Phe Tyr Gln Ser Thr Cys
1 5 10 15

Ser Ala Val Ser Lys Gly Tyr Leu Ser Ala Leu Arg Thr Gly Trp Tyr
20 25 30

Thr Ser Val Ile Thr Ile Glu Leu Ser Asn Ile Lys Lys Asn Lys Cys
35 40 45

Asn Gly Thr Asp Ala Lys Val Lys Leu Ile Lys Gln Glu Leu Asp Lys
50 55 60

Tyr Lys Asn Ala Val Thr Glu Leu Gln Leu Leu Met Gln Ser Thr Gln
65 70 75 80

Ala Thr Asn Asn Arg Ala Arg Arg Glu Leu Pro Arg Phe Met Asn Tyr
85 90 95

Thr Leu Asn Asn Ala Lys Lys Thr Asn Val Thr Leu Ser Lys Lys Arg
100 105 110

Lys Arg Arg Phe Leu Gly Phe Leu Leu Gly Val Gly Ser Ala Ile Ala
115 120 125

Ser Gly Val Ala Val Ser Lys Val Leu His Leu Glu Gly Glu Val Asn
130 135 140

Lys Ile Lys Ser Ala Leu Leu Ser Thr Asn Lys Ala Val Val Ser Leu
145 150 155 160

Ser Asn Gly Val Ser Val Leu Thr Ser Lys Val Leu Asp Leu Lys Asn
165 170 175

Tyr Ile Asp Lys Gln Leu Leu Pro Ile Val Asn Lys Gln Ser Cys Ser
180 185 190

Ile Ser Asn Ile Glu Thr Val Ile Glu Phe Gln Gln Lys Asn Asn Arg

```
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445

Lys Gly Glu Pro Ile Ile Asn Phe Tyr Asp Pro Leu Val Phe Pro Ser
    450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu His Asn Val Asn
                485                 490                 495

Ala Gly Lys Ser Thr Thr Asn Ile Met Ile Thr Thr Ile Ile Ile Val
            500                 505                 510

Ile Ile Val Ile Leu Leu Ser Leu Ile Ala Val Gly Leu Leu Leu Tyr
        515                 520                 525

Cys Lys Ala Arg Ser Thr Pro Val Thr Leu Ser Lys Asp Gln Leu Ser
    530                 535                 540

Gly Ile Asn Asn Ile Ala Phe Ser Asn
545                 550
```

<210> SEQ ID NO 291
<211> LENGTH: 553
<212> TYPE: PRT
<213> ORGANISM: Artificial Sequence
<220> FEATURE:
<223> OTHER INFORMATION: Synthetic Polypeptide

<400> SEQUENCE: 291

```
Phe Ala Ser Gly Gln Asn Ile Thr Glu Glu Phe Tyr Gln Ser Thr Cys
```

-continued

```
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Glu Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Pro
65                  70                  75                  80

Ala Thr Asn Asn Arg Ala Arg Arg Glu Leu Pro Arg Phe Met Asn Tyr
                85                  90                  95

Thr Leu Asn Asn Ala Lys Lys Thr Asn Val Thr Leu Ser Lys Lys Arg
            100                 105                 110

Lys Arg Arg Phe Leu Gly Phe Leu Leu Gly Val Gly Ser Ala Ile Ala
        115                 120                 125

Ser Gly Val Ala Val Cys Lys Val Leu His Leu Glu Gly Glu Val Asn
    130                 135                 140

Lys Ile Lys Ser Ala Leu Leu Ser Thr Asn Lys Ala Val Val Ser Leu
145                 150                 155                 160

Ser Asn Gly Val Ser Val Leu Thr Phe Lys Val Leu Asp Leu Lys Asn
                165                 170                 175

Tyr Ile Asp Lys Gln Leu Leu Pro Ile Leu Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Cys Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430
```

Asn Thr Leu Tyr Tyr Val Asn Lys Gln Glu Gly Lys Ser Leu Tyr Val
435 440 445

Lys Gly Glu Pro Ile Ile Asn Phe Tyr Asp Pro Leu Val Phe Pro Ser
450 455 460

Asp Glu Phe Asp Ala Ser Ile Ser Gln Val Asn Glu Lys Ile Asn Gln
465 470 475 480

Ser Leu Ala Phe Ile Arg Lys Ser Asp Glu Leu Leu His Asn Val Asn
485 490 495

Ala Gly Lys Ser Thr Thr Asn Ile Met Ile Thr Thr Ile Ile Ile Val
500 505 510

Ile Ile Val Ile Leu Leu Ser Leu Ile Ala Val Gly Leu Leu Leu Tyr
515 520 525

Cys Lys Ala Arg Ser Thr Pro Val Thr Leu Ser Lys Asp Gln Leu Ser
530 535 540

Gly Ile Asn Asn Ile Ala Phe Ser Asn
545 550

<210> SEQ ID NO 292
<211> LENGTH: 480
<212> TYPE: PRT
<213> ORGANISM: Artificial Sequence
<220> FEATURE:
<223> OTHER INFORMATION: Synthetic Polypeptide

<400> SEQUENCE: 292

Phe Ala Ser Gly Gln Asn Ile Thr Glu Glu Phe Tyr Gln Ser Thr Cys
1 5 10 15

Ser Ala Val Ser Lys Gly Tyr Leu Ser Ala Leu Arg Thr Gly Trp Tyr
20 25 30

Thr Ser Val Ile Thr Ile Glu Leu Ser Asn Ile Lys Lys Asn Lys Cys
35 40 45

Asn Gly Thr Asp Ala Lys Val Lys Leu Ile Lys Gln Glu Leu Asp Lys
50 55 60

Tyr Lys Asn Ala Val Thr Glu Leu Gln Leu Leu Met Gln Ser Thr Gln
65 70 75 80

Ala Thr Asn Asn Arg Ala Arg Gln Gln Gln Gln Arg Phe Leu Gly Phe
85 90 95

Leu Leu Gly Val Gly Ser Ala Ile Ala Ser Gly Val Ala Val Ser Lys
100 105 110

Val Leu His Leu Glu Gly Glu Val Asn Lys Ile Lys Ser Ala Leu Leu
115 120 125

Ser Thr Asn Lys Ala Val Val Ser Leu Ser Asn Gly Val Ser Val Leu
130 135 140

Thr Ser Lys Val Leu Asp Leu Lys Asn Tyr Ile Asp Lys Gln Leu Leu
145 150 155 160

Pro Ile Val Asn Lys Gln Ser Cys Ser Ile Ser Asn Ile Glu Thr Val
165 170 175

Ile Glu Phe Gln Gln Lys Asn Asn Arg Leu Leu Glu Ile Thr Arg Glu
180 185 190

Phe Ser Val Asn Ala Gly Val Thr Thr Pro Val Ser Thr Tyr Met Leu
195 200 205

Thr Asn Ser Glu Leu Leu Ser Leu Ile Asn Asp Met Pro Ile Thr Asn
210 215 220

Asp Gln Lys Lys Leu Met Ser Asn Asn Val Gln Ile Val Arg Gln Gln
225 230 235 240

```
Ser Tyr Ser Ile Met Ser Ile Ile Lys Glu Glu Val Leu Ala Tyr Val
                245                 250                 255

Val Gln Leu Pro Leu Tyr Gly Val Ile Asp Thr Pro Cys Trp Lys Leu
            260                 265                 270

His Thr Ser Pro Leu Cys Thr Thr Asn Thr Lys Glu Gly Ser Asn Ile
        275                 280                 285

Cys Leu Thr Arg Thr Asp Arg Gly Trp Tyr Cys Asp Asn Ala Gly Ser
    290                 295                 300

Val Ser Phe Phe Pro Gln Ala Glu Thr Cys Lys Val Gln Ser Asn Arg
305                 310                 315                 320

Val Phe Cys Asp Thr Met Asn Ser Leu Thr Leu Pro Ser Glu Val Asn
                325                 330                 335

Leu Cys Asn Val Asp Ile Phe Asn Pro Lys Tyr Asp Cys Lys Ile Met
            340                 345                 350

Thr Ser Lys Thr Asp Val Ser Ser Ser Val Ile Thr Ser Leu Gly Ala
        355                 360                 365

Ile Val Ser Cys Tyr Gly Lys Thr Lys Cys Thr Ala Ser Asn Lys Asn
    370                 375                 380

Arg Gly Ile Ile Lys Thr Phe Ser Asn Gly Cys Asp Tyr Val Ser Asn
385                 390                 395                 400

Lys Gly Val Asp Thr Val Ser Val Gly Asn Thr Leu Tyr Tyr Val Asn
                405                 410                 415

Lys Gln Glu Gly Lys Ser Leu Tyr Val Lys Gly Glu Pro Ile Ile Asn
            420                 425                 430

Phe Tyr Asp Pro Leu Val Phe Pro Ser Asp Glu Phe Asp Ala Ser Ile
        435                 440                 445

Ser Gln Val Asn Glu Lys Ile Asn Gln Ser Leu Ala Phe Ile Arg Lys
    450                 455                 460

Ser Asp Glu Leu Leu His Asn Val Asn Ala Gly Lys Ser Thr Thr Asn
465                 470                 475                 480


<210> SEQ ID NO 293
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 293

Phe Ala Ser Gly Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Lys Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Gln
65                  70                  75                  80

Ala Thr Asn Asn Arg Ala Arg Gln Gln Gln Gln Arg Phe Leu Gly Phe
                85                  90                  95

Leu Leu Gly Val Gly Ser Ala Ile Ala Ser Gly Val Ala Val Ser Lys
            100                 105                 110

Val Leu His Leu Glu Gly Glu Val Asn Lys Ile Lys Ser Ala Leu Leu
        115                 120                 125
```

```
Ser Thr Asn Lys Ala Val Val Ser Leu Ser Asn Gly Val Ser Val Leu
    130                 135                 140

Thr Ser Lys Val Leu Asp Leu Lys Asn Tyr Ile Asp Lys Gln Leu Leu
145                 150                 155                 160

Pro Ile Val Asn Lys Gln Ser Cys Ser Ile Ser Asn Ile Glu Thr Val
                165                 170                 175

Ile Glu Phe Gln Gln Lys Asn Asn Arg Leu Leu Glu Ile Thr Arg Glu
            180                 185                 190

Phe Ser Val Asn Ala Gly Val Thr Thr Pro Val Ser Thr Tyr Met Leu
        195                 200                 205

Thr Asn Ser Glu Leu Leu Ser Leu Ile Asn Asp Met Pro Ile Thr Asn
    210                 215                 220

Asp Gln Lys Lys Leu Met Ser Asn Asn Val Gln Ile Val Arg Gln Gln
225                 230                 235                 240

Ser Tyr Ser Ile Met Ser Ile Ile Lys Glu Glu Val Leu Ala Tyr Val
                245                 250                 255

Val Gln Leu Pro Leu Tyr Gly Val Ile Asp Thr Pro Cys Trp Lys Leu
            260                 265                 270

His Thr Ser Pro Leu Cys Thr Thr Asn Thr Lys Glu Gly Ser Asn Ile
        275                 280                 285

Cys Leu Thr Arg Thr Asp Arg Gly Trp Tyr Cys Asp Asn Ala Gly Ser
    290                 295                 300

Val Ser Phe Phe Pro Gln Ala Glu Thr Cys Lys Val Gln Ser Asn Arg
305                 310                 315                 320

Val Phe Cys Asp Thr Met Asn Ser Leu Thr Leu Pro Ser Glu Val Asn
                325                 330                 335

Leu Cys Asn Val Asp Ile Phe Asn Pro Lys Tyr Asp Cys Lys Ile Met
            340                 345                 350

Thr Ser Lys Thr Asp Val Ser Ser Ser Val Ile Thr Ser Leu Gly Ala
        355                 360                 365

Ile Val Ser Cys Tyr Gly Lys Thr Lys Cys Thr Ala Ser Asn Lys Asn
    370                 375                 380

Arg Gly Ile Ile Lys Thr Phe Ser Asn Gly Cys Asp Tyr Val Ser Asn
385                 390                 395                 400

Lys Gly Val Asp Thr Val Ser Val Gly Asn Thr Leu Tyr Tyr Val Asn
                405                 410                 415

Lys Gln Glu Gly Lys Ser Leu Tyr Val Lys Gly Glu Pro Ile Ile Asn
            420                 425                 430

Phe Tyr Asp Pro Leu Val Phe Pro Ser Asp Glu Phe Asp Ala Ser Ile
        435                 440                 445

Ser Gln Val Asn Glu Lys Ile Asn Gln Ser Leu Ala Phe Ile Arg Lys
    450                 455                 460

Ser Asp Glu Leu Leu
465
```

<210> SEQ ID NO 294
<211> LENGTH: 543
<212> TYPE: PRT
<213> ORGANISM: Artificial Sequence
<220> FEATURE:
<223> OTHER INFORMATION: Synthetic Polypeptide

<400> SEQUENCE: 294

```
Phe Ala Ser Gly Gln Asn Ile Thr Glu Glu Phe Tyr Gln Ser Thr Cys
1               5                   10                  15
```

```
Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Glu Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Pro
65                  70                  75                  80

Ala Thr Asn Asn Arg Ala Arg Arg Glu Leu Pro Arg Phe Met Asn Tyr
                85                  90                  95

Thr Leu Asn Asn Ala Lys Lys Thr Asn Val Thr Leu Ser Lys Lys Gln
            100                 105                 110

Lys Gln Gln Ala Ile Ala Ser Gly Val Ala Val Ser Lys Val Leu His
        115                 120                 125

Leu Glu Gly Glu Val Asn Lys Ile Lys Ser Ala Leu Leu Ser Thr Asn
    130                 135                 140

Lys Ala Val Val Ser Leu Ser Asn Gly Val Ser Val Leu Thr Ser Lys
145                 150                 155                 160

Val Leu Asp Leu Lys Asn Tyr Ile Asp Lys Gln Leu Leu Pro Ile Val
                165                 170                 175

Asn Lys Gln Ser Cys Ser Ile Ser Asn Ile Glu Thr Val Ile Glu Phe
            180                 185                 190

Gln Gln Lys Asn Asn Arg Leu Leu Glu Ile Thr Arg Glu Phe Ser Val
        195                 200                 205

Asn Ala Gly Val Thr Thr Pro Val Ser Thr Tyr Met Leu Thr Asn Ser
    210                 215                 220

Glu Leu Leu Ser Leu Ile Asn Asp Met Pro Ile Thr Asn Asp Gln Lys
225                 230                 235                 240

Lys Leu Met Ser Asn Asn Val Gln Ile Val Arg Gln Gln Ser Tyr Ser
                245                 250                 255

Ile Met Ser Ile Ile Lys Glu Glu Val Leu Ala Tyr Val Val Gln Leu
            260                 265                 270

Pro Leu Tyr Gly Val Ile Asp Thr Pro Cys Trp Lys Leu His Thr Ser
        275                 280                 285

Pro Leu Cys Thr Thr Asn Thr Lys Glu Gly Ser Asn Ile Cys Leu Thr
    290                 295                 300

Arg Thr Asp Arg Gly Trp Tyr Cys Asp Asn Ala Gly Ser Val Ser Phe
305                 310                 315                 320

Phe Pro Gln Ala Glu Thr Cys Lys Val Gln Ser Asn Arg Val Phe Cys
                325                 330                 335

Asp Thr Met Asn Ser Leu Thr Leu Pro Ser Glu Val Asn Leu Cys Asn
            340                 345                 350

Val Asp Ile Phe Asn Pro Lys Tyr Asp Cys Lys Ile Met Thr Ser Lys
        355                 360                 365

Thr Asp Val Ser Ser Ser Val Ile Thr Ser Leu Gly Ala Ile Val Ser
    370                 375                 380

Cys Tyr Gly Lys Thr Lys Cys Thr Ala Ser Asn Lys Asn Arg Gly Ile
385                 390                 395                 400

Ile Lys Thr Phe Ser Asn Gly Cys Asp Tyr Val Ser Asn Lys Gly Val
                405                 410                 415

Asp Thr Val Ser Val Gly Asn Thr Leu Tyr Tyr Val Asn Lys Gln Glu
            420                 425                 430
```

```
Gly Lys Ser Leu Tyr Val Lys Gly Glu Pro Ile Ile Asn Phe Tyr Asp
        435                 440                 445

Pro Leu Val Phe Pro Ser Asp Glu Phe Asp Ala Ser Ile Ser Gln Val
    450                 455                 460

Asn Glu Lys Ile Asn Gln Ser Leu Ala Phe Ile Arg Lys Ser Asp Glu
465                 470                 475                 480

Leu Leu His Asn Val Asn Ala Gly Lys Ser Thr Thr Asn Ile Met Ile
                485                 490                 495

Thr Thr Ile Ile Ile Val Ile Ile Val Ile Leu Leu Ser Leu Ile Ala
            500                 505                 510

Val Gly Leu Leu Leu Tyr Cys Lys Ala Arg Ser Thr Pro Val Thr Leu
        515                 520                 525

Ser Lys Asp Gln Leu Ser Gly Ile Asn Asn Ile Ala Phe Ser Asn
    530                 535                 540


<210> SEQ ID NO 295
<211> LENGTH: 464
<212> TYPE: PRT
<213> ORGANISM: Artificial Sequence
<220> FEATURE:
<223> OTHER INFORMATION: Synthetic Polypeptide

<400> SEQUENCE: 295

Phe Ala Ser Ser Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Glu Asn Lys Cys
        35                  40                  45

Asn Gly Thr Asp Ala Lys Val Lys Leu Ile Lys Gln Glu Leu Asp Lys
    50                  55                  60

Tyr Lys Ser Ala Val Thr Glu Leu Gln Leu Leu Met Gln Ser Thr Pro
65                  70                  75                  80

Ala Thr Asn Asn Lys Phe Leu Gly Phe Leu Gln Gly Val Gly Ser Ala
                85                  90                  95

Ile Ala Ser Gly Ile Ala Val Ser Lys Val Leu His Leu Glu Gly Glu
            100                 105                 110

Val Asn Lys Ile Lys Ser Ala Leu Leu Ser Thr Asn Lys Ala Val Val
        115                 120                 125

Ser Leu Ser Asn Gly Val Ser Val Leu Thr Ser Lys Val Leu Asp Leu
    130                 135                 140

Lys Asn Tyr Ile Asp Lys Gln Leu Leu Pro Ile Val Asn Lys Gln Ser
145                 150                 155                 160

Cys Ser Ile Ser Asn Ile Glu Thr Val Ile Glu Phe Gln Gln Lys Asn
                165                 170                 175

Asn Arg Leu Leu Glu Ile Thr Arg Glu Phe Ser Val Asn Ala Gly Val
            180                 185                 190

Thr Thr Pro Val Ser Thr Tyr Met Leu Thr Asn Ser Glu Leu Leu Ser
        195                 200                 205

Leu Ile Asn Asp Met Pro Ile Thr Asn Asp Gln Lys Lys Leu Met Ser
    210                 215                 220

Asn Asn Val Gln Ile Val Arg Gln Gln Ser Tyr Ser Ile Met Ser Ile
225                 230                 235                 240

Ile Lys Glu Glu Val Leu Ala Tyr Val Val Gln Leu Pro Leu Tyr Gly
                245                 250                 255
```

Val Ile Asp Thr Pro Cys Trp Lys Leu His Thr Ser Pro Leu Cys Thr
260 265 270

Thr Asn Thr Lys Glu Gly Ser Asn Ile Cys Leu Thr Arg Thr Asp Arg
275 280 285

Gly Trp Tyr Cys Asp Asn Ala Gly Ser Val Ser Phe Phe Pro Leu Ala
290 295 300

Glu Thr Cys Lys Val Gln Ser Asn Arg Val Phe Cys Asp Thr Met Asn
305 310 315 320

Ser Leu Thr Leu Pro Ser Glu Val Asn Leu Cys Asn Ile Asp Ile Phe
325 330 335

Asn Pro Lys Tyr Asp Cys Lys Ile Met Thr Ser Lys Thr Asp Val Ser
340 345 350

Ser Ser Val Ile Thr Ser Leu Gly Ala Ile Val Ser Cys Tyr Gly Lys
355 360 365

Thr Lys Cys Thr Ala Ser Asn Lys Asn Arg Gly Ile Ile Lys Thr Phe
370 375 380

Ser Asn Gly Cys Asp Tyr Val Ser Asn Lys Gly Val Asp Thr Val Ser
385 390 395 400

Val Gly Asn Thr Leu Tyr Tyr Val Asn Lys Gln Glu Gly Lys Ser Leu
405 410 415

Tyr Val Lys Gly Glu Pro Ile Ile Asn Phe Tyr Asp Pro Leu Val Phe
420 425 430

Pro Ser Asp Glu Phe Asp Ala Ser Ile Ser Gln Val Asn Glu Lys Ile
435 440 445

Asn Gly Thr Leu Ala Phe Ile Arg Lys Ser Asp Glu Lys Leu His Asn
450 455 460

<210> SEQ ID NO 296
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 296

Phe Ala Ser Gly Gln Asn Ile Thr Glu Glu Phe Tyr Gln Ser Thr Cys
1 5 10 15

Ser Ala Val Ser Lys Gly Tyr Leu Ser Ala Leu Arg Thr Gly Trp Tyr
20 25 30

Thr Ser Val Ile Thr Ile Glu Leu Ser Asn Ile Lys Lys Asn Lys Cys
35 40 45

Asn Gly Thr Asp Ala Lys Val Lys Leu Ile Lys Gln Glu Leu Asp Lys
50 55 60

Tyr Lys Asn Ala Val Thr Glu Leu Gln Leu Leu Met Gln Ser Thr Gln
65 70 75 80

Ala Thr Asn Asn Arg Ala Arg Arg Glu Leu Pro Arg Phe Met Asn Tyr
85 90 95

Thr Leu Asn Asn Ala Lys Lys Thr Asn Val Thr Leu Ser Lys Lys Arg
100 105 110

Lys Arg Arg Phe Leu Gly Phe Leu Leu Gly Val Gly Ser Ala Ile Ala
115 120 125

Ser Gly Val Ala Val Ser Lys Val Leu His Leu Glu Gly Glu Val Asn
130 135 140

Lys Ile Lys Ser Ala Leu Leu Ser Thr Asn Lys Ala Val Val Ser Leu
145 150 155 160

-continued

```
Ser Asn Gly Val Ser Val Leu Thr Ser Lys Val Leu Asp Leu Lys Asn
                165                 170                 175

Tyr Ile Asp Lys Gln Leu Leu Pro Ile Val Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445

Lys Gly Glu Pro Ile Ile Asn Phe Tyr Asp Pro Leu Val Phe Pro Ser
    450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu
                485                 490
```

<210> SEQ ID NO 297
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 297

```
Phe Ala Ser Gly Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30
```

-continued

```
Thr Ser Val Ile Thr Ile Glu Leu Ser Asn Ile Lys Glu Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Pro
65                  70                  75                  80

Ala Thr Asn Asn Arg Ala Arg Arg Glu Leu Pro Arg Phe Met Asn Tyr
                85                  90                  95

Thr Leu Asn Asn Ala Lys Lys Thr Asn Val Thr Leu Ser Lys Lys Arg
            100                 105                 110

Lys Arg Arg Phe Leu Gly Phe Leu Leu Gly Val Gly Ser Ala Ile Ala
        115                 120                 125

Ser Gly Val Ala Val Cys Lys Val Leu His Leu Glu Gly Glu Val Asn
    130                 135                 140

Lys Ile Lys Ser Ala Leu Leu Ser Thr Asn Lys Ala Val Val Ser Leu
145                 150                 155                 160

Ser Asn Gly Val Ser Val Leu Thr Phe Lys Val Leu Asp Leu Lys Asn
                165                 170                 175

Tyr Ile Asp Lys Gln Leu Leu Pro Ile Leu Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Cys Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445

Lys Gly Glu Pro Ile Ile Asn Phe Tyr Asp Pro Leu Val Phe Pro Ser
```

```
    450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu
                485                 490


<210> SEQ ID NO 298
<211> LENGTH: 480
<212> TYPE: PRT
<213> ORGANISM: Artificial Sequence
<220> FEATURE:
<223> OTHER INFORMATION: Synthetic Polypeptide

<400> SEQUENCE: 298

Phe Ala Ser Gly Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Lys Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Gln
65                  70                  75                  80

Ala Thr Asn Asn Arg Ala Arg Gln Gln Gln Gln Arg Phe Leu Gly Phe
                85                  90                  95

Leu Leu Gly Val Gly Ser Ala Ile Ala Ser Gly Val Ala Val Ser Lys
            100                 105                 110

Val Leu His Leu Glu Gly Glu Val Asn Lys Ile Lys Ser Ala Leu Leu
        115                 120                 125

Ser Thr Asn Lys Ala Val Val Ser Leu Ser Asn Gly Val Ser Val Leu
    130                 135                 140

Thr Ser Lys Val Leu Asp Leu Lys Asn Tyr Ile Asp Lys Gln Leu Leu
145                 150                 155                 160

Pro Ile Val Asn Lys Gln Ser Cys Ser Ile Ser Asn Ile Glu Thr Val
                165                 170                 175

Ile Glu Phe Gln Gln Lys Asn Asn Arg Leu Leu Glu Ile Thr Arg Glu
            180                 185                 190

Phe Ser Val Asn Ala Gly Val Thr Thr Pro Val Ser Thr Tyr Met Leu
        195                 200                 205

Thr Asn Ser Glu Leu Leu Ser Leu Ile Asn Asp Met Pro Ile Thr Asn
    210                 215                 220

Asp Gln Lys Lys Leu Met Ser Asn Asn Val Gln Ile Val Arg Gln Gln
225                 230                 235                 240

Ser Tyr Ser Ile Met Ser Ile Ile Lys Glu Glu Val Leu Ala Tyr Val
                245                 250                 255

Val Gln Leu Pro Leu Tyr Gly Val Ile Asp Thr Pro Cys Trp Lys Leu
            260                 265                 270

His Thr Ser Pro Leu Cys Thr Thr Asn Thr Lys Glu Gly Ser Asn Ile
        275                 280                 285

Cys Leu Thr Arg Thr Asp Arg Gly Trp Tyr Cys Asp Asn Ala Gly Ser
    290                 295                 300

Val Ser Phe Phe Pro Gln Ala Glu Thr Cys Lys Val Gln Ser Asn Arg
305                 310                 315                 320

Val Phe Cys Asp Thr Met Asn Ser Leu Thr Leu Pro Ser Glu Val Asn
```

```
                325                 330                 335

Leu Cys Asn Val Asp Ile Phe Asn Pro Lys Tyr Asp Cys Lys Ile Met
            340                 345                 350

Thr Ser Lys Thr Asp Val Ser Ser Ser Val Ile Thr Ser Leu Gly Ala
        355                 360                 365

Ile Val Ser Cys Tyr Gly Lys Thr Lys Cys Thr Ala Ser Asn Lys Asn
    370                 375                 380

Arg Gly Ile Ile Lys Thr Phe Ser Asn Gly Cys Asp Tyr Val Ser Asn
385                 390                 395                 400

Lys Gly Val Asp Thr Val Ser Val Gly Asn Thr Leu Tyr Tyr Val Asn
                405                 410                 415

Lys Gln Glu Gly Lys Ser Leu Tyr Val Lys Gly Glu Pro Ile Ile Asn
            420                 425                 430

Phe Tyr Asp Pro Leu Val Phe Pro Ser Asp Glu Phe Asp Ala Ser Ile
        435                 440                 445

Ser Gln Val Asn Glu Lys Ile Asn Gln Ser Leu Ala Phe Ile Arg Lys
    450                 455                 460

Ser Asp Glu Leu Leu His Asn Val Asn Ala Gly Lys Ser Thr Thr Asn
465                 470                 475                 480


<210> SEQ ID NO 299
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 299

Phe Ala Ser Gly Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Lys Asn Lys Cys
        35                  40                  45

Asn Gly Thr Asp Ala Lys Val Lys Leu Ile Lys Gln Glu Leu Asp Lys
    50                  55                  60

Tyr Lys Asn Ala Val Thr Glu Leu Gln Leu Leu Met Gln Ser Thr Gln
65                  70                  75                  80

Ala Thr Asn Asn Arg Ala Arg Gln Gln Gln Gln Arg Phe Leu Gly Phe
                85                  90                  95

Leu Leu Gly Val Gly Ser Ala Ile Ala Ser Gly Val Ala Val Ser Lys
            100                 105                 110

Val Leu His Leu Glu Gly Glu Val Asn Lys Ile Lys Ser Ala Leu Leu
        115                 120                 125

Ser Thr Asn Lys Ala Val Val Ser Leu Ser Asn Gly Val Ser Val Leu
    130                 135                 140

Thr Ser Lys Val Leu Asp Leu Lys Asn Tyr Ile Asp Lys Gln Leu Leu
145                 150                 155                 160

Pro Ile Val Asn Lys Gln Ser Cys Ser Ile Ser Asn Ile Glu Thr Val
                165                 170                 175

Ile Glu Phe Gln Gln Lys Asn Asn Arg Leu Leu Glu Ile Thr Arg Glu
            180                 185                 190

Phe Ser Val Asn Ala Gly Val Thr Thr Pro Val Ser Thr Tyr Met Leu
        195                 200                 205

Thr Asn Ser Glu Leu Leu Ser Leu Ile Asn Asp Met Pro Ile Thr Asn
```

```
    210                 215                 220

Asp Gln Lys Lys Leu Met Ser Asn Asn Val Gln Ile Val Arg Gln Gln
225                 230                 235                 240

Ser Tyr Ser Ile Met Ser Ile Ile Lys Glu Glu Val Leu Ala Tyr Val
                245                 250                 255

Val Gln Leu Pro Leu Tyr Gly Val Ile Asp Thr Pro Cys Trp Lys Leu
            260                 265                 270

His Thr Ser Pro Leu Cys Thr Thr Asn Thr Lys Glu Gly Ser Asn Ile
        275                 280                 285

Cys Leu Thr Arg Thr Asp Arg Gly Trp Tyr Cys Asp Asn Ala Gly Ser
    290                 295                 300

Val Ser Phe Phe Pro Gln Ala Glu Thr Cys Lys Val Gln Ser Asn Arg
305                 310                 315                 320

Val Phe Cys Asp Thr Met Asn Ser Leu Thr Leu Pro Ser Glu Val Asn
                325                 330                 335

Leu Cys Asn Val Asp Ile Phe Asn Pro Lys Tyr Asp Cys Lys Ile Met
            340                 345                 350

Thr Ser Lys Thr Asp Val Ser Ser Ser Val Ile Thr Ser Leu Gly Ala
        355                 360                 365

Ile Val Ser Cys Tyr Gly Lys Thr Lys Cys Thr Ala Ser Asn Lys Asn
    370                 375                 380

Arg Gly Ile Ile Lys Thr Phe Ser Asn Gly Cys Asp Tyr Val Ser Asn
385                 390                 395                 400

Lys Gly Val Asp Thr Val Ser Val Gly Asn Thr Leu Tyr Tyr Val Asn
                405                 410                 415

Lys Gln Glu Gly Lys Ser Leu Tyr Val Lys Gly Glu Pro Ile Ile Asn
            420                 425                 430

Phe Tyr Asp Pro Leu Val Phe Pro Ser Asp Glu Phe Asp Ala Ser Ile
        435                 440                 445

Ser Gln Val Asn Glu Lys Ile Asn Gln Ser Leu Ala Phe Ile Arg Lys
    450                 455                 460

Ser Asp Glu Leu Leu
465


<210> SEQ ID NO 300
<211> LENGTH: 464
<212> TYPE: PRT
<213> ORGANISM: Artificial Sequence
<220> FEATURE:
<223> OTHER INFORMATION: Synthetic Polypeptide

<400> SEQUENCE: 300

Phe Ala Ser Ser Gln Asn Ile Thr Glu Glu Phe Tyr Gln Ser Thr Cys
1               5                   10                  15

Ser Ala Val Ser Lys Gly Tyr Leu Ser Ala Leu Arg Thr Gly Trp Tyr
            20                  25                  30

Thr Ser Val Ile Thr Ile Glu Leu Ser Asn Ile Lys Glu Asn Lys Cys
        35                  40                  45

Asn Gly Thr Asp Ala Lys Val Lys Leu Ile Lys Gln Glu Leu Asp Lys
    50                  55                  60

Tyr Lys Ser Ala Val Thr Glu Leu Gln Leu Leu Met Gln Ser Thr Pro
65                  70                  75                  80

Ala Thr Asn Asn Lys Phe Leu Gly Phe Leu Gln Gly Val Gly Ser Ala
                85                  90                  95

Ile Ala Ser Gly Ile Ala Val Ser Lys Val Leu His Leu Glu Gly Glu
```

-continued

```
            100                 105                 110

Val Asn Lys Ile Lys Ser Ala Leu Leu Ser Thr Asn Lys Ala Val Val
        115                 120                 125

Ser Leu Ser Asn Gly Val Ser Val Leu Thr Ser Lys Val Leu Asp Leu
    130                 135                 140

Lys Asn Tyr Ile Asp Lys Gln Leu Leu Pro Ile Val Asn Lys Gln Ser
145                 150                 155                 160

Cys Ser Ile Ser Asn Ile Glu Thr Val Ile Glu Phe Gln Gln Lys Asn
                165                 170                 175

Asn Arg Leu Leu Glu Ile Thr Arg Glu Phe Ser Val Asn Ala Gly Val
            180                 185                 190

Thr Thr Pro Val Ser Thr Tyr Met Leu Thr Asn Ser Glu Leu Leu Ser
        195                 200                 205

Leu Ile Asn Asp Met Pro Ile Thr Asn Asp Gln Lys Lys Leu Met Ser
    210                 215                 220

Asn Asn Val Gln Ile Val Arg Gln Gln Ser Tyr Ser Ile Met Ser Ile
225                 230                 235                 240

Ile Lys Glu Glu Val Leu Ala Tyr Val Val Gln Leu Pro Leu Tyr Gly
                245                 250                 255

Val Ile Asp Thr Pro Cys Trp Lys Leu His Thr Ser Pro Leu Cys Thr
            260                 265                 270

Thr Asn Thr Lys Glu Gly Ser Asn Ile Cys Leu Thr Arg Thr Asp Arg
        275                 280                 285

Gly Trp Tyr Cys Asp Asn Ala Gly Ser Val Ser Phe Phe Pro Leu Ala
    290                 295                 300

Glu Thr Cys Lys Val Gln Ser Asn Arg Val Phe Cys Asp Thr Met Asn
305                 310                 315                 320

Ser Leu Thr Leu Pro Ser Glu Val Asn Leu Cys Asn Ile Asp Ile Phe
                325                 330                 335

Asn Pro Lys Tyr Asp Cys Lys Ile Met Thr Ser Lys Thr Asp Val Ser
            340                 345                 350

Ser Ser Val Ile Thr Ser Leu Gly Ala Ile Val Ser Cys Tyr Gly Lys
        355                 360                 365

Thr Lys Cys Thr Ala Ser Asn Lys Asn Arg Gly Ile Ile Lys Thr Phe
    370                 375                 380

Ser Asn Gly Cys Asp Tyr Val Ser Asn Lys Gly Val Asp Thr Val Ser
385                 390                 395                 400

Val Gly Asn Thr Leu Tyr Tyr Val Asn Lys Gln Glu Gly Lys Ser Leu
                405                 410                 415

Tyr Val Lys Gly Glu Pro Ile Ile Asn Phe Tyr Asp Pro Leu Val Phe
            420                 425                 430

Pro Ser Asp Glu Phe Asp Ala Ser Ile Ser Gln Val Asn Glu Lys Ile
        435                 440                 445

Asn Gly Thr Leu Ala Phe Ile Arg Lys Ser Asp Glu Lys Leu His Asn
    450                 455                 460
```